US008513186B2

(12) United States Patent
Cottell et al.

(10) Patent No.: US 8,513,186 B2
(45) Date of Patent: Aug. 20, 2013

(54) ANTIVIRAL COMPOUNDS

(75) Inventors: Jeromy J. Cottell, Redwood City, CA (US); John O. Link, San Francisco, CA (US); Scott D. Schroeder, Foster City, CA (US); James Taylor, Burlingame, CA (US); Winston C. Tse, San Mateo, CA (US); Randall W. Vivian, San Mateo, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 881 days.

(21) Appl. No.: 12/215,601

(22) Filed: Jun. 26, 2008

(65) Prior Publication Data

US 2009/0186869 A1 Jul. 23, 2009

Related U.S. Application Data

(60) Provisional application No. 60/937,752, filed on Jun. 29, 2007, provisional application No. 60/959,698, filed on Jul. 16, 2007.

(51) Int. Cl.
*A61K 38/00* (2006.01)

(52) U.S. Cl.
USPC .......................................................... 514/4.3

(58) Field of Classification Search
None
See application file for complete search history.

(56) References Cited

U.S. PATENT DOCUMENTS

| | | | |
|---|---|---|---|
| 5,633,388 A | 5/1997 | Diana et al. |
| 5,866,684 A | 2/1999 | Attwood et al. |
| 5,869,253 A | 2/1999 | Draper |
| 6,018,020 A | 1/2000 | Attwood et al. |
| 6,225,284 B1 | 5/2001 | Albert et al. |
| 6,265,380 B1 | 7/2001 | Tung et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Llinas-Brunet et al. |
| 6,608,027 B1 | 8/2003 | Tsantrizos et al. |
| 6,642,204 B2 | 11/2003 | Llinas-Brunet et al. |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,908,901 B2 | 6/2005 | Bailey et al. |
| 6,919,423 B2 | 7/2005 | Llinas-Brunet |
| 7,041,698 B2 | 5/2006 | Ripka et al. |
| 7,148,347 B2 | 12/2006 | Brandenburg et al. |
| 2003/0191067 A1 | 10/2003 | Llinas-Brunet et al. |

FOREIGN PATENT DOCUMENTS

| | | |
|---|---|---|
| CA | 2429359 | 8/2002 |
| CA | 2486308 | 12/2004 |
| EP | 1162196 | 12/2001 |
| EP | 1437362 | 7/2004 |
| WO | WO-95/33764 | 12/1995 |
| WO | WO-97/06804 | 2/1997 |
| WO | WO-97/43310 | 11/1997 |
| WO | WO-98/17679 | 4/1998 |
| WO | WO-98/22496 | 5/1998 |
| WO | WO-98/46597 | 10/1998 |
| WO | WO-98/46630 | 10/1998 |
| WO | WO-99/07733 | 2/1999 |
| WO | WO-99/07734 | 2/1999 |
| WO | WO-99/38888 | 8/1999 |
| WO | WO-99/50230 | 10/1999 |
| WO | WO-99/64442 | 12/1999 |
| WO | WO-00/06529 | 2/2000 |
| WO | WO-00/09543 | 2/2000 |
| WO | WO-00/09558 | 2/2000 |
| WO | WO-00/10573 | 3/2000 |
| WO | WO-00/13708 | 3/2000 |
| WO | WO-00/18231 | 4/2000 |
| WO | WO-00/59929 | 10/2000 |
| WO | WO-01/32153 | 5/2001 |
| WO | WO-01/85172 | 11/2001 |
| WO | WO-02/04425 | 1/2002 |
| WO | WO-02/06246 | 1/2002 |
| WO | WO-02/060926 | 8/2002 |
| WO | WO-03/053349 | 7/2003 |
| WO | WO-03/064416 | 8/2003 |
| WO | WO-03/064455 | 8/2003 |
| WO | WO-03/064456 | 8/2003 |
| WO | WO-03/066103 | 8/2003 |
| WO | WO-03/099274 | 12/2003 |
| WO | WO-03/099316 | 12/2003 |
| WO | WO-2004/032827 | 4/2004 |
| WO | WO-2004/094452 | 4/2004 |
| WO | WO-2004/043339 | 5/2004 |
| WO | WO-2004/072243 | 8/2004 |
| WO | WO-2004/093798 A2 | 11/2004 |
| WO | WO-2004/101602 | 11/2004 |

(Continued)

OTHER PUBLICATIONS

Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008 ; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*

(Continued)

*Primary Examiner* — Thomas Heard
(74) *Attorney, Agent, or Firm* — Foley & Lardner LLP

(57) ABSTRACT

The invention is related to anti-viral compounds, compositions containing such compounds, and therapeutic methods that include the administration of such compounds, as well as to processes and intermediates useful for preparing such compounds.

37 Claims, No Drawings

(56) References Cited

FOREIGN PATENT DOCUMENTS

| WO | WO-2004/103996 | 12/2004 |
|---|---|---|
| WO | WO-2004/113365 | 12/2004 |
| WO | WO-2005/010029 | 2/2005 |
| WO | WO-2005/037214 | 4/2005 |
| WO | WO-2005/046712 | 5/2005 |
| WO | WO-2005/070955 | 8/2005 |
| WO | WO-2005/095403 | 10/2005 |
| WO | WO-2006/007700 | 1/2006 |
| WO | WO-2006/007708 | 1/2006 |
| WO | WO-2006/020276 | 2/2006 |
| WO | WO-2007/015824 | 7/2006 |
| WO | WO-2006/086381 | 8/2006 |
| WO | WO-2006/122188 | 11/2006 |
| WO | WO-2007/001406 A2 | 1/2007 |
| WO | WO-2007/008657 | 1/2007 |
| WO | WO-2007/009109 | 1/2007 |
| WO | WO-2007/011658 | 1/2007 |
| WO | WO-2007/044933 A1 | 4/2007 |

OTHER PUBLICATIONS

Testa Prodrug research: futile or fertile? Biochemical Pharmacology (2004) 2097-2106.*
Office Action for Australian Application No. 2008271116 dated Jun. 14, 2012.
Office Action for Chinese Application No. 200880104726.2 dated Jun. 13, 2012.
Office Action for Eurasian Application No. 200971074 dated Aug. 3, 2012.
Office Action for New Zealand Application No. 600527 dated Aug. 2, 2012.
Office Action for Thailand Application No. 0801003323 dated Aug. 13, 2012.
Lauer, G. et al. (2001) "Hepatitis C Virus Infection," New England Journal of Medicine, 345 (1): 41-52.
Weinstein, (1983), "Chemistry and Biochemistry of Amino Acids, Peptides and Proteins, Passage", Chemistry and Biochemistry of Amino Acids, Peptides and Proteins, 7, pp. 266-357.
Office Action for Chinese Application No. 20880104330.8 dated Jul. 4, 2011.
Office Action for Eurasian Application No. 200971074/28 dated May 4, 2011.
Office Action for New Zealand Application No. 582091 dated Dec. 8, 2010.
Office Action for Thailand Application No. 0801003326 dated Mar. 21, 2011.
Beaulieu, P. et al. (2005) "Synthesis of (1R,2S)-1-amino-2-vinylcyclopropanecarboxylic acid vinyl-ACCA) Derivatives: Key Intermediates for the Preparation of Inhibitors in the Hepatitis C Virus NS3 Protease" Journal of Organic Chemistry, 70:5869-5879.
Belokon, Y. et al. (1990) "General Method for the Asymmetric Synthesis of *anti*-Diasteroisomers of β-substituted L-2-aminobutanoic acids via chiral nickel-II Schiff's base complexes of dehydroaminobutanoic acid. X-Ray Crystal and Molecular Structure of the nickel(II) complex of the Schiff's base from [(benzylpropyl)amino]benzophenone and dehydroaminobutanoic acid" Journal of the Chemical Society Perkin Transactions I, 2301-2310.
Chu, M. et al. (1996) "Structure of Sch 68631: A New Hepatic C Virus Proteinase Inhibitor from *Streptmoyces* sp.", Tetrahedron Letters 37 (40):7229-7232.
Galgoci (1994) "A convenient synthesis of methyl (z)-1-carbamoyl-2-ethenylcyclopropanecarboxylate and (Z)-1-carbamoyl-2-ethenylcyclopropanecarboxylic acid" Synthetic Communications, 24:2477-2483.
Ingallinella, P. et al. (1998) "Potent Peptide Inhibitors of Human Hepatitis C Virus NS3 Protease Are Obtained by Optimizing the Cleavage Products," Biochemistry, 37:8906-8914.
International Search Report for PCT/US2008/007928, Jan. 14, 2009.
Llinas-Brunet, M. et al. (1998) "Peptide-Based Inhibitors of the Hepatitis C Virus Serine Protease," Bioorganic & Medicinal Chemistry Letters, 8:1713-1718.
Llinas-Brunet, M. et al. (2004) "A Systematic Approach to the Optimization of Substrate-Based Inhibitors of the Hepatitis C Virus NS3 Protease: Discovery of Potent and Specific Tripeptide Inhibitors," Journal of Medicinal Chemistry , 47:6584-6594.
Matsumoto, Y. et al. (1996) "3D Modeling of HCV Protease and Computer Screening of Its Inhibitors," Antiviral Research, Oreal Session III—Hepadnavirus, Papillomavirus, Other Infections. Abstract 19, p. A23.
Poupart, M. et al. (2001) "Solid-Phase Synthesis of Peptidomimetic Inhibitors for the Hepatitis C Virus NS3 Protease," The Journal of Organic Chemistry, 66 (14):4743-4751.
Poynard, T. et al. (1998), "Randomised Trial of Interferon ∝2b Plus Ribarvirin for 48 Weeks or for 24 Weeks Versus Interferon ∝2b Plus Placebo for 48 Weeks for Treatment of Chronic Infection with Hepatitis C Virus," The Lancet, 352:1426-1432.
Spatola, A. (1983) "Peptide Backbone Modifications: A Structure-Activity Analysis of Peptides Containing Amide Bond Surrogates, Conformational Constraints and Rela," Chemistry and Biochemistry of Amino Acids, Peptides, and Proteins. A Survey of Recent Developments. 7:267-357. Marcell Dekker, Inc. New York, NY.
Steinkuhler, C. et al. (1998) "Product Inhibition of the Hepatitis C Virus NS3 Protease," Biochemistry 37:8899-8905.
Tsantrizos, Y. et al. (2003) "Macrocyclic Inhibitors of the NS3 Protease as Potential Therapeutic Agents of Hepatitis C Virus Infection," Angewandte Chemie Int. Ed., 42 (12):1356-1360.
Zeuzem, S. et al. (2000) "Peginterferon Alfa-2a In Patients with Chronic Hepatitis C," The New England Journal of Medicine. 343(23):1666-1672.
International Search Report for PCT/US/2008/007927, Jan. 20, 2009.

* cited by examiner

ANTIVIRAL COMPOUNDS

PRIORITY OF INVENTION

This application claims priority under 35 U.S.C. §119(e) to U.S. Provisional Patent Application No. 60/937,752, filed 29 Jun. 2007; and to U.S. Provisional Patent Application No. 60/959,698, filed on 16 Jul. 2007. The entire content of each of these provisional patent applications is hereby incorporated herein by reference.

FIELD OF THE INVENTION

The invention relates generally to compounds with HCV inhibitory activity.

BACKGROUND OF THE INVENTION

Hepatitis C is recognized as a chronic viral disease of the liver which is characterized by liver disease. Although drugs targeting the liver are in wide use and have shown effectiveness, toxicity and other side effects have limited their usefulness. Inhibitors of HCV are useful to limit the establishment and progression of infection by HCV as well as in diagnostic assays for HCV.

There is a need for new HCV therapeutic agents.

SUMMARY OF THE INVENTION

In one embodiment the invention provides a compound of the invention which is a compound of formula I:

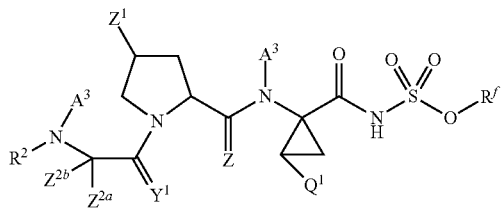

(I)

or a pharmaceutically acceptable salt, or prodrug thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from,
a) —C($Y^1$)($A^3$),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
where said alkyl, cycloalkyl and alkyl-cycloalkyl may optionally be mono- or di-substituted with substituents selected from hydroxy and O—(C1-4)alkyl, or
where each of said alkyl-groups may optionally be mono-, di- or tri-substituted with halogen, or
where each of said cycloalkyl groups being 5-, 6- or 7-membered, one or two —CH$_2$— groups not being directly linked to each other may be optionally replaced by —O— such that the O-atom is linked to the N atom to which $R^2$ is attached via at least two C-atoms, c) phenyl, (C1-3)alkyl-phenyl, heteroaryl or (C1-3)alkyl-heteroaryl,
wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen;
d) —S(O)$_2$($A^3$); or
e) —C($Y^1$)—X—Y;

$R^3$ is H or (C1-6)alkyl;

$Y^1$ is independently O, S, N($A^3$), N(O)($A^3$), N(O$A^3$), N(O)(O$A^3$) or N(N($A^3$)($A^3$));

Z is O, S, or N$R^3$;

$Z^1$ is an organic group having a three dimensional shape that will fit the extended S2 region of the HCV NS3 serine protease domain;

$Z^{2b}$ is H, (C1-10)alkyl, (C2-10)alkenyl, (C2-10)alkynyl;

$Q^1$ is $A^3$; or $Q^1$ and $Z^{2a}$ taken together with the atoms to which they are attached form a heterocycle, which heterocycle may optionally be substituted with one or more oxo (=O), $R^4$, or $A^3$;

each X is independently a bond, O, S, or N$R^3$;

Y is a polycarbocycle or a polyheterocycle, which polycarbocycle or a polyheterocycle is optionally substituted with one or more $R^4$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$, SR$_r$, S(O)R$_r$, or S(O)$_2$R$_r$;

each $R^4$ is independently —P($Y^3$)(O$A^2$)(O$A^2$), —P($Y^3$)(O$A^2$)(N($A^2$)$_2$), —P($Y^3$)($A^2$)(O$A^2$), —P($Y^3$)($A^2$)(N($A^2$)$_2$), or P($Y^3$)(N($A^2$)$_2$)(N($A^2$)$_2$);

each $Y^3$ is independently O, S, or N$R^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl, or (C1-10)alkoxycarbonyl;

$Z^{2a}$ is H, (C1-10)alkyl, (C2-10)alkenyl, (C2-10)alkynyl, haloalkyl, (C1-10)alkyl-S(=O)$_2$—(C1-10)alkyl, or cycloalkyl, wherein any carbon atom of $Z^{2a}$ may optionally be replaced with a heteroatom selected from O, S, S(=O), S(=O)$_2$, or N and wherein any cycloalkyl is optionally substituted with one or more (C1-10)alkyl, (C2-10)alkenyl, (C2-10)alkynyl, haloalkyl, F, Cl, Br, or I; or $Z^{2a}$ optionally forms a heterocycle with one or more $R^1$, $R^2$, $Q^1$, or $A^3$;

$A^3$ is independently selected from PRT, H, —OH, —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, —C($A^2$)$_3$, —C($A^2$)$_2$-C(O)$A^2$, —C(O)$A^2$, —C(O)O$A^2$, —O($A^2$), —N($A^2$)$_2$, —S($A^2$), —CH$_2$P($Y^1$)($A^2$)(O$A^2$), —CH$_2$P($Y^1$)($A^2$)(N($A^2$)$_2$), —CH$_2$P($Y^1$)(O$A^2$)(O$A^2$), —OCH$_2$P $(Y^1)(OA^2)(OA^2)$, $-OCH_2P(Y^1)(A^2)(OA^2)$, $-OCH_2P(Y^1)(A^2)(N(A^2)_2)$, $-C(O)OCH_2P(Y^1)(OA^2)(OA^2)$, $-C(O)OCH_2P(Y^1)(A^2)(OA^2)$, $-C(O)OCH_2P(Y^1)(A^2)(N(A^2)_2)$, $-OCH_2P(Y^1)(OA^2)(N(A^2)_2)$, $-C(O)OCH_2P(Y^1)(OA^2)(N(A^2)_2)$, $-CH_2P(Y^1)(N(A^2)_2)(N(A^2)_2)$, $-C(O)OCH_2P(Y^1)(N(A^2)_2)(N(A^2)_2)$, $-OCH_2P(Y^1)(N(A^2)_2)(N(A^2)_2)$, $-(CH_2)_m$-heterocycle, $-(CH_2)_mC(O)Oalkyl$, $-O-(CH_2)_m-O-C(O)-Oalkyl$, $-O-(CH_2)_r-O-C(O)-(CH_2)_m$-alkyl, $-(CH_2)_mO-C(O)-O$-alkyl, $-(CH_2)_mO-C(O)-O$-cycloalkyl, $-N(H)C(Me)C(O)O$-alkyl, $SR_r$, $S(O)R_r$, $S(O)_2R_r$, or alkoxy arylsulfonamide, wherein each $A^3$ may be optionally substituted with 1 to 4

$-R^1$, $-P(Y^1)(OA^2)(OA^2)$, $-P(Y^1)(OA^2)(N(A^2)_2)$, $-P(Y^1)(A^2)(OA^2)$, $-P(Y^1)(A^2)(N(A^2)_2)$, or $P(Y^1)(N(A^2)_2)(N(A^2)_2)$, $-C(=O)N(A^2)_2)$, halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, $-(CH_2)_m$heterocycle, $-(CH_2)_m-C(O)O$-alkyl, $-O(CH_2)_mOC(O)Oalkyl$, $-O-(CH_2)_m-O-C(O)-(CH_2)_m$-alkyl, $-(CH_2)_m-O-C(O)-O$-alkyl, $-(CH_2)_m-O-C(O)-O$-cycloalkyl, $-N(H)C(CH_3)C(O)O$-alkyl, or alkoxy arylsulfonamide, optionally substituted with $R^1$;

optionally each independent instance of $A^3$ and $Q^1$ can be taken together with one or more $A^3$ or $Q^1$ groups to form a ring; and $A^2$ is independently, selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each $A^2$ is optionally substituted with $A^3$.

$R^f$ is $A^3$; and m is 0 to 6.

The present invention also provides a pharmaceutical composition comprising a compound of the invention and at least one pharmaceutically acceptable carrier.

The present invention also provides a pharmaceutical composition for use in treating disorders associated with HCV.

The present invention also provides a pharmaceutical composition further comprising a nucleoside analog.

The present invention also provides for a pharmaceutical composition further comprising an interferon or pegylated interferon.

The present invention also provides for a pharmaceutical composition wherein said nucleoside analogue is selected from ribavirin, viramidine levovirin, a L-nucleoside, and isatoribine and said interferon is a-interferon or pegylated interferon.

The present invention also provides for a method of treating disorders associated with hepatitis C, said method comprising administering to an individual a pharmaceutical composition which comprises a therapeutically effective amount of a compound of the invention.

The present invention also provides a method of inhibiting HCV, comprising administering to a mammal afflicted with a condition associated with HCV activity, an amount of a compound of the invention, effective to inhibit HCV.

The present invention also provides a compound of the invention for use in medical therapy (preferably for use in inhibiting HCV or treating a condition associated with HCV activity), as well as the use of a compound of the invention for the manufacture of a medicament useful for inhibiting HCV or the treatment of a condition associated with HCV activity in a mammal.

The present invention also provides synthetic processes and novel intermediates disclosed herein which are useful for preparing compounds of the invention. Some of the compounds of the invention are useful to prepare other compounds of the invention.

In another aspect the invention provides a compound of formula I, or a pharmaceutically acceptable salt or prodrug thereof, for use in the prophylactic or therapeutic treatment of hepatitis C or a hepatitis C associated disorder.

In another aspect the invention provides a method of inhibiting HCV activity in a sample comprising treating the sample with a compound of the invention.

In one embodiment the invention provides a compound having improved inhibitory or pharmacokinetic properties, including enhanced activity against development of viral resistance, improved oral bioavailability, greater potency or extended effective half-life in vivo. Certain compounds of the invention may have fewer side effects, less complicated dosing schedules, or be orally active.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compounds of the Invention

The compounds of the invention exclude compounds heretofore known. However it is within the invention to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "$R^1$" or "$A^3$", then it will be understood that the groups may be the same or different, i.e., each group is independently selected.

"Alkyl" is $C_1$-$C_{18}$ hydrocarbon containing normal, secondary, tertiary or cyclic carbon atoms. Examples are methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl (—CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃, and cyclopropylmethyl

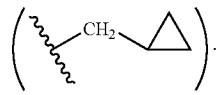

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—CH=CH₂), allyl (—CH₂CH=CH₂), cyclopentenyl (—C₅H₇), and 5-hexenyl (—CH₂ CH₂CH₂CH₂CH=CH₂).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH₂C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "polycarbocycle" refers to a saturated or unsaturated polycyclic ring system having from about 6 to about 25 carbon atoms and having two or more rings (e.g. 2, 3, 4, or 5 rings). The rings can be fused and/or bridged to form the polycyclic ring system. For example, the term includes bicyclo [4,5], [5,5], [5,6] or [6,6] ring systems, as well as the following bridged ring systems:

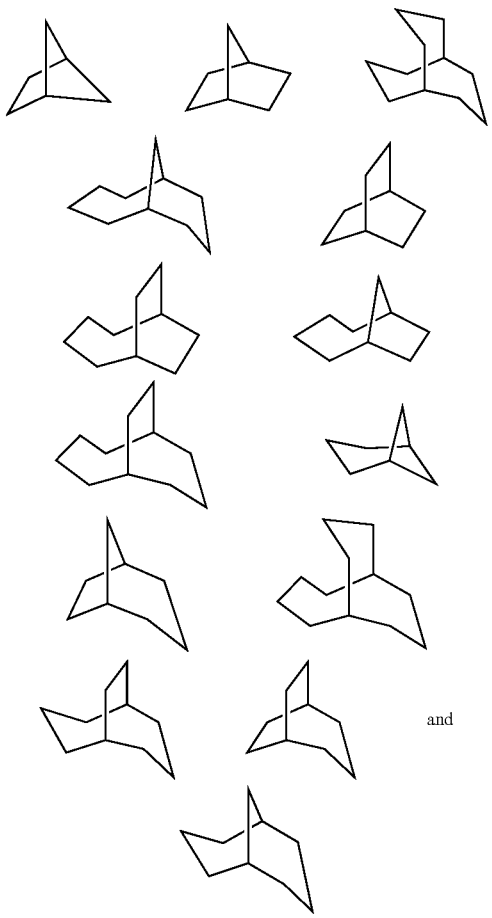

and (i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" refers to a polycarbocycle as defined herein, wherein one or more carbon atoms is replaced with a heteroatom (e,g, O, S, S(O), S(O)₂, N⁺(O⁻)$R_x$, or N$R_x$); wherein each $R_x$ is independently H, (C1-10)alkyl, (C2-10)alkenyl, (C2-10)alkynyl, (C1-10)alkanoyl, S(O)₂NR$_n$R$_p$, S(O)₂R$_x$, or (C1-10)alkoxy, wherein each (C1-10)alkyl, (C2-10)alkenyl, (C2-10)alkynyl, (C1-10)alkanoyl, and (C1-10) alkoxy is optionally substituted with one or more halo).

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NRR—S(=O)₂O⁻, —S(=O)₂OH, —S(=O)₂R, —OS(=O)₂OR, —S(=O)₂NR, —S(=O)R, —OP(=O)O₂RR, —P(=O)O₂RR—P(=O)(O⁻)₂, —P(=O)(OH)₂, —C(=O)R, —C(=O)X, —C(S)R, —C(O)OR, —C(O)O—, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

The term "optionally substituted" in reference to a particular moiety of the compound of formula I, (e.g., an optionally substituted aryl group) refers to a moiety having 0, 1, 2, or more substituents.

The symbol "- - -" means that a bond is a single or double bond. In a non-limiting example,

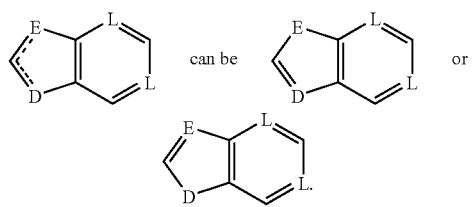

"Haloalkyl" as used herein includes an alkyl group substituted with one or more halogens (e.g. F, Cl, Br, or I). Representative examples of haloalkyl include trifluoromethyl, 2,2,2-trifluoroethyl, and 2,2,2-trifluoro-1-(trifluoromethyl)ethyl.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs* (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

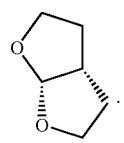

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo[4,5], [5,5], [5,6] or [6,6] system, or 9 or 10 ring atoms arranged as a bicyclo [5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. When $Q^1$ and $Z^{2a}$ taken together with the atoms to which they are attached form a heterocycle, the heterocycle formed by $Q^1$ and $Z^{2a}$ taken together with the atoms to which they are attached may typically comprise up to about 25 atoms.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "PRT" is selected from the terms "prodrug moiety" and "protecting group" as defined herein.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

$Z^1$ Groups

The compounds of the invention have inhibitory activity toward HCV protease. Unexpectedly, it has been found that compounds possessing the acyl sulfamate group of the following formula:

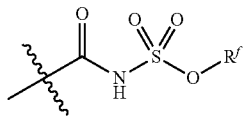

are suitably stable under physiological conditions. Additionally, it has been determined that representative compounds possessing this sulfamate group are unexpectedly potent inhibitors of HCV polymerase.

The crystal structure of the S2 region of the HCV NS3 serine protease is known. See for example Y. S. Tsantrizos et al., *Angew. Chem. Int. Ed.* 2003, 42, 12, 1356-1360. The extended S2 region of the HCV NS3 serine protease domain interacts with the P2 group of several classes of inhibitors which act by competing with the natural viral peptide substrates for binding to the substrate binding site and active site of the protease. Specifically, crystal structure analysis reveals that the NS3 residues, aspartic acid (Asp) 168 and arginine (Arg) 155, form a salt bridge which orients the planes of the carboxylic acid moiety of Asp 168 and the guanidinium moiety of Arg 155 parallel to the plane of the P2 group when the inhibitor is bound. This flat stacking interaction likely includes a combination of Van der Waals and hydrophobic forces that help promote the formation of a complex between the NS3 protein and the inhibitor.

The 7-methoxy group of several known inhibitors may also form favorable electronic interactions with the coplanar guanidinium moiety of Arg 155 (~3.5 Å between the two planes of atoms) which also helps stabilize the complex. Similarly, the orientation of NS3 residues, Asp 81 and histidine (His) 57, of the catalytic triad form a flat surface against which a portion of the inhibitor P2 group can pack. Again, the coplanar stacking arrangement between the inhibitor P2 group and NS3 residues 81 and 57 likely provide a combination of attractive Van der Waals and hydrophobic forces that help increase the affinity between the protease and the inhibitor. For more elaborated P2 groups, the backbone carbonyl oxygens of residues valine (Val) 78 and Asp 79 come in close contact to substitutions at the 8-position of the isoquinoline ring. Larger substitutions off of the 2-position of the isoquinoline ring, such as isopropyl aminothiazoles, come in close proximity to tyrosine (Tyr) 56.

In light of this understanding regarding the S2 region of the HCV NS3 serine protease, one skilled in the art can identify $Z^1$ groups that have a three dimensional shape that will fit the extended S2 region of the HCV NS3 serine protease domain to provide a serine protease inhibitor of formula I that possesses the benefits of the acyl sulfamate group discussed above. Accordingly, the structure of $Z^1$ in the compounds of formula (I) can vary considerably, provided $Z^1$ has a three dimensional shape that will fit the extended S2 region of the HCV NS3 serine protease domain to provide a compound with serine protease inhibiting activity. In one embodiment of the invention, $Z^1$ is an organic group having a three dimensional shape that will fit the extended S2 region of the HCV NS3 serine protease domain.

Additionally, it is known that it can be desirable for protease inhibitors to have favorable interactions (e.g. interactions such as Van der Waals or hydrophobic interactions) with one or more residues corresponding to Histidine 57, Aspartic acid 81, Arginine 155, and Aspartic acid 168 of the extended S2 region of the HCV NS3 serine protease domain. In another embodiment, the invention $Z^1$ is an organic group that has favorable interactions (e.g. interactions such as Van der Waals or hydrophobic interactions) with one or more residues corresponding to Histidine 57, Aspartic acid 81, Arginine 155, and Aspartic acid 168 of the extended S2 region of the HCV NS3 serine protease domain.

Additionally, it is known that it can be desirable for protease inhibitors to have favorable interactions with one or more residues corresponding to Tyrosine 56, Valine 78, and Aspartic acid 79 of the extended S2 region of the HCV NS3 serine protease domain. In another embodiment, the invention $Z^1$ is an organic group that has favorable interactions (e.g. interactions such as Van der Waals or hydrophobic interactions) with one or more residues corresponding to Tyrosine 56, Valine 78, and Aspartic acid 79 of the extended S2 region of the HCV NS3 serine protease domain.

A large number of pyrole cyclopropyl based compounds have been reported to possess activity as protease inhibitors. Based on the variety of structures tested to date, it is believed that the potency of this class of pyrole cyclopropyl compounds can be improved by incorporating the above sulfamate group into this class of compounds.

For example, the above sulfamate group can be incorporated into the compounds reported in International Patent Application Publication Number WO 2006/007700 and WO 2006/007708 in place of the —C(=O)NHSO$_n$—R$^4$ group of formula (I) therein; the above sulfamate group can be incorporated into the compounds reported in WO 2004/113365, WO 2005/010029, and WO 2004/072243 in place of the —C(=O)G group of formula (I) therein; the above sulfamate group can be incorporated into the compounds reported in WO 2006/086381 in place of the —C(=O)W group of formula (I) therein; the above sulfamate group can be incorporated into the compounds reported in U.S. Pat. No. 6,878,722 in place of the group

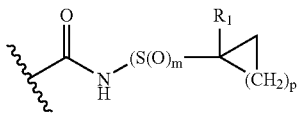

of formula (I) therein; the above sulfamate group can be incorporated into the compounds reported in WO 2003/099274 in place of the —C(=O)N(H)SO$_m$R$_1$ group of formula (I) therein; the above sulfamate group can be incorporated into the compounds reported in WO 2004/094452 in place of the —C(=O)W group of formula (I) therein; the above sulfamate group can be incorporated into the compounds reported in WO 2005/095403 in place of the —Y group of formula (I) therein; and the above sulfamate group can be incorporated into the compounds reported in WO 2007/015824 in place of the —C(=O)—R$^2$ group of formula (I) therein.

In one embodiment, the invention provides a compound of formula (I) as described herein, wherein Z$^1$ has any of the values defined for R$^2$ in WO 2006/007700 or WO 2006/007708.

In one embodiment, the invention provides a compound of formula (I) as described herein, wherein Z$^1$ has any of the values defined for W in WO 2004/113365.

In one embodiment, the invention provides a compound of formula (I) as described herein, wherein Z$^1$ has any of the values defined for -M-Q in WO 2005/010029.

In one embodiment, the invention provides a compound of formula (I) as described herein, wherein Z$^1$ has any of the values defined for W in WO 2004/072243.

In one embodiment, the invention provides a compound of formula (I) as described herein, wherein Z$^1$ has any of the values defined for —O-L-R$^1$ in WO 2006/086381.

In one embodiment, the invention provides a compound of formula (I) as described herein, wherein Z$^1$ has any of the values defined for

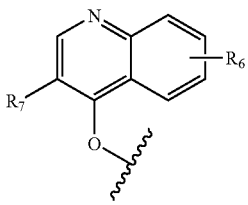

in U.S. Pat. No. 6,878,722.

In one embodiment, the invention provides a compound of formula (I) as described herein, wherein Z$^1$ has any of the values defined for —X—R' in WO 2003/099274.

In one embodiment, the invention provides a compound of formula (I) as described herein, wherein Z$^1$ has any of the values defined for

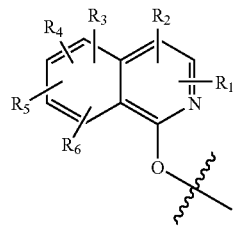

in WO 2004/094452.

In one embodiment, the invention provides a compound of formula (I) as described herein, wherein Z$^1$ has any of the values defined for —W—C(=V)-Q in WO 2005/095403.

In one embodiment, the invention provides a compound of formula (I) as described herein, wherein Z$^1$ has any of the values defined for R$^1$ in WO 2007/015824.

The entire content of International Patent Application Publication Numbers WO 2006/007700, WO 2006/007708, WO 2004/113365, WO 2005/010029, WO 2004/072243, WO 2006/086381, WO 2003/099274, WO 2004/094452, WO 2005/095403, and WO 2007/015824 as well as the entire content of U.S. Pat. No. 6,878,722 is hereby incorporated herein by reference. In particular, the definitions for the groups substituted at the 3-position of the pyrole rings in formulae (I) therein as well as information relating to suitable synthetic routes for preparing the compounds of formulae (I) therein are hereby incorporated herein by reference.

Prodrugs

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —CH$_2$C(=O)R$^9$ and acyloxymethyl carbonates —CH$_2$C(=O)OR$^9$ where R$^9$ is C$_1$-C$_6$ alkyl, C$_1$-C$_6$ substituted alkyl, C$_6$-C$_{20}$ aryl or C$_6$-C$_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM)-CH$_2$C(=O)C(CH$_3$)$_3$. An exemplary acyloxymethyl carbonate prodrug moiety is pivaloyloxymethylcarbonate (POC)—CH$_2$C(=O)OC(CH$_3$)$_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

By way of example and not limitation, A$^3$, A$^2$ and R$^1$ are all recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. Whenever a compound described herein is substituted with more than one of the same designated group, e.g., "R$^1$" or "A$^3$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Cellular Accumulation

In one embodiment, the invention provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this embodiment may further comprise a phosphonate or phosphonate prodrug. More typically, the phosphonate or phosphonate prodrug can have the structure $A^3$ as described herein.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of HCV. Accordingly, the invention relates to methods of detecting NS3 in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (I) that comprises or that is bound or linked to one or more detectable labels. Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in man.

However, in screening compounds capable of inhibiting HCV it should be kept in mind that the results of enzyme assays may not always correlate with cell culture assays. Thus, a cell based assay should typically be the primary screening tool.

Screens for HCV Inhibitors

Compounds of the invention are screened for inhibitory activity against HCV by any of the conventional techniques for evaluating enzyme activity. Within the context of the invention, typically compounds are first screened for inhibition of HCV in vitro and compounds showing inhibitory activity are then screened for activity in vivo. Compounds having in vitro Ki (inhibitory constants) of less then about $5\times10^{-6}$ M, typically less than about $1\times10^{-7}$ M and preferably less than about $5\times10^{-8}$ M are preferred for in vivo use. Useful in vitro screens have been described in detail.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salkylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention can also be used in combination with other active ingredients. Such combinations are selected based on the condition to be treated, cross-reactivities of ingredients and pharmaco-properties of the combination.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Suitable active therapeutic agents or ingredients which can be combined with the compounds of formula I can include interferons, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon; ribavirin analogs, e.g., rebetol, copegus, levovirin VX-497, and viramidine (taribavirin); NS5a inhibitors, e.g., A-831 and A-689; NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-21-25; NS3 protease inhibitors, e.g., SCH-503034 (SCH-7), VX-950 (Telaprevir), ITMN-191, and BILN-2065; alpha-glucosidase I inhibitors, e.g., MX-3253 (celgosivir) and UT-231B; hepatoprotectants, e.g., IDN-6556, ME 3738, MitoQ, and LB-84451; non-nucleoside inhibitors of HCV, e.g., benzimidazole derivatives, benzo-1,2,4-thiadiazine derivatives, and phenylalanine derivatives; and other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-68.65, ANA 971, NOV-205, tarvacin, EHC-18, and NIM811.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of formula I and additional active therapeutic agents may be selected to treat patients infected with HCV and other conditions such as HIV infections. Accordingly, the compounds of formula I may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+ actimmune, IFN-omega with DUROS, and albuferon, 12) ribavirin analogs, e.g., rebetol, copegus, levovirin, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 19) pharmacokinetic enhancers, e.g., BAS-100 and SPI452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV-inhibitory activity of their own.

Methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry*. In 9 Volumes, Barry M. Trost, Editor-in-Chief (Pergamon Press, New York, 1993 printing). Other methods suitable for preparing compounds of the invention are described in International Patent Application Publication Number WO 2006/020276.

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113, 3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Specific Embodiments of the Invention

In one specific embodiment the invention $Z^1$ is $A^3$.

In one specific embodiment the invention $Z^1$ is selected from $A^3$.

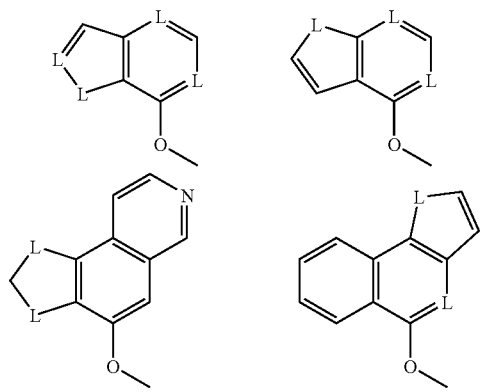

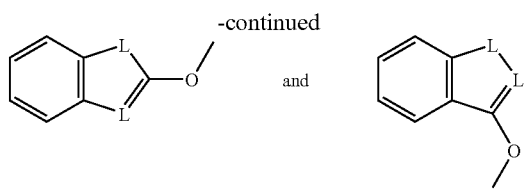

wherein each L is independently CH or N; and wherein each $Z^1$ is optionally substituted with one or more $A^3$.

In one specific embodiment the invention $Z^1$ is a group $—Z^3$-Q, wherein: $Z^3$ is a direct bond, —O—, —S—, —S(=O)—, —S(=O)$_2$, —C(=O)—, —C(=O)O—, or —OC(=O)—; and Q is a bicyclic [4.4.0] ring system wherein at least one ring is aromatic, which ring system comprises one or more carbon atoms and optionally comprises one or more O, S, S(=O), S(=O)$_2$, —N=, or —N($A^5$)- in the ring system; wherein each $A^5$ is independently $A^3$ or the point of attachment to $Z^3$; and wherein the ring system is optionally substituted on one or more carbon atoms with $A^3$.

In one specific embodiment the invention $Z^1$ is a group $—Z^3$-Q, wherein: $Z^3$ is a direct bond, —O—, —S—, —C(=O)—, —C(=O)O—, or —OC(=O)—; and Q is a bicyclic [4.4.0] ring system wherein at least one ring is aromatic, which ring system comprises one or more carbon atoms and optionally comprises one or more —N= or —N($A^5$)- in the ring system, and which ring system is optionally substituted on one or more carbon atoms with $A^3$.

In one specific embodiment the invention $Z^1$ is a group $—Z^3$-Q, wherein: $Z^3$ is a direct bond, —O—, —S—, —C(=O)—, —C(=O)O—, or —OC(=O)—; and Q is a bicyclic [4.4.0] ring system wherein both rings are aromatic, which ring system comprises one or more carbon atoms and optionally comprises one or more —N= in the ring system, and which ring system is optionally substituted on one or more carbon atoms with $A^3$.

In one specific embodiment the invention $Z^1$ is a group $—Z^3$-Q, wherein: $Z^3$ is a direct bond, —O—, —S—, —C(=O)—, —C(=O)O—, or —OC(=O)—; and Q is a bicyclic [4.4.0] ring system wherein both rings are aromatic, which ring system comprises one or more carbon atoms and comprises 1, 2, 3, or 4 —N= in the ring system, and which ring system is optionally substituted on one or more carbon atoms with $A^3$.

In one specific embodiment the invention $Z^1$ is a group $—Z^3$-Q, wherein: $Z^3$ is a direct bond, —O—, —S—, —C(=O)—, —C(=O)O—, or —OC(=O)—; and Q is a bicyclic [4.4.0] ring system wherein both rings are aromatic, which ring system comprises one or more carbon atoms and comprises 1 or 2 —N= in the ring system, and which ring system is optionally substituted on one or more carbon atoms with $A^3$.

In one specific embodiment the invention $Z^1$ is a group $—Z^3$-Q, wherein: $Z^3$ is a direct bond, —O—, —S—, —C(=O)—, —C(=O)O—, or —OC(=O)—; and Q is a 1-naphthyl or 2-naphthyl ring system that is optionally substituted with one or more $A^3$.

In one specific embodiment the invention $Z^1$ is a group $—Z^3$-Q, wherein: $Z^3$ is a direct bond, —O—, —S—, —S(=O)—, —S(=O)$_2$, —C(=O)—, —C(=O)O—, or —OC(=O)—; and Q is a bicyclic [4.3.0] ring system wherein at least one ring is aromatic, which ring system comprises one or more carbon atoms and optionally comprises one or more O, S, S(=O), S(=O)$_2$, —N=, or —N($A^5$)- in the ring system; wherein each $A^5$ is independently $A^3$ or the point of attachment to $Z^3$; and wherein the ring system is optionally substituted on one or more carbon atoms with $A^3$. In one specific embodiment the invention $Z^3$ is a direct bond, —O—, or —OC(=O)—. In one specific embodiment the invention $Z^3$ is a direct bond. In one specific embodiment the invention $Z^3$ is —O—. In one specific embodiment the invention $Z^3$ is —C(=O)O—.

In one specific embodiment the invention $Z^1$ is selected from:

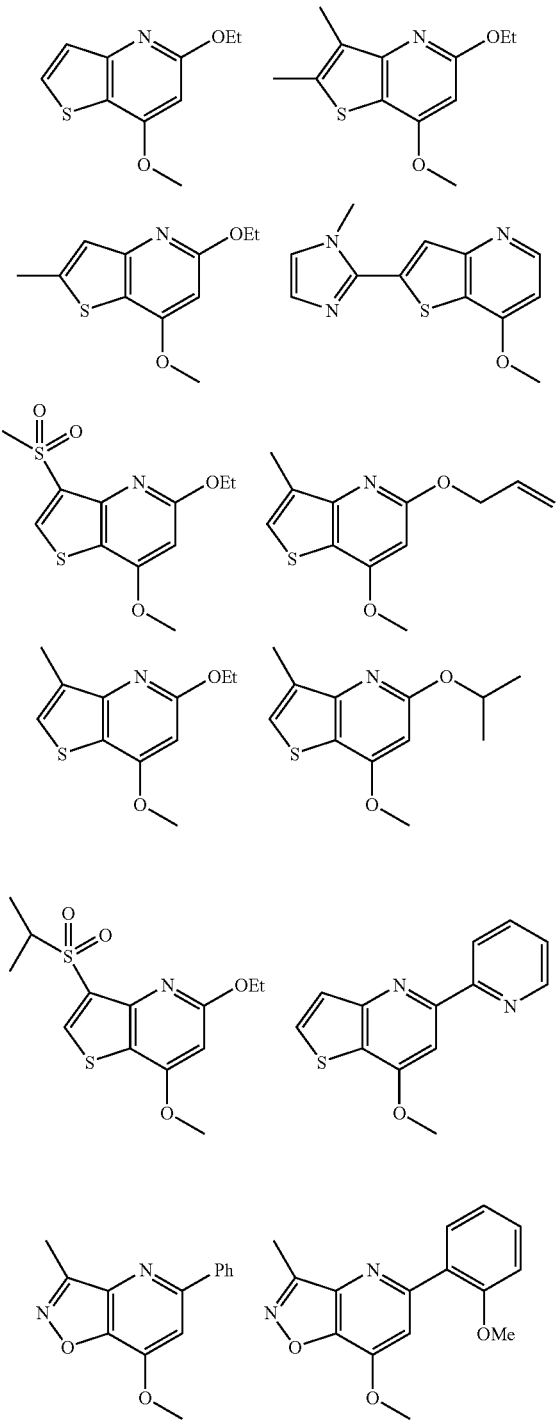

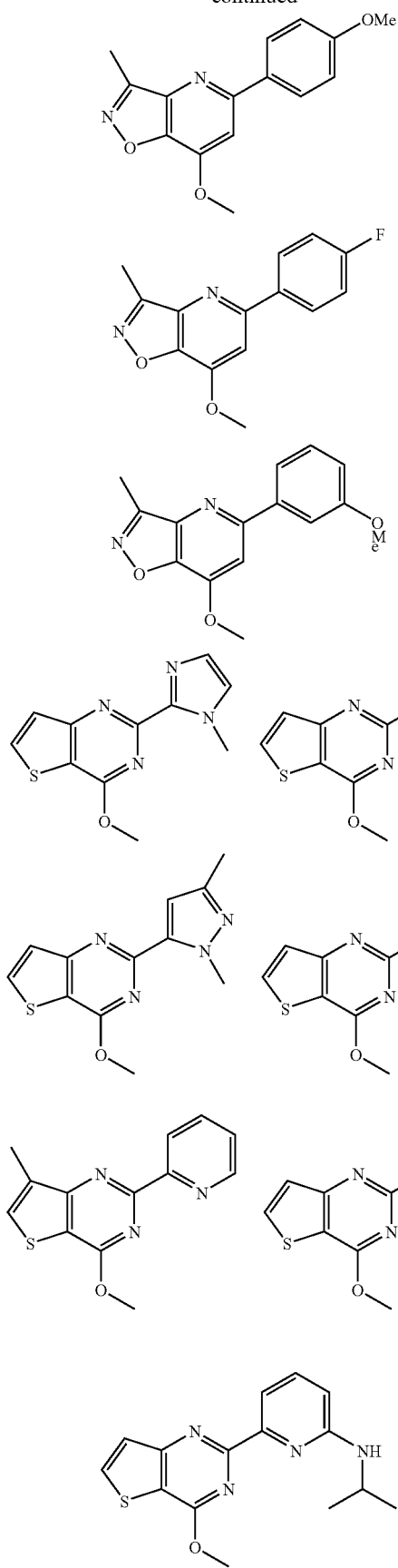
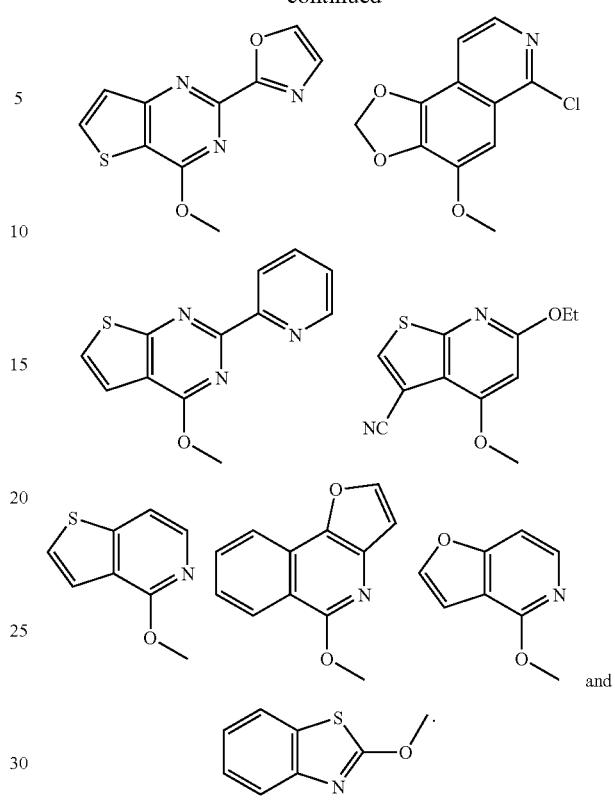
In one specific embodiment the invention $Z^1$ is selected from:
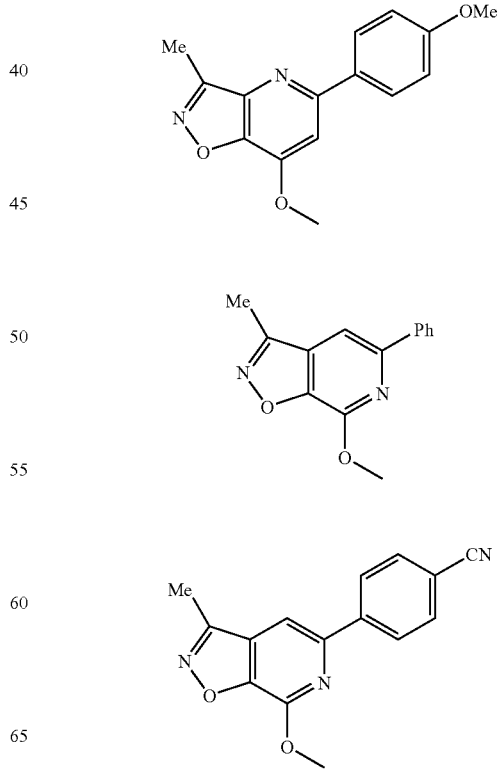

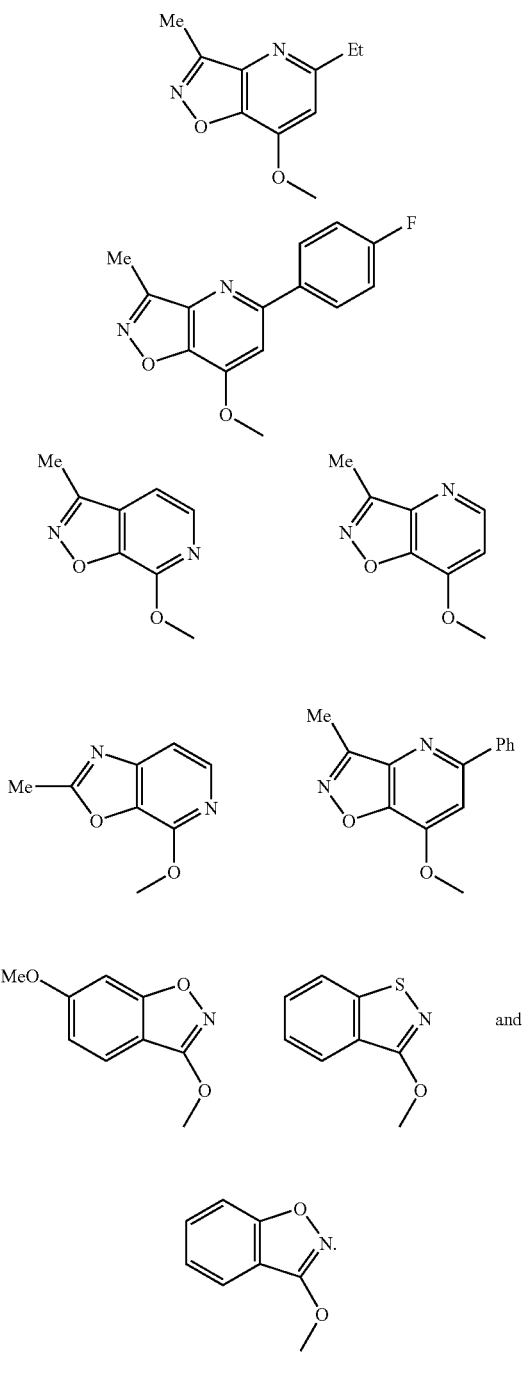
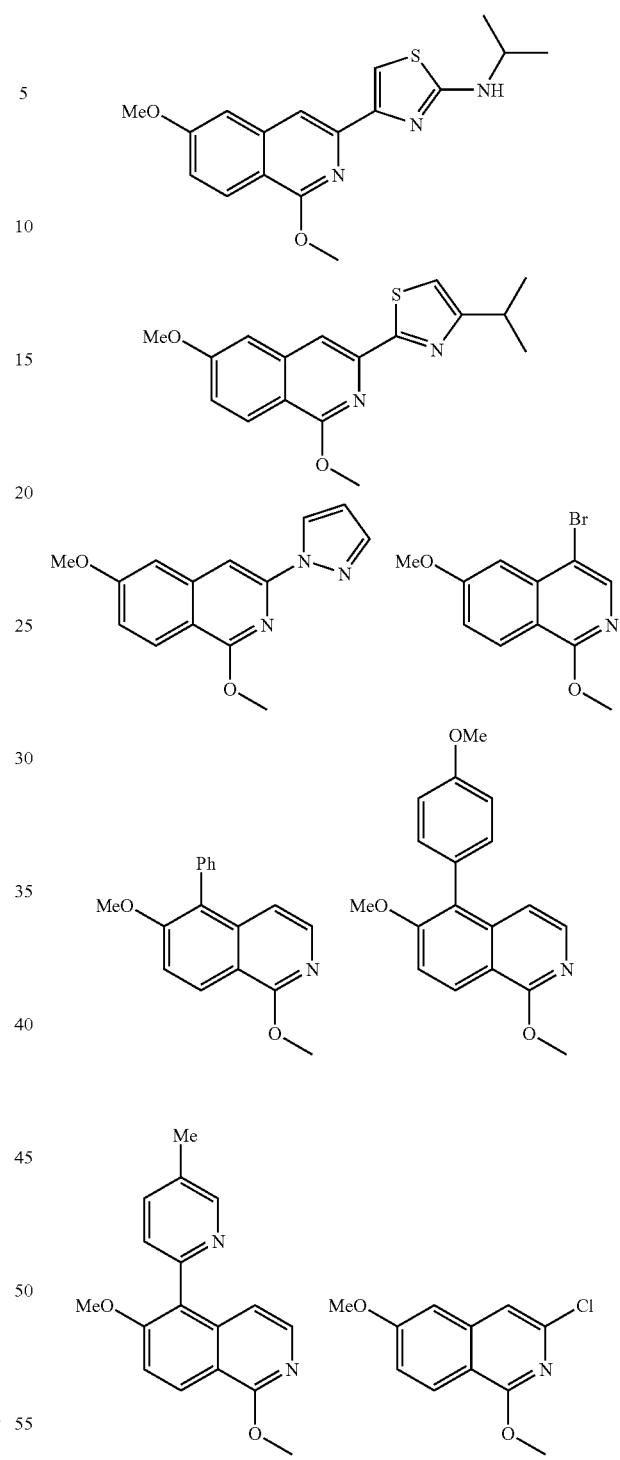
In one specific embodiment the invention $Z^1$ is selected from:
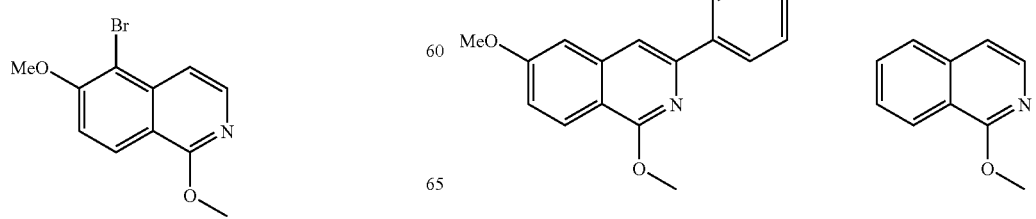

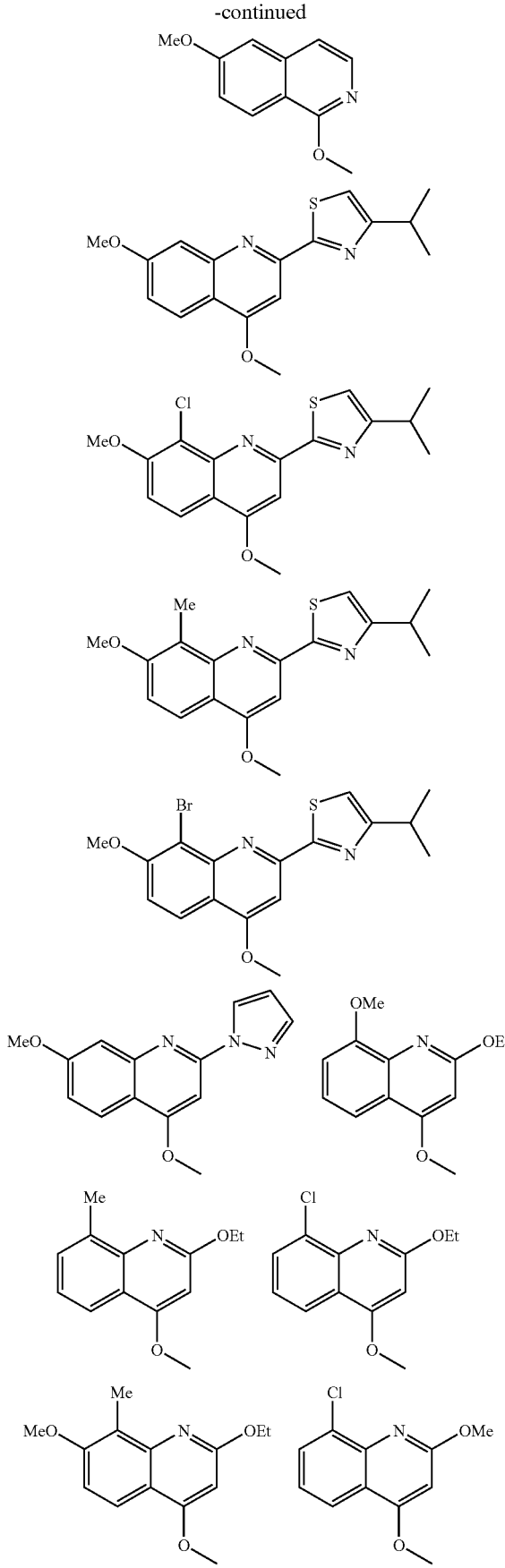
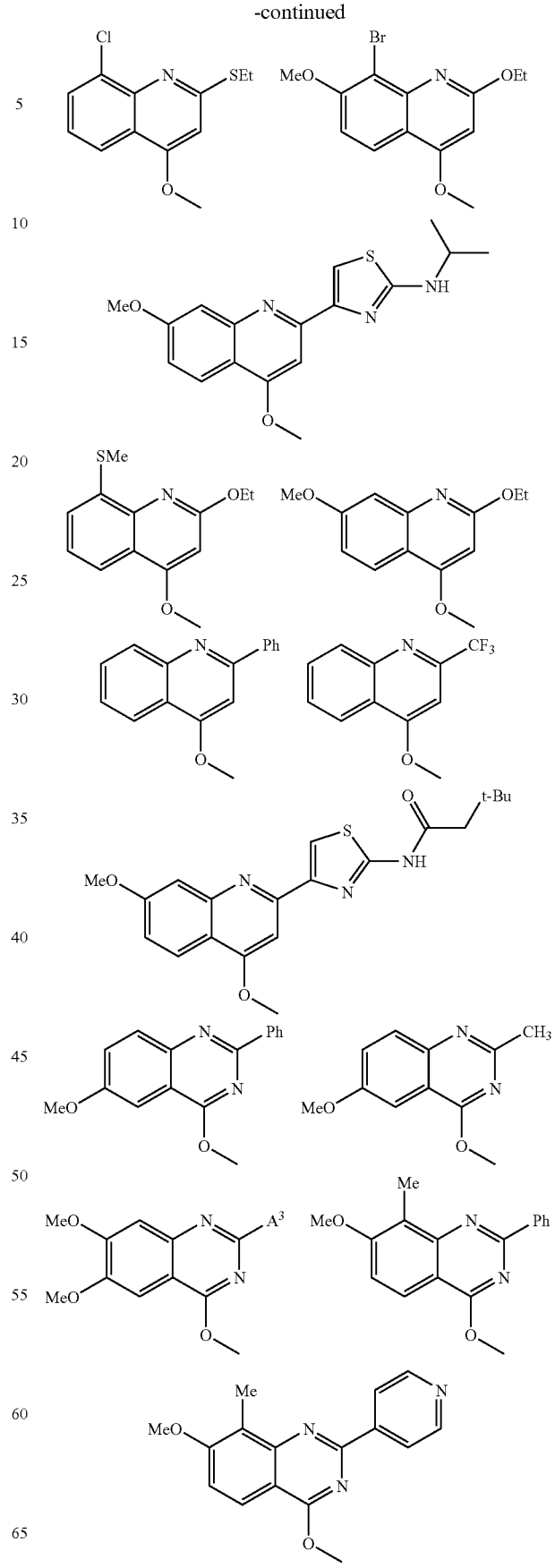

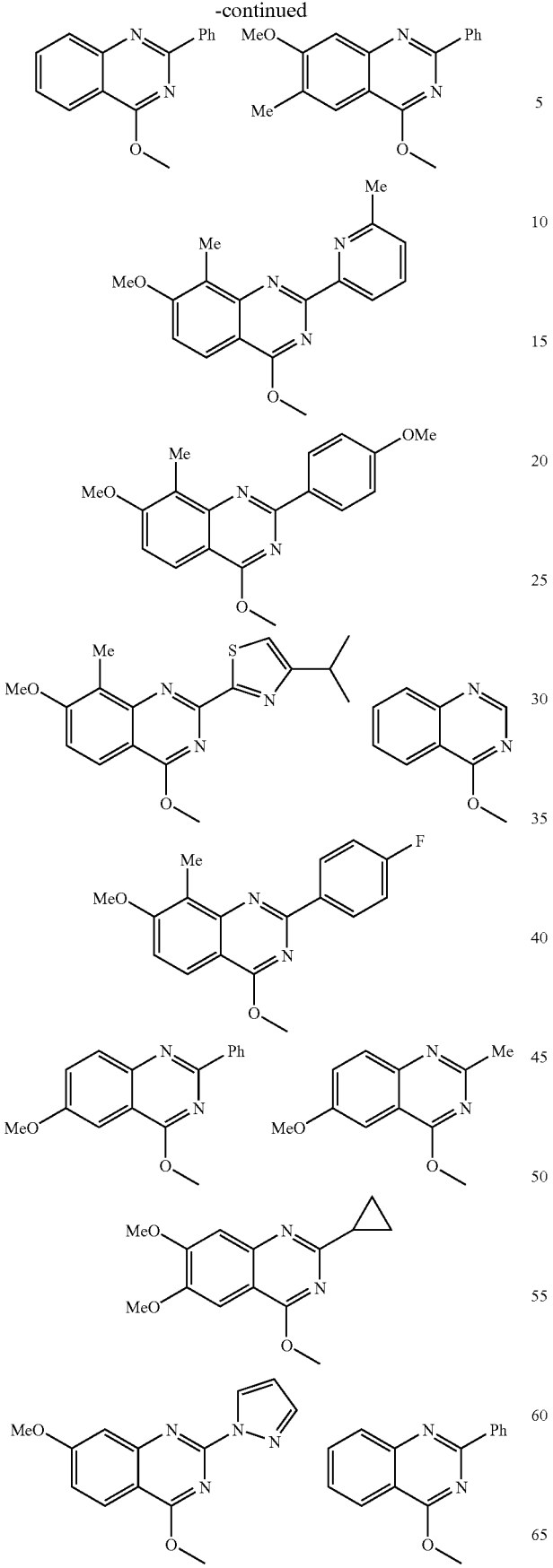
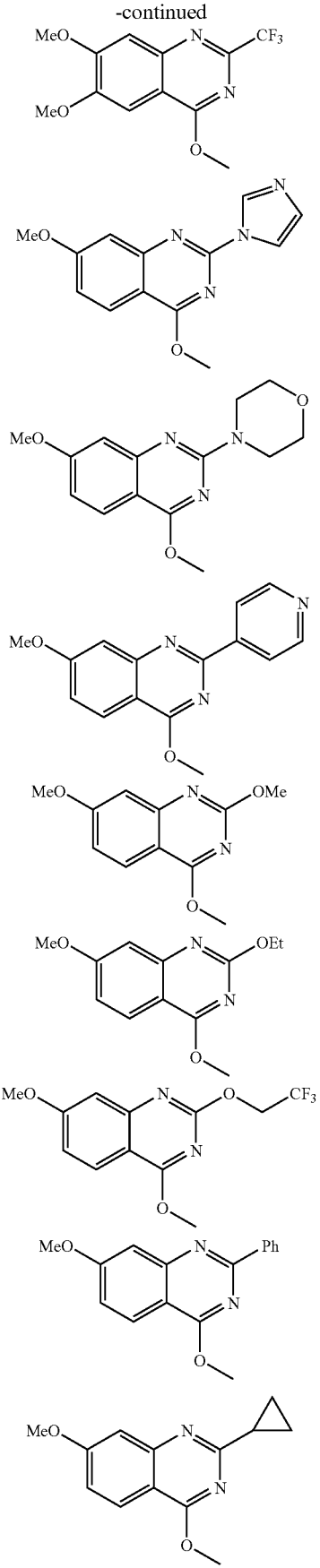

-continued
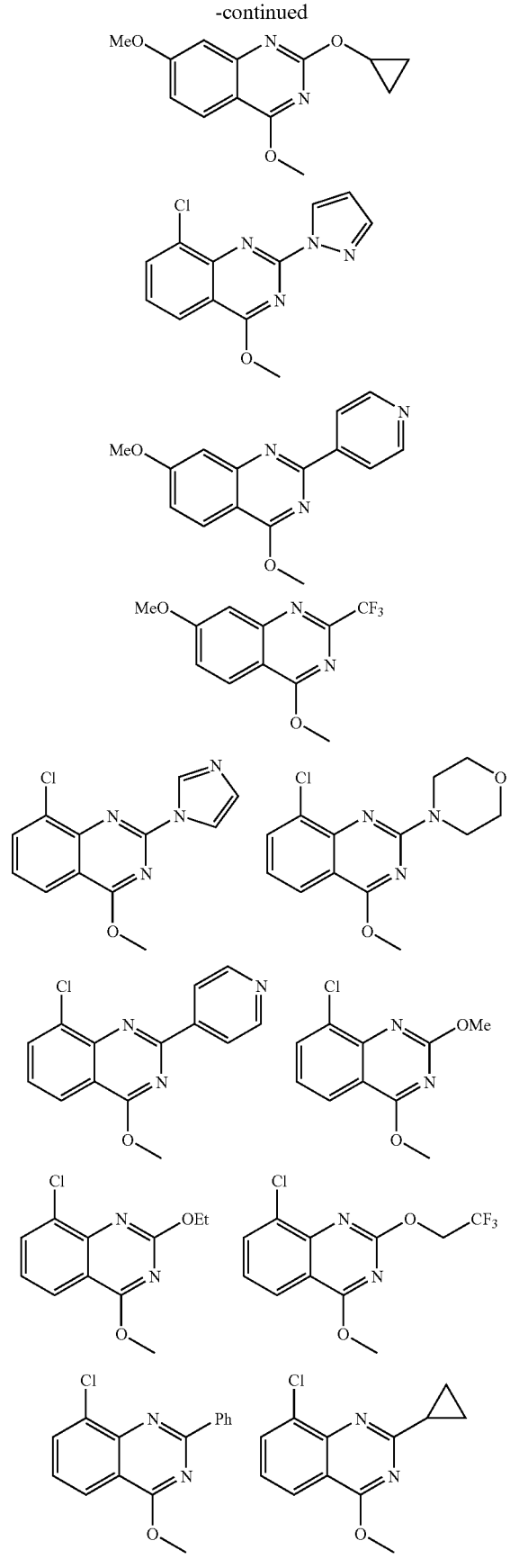
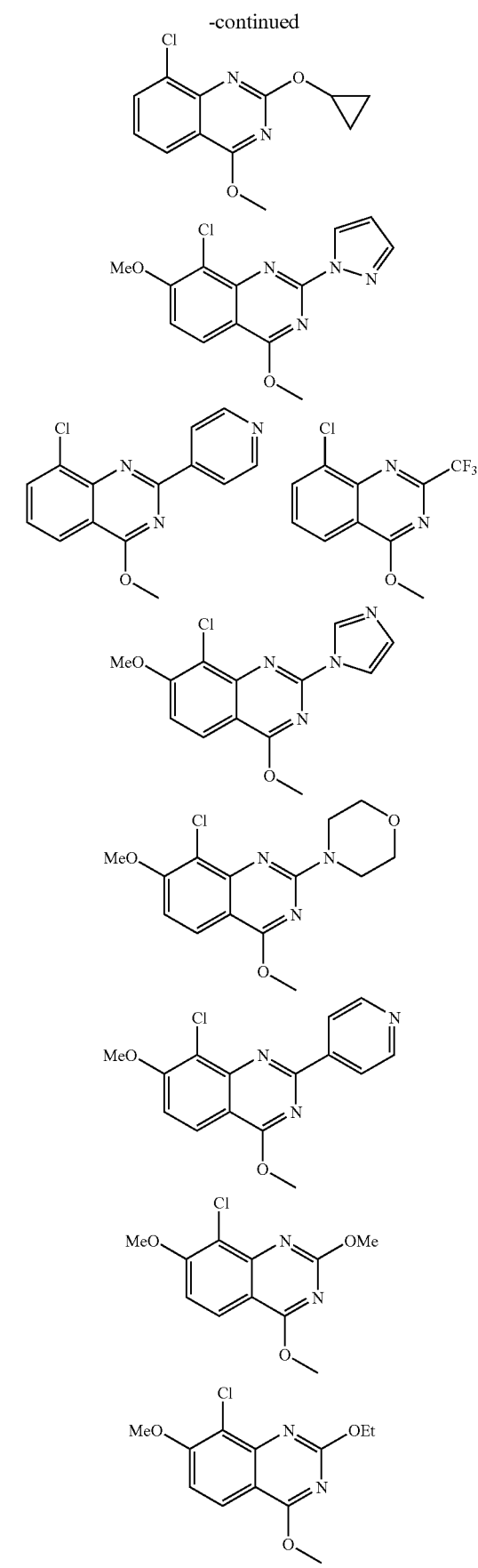

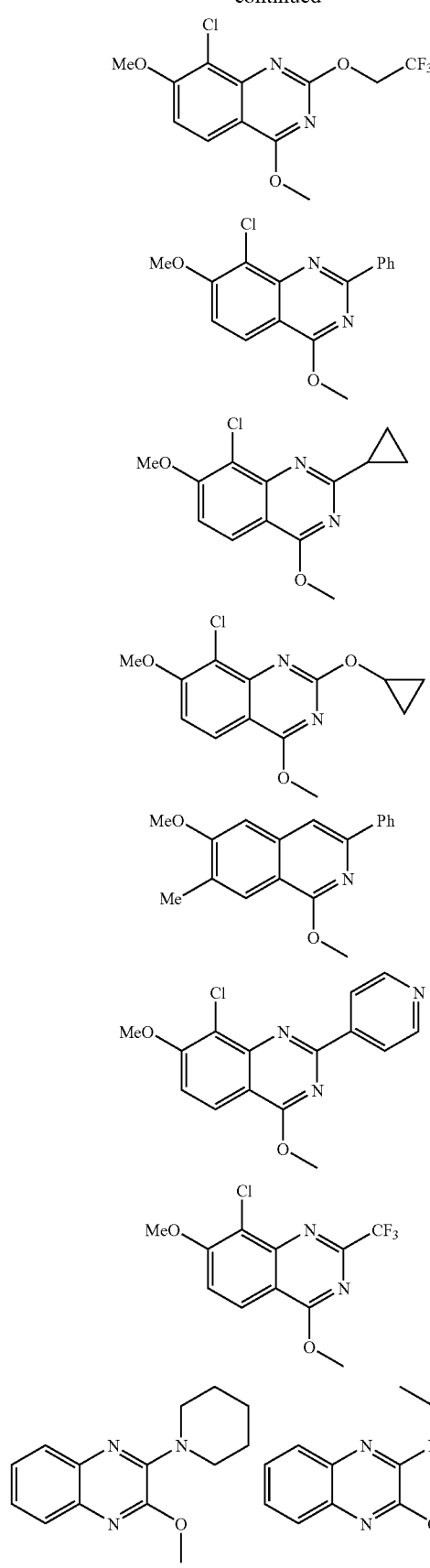
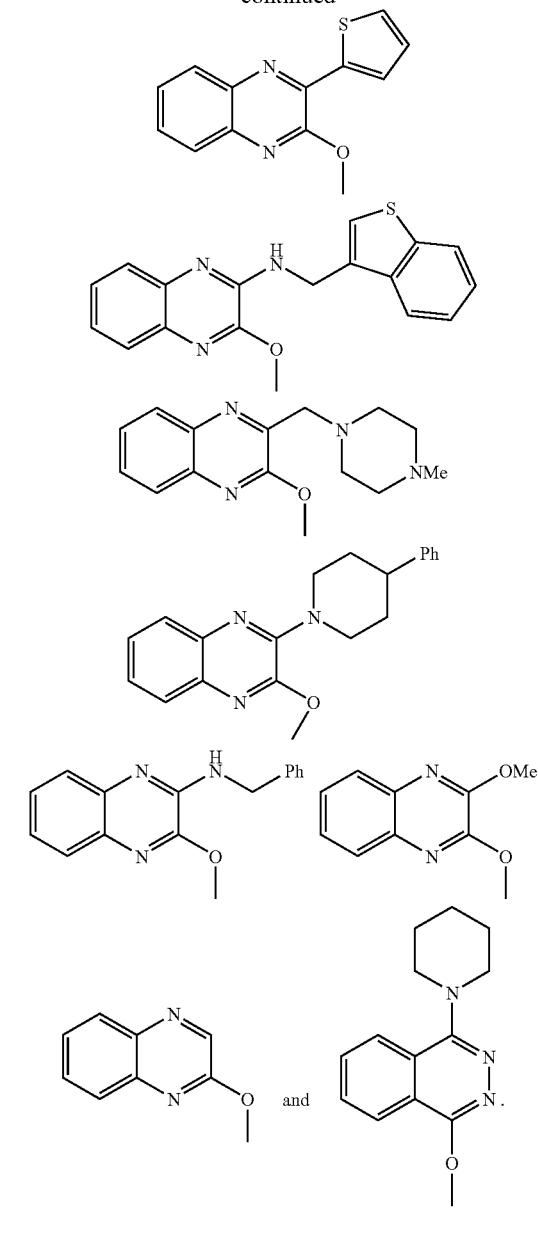
In one specific embodiment the invention $Z^1$ is selected from:
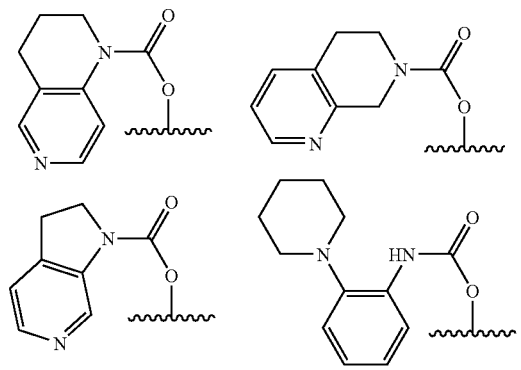

-continued

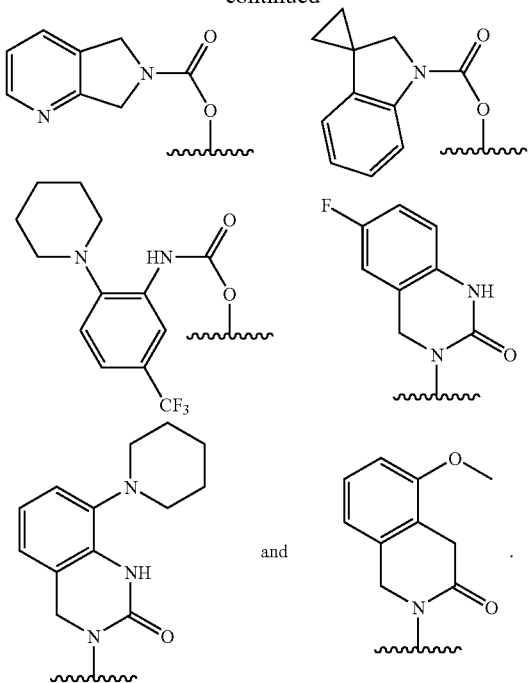

In one specific embodiment the invention provides a compound of formula I:

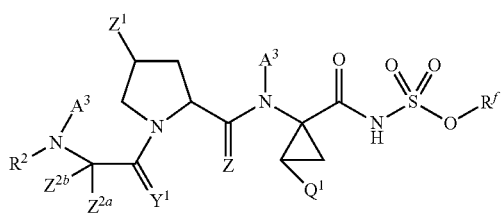

(I)

or a pharmaceutically acceptable salt, or prodrug thereof, wherein:

R$^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more A$^3$;

R$^2$ is selected from,
a) —C(Y$^1$)(A$^3$),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
where said alkyl, cycloalkyl and alkyl-cycloalkyl may optionally be mono- or di-substituted with substituents selected from hydroxy and O—(C1-4)alkyl, or
where each of said alkyl-groups may optionally be mono-, di- or tri-substituted with halogen, or
where each of said cycloalkyl groups being 5-, 6- or 7-membered, one or two —CH$_2$— groups not being directly linked to each other may be optionally replaced by —O— such that the O-atom is linked to the N atom to which R$^2$ is attached via at least two C-atoms, c) phenyl, (C1-3)alkyl-phenyl, heteroaryl or (C1-3)alkyl-heteroaryl,
wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen;
d) —S(O)$_2$(A$^3$); or
e) —C(Y$^1$)—X—Y;

R$^3$ is H or (C1-6)alkyl;
Y$^1$ is independently O, S, N(A$^3$), N(O)(A$^3$), N(OA$^3$), N(O)(OA$^3$) or N(N(A$^3$)(A$^3$));
Z is O, S, or NR$^3$;
Z$^1$ is selected from the following structures:

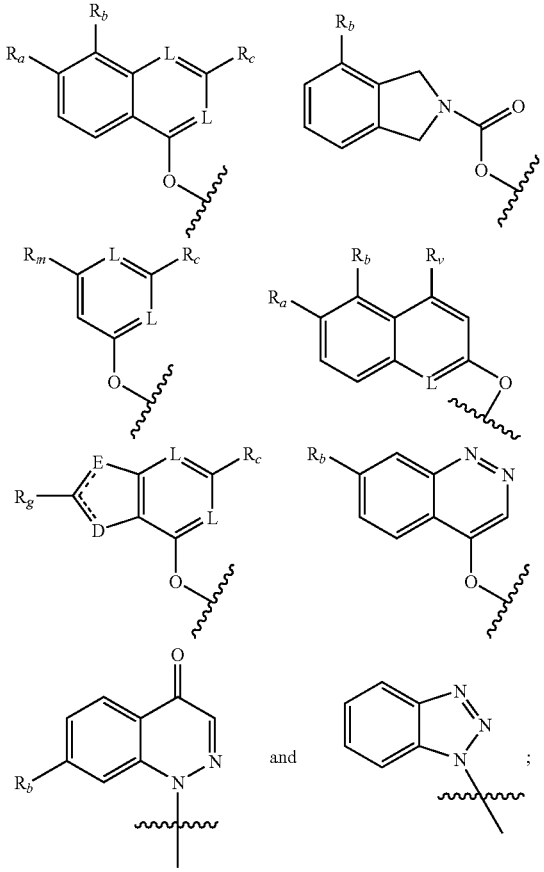

each R$_a$ is R$^4$, H, halo, —O(A$^2$), trifluoromethoxy, NR$_s$R$_t$, C(=O)NR$_s$R$_t$,
S((=O)NR$_s$R$_t$ or (C1-10)alkyl, wherein one or more carbon atoms of said (C1-10)alkyl is optionally replaced by O, S, S(=O), S(=O)$_2$ or NR$_k$ and which (C1-10)alkyl is optionally substituted with one or more hydroxy, halo, cyano, NR$_n$R$_p$, C(=O)NR$_n$R$_p$, (C1-10)alkoxy, carboxy, (C1-10)alkoxycarbonyl, aryl, heteroaryl, or heterocyclyl; or R$_a$ and R$_b$ taken together with the atoms to which they are attached form a 5 or 6 membered hetero cyclic ring containing one or more O, S, or NR$_k$;

each $R_b$ is $R^4$, H, F, Cl, Br, I, $CF_3$, (C1-10)alkyl, or $XR^3$;

each $R_c$ is $R^4$, H, cyano, F, Cl, Br, I, —C(=O)$NR_dR_e$, C(=O)$NR_sR_t$, $NR_sR_t$, $SR_r$, S(O)$R_r$, or S(O)$_2R_r$, S(=O)$_2$ $NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, S(O)$R_r$, or S(O)$_2R_r$; wherein any (C1-10)alkoxy of $R_c$ is optionally substituted with one or more halo, (C1-6) alkoxy, or $NR_wR_x$;

$R_d$ and $R_e$ are each independently H, (C1-10)alkyl, or aryl, which is optionally substituted with one or more halo;

each $R_y$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)$_2R_r$;

each $R_k$ is H, $NR_sR_t$, C(=O)$NR_sR_t$, S(=O)$_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)$_2R_r$;

each $R_u$ is H, $A^3$, C(=O)$NR_sR_t$, or S(=O)$_2NR_sR_t$;

each $R_m$ is H, cyano, F, Cl, Br, I, —C(=O)$NR_dR_e$, —C(=O)$NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_y$ and the other E or D is $CR_u$ or N;

$Z^{2b}$ is H, (C1-10)alkyl, (C2-10)alkenyl, (C2-10)alkynyl;

$Q^1$ is (C1-10)alkyl, (C2-10)alkenyl or (C2-10)alkynyl which $Q^1$ is optionally substituted with $R_c$; or $Q^1$ and $Z^{2a}$ taken together with the atoms to which they are attached form a heterocycle, which heterocycle may optionally be substituted with one or more oxo (=O), $R^4$, or $A^3$;

each X is independently a bond, O, S, or $NR^3$;

Y is a polycarbocycle or a polyheterocycle, which polycarbocycle or a polyheterocycle is optionally substituted with one or more $R^4$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)$_2R_r$;

each $R^4$ is independently —P($Y^3$)(O$A^2$)(O$A^2$), —P($Y^3$)(O$A^2$)(N($A^2$)$_2$), —P($Y^3$)($A^2$)(O$A^2$), —P($Y^3$)($A^2$)(N($A^2$)$_2$), or P($Y^3$)(N($A^2$)$_2$)(N($A^2$)$_2$);

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl, or (C1-10)alkoxycarbonyl;

each $R_s$ and $R_t$ is independently H, (C1-10)alkyl, (C2-10)alkenyl, (C2-10)alkynyl, (C1-10)alkanoyl, S(=O)$_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O);

each $R_v$ is $R^4$, H, F, Cl, Br, I, $CF_3$, (C1-10)alkyl, of $XR^3$ each $R_w$ and $R_x$ is independently H or (C1-10)alkyl or $R_w$ and $R_x$ together with the nitrogen to which they are attached form a azetidine, pyrrolidine, piperidine, piperazine, morpholine, or thiomorpholine ring which ring is optionally substituted with hydroxy;

$Z^{2a}$ is H, (C1-10)alkyl, (C2-10)alkenyl, (C2-10)alkynyl, haloalkyl, (C1-10)alkyl-S(=O)$_2$—(C1-10)alkyl, or cycloalkyl, wherein any carbon atom of $Z^{2a}$ may optionally be replaced with a heteroatom selected from O, S, S(=O), S(=O)$_2$, or N and wherein any cycloalkyl is optionally substituted with one or more (C1-10)alkyl, (C2-10)alkenyl, (C2-10)alkynyl, haloalkyl, F, Cl, Br, or I; or $Z^{2a}$ optionally forms a heterocycle with one or more $R^1$, $R^2$, $Q^1$, or $A^3$;

$A^3$ is independently selected from PRT, H, —OH, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —C($A^2$)$_3$, —C($A^2$)$_2$-C(O)$A^2$, —C(O)$A^2$, —C(O)O$A^2$, —O($A^2$), —N($A^2$), —S($A^2$), —CH$_2$P($Y^1$)($A^2$)(O$A^2$), —CH$_2$P($Y^1$)($A^2$)(N($A^2$)$_2$), —CH$_2$P($Y^1$)(O$A^2$)(O$A^2$), —OCH$_2$P($Y^1$)(O$A^2$)(O$A^2$), OCH$_2$P($Y^1$)($A^2$)(O$A^2$), —OCH$_2$P($Y^1$)($A^2$)(N($A^2$)$_2$), —C(O)OCH$_2$P($Y^1$)(O$A^2$)(OA), —C(O)OCH$_2$P($Y^1$)($A^2$)(O$A^2$), —C(O)OCH$_2$P($Y^1$)($A^2$)(N($A^2$)$_2$), —CH$_2$P($Y^1$)(O$A^2$)(N($A^2$)$_2$), —OCH$_2$P($Y^1$)(O$A^2$)(N($A^2$)$_2$), —C(O)OCH$_2$P($Y^1$)(O$A^2$)(N($A^2$)$_2$), —CH$_2$P($Y^1$)(N($A^2$)$_2$)(N($A^2$)$_2$), —C(O)OCH$_2$P($Y^1$)(N($A^2$)$_2$)(N($A^2$)$_2$), —OCH$_2$P($Y^1$)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, $SR_r$, S(O)$R_r$, S(O)$_2R_r$, or alkoxy arylsulfonamide, wherein each $A^3$ may be optionally substituted with 1 to 4

—$R^1$, —P($Y^1$)(O$A^2$)(O$A^2$), —P($Y^1$)(O$A^2$)(N($A^2$)$_2$), —P($Y^1$)($A^2$)(O$A^2$), —P($Y^1$)($A^2$)(N($A^2$)$_2$), or P($Y^1$)(N($A^2$)$_2$)(N($A^2$)$_2$), —C(=O)N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with $R^1$;

optionally each independent instance of $A^3$ and $Q^1$ can be taken together with one or more $A^3$ or $Q^1$ groups to form a ring;

$A^2$ is independently selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each $A^2$ is optionally substituted with $A^3$;

$R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or more halo, alkoxy, or cyano;

each $R_h$ and $R_i$ is independently H, alkyl, or haloalkyl; and m is 0 to 6.

In one specific embodiment the invention provides a compound of formula I:

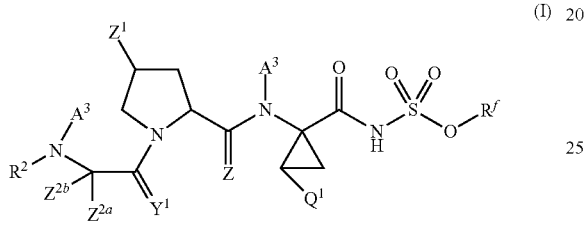
(I)

or a pharmaceutically acceptable salt, or prodrug thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from,
a) —C($Y^1$)($A^3$),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
where said alkyl, cycloalkyl and alkyl-cycloalkyl may optionally be mono- or di-substituted with substituents selected from hydroxy and O—(C1-4)alkyl, or
where each of said alkyl-groups may optionally be mono-, di- or tri-substituted with halogen, or
where each of said cycloalkyl groups being 5-, 6- or 7-membered, one or two —CH$_2$— groups not being directly linked to each other may be optionally replaced by —O— such that the O-atom is linked to the N atom to which $R^2$ is attached via at least two C-atoms,
c) phenyl, (C1-3)alkyl-phenyl, heteroaryl or (C1-3)alkyl-heteroaryl,
wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen;
d) —S(O)$_2$($A^3$); or
e) —C($Y^1$)—X—Y;

$R^3$ is H or (C1-6)alkyl;
$Y^1$ is independently O, S, N($A^3$), N(O)($A^3$), N($OA^3$), N(O)($OA^3$) or N(N($A^3$)($A^3$));
Z is O, S, or $NR^3$;
$Z^1$ is selected from the following structures:

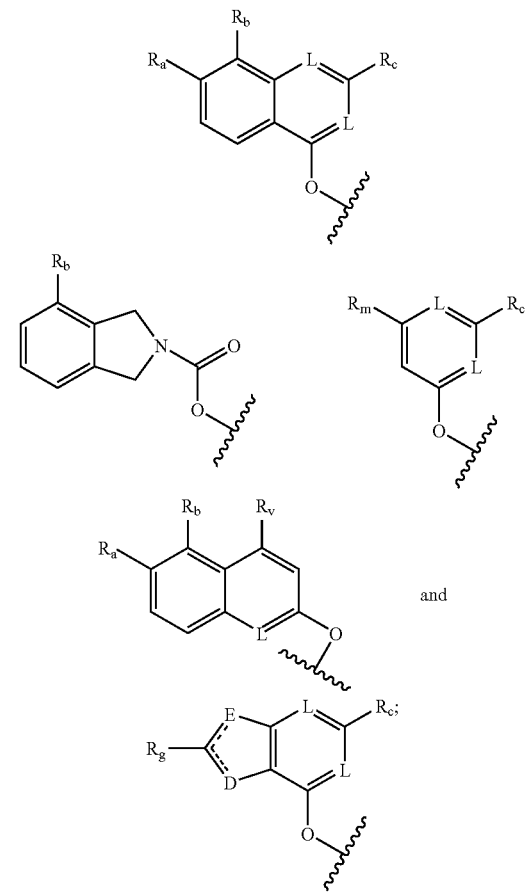

each $R_a$ is $R^4$, H, halo, —O($A^2$), trifluoromethoxy, $NR_sR_t$, C(=O)$NR_sR_t$, S(=O)$_2NR_sR_t$, or (C1-10)alkyl, wherein one or more carbon atoms of said (C1-10)alkyl is optionally replaced by O, S, S(=O), S(=O)$_2$ or $NR_k$ and which (C1-10)alkyl is optionally substituted with one or more hydroxy, halo, cyano, $NR_nR_p$, C(=O)$NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_k$;

each $R_b$ is $R^4$, H, F, Cl, Br, I, CF$_3$, (C1-10)alkyl, or $XR^3$;

each $R_c$ is $R^4$, H, cyano, F, Cl, Br, I, —C(=O)$NR_dR_e$, C(=O)$NR_sR_t$, $NR_sR_t$, $SR_r$, S(O)$R_r$, or S(O)$_2R_r$, S(=O)$_2$ $NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, S(O)$R_r$, or S(O)$_2R_r$; wherein any (C1-10)alkoxy of $R_c$ is optionally substituted with one or more halo, (C1-6)alkoxy, or $NR_wR_x$;

$R_d$ and $R_e$ are each independently H, (C1-10)alkyl, or aryl, which is optionally substituted with one or more halo;

each $R_y$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_k$ is H, $NR_sR_t$, $C(=O)NR_sR_t$, $S(=O)_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_u$ is H, $A^3$, $C(=O)NR_sR_t$, or $S(=O)_2NR_sR_t$;

each $R_m$ is H, cyano, F, Cl, Br, I, —$C(=O)NR_dR_e$, —$C(=O)NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_y$ and the other E or D is $CR_u$ or N;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R_c$; or $Q^1$ and $Z^{2a}$ taken together with the atoms to which they are attached form a heterocycle, which heterocycle may optionally be substituted with one or more oxo (=O), $R^4$, or $A^3$;

each X is independently a bond, O, S, or $NR^3$;

Y is a polycarbocycle or a polyheterocycle, which polycarbocycle or a polyheterocycle is optionally substituted with one or more $R^4$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R^4$ is independently —$P(Y^3)(OA^2)(OA^2)$, —$P(Y^3)(OA^2)(N(A^2)_2)$, —$P(Y^3)(A^2)(OA^2)$, —$P(Y^3)(A^2)(N(A^2)_2)$, or $P(Y^3)(N(A^2)_2)(N(A^2)_2)$;

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl, or (C1-10)alkoxycarbonyl;

each $R_s$ and $R_t$ is independently H, (C1-10)alkyl, (C2-10)alkenyl, (C2-10)alkynyl, (C1-10)alkanoyl, $S(=O)_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by $S(=O)$, $S(=O)_2$, or $C(=O)$;

each $R_v$ is $R^4$, H, F, Cl, Br, I, $CF_3$, (C1-10)alkyl, or $XR^3$ each $R_w$ and $R_x$ is independently H or (C1-10)alkyl or $R_w$ and $R_x$ together with the nitrogen to which they are attached form a azetidine, pyrrolidine, piperidine, piperazine, morpholine, or thiomorpholine ring which ring is optionally substituted with hydroxy;

$Z^{2a}$ is H, (C1-10)alkyl, (C2-10)alkenyl, (C2-10)alkynyl, haloalkyl, (C1-10)alkyl-S(=O)$_2$—(C1-10)alkyl, or cycloalkyl, wherein any carbon atom of $Z^{2a}$ may optionally be replaced with a heteroatom selected from O, S, S(=O), S(=O)$_2$, or N and wherein any cycloalkyl is optionally substituted with one or more (C1-10)alkyl, (C2-10)alkenyl, (C2-10)alkynyl, haloalkyl, F, Cl, Br, or I; or $Z^{2a}$ optionally forms a heterocycle with one or more $R^1$, $R^2$, $Q^1$, or $A^3$;

$A^3$ is independently selected from PRT, H, —OH, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —$C(A^2)_3$, —$C(A^2)_2$-$C(O)A^2$, —$C(O)A^2$, —$C(O)OA^2$, —$O(A^2)$, —$N(A^2)_2$, —$S(A^2)$, —$CH_2P(Y^1)(A^2)(OA^2)$, —$CH_2P(Y^1)(A^2)(N(A^2)_2)$, —$CH_2P(Y^1)(OA^2)(OA^2)$, —$OCH_2P(Y^1)(OA^2)(OA^2)$, —$OCH_2P(Y^1)(A^2)(OA^2)$, —$OCH_2P(Y^1)(A^2)(N(A^2)_2)$, —$C(O)OCH_2P(Y^1)(OA^2)(OA^2)$, —$C(O)OCH_2P(Y^1)(A^2)(OA^2)$, —$C(O)OCH_2P(Y^1)(A^2)(N(A^2)_2)$, —$CH_2P(Y^1)(OA^2)(N(A^2)_2)$, —$OCH_2P(Y^1)(OA^2)(N(A^2)_2)$, —$C(O)OCH_2P(Y^1)(OA^2)(N(A^2)_2)$, —$CH_2P(Y^1)(N(A^2)_2)(N(A^2)_2)$, —$C(O)OCH_2P(Y^1)(N(A^2)_2)(N(A^2)_2)$, —$OCH_2P(Y^1)(N(A^2)_2)(N(A^2)_2)$, —$(CH_2)_m$-heterocycle, —$(CH_2)_mC(O)Oalkyl$, —O—$(CH_2)_m$—O—C(O)—Oalkyl, —O—$(CH_2)_r$—O—C(O)—$(CH_2)_m$-alkyl, —$(CH_2)_m$O—C(O)—O-alkyl, —$(CH_2)_m$O—C(O)—O-cycloalkyl, —N(H)C(Me)C(O)O-alkyl, $SR_r$, $S(O)R_r$, $S(O)_2R_r$, or alkoxy arylsulfonamide, wherein each $A^3$ may be optionally substituted with 1 to 4
—$R^1$, —$P(Y^1)(OA^2)(OA^2)$, —$P(Y^1)(OA^2)(N(A^2)_2)$, —$P(Y^1)(A^2)(OA^2)$, —$P(Y^1)(A^2)(N(A^2)_2)$, or $P(Y^1)(N(A^2)_2)(N(A^2)_2)$, —$C(=O)N(A^2)_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —$(CH_2)_m$heterocycle, —$(CH_2)_m$—C(O)O-alkyl, —$O(CH_2)_m$OC(O)Oalkyl, —O—$(CH_2)_m$—O—C(O)—$(CH_2)_m$-alkyl, —$(CH_2)_m$—O—C(O)—O-alkyl, —$(CH_2)_m$—O—C(O)—O-cycloalkyl, —N(H)C($CH_3$)C(O)O-alkyl, or alkoxy arylsulfonamide, optionally substituted with $R^1$;

optionally each independent instance of $A^3$ and Q can be taken together with one or more $A^3$ or Q groups to form a ring;

$A^2$ is independently selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each $A^2$ is optionally substituted with $A^3$;

$R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —$C(=O)NR_hR_i$, or —$C(=O)OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or motr halo or cyano;

each $R_h$ and $R_i$ is independently H, alkyl, or haloalkyl; and m is 0 to 6.

In one specific embodiment the invention provides a compound of formula I:

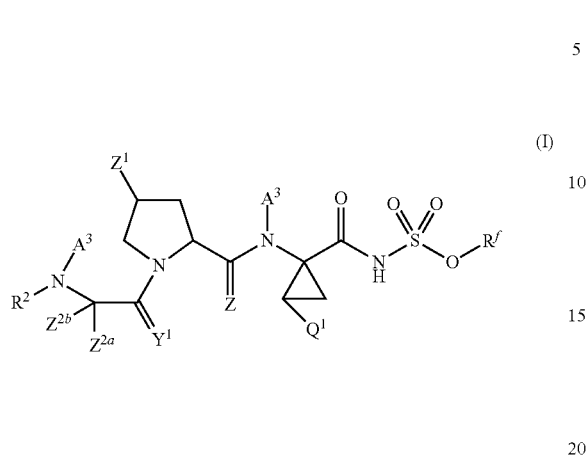

(I)

or a pharmaceutically acceptable salt, or prodrug thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from, a) —C($Y^1$)($A^3$), b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or where said alkyl, cycloalkyl and alkyl-cycloalkyl may optionally be mono- or di-substituted with substituents selected from hydroxy and O—(C1-4)alkyl, or where each of said alkyl-groups may optionally be mono-, di- or tri-substituted with halogen, or where each of said cycloalkyl groups being 5-, 6- or 7-membered, one or two —CH$_2$— groups not being directly linked to each other may be optionally replaced by —O— such that the O-atom is linked to the N atom to which $R^2$ is attached via at least two C-atoms, c) phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen;

d) —S(O)$_2$($A^3$); or e) —C($Y^1$)—X—Y;

$R^3$ is H or (C1-6)alkyl;

$Y^1$ is independently O, S, N($A^3$), N(O)($A^3$), N(O$A^3$), N(O)(O$A^3$) or N(N($A^3$)($A^3$));

Z is O, S, or N$R^3$;

$Z^1$ is selected from the following structures:

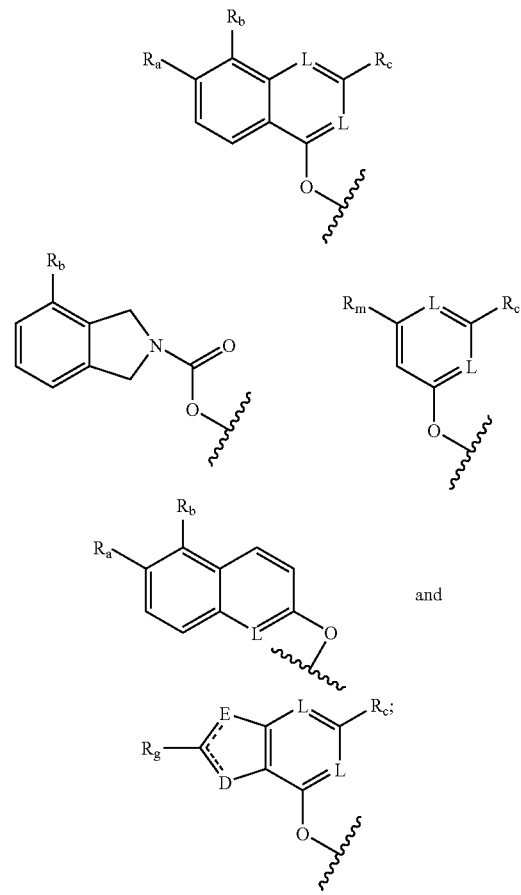

and each $R_a$ is $R^4$, H, halo, trifluoromethoxy, NR$_s$R$_t$, C(=O)NR$_s$R$_t$, S(=O)$_2$NR$_s$R$_t$ or (C1-10)alkyl, wherein one or more carbon atoms of said (C1-10)alkyl is optionally replaced by O, S, S(=O), S(=O)$_2$ or NR$_k$ and which (C1-10)alkyl is optionally substituted with one or more hydroxy, halo, cyano, NR$_n$R$_p$, C(=O)NR$_n$R$_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or NR$_k$;

each $R_b$ is $R^4$, H, F, Cl, Br, I, CF$_3$, (C1-10)alkyl, or XR$^3$;

each $R_c$ is $R^4$, H, cyano, F, Cl, Br, I, —C(=O)NR$_d$R$_e$, C(=O)NR$_s$R$_t$, NR$_s$R$_t$, S(=O)—$_2$NR$_s$R$_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$; SR$_r$, S(O)R$_r$, or S(O)$_2$R$_r$;

$R_d$ and $R_e$ are each independently H or (C1-10)alkyl;

each $R_y$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$, SR$_r$, S(O)R$_r$, or S(O)$_2$R$_r$;

each $R_k$ is H, NR$_s$R$_t$, C(=O)NR$_s$R$_t$, S(=O)$_2$NR$_s$R$_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$, SR$_r$, S(O)R$_r$, or S(O)$_2$R$_r$;

each $R_u$ is H, $A^3$, $C(=O)NR_sR_t$, or $S(=O)_2NR_sR_t$;

each $R_m$ is H, cyano, F, Cl, Br, I, —C(=O)$NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_y$ and the other E or D is $CR_u$ or N;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R^4$ or $R_c$; or $Q^1$ and $Z^{2a}$ taken together with the atoms to which they are attached form a heterocycle, which heterocycle may optionally be substituted with one or more oxo (=O), $R^4$, or $A^3$;

each X is independently a bond, O, S, or $NR^3$;

Y is a polycarbocycle or a polyheterocycle, which polycarbocycle or a polyheterocycle is optionally substituted with one or more $R^4$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R^4$ is independently —P($Y^3$)($OA^2$)($OA^2$), —P($Y^3$)($OA^2$)(N($A^2$)$_2$), —P($Y^3$)($A^2$)($OA^2$), —P($Y^3$)($A^2$)N($A^2$)$_2$), or P($Y^3$)(N($A^2$)$_2$)(N($A^2$)$_2$);

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl, or (C1-10)alkoxycarbonyl;

each $R_s$ and $R_t$ is independently H, (C1-10)alkyl, (C2-10)alkenyl, (C2-10)alkynyl, (C1-10)alkanoyl, $S(=O)_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), $S(=O)_2$, or C(=O);

$Z^{2a}$ is H, (C1-10)alkyl, (C2-10)alkenyl, (C2-10)alkynyl, haloalkyl, (C1-10)alkyl-S(=O)$_2$—(C1-10)alkyl, or cycloalkyl, wherein any carbon atom of $Z^{2a}$ may optionally be replaced with a heteroatom selected from O, S or N and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with one or more $R^1$, $R^2$, $Q^1$, or $A^3$;

$A^3$ is independently selected from PRT, H, —OH, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —C($A^2$)$_3$, —C($A^2$)$_2$-C(O)$A^2$, —C(O)$A^2$, —C(O)$OA^2$, —O($A^2$), —N($A^2$)$_2$, —S($A^2$), —CH$_2$P($Y^1$)($A^2$)($OA^2$), —CH$_2$P($Y^1$)($A^2$)(N($A^2$)$_2$), —CH$_2$P($Y^1$)($OA^2$)($OA^2$), —OCH$_2$P($Y^1$)($OA^2$)($OA^2$), —OCH$_2$P($Y^1$)($A^2$)($OA^2$), —OCH$_2$P($Y^1$)($A^2$)(N($A^2$)$_2$), —C(O)OCH$_2$P($Y^1$)($OA^2$)($OA^2$), —C(O)OCH$_2$P($Y^1$)($A^2$)($OA^2$), —C(O)OCH$_2$P($Y^1$)($A^2$)(N($A^2$)$_2$), —CH$_2$P($Y^1$)($OA^2$)(N($A^2$)$_2$), —OCH$_2$P($Y^1$)($OA^2$)(N($A^2$)$_2$), —C(O)OCH$_2$P($Y^1$)($OA^2$)(N($A^2$)$_2$), —CH$_2$P($Y^1$)(N($A^2$)$_2$)(N($A^2$)$_2$), —C(O)OCH$_2$P($Y^1$)(N($A^2$)$_2$)(N($A^2$)$_2$), —OCH$_2$P($Y^1$)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, $SR_r$, $S(O)R_r$, $S(O)_2R_r$, or alkoxy arylsulfonamide, wherein each $A^3$ may be optionally substituted with 1 to 4

—$R^1$, —P($Y^1$)($OA^2$)($OA^2$), —P($Y^1$)($OA^2$)(N($A^2$)$_2$), —P($Y^1$)($A^2$)($OA^2$), —P($Y^1$)($A^2$)(N($A^2$)$_2$), or P($Y^1$)(N($A^2$)$_2$)(N($A^2$)$_2$), —C(=O)N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with $R^1$;

optionally each independent instance of $A^3$ and Q can be taken together with one or more $A^3$ or Q groups to form a ring;

$A^2$ is independently selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each $A^2$ is optionally substituted with $A^3$;

$R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy;

each $R_h$ and $R_i$ is independently H, alkyl, or haloalkyl; and m is 0 to 6.

In one specific embodiment of the invention $Z^1$ is selected from the following structures:
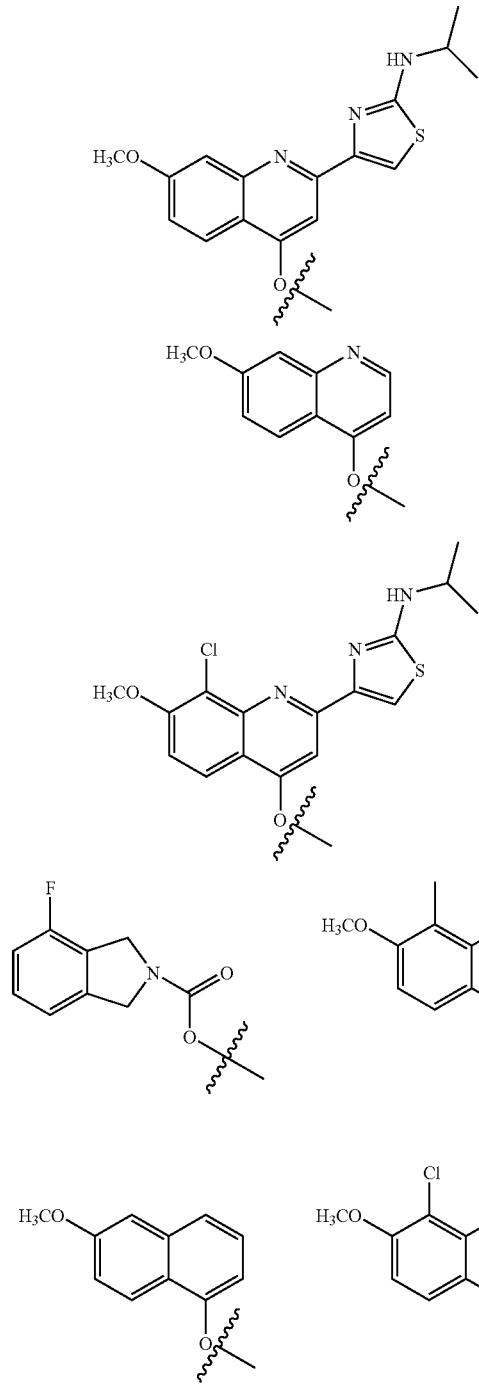
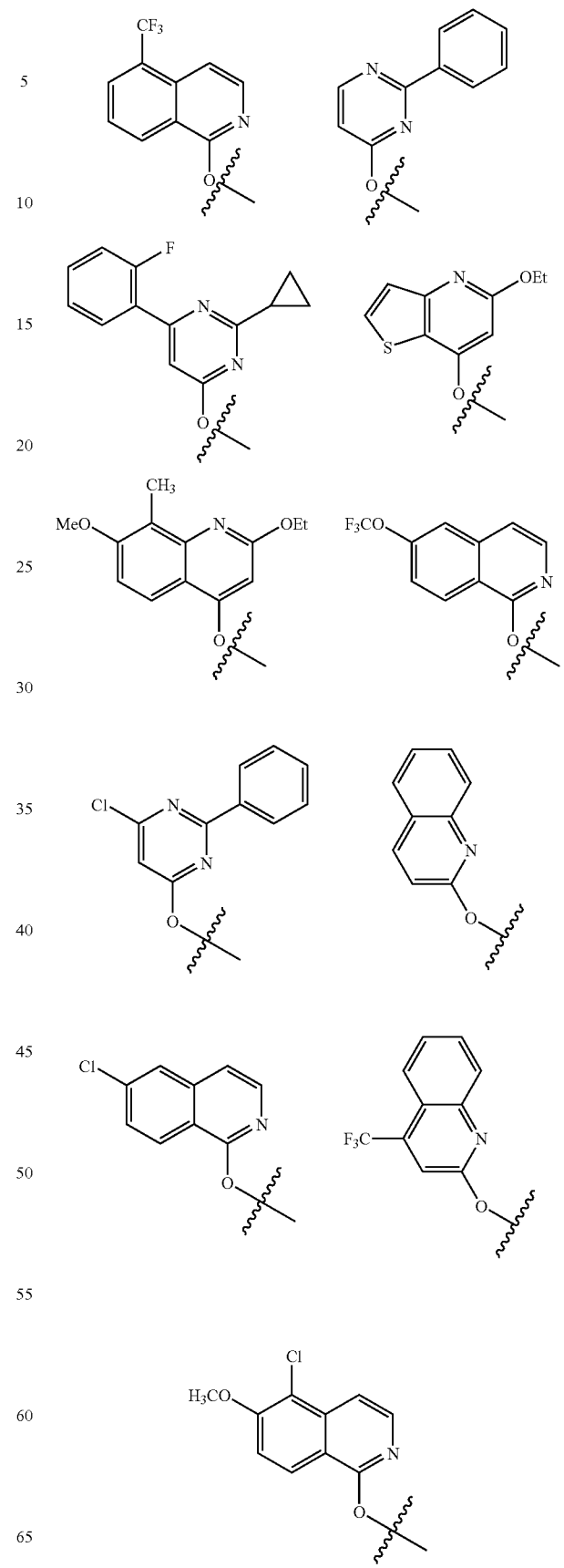

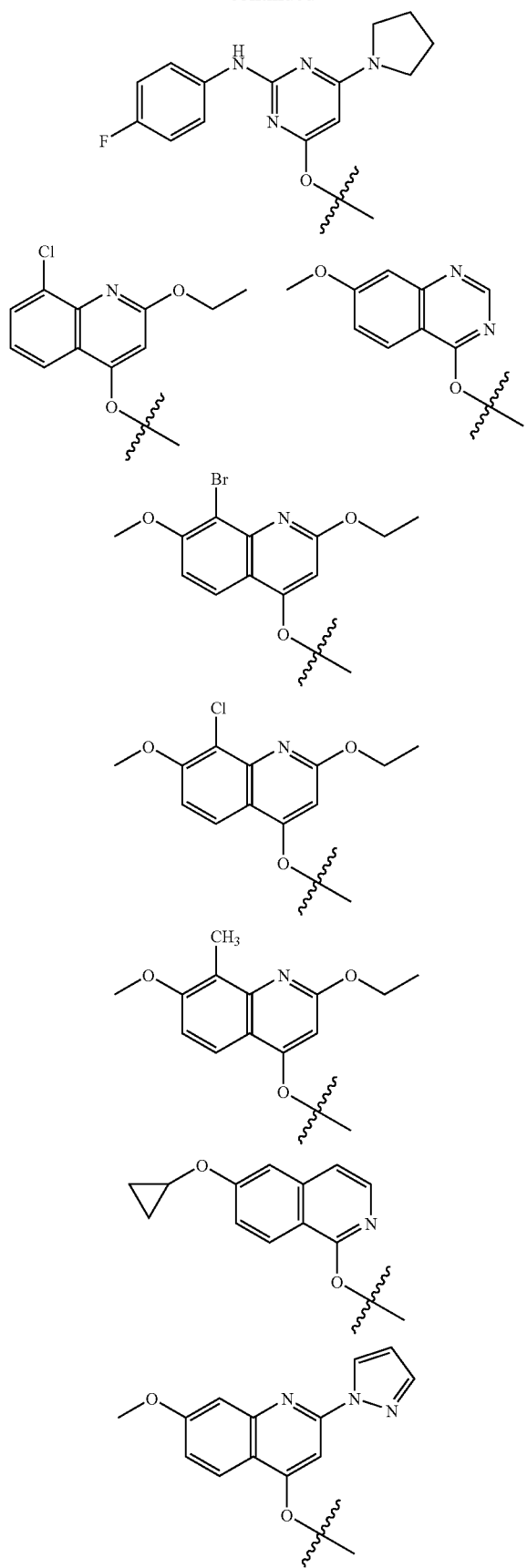
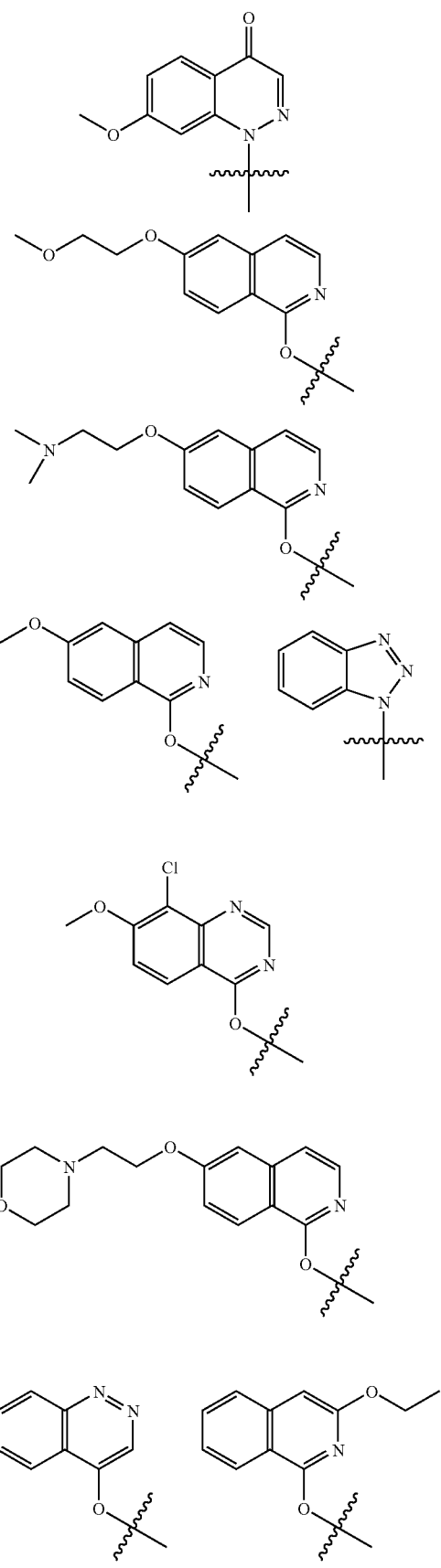

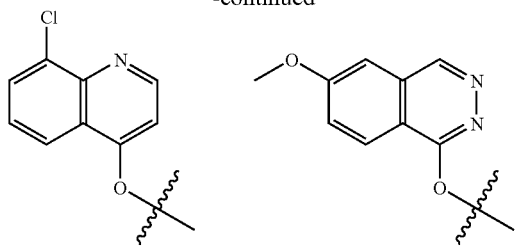
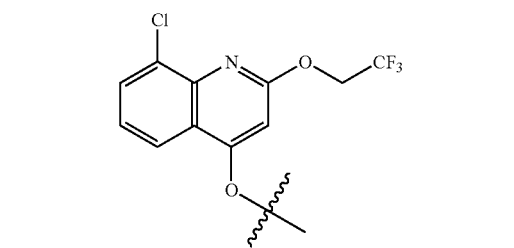
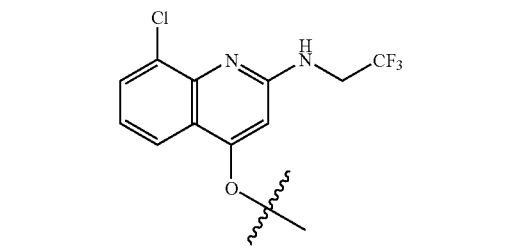
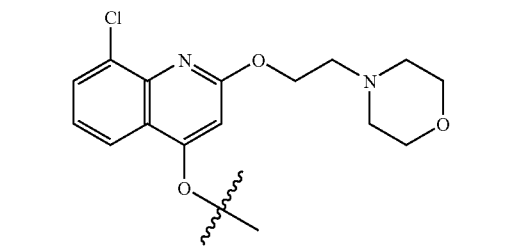
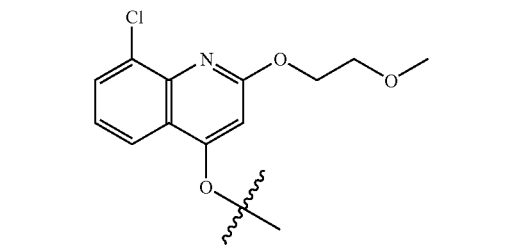
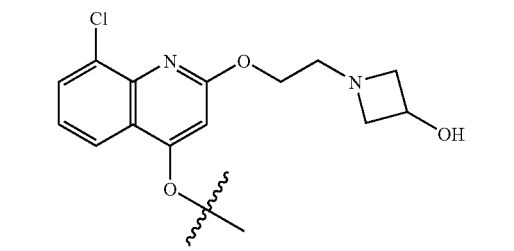
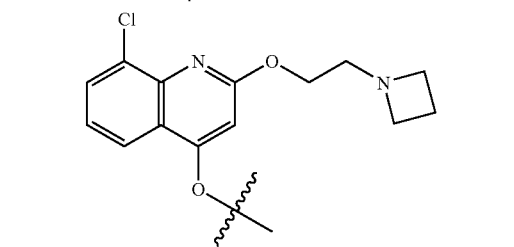
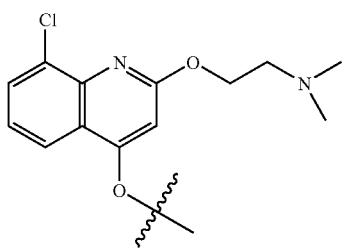
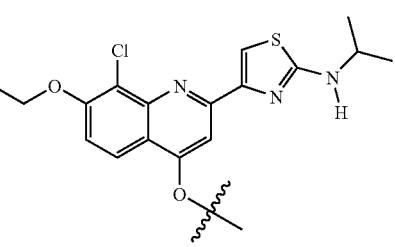
and
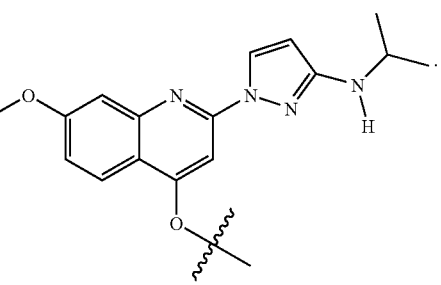
In a specific embodiment of the invention $Z^1$ is selected from the following structures:
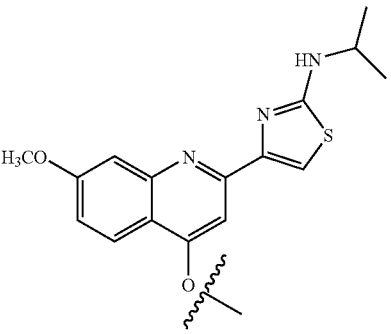
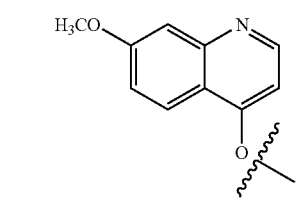

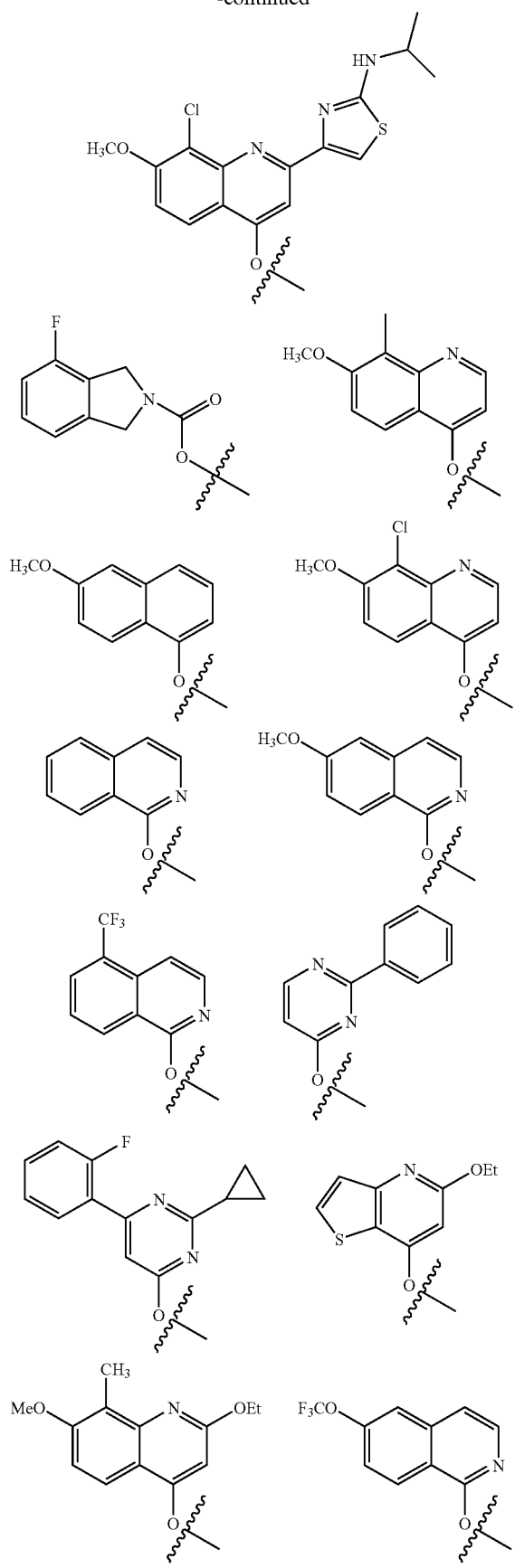
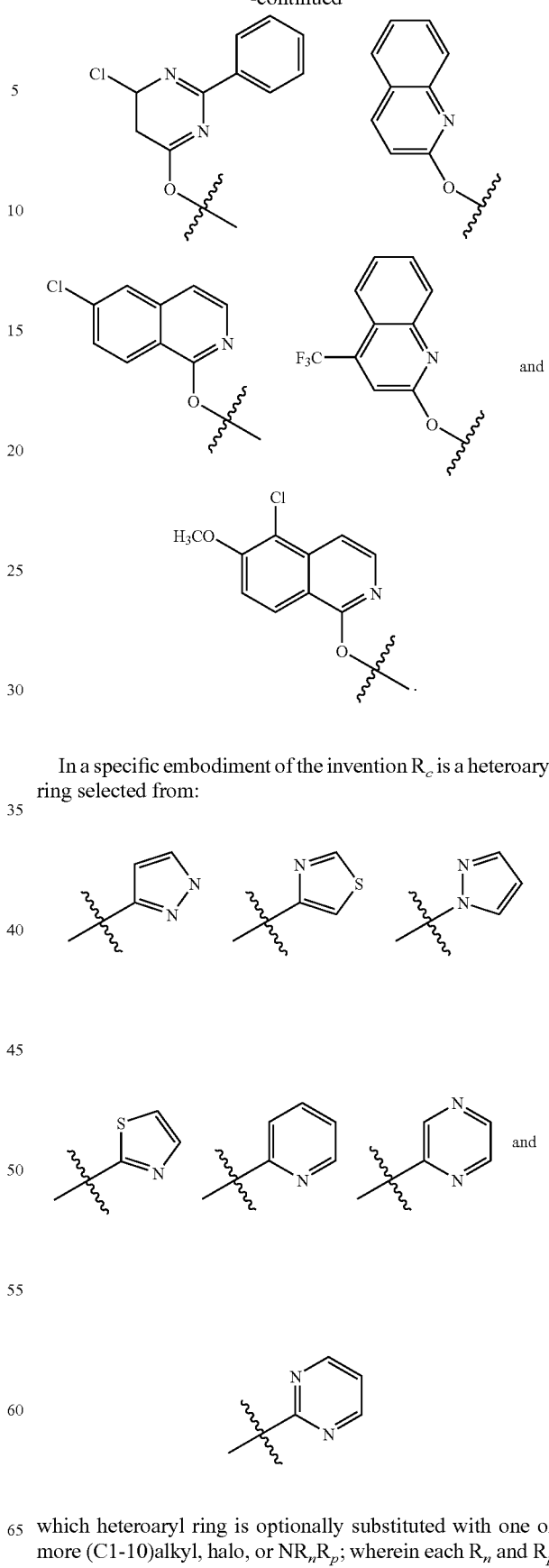
In a specific embodiment of the invention $R_c$ is a heteroaryl ring selected from:
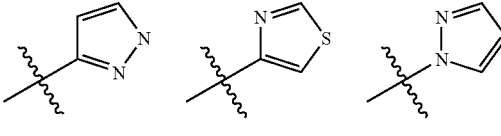
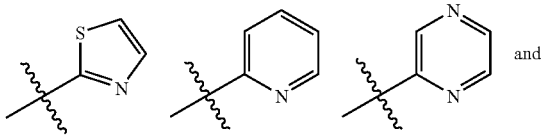
which heteroaryl ring is optionally substituted with one or more (C1-10)alkyl, halo, or $NR_nR_p$; wherein each $R_n$ and $R_p$ is independently H or (C1-10)alkyl.

In a specific embodiment of the invention $R_c$ is selected from:
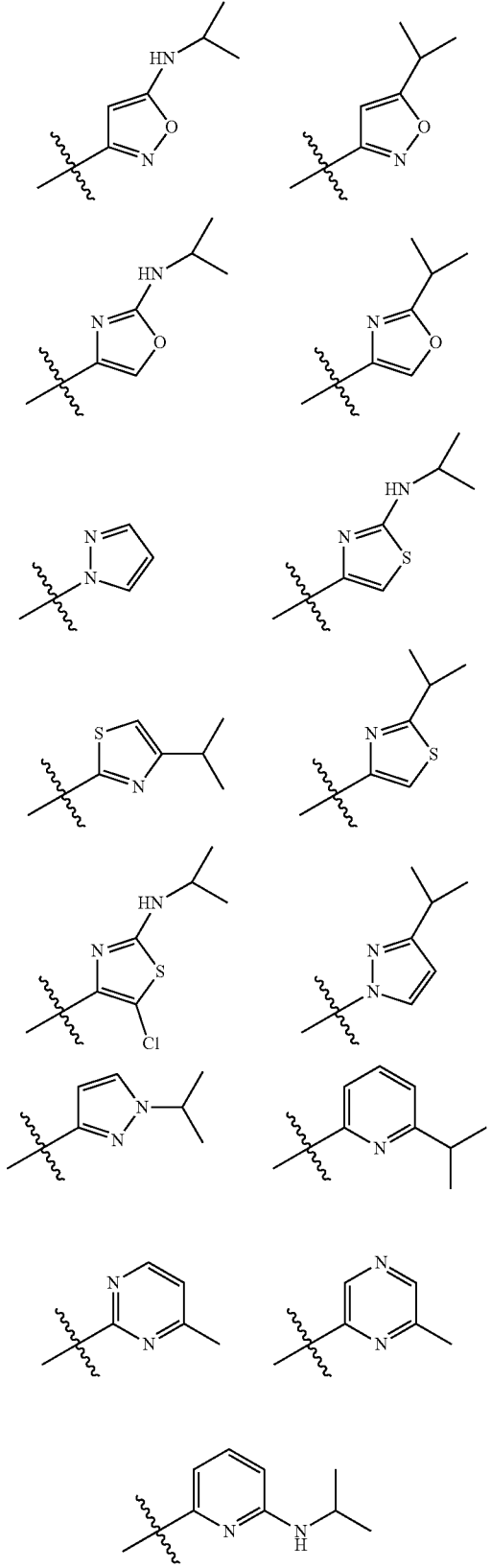
In a specific embodiment of the invention $R_c$ is selected from:
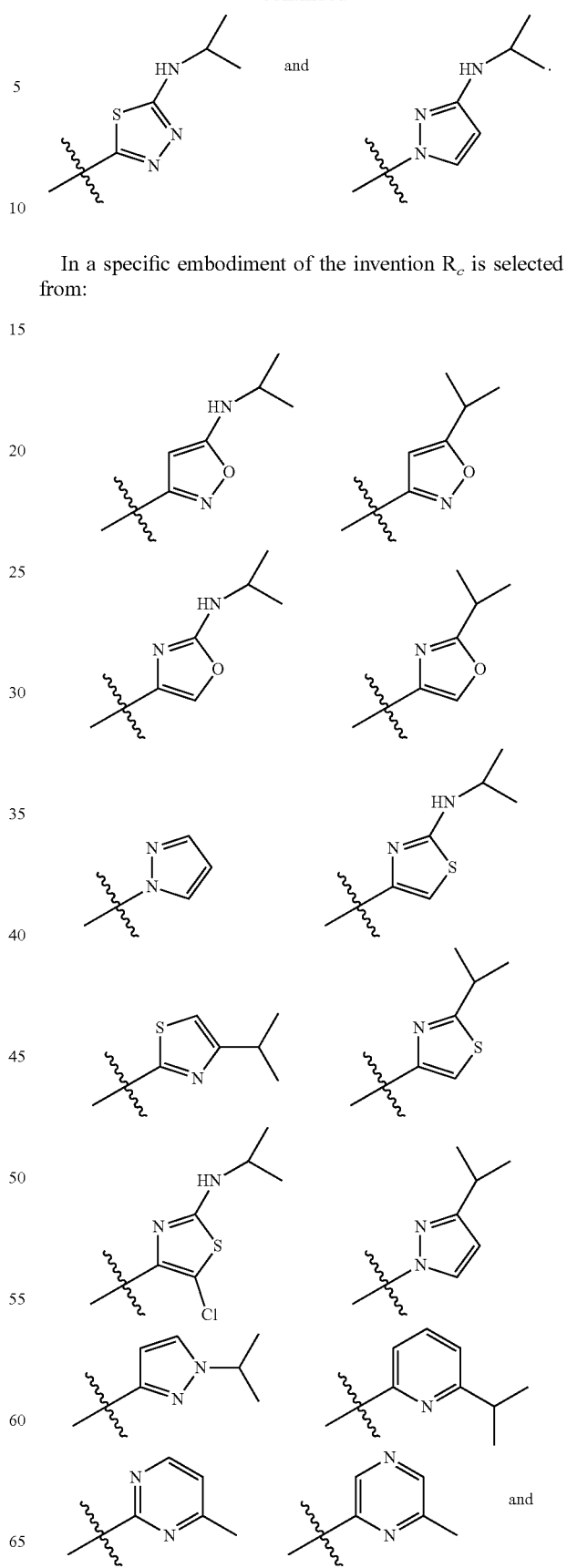

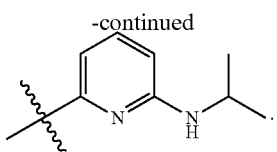

In a specific embodiment of the invention $R_b$ is H, F, Cl, Br, methyl or trifluoromethyl.

In a specific embodiment of the invention $R_b$ is H, F, Cl, methyl or trifluoromethyl.

In a specific embodiment of the invention $R_a$ is H, methoxy, trifluoromethoxy, chloro, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, 2-morpholinoethoxy, cyclopropyloxy 2,2,2-trifluoroethoxy or 2-(N,N-diemthylamino)ethoxy.

In a specific embodiment of the invention $R_a$ is H, methoxy, trifluoromethoxy, chloro, N-(2-cyano ethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, or 2-morpholinoethoxy.

In a specific embodiment of the invention $Z^1$ is selected from the following structures:

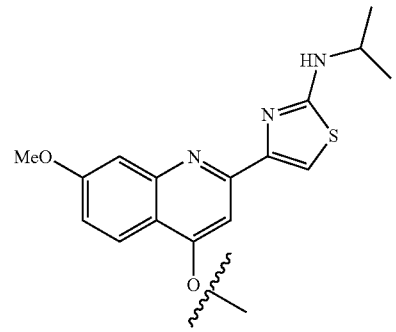

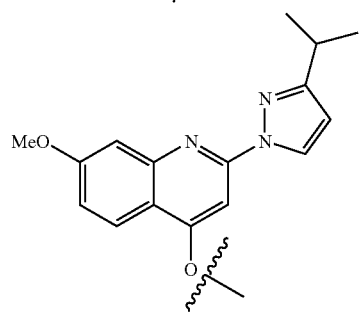

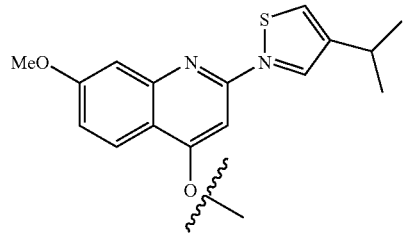

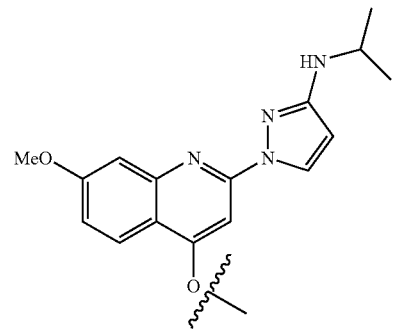

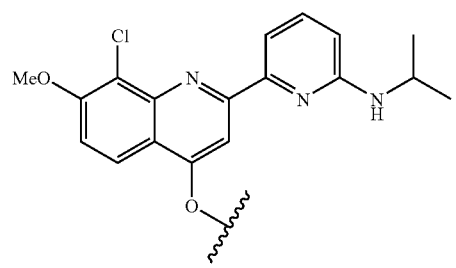

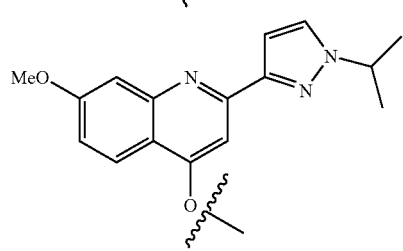

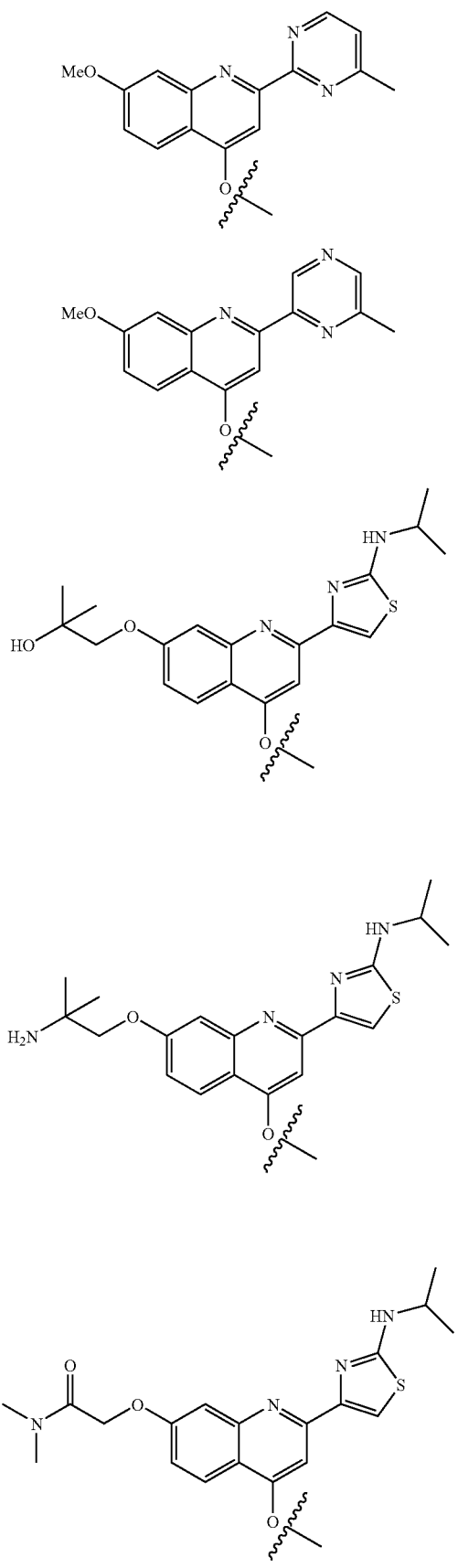
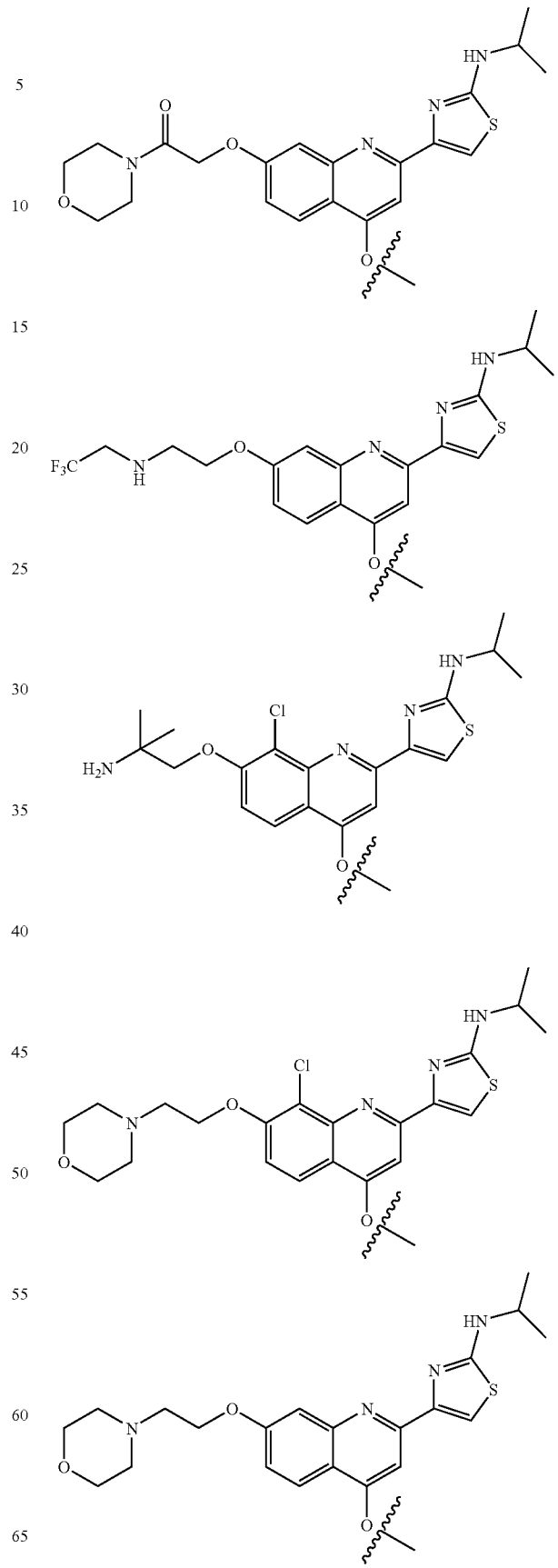

-continued
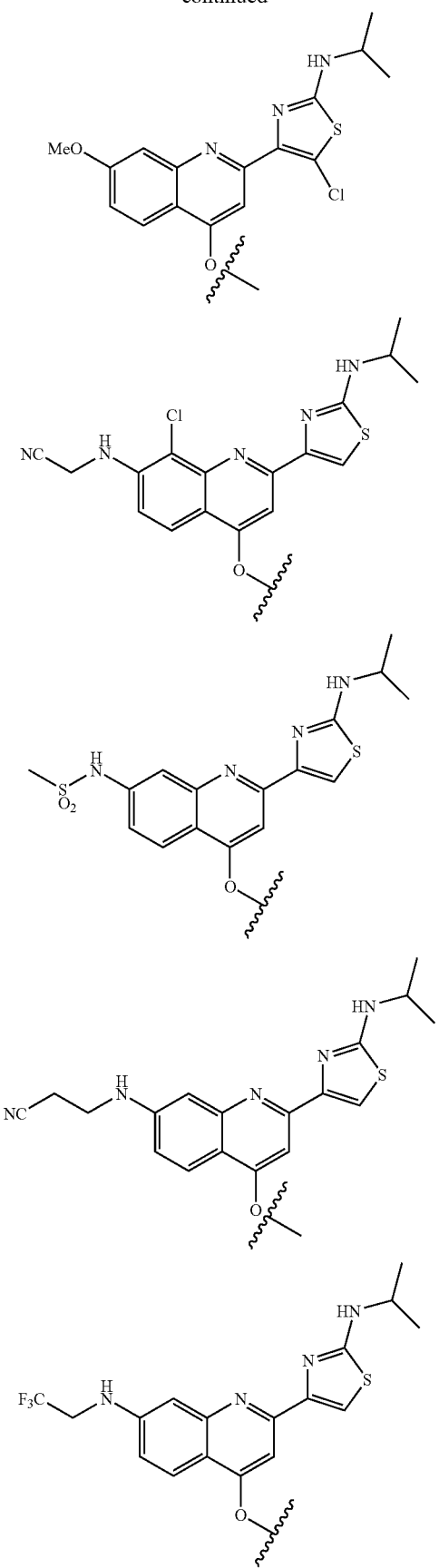
-continued
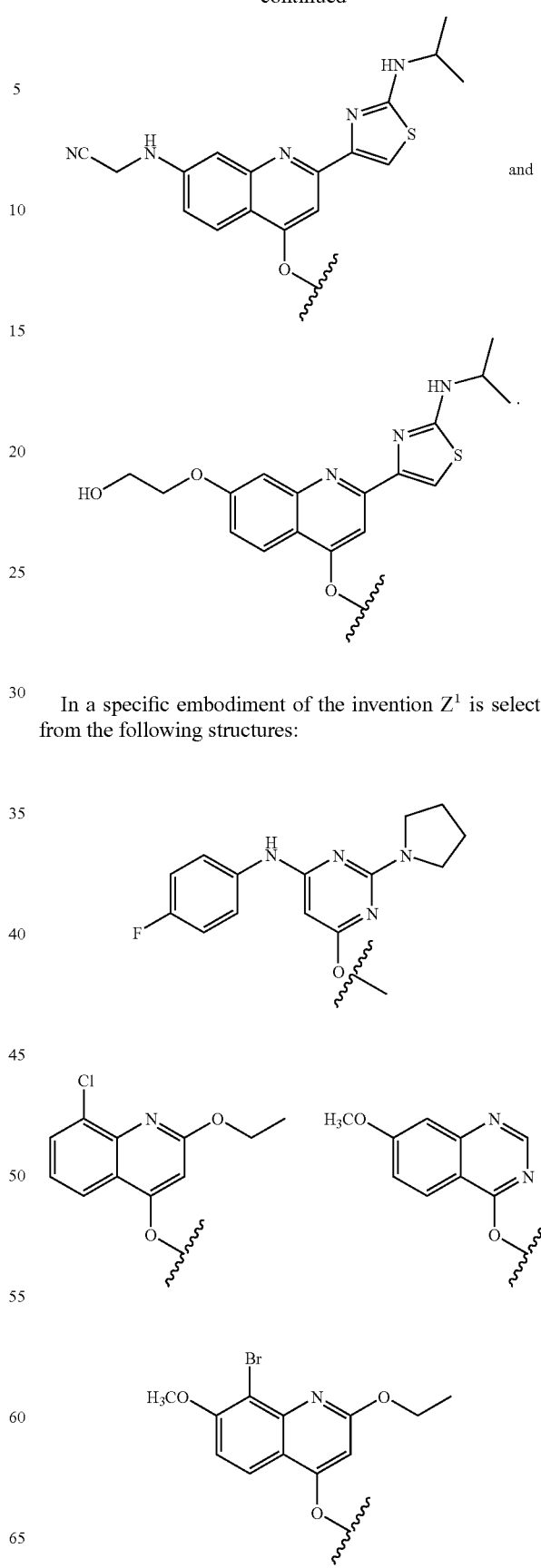
In a specific embodiment of the invention $Z^1$ is selected from the following structures:
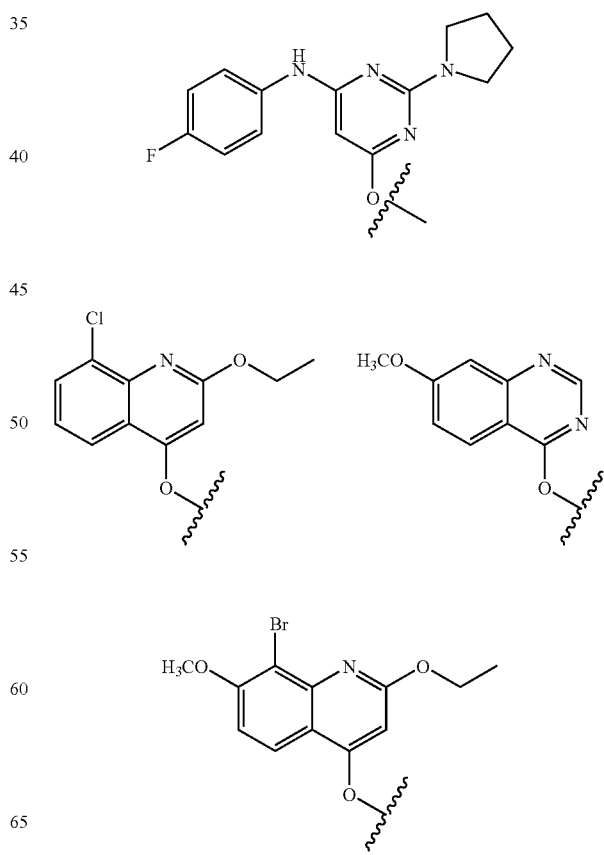

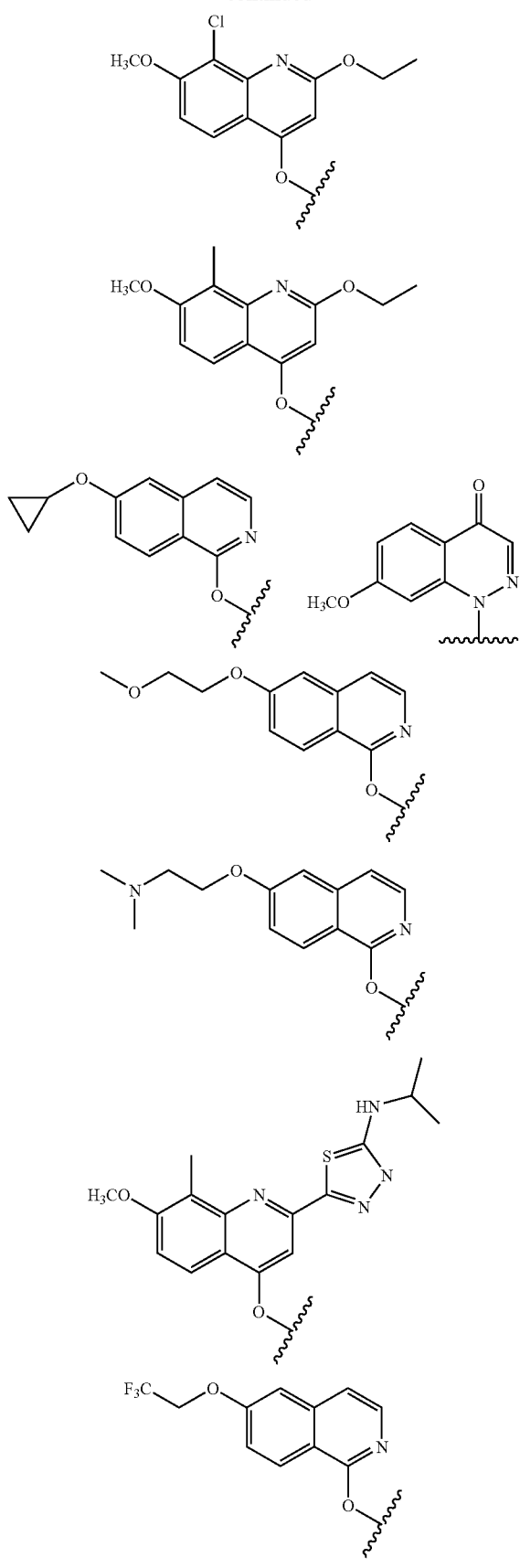
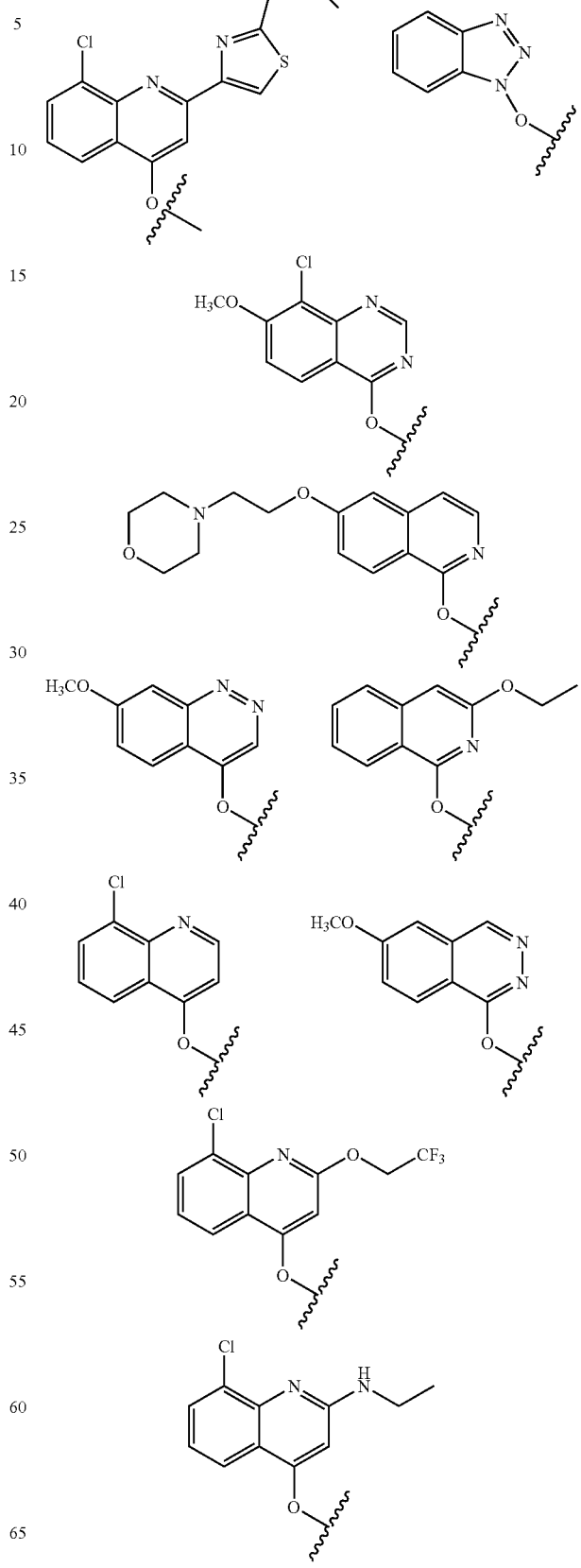

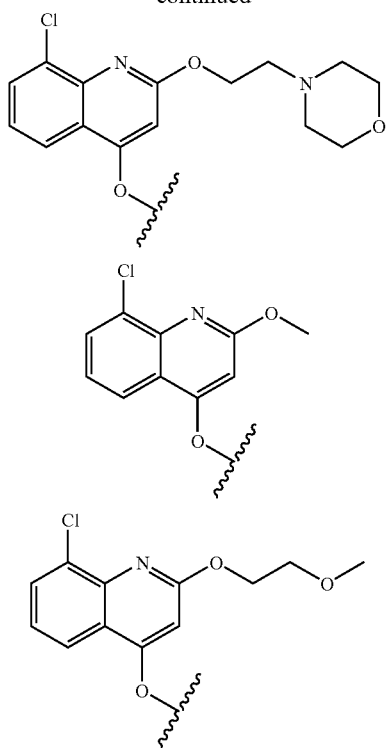

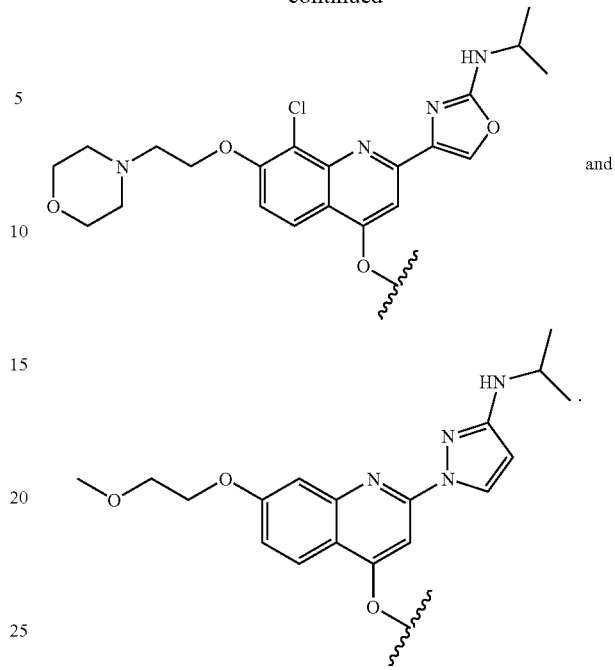

In a specific embodiment of the invention $R_c$ is selected from:

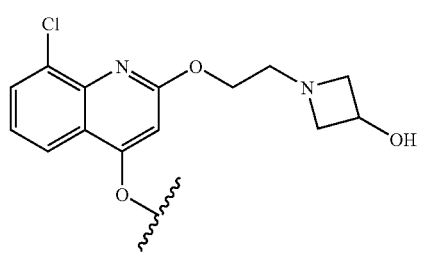

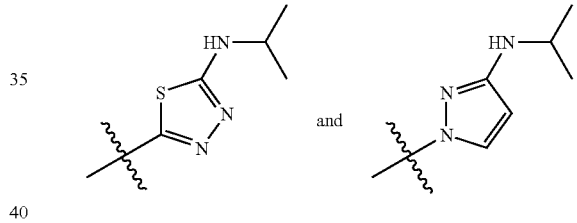

In a specific embodiment of the invention $R^f$ is aryl, heteroaryl, or cycloalkyl, which $R^f$ is optionally substituted with one to three A3.

In a specific embodiment of the invention $R^f$ is cyclopropyl which $R^f$ is optionally substituted by up to four A3.

In a specific embodiment of the invention $R^f$ is cyclopropyl which $R^f$ is optionally substituted by one A3.

In a specific embodiment of the invention $R^f$ is H, alkyl, alkenyl, alkynyl, aryl, heteroaryl, or cycloalkyl, which $R^f$ is optionally substituted with one or more $R_g$;

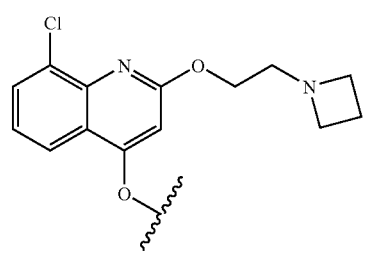

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or motr halo or cyano; and each $R_h$ and $R_i$ is independently H, alkyl, or haloalkyl.

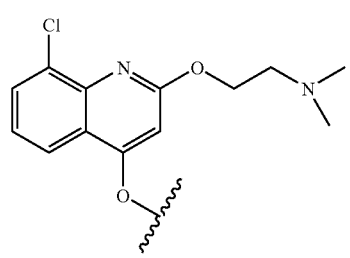

In a specific embodiment of the invention $R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy;
each $R_h$ and $R_i$ is independently H, alkyl, or haloalkyl;

In a specific embodiment of the invention $R^f$ is phenyl, cyclopropyl, 2-fluorophenyl, 4-chlorophenyl, 2-chlorophenyl, 2,6-dimethylphenyl, 2-methylphenyl, 2,2-dimethylpropyl, 2,2-difluoroethyl, 2,2,2-trifluoroethyl, or 1-methylcyclopropyl.

In a specific embodiment of the invention f is cyclopropyl.

In a specific embodiment of the invention $R^f$ is 1-methylcyclopropyl.

In a specific embodiment the invention provides a compound of formula I which is a compound of formula (II):

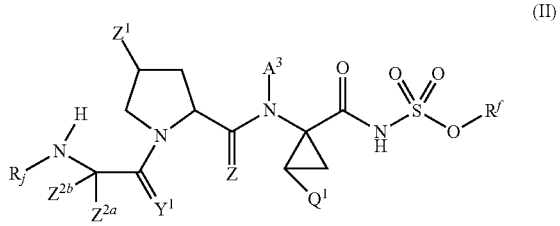

(II)

or a pharmaceutically acceptable salt, or prodrug thereof, wherein: $R_j$ is tert-butoxycarbonyl, cyclopentyloxycarbonyl, 2,2,2-trifluoro-1,1-dimethylethyloxycarbonyl, tert-butylaminocarbonyl, 1-methylcyclopropyloxycarbonyl, 2-(N,N-dimethylamino)-1-1-dimethylethoxycarbonyl, 2-morpholino-1-1-dimethylethoxycarbonyl, tetrahydrofur-3-yloxycarbonyl, or

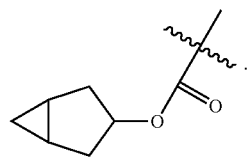

In a specific embodiment of the invention $Q^1$ is (C1-10)alkyl, (C2-10)alkenyl, or (C2-10)alkynyl which $Q^1$ is optionally substituted with $R_c$; or $Q^1$ and $Z^{2a}$ taken together with the atoms to which they are attached form a heterocycle, which heterocycle may optionally be substituted with one or more oxo (═O), $R^4$, or $A^3$; each $R_c$ is $R^4$, H, cyano, F, Cl, Br, I, —C(═O)$NR_dR_e$, C(═O)$NR_sR_t$, $NR_sR_t$, $SR_r$, S(O)$R_r$, or S(O)$_2R_r$, S(═O)$_2NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, S(O)$R_r$, or S(O)$_2R_r$; wherein any (C1-10)alkoxy of $R_c$ is optionally substituted with one or more halo, (C1-6)alkoxy, or $NR_wR_x$; $R_d$ and $R_e$ are each independently H, (C1-10)alkyl, or aryl, which is optionally substituted with one or more halo; each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;
each $R_r$ is independently H, (C1-10)alkyl, (C2-10)alkenyl, (C2-10)alkynyl, (C1-10)alkanoyl, or (C1-10)alkoxycarbonyl; each $R_s$ and $R_t$ is independently H, (C1-10)alkyl, (C2-10)alkenyl, (C2-10)alkynyl, (C1-10)alkanoyl, S(═O)$_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(═O), S(═O)$_2$, or C(═O) and; each $R_w$ and $R_x$ is independently H or (C1-10)alkyl or $R_w$ and $R_x$ together with the nitrogen to which they are attached form a azetidine, pyrrolidine, piperidine, piperazine, morpholine, or thiomorpholine ring which ring is optionally substituted with hydroxyl.

In a specific embodiment of the invention Z is O; $Y^1$ is O; and one of $Z^{2a}$ or $Z^{2b}$ is hydrogen.

In a specific embodiment of the invention $Q^1$ is vinyl, ethyl, cyanomethyl, propyl, 2-fluoroethyl, 2,2-difluoroethyl, or 2-cyanoethyl.

In a specific embodiment of the invention $Q^1$ and $Z^{2a}$ taken together with the atoms to which they are attached form a 12-18 membered heterocycle, which heterocycle may optionally be substituted with one or more oxo (═O) or $A^3$.

In a specific embodiment of the invention $Q^1$ is H.

In a specific embodiment the invention provides a compound of formula I which is a compound of formula (III):

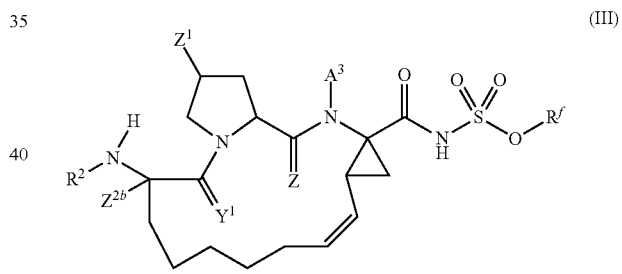

(III)

or a pharmaceutically acceptable salt, or prodrug thereof.

In a specific embodiment the invention provides a compound of formula I which is a compound of formula (IV):

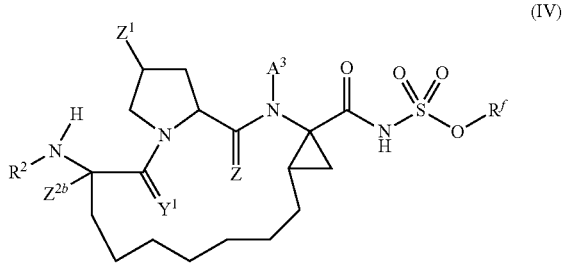

(IV)

or a pharmaceutically acceptable salt, or prodrug thereof.

In a specific embodiment of the invention $Z^{2a}$ is tert-butyl, 1-methylcyclohexyl, tetrahydropyran-4-yl, 1-methylcyclohexyl, 4,4-difluorocyclohexyl, 2,2,2-trifluoro-1-trifluoromethylethyl, or cyclopropyl.

In a specific embodiment the invention provides a compound of formula I, or a pharmaceutically acceptable salt, or prodrug thereof,
wherein:
R¹ is independently selected from H, alkyl, alkenyl, alkynyl, aryl, cycloalkyl, heterocycle, halogen, haloalkyl, alkylsulfonamido, arylsulfonamido, —C(O)NHS(O)₂—, or —S(O)₂—, optionally substituted with one or more A³;
R² is selected from,
a) —C(Y¹)(A³),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
where said alkyl, cycloalkyl and alkyl-cycloalkyl may optionally be mono- or di-substituted with substituents selected from hydroxy and O—(C1-4)alkyl, or
where each of said alkyl-groups may optionally be mono-, di- or tri-substituted with halogen, or
where each of said cycloalkyl groups being 5-, 6- or 7-membered, one or two —CH₂— groups not being directly linked to each other may be optionally replaced by —O— such that the O-atom is linked to the N atom to which R² is attached via at least two C-atoms,
c) phenyl, (C1-3)alkyl-phenyl, heteroaryl or (C1-3)alkyl-heteroaryl,
wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH₂, —CF₃, —NH((C1-4)alkyl) and —N((C1-4)alkyl)₂, —CONH₂ and —CONH—(C1-4)alkyl; and wherein said (C1-3)alkyl may optionally be substituted with one or more halogen;
d) —S(O)₂(A³); or
e) —C(Y¹)—X—Y;
R³ is H or (C1-6)alkyl;
Y¹ is independently O, S, N(A³), N(O)(A³), N(OA³), N(O)(OA³) or N(N(A³)(A³));
Z is O, S, or NR³;
Z¹ is selected from the following structures:

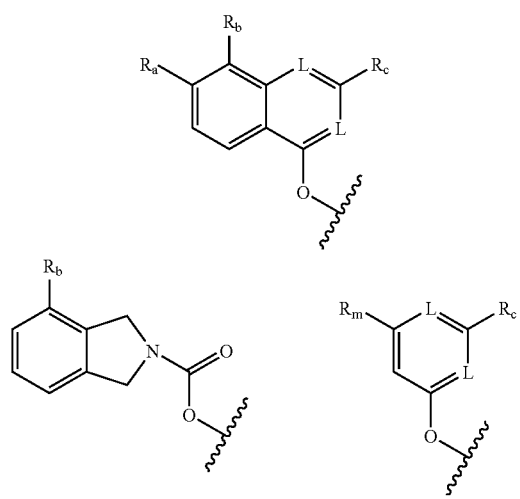

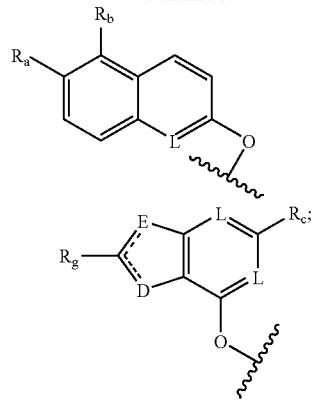

each $R_a$ is $R^4$, H, halo, trifluoromethoxy, $NR_sR_t$, C(=O)$NR_sR_t$, S(=O)₂$NR_sR_t$ or (C1-10)alkyl, wherein one or more carbon atoms of said (C1-10)alkyl is optionally replaced by O, S, S(=O), S(=O)₂ or $NR_k$ and which (C1-10)alkyl is optionally substituted with one or more hydroxy, halo, cyano, $NR_nR_p$, C(=O)$NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_k$;
each $R_b$ is $R^4$, H, F, Cl, Br, I, CF₃, (C1-10)alkyl, or $XR^3$;
each $R_c$ is $R^4$, H, cyano, F, Cl, Br, I, —C(=O)$NR_dR_e$, C(=O)$NR_sR_t$, $NR_sR_t$, S(=O)—₂$NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, S(O)$R_r$, or S(O)₂$R_r$;
$R_d$ and $R_e$ are each independently H or (C1-10)alkyl;
each $R_y$ is H, hydroxy, carboxy, cyano, (C1-10)alkyl, (C2-10)alkenyl, (C2-10) alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)₂$R_r$;
each $R_k$ is H, $NR_sR_t$, C(=O)$NR_sR_t$, S(=O)₂$NR_sR_t$, A², hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)₂$R_r$;
each $R_u$ is H, A³, C(=O)$NR_sR_t$, or S(=O)₂$NR_sR_t$;
each $R_m$ is H, cyano, F, Cl, Br, I, —C(=O)$NR_dR_e$, (C1-10)alkoxy, cycloalkyl, or phenyl that is optionally substituted with one or more F, Cl, Br, I, (C1-10)alkyl, or (C1-10)alkoxy;
each L is independently CH or N;
one of E or D is O, S, or $NR_y$ and the other E or D is $CR_u$ or N;
$Z^{2b}$ is H, (C1-10)alkyl, (C2-10)alkenyl, (C2-10)alkynyl;
Q¹ is (C1-10)alkyl, (C2-10)alkenyl, or (C2-10)alkynyl which Q¹ is optionally substituted with $R^4$ or $R_c$; or Q¹ and $Z^{2a}$ taken together with the atoms to which they are attached form a heterocycle, which heterocycle may optionally be substituted with one or more oxo (=O), $R^4$, or A³;
each X is independently a bond, O, S, or $NR^3$;
Y is a polycarbocycle or a polyheterocycle, which polycarbocycle or a polyheterocycle is optionally substituted with one or more $R^4$, halo, carboxy, hydroxy, (C1-10)

alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R^4$ is independently —$P(Y^3)(OA^2)(OA^2)$, —$P(Y^3)(OA^2)(N(A^2)_2)$, —$P(Y^3)(A^2)(OA^2)$, —$P(Y^3)(A^2)(N(A^2)_2)$, or $P(Y^3)(N(A^2)_2)(N(A^2)_2)$;

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl, or (C1-10)alkoxycarbonyl;

each $R_s$ and $R_t$ is independently H, (C1-10)alkyl, (C2-10)alkenyl, (C2-10)alkynyl, (C1-10)alkanoyl, $S(=O)_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by $S(=O)$, $S(=O)_2$, or $C(=O)$;

$Z^{2a}$ is H, (C1-10)alkyl, (C2-10)alkenyl, (C2-10)alkynyl, haloalkyl, (C1-10)alkyl-$S(=O)_2$—(C1-10)alkyl, or cycloalkyl, wherein any carbon atom of $Z^{2a}$ may optionally be replaced with a heteroatom selected from O, S or N and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with one or more $R^1$, $R^2$, $Q^1$, or $A^3$;

$A^3$ is independently selected from PRT, H, —OH, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —$C(A^2)_3$, —$C(A^2)_2$-$C(O)A^2$, —$C(O)A^2$, —$C(O)OA^2$, —$O(A^2)$, —$N(A^2)_2$, —$S(A^2)$, —$CH_2P(Y^1)(A^2)(OA^2)$, —$CH_2P(Y^1)(A^2)(N(A^2)_2)$, —$CH_2P(Y^1)(OA^2)(OA^2)$, —$OCH_2P(Y^1)(OA^2)(OA^2)$, —$OCH_2P(Y^1)(A^2)(OA^2)$, —$OCH_2P(Y^1)(A^2)(N(A^2)_2)$, —$C(O)OCH_2P(Y^1)(OA^2)(OA^2)$, —$C(O)OCH_2P(Y^1)(A^2)(OA^2)$, —$C(O)OCH_2P(Y^1)(A^2)(N(A^2)_2)$, —$CH_2P(Y^1)(OA^2)(N(A^2)_2)$, —$OCH_2P(Y^1)(OA^2)(N(A^2)_2)$, —$C(O)OCH_2P(Y^1)(OA^2)(N(A^2)_2)$, —$CH_2P(Y^1)(N(A^2)_2)(N(A^2)_2)$, —$C(O)OCH_2P(Y^1)(N(A^2)_2)(N(A^2)_2)$, —$OCH_2P(Y^1)(N(A^2)_2)(N(A^2)_2)$, —$(CH_2)_m$-heterocycle, —$(CH_2)_mC(O)O$alkyl, —O—$(CH_2)_m$—O—$C(O)$—Oalkyl, —O—$(CH_2)_r$—O—$C(O)$—$(CH_2)_m$-alkyl, —$(CH_2)_mO$—$C(O)$—O-alkyl, —$(CH_2)_mO$—$C(O)$—O-cycloalkyl, —$N(H)C(Me)C(O)O$-alkyl, $SR_r$, $S(O)R_r$, $S(O)_2R_r$, or alkoxy arylsulfonamide, wherein each $A^3$ may be optionally substituted with 1 to 4

—$R^1$, —$P(Y^1)(OA^2)(OA^2)$, —$P(Y^1)(OA^2)(N(A^2)_2)$, —$P(Y^1)(A^2)(OA^2)$, —$P(Y^1)(A^2)(N(A^2)_2)$, or $P(Y^1)(N(A^2)_2)(N(A^2)_2)$, —$C(=O)N(A^2)_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —$(CH_2)_m$heterocycle, —$(CH_2)_m$—$C(O)O$-alkyl, —$O(CH_2)_mOC(O)Oalkyl$, —O—$(CH_2)_m$—O—$C(O)$—$(CH_2)_m$-alkyl, —$(CH_2)_m$—O—$C(O)$—O-alkyl, —$(CH_2)_m$—O—$C(O)$—O-cycloalkyl, —$N(H)C(CH_3)C(O)O$-alkyl, or alkoxy arylsulfonamide, optionally substituted with $R^1$;

optionally each independent instance of $A^3$ and $Q^1$ can be taken together with one or more $A^3$ or $Q^1$ groups to form a ring;

$A^2$ is independently selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each $A^2$ is optionally substituted with $A^3$;

$R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —$C(=O)NR_hR_i$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy;

each $R_h$ and $R_i$ is independently H, alkyl, or haloalkyl; and m is 0 to 6.

In a specific embodiment of the invention X is O, S, or $NR^3$.

In a specific embodiment of the invention X is O.

In a specific embodiment of the invention Y is a polycarbocycle.

In a specific embodiment of the invention Y is polyheterocycle.

In a specific embodiment of the invention Y is a fused carbocyclic ring system.

In a specific embodiment of the invention Y is a fused heterocyclic ring system.

In a specific embodiment of the invention Y is a fused carbocyclic ring system comprising one or more double bonds.

In a specific embodiment of the invention Y is a fused heterocyclic ring system comprising one or more double bonds.

In a specific embodiment of the invention Y is a bridged carbocyclic ring system.

In a specific embodiment of the invention Y is a bridged heterocyclic ring system.

In a specific embodiment of the invention Y is a bridged carbocyclic ring system comprising one or more double bonds.

In a specific embodiment of the invention Y is a bridged heterocyclic ring system comprising one or more double bonds.

In a specific embodiment of the invention Y comprises a bridged ring system

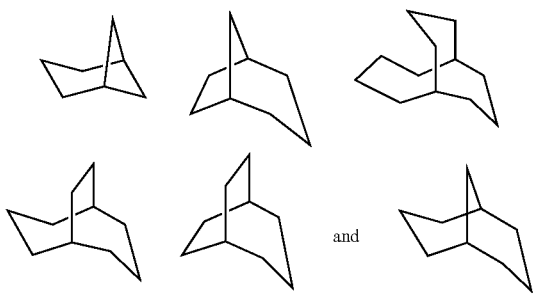

selected from:
wherein one or more carbon atoms in the bridged ring system is optionally replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo; and wherein the ring system optionally comprises one or more double bonds. In a specific embodiment of the invention the ring system comprises one or more double bonds. In a specific embodiment of the invention one or more carbon atoms in the bridged ring system is replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

In a specific embodiment of the invention Y comprises a fused ring system selected from:

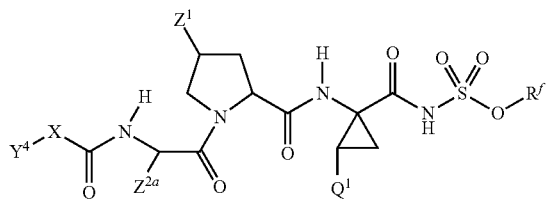

wherein one or more carbon atoms in the fused ring system is optionally replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo; and wherein the ring system optionally comprises one or more double bonds. In a specific embodiment of the invention one or more carbon atoms in the fused ring system is replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

In a specific embodiment of the invention Y is selected from:

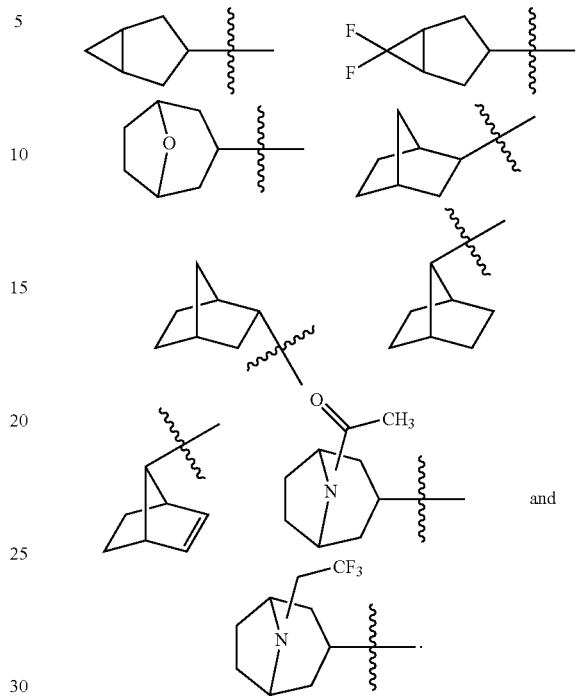

In a specific embodiment the invention provides a compound of formula (V):

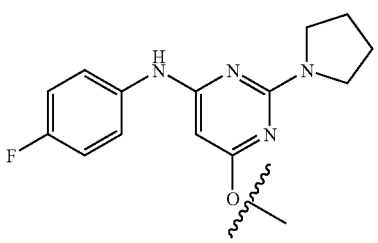

(V)

wherein Z$^1$ is selected from the following structures:

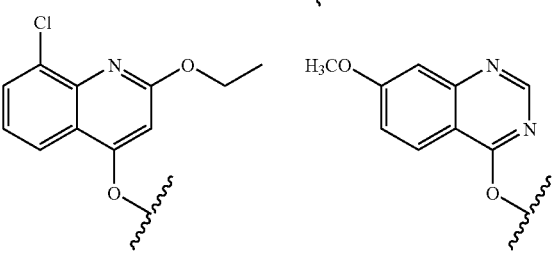

-continued
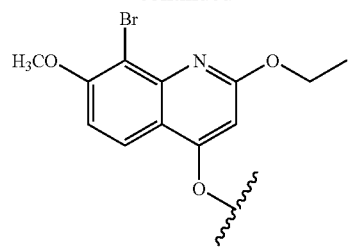
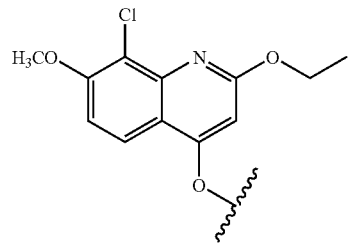
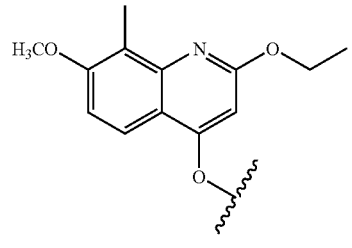
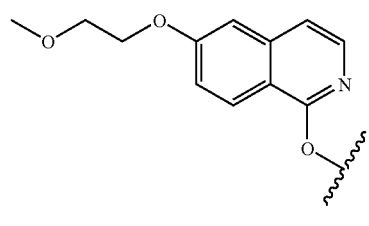
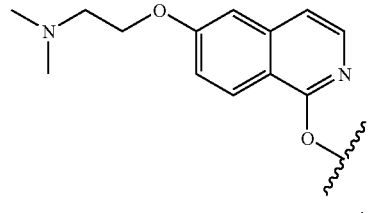
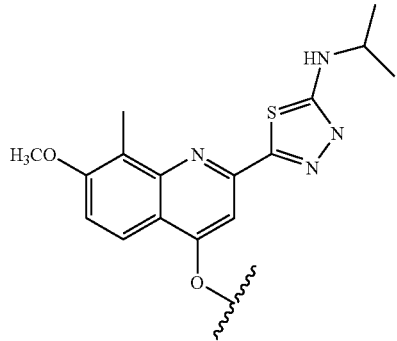
-continued
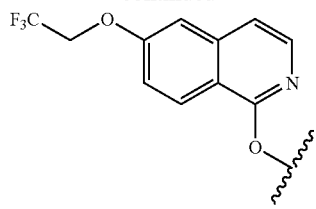
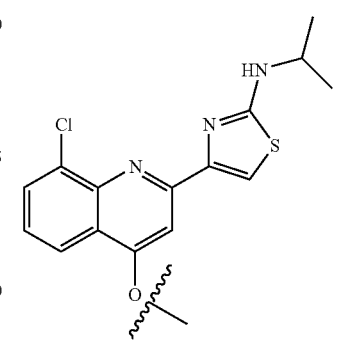
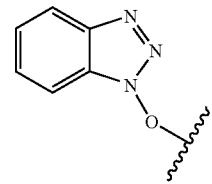
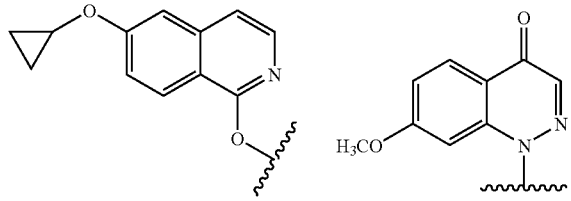
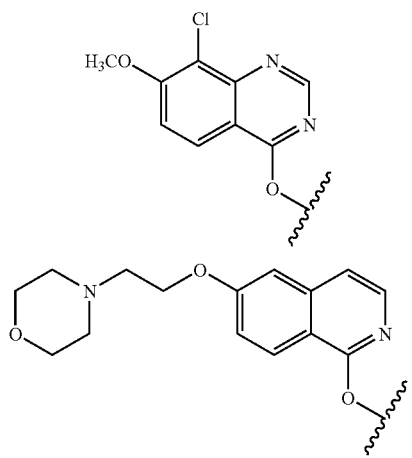
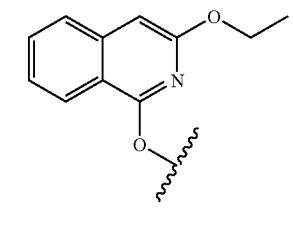
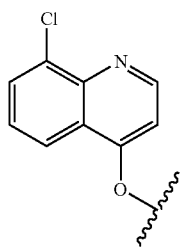
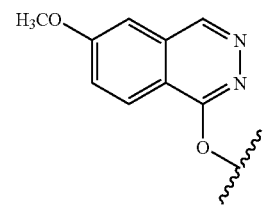
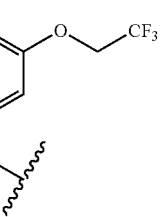

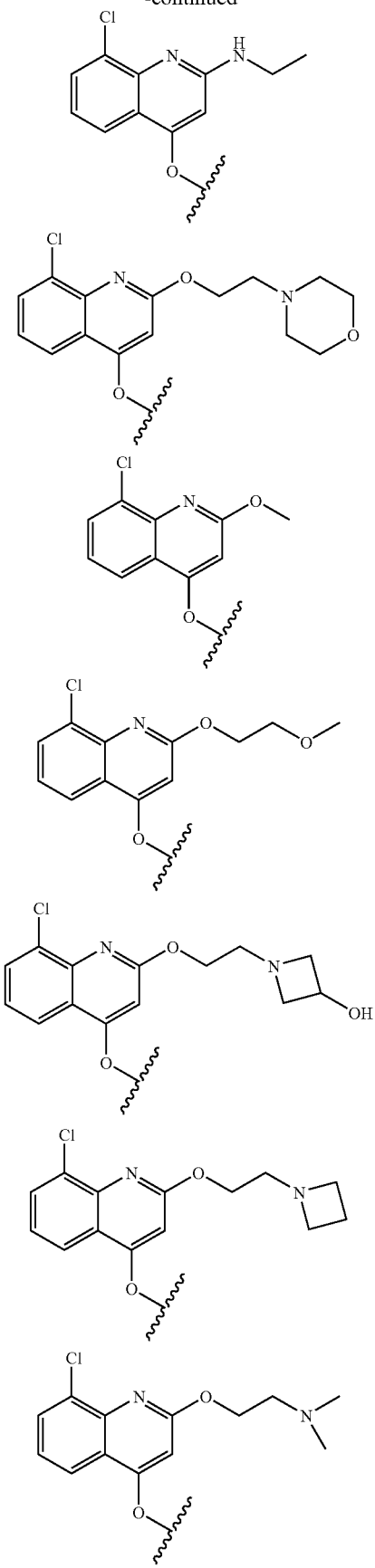

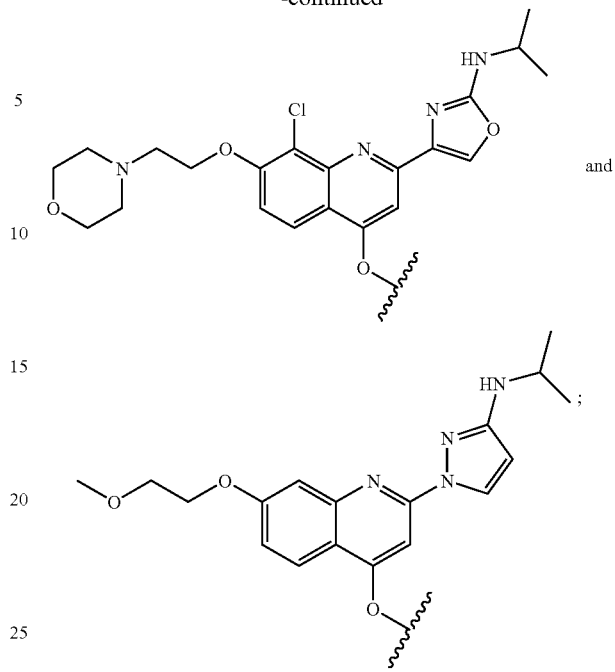

$R^f$ is H, alkyl, alkenyl, alkynyl, aryl, heteroaryl, or cycloalkyl, which $R^f$ is optionally substituted with one or more $R_g$;

$Q^1$ is H, (C1-10)alkyl, (C2-10)alkenyl, or (C2-10)alkynyl which (C1-10)alkyl, (C2-10)alkenyl, or (C2-10)alkynyl is optionally substituted with one or more $R_c$; or $Q^1$ and $Z^{2a}$ taken together with the atoms to which they are attached form a heterocycle, which heterocycle may optionally be substituted with one or more oxo (=O) or halo;

$R^2$ is —C(=O)—X—Y;

X is a bond, O, S, or NH;

$Y^4$ is (C2-10)alkyl, (C3-7)cycloalkyl, heterocycle, polycarbocycle, or polyheterocycle, which (C2-10)alkyl, (C3-7)cycloalkyl, heterocycle, polycarbocycle, or polyheterocycle is optionally substituted with one or more (C1-10)alkyl, halo, carboxy, hydroxy, (C1-10)alkanoyl, (C1-10)alkoxy, (C1-10)alkanoyloxy, (C1-10)alkoxycarbonyl, trifluoromethyl, $NR_nR_p$, $SR_r$, $S(O)R_r$, or $S(O)_2 R_r$;

each $R_c$ cyano, F, Cl, Br, $S(O)_2R_r$, (C1-10)alkoxy, or cycloalkyl;

each $R_d$ is independently H, (C1-10)alkyl, or aryl, which is optionally substituted with one or more halo;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or motr halo, alkoxy, or cyano;

each $R_h$ and $R_i$ is independently H, alkyl, or haloalkyl;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring; and each $R_r$ is independently (C1-10)alkyl.

In a specific embodiment of the invention X is a bond; and $Y^4$ is pyrrol-1-yl, morpholino, or (C2-10)alkyl.

In a specific embodiment of the invention $R^2$ is pyrrol-1-ylcarbonyl, morpholinocarbonyl, or 3,3-dimethylbutanoyl.

In a specific embodiment of the invention X is O; and $Y^4$ is tert-butyl, cyclopentyl, 1,1-dimethylethyl, cyclopropyl, tetrahydrofuranyl, isopropyl, 2,2-dimethylpropyl, cyclobutyl or

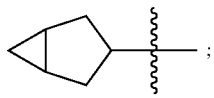 [SMILES: *C1CC2CC2C1]

which $Y^4$ is optionally substituted with one or more (C1-10) alkyl, halo, (C1-10)alkoxy, trifluoromethyl, or $NR_nR_p$.

In a specific embodiment of the invention $R^2$ is tert-butoxycarbonyl, cyclopentoxycarbonyl, 1,1-dimethyl-2,2,2-trifluoroethoxy, 1-methylcyclopropyloxycarbonyl, 2-(N,N-dimethylamino)-1,1dimethylethoxycarbonyl, 2-morpholino-1,1dimethylethoxycarbonyl, 3-tetrahydrofuranyloxycarbonyl, isopropoxycarbonyl, 2-methoxy-1,1-dimethylethoxycarbonyl, 2,2-dimethylpropoxycarbonyl, 1-trifluoromethylcyclobutyloxycarbonyl, cyclobutyloxycarbonyl, 1-methylcyclopentyloxycarbonyl, 1-trifluoromethylcyclopentyloxycarbonyl, 1-trifluoromethylcyclobutyloxycarbonyl, and

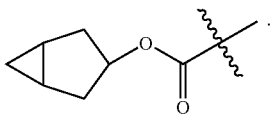 [SMILES: *C(=O)OC1CC2CC2C1]

In a specific embodiment of the invention X is NH; and $Y^4$ (C2-10)alkyl that is optionally substituted with one or more halo.

In a specific embodiment of the invention $R^2$ is tert-butylaminocarbonyl, or 1,1-dimethyl-2,2,2-trifluoroethylaminocarbonyl.

In a specific embodiment of the invention $R^f$ is alkyl, aryl, cycloalkyl, which $R^f$ is optionally substituted with one or more $R_g$ independently selected from alkyl, halo, —C(=O)$OR_d$, or trifluoromethyl, wherein each alkyl of $R_g$ is optionally substituted with one or more halo, alkoxy, or cyano.

In a specific embodiment of the invention $R^f$ is phenyl, cyclopropyl, 2-fluorophenyl, 4-chlorophenyl, 2-chlorophenyl, 2,6-dimethylphenyl, 2-methylphenyl, 2,2-dimethylpropyl, 2,2-difluoroethyl, 2,2,2-trifluoroethyl, 1-methylcyclopropyl, 1-isopropylcyclopropyl, 1-propylcyclopropyl, 2,2,2-trifluoro-1,1-dimethylethyl, 1-(methoxycarbonyl)cyclopropyl, 1-ethylcyclopropyl, 1-trifluoromethylcyclobutyl, 1-(methoxymethyl)cyclopropyl, 1-(2-cyanoethyl)cyclopropyl, or 1-(2,2,2-trifluoroethyl) cyclopropyl.

In a specific embodiment of the invention $Q^1$ is hydrogen, methyl, ethyl, vinyl, cyanomethyl, propyl, 2-fluoroethyl, 2,2-difluoroethyl, 2-cyanoethyl, 2-methoxyethyl, 2-methylsulfonylethyl, or cyclopropyl.

In a specific embodiment of the invention $Z^{2a}$ is selected from tert-butyl, tetrahydropyran-4-yl, 1-methylcyclohexyl, 4,4-difluorocyclohexyl, cyclohexyl, cyclopentyl, 1-trifluoromethylcyclopropyl, and

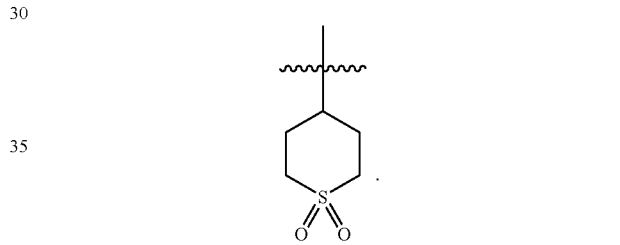

In a specific embodiment the invention provides a compound selected from:

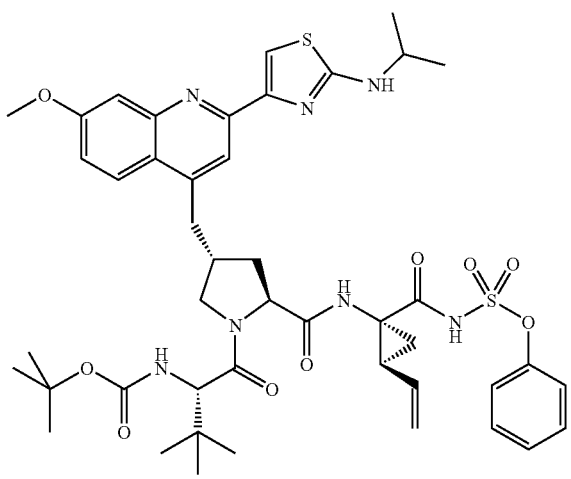

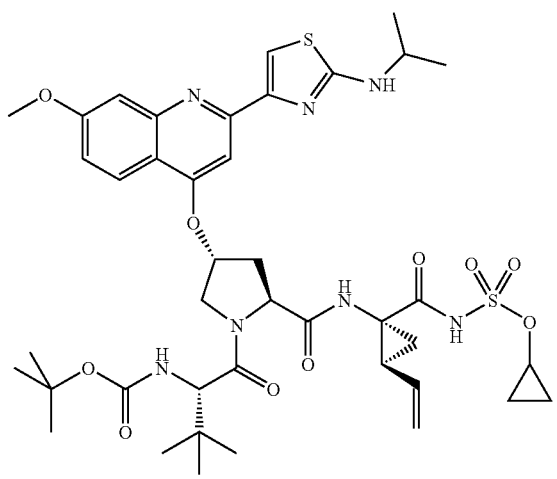

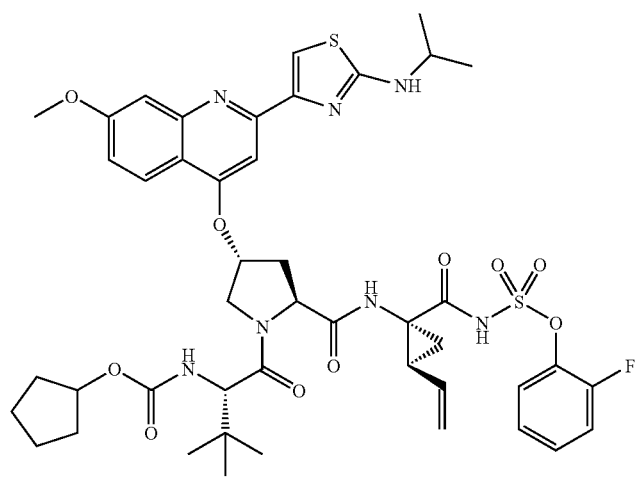
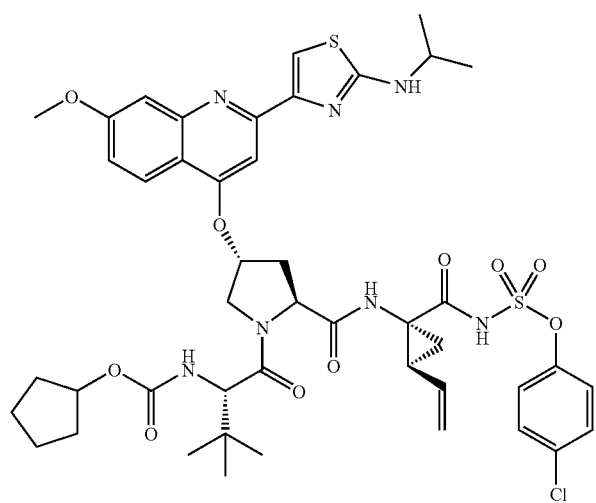
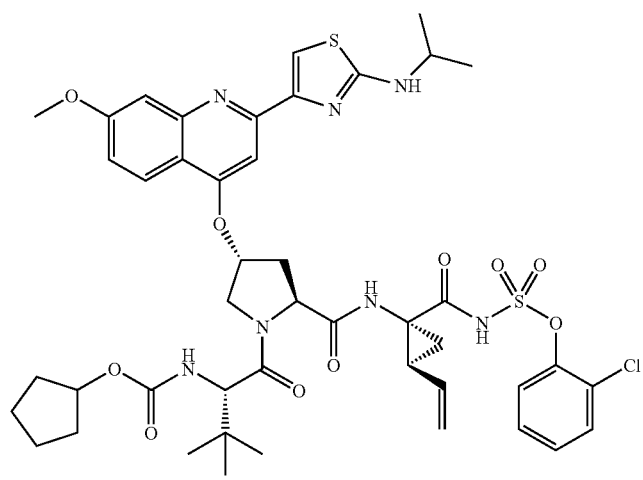

91 92
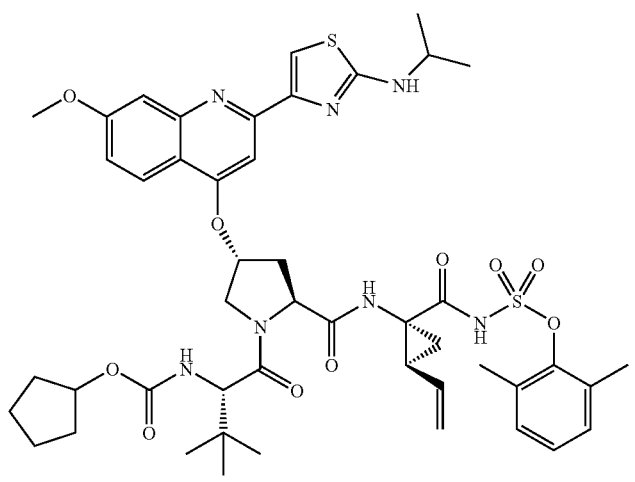
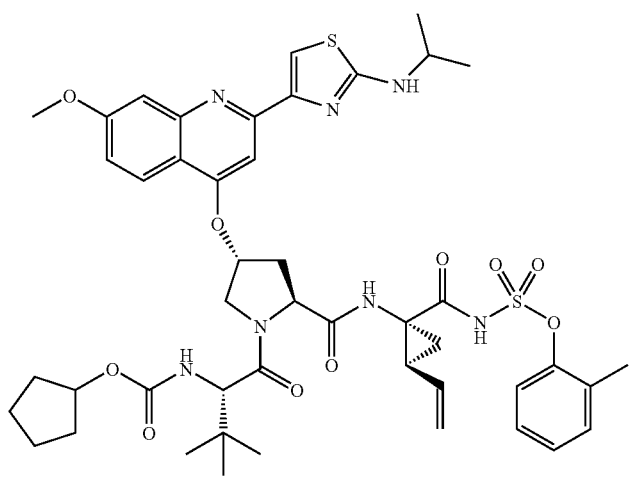
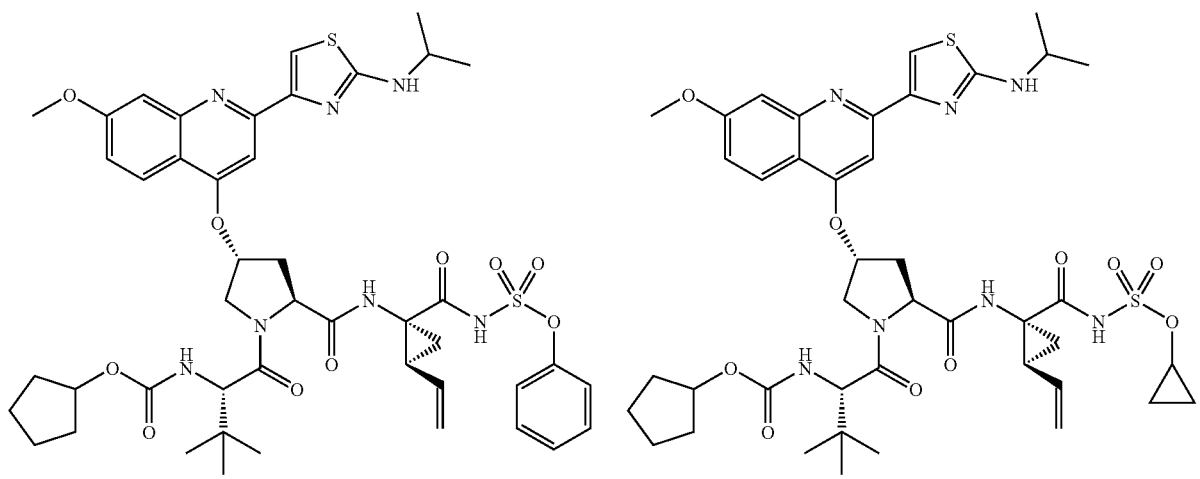

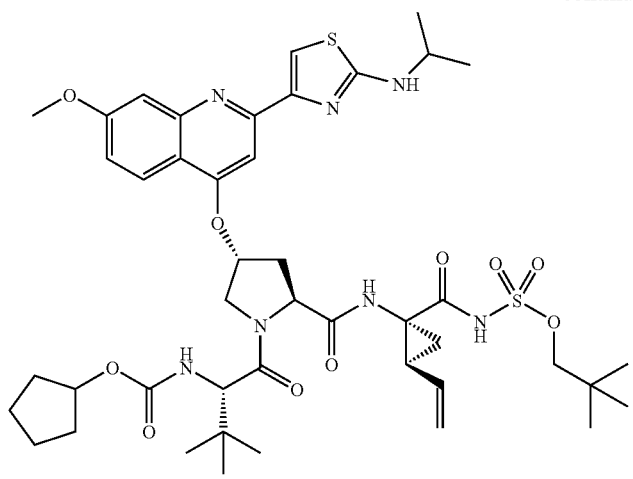
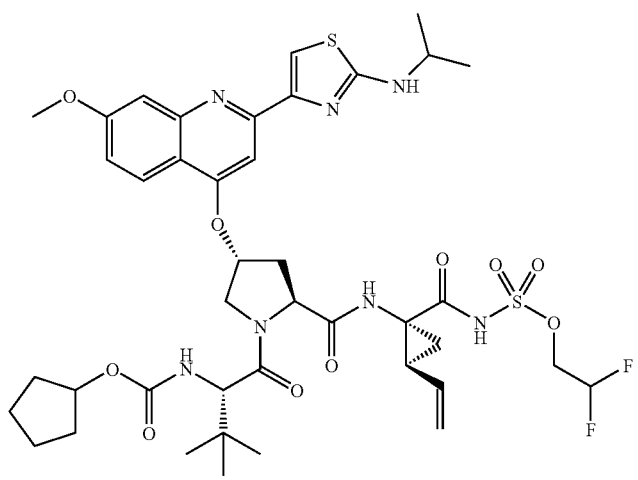
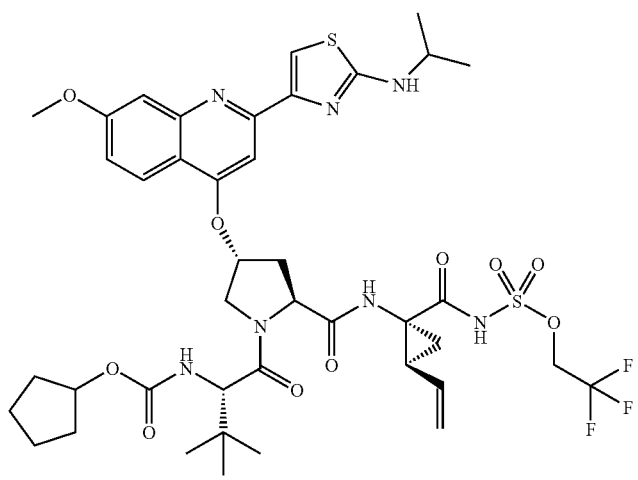

95
96
-continued
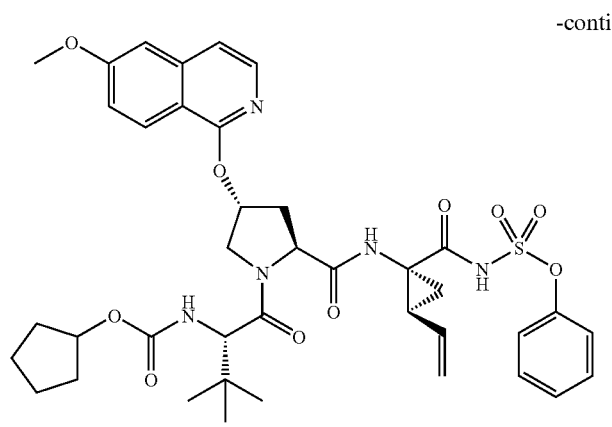
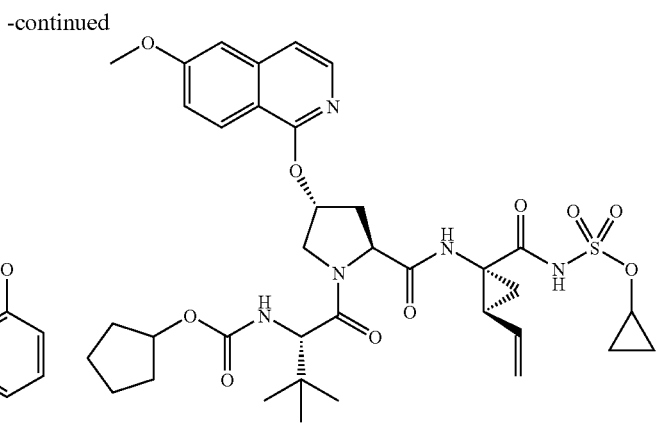
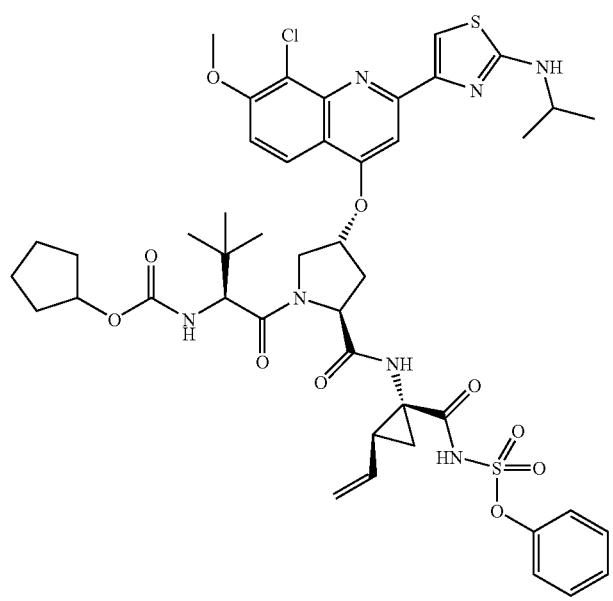
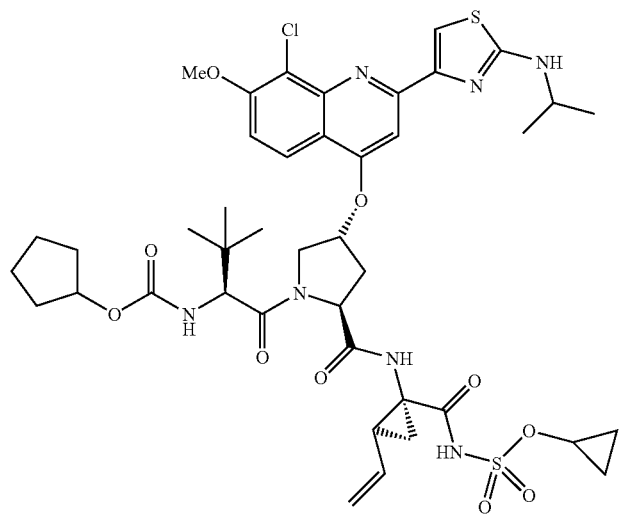

-continued
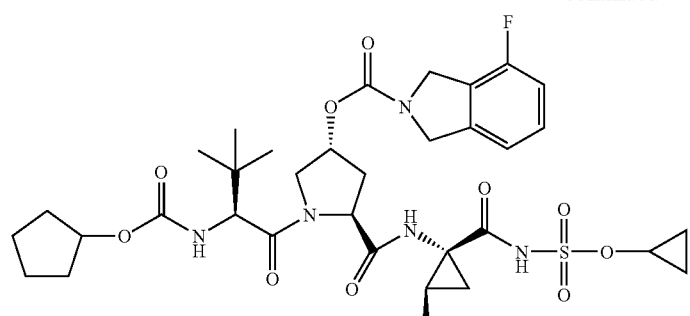
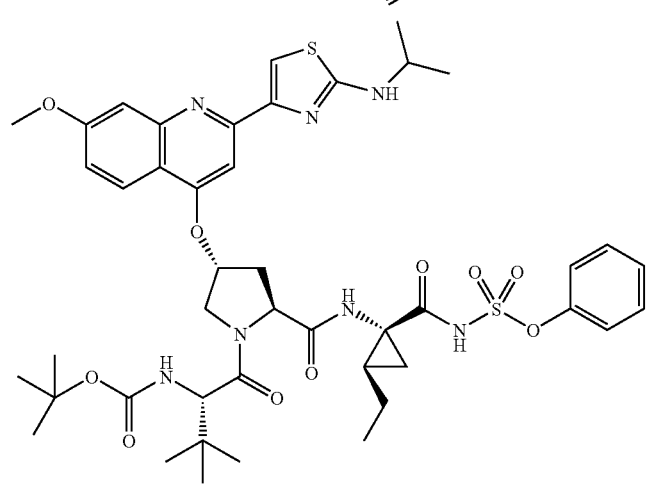
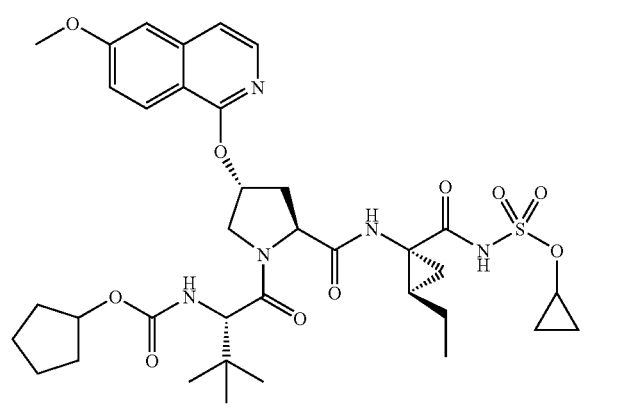
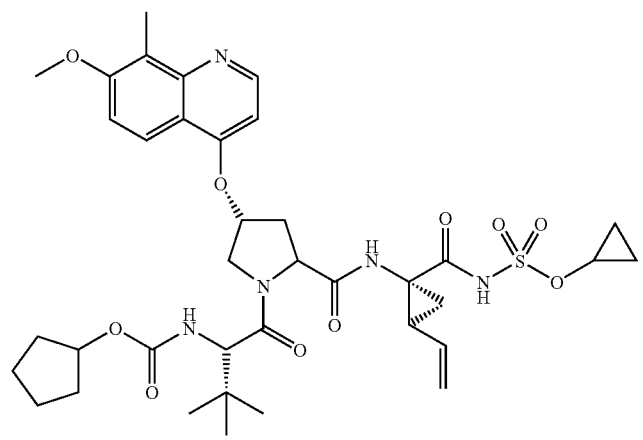

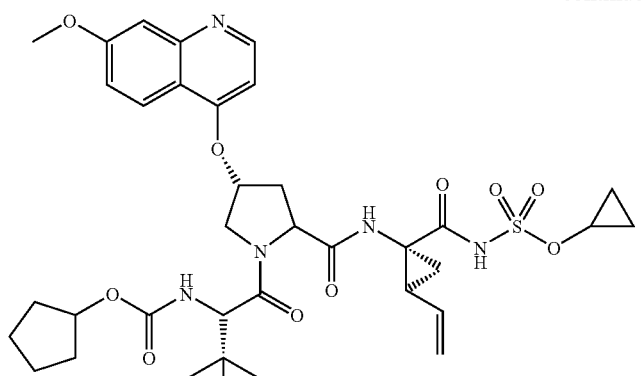
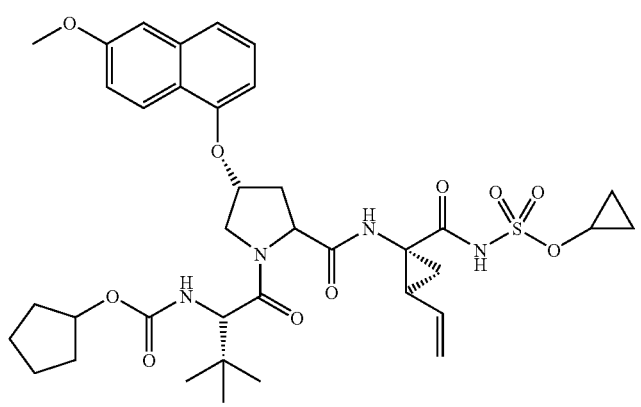
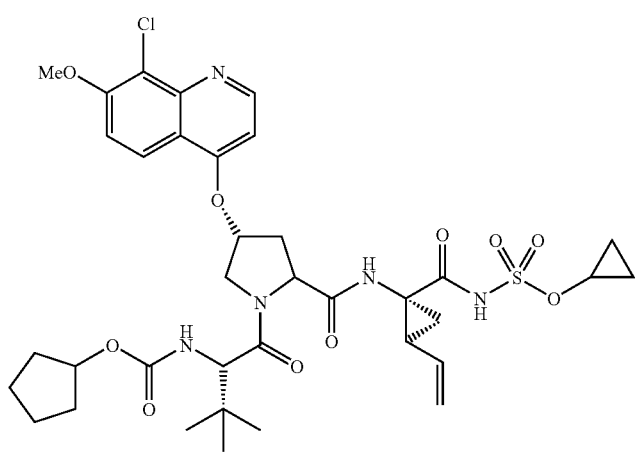
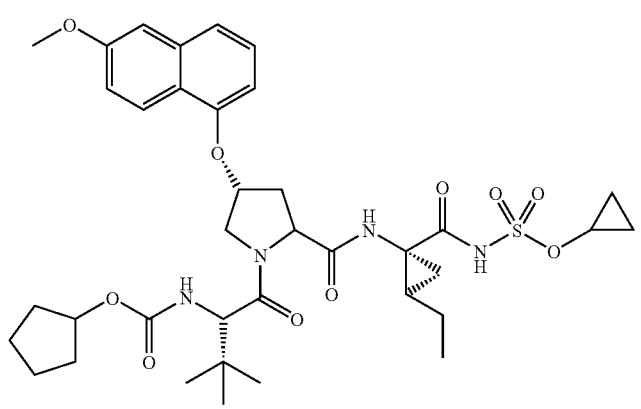

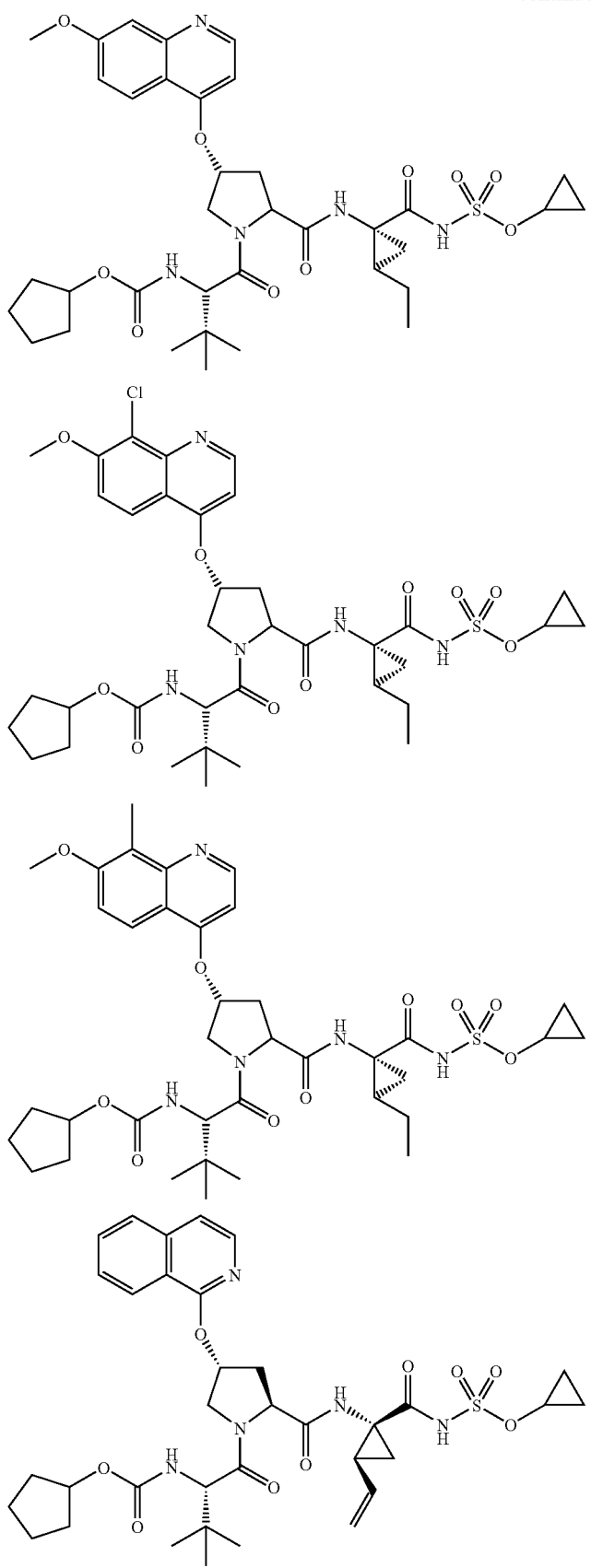

103 104
-continued
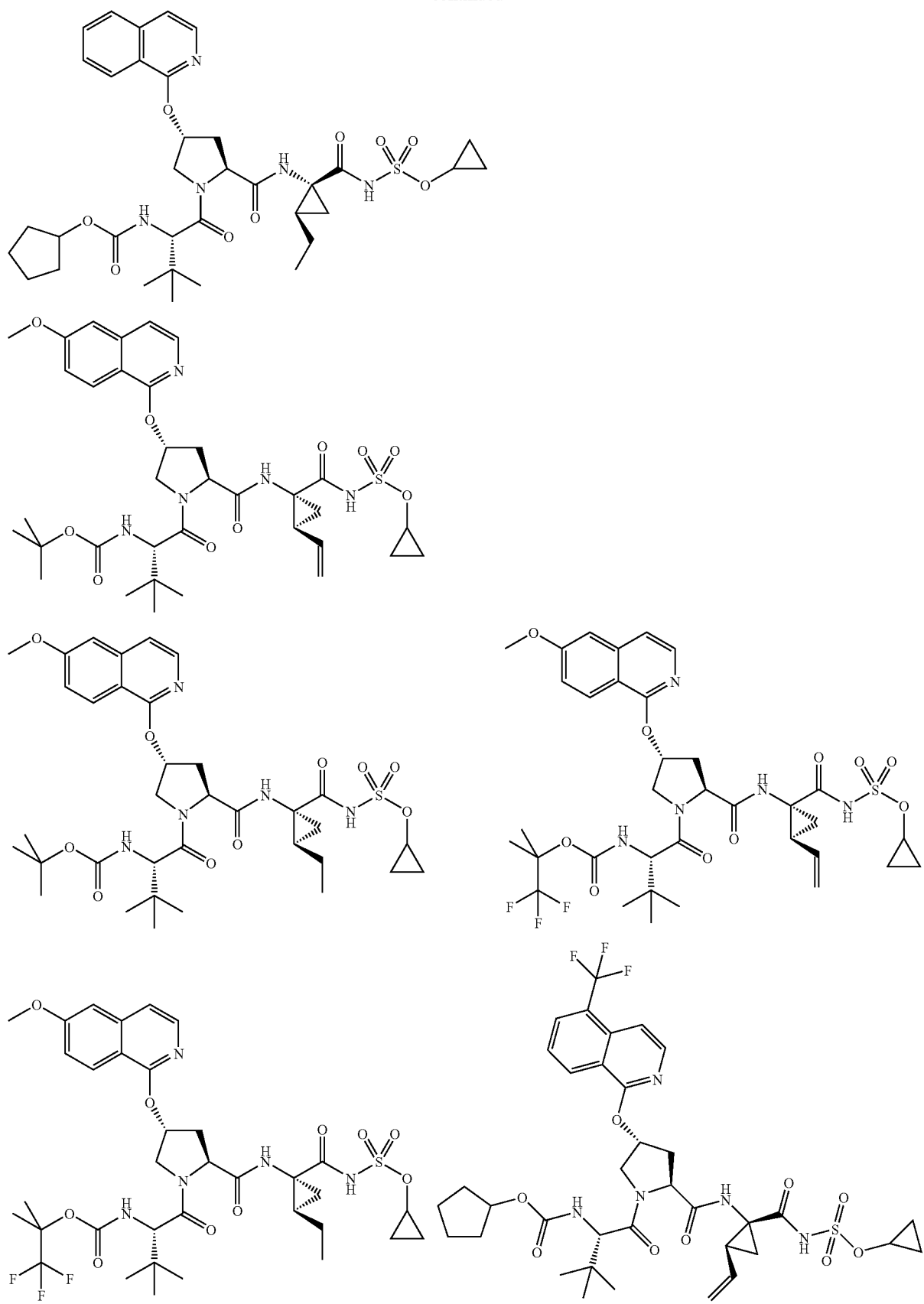

-continued
| 105 | 106 |
|---|---|
| 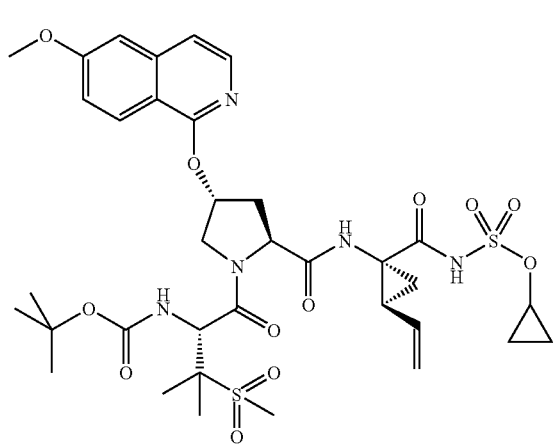 | 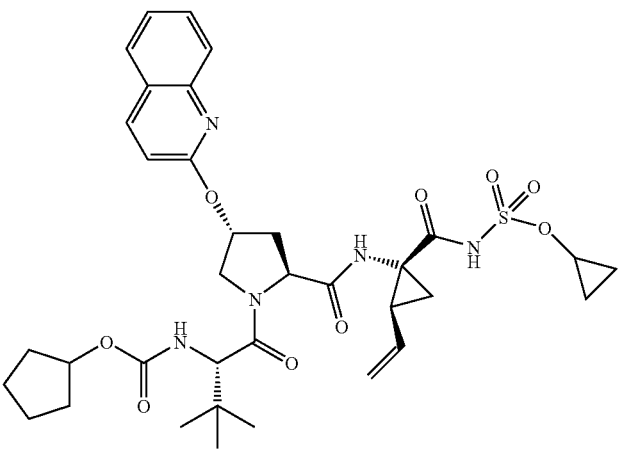 |
| 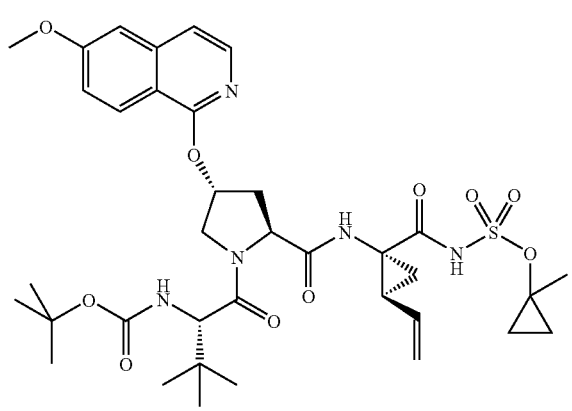 | 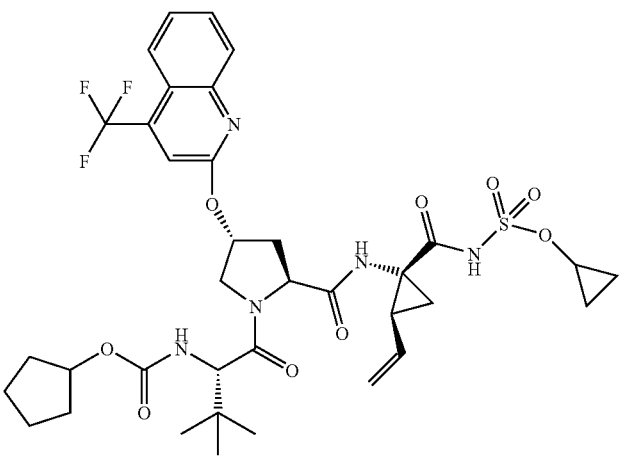 |
| 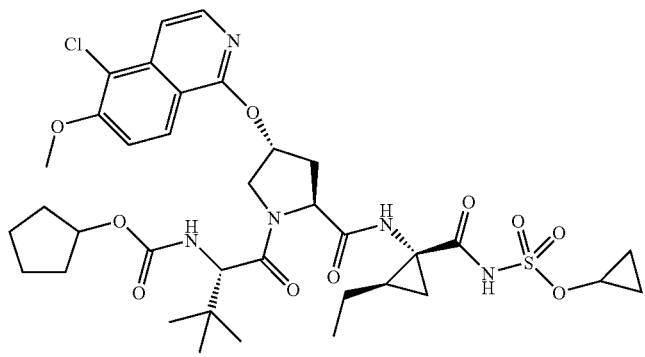 | |
| 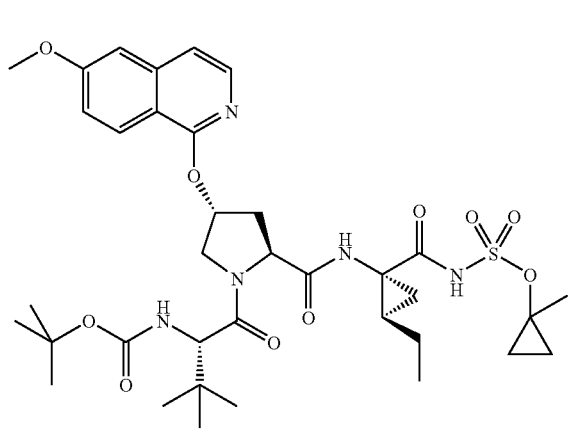 | 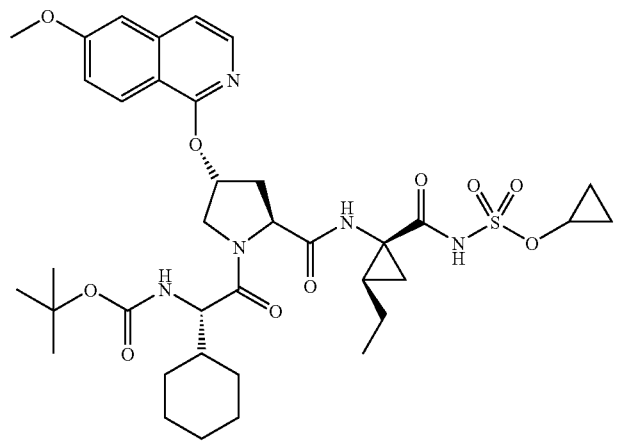 |

-continued
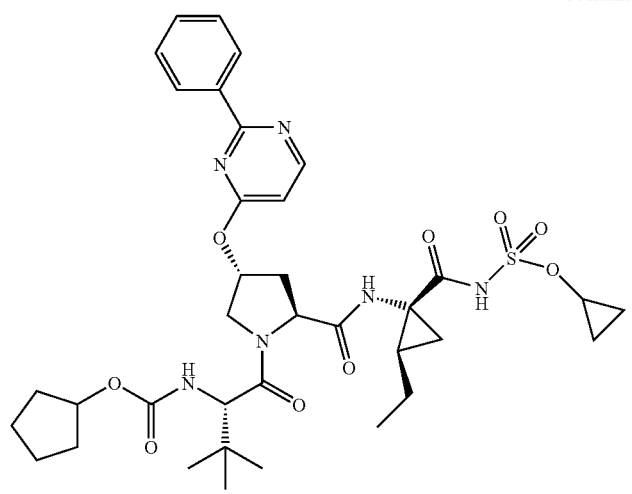
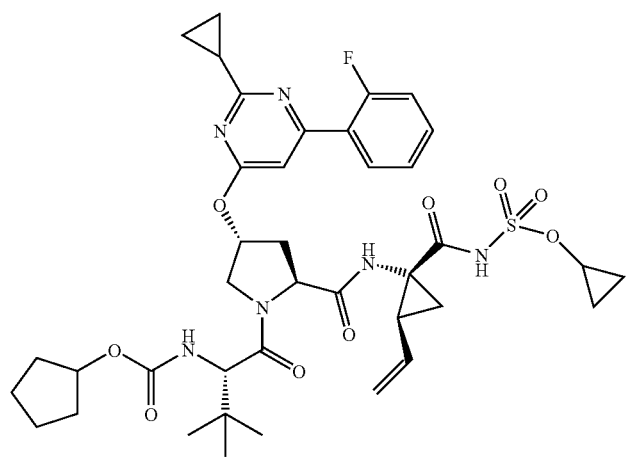
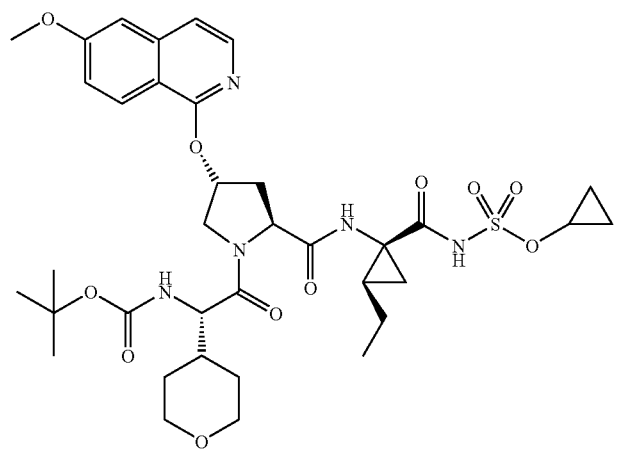

109
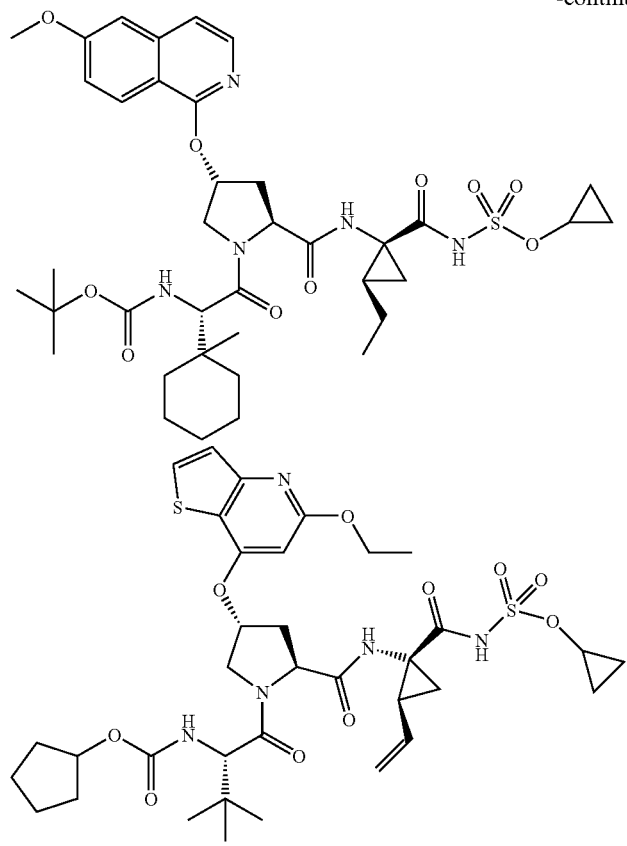
110
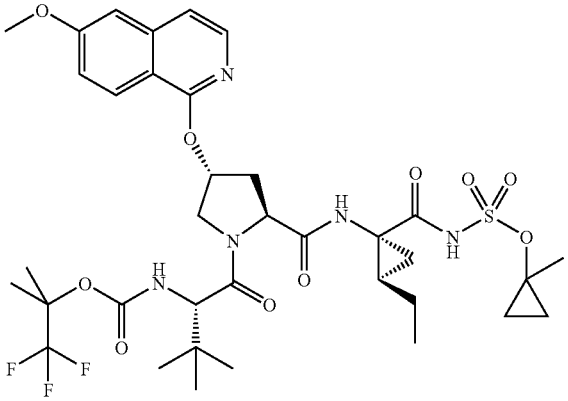
-continued
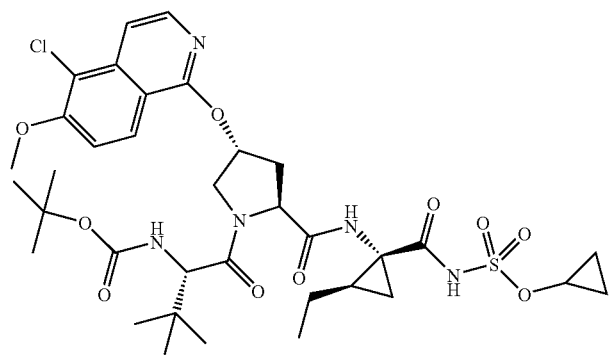
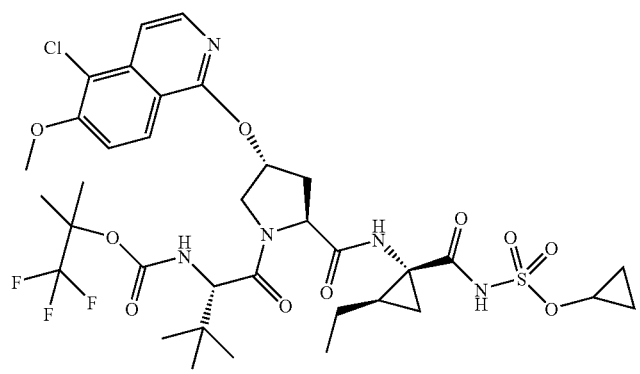

-continued
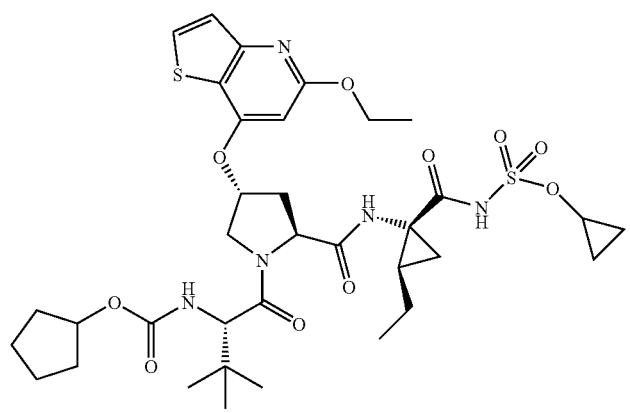
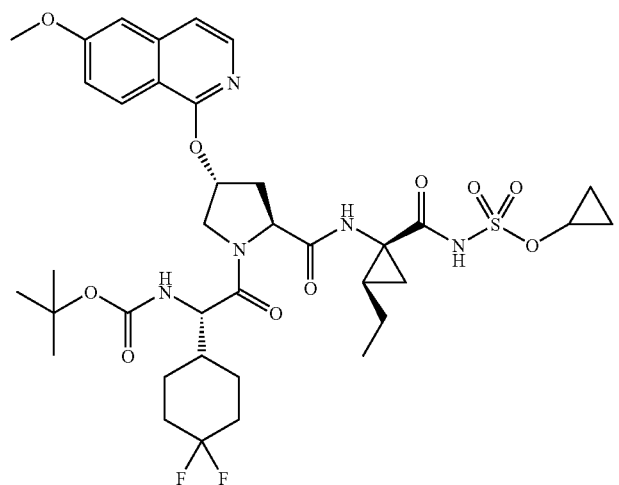
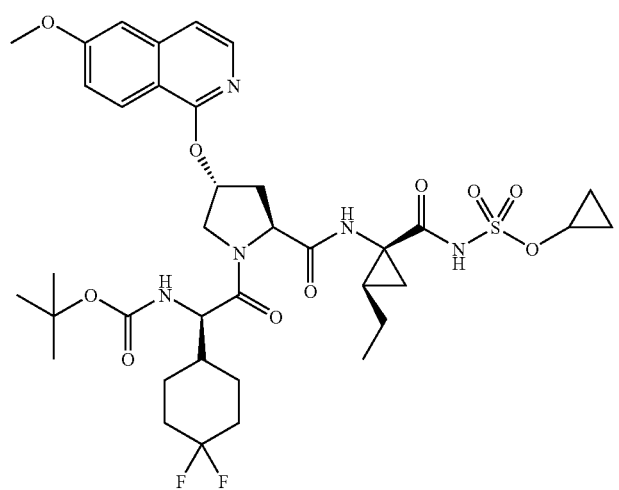

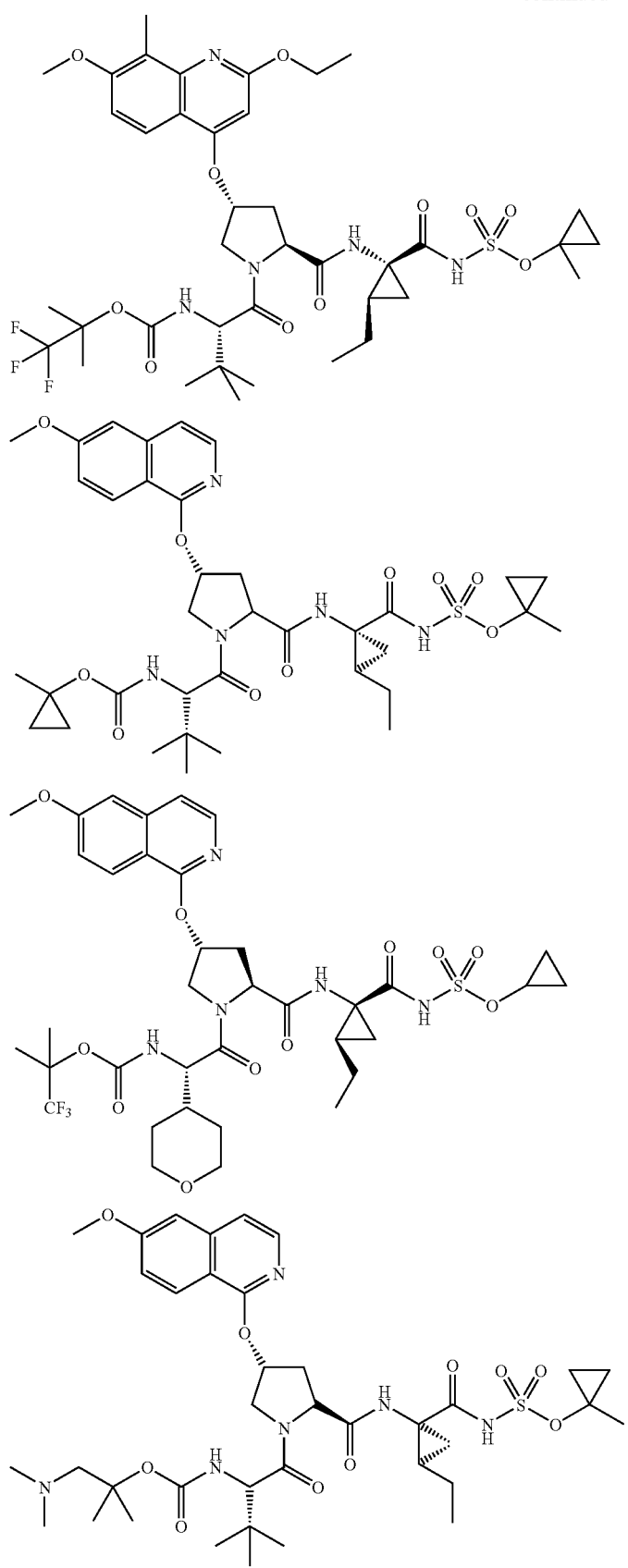

-continued
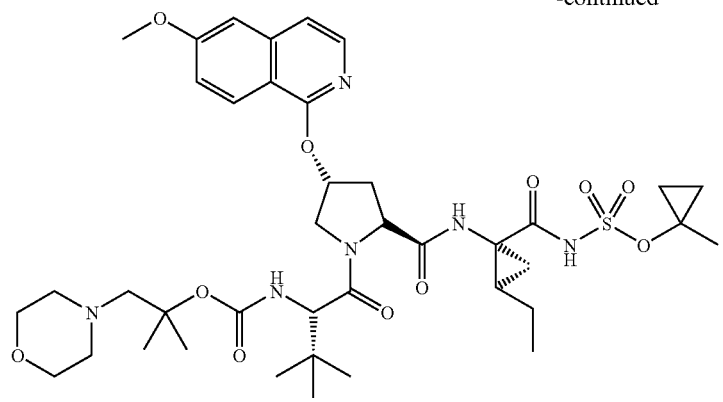
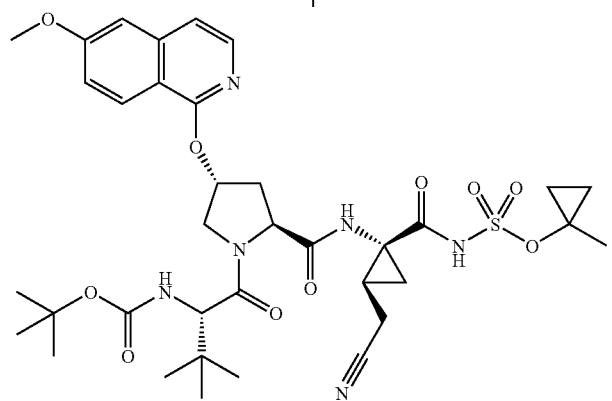
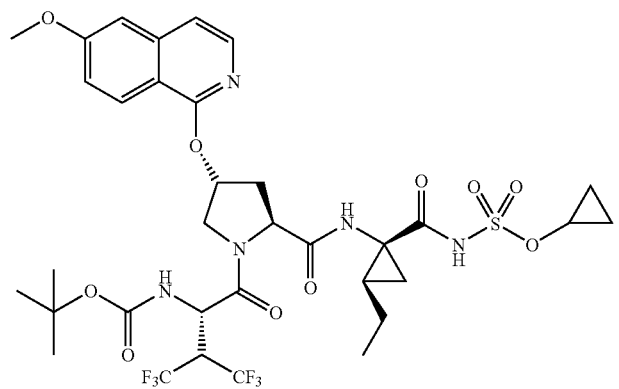
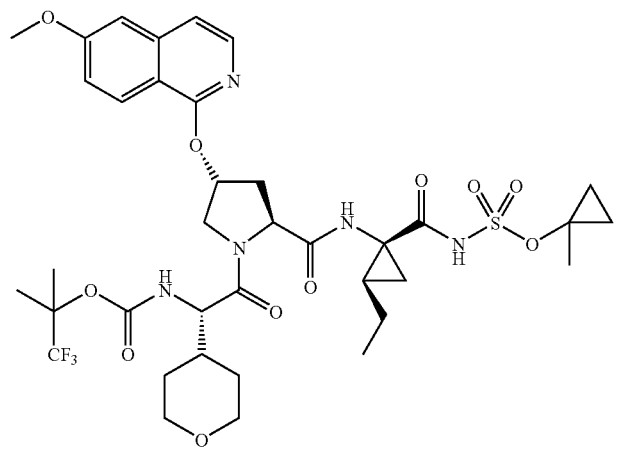

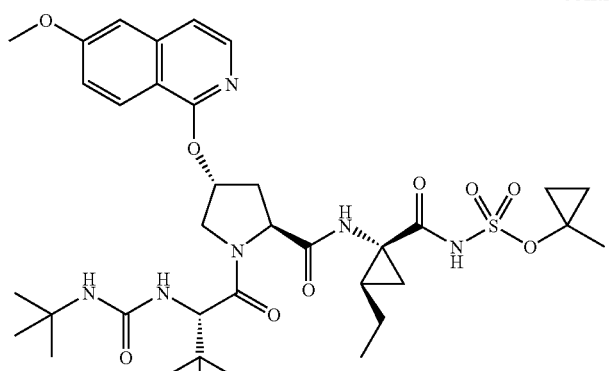
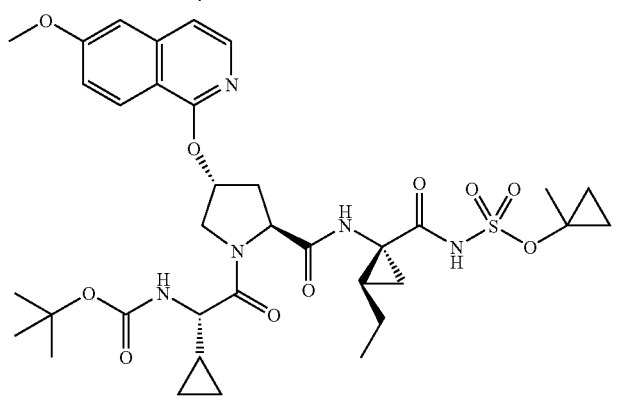
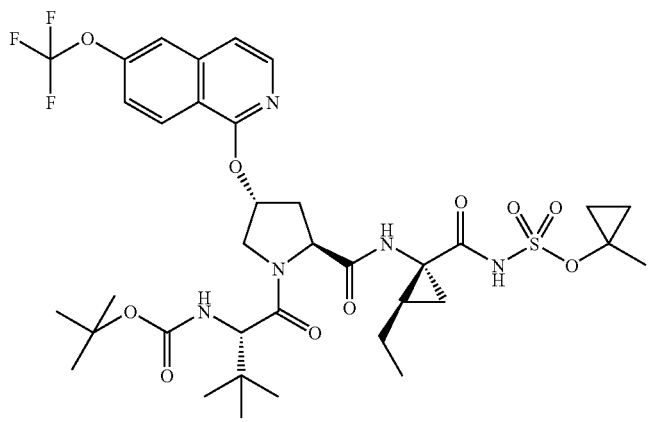
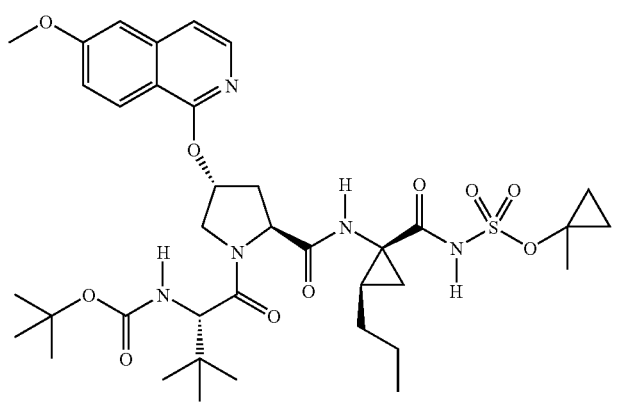

-continued
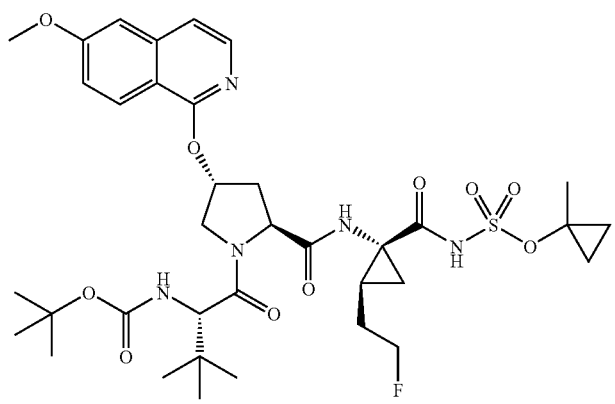
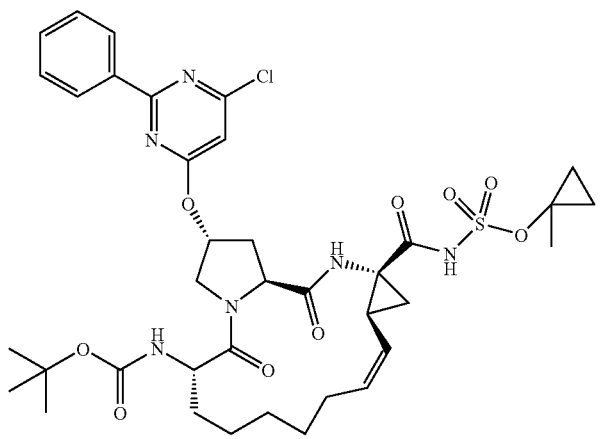
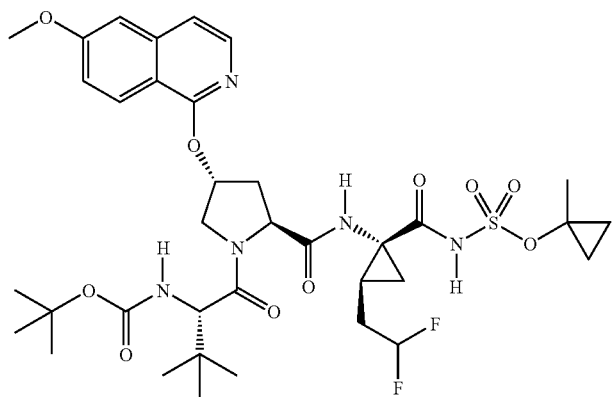
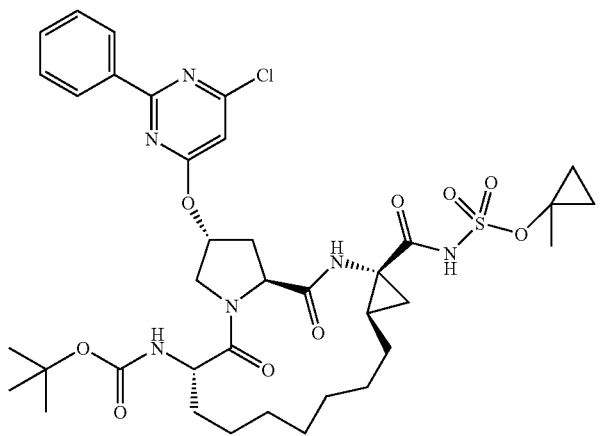

-continued
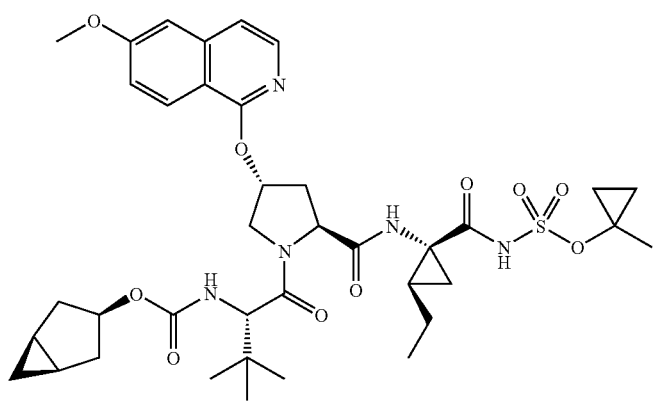
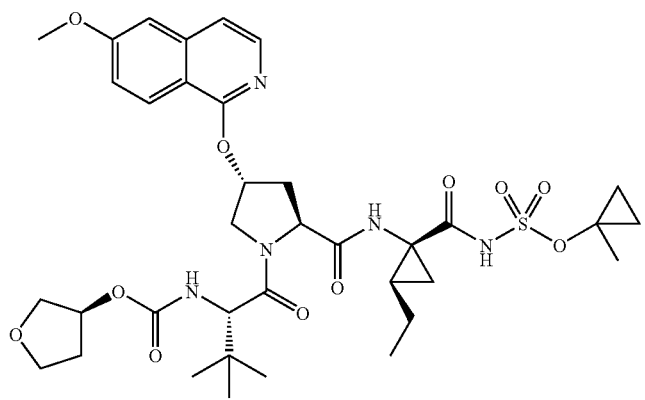
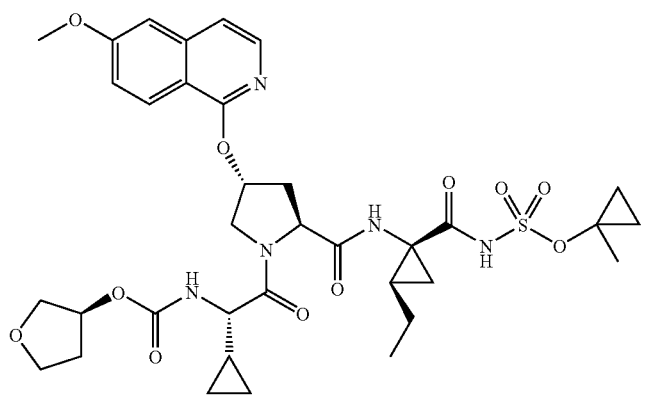
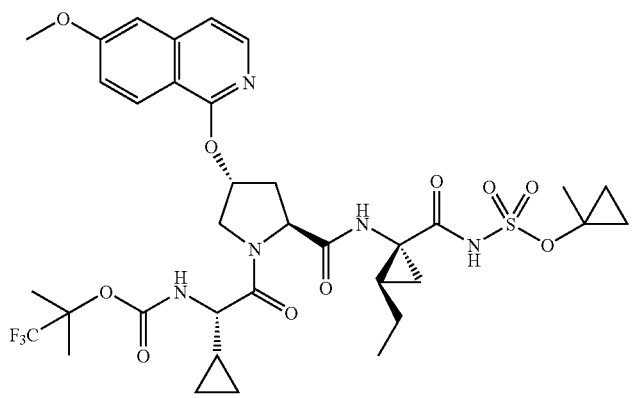

-continued
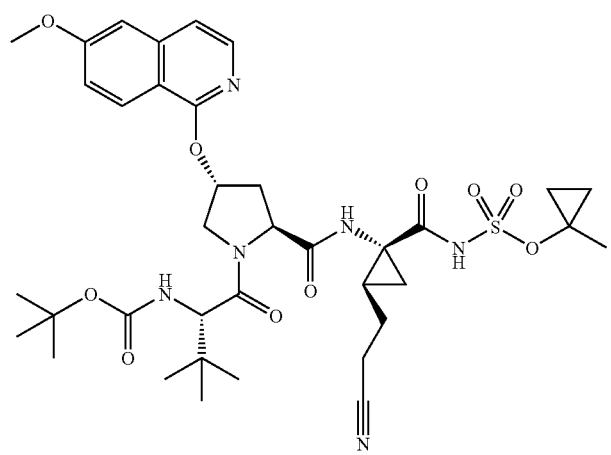
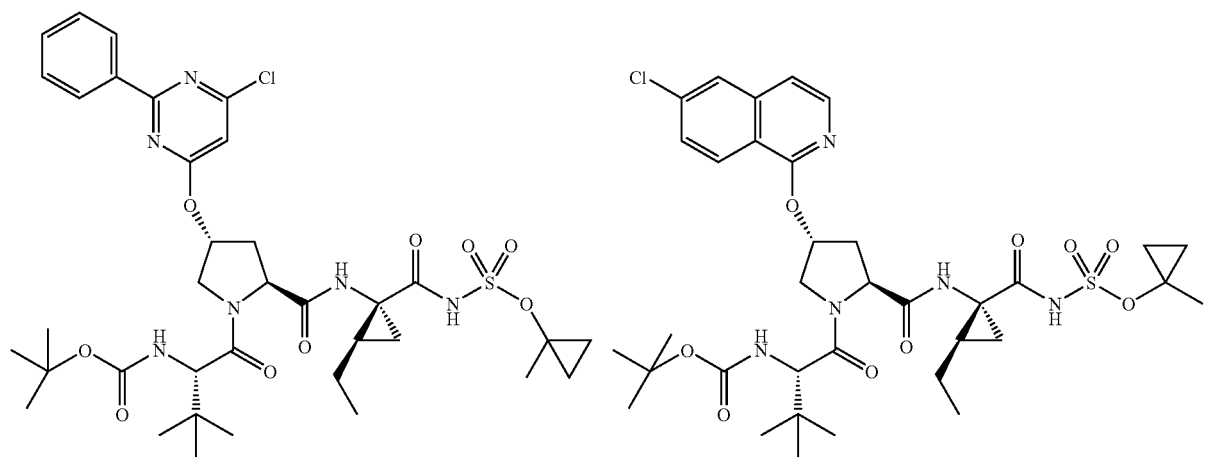
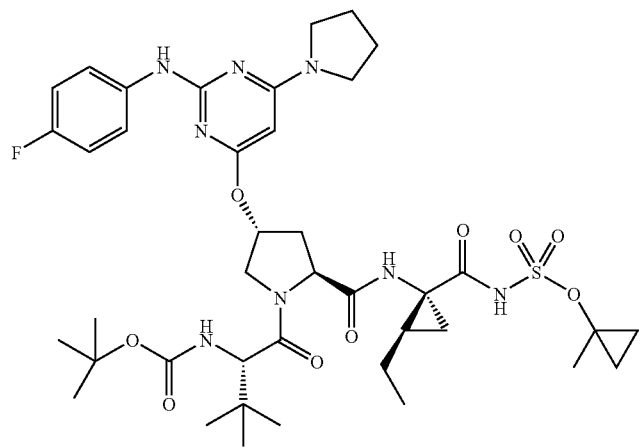

-continued
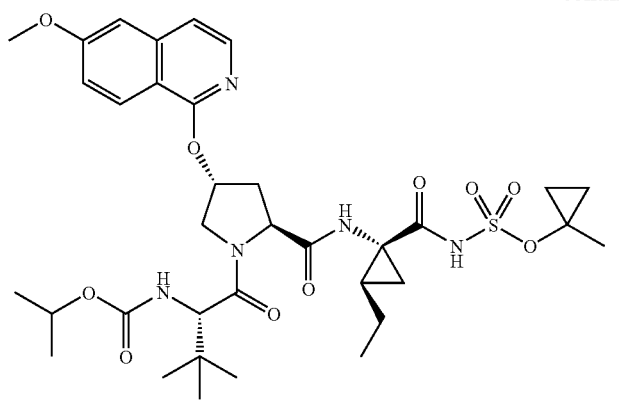
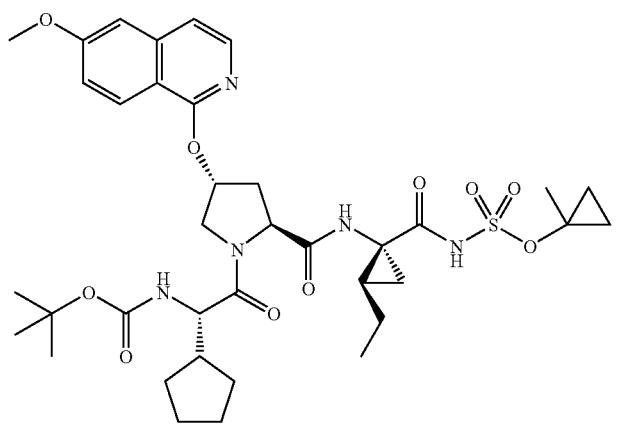
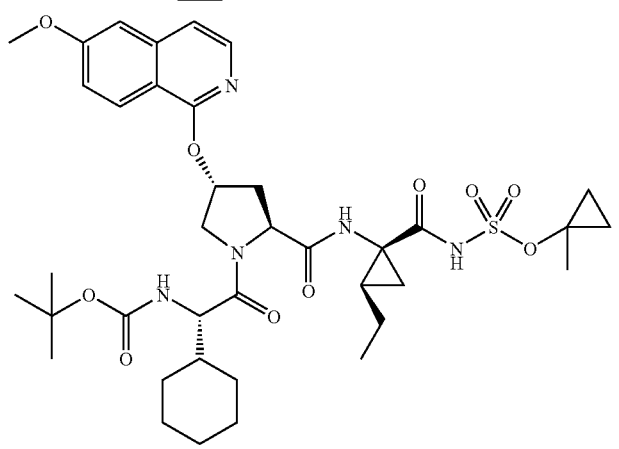

-continued
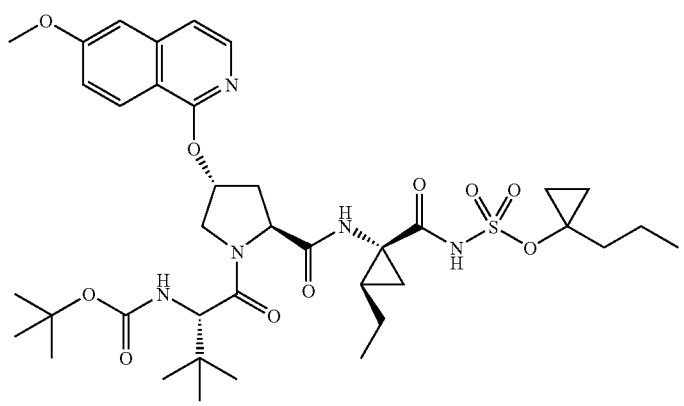
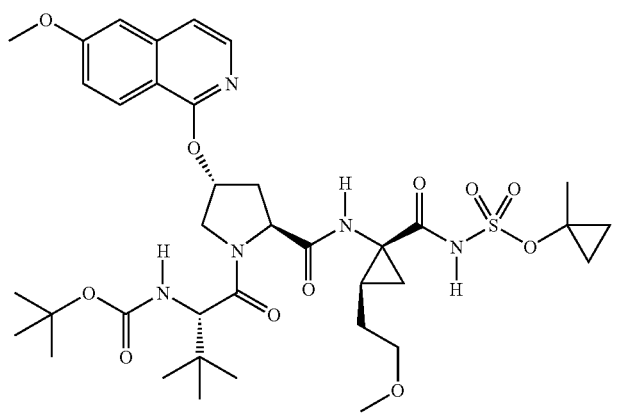
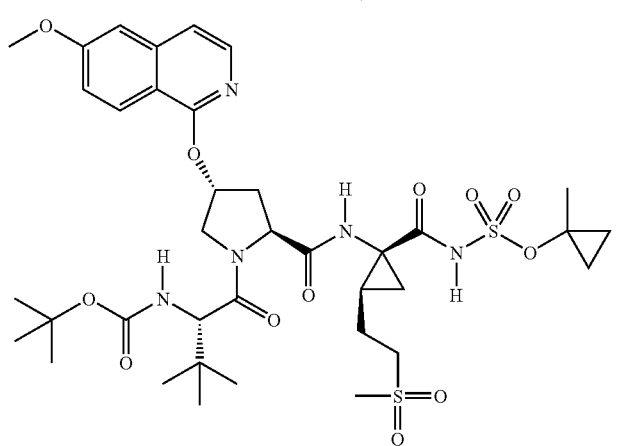
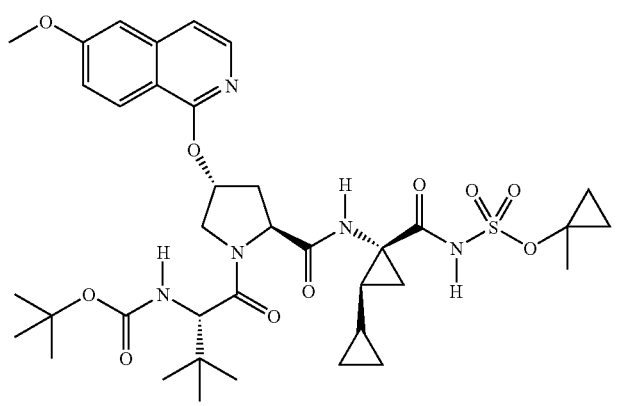

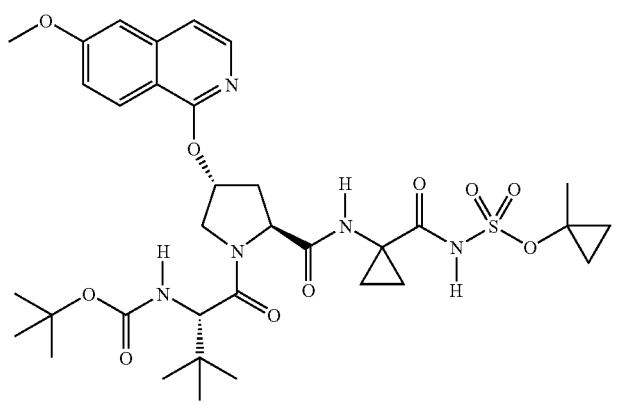
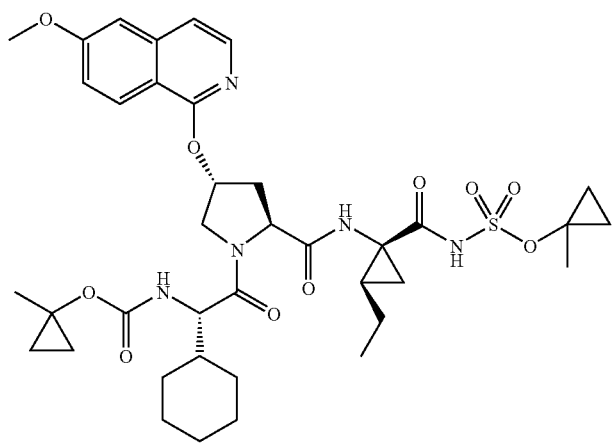
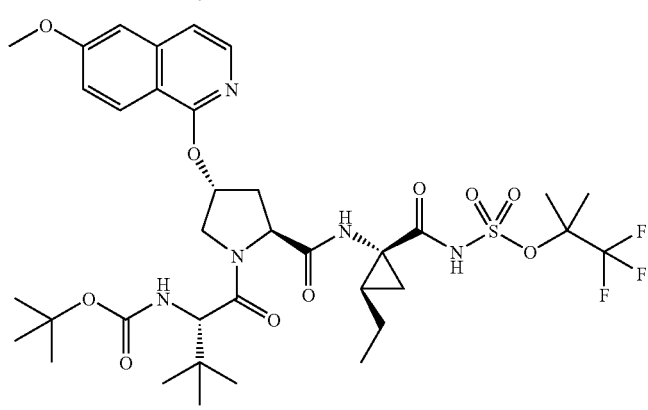
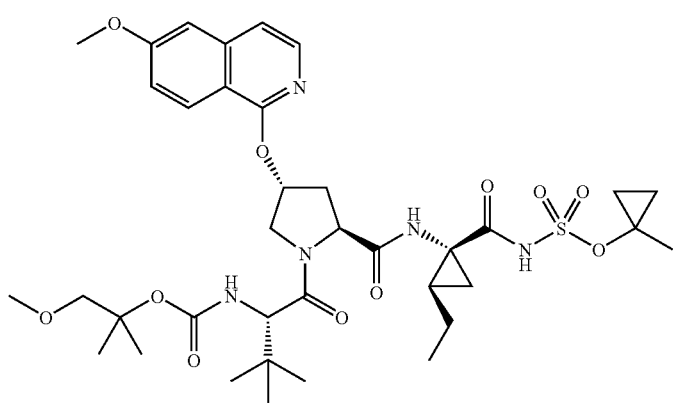

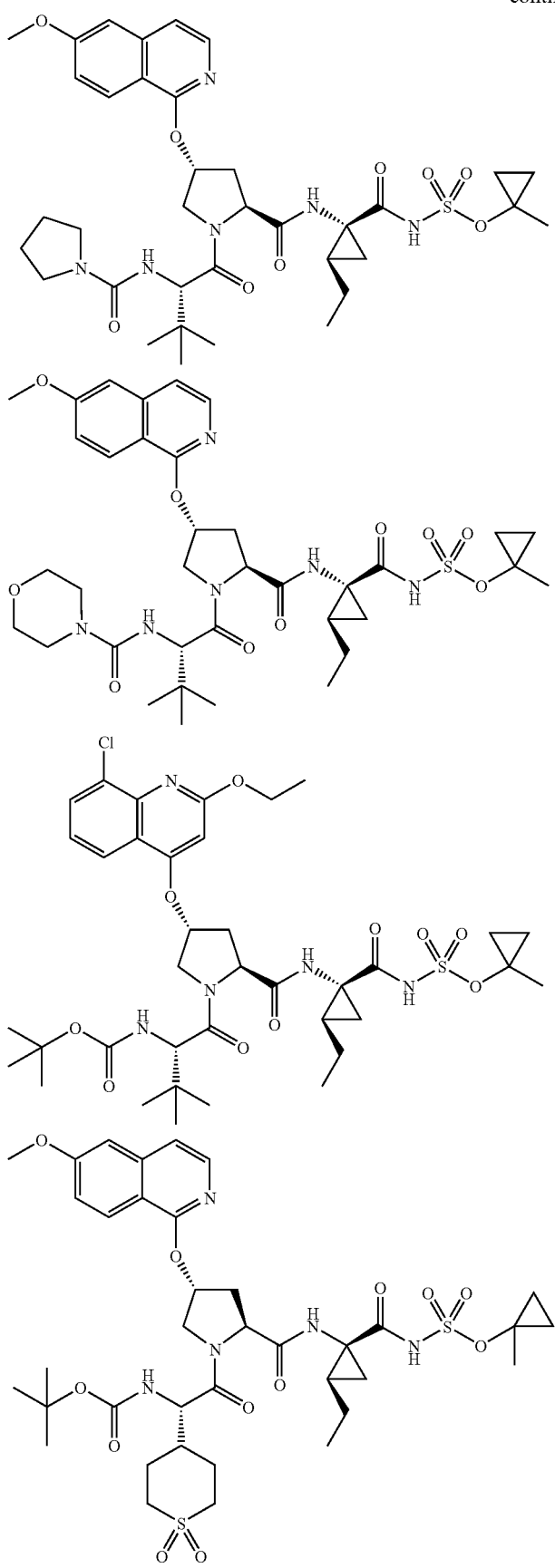

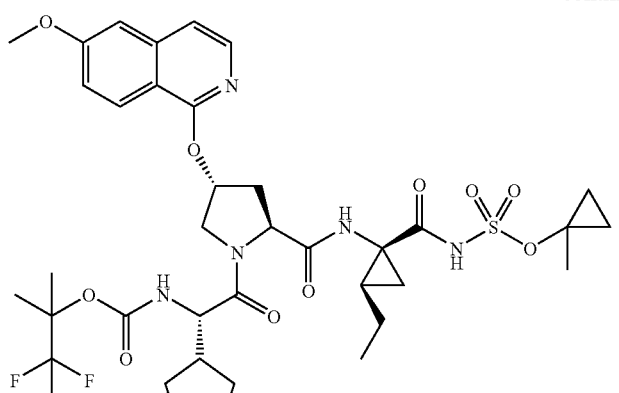
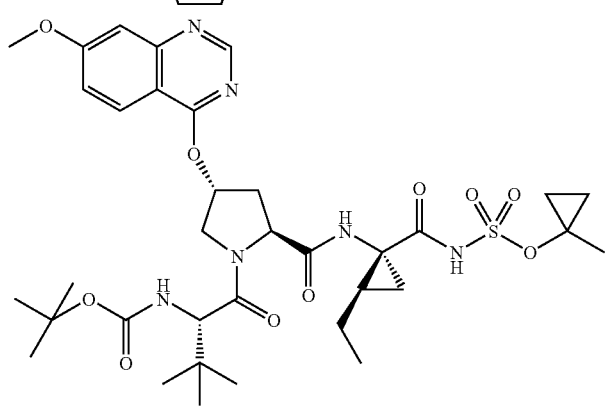
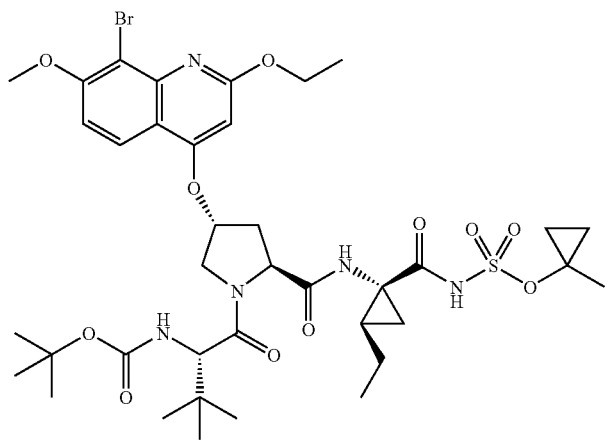
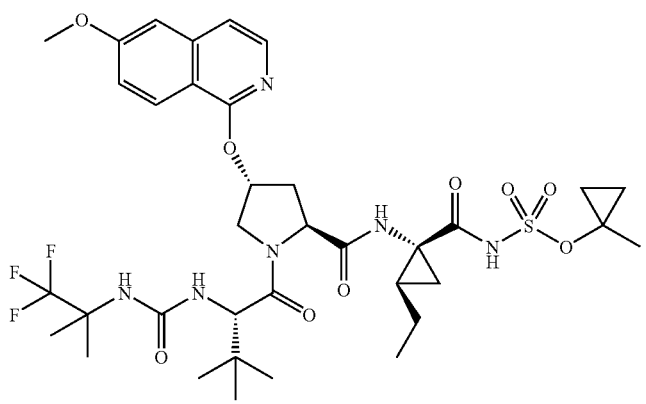

-continued
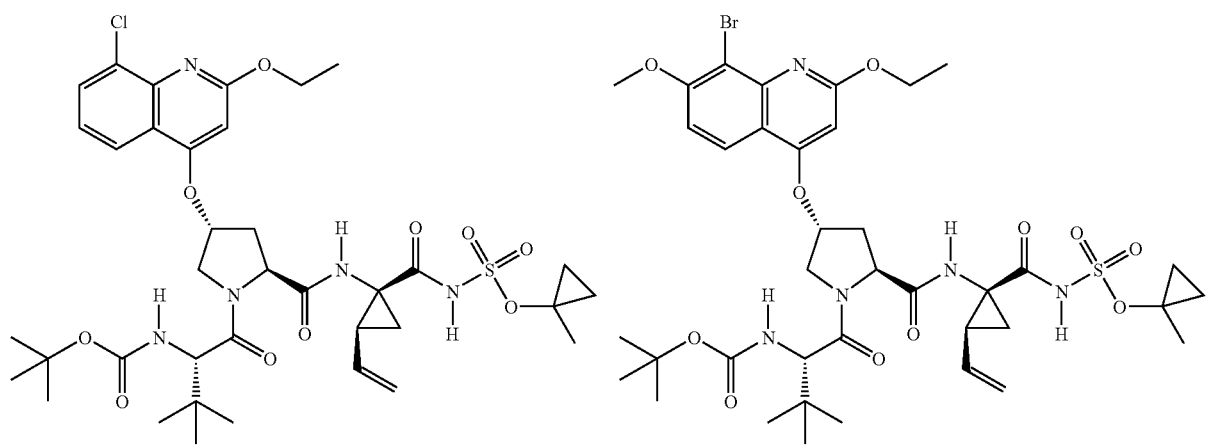
135
136
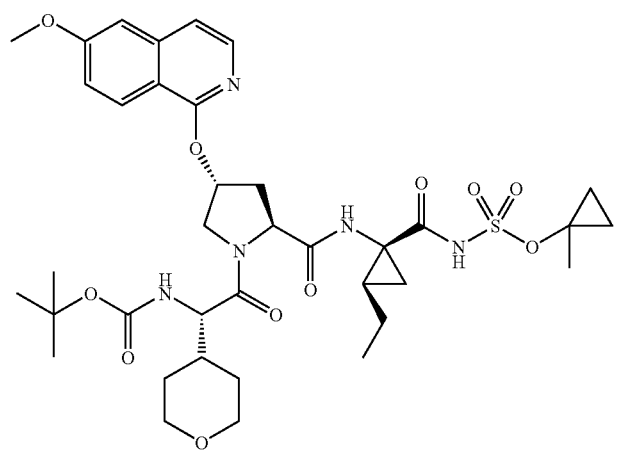
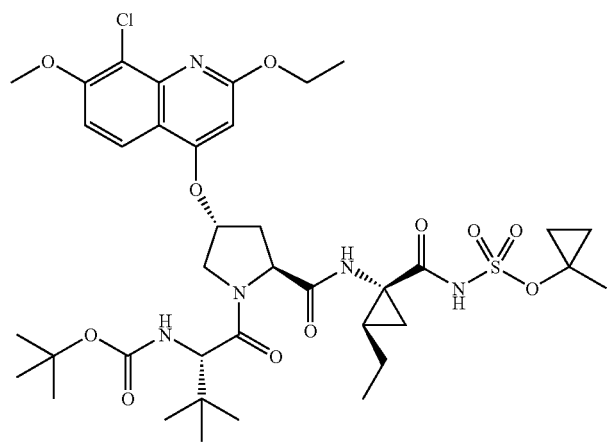

-continued
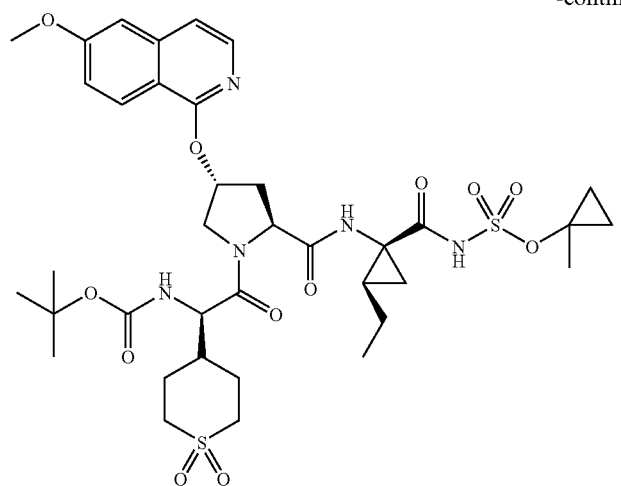
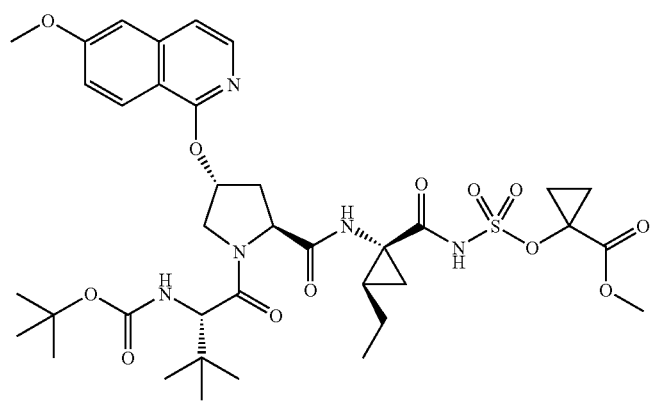
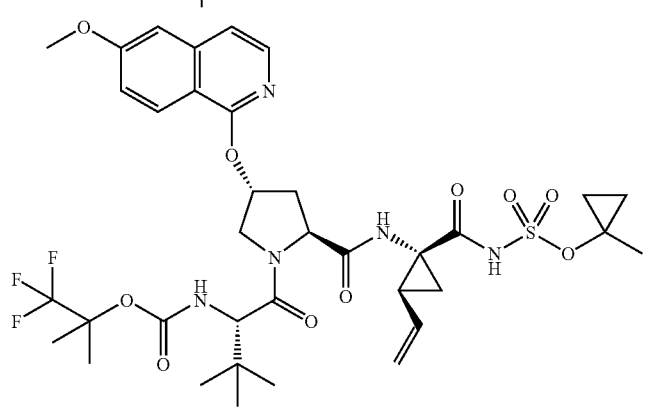
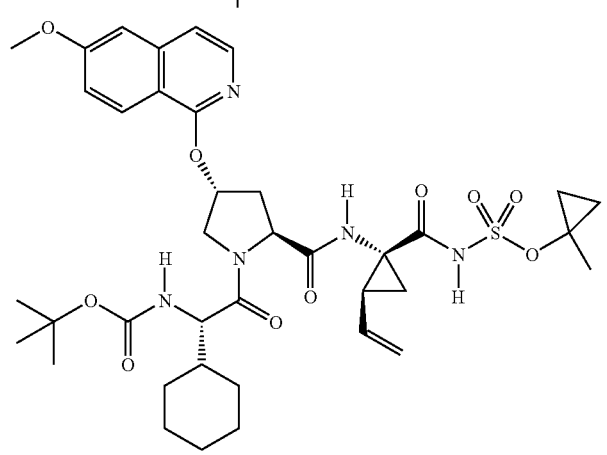

-continued
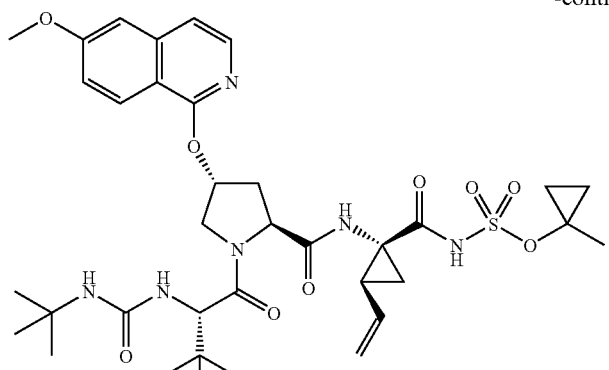
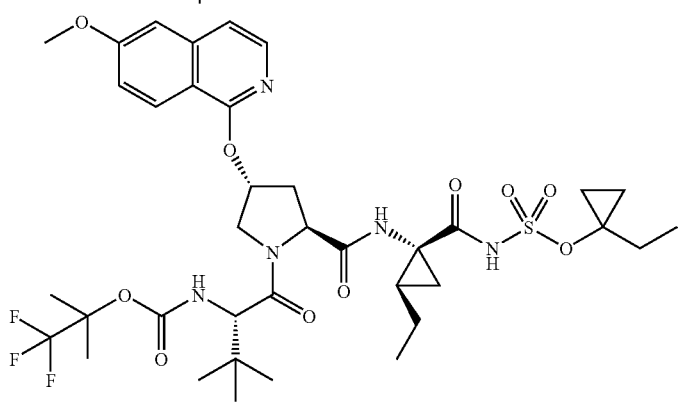
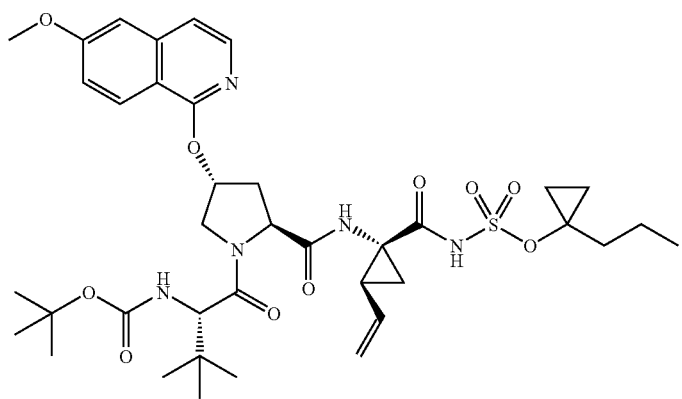
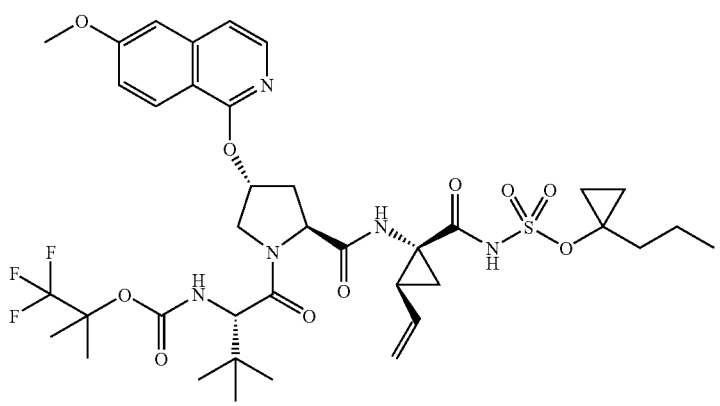

-continued
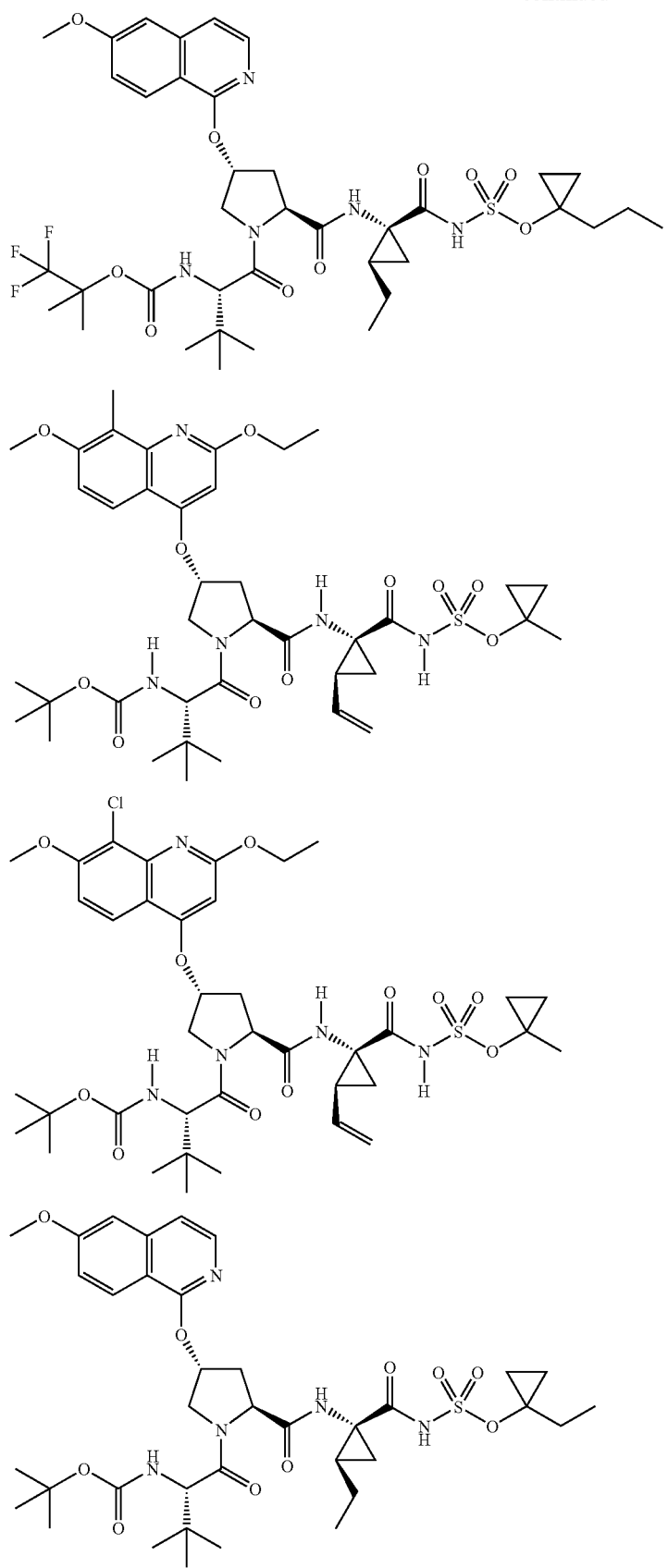

-continued
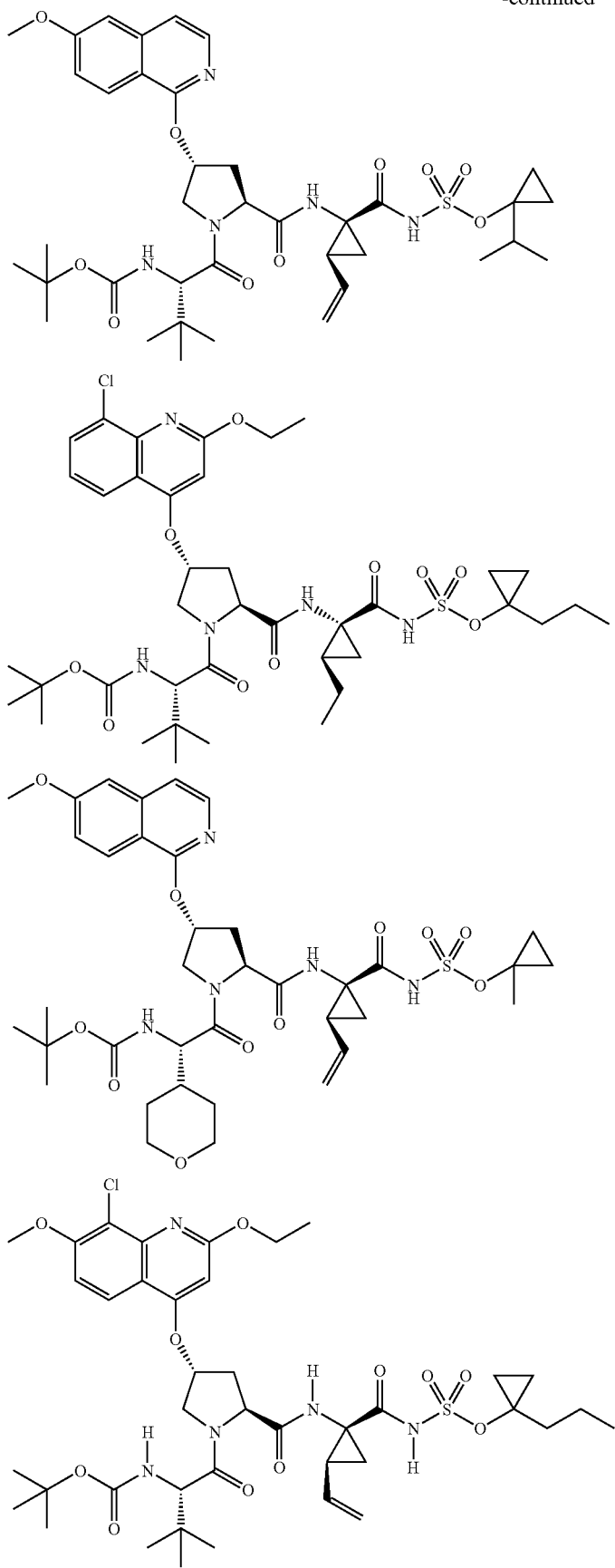

-continued
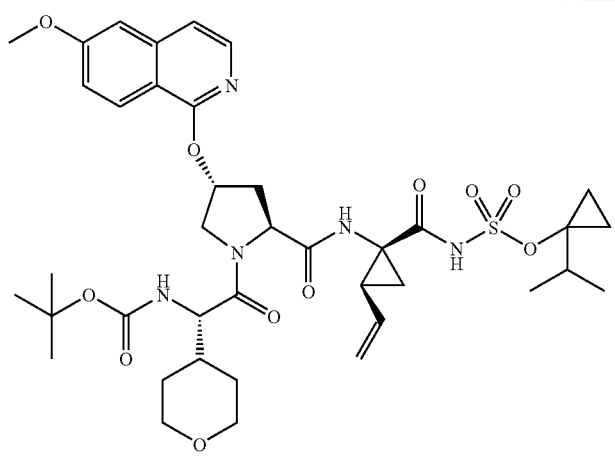
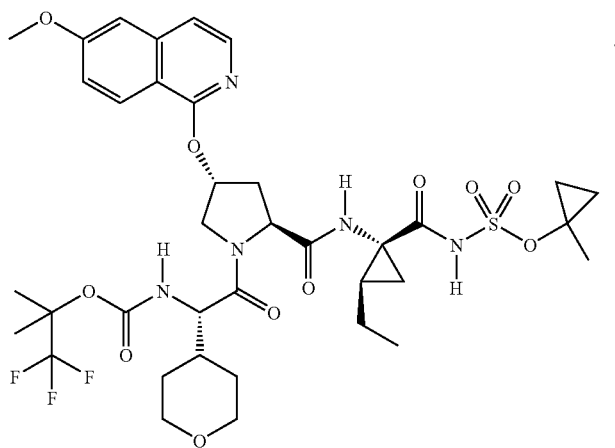
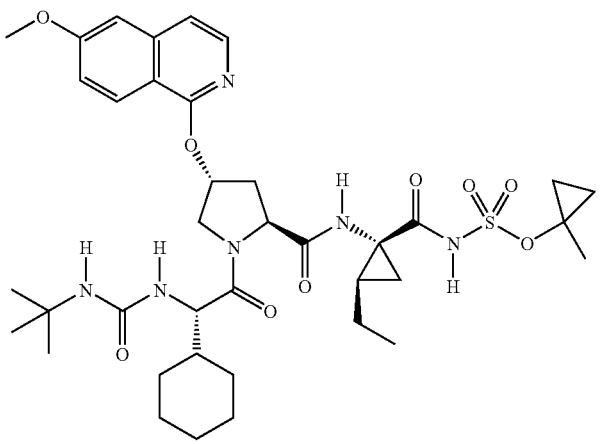
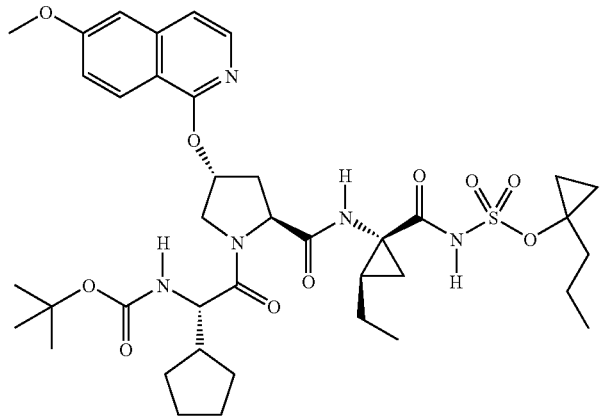
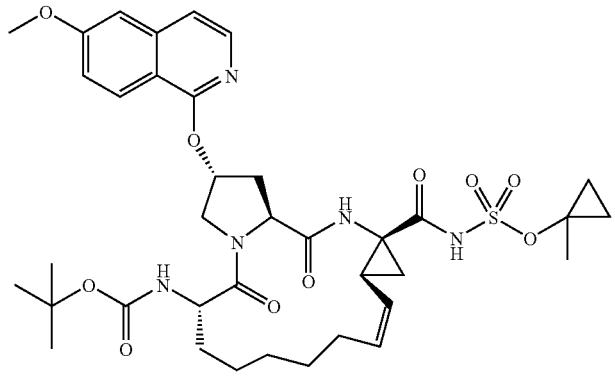

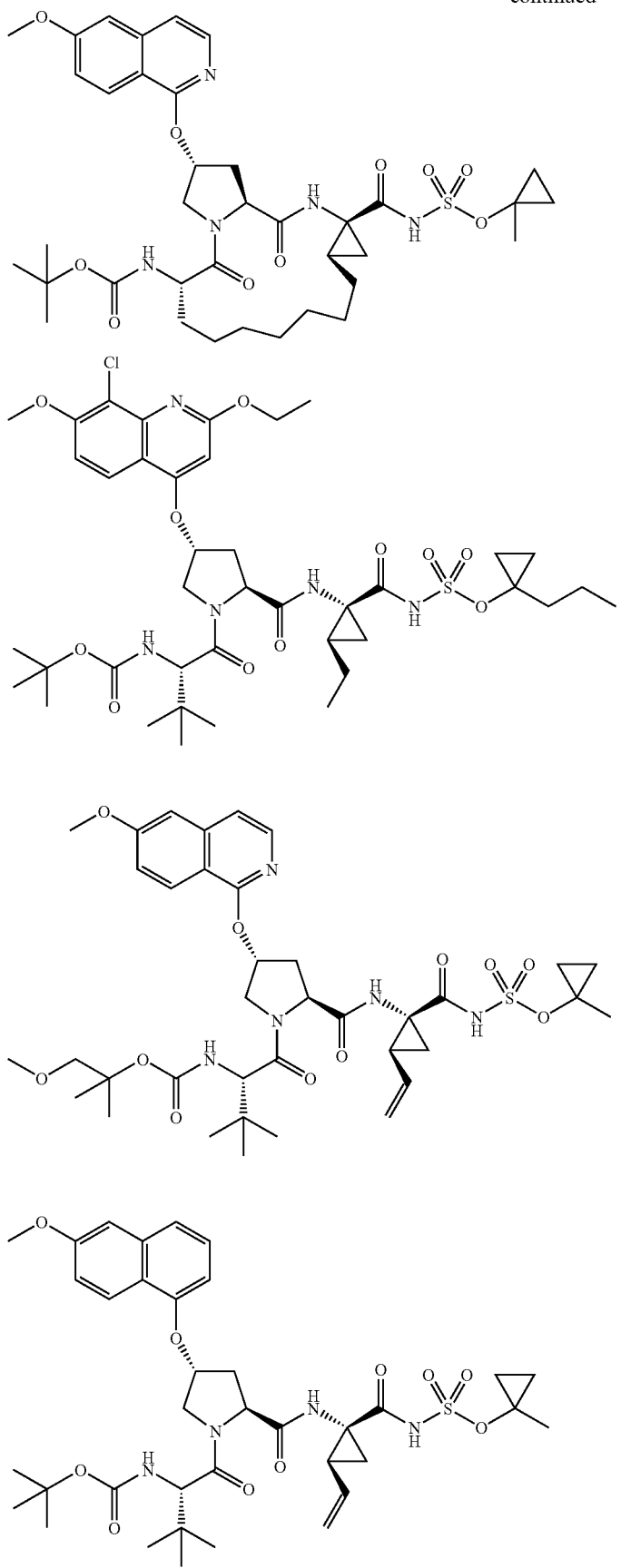

-continued
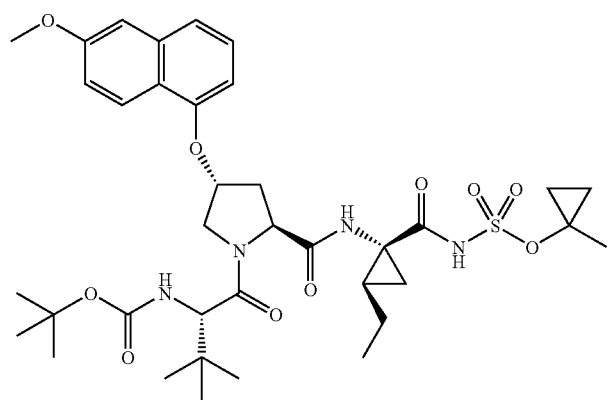
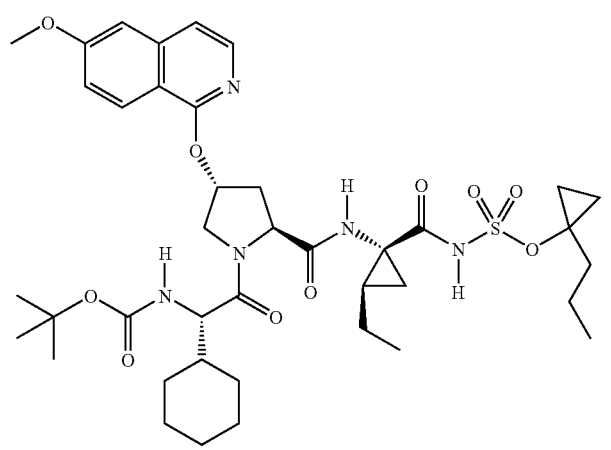
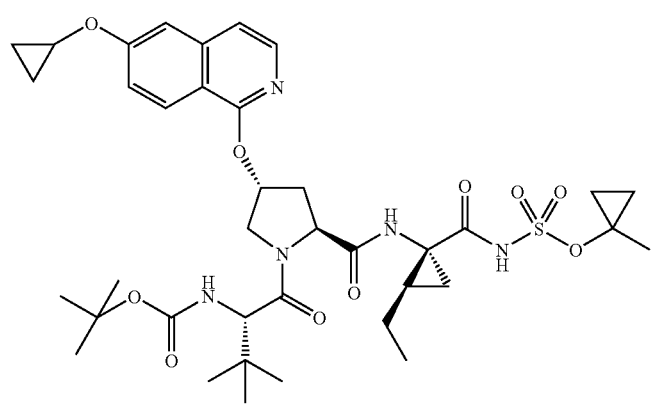
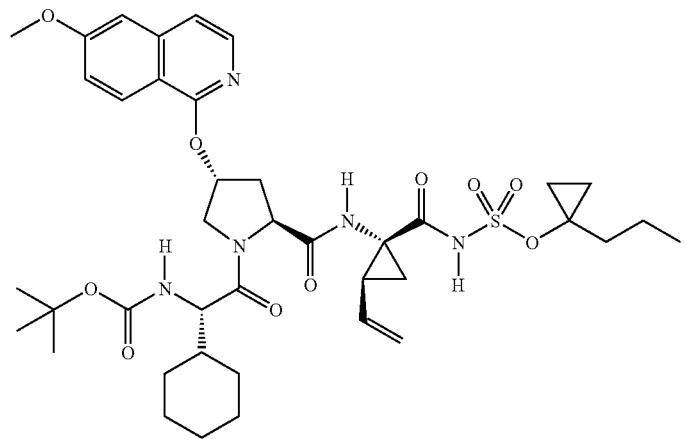

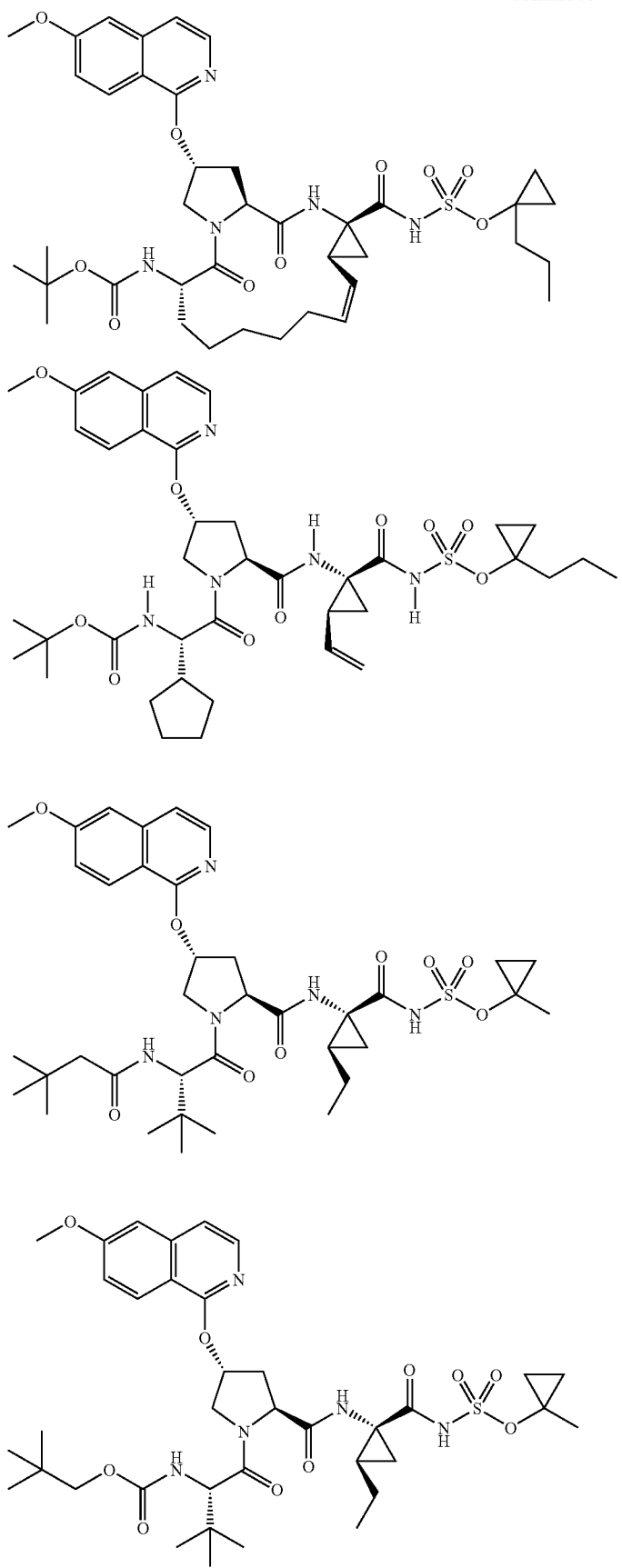

-continued
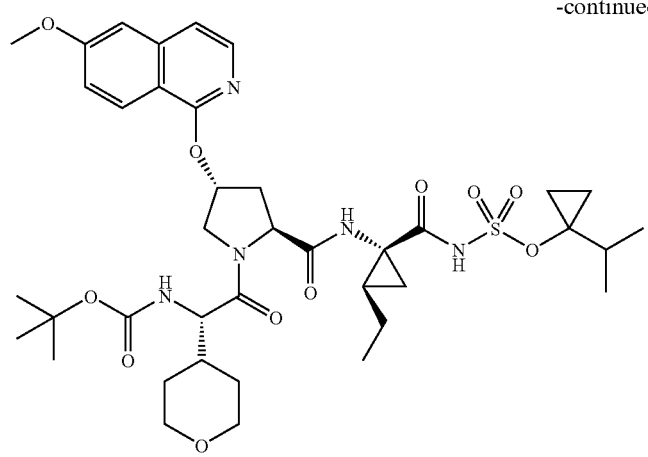
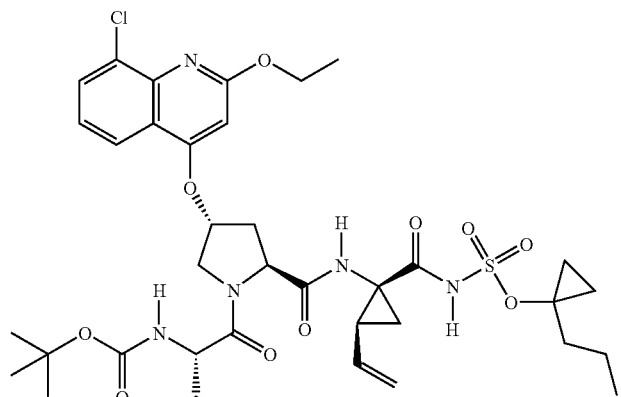
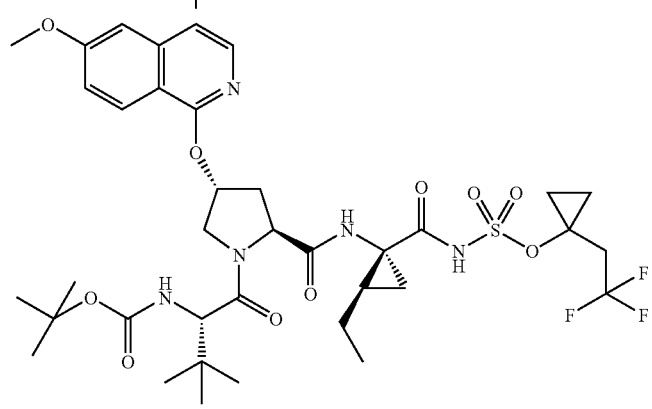
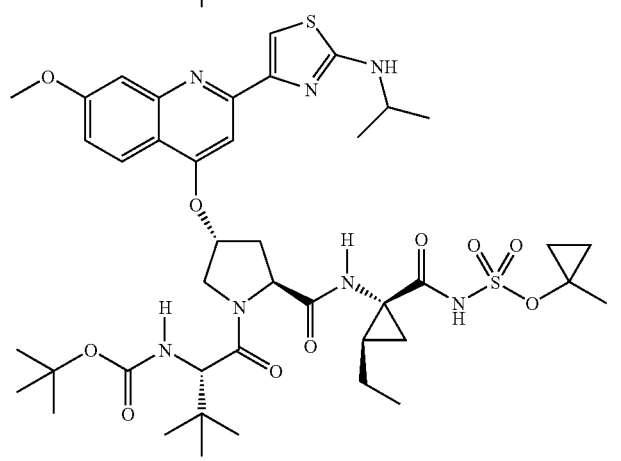

-continued
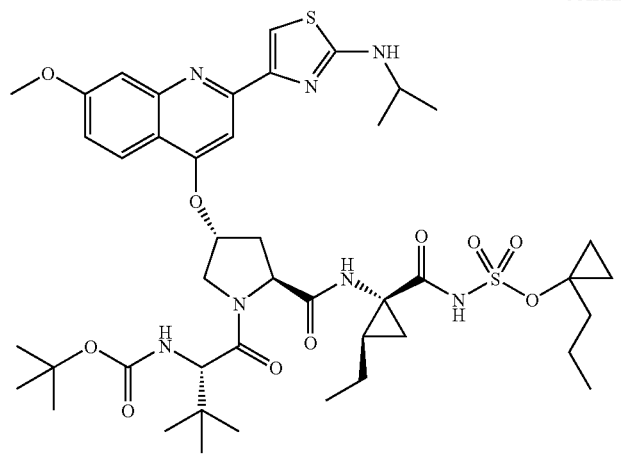
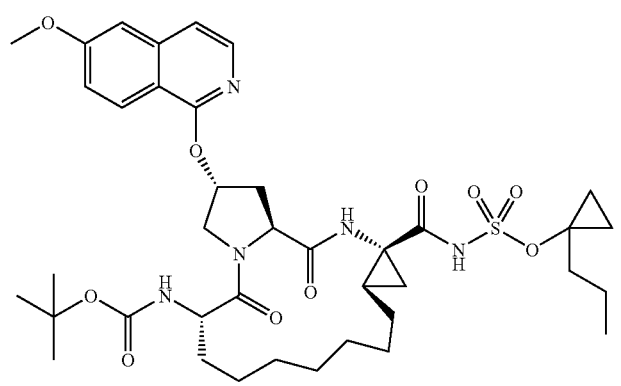
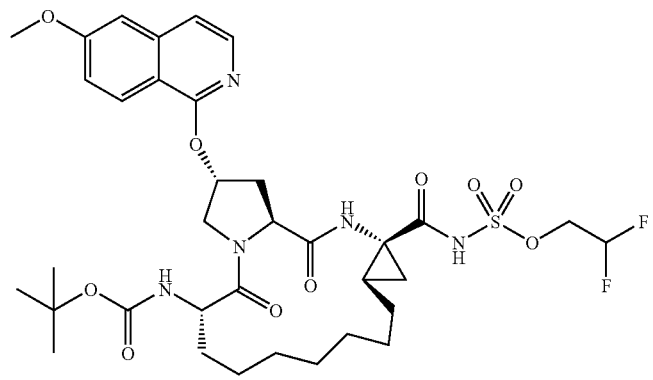
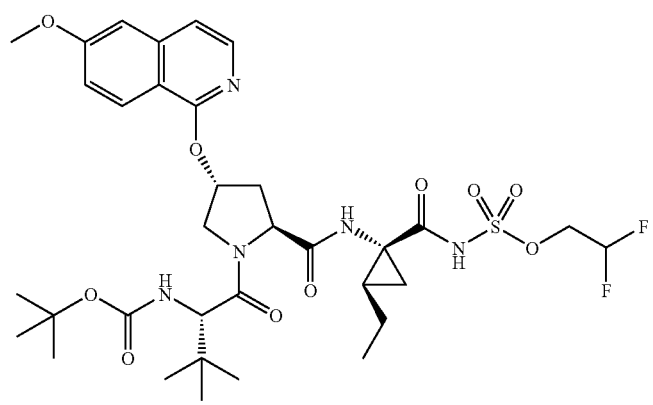

-continued
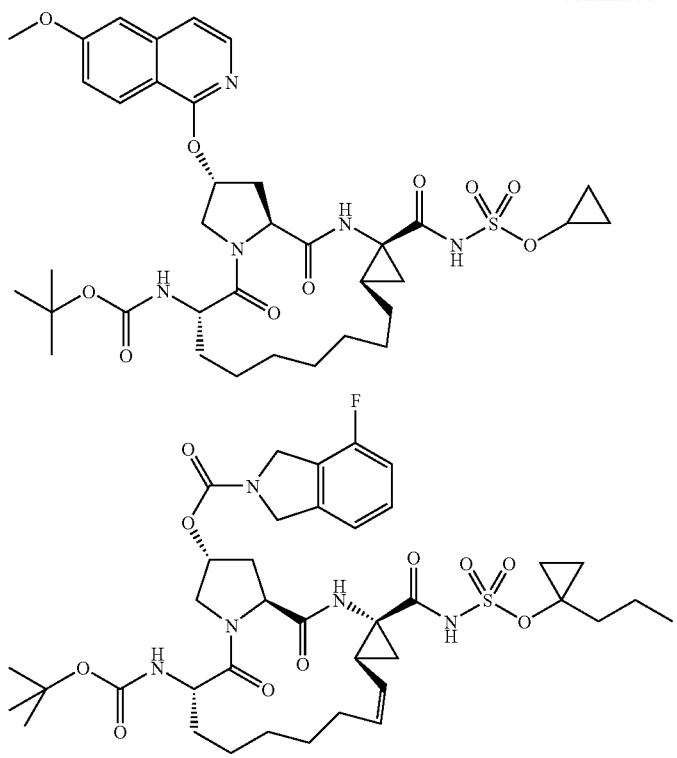
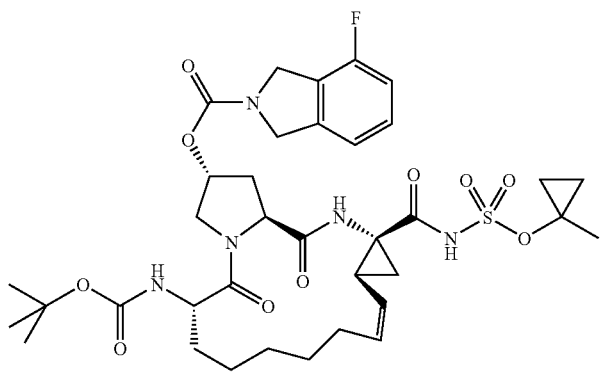
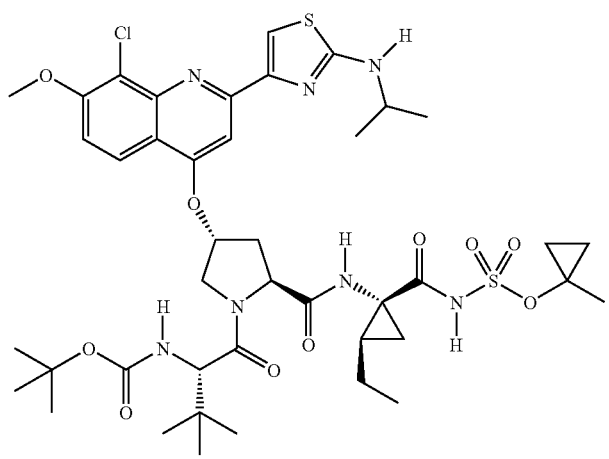

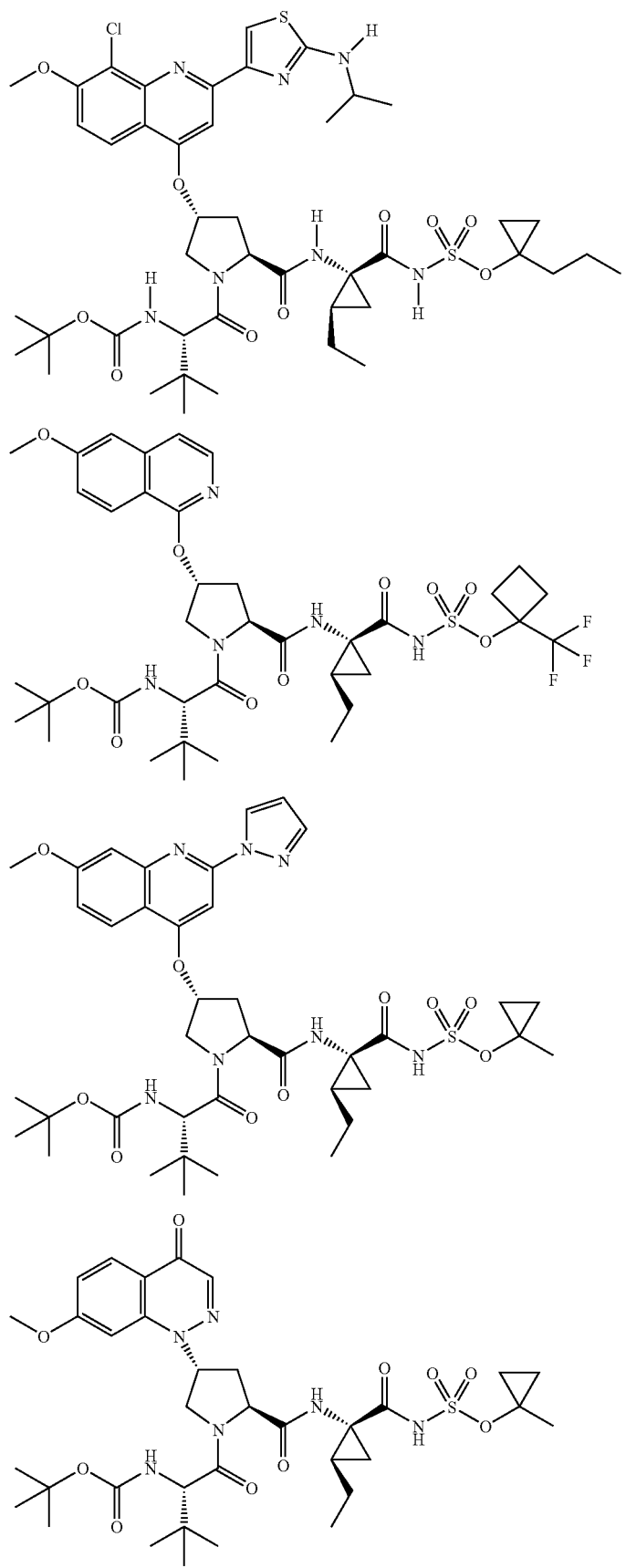

-continued
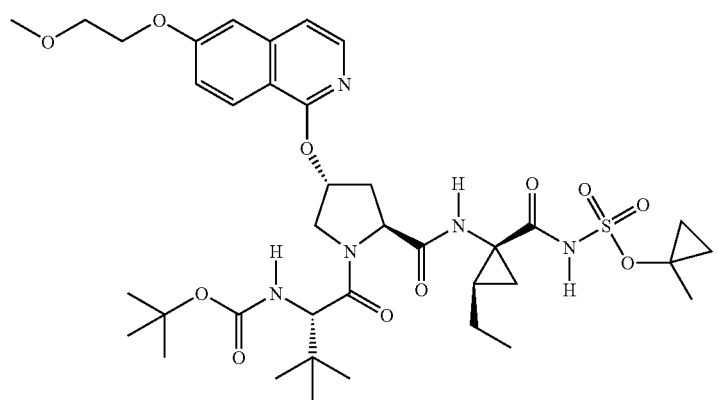
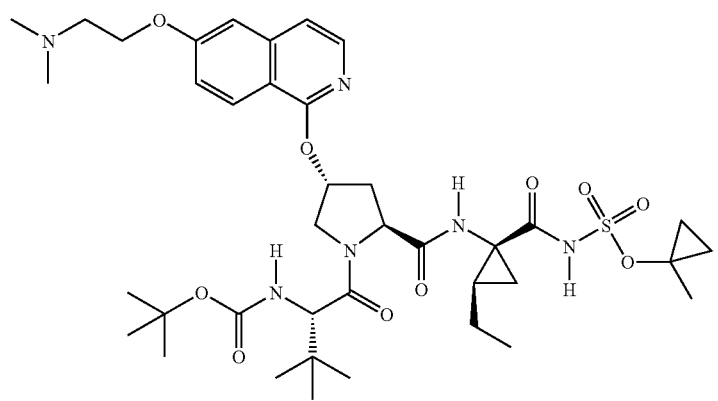
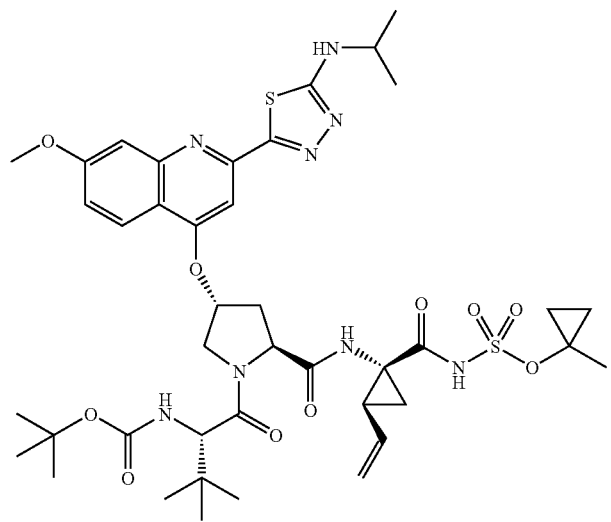

-continued
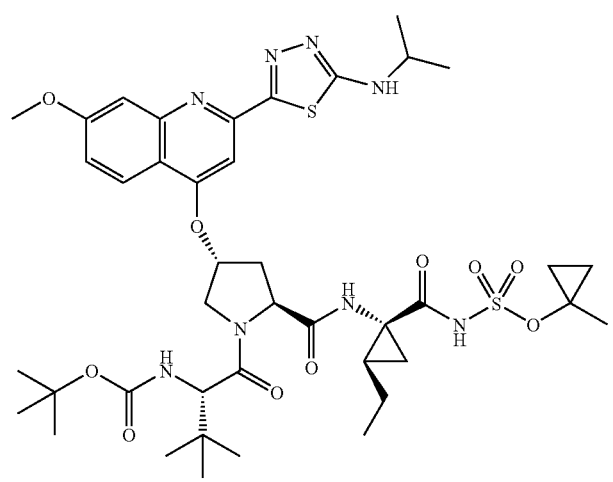
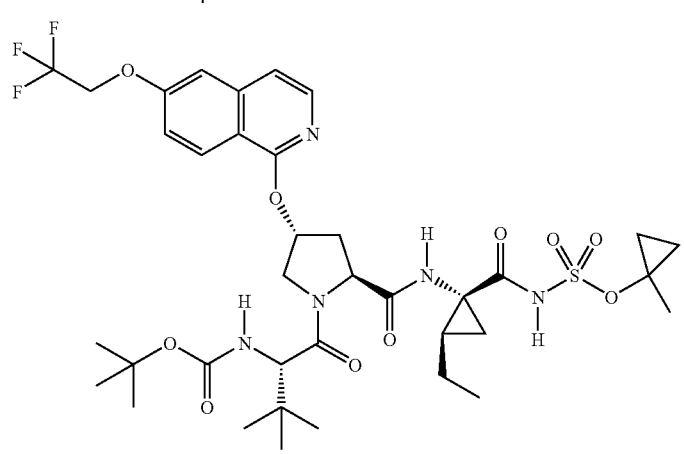
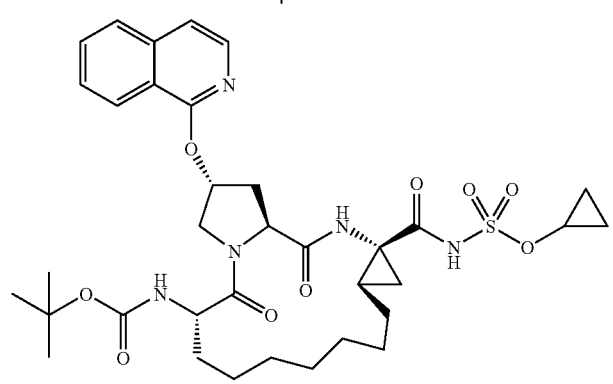
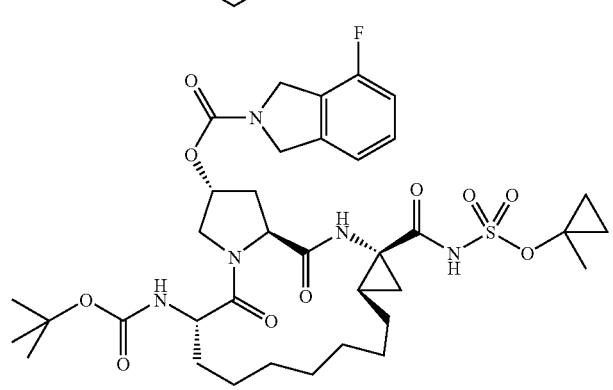

-continued
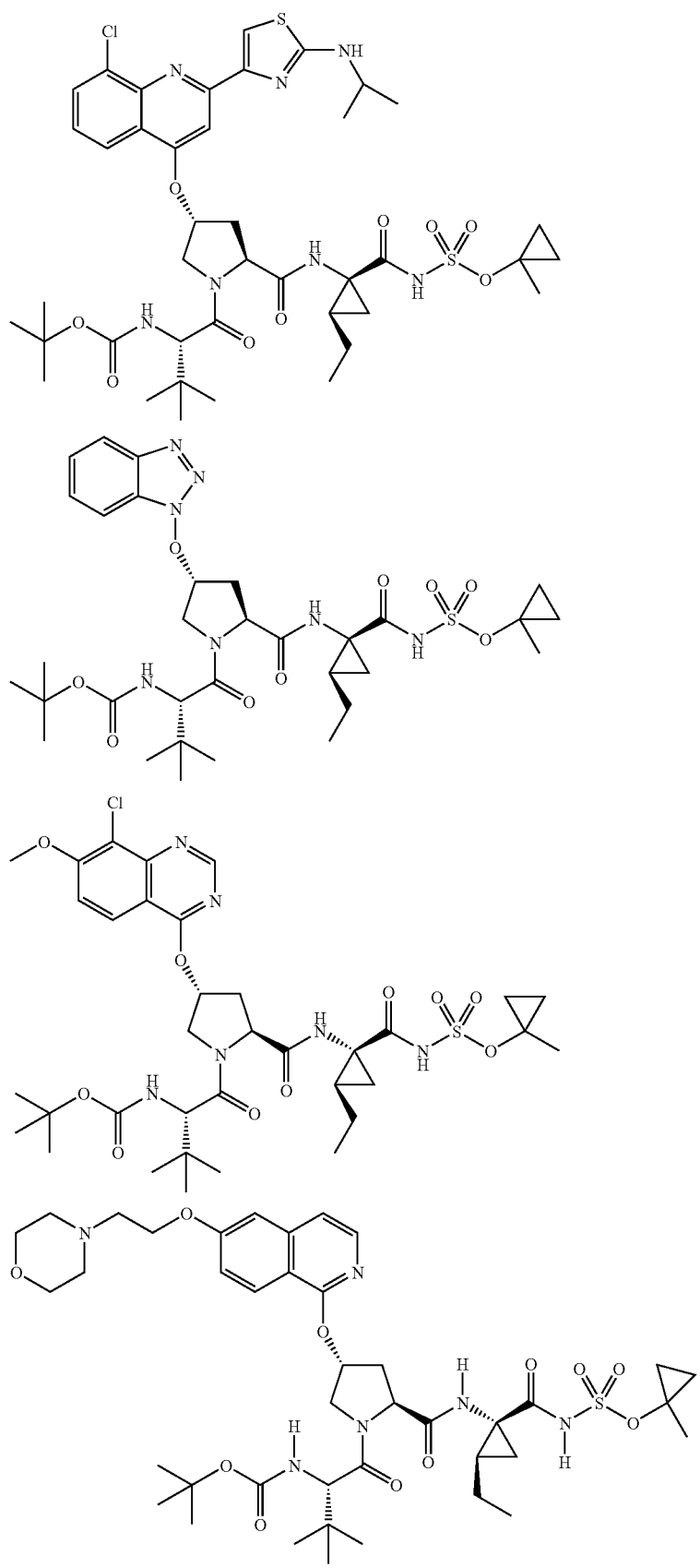

-continued
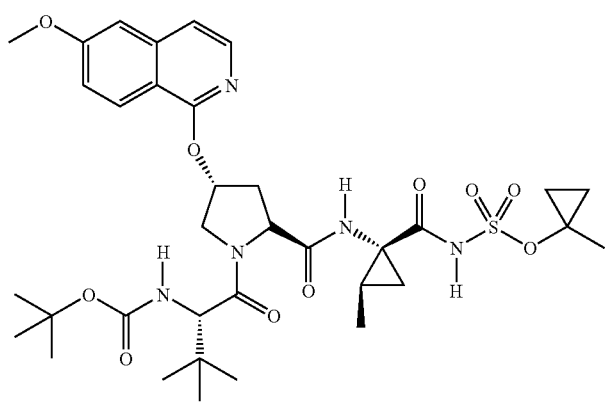
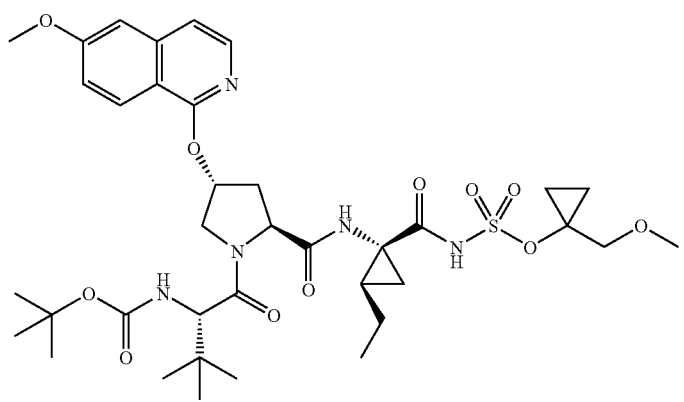
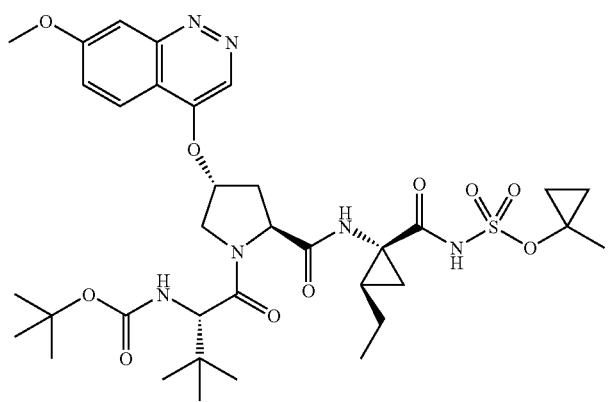
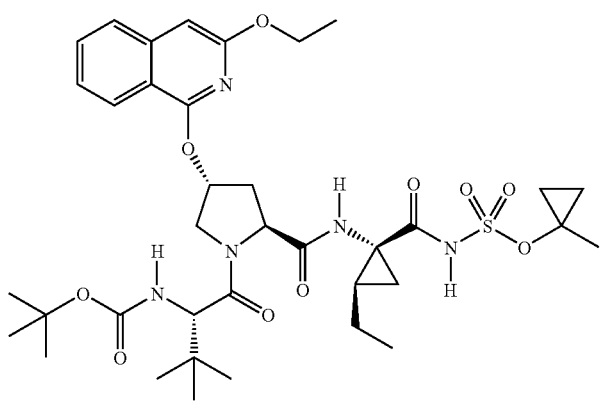

-continued
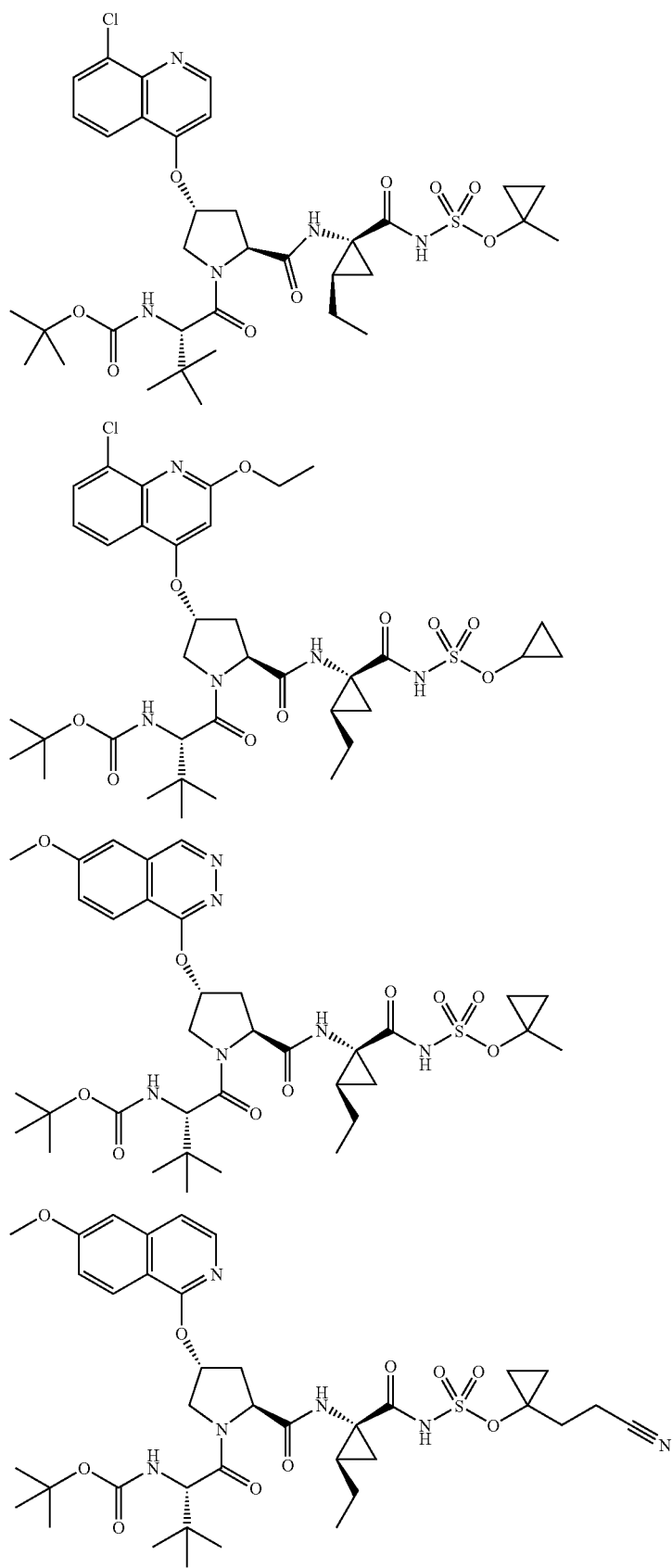

-continued
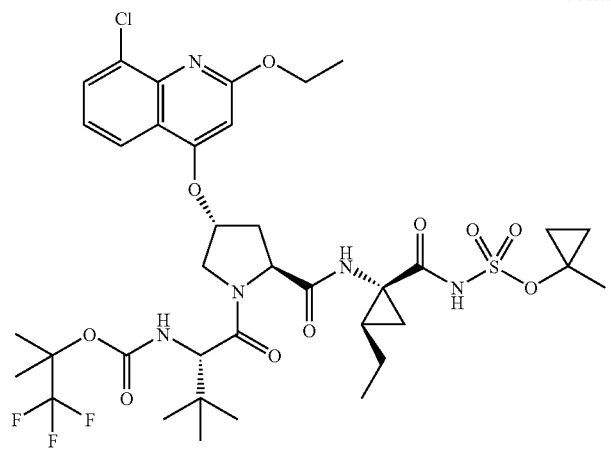
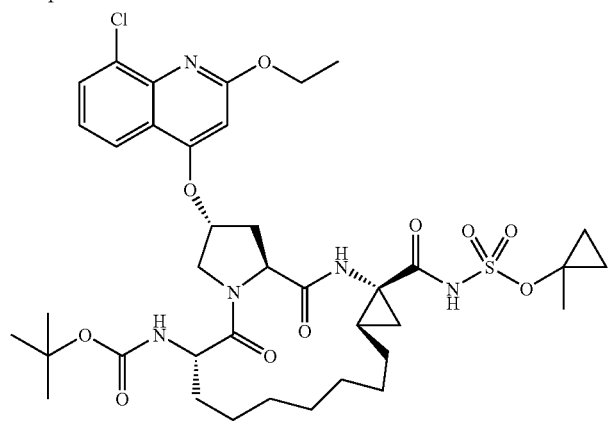
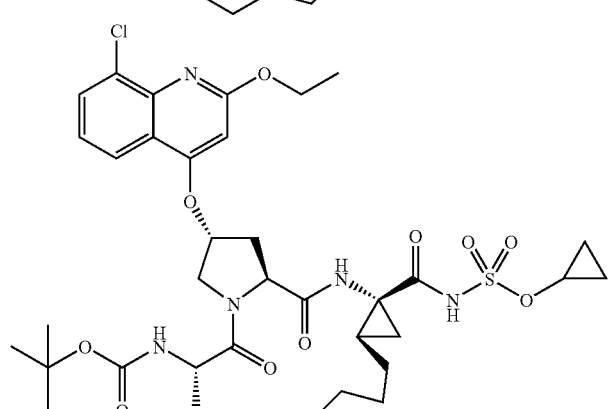
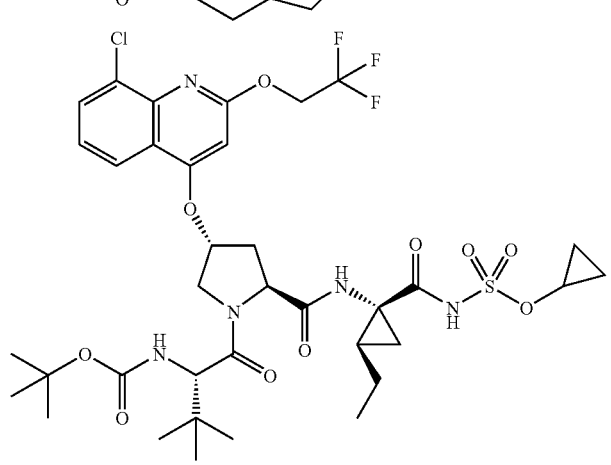

-continued
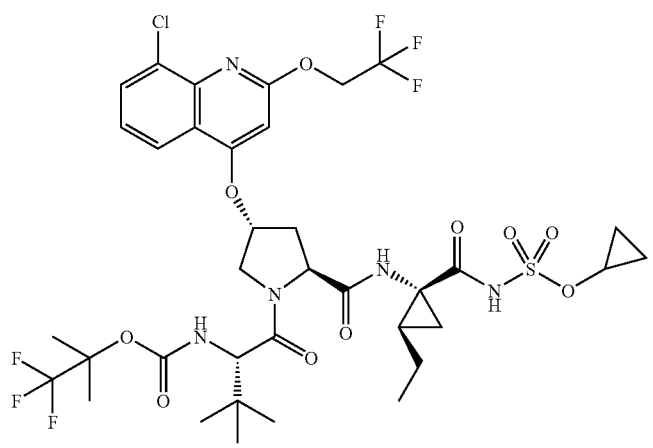
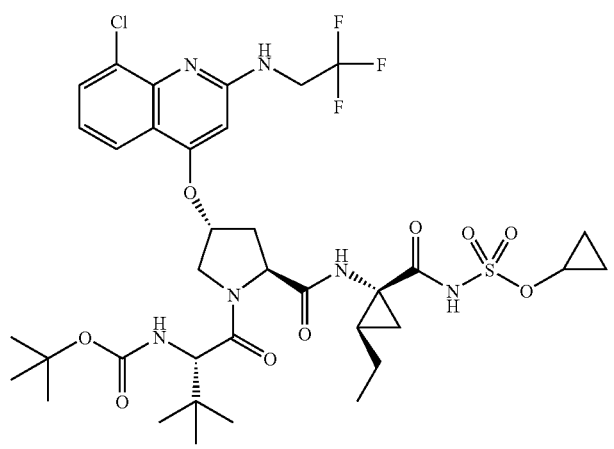
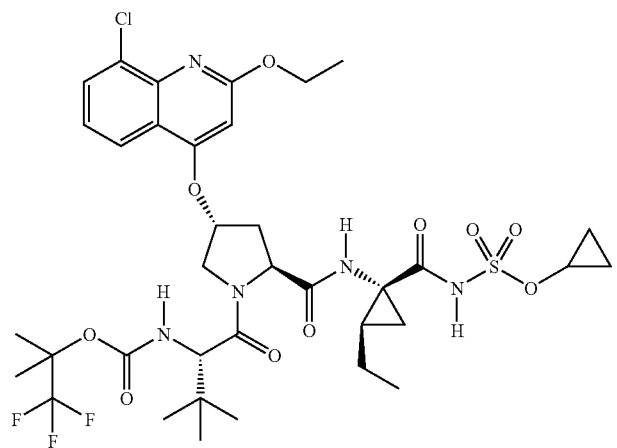

-continued
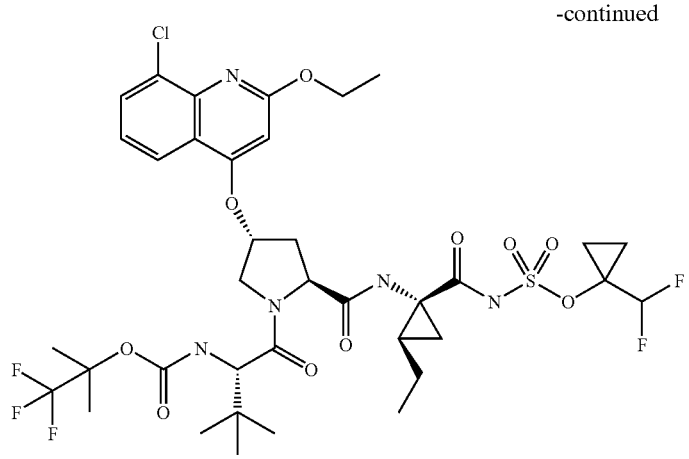
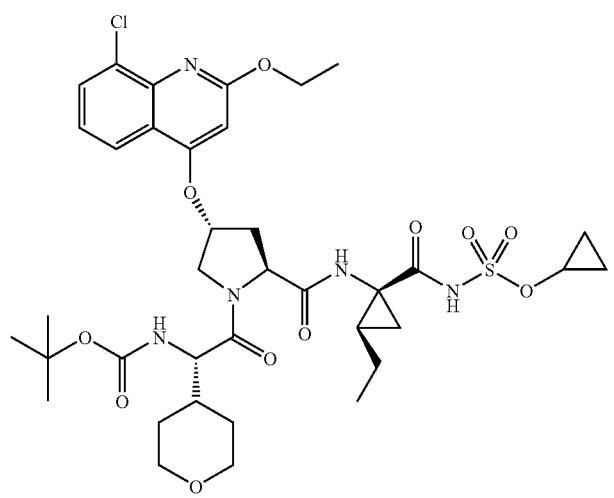
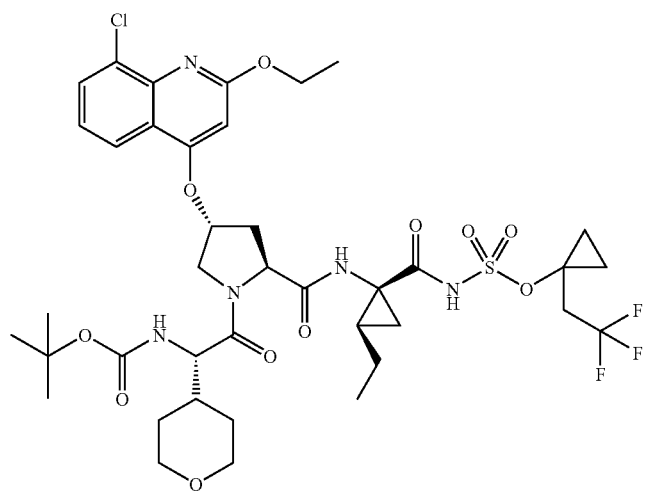

-continued
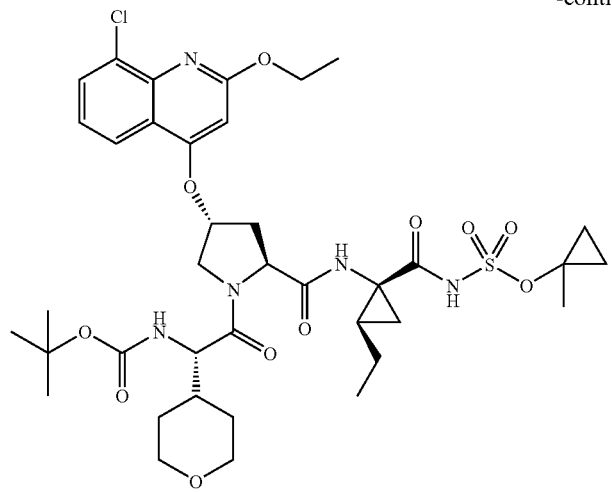
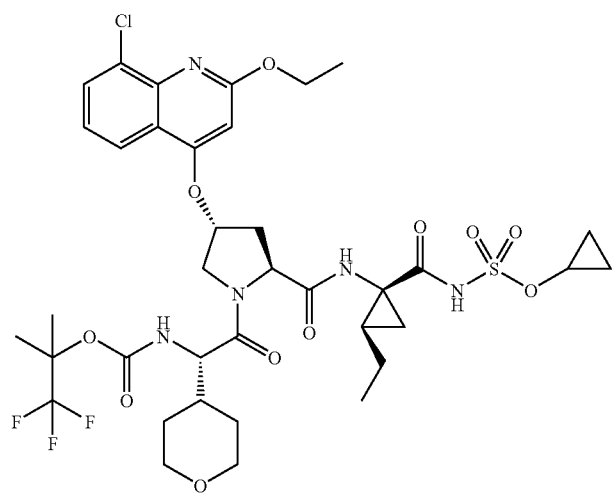
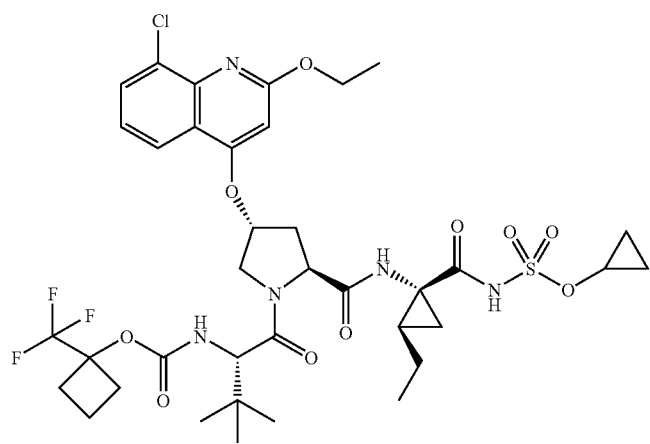

-continued
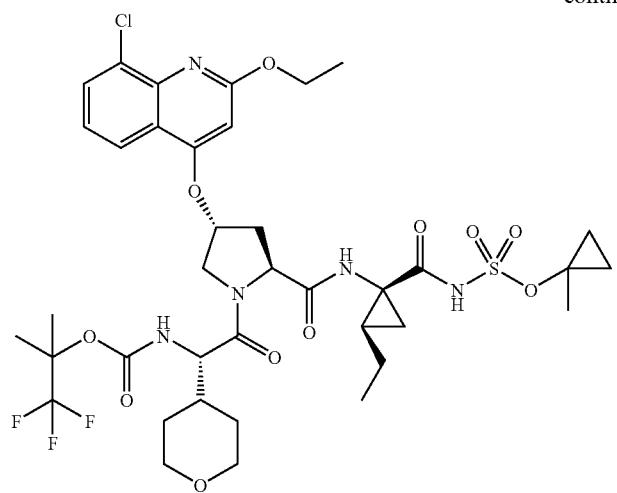
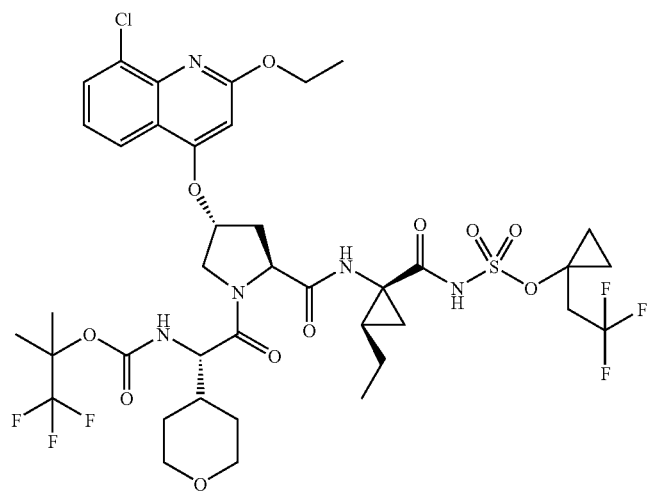
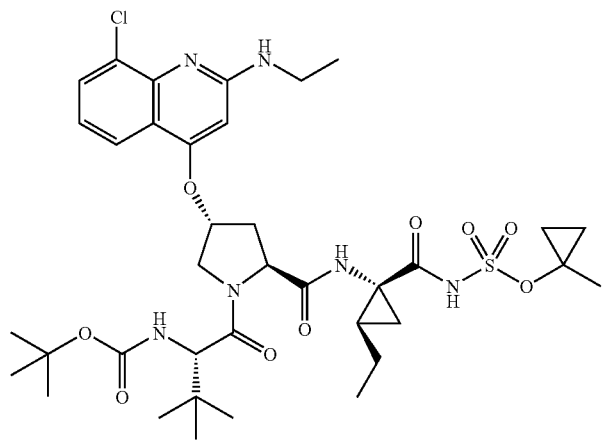

181
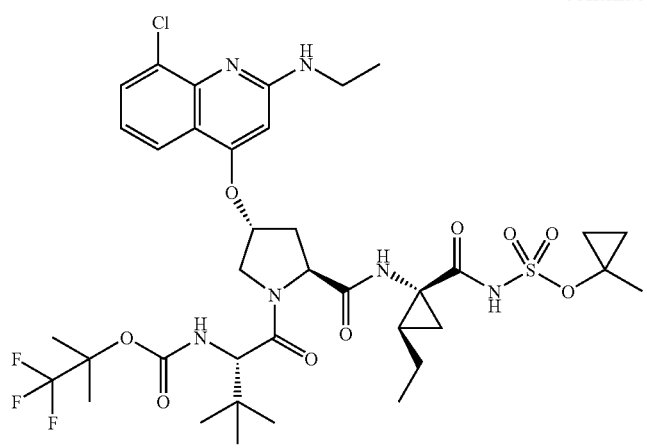
-continued
182
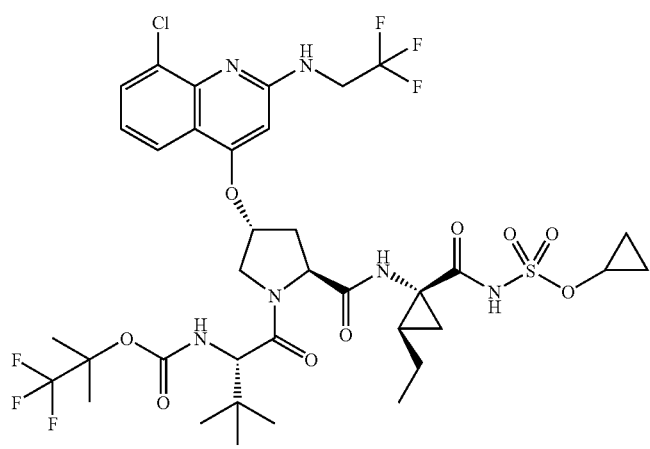
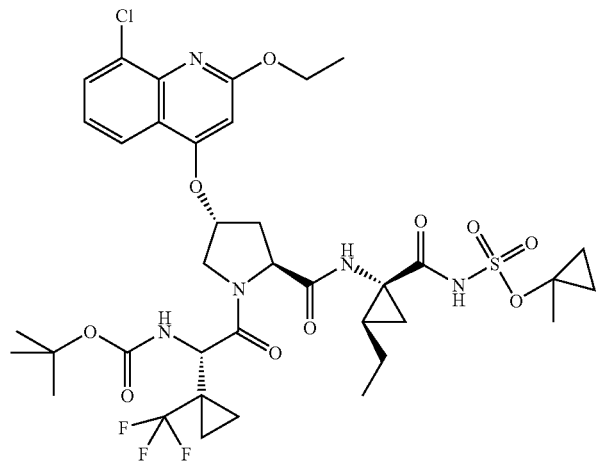
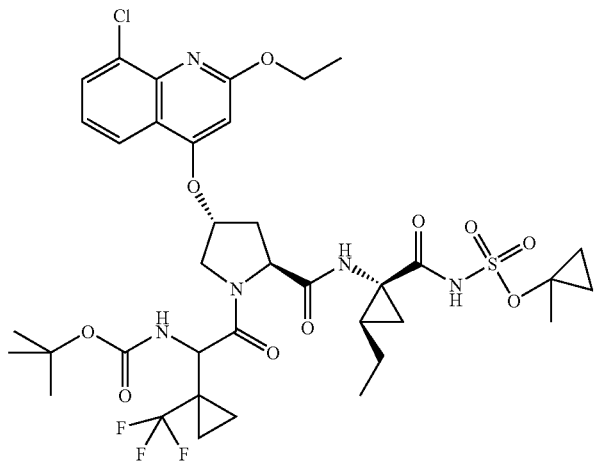

-continued
183 184
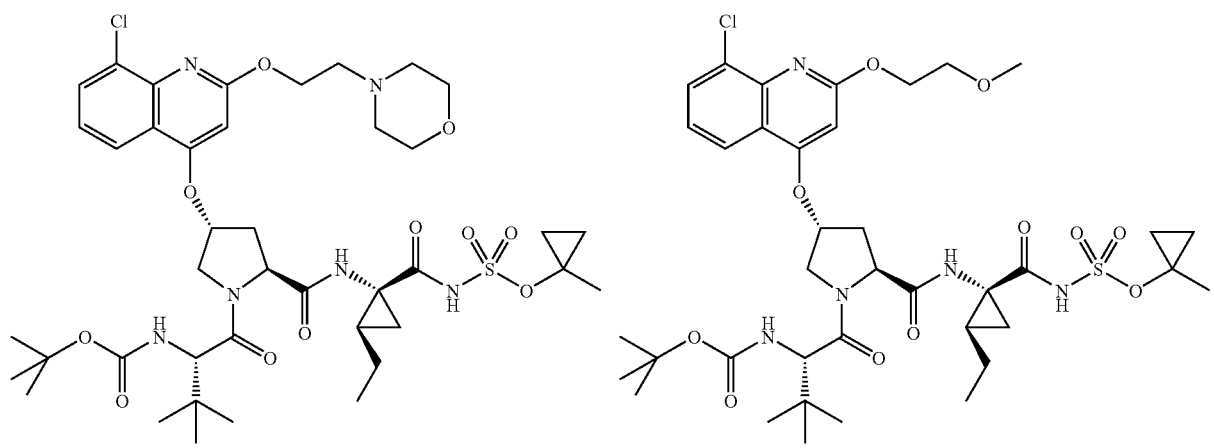
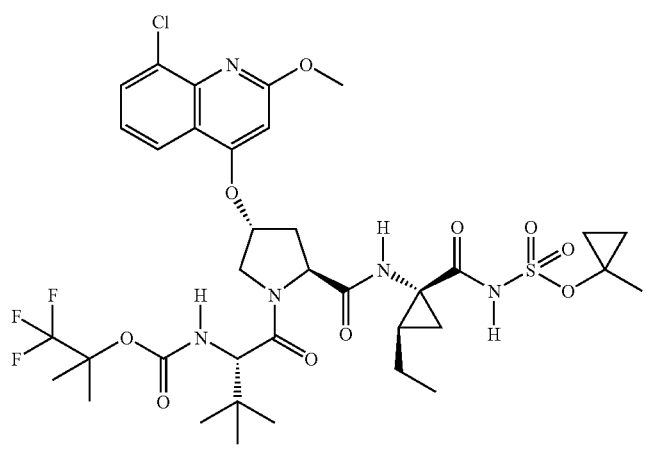
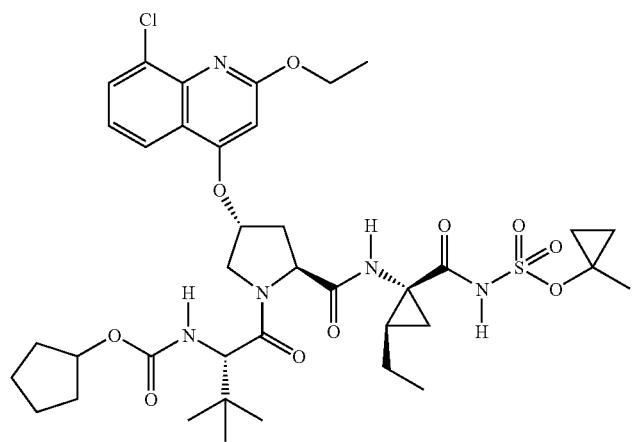

-continued
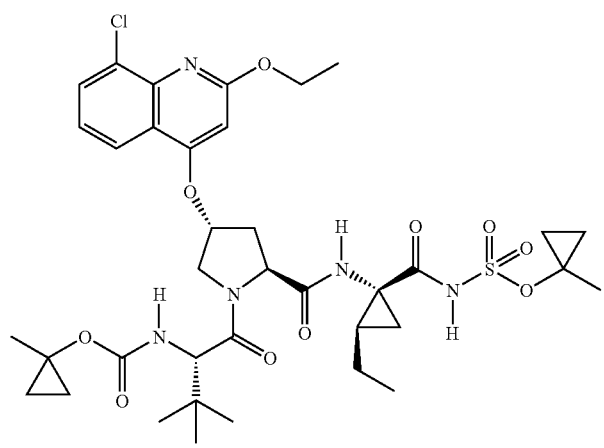
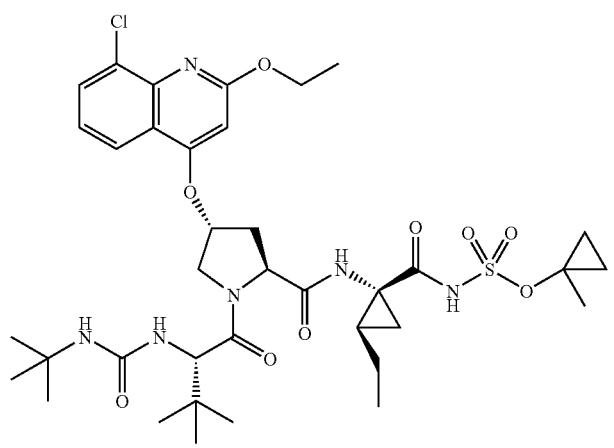
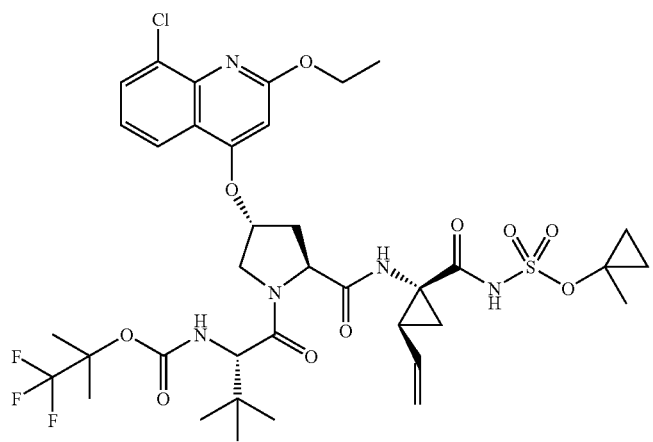

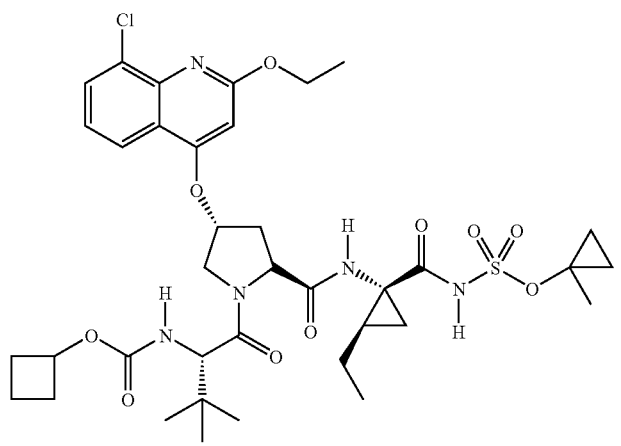
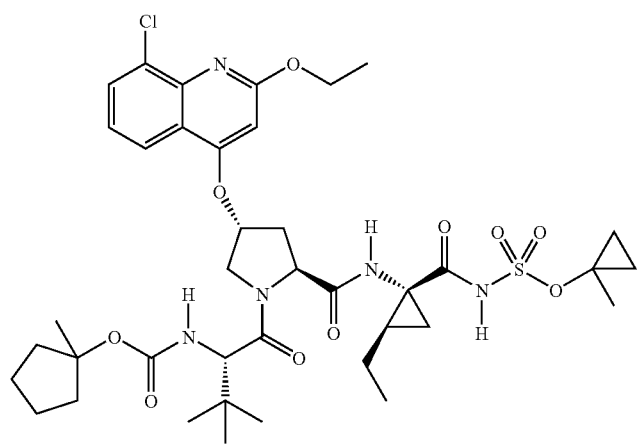
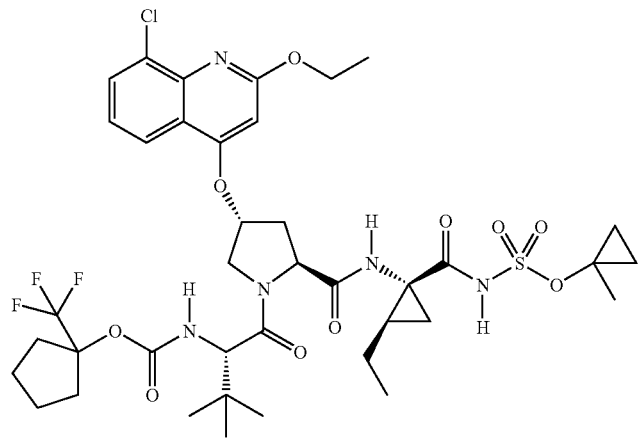

-continued
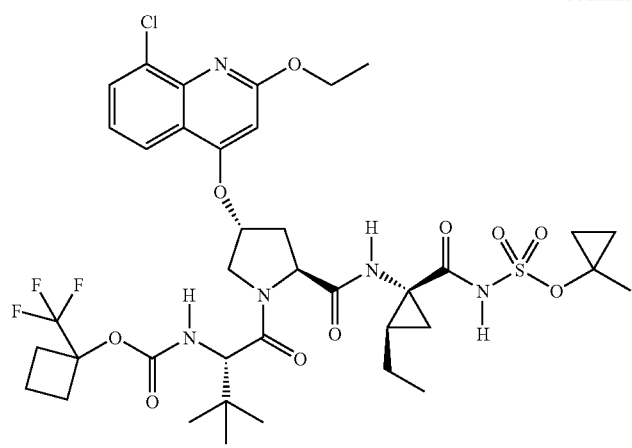
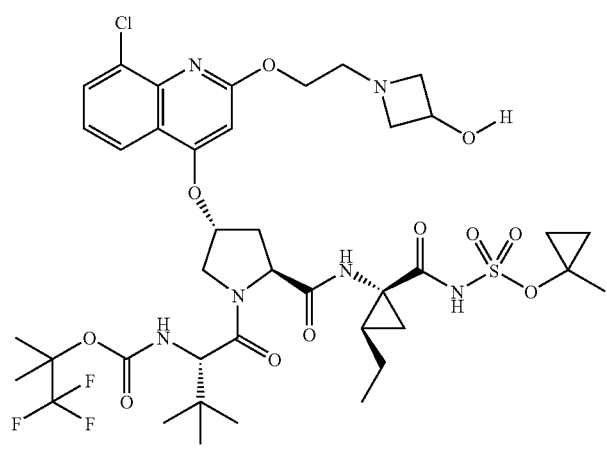
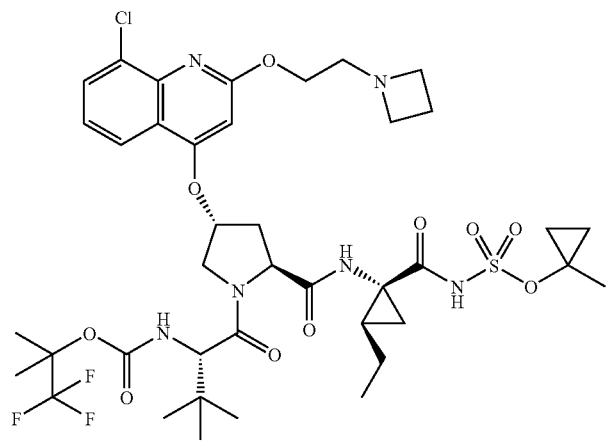

-continued
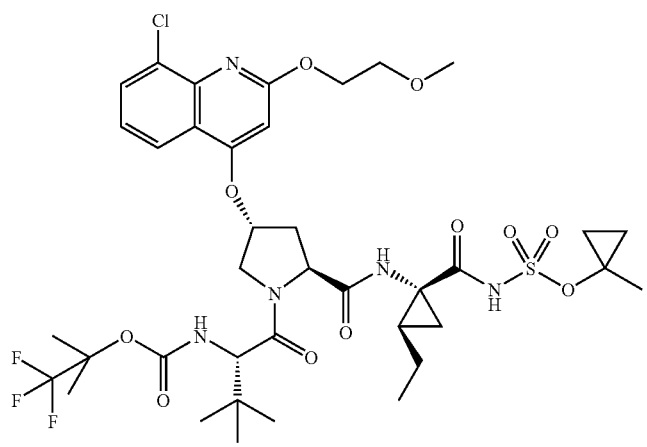
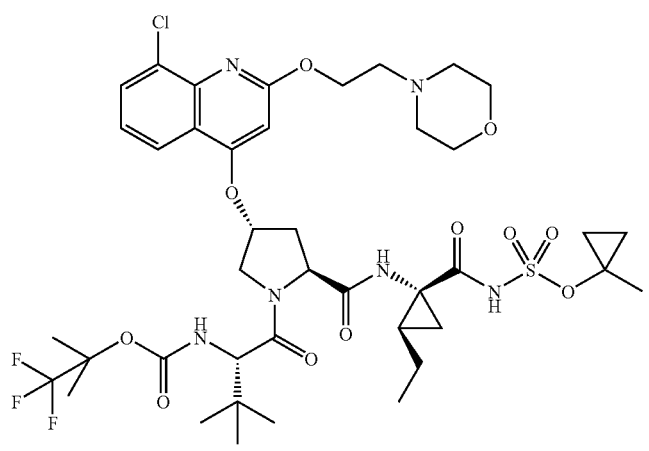
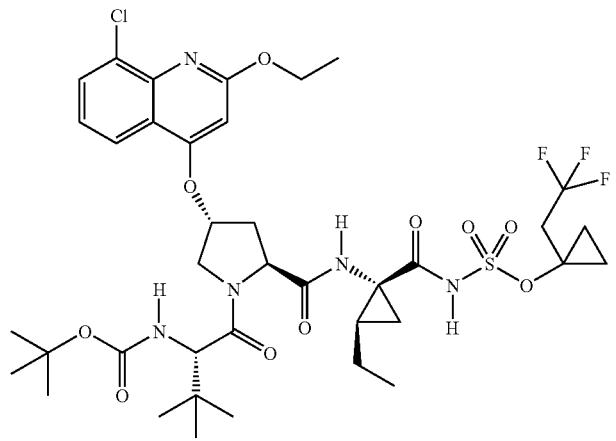

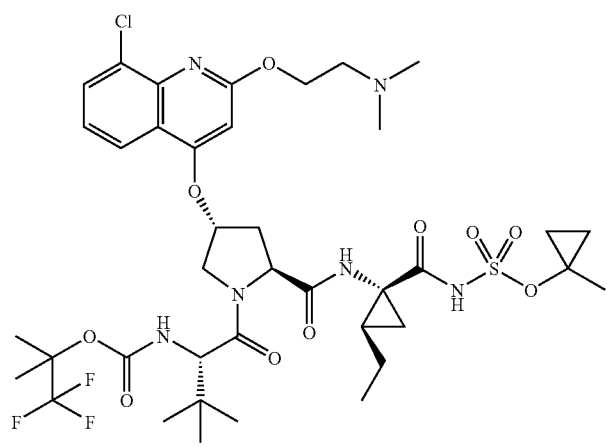
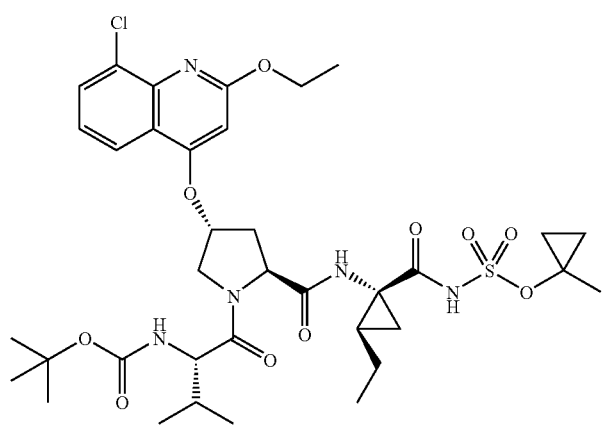
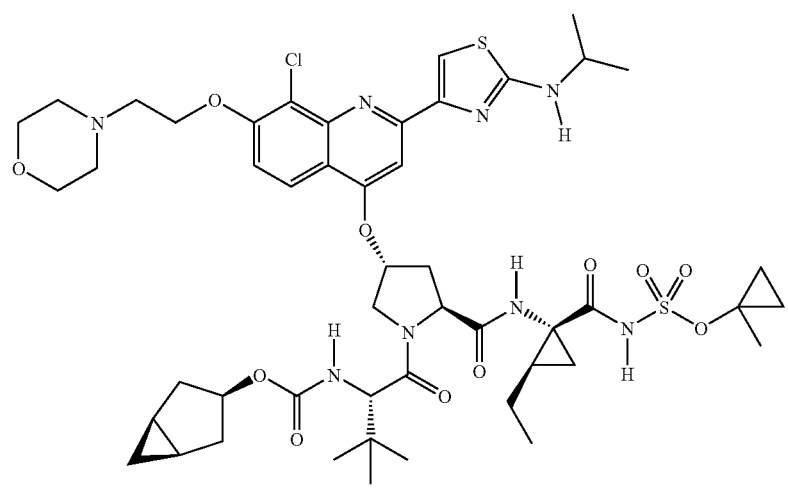

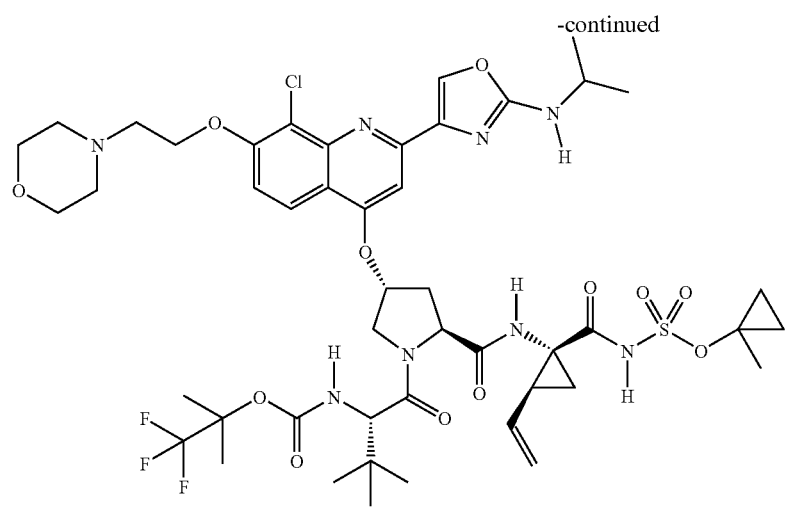
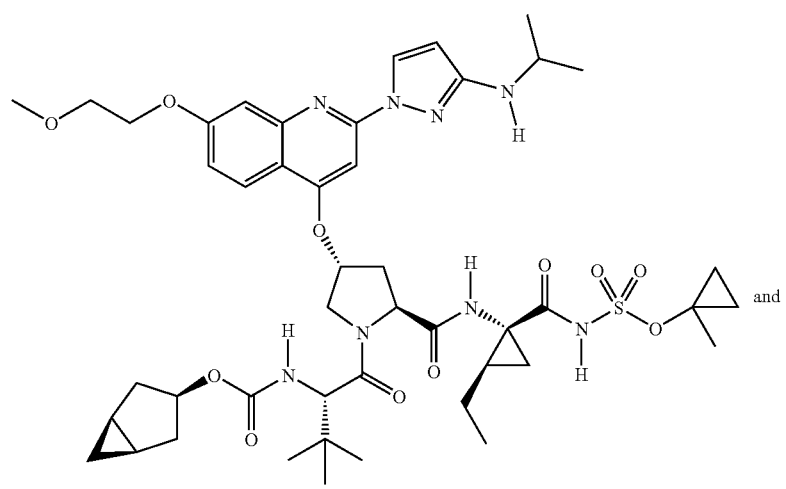
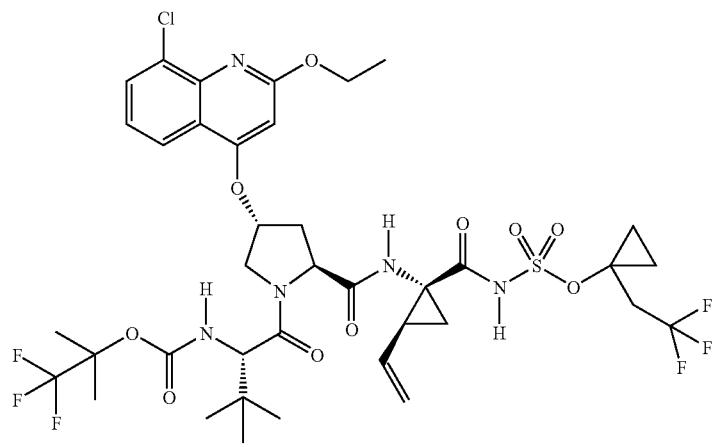
or a pharmaceutically acceptable salt, or prodrug thereof.

In a specific embodiment the invention provides a compound selected from:
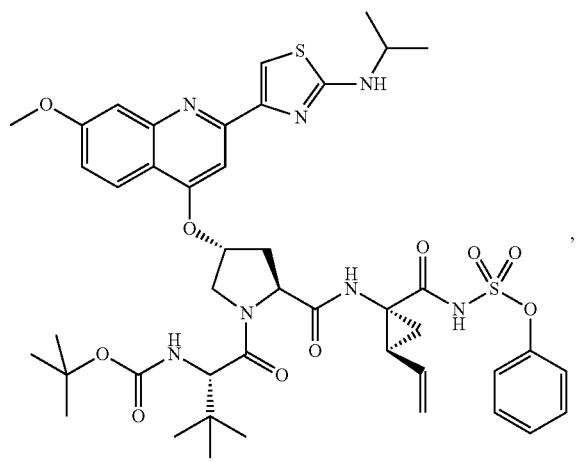
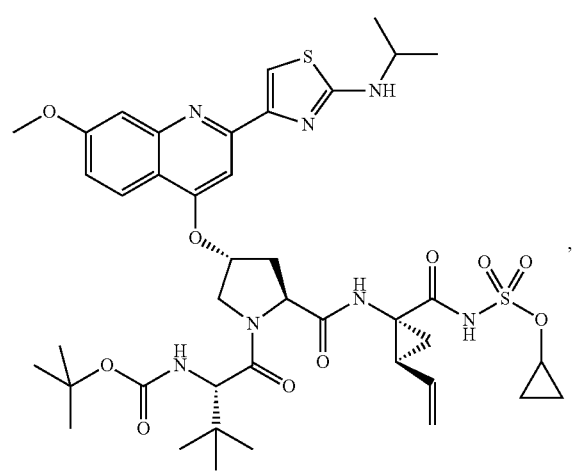
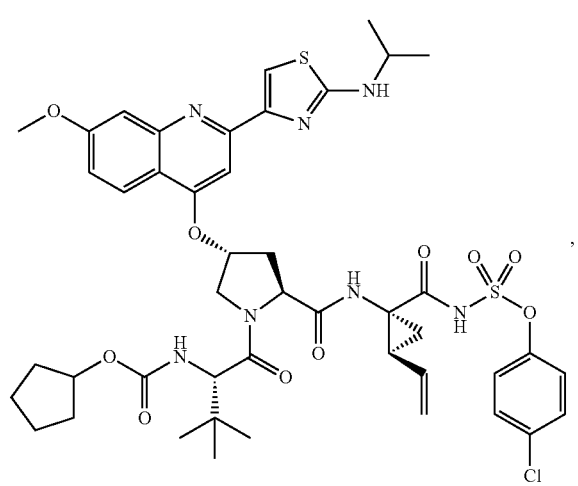
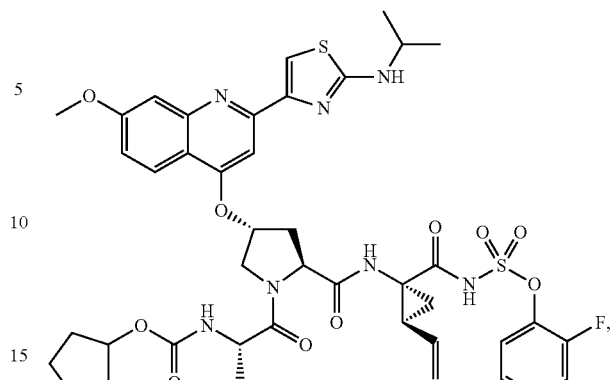
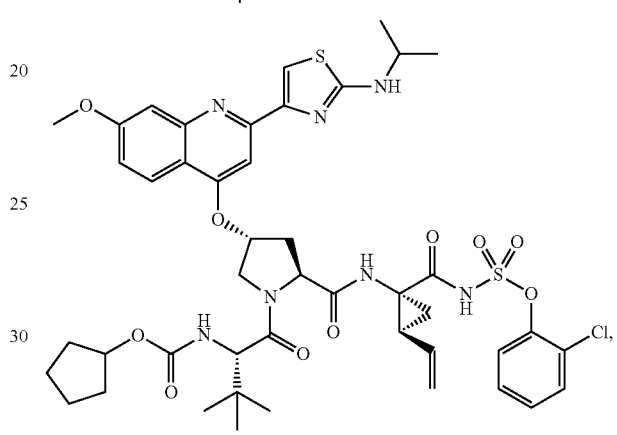
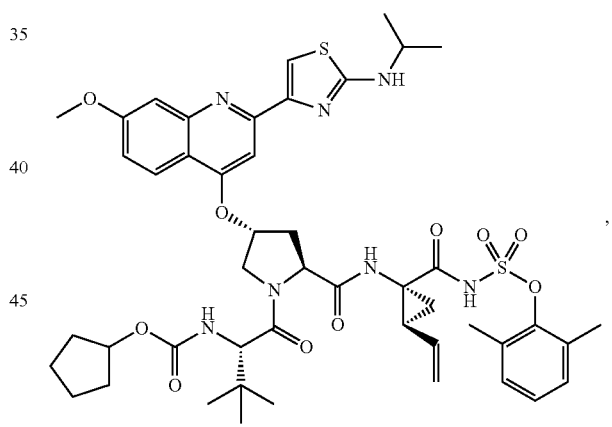
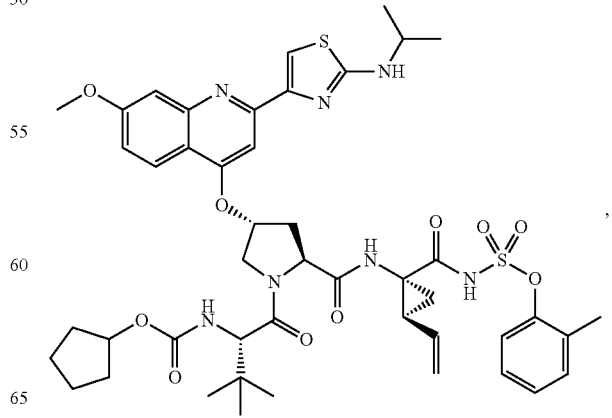

199
-continued
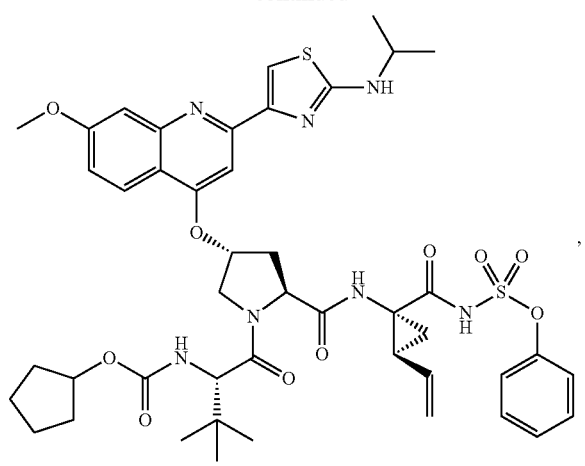
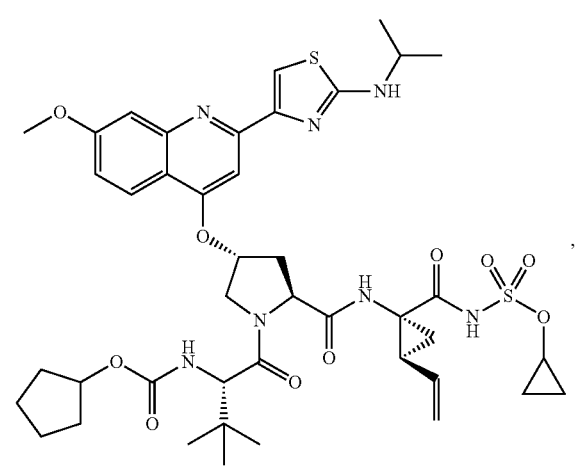
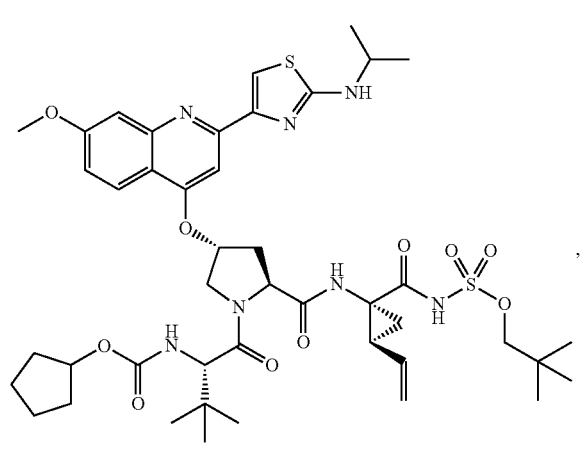
200
-continued
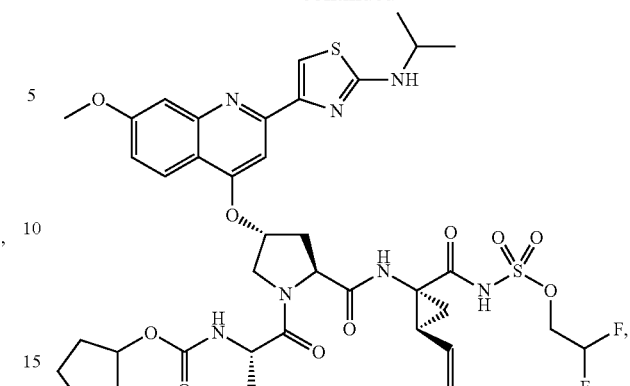
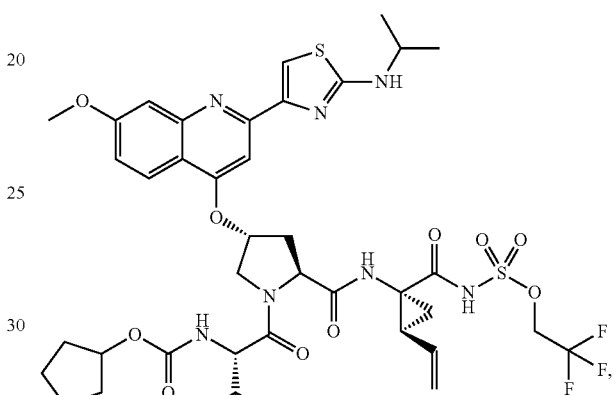
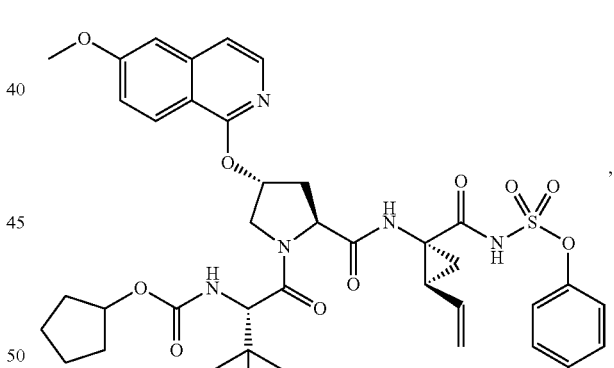
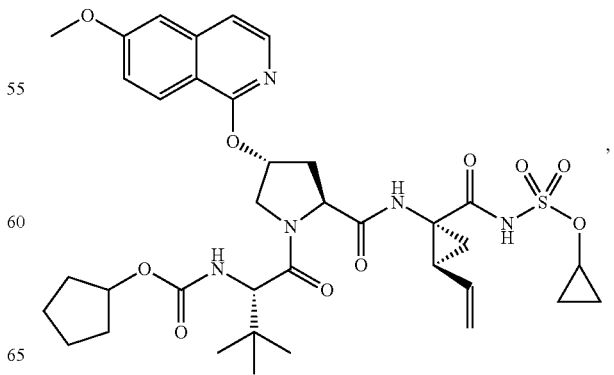

201
-continued
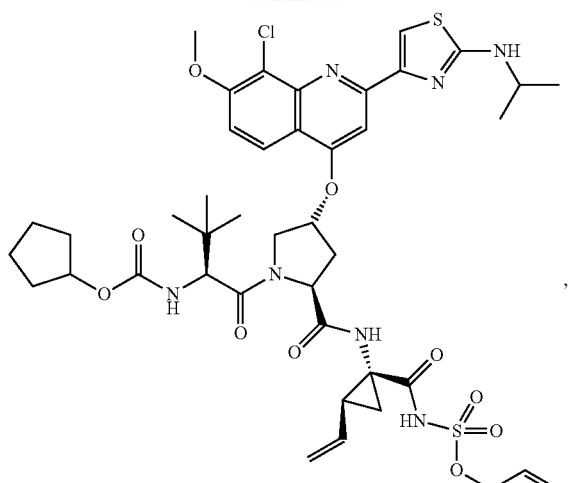
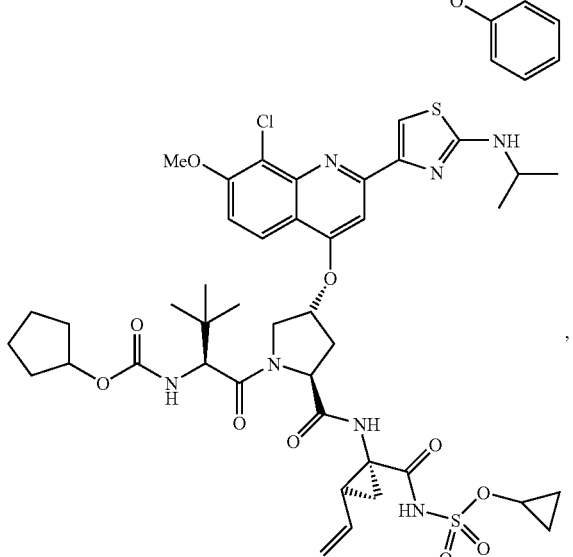
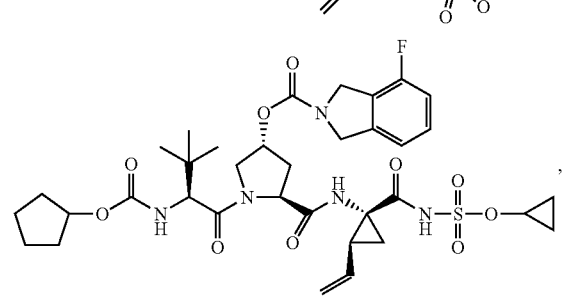
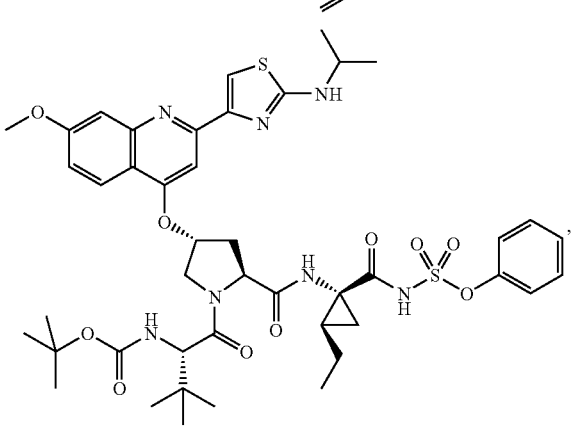
202
-continued
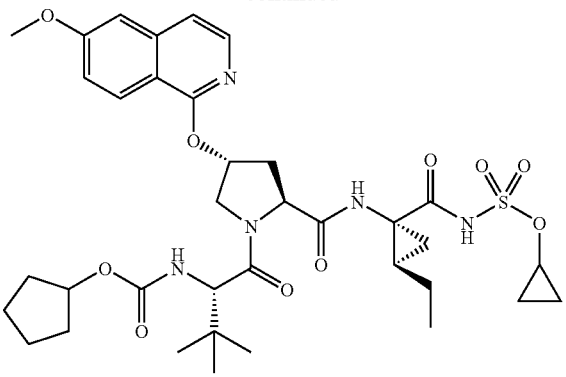
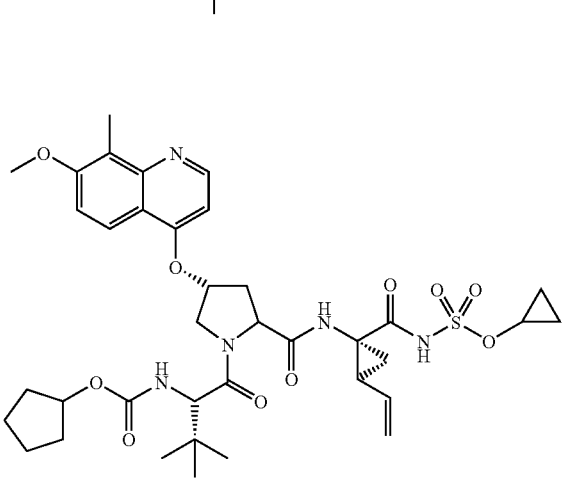
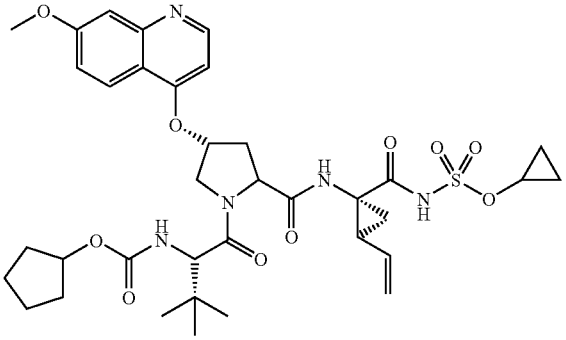
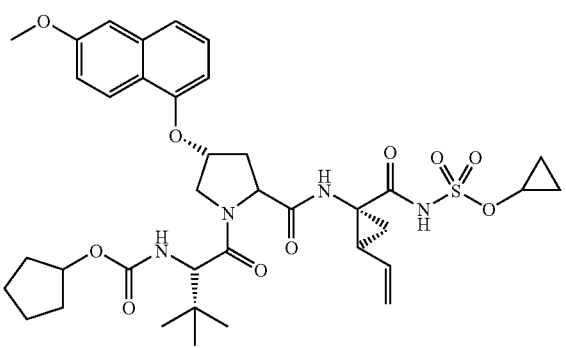

203
-continued
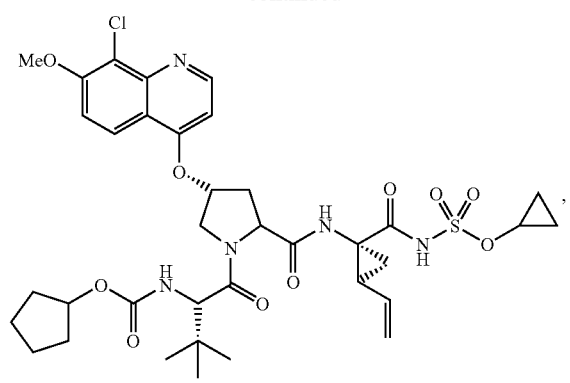
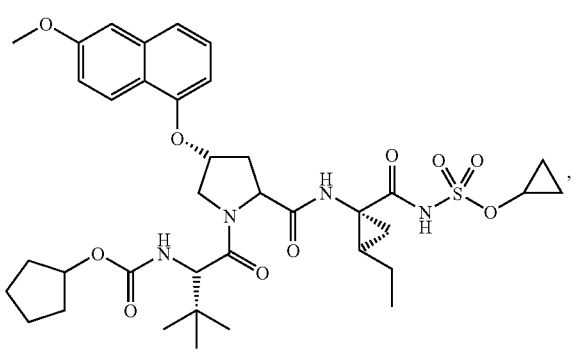
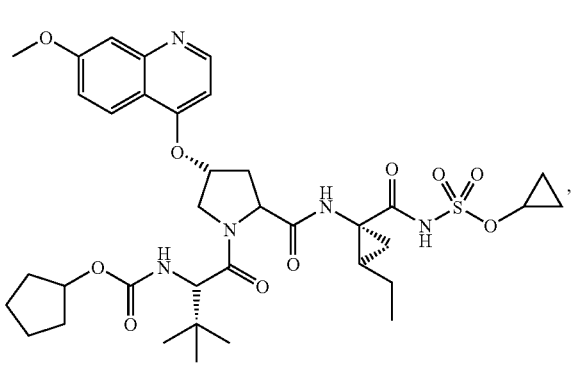
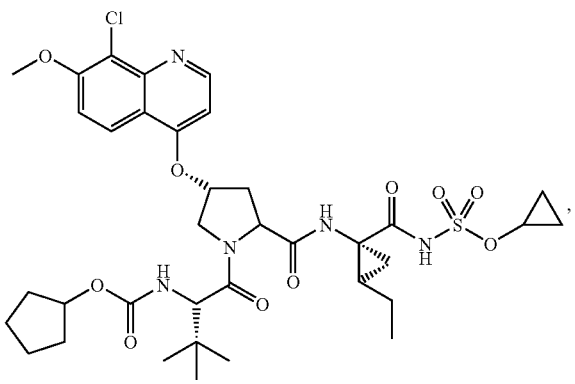
204
-continued
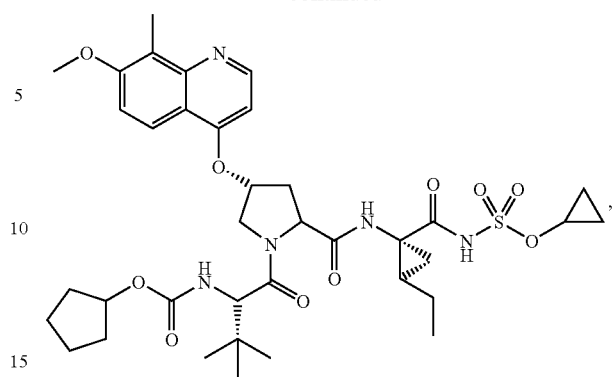
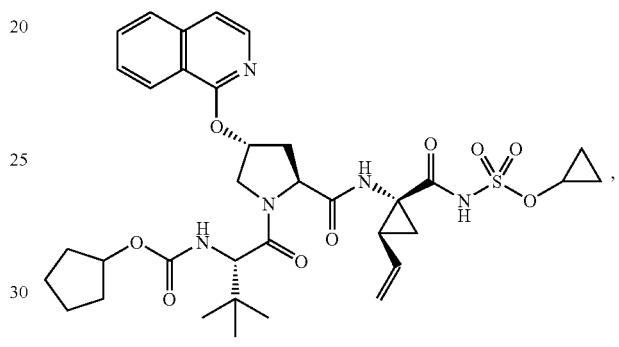
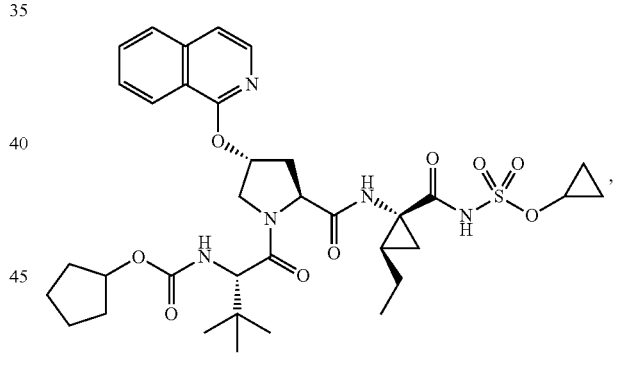
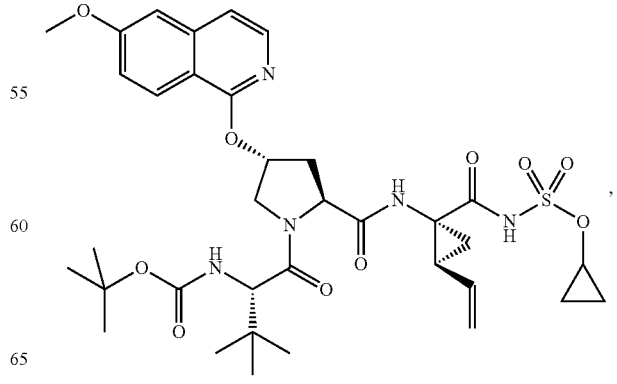

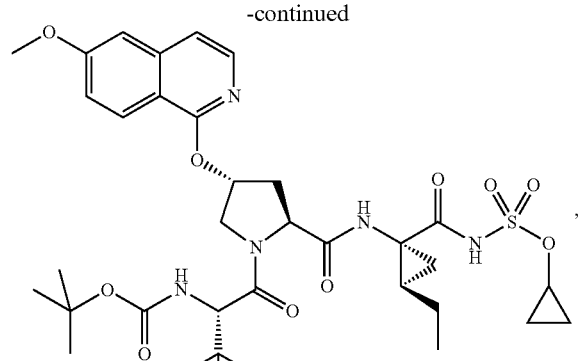
,
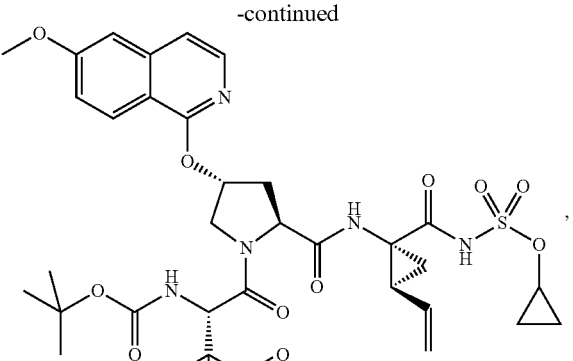
,
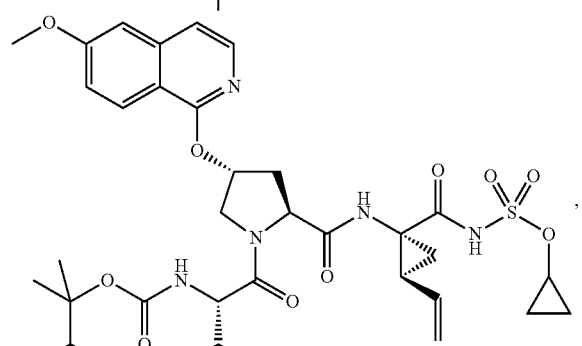
,
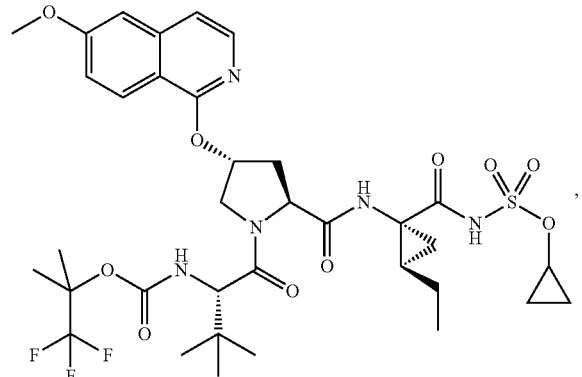
,
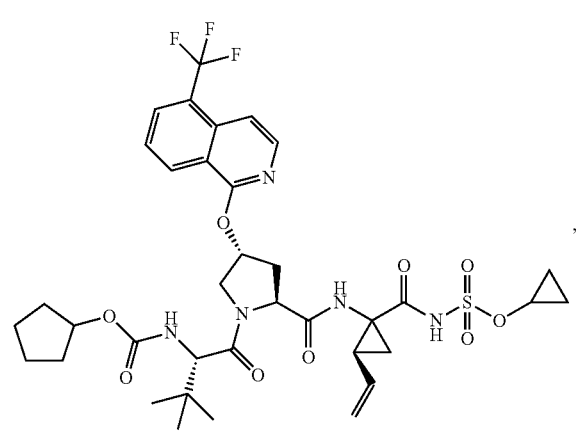
,
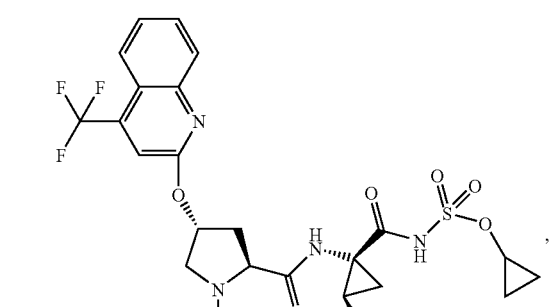
,

207
-continued
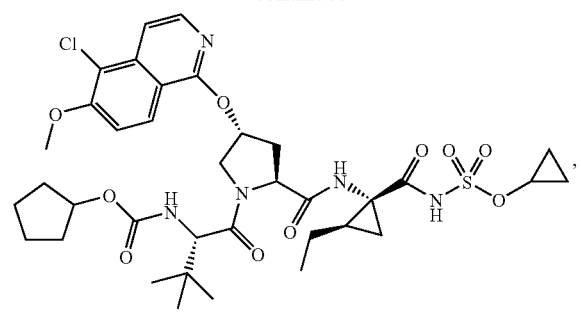
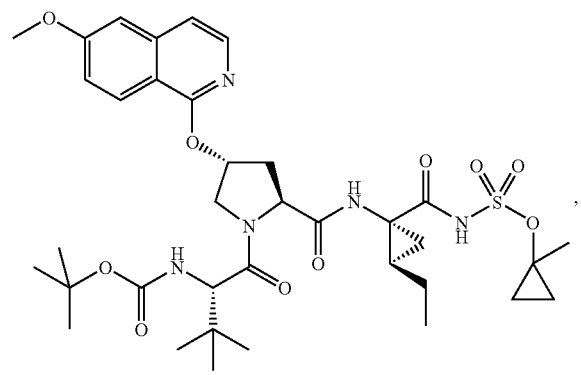
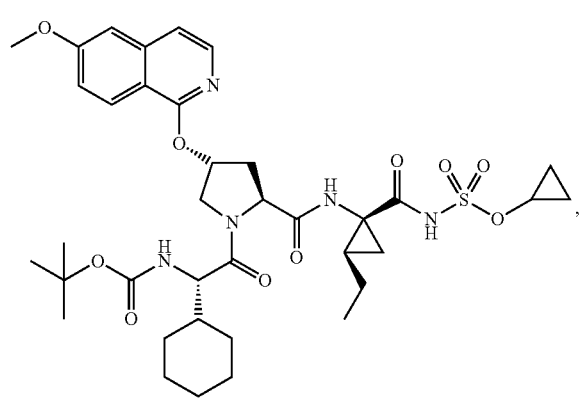
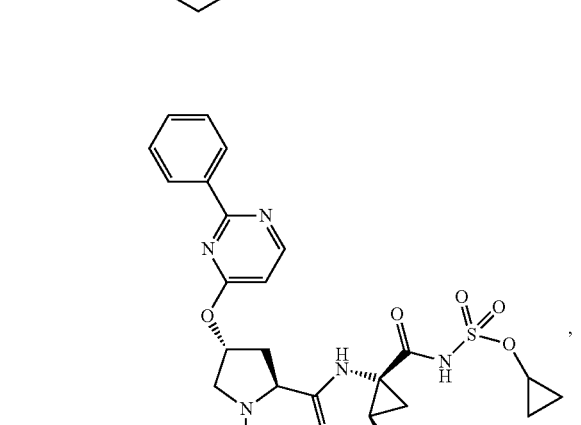
208
-continued
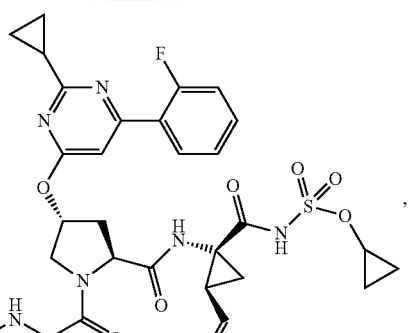
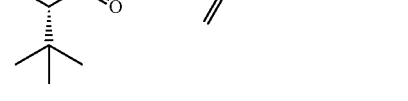

209
-continued
210
-continued
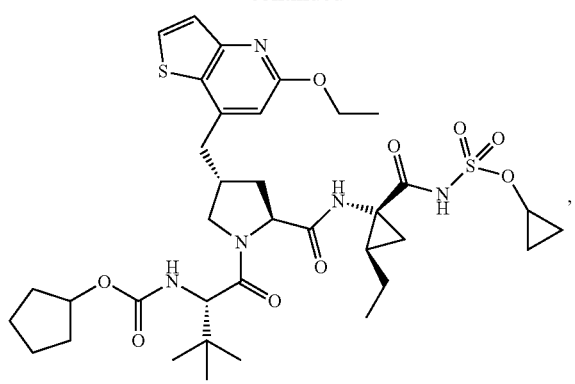
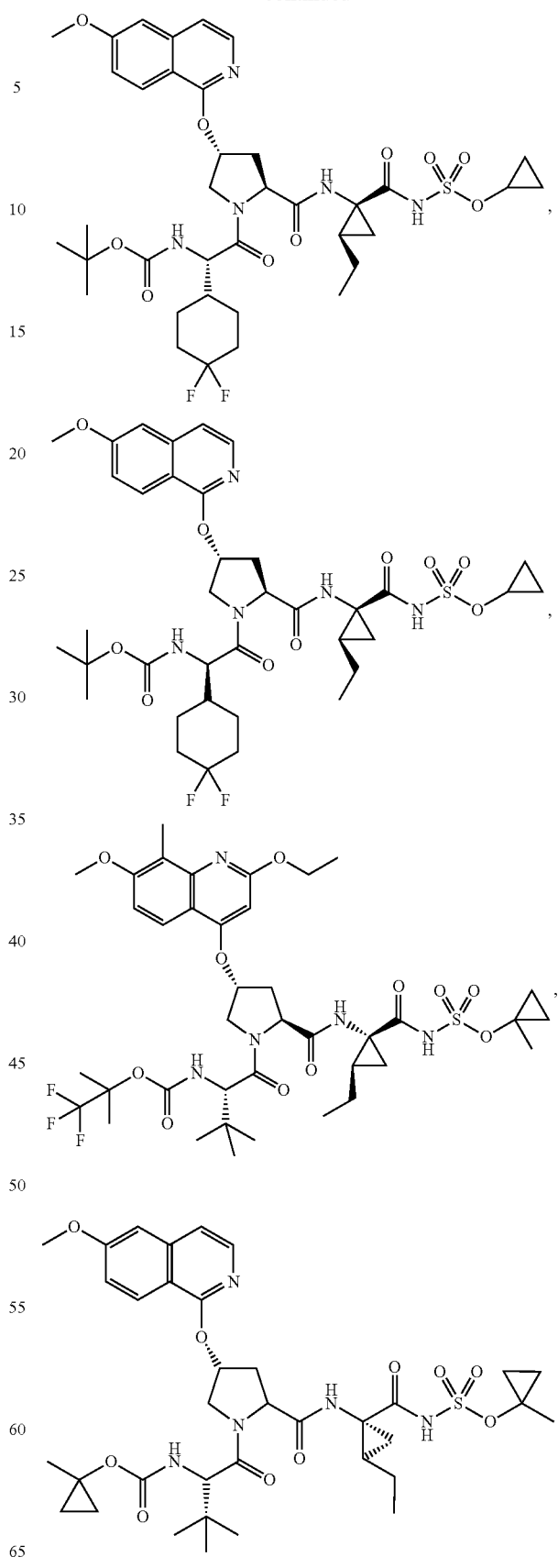

211
-continued
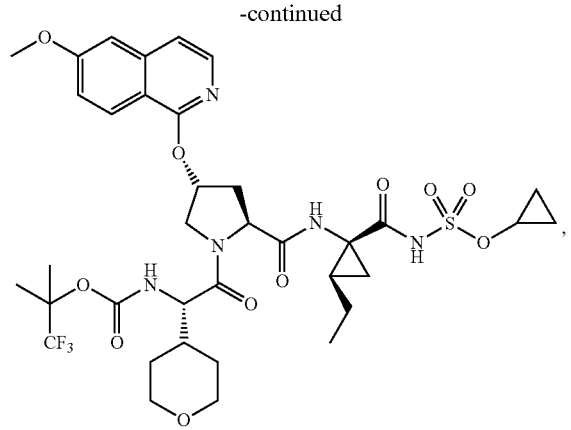
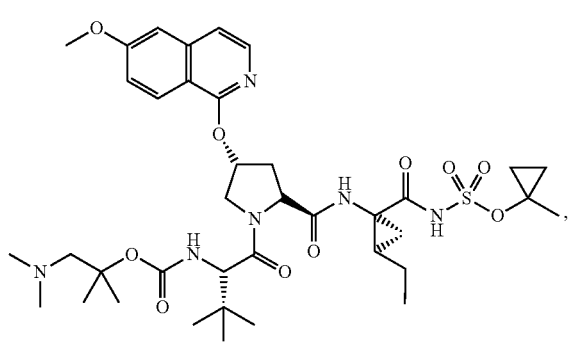
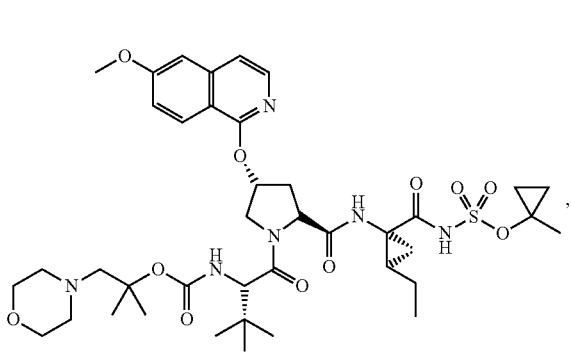
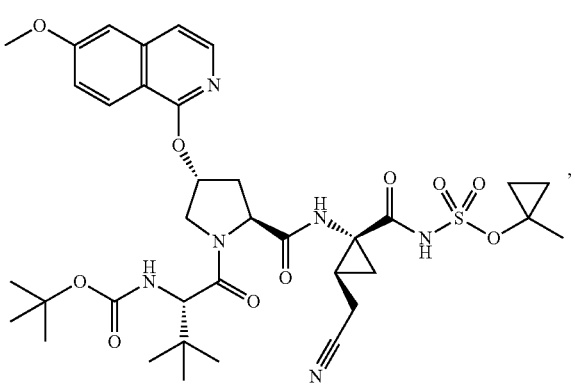
212
-continued
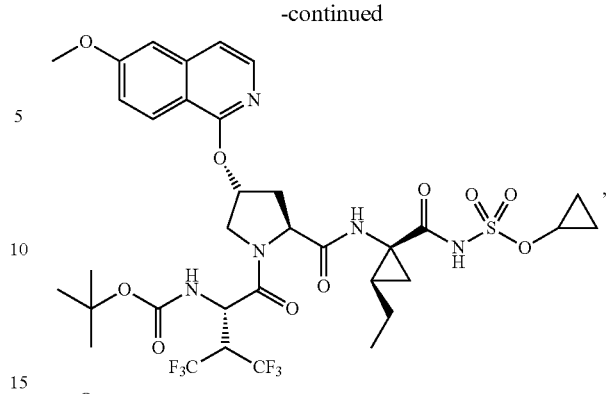
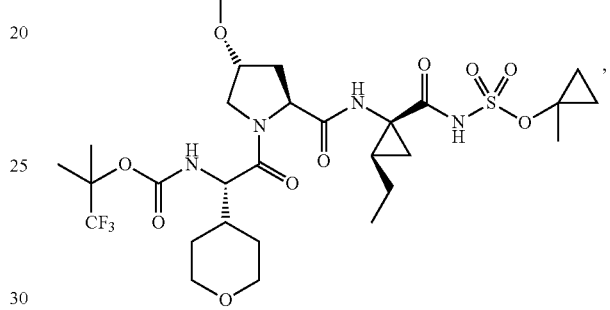
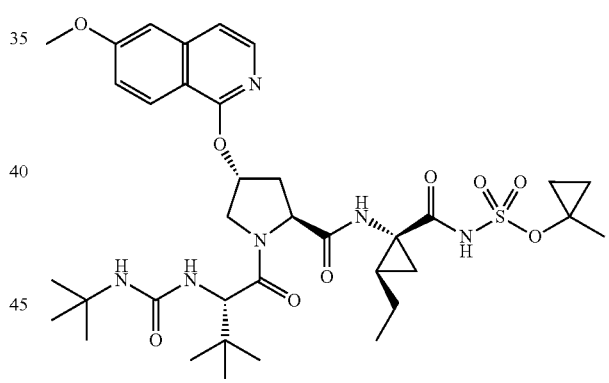
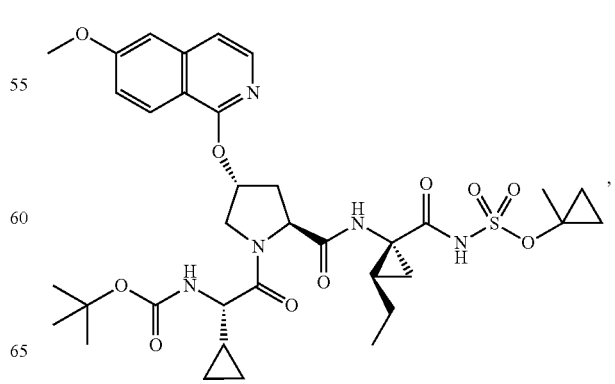

213
-continued
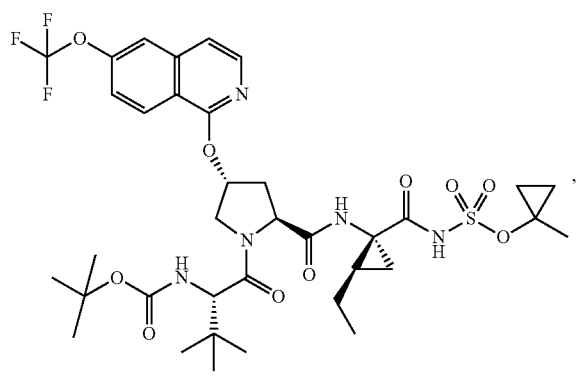
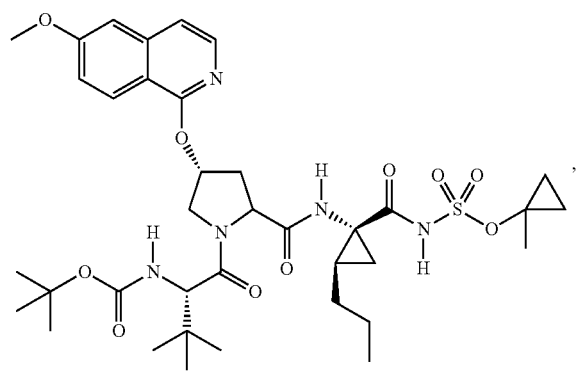
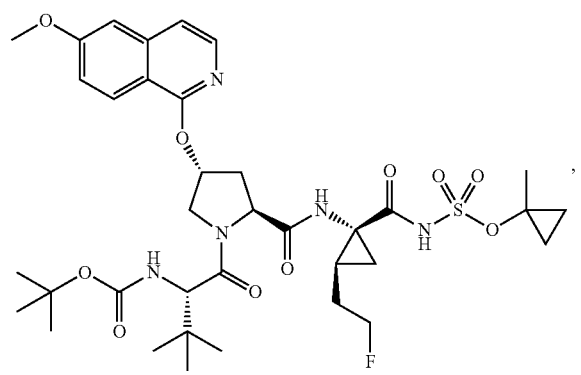
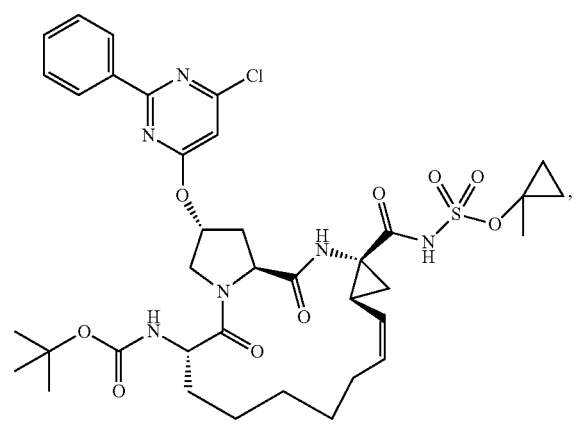
214
-continued
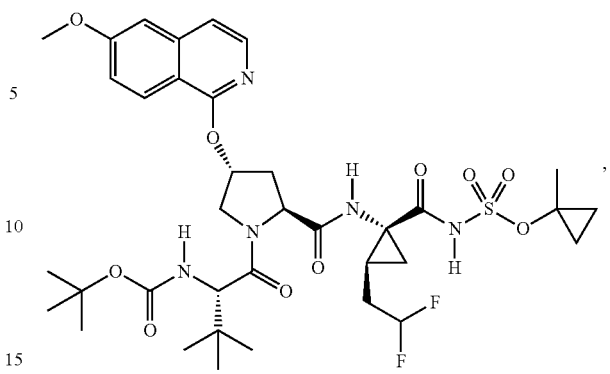
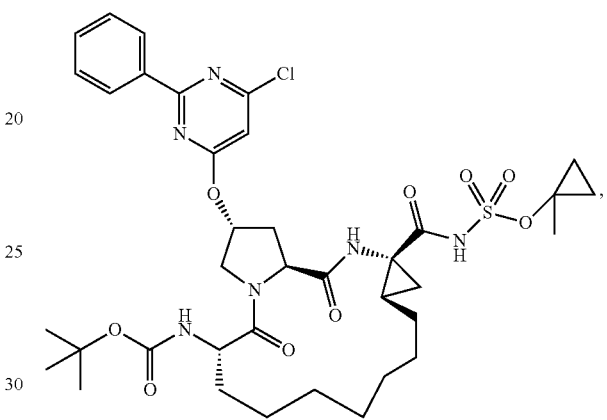
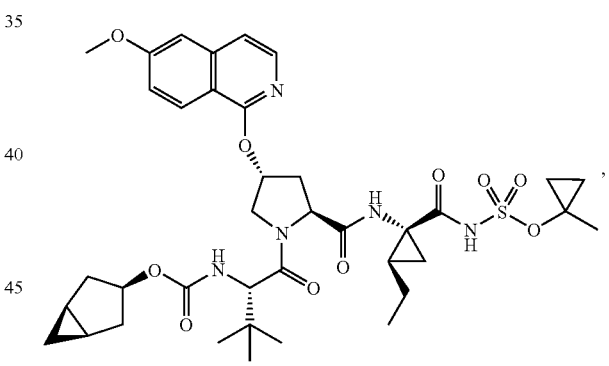
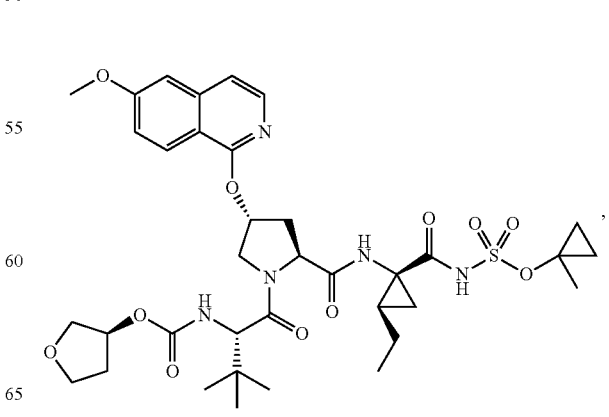

-continued

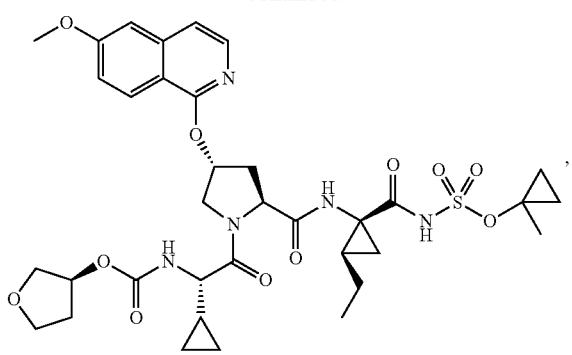

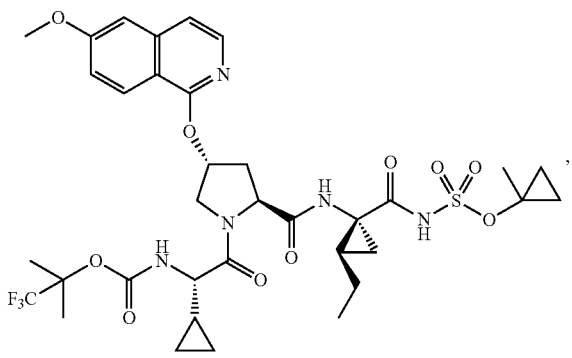

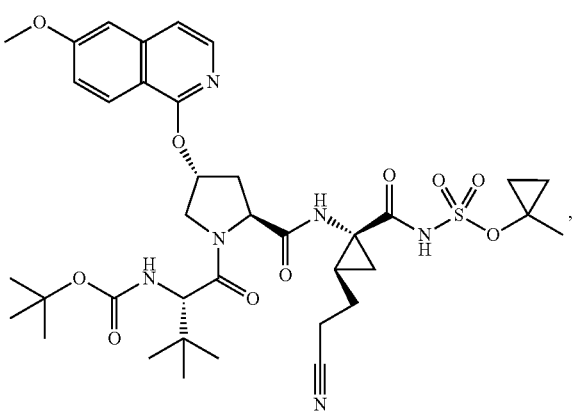

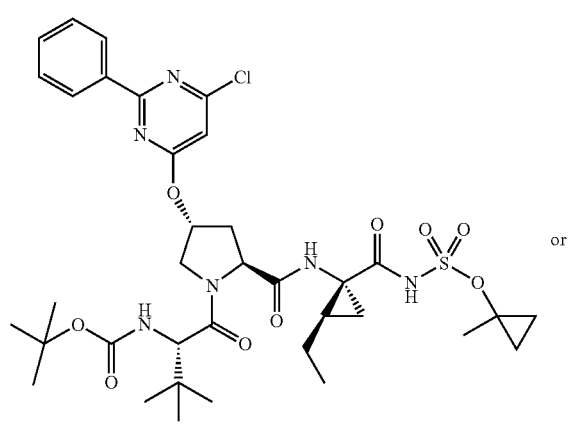

-continued

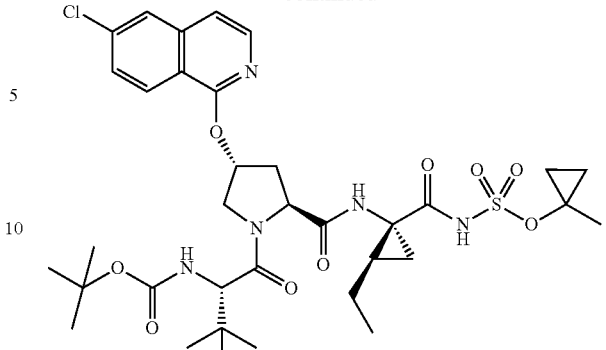

or a pharmaceutically acceptable salt, or prodrug thereof.

In one embodiment, the compounds of the invention exclude the compound:

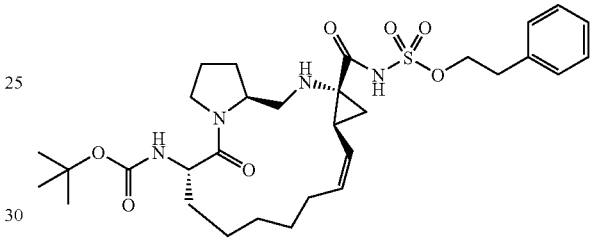

as well as pharmaceutically acceptable salts and prodrugs thereof.

In one embodiment, the compounds of the invention exclude compounds of formula III wherein $Z^1$ is hydrogen.

In one embodiment, the compounds of the invention exclude compounds of formula III wherein $Z^1$ is hydrogen or alkyl.

In one embodiment, the compounds of the invention exclude compounds of formula III wherein $R^f$ is phenethyl.

In one embodiment, the compounds of the invention exclude compounds of formula III wherein $R^f$ is phenethyl, benzyl, or 3-phenylpropyl.

In one embodiment, the compounds of the invention exclude compounds of formula I wherein $Z^1$ is hydrogen.

In one embodiment, the compounds of the invention exclude compounds of formula I wherein $Z^1$ is hydrogen or alkyl.

In one embodiment, the compounds of the invention exclude compounds of formula I wherein $R^f$ is phenethyl.

In one embodiment, the compounds of the invention exclude compounds of formula I wherein $R^f$ is phenethyl, benzyl, or 3-phenylpropyl.

In one embodiment, the compounds of the invention exclude compounds of formula I wherein $R^f$ is aryl optionally substituted with one or more alkyl.

In one embodiment, the compounds of the invention exclude compounds of formula I wherein $Z^1$ is —O(C=O)—N($R_1$)($R_2$) wherein $R_1$ is H, alkyl, alkenyl, or aryl, all of which are optionally substituted with halo, cyano, nitro, alkoxy, amido, amino, or phenyl; and $R_2$ is (i) alkyl; alkyl substituted with carboxy(alkyl); cycloalkyl; cycloalkyl(aryl); alkenyl; alkyl(aryl); all of which may be substituted from one to three times with halo, alkyl, or alkoxy; or $R_2$ is heterocycle which may be substituted from one to three times with halo, alkyl, alkyl(carboxy or phenyl; or (ii) aryl, which may be substituted from one to three times with halo; alkyl, which may itself be substituted with one to three halo; alkoxy; nitro; thio(alkyl); phenyl; alkanoyl; benzoyl; benzoyl oxime; carboxy; carboxy (alkyl); (alkyl) carboxy; phenoxy; (alkyl) carboxy(alkyl) or aryl, which may be substitutes with heterocycle, which heterocycle includes one to three nitrogen, oxygen, or sulfur atoms and which heterocycle itself may be substituted with alkyl, alkoxy, trifluoromethyl, or alkyl (carboxy); or $R_1$ and $R_2$ may join to form a 5 or 6 membered heterocycle, or join to form a 5 or 6 membered heterocycle fused with one or two aryl groups.

In one embodiment, the compounds of the invention exclude compounds of formula I wherein $Z^1$ is linked to the remainder of formula I through the oxygen of a —O(C=O)—N linkage.

The invention also includes the following Specific Embodiments 1-79.

Specific Embodiment 1. In one specific embodiment the invention provides a compound of formula I:

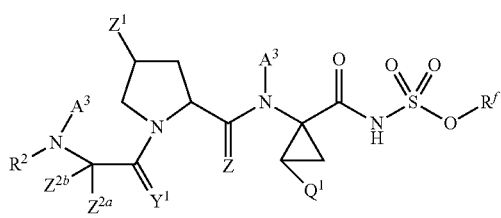

(I)

or a pharmaceutically acceptable salt, or prodrug thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from,
a) —C(Y$^1$)(A$^3$),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
  where said alkyl, cycloalkyl and alkyl-cycloalkyl may optionally be mono- or di-substituted with substituents selected from hydroxy and O—(C1-4)alkyl, or
  where each of said alkyl-groups may optionally be mono-, di- or tri-substituted with halogen, or
  where each of said cycloalkyl groups being 5-, 6- or 7-membered, one or two —CH$_2$— groups not being directly linked to each other may be optionally replaced by —O— such that the O-atom is linked to the N atom to which $R^2$ is attached via at least two C-atoms,
c) phenyl, (C1-3)alkyl-phenyl, heteroaryl or (C1-3)alkyl-heteroaryl,
  wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen;

d) —S(O)$_2$(A$^3$); or
e) —C(Y$^1$)—X—Y;

$R^3$ is H or (C1-6)alkyl;

$Y^1$ is independently O, S, N(A$^3$), N(O)(A$^3$), N(OA$^3$), N(O)(OA$^3$) or N(N(A$^3$)(A$^3$));

Z is O, S, or NR$^3$;

$Z^1$ is an organic group having a three dimensional shape that will fit the extended S2 region of the HCV NS3 serine protease domain;

$Z^{2b}$ is H, (C1-10)alkyl, (C2-10)alkenyl, (C2-10)alkynyl;

$Q^1$ is A$^3$; or $Q^1$ and $Z^{2a}$ taken together with the atoms to which they are attached form a heterocycle, which heterocycle may optionally be substituted with one or more oxo (=O), R$^4$, or A$^3$;

each X is independently a bond, O, S, or NR$^3$;

Y is a polycarbocycle or a polyheterocycle, which polycarbocycle or a polyheterocycle is optionally substituted with one or more R$^4$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$, SR$_r$, S(O)R$_r$, or S(O)$_2$R$_r$;

each R$^4$ is independently —P(Y$^3$)(OA$^2$)(OA$^2$), —P(Y$^3$)(OA$^2$)(N(A$^2$)$_2$), —P(Y$^3$)(A$^2$)(OA$^2$), —P(Y$^3$)(A$^2$)(N(A$^2$)$_2$), or P(Y$^3$)(N(A$^2$)$_2$)(N(A$^2$)$_2$);

each Y$^3$ is independently O, S, or NR$^3$;

each R$_n$ and R$_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more R$^4$, halo, hydroxy, carboxy, cyano, or (C1-10)alkoxy; or R$_n$ and R$_p$ together with the nitrogen to which they are attached form a pyrrolidine, piperidine, piperazine, morpholino, or thiomorpholino ring;

each R$_r$ is independently H, (C1-10)alkyl, (C2-10)alkenyl, (C2-10)alkynyl, (C1-10)alkanoyl, or (C1-10)alkoxycarbonyl;

$Z^{2a}$ is H, (C1-10)alkyl, (C2-10)alkenyl, (C2-10)alkynyl, haloalkyl, (C1-10)alkyl-S(=O)$_2$—(C1-10)alkyl, or cycloalkyl, wherein any carbon atom of Z$^{2a}$ may optionally be replaced with a heteroatom selected from O, S, S(=O), S(=O)$_2$, or N and wherein any cycloalkyl is optionally substituted with one or more (C1-10)alkyl, (C2-10)alkenyl, (C2-10)alkynyl, haloalkyl, F, Cl, Br, or I; or Z$^{2a}$ optionally forms a heterocycle with one or more R$^1$, R$^2$, Q$^1$, or A$^3$;

A$^3$ is independently selected from PRT, H, —OH, —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, —C(A$^2$)$_3$, —C(A$^2$)$_2$-C(O)A$^2$, —C(O)A$^2$, —C(O)OA$^2$, —O(A$^2$), —N(A$^2$)$_2$, —S(A$^2$), —CH$_2$P(Y$^1$)(A$^2$)(OA$^2$), —CH$_2$P(Y$^1$)(A$^2$)(N(A$^2$)$_2$), —CH$_2$P(Y$^1$)(OA$^2$)(OA$^2$), —OCH$_2$P(Y$^1$)(OA$^2$)(OA$^2$), —OCH$_2$P(Y$^1$)(A$^2$)(OA$^2$), —OCH$_2$P(Y$^1$)(A$^2$)(N(A$^2$)$_2$), —C(O)OCH$_2$P(Y$^1$)(OA$^2$)(OA$^2$), —C(O)OCH$_2$P(Y$^1$)(A$^2$)(OA$^2$), —C(O)OCH$_2$P(Y$^1$)(A$^2$)(N(A$^2$)$_2$), —CH$_2$P(Y$^1$)(OA$^2$)(N(A$^2$)$_2$), —OCH$_2$P(Y$^1$)(OA$^2$)(N(A$^2$)$_2$), —C(O)OCH$_2$P(Y$^1$)(OA$^2$)(N(A$^2$)$_2$), —CH$_2$P(Y$^1$)(N(A$^2$)$_2$)(N(A$^2$)$_2$), —C(O)OCH$_2$P(Y$^1$)(N(A$^2$)$_2$)(N(A$^2$)$_2$), —OCH$_2$P(Y$^1$)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O- alkyl, —(CH$_2$)$_m$—O—C(O)—O-cycloalkyl, —N(H)C(Me)C(O)O-alkyl, SR$_{r'}$, S(O)R$_{r'}$, S(O)$_2$R$_{r'}$, or alkoxy arylsulfonamide, wherein each A$^3$ may be optionally substituted with 1 to 4

—R$^1$, —P(Y$^1$)(OA$^2$)(OA$^2$), —P(Y$^1$)(OA$^2$)(N(A$^2$)$_2$), —P(Y$^1$)(A$^2$)(OA$^2$), —P(Y$^1$)(A$^2$)(N(A$^2$)$_2$), or P(Y$^1$)(N(A$^2$)$_2$)(N(A$^2$)$_2$), —C(=O)N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$;

optionally each independent instance of A$^3$ and Q$^1$ can be taken together with one or more A$^3$ or Q$^1$ groups to form a ring; and A$^2$ is independently selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each A$^2$ is optionally substituted with A$^3$.

R$^f$ is A$^3$; and m is 0 to 6;

provided the compound of formula I is not the compound:

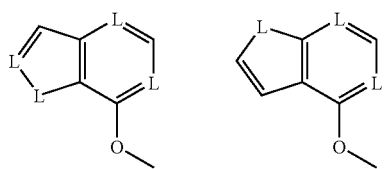

Specific Embodiment 2. The compound of specific embodiment 1 wherein Z$^1$ is an organic group that has favorable interations with one or more residues corresponding to Histidine 57, Aspartic acid 81, Arginine 155, and Aspartic acid 168 of the extended S2 region of the HCV NS3 serine protease domain.

Specific Embodiment 3. The compound of specific embodiment 1 wherein Z$^1$ is an organic group that has favorable interactions with one or more residues corresponding to Tyrosine 56, Valine 78, and Aspartic acid 79 of the extended S2 region of the HCV NS3 serine protease domain.

Specific Embodiment 4. The compound of specific embodiment 1 wherein Z$^1$ is A$^3$.

Specific Embodiment 5. The compound of specific embodiment 1 wherein Z$^1$ is selected from:

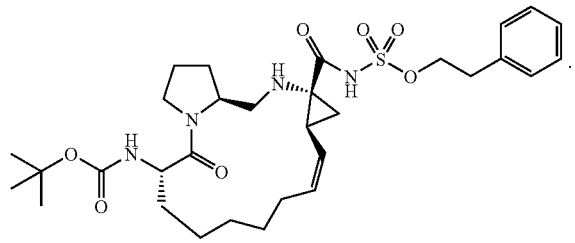

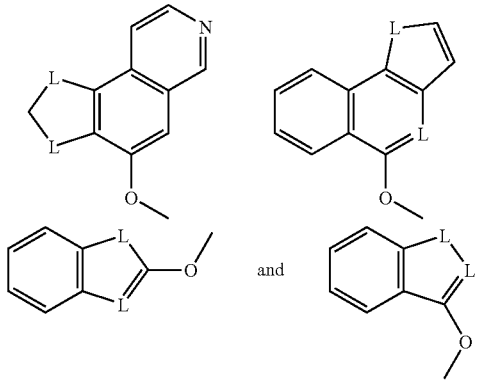

wherein each L is independently CH or N; and wherein each Z$^1$ is optionally substituted with one or more A$^3$.

Specific Embodiment 6. The compound of specific embodiment 1 wherein Z$^1$ is a group —Z$^3$-Q, wherein: Z$^3$ is a direct bond, —O—, —S—, —S(=O), —S(=O)$_2$, —C(=O)—, —C(=O)O—, or —OC(=O)—; and Q is a bicyclic [4.4.0] ring system wherein at least one ring is aromatic, which ring system comprises one or more carbon atoms and optionally comprises one or more O, S, S(=O), S(=O)$_2$, —N=, or —N(A$^5$)- in the ring system; wherein each A$^5$ is independently A$^3$ or the point of attachment to Z$^3$; and wherein the ring system is optionally substituted on one or more carbon atoms with A$^3$.

Specific Embodiment 7. The compound of specific embodiment 1 wherein Z$^1$ is a group —Z$^3$-Q, wherein: Z$^3$ is a direct bond, —O—, —S—, —C(=O)—, —C(=O)O—, or —OC(=O)—; and Q is a bicyclic [4.4.0] ring system wherein at least one ring is aromatic, which ring system comprises one or more carbon atoms and optionally comprises one or more —N= or —N(A$^5$)- in the ring system, and which ring system is optionally substituted on one or more carbon atoms with A$^3$.

Specific Embodiment 8. The compound of specific embodiment 1 wherein Z$^1$ is a group —Z$^3$-Q, wherein: Z$^3$ is a direct bond, —O—, —S—, —C(=O)—, —C(=O)O—, or —OC(=O)—; and Q is a bicyclic [4.4.0] ring system wherein both rings are aromatic, which ring system comprises one or more carbon atoms and optionally comprises one or more —N= in the ring system, and which ring system is optionally substituted on one or more carbon atoms with A$^3$.

Specific Embodiment 9. The compound of specific embodiment 1 wherein Z$^1$ is a group —Z$^3$-Q, wherein: Z$^3$ is a direct bond, —O—, —S—, —C(=O)—, —C(=O)O—, or —OC(=O)—; and Q is a bicyclic [4.4.0] ring system wherein both rings are aromatic, which ring system comprises one or more carbon atoms and comprises 1, 2, 3, or 4 —N= in the ring system, and which ring system is optionally substituted on one or more carbon atoms with A$^3$.

Specific Embodiment 10. The compound of specific embodiment 1 wherein Z$^1$ is a group —Z$^3$-Q, wherein: Z$^3$ is a direct bond, —O—, —S—, —C(=O)—, —C(=O)O—, or —OC(=O)—; and Q is a bicyclic [4.4.0] ring system wherein both rings are aromatic, which ring system comprises one or more carbon atoms and comprises 1 or 2 —N= in the ring system, and which ring system is optionally substituted on one or more carbon atoms with A$^3$.

Specific Embodiment 11. The compound of specific embodiment 1 wherein Z$^1$ is a group —Z$^3$-Q, wherein: Z$^3$ is a direct bond, —O—, —S—, —C(=O)—, —C(=O)O—, or —OC(=O)—; and Q is a 1-naphthyl or 2-naphthyl ring system that is optionally substituted with one or more $A^3$.

Specific Embodiment 12. The compound of specific embodiment 1 wherein $Z^1$ is a group —$Z^3$-Q, wherein: $Z^3$ is a direct bond, —O—, —S—, —S(=O)—, —S(=O)$_2$—, —C(=O)—, —C(=O)O—, or —OC(=O)—; and Q is a bicyclic [4.3.0] ring system wherein at least one ring is aromatic, which ring system comprises one or more carbon atoms and optionally comprises one or more O, S, S(=O), S(=O)$_2$, —N=, or —N($A^5$)- in the ring system; wherein each $A^5$ is independently $A^3$ or the point of attachment to $Z^3$; and wherein the ring system is optionally substituted on one or more carbon atoms with $A^3$.

Specific Embodiment 13. The compound of any one of specific embodiments 6-12 wherein $Z^3$ is a direct bond, —O—, or —OC(=O)—.

Specific Embodiment 14. The compound of any one of specific embodiments 6-12 wherein $Z^3$ is a direct bond.

Specific Embodiment 15. The compound of any one of specific embodiments 6-12 wherein $Z^3$ is —O—.

Specific Embodiment 16. The compound of any one of specific embodiments 6-12 wherein $Z^3$ is —C(=O)O—.

Specific Embodiment 17. The compound of formula (I) as described in specific embodiment 1 or a pharmaceutically acceptable salt, or prodrug thereof, wherein $Z^1$ is selected from:

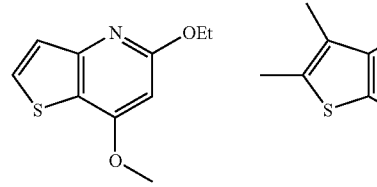

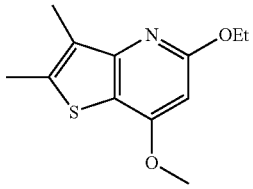

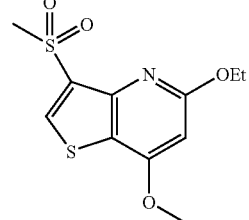

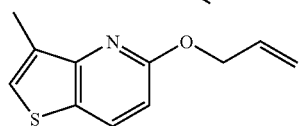

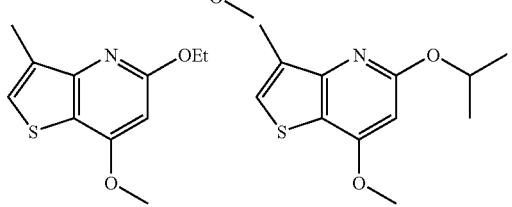

-continued

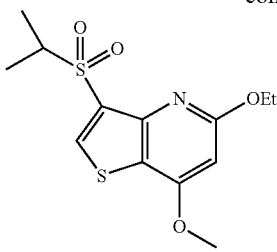

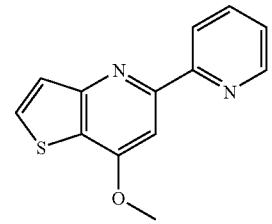

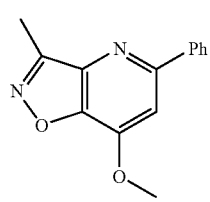

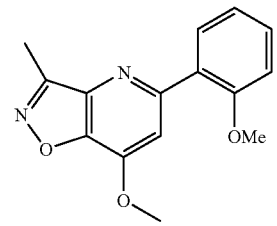

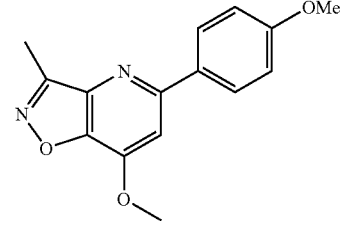

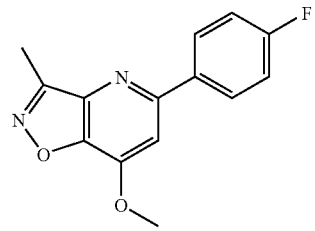

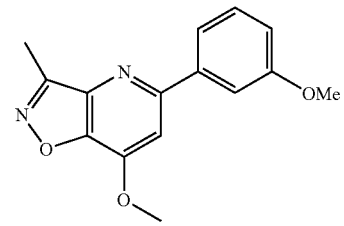

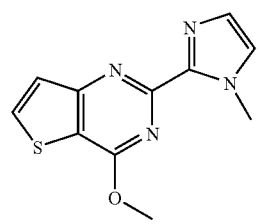

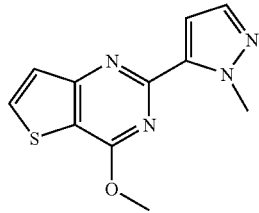

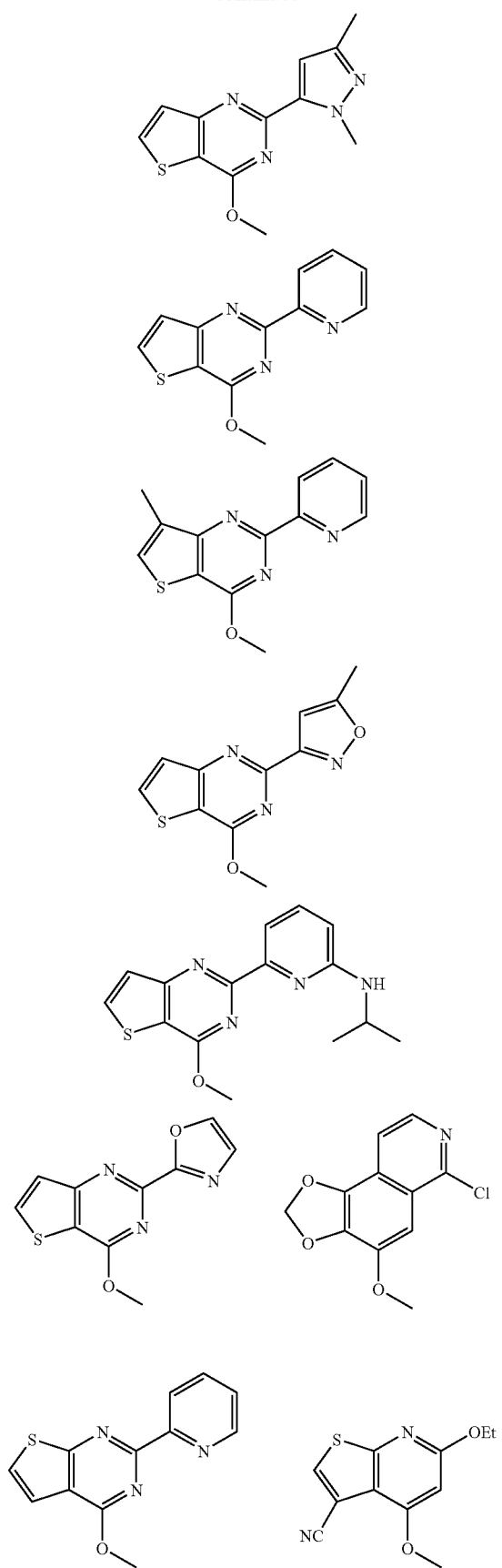
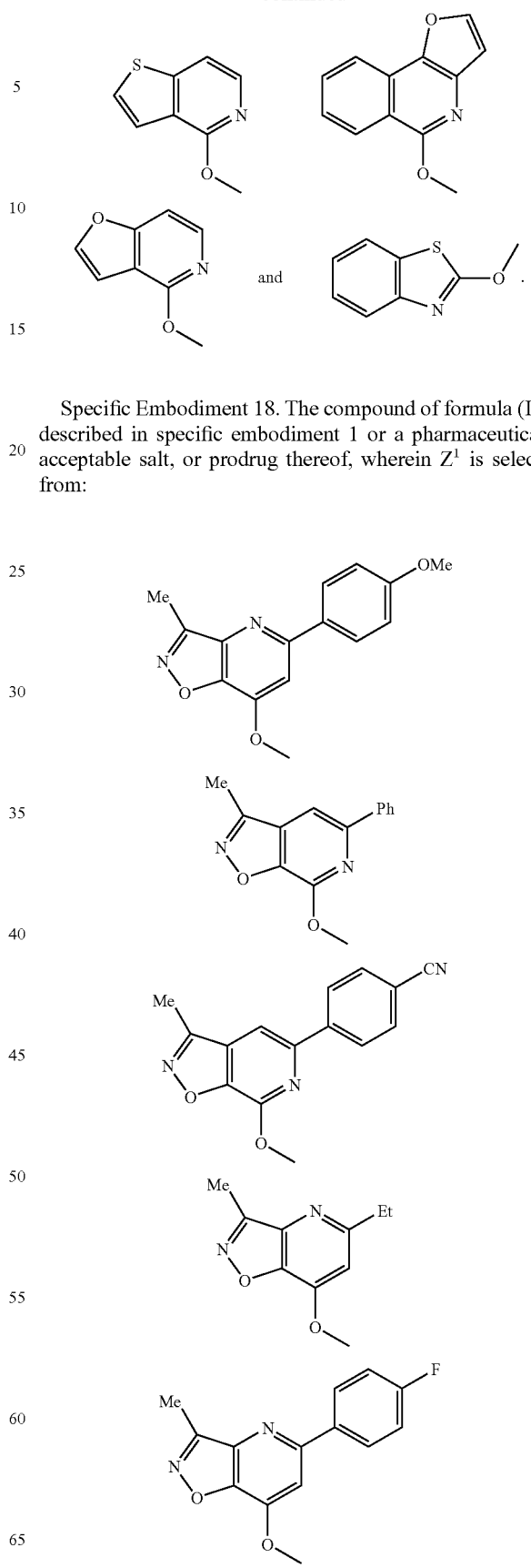
Specific Embodiment 18. The compound of formula (I) as described in specific embodiment 1 or a pharmaceutically acceptable salt, or prodrug thereof, wherein $Z^1$ is selected from:

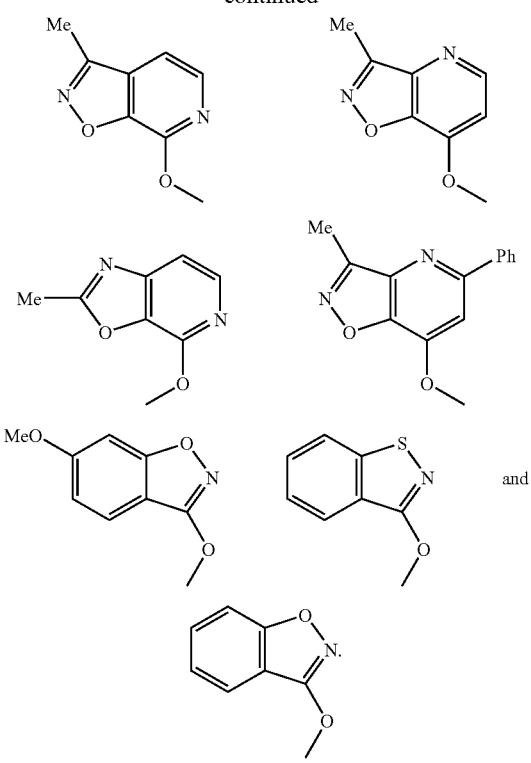
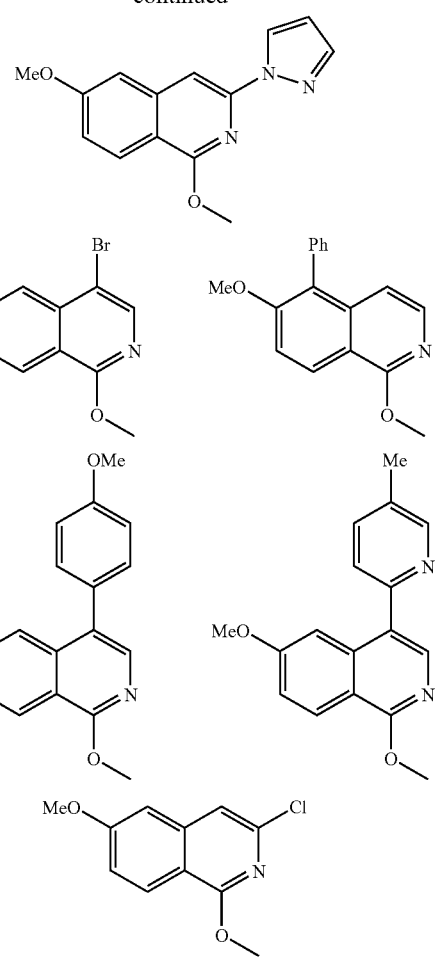
Specific Embodiment 19. The compound of formula (I) as described in specific embodiment 1 or a pharmaceutically acceptable salt, or prodrug thereof, wherein $Z^1$ is selected from:
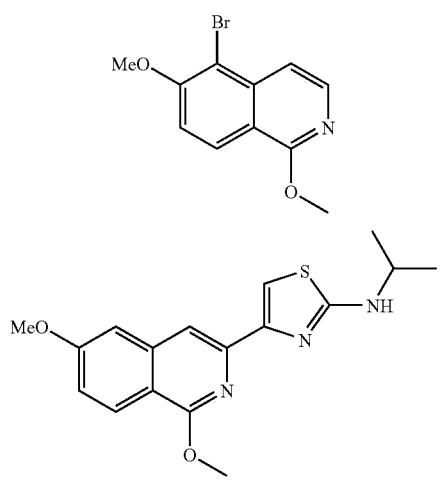
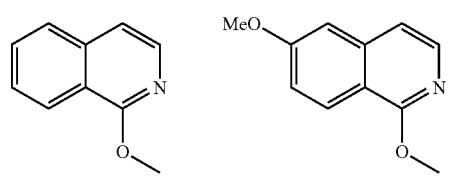
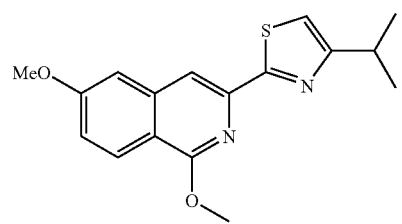
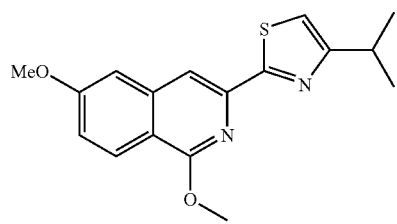

227
-continued
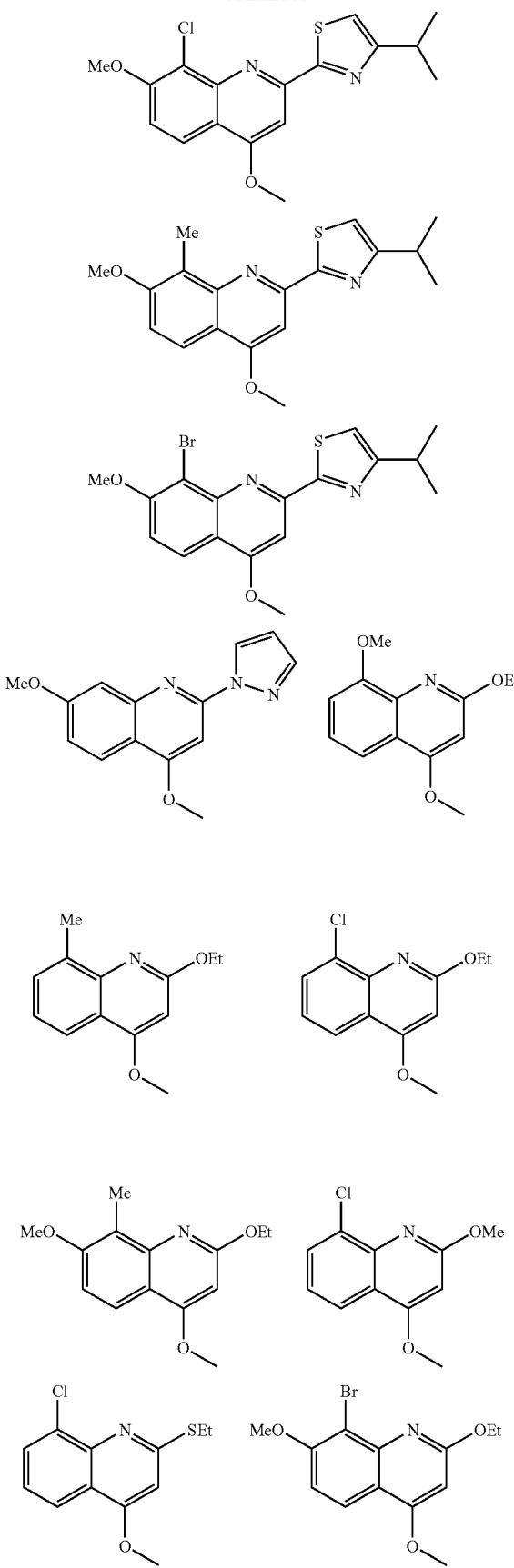
228
-continued
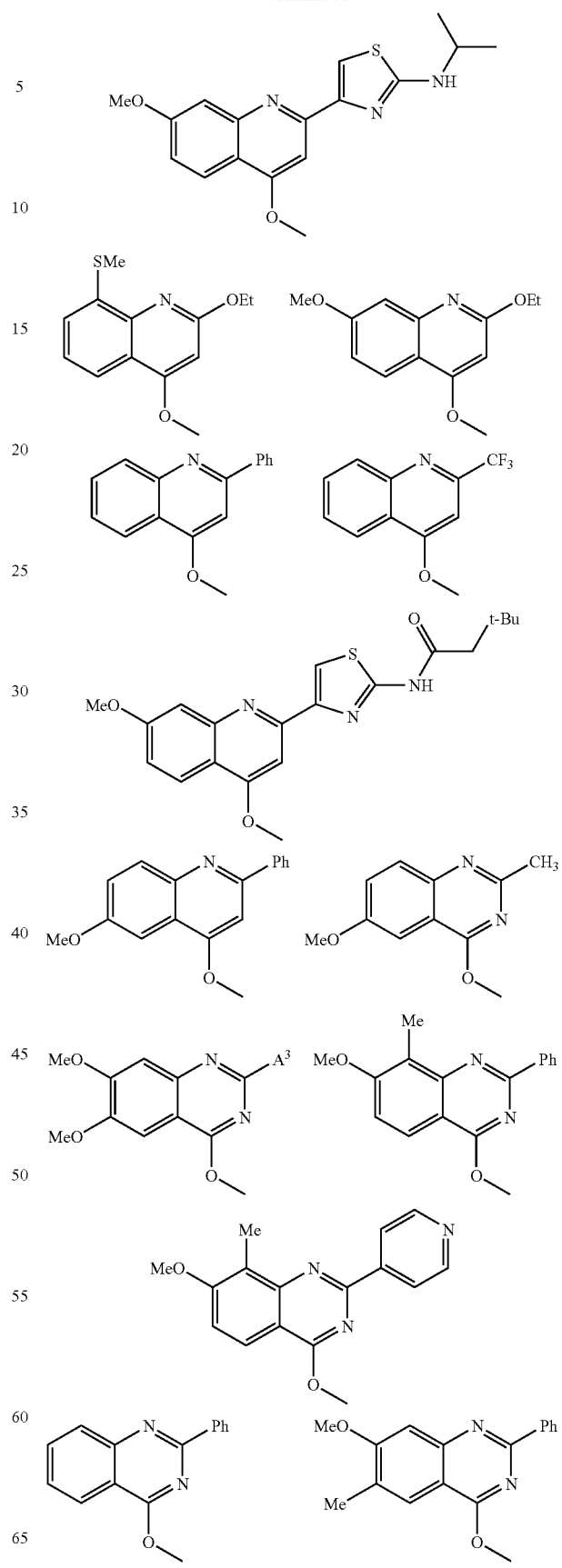

-continued
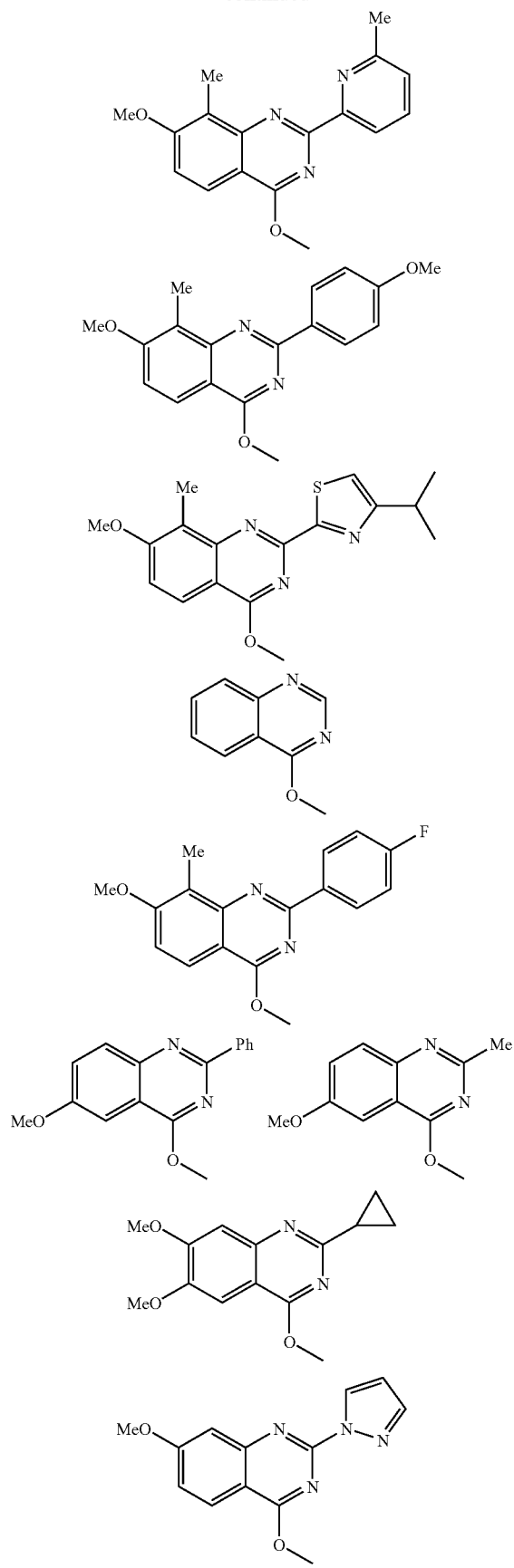
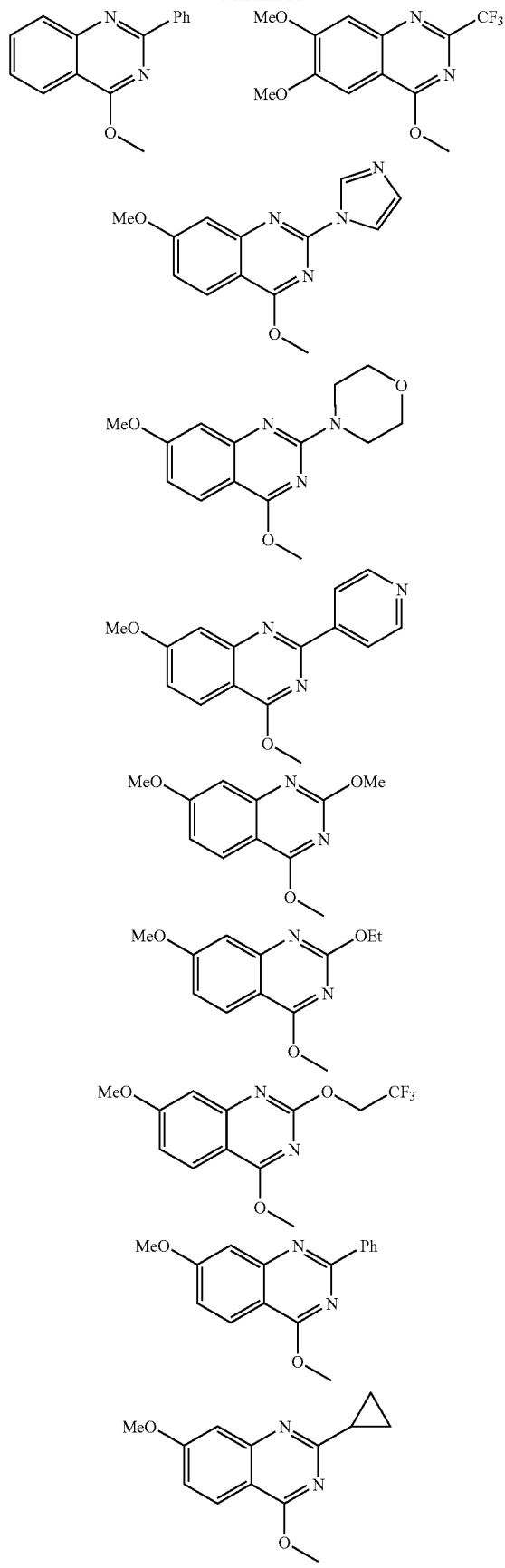

-continued
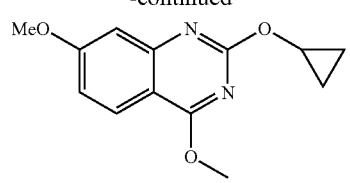
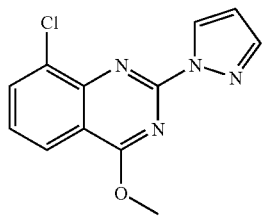
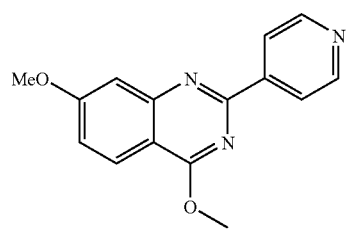
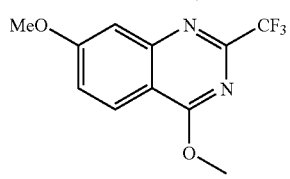
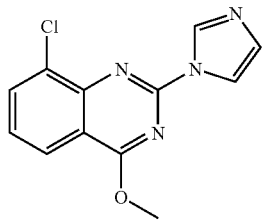
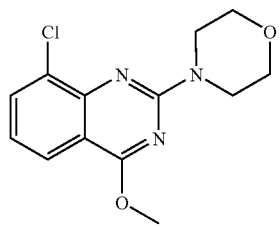
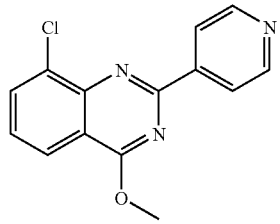
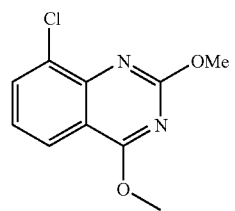
-continued
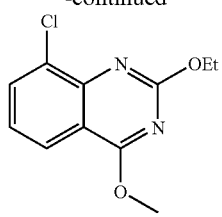
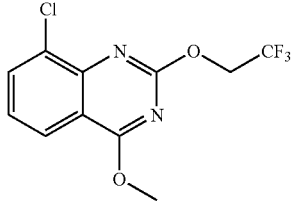
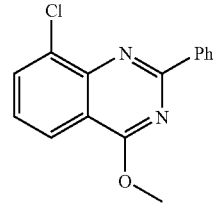
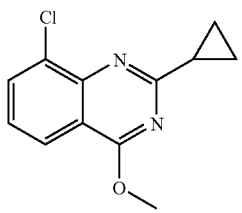
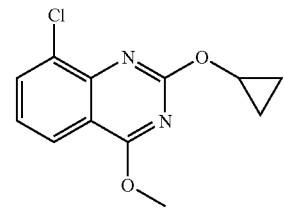
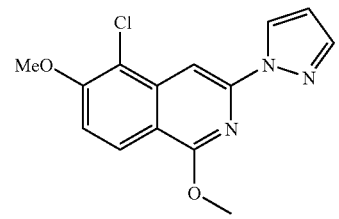
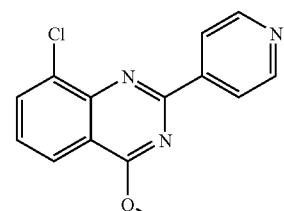
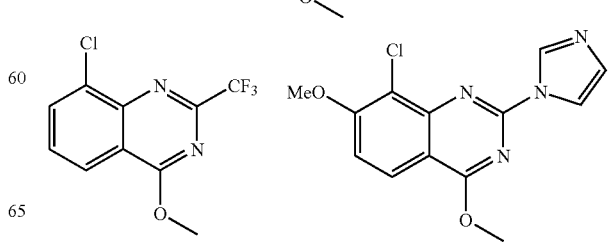

-continued
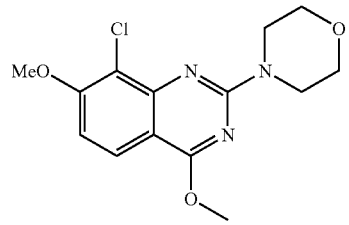
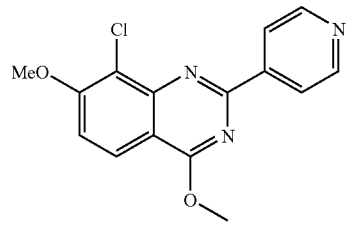
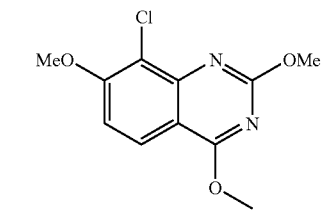
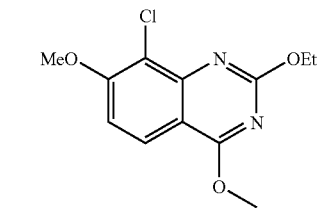
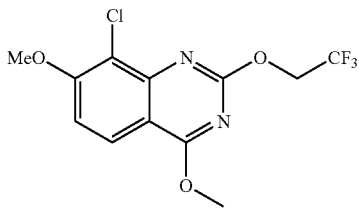
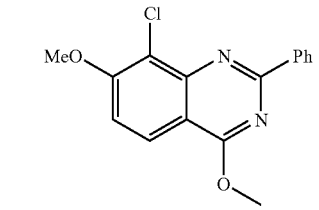
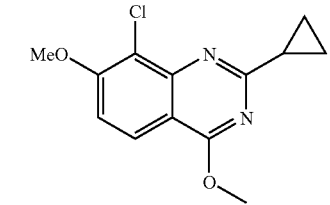
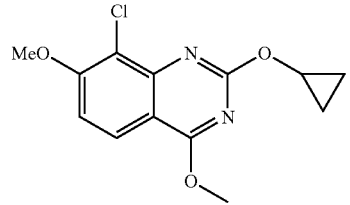
-continued
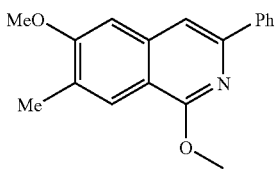
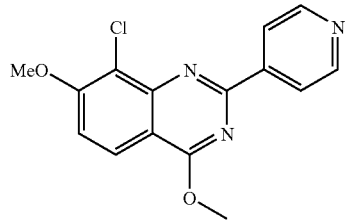
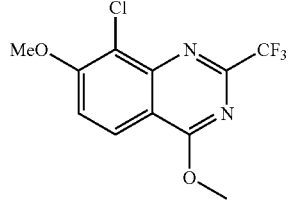
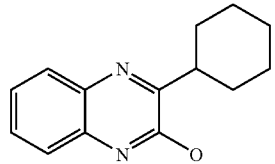
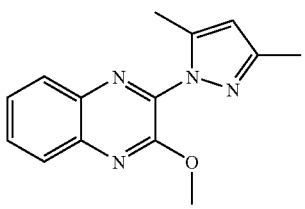
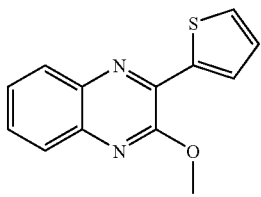
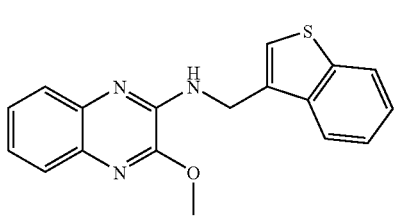
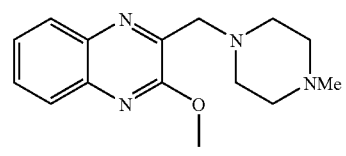

-continued
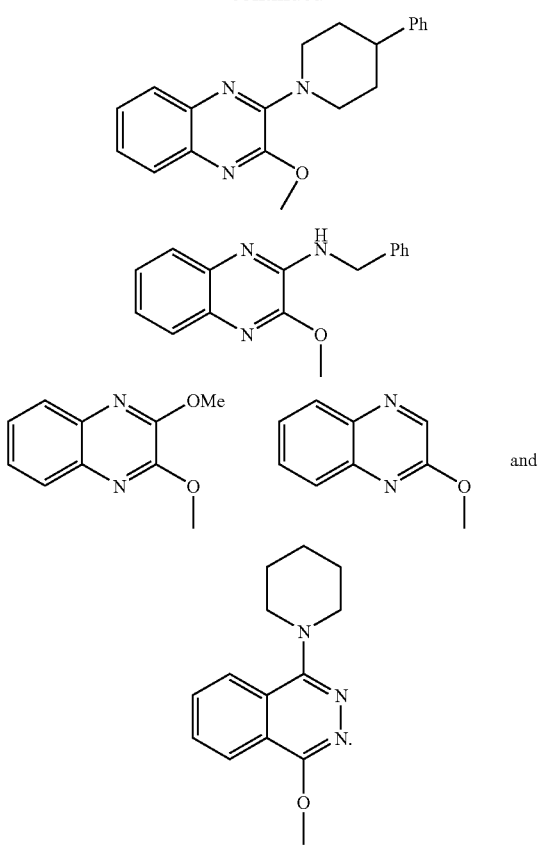
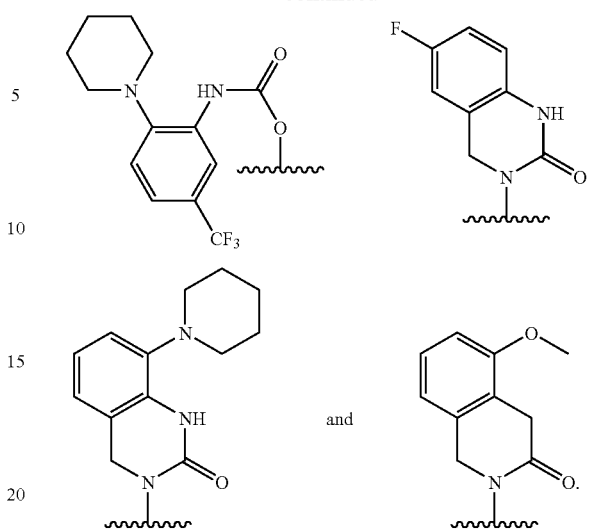
Specific Embodiment 21. The compound of formula (I) as described in specific embodiment 1 or a pharmaceutically acceptable salt, or prodrug thereof, wherein $Z^1$ is selected from the following structures:
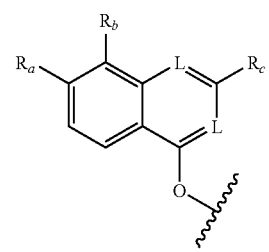
Specific Embodiment 20. The compound of specific embodiment 1 wherein $Z^1$ is selected from:
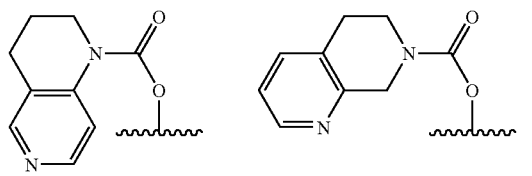
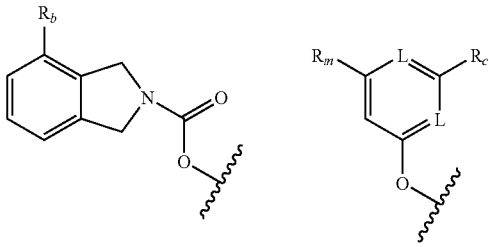
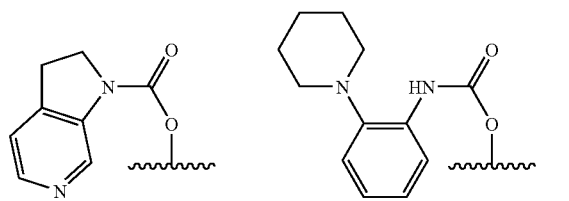
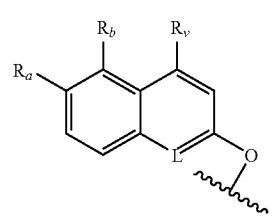
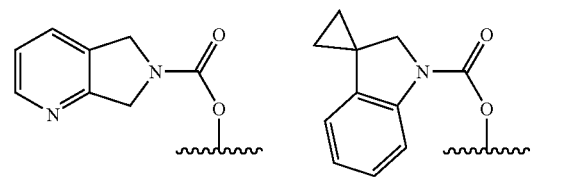
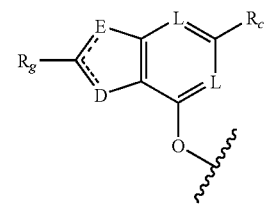

-continued

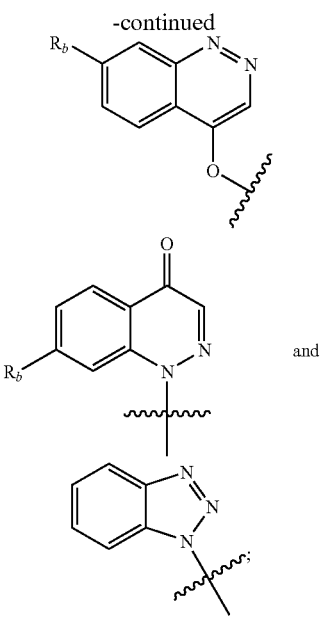

wherein:
each $R_a$ is $R^4$, H, halo, —O(A²), trifluoromethoxy, $NR_sR_t$, C(=O)$NR_sR_t$, S(=O)$_2NR_sR_t$ or (C1-10)alkyl, wherein one or more carbon atoms of said (C1-10)alkyl is optionally replaced by O, S, S(=O), S(=O)$_2$ or $NR_k$ and which (C1-10)alkyl is optionally substituted with one or more hydroxy, halo, cyano, $NR_nR_p$, C(=O)$NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_k$;
each $R_b$ is $R^4$, H, F, Cl, Br, I, CF$_3$, (C1-10)alkyl, or XR³;
each $R_c$ is $R^4$, H, cyano, F, Cl, Br, I, —C(=O)$NR_dR_e$, C(=O)$NR_sR_t$, $NR_sR_t$, $SR_r$, S(O)$R_r$, or S(O)$_2R_r$, S(=O)$_2$ $NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10) alkanoyloxy, (C1-10)alkoxycarbonyl, $NR_nR_p$; $SR_r$, S(O)$R_r$, or S(O)$_2R_r$; wherein any (C1-10)alkoxy of $R_c$ is optionally substituted with one or more halo, (C1-6) alkoxy, or $NR_wR_x$;
$R_d$ and $R_e$ are each independently H, (C1-10)alkyl, or aryl, which is optionally substituted with one or more halo;
each $R_y$ is H, hydroxy, carboxy, cyano, (C1-10)alkyl, (C2-10)alkenyl, (C2-10)alkynyl, (C1-10)alkanoyl, (C1-10) alkoxy, (C1-10)alkanoyloxy, (C1-10)alkoxycarbonyl, $NR_nR_p$, $SR_r$, S(O)$R_r$, or S(O)$_2R_r$;
each $R_k$ is H, $NR_sR_t$, C(=O)$NR_sR_t$, S(=O)$_2NR_sR_t$, A², hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)$_2R_r$;
each $R_u$ is H, A³, C(=O)$NR_sR_t$, or S(=O)$_2NR_sR_t$;
each $R_m$ is H, cyano, F, Cl, Br, I, —C(=O)$NR_dR_e$, —C(=O)$NR_dR_e$, (C1-10)alkoxy, cycloalkyl, or phenyl that is optionally substituted with one or more F, Cl, Br, I, (C1-10)alkyl, or (C1-10)alkoxy;
each L is independently CH or N;
one of E or D is O, S, or $NR_y$ and the other E or D is $CR_u$ or N;
each $R_s$ and $R_t$ is independently H, (C1-10)alkyl, (C2-10) alkenyl, (C2-10)alkynyl, (C1-10)alkanoyl, S(=O)$_2A^2$, (C1-10)alkoxy, (C1-10)alkanoyloxy, or (C1-10)alkoxycarbonyl, which (C1-10)alkyl, (C2-10)alkenyl, (C2-10) alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O);
each $R_v$ is $R^4$, H, F, Cl, Br, I, CF$_3$, (C1-10)alkyl, or XR³
each $R_w$ and $R_x$ is independently H or (C1-10)alkyl or $R_w$ and $R_x$ together with the nitrogen to which they are attached form a azetidine, pyrrolidine, piperidine, piperazine, morpholine, or thiomorpholine ring which ring is optionally substituted with hydroxy;
$R^f$ is H, alkyl, alkenyl, alkynyl, aryl, heteroaryl, or cycloalkyl, which $R^f$ is optionally substituted with one or more $R_g$;
each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or more halo, alkoxy, or cyano; and
each $R_h$ and $R_i$ is independently H, alkyl, or haloalkyl.

Specific Embodiment 22. The compound of formula (I) as described in specific embodiment 1 or a pharmaceutically acceptable salt, or prodrug thereof, wherein:
$Z^1$ is selected from the following structures:

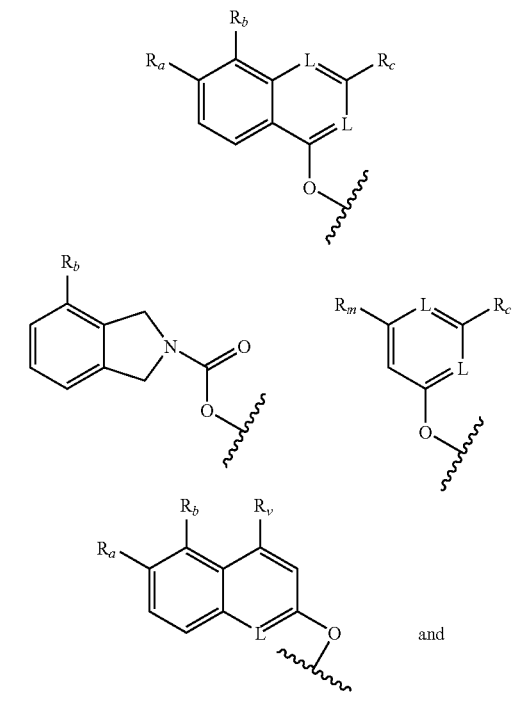

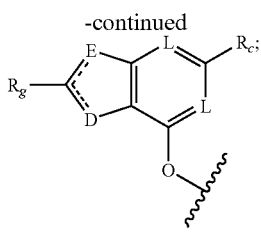

each $R_a$ is $R^4$, H, halo, —O($A^2$), trifluoromethoxy, $NR_sR_t$, C(=O)$NR_sR_t$, S(=O)$_2NR_sR_t$ or (C1-10)alkyl, wherein one or more carbon atoms of said (C1-10)alkyl is optionally replaced by O, S, S(=O), S(=O)$_2$ or $NR_k$ and which (C1-10)alkyl is optionally substituted with one or more hydroxy, halo, cyano, $NR_nR_p$, C(=O)$NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_k$;

each $R_b$ is $R^4$, H, F, Cl, Br, I, $CF_3$, (C1-10)alkyl, or $XR^3$;

each $R_c$ is $R^4$, H, cyano, F, Cl, Br, I, —C(=O)$NR_dR_e$, C(=O)$NR_sR_t$, $NR_sR_t$, $SR_r$, S(O)$R_r$, or S(O)$_2R_r$, S(=O)$_2$ $NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10) alkanoyloxy, (C1-10)alkoxycarbonyl, $NR_nR_p$; $SR_r$, S(O)$R_r$, or S(O)$_2R_r$; wherein any (C1-10)alkoxy of $R_c$ is optionally substituted with one or more halo, (C1-6) alkoxy, or $NR_wR_x$;

$R_d$ and $R_e$ are each independently H, (C1-10)alkyl, or aryl, which is optionally substituted with one or more halo;

each $R_y$ is H, hydroxy, carboxy, cyano, (C1-10)alkyl, (C2-10)alkenyl, (C2-10)alkynyl, (C1-10)alkanoyl, (C1-10) alkoxy, (C1-10)alkanoyloxy, (C1-10)alkoxycarbonyl, $NR_nR_p$, $SR_r$, S(O)$R_r$, or S(O)$_2R_r$;

each $R_k$ is H, $NR_sR_t$, C(=O)$NR_sR_t$, S(=O)$_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, S(O)$R_r$, or S(O)$_2R_r$;

each $R_u$ is H, $A^3$, C(=O)$NR_sR_t$, or S(=O)$_2NR_sR_t$;

each $R_m$ is H, cyano, F, Cl, Br, I, —C(=O)$NR_dR_e$, —C(=O)$NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_y$ and the other E or D is $CR_u$ or N;

each $R_s$ and $R_t$ is independently H, (C1-10)alkyl, (C2-10) alkenyl, (C2-10)alkynyl, (C1-10)alkanoyl, S(=O)$_2A^2$, (C1-10)alkoxy, (C1-10)alkanoyloxy, or (C1-10)alkoxycarbonyl, which (C1-10)alkyl, (C2-10)alkenyl, (C2-10) alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O);

each $R_v$ is $R^4$, H, F, Cl, Br, I, $CF_3$, (C1-10)alkyl, or $XR^3$ each $R_w$ and $R_x$ is independently H or (C1-10)alkyl or $R_w$ and $R_x$ together with the nitrogen to which they are attached form a azetidine, pyrrolidine, piperidine, piperazine, morpholine, or thiomorpholine ring which ring is optionally substituted with hydroxy;

$R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or motr halo or cyano; and each $R_h$ and $R_i$ is independently H, alkyl, or haloalkyl.

Specific Embodiment 23. The compound of formula (I) as described in specific embodiment 21 or a pharmaceutically acceptable salt, or prodrug thereof, wherein $Z^1$ is selected from the following structures:

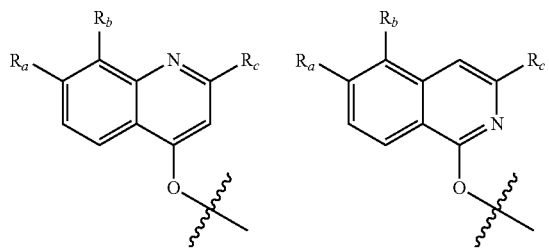

Specific Embodiment 24. The compound of specific embodiment 1 wherein $Z^1$ is selected from the following structures:

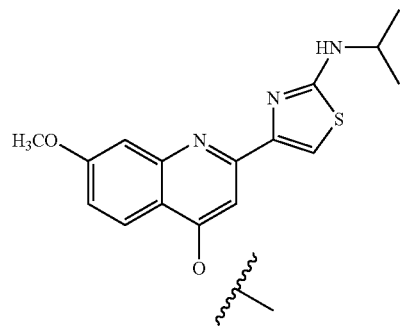

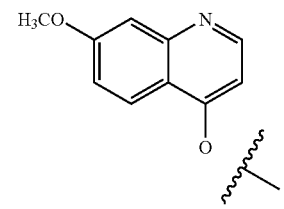

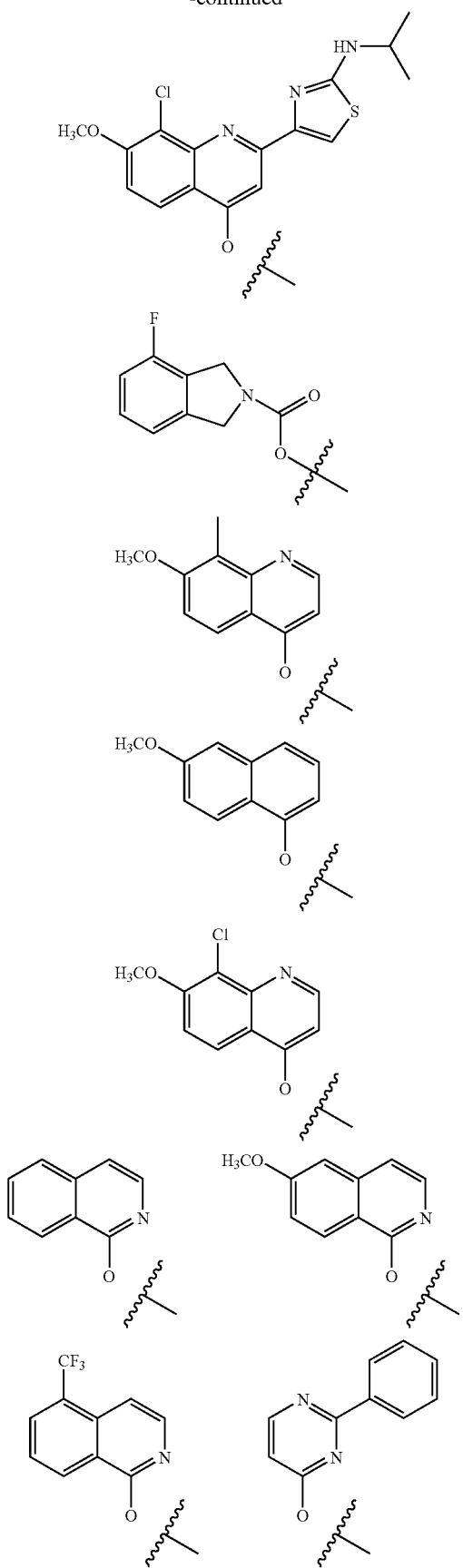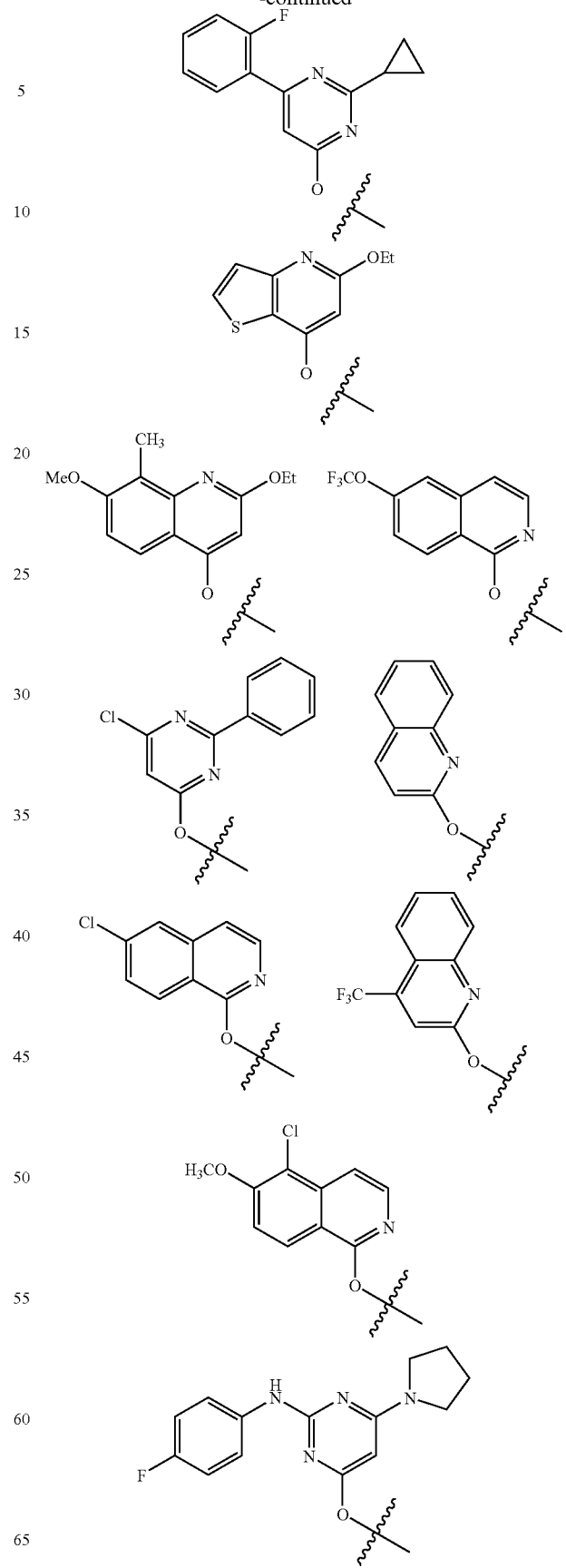

243
-continued
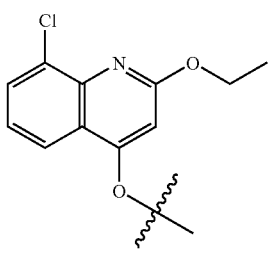
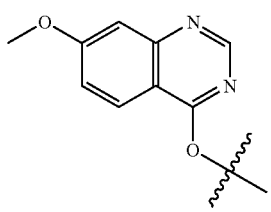
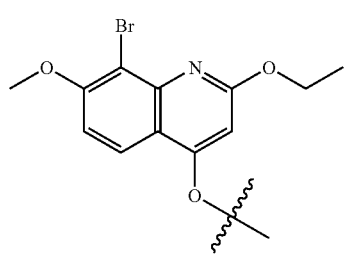
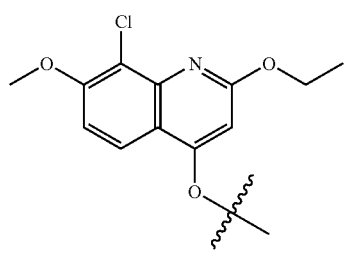
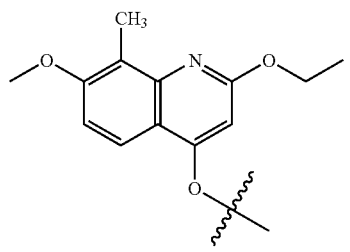
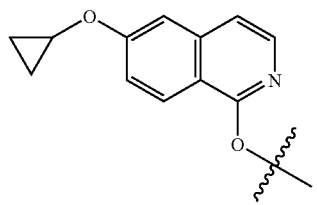
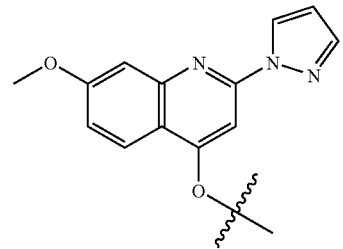
244
-continued
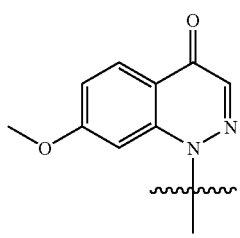
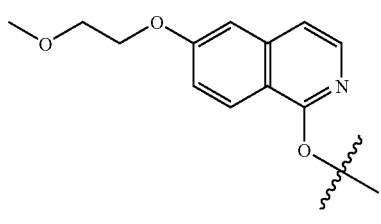
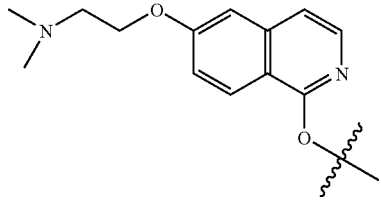
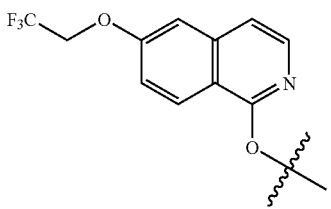
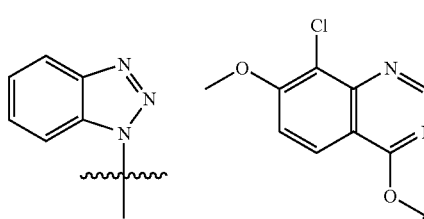
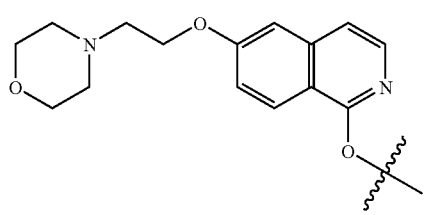
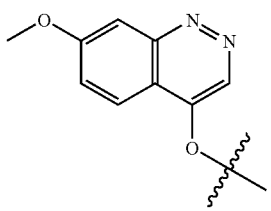

-continued
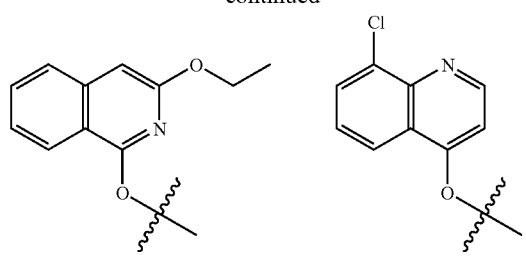
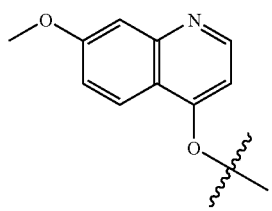
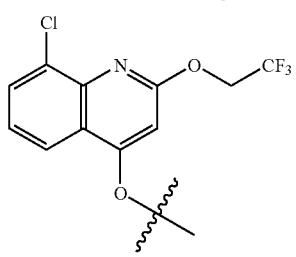
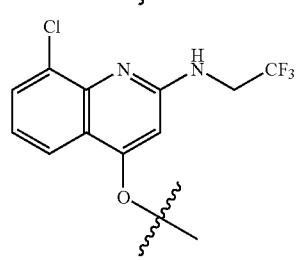
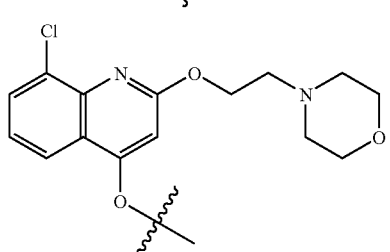
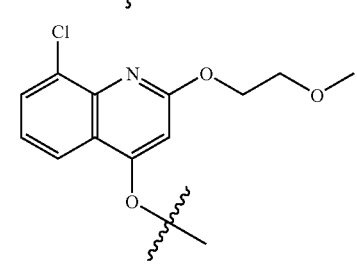
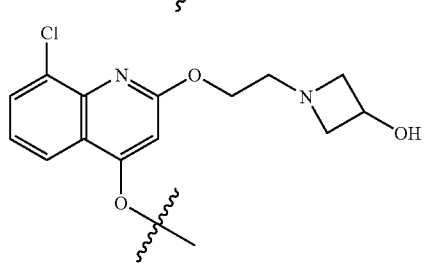
-continued
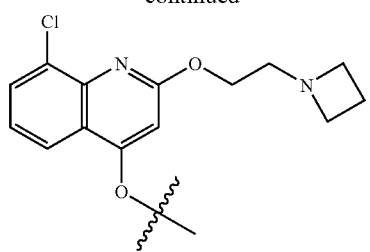
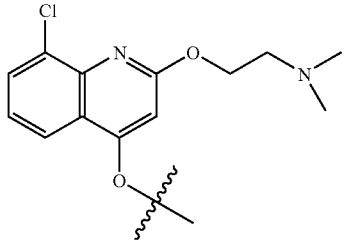
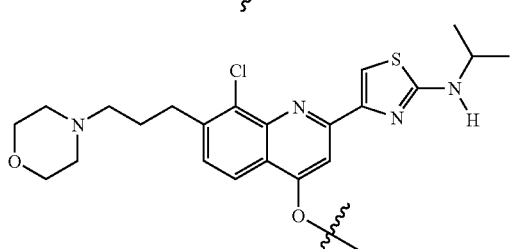
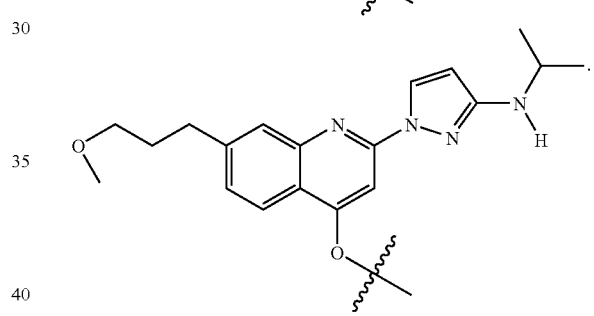
and
Specific Embodiment 25. The compound of any one of specific embodiments 21-23 wherein $R_c$ is a heteroaryl ring selected from:
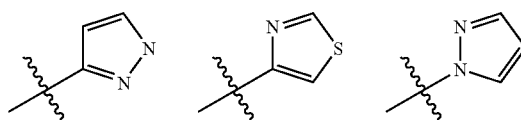
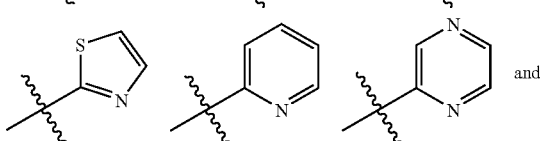 and
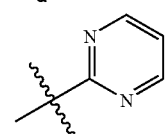
which heteroaryl ring is optionally substituted with one or more (C1-10)alkyl, halo, or $NR_nR_p$; wherein each $R_n$ and $R_p$ is independently H or (C1-10)alkyl.

Specific Embodiment 26. The compound of any one of specific embodiments 21-23 wherein each $R_c$ is selected from:
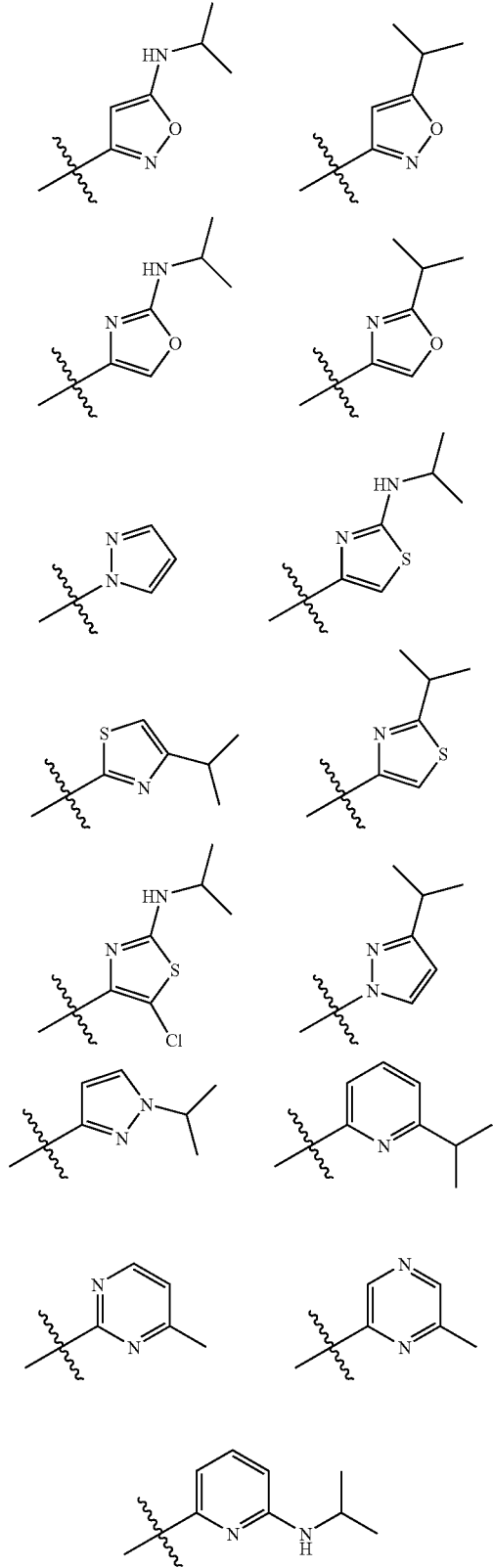
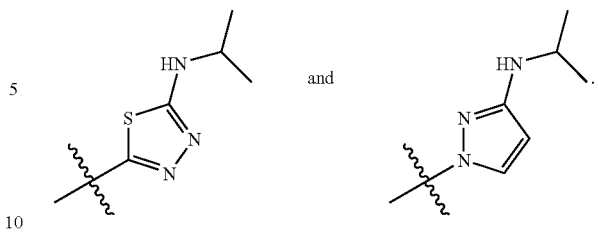
Specific Embodiment 27. The compound of any one of specific embodiments 21-23 wherein each $R_c$ is selected from:
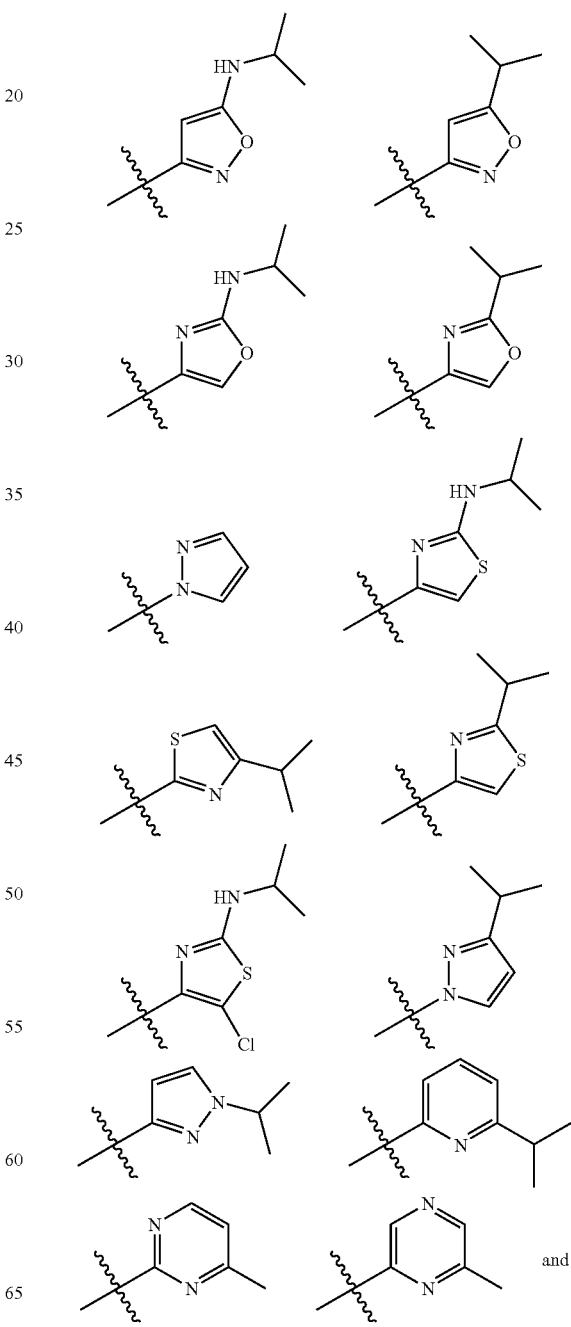

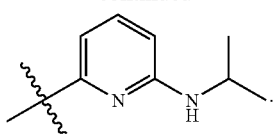

Specific Embodiment 28. The compound of any one of specific embodiments 21-23 wherein $R_b$ is H, F, Cl, Br, methyl or trifluoromethyl.

Specific Embodiment 29. The compound of any one of specific embodiments 21-23 wherein $R_b$ is H, F, Cl, methyl or trifluoromethyl.

Specific Embodiment 30. The compound of any one of specific embodiments 21-23 wherein $R_a$ is H, methoxy, trifluoromethoxy, chloro, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, 2-morpholinoethoxy, cyclopropyloxy 2,2,2-trifluoroethoxy or 2-(N,N-diemthylamino)ethoxy.

Specific Embodiment 31. The compound of any one of specific embodiments 21-23 wherein $R_a$ is H, methoxy, trifluoromethoxy, chloro, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, or 2-morpholinoethoxy.

Specific Embodiment 32. The compound of specific embodiment 1 wherein $Z^1$ is selected from the following structures:

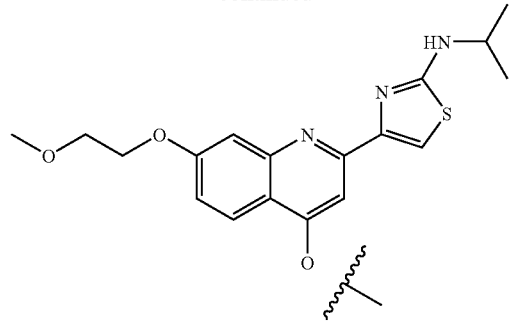

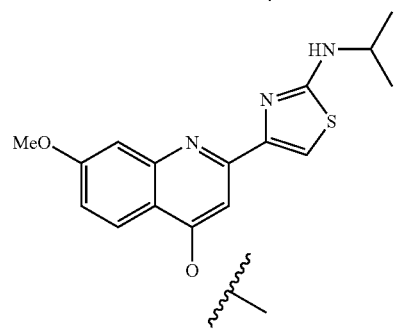

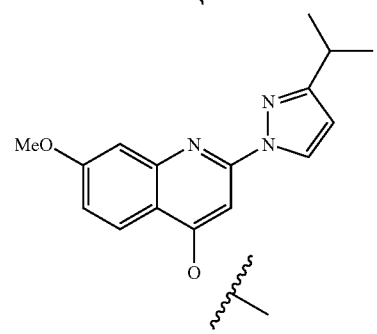

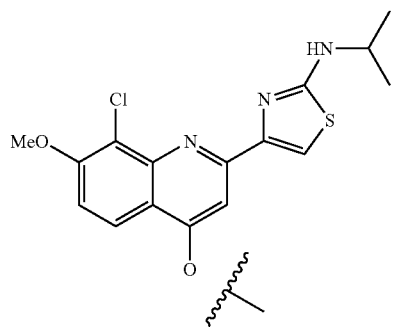

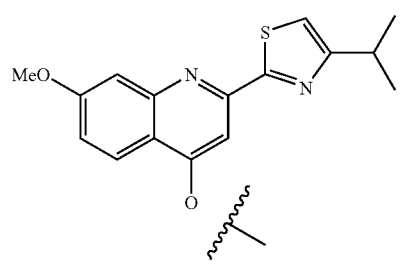

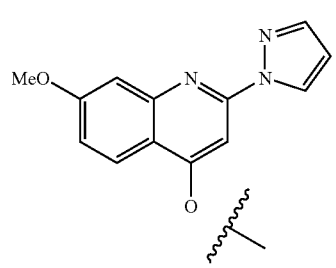

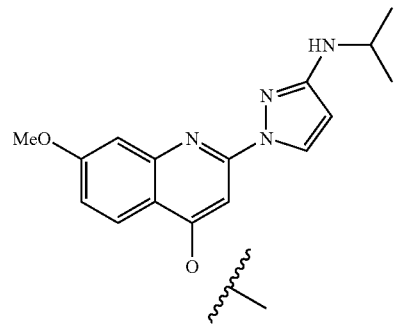

251
-continued
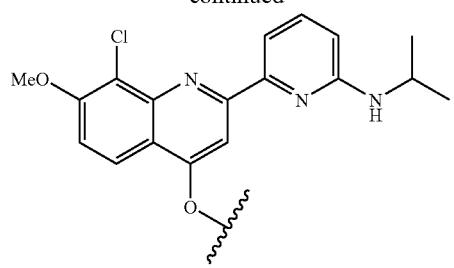
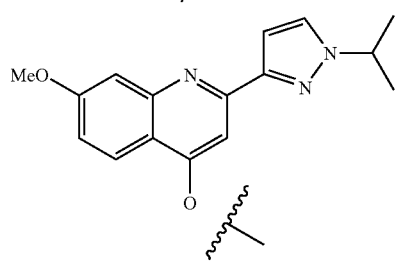
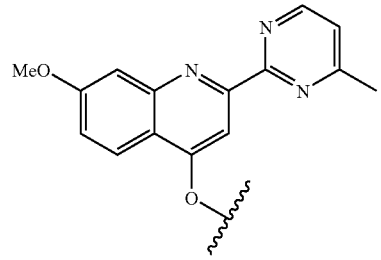
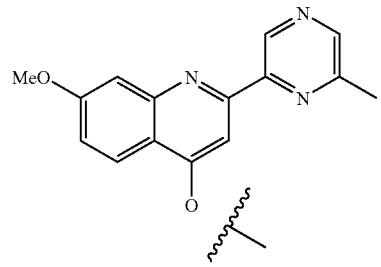
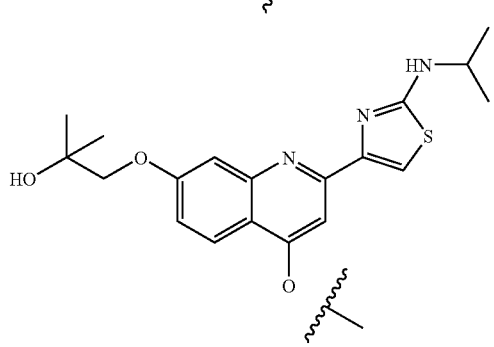
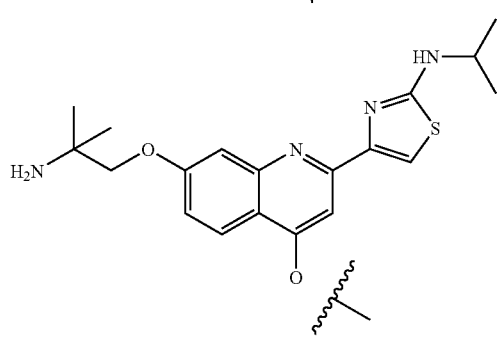
252
-continued
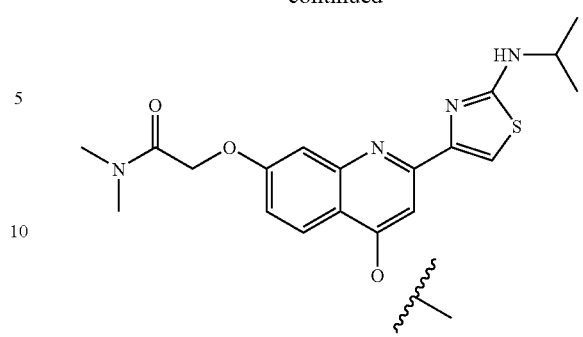
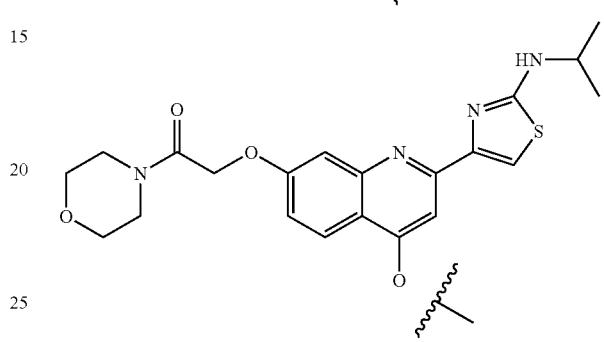
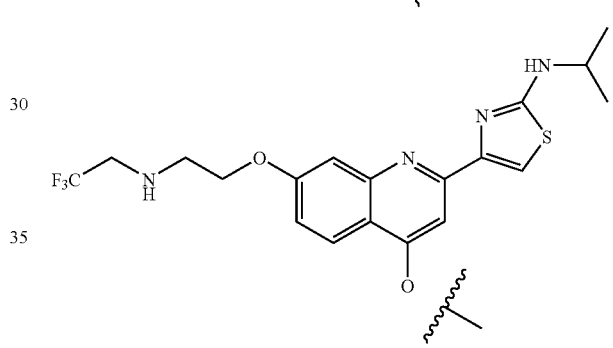
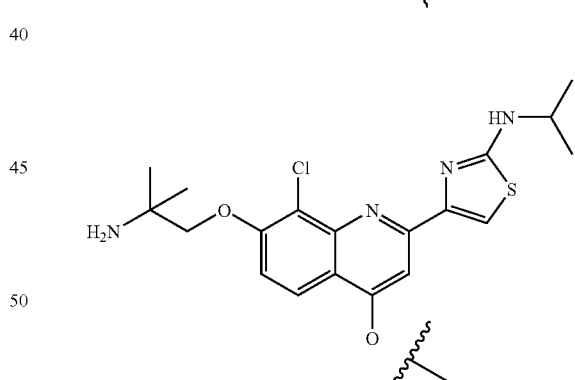
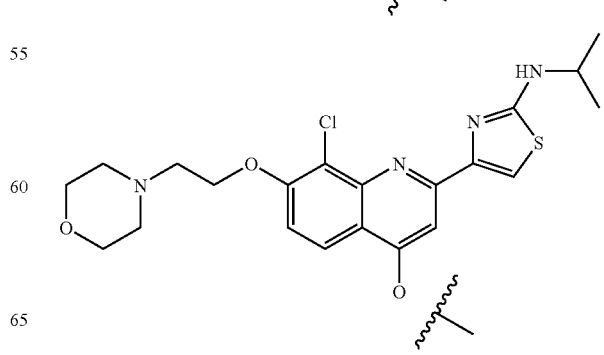

253
-continued
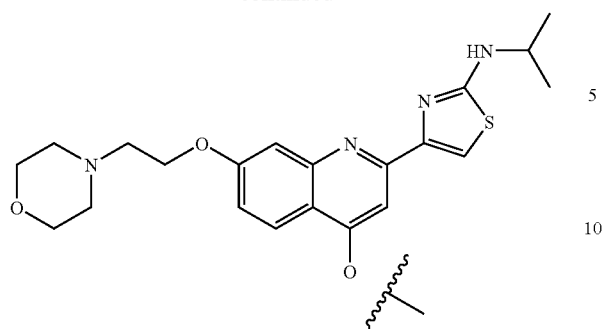
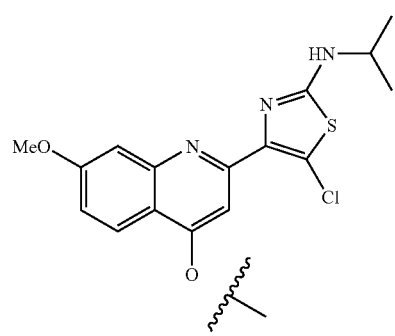
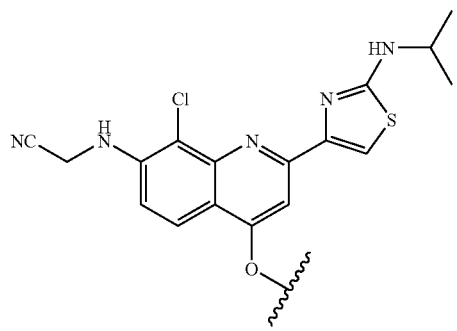
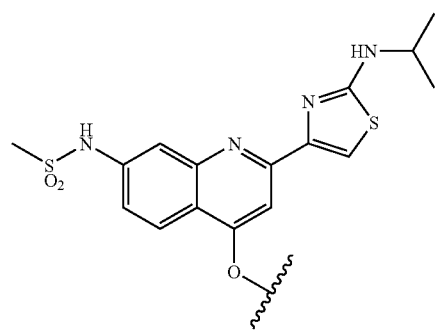
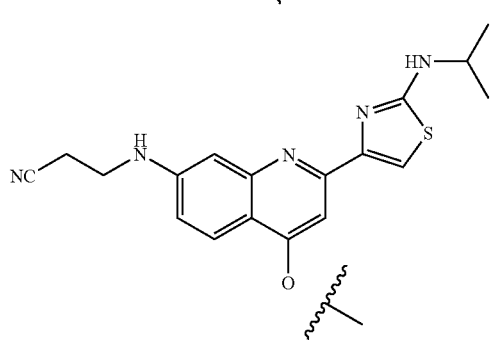
254
-continued
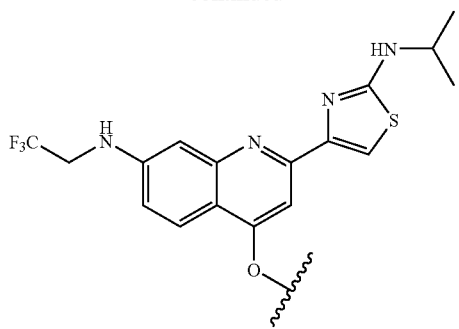
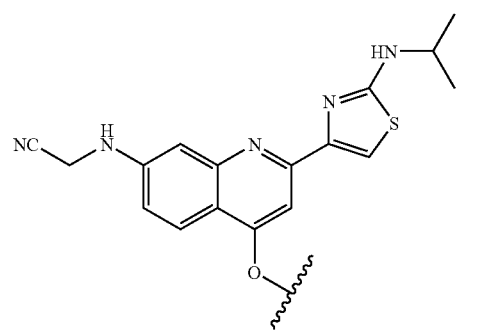
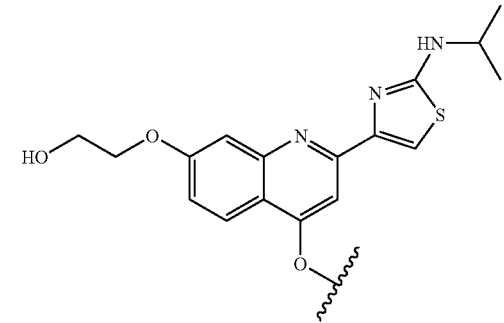 [SMILES: *Oc1cc(-c2csc(NC(C)C)n2)nc2cc(OCCO)ccc12]
and
Specific Embodiment 33. The compound of specific embodiment 1 wherein $Z^1$ is selected from the following structures:
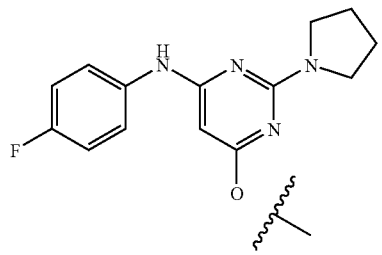
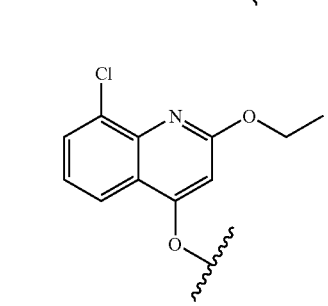

255
-continued
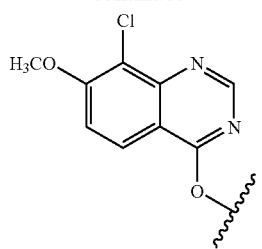
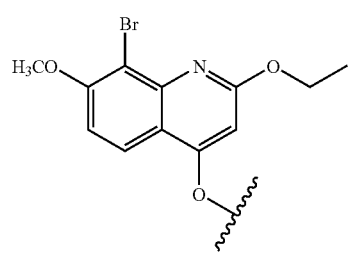
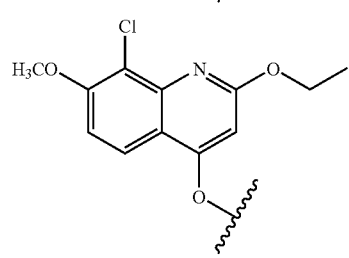
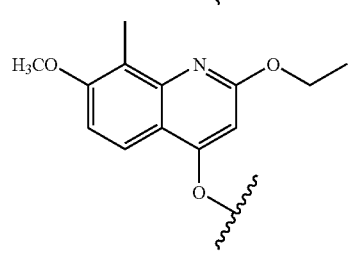
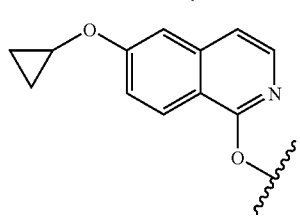
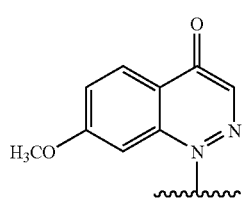
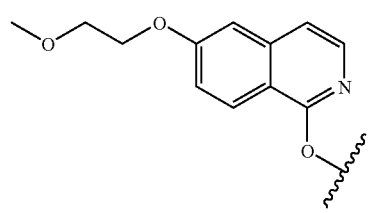
256
-continued
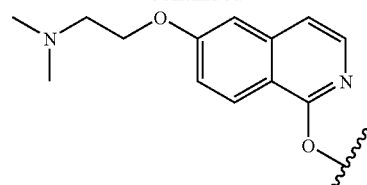
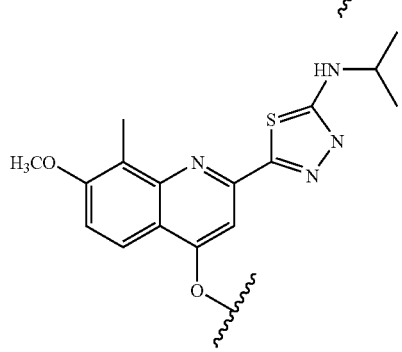
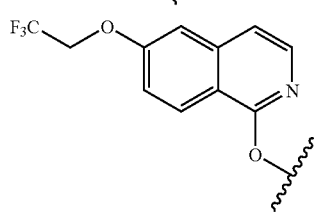
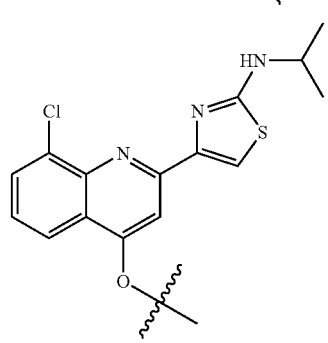
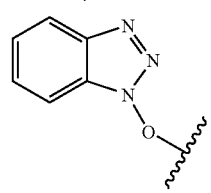
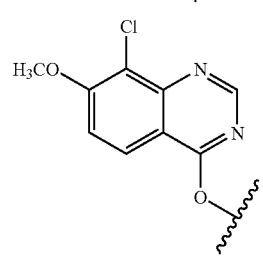
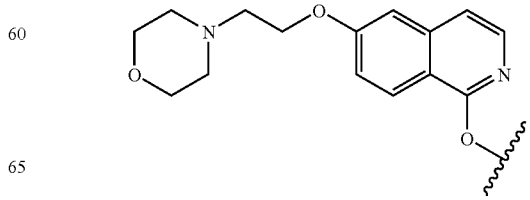

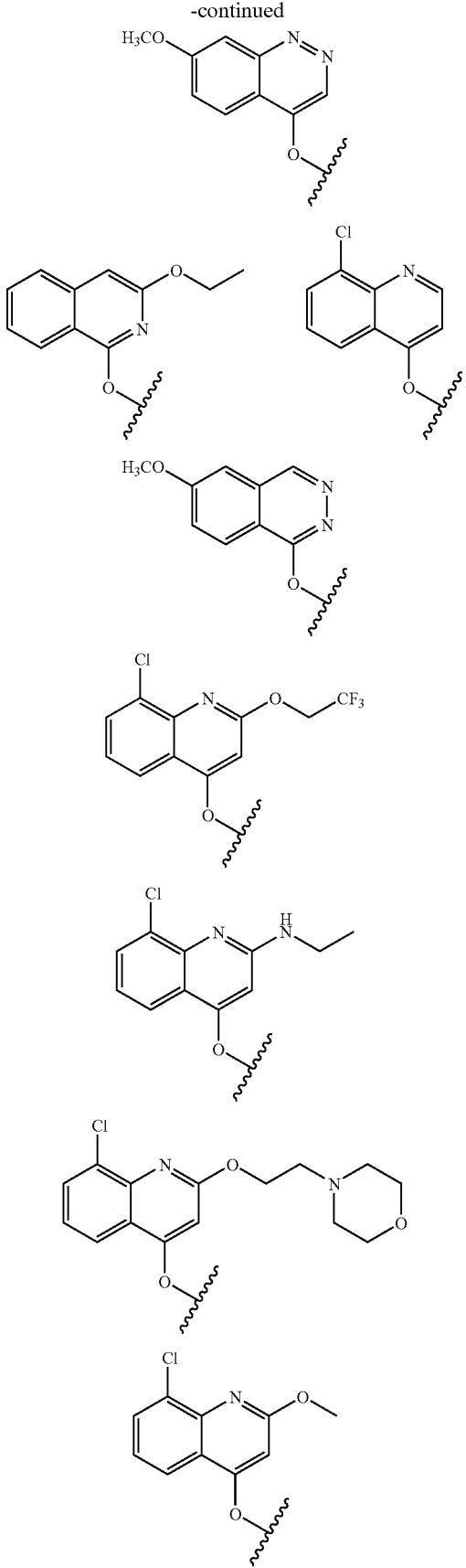
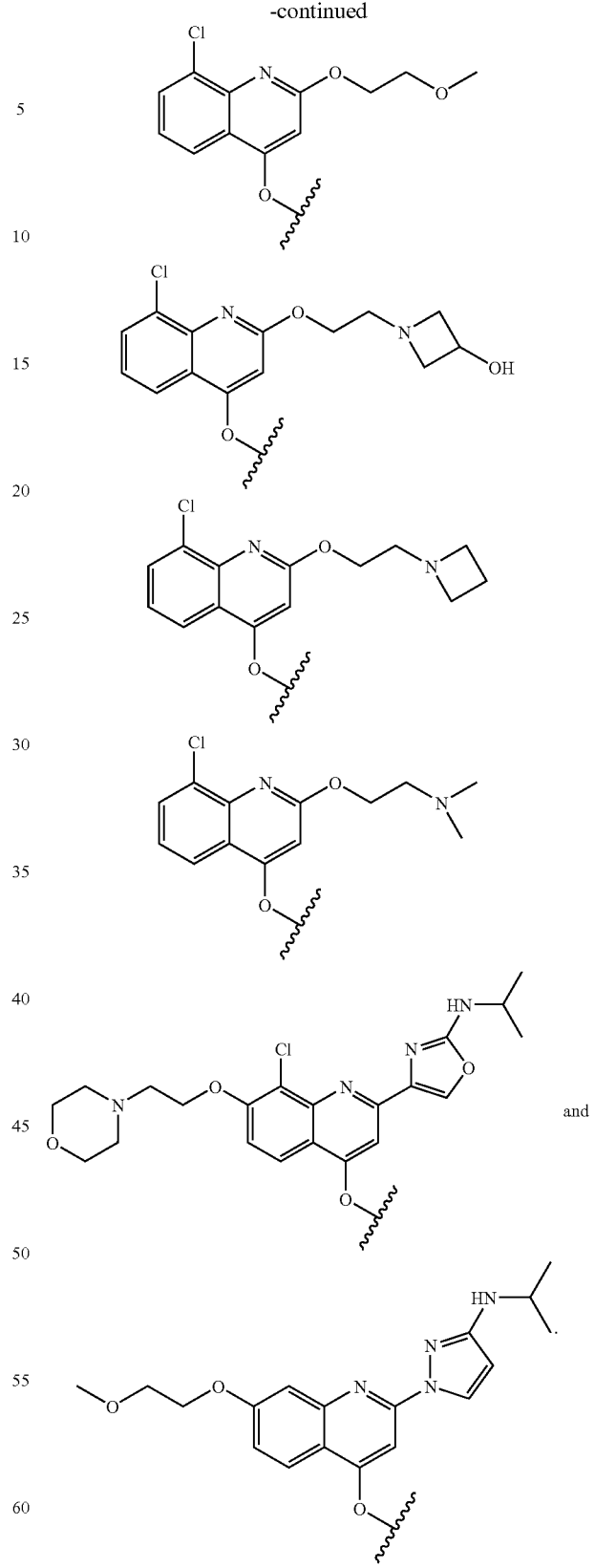
Specific Embodiment 34. The compound of any one of specific embodiments 21-23 wherein each $R_c$ is selected from:

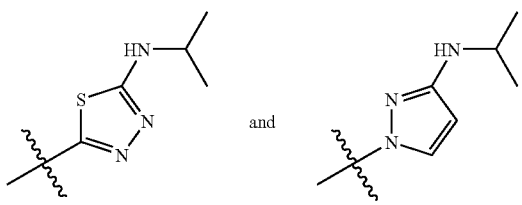 and 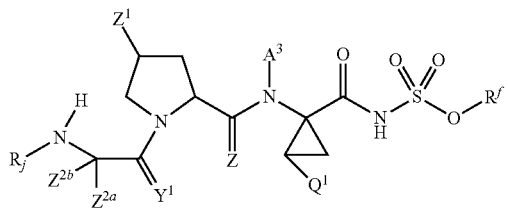

Specific Embodiment 35. The compound of any one of specific embodiments 1-34 wherein $R^f$ is aryl, heteroaryl, or cycloalkyl, which $R^f$ is optionally substituted with one to three $A^3$.

Specific Embodiment 36. The compound of any one of specific embodiments 1-34 wherein $R^f$ is cyclopropyl which $R^f$ is optionally substituted by up to four $A^3$.

Specific Embodiment 37. The compound of any one of specific embodiments 1-34 wherein $R^f$ is cyclopropyl which $R^f$ is optionally substituted by one $A^3$.

Specific Embodiment 38. The compound of any one of specific embodiments 1-34 wherein $R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or motr halo or cyano;

each $R_d$ is independently H, (C1-10)alkyl, or aryl, which is optionally substituted with one or more halo; and each $R_h$ and $R_i$ is independently H, alkyl, or haloalkyl.

Specific Embodiment 39. The compound of any one of specific embodiments 1-34 wherein $R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; and each $R_h$ and $R_i$ is independently H, alkyl, or haloalkyl.

Specific Embodiment 40. The compound of The compound of any one of specific embodiments 1-34 wherein $R^f$ is phenyl, cyclopropyl, 2-fluorophenyl, 4-chlorophenyl, 2-chlorophenyl, 2,6-dimethylphenyl, 2-methylphenyl, 2,2-dimethylpropyl, 2,2-difluoroethyl, 2,2,2-trifluoroethyl, or 1-methylcyclopropyl.

Specific Embodiment 41. The compound of any one of specific embodiments 1-34 wherein $R^f$ is cyclopropyl.

Specific Embodiment 42. The compound of specific embodiment 2 wherein $R^f$ is 1-methylcyclopropyl.

Specific Embodiment 43. The compound of any one of specific embodiments 1-42 which is a compound of formula (II):

(II)

![Formula II structure]

or a pharmaceutically acceptable salt, or prodrug thereof, wherein: $R_j$ is tert-butoxycarbonyl, cyclopentyloxycarbonyl, 2,2,2-trifluoro-1,1-dimethylethyloxycarbonyl, tert-butylaminocarbonyl, 1-methylcyclopropyloxycarbonyl, 2-(N,N-dimethylamino)-1-1-dimethylethoxycarbonyl, 2-morpholino-1-1-dimethylethoxycarbonyl, tetrahydrofur-3-yloxycarbonyl, or

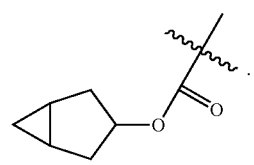 [SMILES: *C(=O)OC1CC2CC2C1 ; "."]

Specific Embodiment 44. The compound of any one of specific embodiments 1-43 wherein:

$Q^1$ is (C1-10)alkyl, (C2-10)alkenyl, or (C2-10)alkynyl which $Q^1$ is optionally substituted with $R_c$; or $Q^1$ and $Z^{2a}$ taken together with the atoms to which they are attached form a heterocycle, which heterocycle may optionally be substituted with one or more oxo (=O), $R^4$, or $A^3$;

each $R_c$ is $R^4$, H, cyano, F, Cl, Br, I, —C(=O)$NR_dR_e$, C(=O)$NR_sR_t$, $NR_sR_t$, $SR_r$, S(O)$R_r$, or S(O)$_2R_r$, S(=O)$_2$ $NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, S(O)$R_r$, or S(O)$_2R_r$; wherein any (C1-10)alkoxy of $R_c$ is optionally substituted with one or more halo, (C1-6) alkoxy, or $NR_wR_x$;

$R_d$ and $F_e$ are each independently H, (C1-10)alkyl, or aryl, which is optionally substituted with one or more halo;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl; or (C1-10)alkoxycarbonyl;

each $R_s$ and $R_t$ is independently H, (C1-10)alkyl, (C2-10)alkenyl, (C2-10)alkynyl, (C1-10)alkanoyl, S(=O)$_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more R$^4$, halo hydroxy, carboxy, cyano, or (C1-10)alkoxy; or R$_s$ and R$_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O) and;

each R$_w$ and R$_x$ is independently H or (C1-10)alkyl or R$_w$ and R$_x$ together with the nitrogen to which they are attached form a azetidine, pyrrolidine, piperidine, piperazine, morpholine, or thiomorpholine ring which ring is optionally substituted with hydroxyl.

Specific Embodiment 45. The compound of specific embodiment 43 wherein Z is O; Y$^1$ is O; and one of Z$^{2a}$ or Z$^{2b}$ is hydrogen.

Specific Embodiment 46. The compound of any one of specific embodiments 1-43 wherein Q$^1$ is vinyl, ethyl, cyanomethyl, propyl, 2-fluoroethyl, 2,2-difluoroethyl, or 2-cyanoethyl.

Specific Embodiment 47. The compound of any one of specific embodiments 1-43 wherein Q$^1$ and Z$^{2a}$ taken together with the atoms to which they are attached form a 12-18 membered heterocycle, which heterocycle may optionally be substituted with one or more oxo (=O) or A$^3$.

Specific Embodiment 48. The compound of any one of specific embodiments 1-43 which is a compound of formula (III):

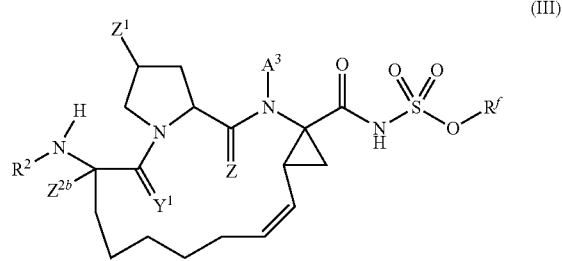

(III)

or a pharmaceutically acceptable salt, or prodrug thereof.

Specific Embodiment 49. The compound of any one of specific embodiments 1-43 which is a compound of formula (IV):

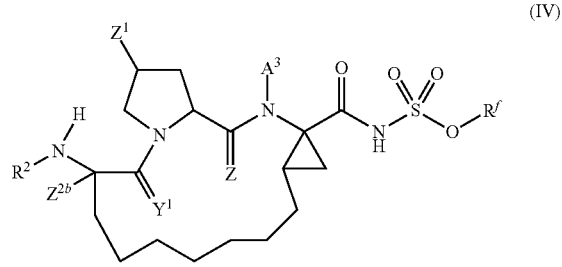

(IV)

or a pharmaceutically acceptable salt, or prodrug thereof.

Specific Embodiment 50. The compound of any one of specific embodiments 1-43 wherein Z$^{2a}$ is tert-butyl, 1-methylcyclohexyl, tetrahydropyran-4-yl, 1-methylcyclohexyl, 4,4-difluorocyclohexyl, 2,2,2-trifluoro-1-trifluoromethyl-ethyl, or cyclopropyl.

Specific Embodiment 51. The compound of specific embodiment 1 or a pharmaceutically acceptable salt, or prodrug thereof, wherein:
R$^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more A R$^2$ is selected from,
a) —C(Y$^1$)(A$^3$),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
where said alkyl, cycloalkyl and alkyl-cycloalkyl may optionally be mono- or di-substituted with substituents selected from hydroxy and O—(C1-4)alkyl, or
where each of said alkyl-groups may optionally be mono-, di- or tri-substituted with halogen, or
where each of said cycloalkyl groups being 5-, 6- or 7-membered, one or two —CH$_2$— groups not being directly linked to each other may be optionally replaced by —O— such that the O-atom is linked to the N atom to which R$^2$ is attached via at least two C-atoms,
c) phenyl, (C1-3)alkyl-phenyl, heteroaryl or (C1-3)alkyl-heteroaryl,
wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen;
d) —S(O)$_2$(A$^3$); or
e) —C(Y$^1$)—X—Y;
R$^3$ is H or (C1-6)alkyl;
Y$^1$ is independently O, S, N(A$^3$), N(O)(A$^3$), N(OA$^3$), N(O)(OA$^3$) or N(N(A$^3$)(A$^3$));
Z is O, S, or NR$^3$;
Z is selected from the following structures:

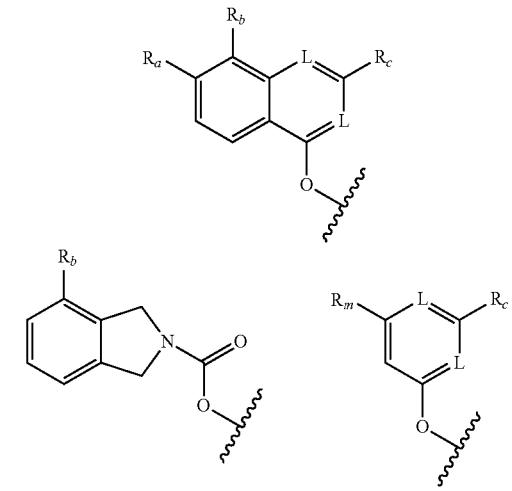

-continued

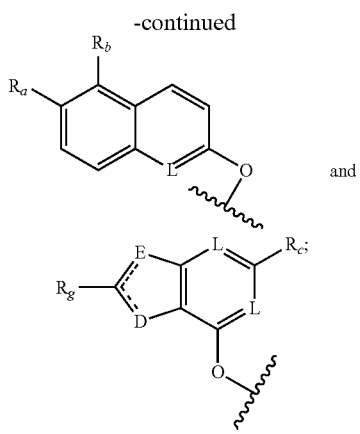

and each $R_a$ is $R^4$, H, halo, trifluoromethoxy, $NR_sR_t$, C(=O)$NR_sR_t$, S(=O)$_2NR_sR_t$, or (C1-10)alkyl, wherein one or more carbon atoms of said (C1-10)alkyl is optionally replaced by O, S, S(=O), S(=O)$_2$ or $NR_k$ and which (C1-10)alkyl is optionally substituted with one or more hydroxy, halo, cyano, $NR_nR_p$, C(=O)$NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_k$;

each $R_b$ is $R^4$, H, F, Cl, Br, I, $CF_3$, (C1-10)alkyl, or $XR^3$;

each $R_c$ is $R^4$, H, cyano, F, Cl, Br, I, —C(=O)$NR_dR_e$, C(=O)$NR_sR_t$, $NR_sR_t$, S(=O)—$_2NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, $S(O)R_r$, or $S(O)_2R_r$;

$R_d$ and $R_e$ are each independently H or (C1-10)alkyl;

each $R_y$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_k$ is H, $NR_sR_t$, C(=O)$NR_sR_t$, S(=O)$_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_u$ is H, $A^3$, C(=O)$NR_sR_t$, or S(=O)$_2NR_sR_t$;

each $R_m$ is H, cyano, F, Cl, Br, I, —C(=O)$NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O S, or $NR_y$ and the other E or D is $CR_u$ or N;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R^4$ or $R_c$; or $Q^1$ and $Z^{2a}$ taken together with the atoms to which they are attached form a heterocycle, which heterocycle may optionally be substituted with one or more oxo (=O), $R^4$, or $A^3$;

each X is independently a bond, O, S, or $NR^3$;

Y is a polycarbocycle or a polyheterocycle, which polycarbocycle or a polyheterocycle is optionally substituted with one or more $R^4$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R^4$ is independently —P($Y^3$)(O$A^2$)(O$A^2$), —P($Y^3$)(O$A^2$)(N($A^2$)$_2$), —P($Y^3$)($A^2$)(O$A^2$), —P($Y^3$)($A^2$)(N($A^2$)$_2$), or P($Y^3$)(N($A^2$)$_2$)(N($A^2$)$_2$);

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring;

each $R_r$ is independently H, (C1-10)alkyl, (C2-10)alkenyl, (C2-10)alkynyl, (C1-10)alkanoyl, or (C1-10)alkoxycarbonyl;

each $R_s$ and $R_t$ is independently H, (C1-10)alkyl, (C2-10)alkenyl, (C2-10)alkynyl, (C1-10)alkanoyl, S(=O)$_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^4$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O);

$Z^{2a}$ is H, (C1-10)alkyl, (C2-10)alkenyl, (C2-10)alkynyl, haloalkyl, (C1-10)alkyl-S(=O)$_2$—(C1-10)alkyl, or cycloalkyl, wherein any carbon atom of $Z^{2a}$ may optionally be replaced with a heteroatom selected from O, S or N and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with one or more $R^1$, $R^2$, $Q^1$, or $A^3$;

$A^3$ is independently selected from PRT, H, —OH, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —C($A^2$)$_3$, —C($A^2$)$_2$-C(O)$A^2$, —C(O)$A^2$, —C(O)O$A^2$, —O($A^2$), —N($A^2$)$_2$, —S($A^2$), —$CH_2$P($Y^1$)($A^2$)(O$A^2$), —$CH_2$P($Y^1$)($A^2$)(N($A^2$)$_2$), —$CH_2$P($Y^1$)(O$A^2$)(O$A^2$), —OC$H_2$P($Y^1$)(O$A^2$)(O$A^2$), —OC$H_2$P($Y^1$)($A^2$)(O$A^2$), —OC$H_2$P($Y^1$)($A^2$)(N($A^2$)$_2$), —C(O)OC$H_2$P($Y^1$)(O$A^2$)(O$A^2$), —C(O)OC$H_2$P($Y^1$)($A^2$)(O$A^2$), —C(O)OC$H_2$P($Y^1$)($A^2$)(N($A^2$)$_2$), —$CH_2$P($Y^1$)(O$A^2$)(N($A^2$)$_2$), —OC$H_2$P($Y^1$)(O$A^2$)(N($A^2$)$_2$), —C(O)OC$H_2$P($Y^1$)(O$A^2$)(N($A^2$)$_2$), —$CH_2$P($Y^1$)(N($A^2$)$_2$)(N($A^2$)$_2$), —C(O)OC$H_2$P($Y^1$)(N($A^2$)$_2$)(N($A^2$)$_2$), —OC$H_2$P($Y^1$)(N($A^2$)$_2$)(N($A^2$)$_2$), —($CH_2$)$_m$-heterocycle, —($CH_2$)$_m$C(O)Oalkyl, —O—($CH_2$)$_m$—O—C(O)—Oalkyl, —O—($CH_2$)$_r$—O—C(O)—($CH_2$)$_m$-alkyl, —($CH_2$)$_m$O—C(O)—O-alkyl, —($CH_2$)$_m$O—C(O)—O-cycloalkyl, —N(H)C(Me)C(O)O-alkyl, $SR_r$, $S(O)R_r$, $S(O)_2R_r$, or alkoxy arylsulfonamide, wherein each $A^3$ may be optionally substituted with 1 to 4 —$R^1$, —P($Y^1$)(O$A^2$)(O$A^2$), —P($Y^1$)(O$A^2$)(N($A^2$)$_2$), —P($Y^1$)($A^2$)(O$A^2$), —P($Y^1$)($A^2$)(N($A^2$)$_2$), or P($Y^1$)

(N(A²)₂)(N(A²)₂), —C(=O)N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH₂)ₘheterocycle, —(CH₂)ₘ—C(O)O-alkyl, —O(CH₂)ₘOC(O)Oalkyl, —O—(CH₂)ₘ—O—C(O)—(CH₂)ₘ-alkyl, —(CH₂)ₘ—O—C(O)—O-alkyl, —(CH₂)ₘ—O—C(O)—O-cycloalkyl, —N(H)C(CH₃)C(O)O-alkyl, or alkoxy arylsulfonamide, optionally substituted with R¹;

optionally each independent instance of A³ and Q¹ can be taken together with one or more A³ or Q¹ groups to form a ring;

A² is independently selected from PRT, H, alkyl, alkenyl, alkynyl, amino, amino acid, alkoxy, aryloxy, cyano, haloalkyl, cycloalkyl, aryl, heteroaryl, heterocycle, alkylsulfonamide, or arylsulfonamide, wherein each A² is optionally substituted with A³

$R^f$ is H, alkyl, alkenyl, alkynyl, aryl, heteroaryl, or cycloalkyl, which $R^f$ is optionally substituted with one or more $R_g$;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy;

each $R_h$ and $R_i$ is independently H, alkyl, or haloalkyl; and m is 0 to 6.

Specific Embodiment 52. The compound of any one of specific embodiments 1-51 wherein X is O, S, or NR³.

Specific Embodiment. 53. The compound of any one of specific embodiments 1-51 wherein X is O.

Specific Embodiment 54. The compound of any one of specific embodiments 1-53 wherein Y is a polycarbocycle.

Specific Embodiment 55. The compound of any one of specific embodiments 1-53 wherein Y is polyheterocycle.

Specific Embodiment 56. The compound of any one of specific embodiments 1-53 wherein Y is a fused carbocyclic ring system.

Specific Embodiment 57. The compound of any one of specific embodiments 1-53 wherein Y is a fused heterocyclic ring system.

Specific Embodiment 58. The compound of any one of specific embodiments 1-53 wherein Y is a fused carbocyclic ring system comprising one or more double bonds.

Specific Embodiment 59. The compound of any one of specific embodiments 1-53 wherein Y is a fused heterocyclic ring system comprising one or more double bonds.

Specific Embodiment 60. The compound of any one of specific embodiments 1-53 wherein Y is a bridged carbocyclic ring system.

Specific Embodiment 61. The compound of any one of specific embodiments 1-53 wherein Y is a bridged heterocyclic ring system.

Specific Embodiment 62. The compound of any one of specific embodiments 1-53 wherein Y is a bridged carbocyclic ring system comprising one or more double bonds.

Specific Embodiment 63. The compound of any one of specific embodiments 1-53 wherein Y is a bridged heterocyclic ring system comprising one or more double bonds.

Specific Embodiment 64. The compound of any one of specific embodiments 1-53 wherein Y comprises a bridged ring system selected from:

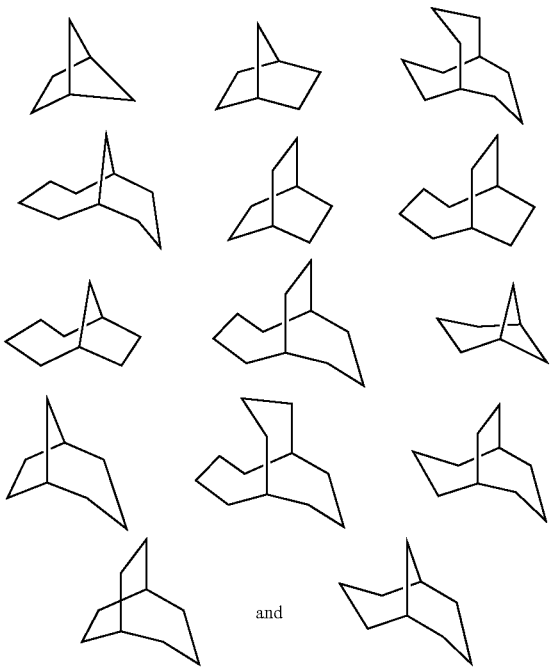

and wherein one or more carbon atoms in the bridged ring system is optionally replaced with O, S, S(O), S(O)₂, N⁺(O⁻)$R_x$, or $NR_x$; wherein each $R_x$ is independently H, (C1-10)alkyl, (C2-10)alkenyl, (C2-10)alkynyl, (C1-10)alkanoyl, S(O)₂$NR_nR_p$, S(O)₂$R_x$, or (C1-10)alkoxy, wherein each (C1-10)alkyl, (C2-10)alkenyl, (C2-10)alkynyl, (C1-10)alkanoyl, and (C1-10) alkoxy is optionally substituted with one or more halo; and wherein the ring system optionally comprises one or more double bonds.

Specific Embodiment 65. The compound of specific embodiment 64 wherein the ring system comprises one or more double bonds.

Specific Embodiment 66. The compound of specific embodiment 64 wherein one or more carbon atoms in the bridged ring system is replaced with O, S, S(O), S(O)₂, N⁺(O⁻)$R_x$, or $NR_x$; wherein each $R_x$ is independently H, (C1-10)alkyl, (C2-10)alkenyl, (C2-10)alkynyl, (C1-10)alkanoyl, S(O)₂$NR_nR_p$, S(O)₂$R_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

Specific Embodiment 67. The compound of any one of specific embodiments 1-53 wherein Y comprises a fused ring system selected from:

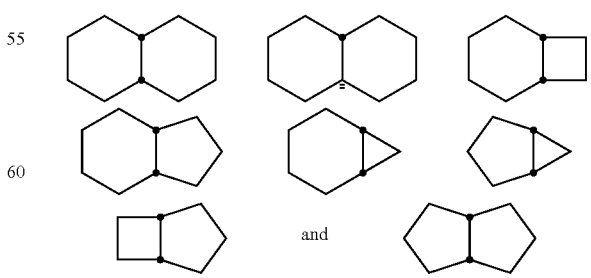

and wherein one or more carbon atoms in the fused ring system is optionally replaced with O, S, S(O), S(O)₂, N⁺(O⁻)$R_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo; and wherein the ring system optionally comprises one or more double bonds.

Specific Embodiment 68. The compound of specific embodiment 67 wherein one or more carbon atoms in the fused ring system is replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

Specific Embodiment 69. The compound of any one of specific embodiments 1-53 wherein Y is selected from:

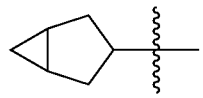 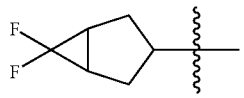

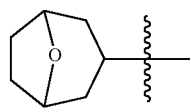 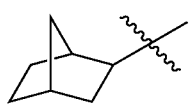

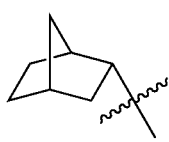 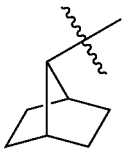 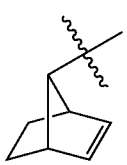

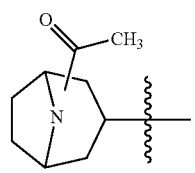 and 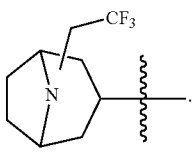.

Specific Embodiment 70. The compound of specific embodiment 1 which is a compound of formula (V):

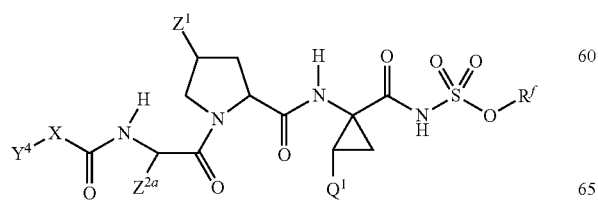

(V)

wherein Z$^1$ is selected from the following structures:

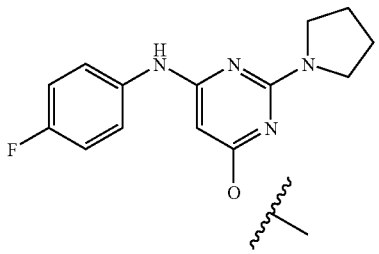

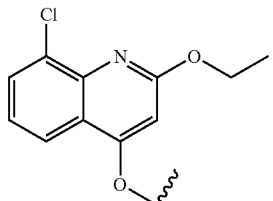

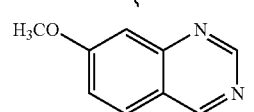

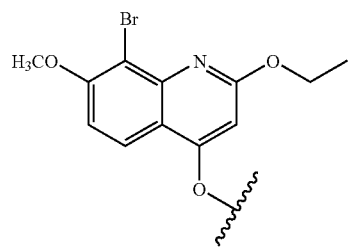

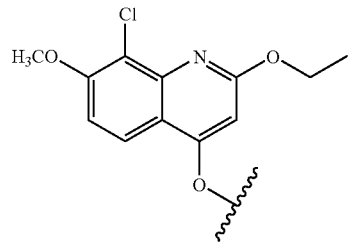

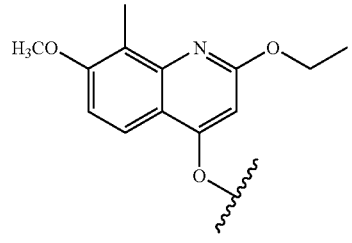

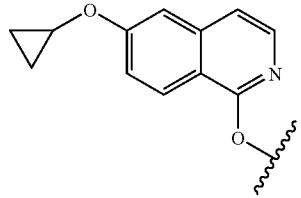

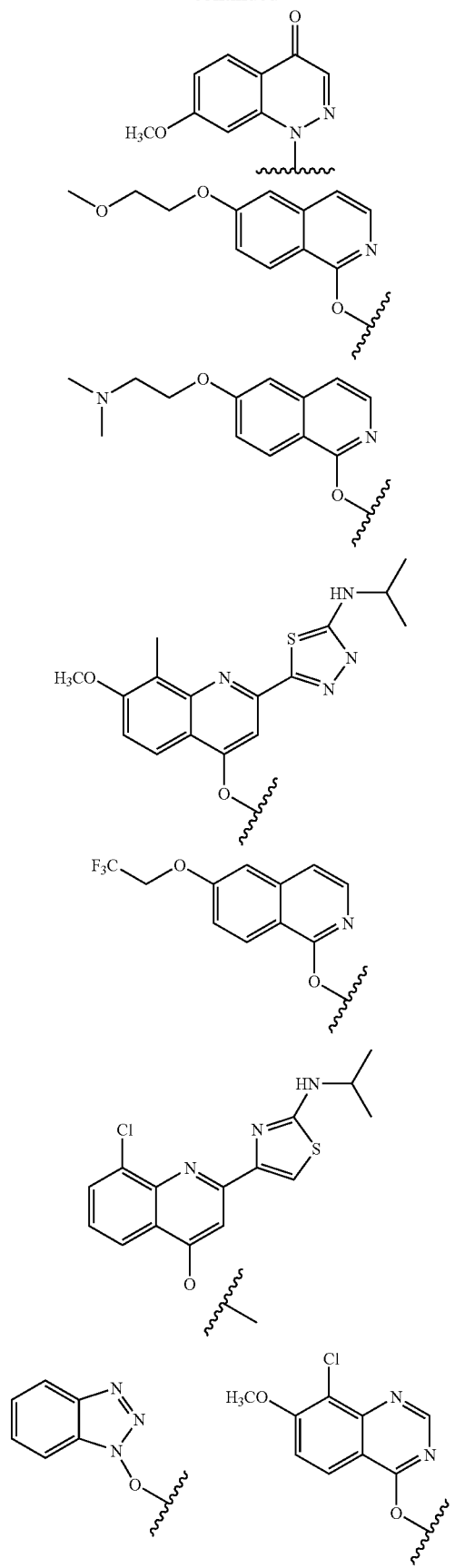

-continued

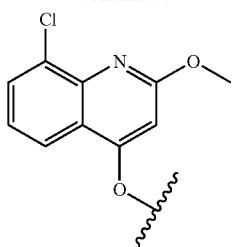
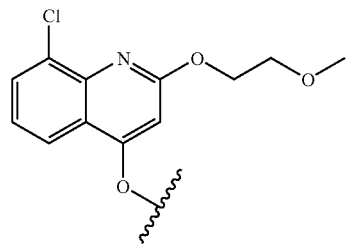
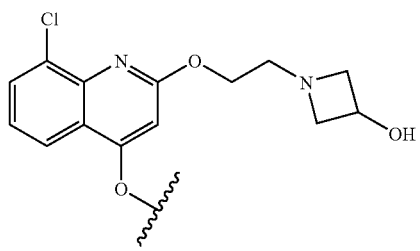
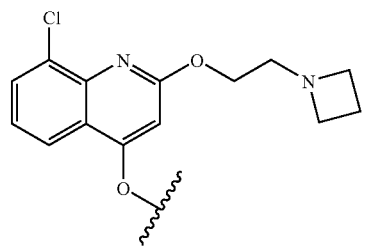
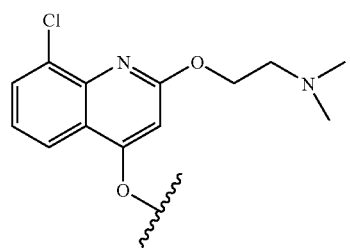
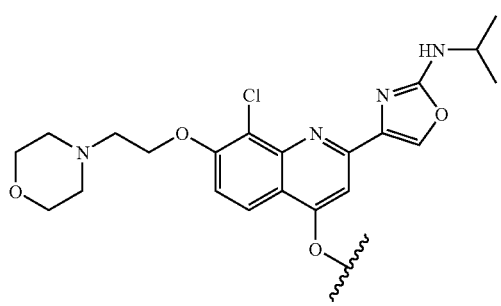

and

-continued

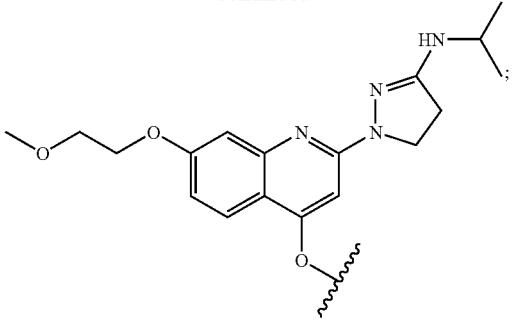

$R^f$ is H, alkyl, alkenyl, alkynyl, aryl, heteroaryl, or cycloalkyl, which $R^f$ is optionally substituted with one or more $R_g$;

$Q^1$ is H, (C1-10)alkyl, (C2-10)alkenyl, or (C2-10)alkynyl which (C1-10)alkyl, (C2-10)alkenyl, or (C2-10)alkynyl is optionally substituted with one or more $R_c$; or $Q^1$ and $Z^{2a}$ taken together with the atoms to which they are attached form a heterocycle, which heterocycle may optionally be substituted with one or more oxo (=O) or halo;

$R^2$ is —C(=O)—X—$Y^4$;

X is a bond O, S, or NH;

$Y^4$ is (C2-10)alkyl, (C3-7)cycloalkyl, heterocycle, polycarbocycle, or polyheterocycle, which (C2-10)alkyl, (C3-7)cycloalkyl, heterocycle, polycarbocycle, or polyheterocycle is optionally substituted with one or more (C1-10)alkyl, halo, carboxy, hydroxy, (C1-10)alkanoyl, (C1-10)alkoxy, (C1-10)alkanoyloxy, (C1-10)alkoxycarbonyl, trifluoromethyl, $NR_nR_p$, $SR_r$, $S(O)R_r$, or $S(O)_2 R_r$;

each $R_c$ cyano, F, Cl, Br, $S(O)_2R_r$, (C1-10)alkoxy, or cycloalkyl;

each $R_d$ is independently H, (C1-10)alkyl, or aryl, which is optionally substituted with one or more halo;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl of $R_g$ is optionally substituted with one or motr halo, alkoxy, or cyano;

each $R_h$ and $R_i$ is independently H, alkyl, or haloalkyl;

each $R_n$ and $R_p$ is independently H, (C1-10)alkyl, (C2-10) alkenyl, (C2-10)alkynyl, (C1-10)alkanoyl, (C1-10) alkoxy, (C1-10)alkanoyloxy, or (C1-10)alkoxycarbonyl, which (C1-10)alkyl, (C2-10)alkenyl, (C2-10) alkynyl, (C1-10)alkanoyl, (C1-10)alkoxy, (C1-10) alkanoyloxy, or (C1-10)alkoxycarbonyl, is optionally substituted with one or more halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring; and each $R_r$ is independently (C1-10)alkyl.

Specific Embodiment 71. The compound of specific embodiment 70 wherein: X is a bond; and $Y^4$ is pyrrol-1-yl, morpholino, or (C2-10)alkyl.

Specific Embodiment 72. The compound of specific embodiment 70 wherein $R^2$ is pyrrol-1-ylcarbonyl, morpholinocarbonyl, or 3,3-dimethylbutanoyl.

Specific Embodiment 73. The compound of specific embodiment 70 wherein: X is O; and $Y^4$ is tert-butyl, cyclopentyl, 1,1-dimethylethyl, cyclopropyl, tetrahydrofuranyl, isopropyl, 2,2-dimethylpropyl, cyclobutyl or

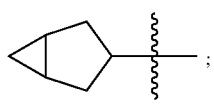 [SMILES: *C1CC2CC2C1]

which $Y^4$ is optionally substituted with one or more (C1-10) alkyl, halo, (C1-10)alkoxy, trifluoromethyl, or $NR_nR_p$.

Specific Embodiment 74. The compound of specific embodiment 70 wherein $R^2$ is tert-butoxycarbonyl, cyclopentoxycarbonyl, 1,1-dimethyl-2,2,2-trifluoroethoxy, 1-methylcyclopropyloxycarbonyl, 2-(N,N-dimethylamino)-1,1dimethylethoxycarbonyl, 2-morpholino-1,1dimethylethoxycarbonyl, 3-tetrahydrofuranyloxycarbonyl, isopropoxycarbonyl, 2-methoxy-1,1-dimethylethoxycarbonyl, 2,2-dimethylpropoxycarbonyl, 1-trifluoromethylcyclobutyloxycarbonyl, cyclobutyloxycarbonyl, 1-methylcyclopentyloxycarbonyl, 1-trifluoromethylcyclopentyloxycarbonyl, 1-trifluoromethylcyclobutyloxycarbonyl, and

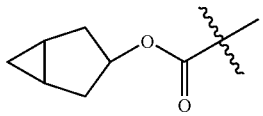

Specific Embodiment 75. The compound of specific embodiment 70 wherein: X is NH; and $Y^4$ (C2-10)alkyl that is optionally substituted with one or more halo.

Specific Embodiment 76. The compound of specific embodiment 70 wherein $R^2$ is tert-butylaminocarbonyl, or 1,1-dimethyl-2,2,2-trifluoroethylaminocarbonyl.

Specific Embodiment 77. The compound of any one of specific embodiments 70-76 wherein: $R^f$ is alkyl, aryl, cycloalkyl, which $R^f$ is optionally substituted with one or more $R^g$ independently selected from alkyl, halo, —C(=O)$OR_d$, or trifluoromethyl, wherein each alkyl of $R^g$ is optionally substituted with one or more halo, alkoxy, or cyano.

Specific Embodiment 78. The compound of any one of specific embodiments 70-76 wherein: $R^f$ is phenyl, cyclopropyl, 2-fluorophenyl, 4-chlorophenyl, 2-chlorophenyl, 2,6-dimethylphenyl, 2-methylphenyl, 2,2-dimethylpropyl, 2,2-difluoroethyl, 2,2,2-trifluoroethyl, 1-methylcyclopropyl, 1-isopropylcyclopropyl, 1-propylcyclopropyl, 2,2,2-trifluoro-1,1-dimethylethyl, 1-(methoxycarbonyl)cyclopropyl, 1-ethylcyclopropyl, 1-trifluoromethylcyclobutyl, 1-(methoxymethyl)cyclopropyl, 1-(2-cyanoethyl)cyclopropyl, or 1-(2,2,2-trifluoroethyl)cyclopropyl.

Specific Embodiment 79. The compound of any one of specific embodiments 70-78 wherein: $Q^1$ is hydrogen, methyl, ethyl, vinyl, cyanomethyl, propyl, 2-fluoroethyl, 2,2-difluoroethyl, 2-cyanoethyl, 2-methoxyethyl, 2-methylsulfonylethyl, or cyclopropyl.

SCHEMES AND EXAMPLES

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention.

EXAMPLES

Example 1

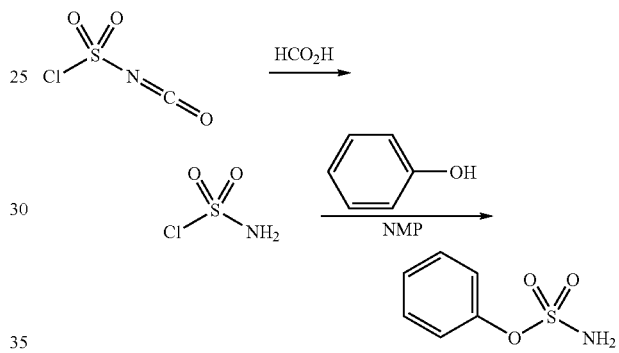

A three necked round bottom equipped with a reflux condensor was charged with chlorosulfonyl isocyanate (5.25 ml, 0.06 mol) and cooled to 0° C. Formic acid (2.25 mL, 0.06 mol) was added dropwise with rapid stirring with rapid gas evolution observed. Upon complete addition of formic acid, the reaction was let warm to room temperature. After 2 h, the resultant reaction vessel containing the solid sulfamoyl chloride was cooled to 0° C. and phenol (1.88 g, 0.02 mol) dissolved in NMP (25 mL) was added dropwise via an addition funnel. The reaction was let warm to room temperature. After 3 h stirring, the reaction mixture was poured into cold saturated aqueous NaCl (120 mL) and extracted with EtOAc. After removal of the separated organic solvent, the crude product was purified by column chromatography on silica (35% EtOAc/hexane) to provide sulfamic acid phenyl ester (2.8 g, 81%): LCMS found 173.9 [M+H]$^+$.

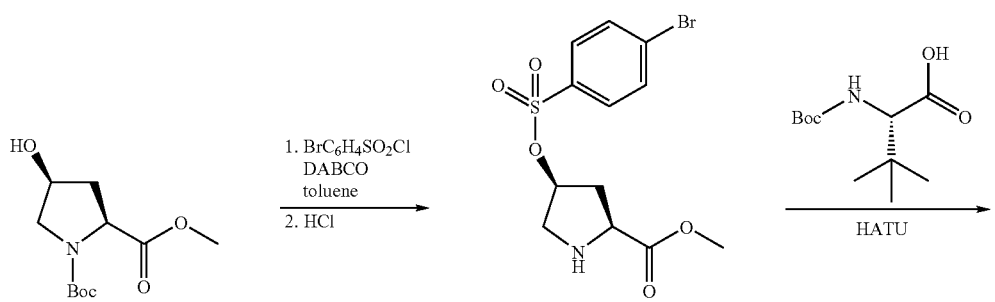

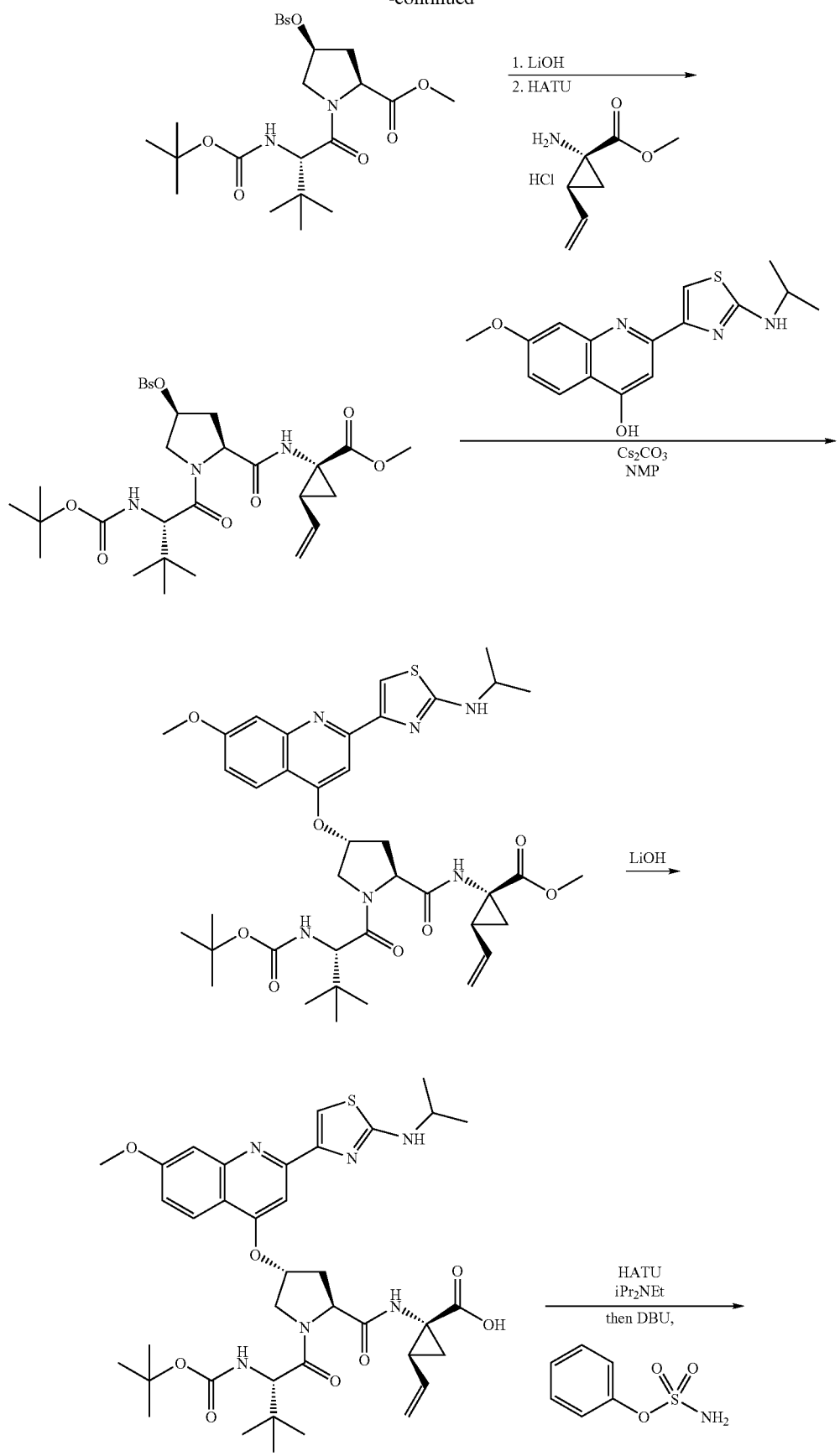

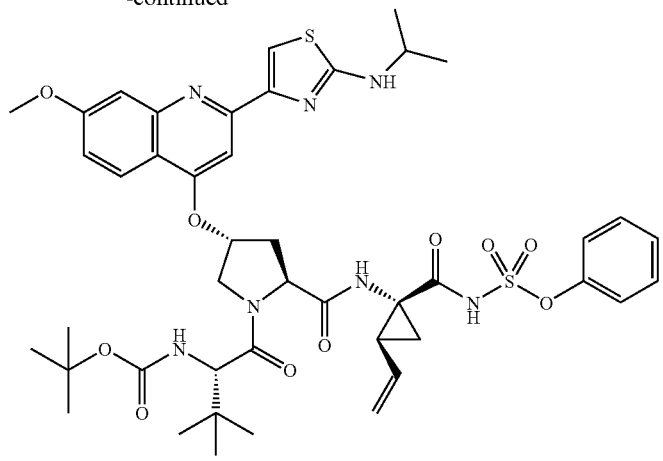

Compound 1

N-t-Boc-cis-4-hydroxy-L-proline methyl ester (100.0 g, 407.7 mmol) and DABCO (1.5 eq, 68.6 g, 611.6 mmol) were dissolved in anhydrous toluene (200 mL) in a 2 L three necked round bottom flask. It was equipped with a mechanical stirrer and an addition funnel. After cooling the solution to 0° C. under nitrogen, 4-bromo-benzenesulfonyl chloride (1.3 eq, 135.6 g, 530.0 mmol) dissolved in 300 mL of toluene was added through addition funnel over a period of in 60 minutes. The reaction solution was stirred and warmed to room temperature overnight. The mixture was slowly poured into 2 L 1M $Na_2CO_3$ (aq.), and was extracted with EtOAc (2 L). The organic phase was washed by 0.5N HCl (2 L), $H_2O$ (1 L) and brine (1 L). It was then dried over $MgSO_4$ and concentrated to give a yellow oily product.

The brosylate (407.7 mmol) was dissolved in dichloromethane (300 mL). 4.0 M HCl in dioxane (500 mL) was added to the reaction solution slowly and the reaction solution was allowed to stir at room temperature for 2 hours at which point ether (500 mL) was added and the reaction stirred for 15 min. The resultant white precipitate was collected by filtration. The solid was washed with ether and hexane and dried under vacuum. It afforded 153.0 g of HCl amine salt (381.8 mmol, 94% over two steps).

To a solution of Boc-tert-butyl-glycine (97.0 g, 420.0 mmol) in DMF (200 mL) and DCM (200 mL) were added HATU (217.76 g, 572.7 mmol) and DIPEA (126 mL, 1145.4 mmol) at room temperature. After the mixture was stirred for 20 min at room temperature, a solution of the previous HCl salt (153.0 g, 381.8 mmol) and Hunig's base (126 mL, 1145.4 mmol) in DMF (200 ml) and dichloromethane (200 mL) was added to the above acid mixture in one portion. The reaction mixture was stirred at room temperature for 3 h, with monitoring by LCMS. The reaction mixture was concentrated to remove dichloromethane under reduced pressure and the white solid that formed was filtered off. The remaining DMF solution was diluted with ethyl acetate (1 L), washed successively with 3% LiCl (aq) (3×650 mL), saturated $NH_4Cl$ (2×500 mL), 0.5N HCl (aq) (2×600 mL), brine (500 mL), saturated $NaHCO_3$ (3×500 mL), and brine (500 mL). The resulting organic fraction was dried ($MgSO_4$) and concentrated to afford crude dipeptide (111 g).

To a solution of the methyl ester (120 g, 207.8 mmol) in THF (300 mL), MeOH (75 mL) was added a solution of LiOH (26.18 g, 623.4 mmol) in $H_2O$ (150 mL). The solution was allowed to stir at room temperature for 4 hours. The mixture was cooled in an ice-bath while acidifying with 3N HCl to pH 5.5, stirred for 10 min, and the resulting white solids were collected by filtration. The solids were washed with more water, ether and hexane. The solids were dried under vacuum at 40° C. overnight to give 95.78 g (82%) of the acid.

To a solution of the carboxylic acid (81.4 g, 144.27 mmol) in DMF (200 mL) and dichloromethane (200 mL) was added HATU (82.3 g, 216.4 mmol) and DIPEA base (47.5 mL, 432.8 mmol) at room temperature. After the mixture was stirred for 20 min at room temperature, a solution of 1-amino-2-vinyl-cyclopropanecarboxylic acid methyl ester (158.7 mmol) and Hunig's base (47.5 mL, 1145.4 mmol) in DMF (200 mL) and dichloromethane (200 mL) was added to the above acid mixture in one portion. The reaction mixture was stirred at room temperature for 3 h and monitored by LCMS. After the mixture was concentrated under reduced pressure to remove dichloromethane, the white solids that formed were filtered off. The remaining DMF solution was diluted with ethyl acetate (600 mL) and successively washed with 3% LiCl (aq) (2×550 mL), saturated $NH_4Cl$ (500 mL), 1N HCl (aq) (500 mL), saturated $NaHCO_3$ (500 mL), and brine (300 mL). The resulting organic fraction was dried ($Na_2SO_4$) and concentrated to afford crude tripeptide 1-{[4-(4-bromo-benzenesulfonyloxy)-1-(2-tert-butoxycarbonylamino-3,3-dimethyl-butyryl)-pyrrolidine-2-carbonyl]-amino}-2-vinyl-cyclopropanecarboxylic acid methyl ester (111 g). LCMS found 685.6 $[M+H]^+$.

2-(2-(Isopropylamino)thiazol-4-yl)-7-methoxyquinolin-4-ol (1.72 g, 5.46 mmol) was dissolved in NMP (10 mL) and treated with $Cs_2CO_3$ (2.54 g, 7.80 mmol) followed by the addition of 1-{[4-(4-bromo-benzenesulfonyloxy)-1-(2-tert-butoxycarbonylamino-3,3-dimethyl-butyryl)-pyrrolidine-2-carbonyl]-amino}-2-vinyl-cyclopropanecarboxylic acid methyl ester (3.0 g, 4.29 mmol) in NMP (7 mL). The reaction mixture was heated to 60° C. for 14 h after which the reaction was cooled to room temperature and diluted with aqueous 5% LiCl. The solution was extracted with EtOAc, washed with saturated aqueous NaCl, and dried over sodium sulfate. After removal of solvent, the crude product was purified by column chromatography on silica (75-95% EtOAc/hexane) to provide the aryl ether (2.8 g, 86%). LCMS found 765.2 $[M+H]^+$.

The methyl ester (200 mg, 0.26 mmol) was dissolved in THF/MeOH (3:1, 2 mL) and treated with LiOH dissolved in $H_2O$ (0.5 mL). The reaction was judged complete by complete consumption of starting material, approximately 2 h at which time the reaction was diluted with H₂O, acidified with 1N aqueous HCl. The solution was extracted with EtOAc, washed with saturated aqueous NaCl, and dried over sodium sulfate. After removal of solvent, the crude product (198 mg,) was used directly in the next reaction. LCMS found 731.2 [M+H]⁺.

The acid (385 mg, 0.51 mmol), sulfamic acid phenyl ester (355 mg, 2.05 mmol), and HATU (214 mg, 0.56 mmol) were combined in DMF (5.1 mL) and treated with iPr₂NEt (0.47 mL, 2.56 mmol), DMAP (251 mg, 2.05 mmol) and DBU (0.38 mL, 2.56 mmol). After stirring for 3 h at room temperature, the reaction was diluted with H₂O. The solution was extracted with EtOAc, washed with saturated aqueous NaHCO₃, and dried over sodium sulfate. After removal of solvent, the crude product was purified by reverse phase column chromatography on C18 (30-95% MeOH/H2O-1% AcOH) to provide the desired product Compound 1 (160 mg, 35%): ¹H NMR (CD₃OD, 300 MHz) δ 9.18 (s, 1H), 8.24 (d, 1H), 8.17 (s, 1H), 7.43 (m, 2H), 7.26-7.43 (m, 6H), 5.78 (m, 2H), 5.35 (d, 1H), 5.21 (d, 1H), 4.58 (m, 2H), 4.16 (m, 3H), 4.05 (s, 3H), 2.70 (m, 1H), 2.41 (m, 1H), 2.85 (dd, 1H), 1.97 (dd, 1H), 1.47 (m, 1H), 1.33 (d, 6H), 1.19 (s, 9H), 1.00 (s, 9H); LCMS found 906.04 [M+H]⁺.

Example 2

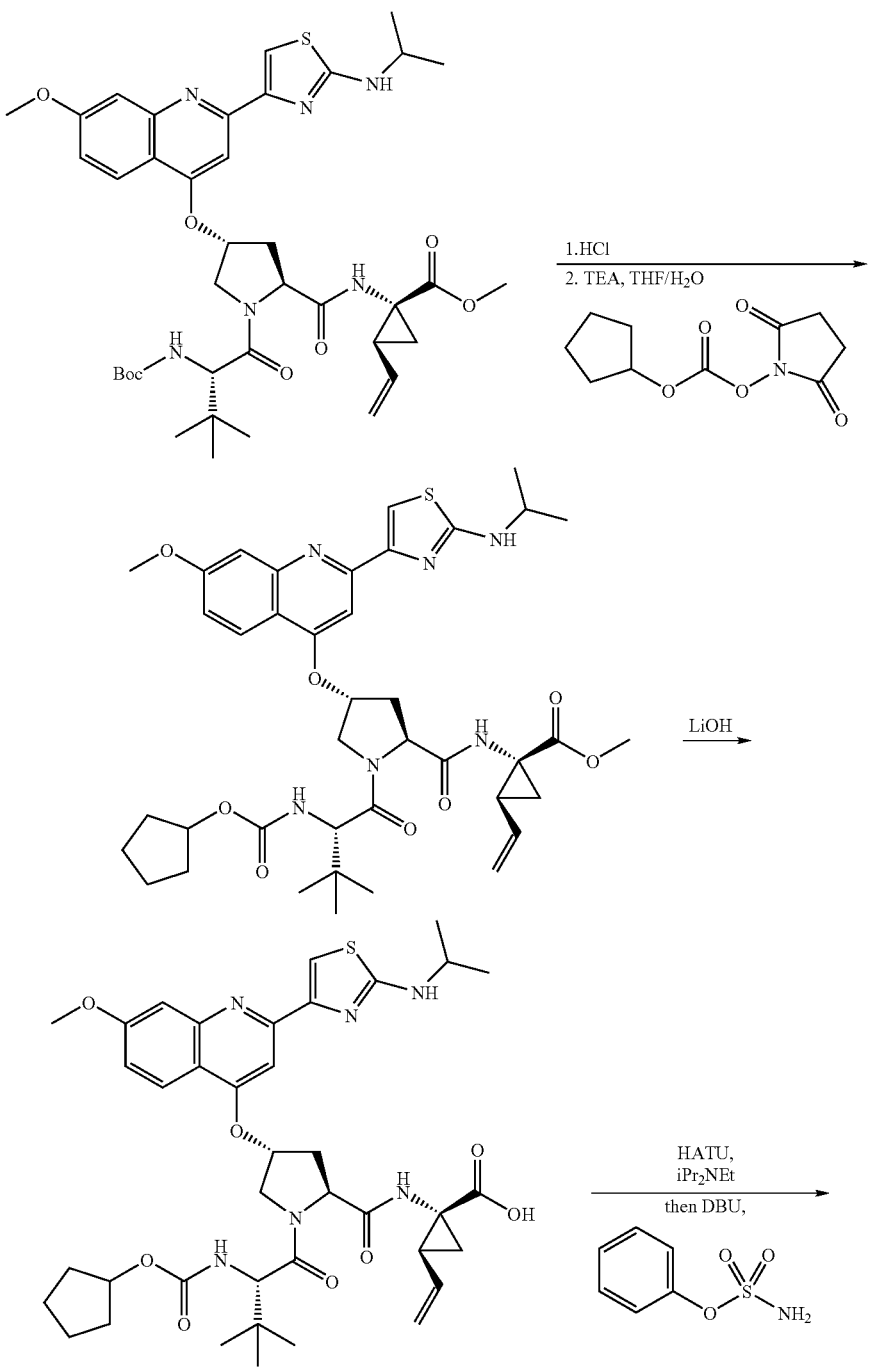

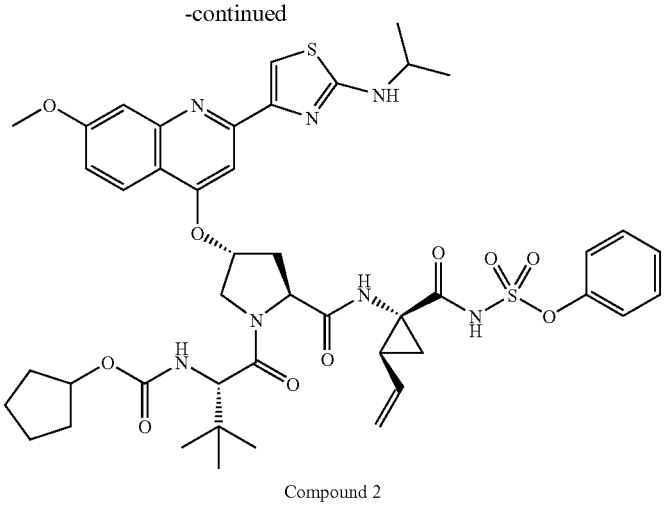

Compound 2

1-({1-(2-tert-Butoxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid methyl ester (1.09 g, 1.40 mmol) was treated with 4N HCl in dioxanes (11 mL) and reacted at room temperature for 1 h. Solvents were removed and the crude residue dried. To the resultant solid was added succinimidyl-cyclopentylcarbonate (340 mg, 1.50 mmol), THF/H$_2$O (6:1, 5.7 mL), and triethylamine (0.2 mL, 1.50 mmol). After stirring for 6 h at room temperature, the reaction was quenched with 0.5N aqueous HCl. The solution was extracted with EtOAc, washed with saturated aqueous NaCl, and dried over sodium sulfate. After removal of solvent, the crude product was purified by column chromatography on silica (5-10% MeOH/CH$_2$Cl$_2$) to provide the cyclopentylcarbamate (0.705 g, 64%).

The methyl ester (300 mg, 0.39 mmol) was dissolved in THF/MeOH (3:1, 3.2 mL) and treated with LiOH dissolved in H$_2$O (0.8 mL). The reaction was judged complete by complete consumption of starting material, approximately 2 h at which time the reaction was diluted with H$_2$O, acidified with 1N aqueous HCl. The solution was extracted with EtOAc, washed with saturated aqueous NaCl, and dried over sodium sulfate. After removal of solvent, the crude product was used directly in the next reaction.

The acid (45 mg, 0.06 mmol), sulfamic acid phenyl ester (41 mg, 0.24 mmol) and HATU (25 mg, 0.07 mmol) were combined in DMF (0.6 mL) to which iPr$_2$NEt (21 µL, 0.12 mmol) was added. After stirring 30 min at room temperature, DBU (36 µL, 0.24 mmol) was added and reacted for 14 h at room temperature. The crude reaction mixture was treated with H$_2$O to reconvert any remaining oxazolone intermediate to the corresponding acid and the crude reaction mixture was taken directly into purification by reverse phase column chromatography on C18 (40-95% ACN/H$_2$O-1% TFA) to provide Compound 2 (10 mg, 16%): $^1$H NMR (CDCl$_3$, 300 MHz) δ 11.45 (bs, 1H), 8.89 (s, 1H), 8.12 (d, 1H), 7.96 (s, 1H), 7.75 (s, 1H), 7.21-7.37 (m, 6H), 5.77 (m, 2H), 5.24 (m, 3H), 4.60 (m, 3H), 4.12 (m, 3H), 4.00 (s, 3H), 3.58 (m, 1H), 2.57-2.70 (m, 2H), 2.11 (m, 1H), 2.02 (m, 1H), 1.50-1.70 (m, 10H), 1.45 (d, 6H), 0.97 (s, 9H); LCMS found 918.7 [M+H]$^+$.

Example 3

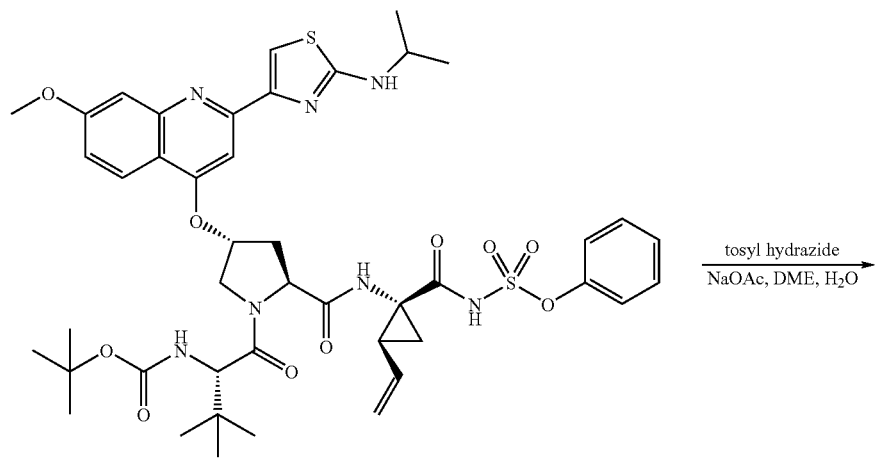

Compound 1

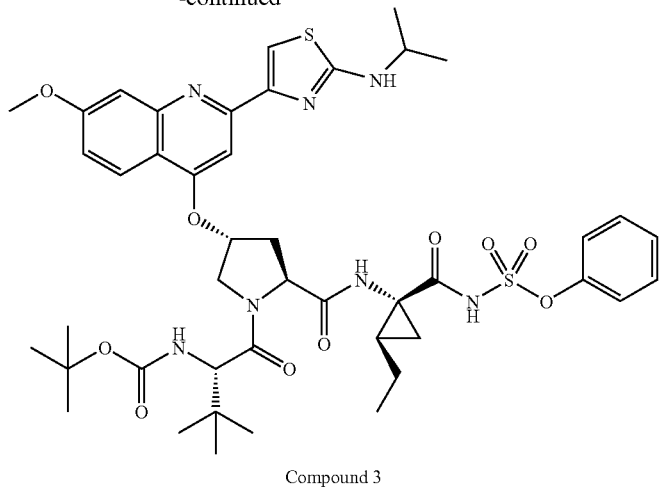

Compound 3

A round bottom flask was charged with Compound 1 (20 mg, 0.022 mmol) from Example 1 and dissolved in DME (1 mL) and water (1 mL). To the stirring mixture tosyl hydrazide (30.8 mg, 0.17 mmol) and sodium acetate (27.1 mg, 0.33 mmol) were added and the reaction was heated to 95° C. for 1 hour. The reaction mixture was diluted with water and extracted with dichloromethane. The organic layer was dried over sodium sulfate, filtered, and concentrated. The crude mixture was purified by reverse phase HPLC to provide Compound 3 (3.7 mg, 19%): $^1$H NMR (CDCl$_3$, 300 MHz) δ 11.46 (bs, 1H), 8.77 (s, 1H), 8.13 (d, 1H), 7.85 (s, 1H), 7.75 (s, 1H), 7.21-7.38 (m, 6H), 5.75 (s, 2H), 5.18 (m, 1H), 4.58 (m, 2H), 4.06 (m, 7H), 3.59 (m, 1H), 2.50-2.71 (m, 2H), 2.01 (m, 1H), 1.47 (d, 3H), 1.25-1.48 (m, 10H), 1.24 (d, 6H), 0.95 (s, 9H), 0.90 (s, 2H); LCMS found 908.10 [M+H]$^+$.

panol (synthesized by methods reported in *JOC* 1980, 45, 4129-35) to obtain sulfamic acid cyclopropyl ester.

Compound 4 was prepared according to the method presented in the final synthetic step of Example 1. Treatment of 1-({1-(2-tert-butoxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions adjusted for scale and with the exception of utilizing sulfamic acid cyclopropyl ester (55 mg, 0.40 mmol) provided the desired product (4 mg, 5%): $^1$H NMR (CD$_3$OD, 300 MHz, diagnostic peaks) δ 4.16 (m, 1H), 0.94 (m, 2H), 0.75 (m, 2H); LCMS found 870.11 [N+H]$^+$.

Example 4

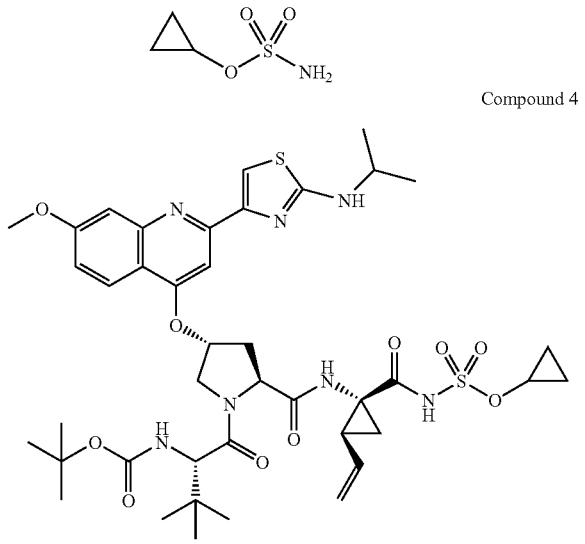

Compound 4

Cyclopropylsulfamate was synthesized according to the method presented in the synthesis of sulfamic acid phenyl ester in Example 1 with the exception of utilizing cyclopro- Example 5

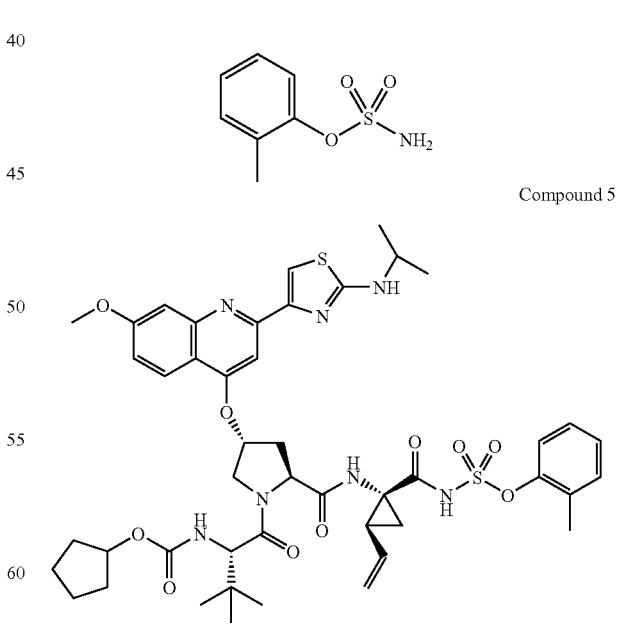

Compound 5 o-Tolylsulfamate was synthesized according to the method presented in the synthesis of sulfamic acid cyclopropyl ester in Example 1 with the exception of utilizing o-creol to obtain sulfamic acid o-tolyl ester.

Compound 5 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy])-pyrrolidine-2-carbonyl}-amino)-2-vinyl-cyclopropanecarboxylic acid under the same conditions with the exception of utilizing sulfamic acid o-tolyl ester (44 mg, 0.24 mmol) provided the desired product (6.8 mg, 11%): $^1$H NMR (CDCl$_3$, 300 MHz, diagnostic peaks) δ 2.37 (s, 3H); LCMS found 932.7 [M+H]$^+$.

Example 6

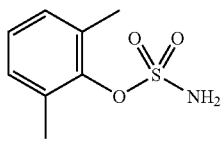

Compound 6

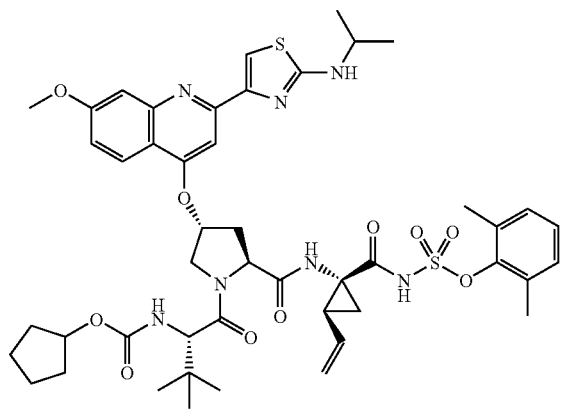

2,6-Dimethylphenylsulfamate was synthesized according to the method presented in the synthesis of sulfamic acid cyclopropyl ester in Example 1 with the exception of utilizing 2,6-dimethylphenol to obtain sulfamic acid 2,6-dimethyl-phenyl ester.

Compound 6 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions with the exception of utilizing sulfamic acid 2,6-dimethyl-phenyl ester (47 mg, 0.24 mmol) provided the desired product (23 mg, 36%): $^1$H NMR (CDCl$_3$, 300 MHz, diagnostic peaks) δ 7.04 (m, 3H), 2.36 (s, 6H); LCMS found 946.7 [M+H]$^+$.

Example 7

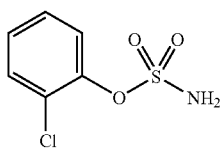

Compound 7

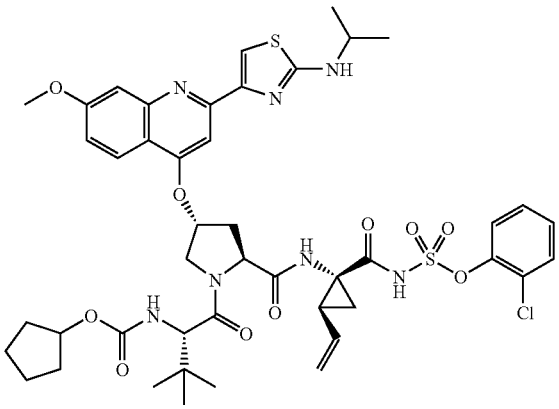

2-Chlorophenylsulfamate was synthesized according to the method presented in the synthesis of Sulfamic acid cyclopropyl ester in Example 1 with the exception of utilizing 2-chlorophenol to obtain sulfamic acid 2-chloro-phenyl ester.

Compound 7 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions with the exception of utilizing sulfamic acid 2-chloro-phenyl ester (49 mg, 0.24 mmol) provided the desired product (8 mg, 13%): $^1$H NMR (CDCl$_3$, 300 MHz, diagnostic peaks) 6 phenyl H obscured by solvent peak; LCMS found 952.7 [M+H]$^+$.

Example 8

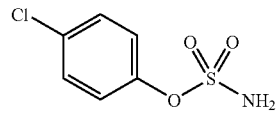

Compound 8

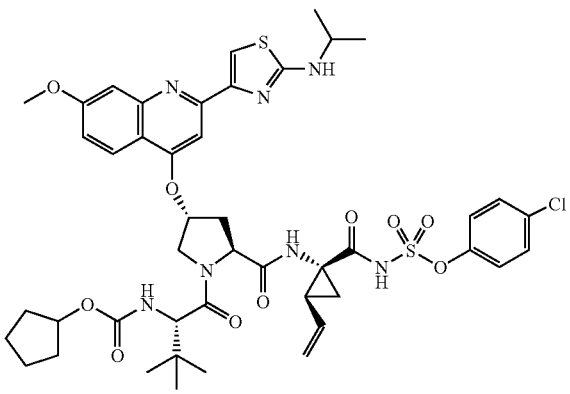

4-Chlorophenylsulfamate was synthesized according to the method presented in the synthesis of Sulfamic acid cyclopropyl ester in Example 1 with the exception of utilizing 4-chlorophenol to obtain sulfamic acid 4-chloro-phenyl ester.

Compound 8 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions with the exception of utilizing sulfamic acid 4-chloro-phenyl ester (49 mg, 0.24 mmol) provided the desired product (4 mg, 7%): $^1$H NMR (CDCl$_3$, 300 MHz, diagnostic peaks) δ 7.30 (d, 2H), 2.25 (d, 2H); LCMS found 952.7 [M+H]$^+$.

Example 9

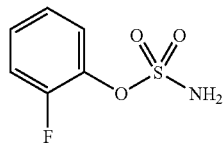

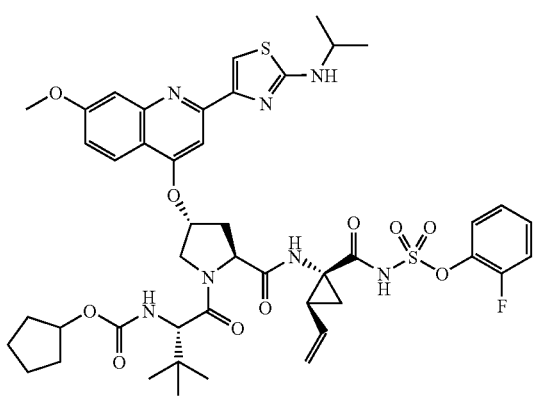

Compound 9

2-Fluorophenylsulfamate was synthesized according to the method presented in the synthesis of Sulfamic acid cyclopropyl ester in Example 1 with the exception of utilizing 2-fluorophenol to obtain sulfamic acid 2-fluoro-phenyl ester.

Compound 9 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions with the exception of utilizing sulfamic acid 2-fluoro-phenyl ester (45 mg, 0.24 mmol) provided the desired product (9 mg, 14%): $^1$H NMR (CDCl$_3$, 300 MHz, diagnostic peaks) δ 7.10-7.25 (m, 4H); LCMS found 936.7 [M+H]$^+$.

Example 10

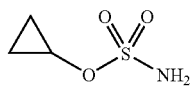

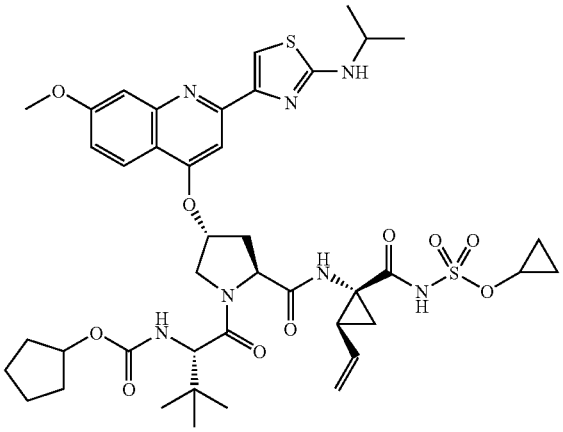

Compound 10

Compound 10 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions adjusted for scale and with the exception of utilizing sulfamic acid cyclopropyl ester (74 mg, 0.54 mmol) provided the desired product (21 mg, 18%): $^1$H NMR (CD$_3$OD, 300 MHz, diagnostic peaks) δ 4.16 (m, 1H), 0.93 (m, 2H), 0.74 (m, 2H); LCMS found 882.5 [M+H]$^+$.

Example 11

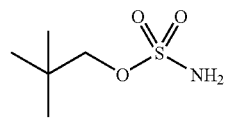

Compound 11

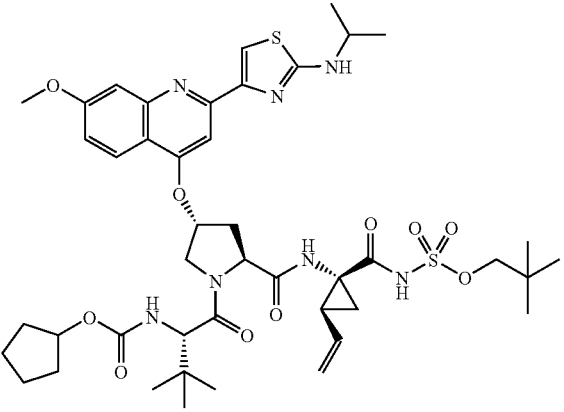

Neopenylsulfamate was synthesized according to the method presented in the synthesis of sulfamic acid cyclopropyl ester in Example 1 with the exception of utilizing neopentylalcohol to obtain sulfamic acid 2,2-dimethyl-propyl ester.

Compound 11 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions adjusted for scale and with the exception of utilizing sulfamic acid 2,2-dimethyl-propyl ester (45 mg, 0.27 mmol) provided the desired product (5 mg, 8%): $^1$H NMR (CD$_3$OD, 300 MHz, diagnostic peaks) δ 3.93 (m, 2H), 0.98 (s, 9H); LCMS found 912.7 [M+H]$^+$.

Example 12

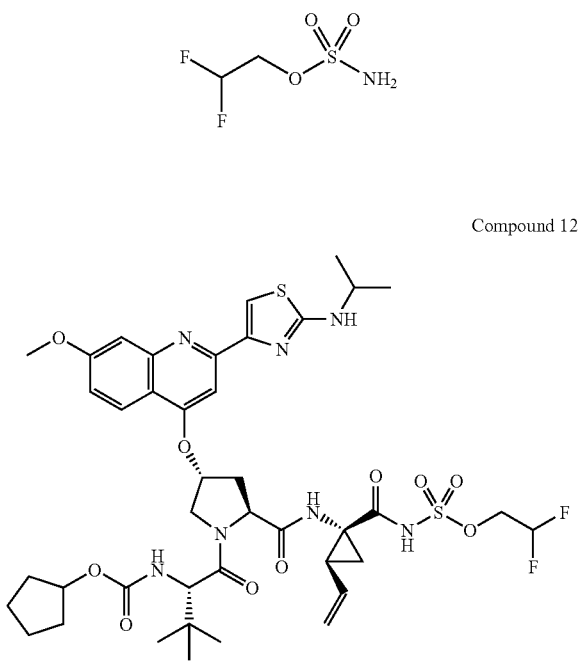

Compound 12

2,2-Difluoroethylsulfamate was synthesized according to the method presented in the synthesis of sulfamic acid cyclopropyl ester in Example 1 with the exception of utilizing 2,2-difluoroethylalcohol to obtain sulfamic acid 2,2-difluoro-ethyl ester.

Compound 12 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions adjusted for scale and with the exception of utilizing sulfamic acid 2,2-difluoro-ethyl ester (43 mg, 0.27 mmol) provided the desired product (6 mg, 10%): $^1$H NMR (CD$_3$OD, 300 MHz, diagnostic peaks) δ 6.10 (m, 1H), 4.45 (m, 2H); LCMS found 906.5 [M+H]$^+$.

Example 13

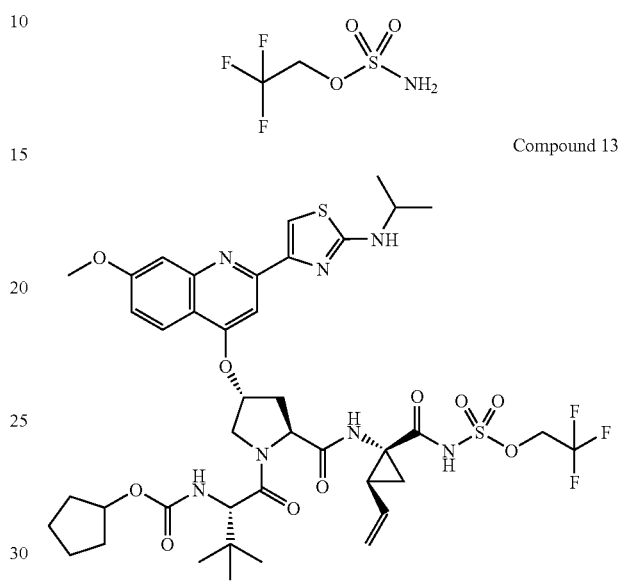

Compound 13

2,2,2-Trifluoroethylsulfamate was synthesized according to the method presented in the synthesis of sulfamic acid cyclopropyl ester in Example 1 with the exception of utilizing 2,2,2-trifluoroethylalcohol to obtain sulfamic acid 2,2,2-trifluoro-ethyl ester.

Compound 13 was prepared according to the method presented in the final synthetic step of Example 2. Treatment of 1-({1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-vinyl-cyclopropanecarboxylic acid under the same conditions adjusted for scale and with the exception of utilizing sulfamic acid 2,2,2-trifluoro-ethyl ester (48 mg, 0.27 mmol) provided the desired product (5 mg, 8%): $^1$H NMR (CD$_3$OD, 300 MHz, diagnostic peaks) δ 4.77 (m, 2H); LCMS found 924.5 [M+H]$^+$.

Example 14

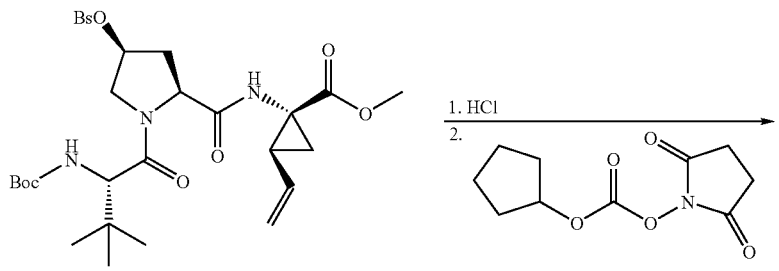

-continued
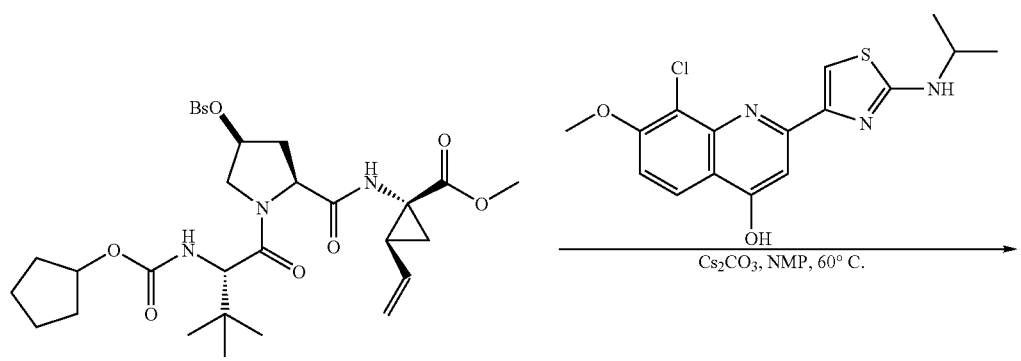
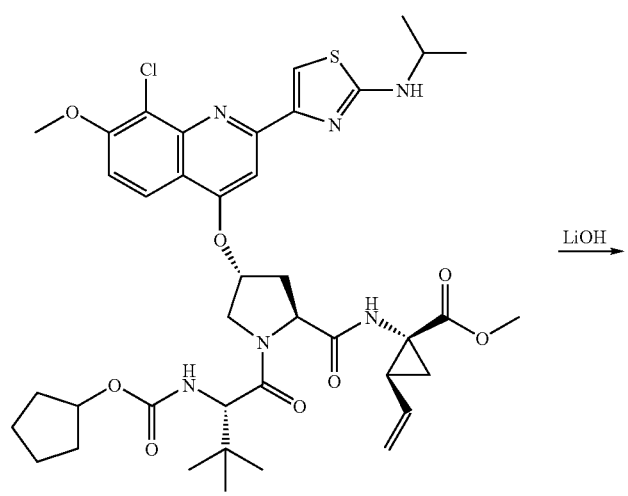
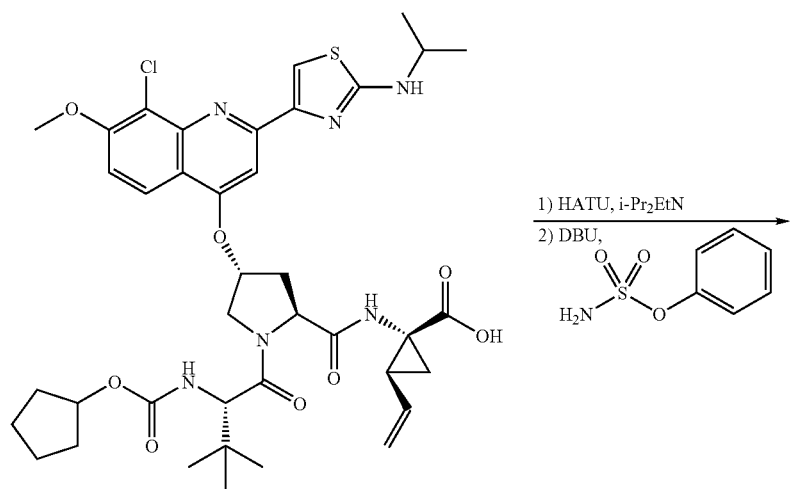

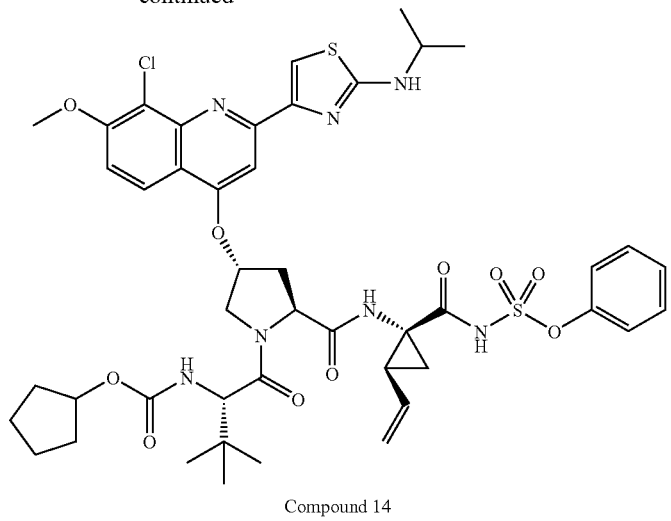

Compound 14

1-{[4-(4-Bromo-benzenesulfonyloxy)-1-(2-tert-butoxy-carbonylamino-3,3-dimethyl-butyryl)-pyrrolidine-2-carbonyl]-amino}-2-vinyl-cyclopropanecarboxylic acid methyl ester (2.57 g, 3.67 mmol) from Example 1 was dissolved in CH$_2$Cl$_2$ (9 mL), treated with 4N HCl in dioxanes (9 mL), and reacted at room temperature for 2 h. Solvents were removed and the crude residue dried. To the resultant solid was added succinimidyl-cyclopentylcarbonate (894 mg, 3.93 mmol), THF/H$_2$O (6:1, 15 mL), and triethylamine (0.55 mL, 3.93 mmol). After stirring for 2 h at room temperature, the reaction was quenched with 0.5N aqueous HCl. The solution was extracted with EtOAc, washed with saturated aqueous NaCl, and dried over sodium sulfate. After removal of solvent, the crude product cyclopentylcarbamate (2.60 g, >99%) was used directly in the next reaction.

To a solution of 1-{[4-(4-bromo-benzenesulfonyloxy)-1-(2-cyclopentyloxycarbonylamino-3,3-dimethyl-butyryl)-pyrrolidine-2-carbonyl]-amino}-2-vinyl-cyclopropanecarboxylic acid methyl ester (371.5 mg, 0.53 mmol) in NMP (1.8 mL) was added 8-chloro-2-(2-(isopropylamino)thiazol-4-yl)-7-methoxyquinolin-4-ol (252.3 mg, 0.58 mmol) and cesium carbonate (440.4 mg, 1.35 mmol). The resulting slurry was heated to 60° C. (external temperature, oil bath), and stirred vigorously for 22 h. Upon cooling to room temperature, the reaction mixture was diluted with EtOAc and washed with saturated ammonium chloride (2×) and then brine. The resulting organic layer was dried over sodium sulfate and concentrated to a brown oil. The crude product was purified by column chromatography (30%→100% EtOAc/hexanes) to provide the aryl ether (297.8 mg, 69%).

To a solution of 1-{[4-[8-chloro-2-(2-isopropylamino-thiazol-4-yl)-7-methoxy-quinolin-4-yloxy]-1-(2-cyclopentyloxycarbonylamino-3,3-dimethyl-butyryl)-pyrrolidine-2-carbonyl]-amino}-2-vinyl-cyclopropanecarboxylic acid methyl ester (297.8 mg, 0.37 mmol) in a 2:1:1 mixture of THF:MeOH:H$_2$O (3 µL) was added lithium hydroxide (77.9 mg, 1.86 mmol). The resulting slurry was stirred at room temperature for 16 h. The reaction mixture was then diluted with EtOAc and washed with aqueous HCl (0.5 N) and brine. The crude product was precipitated from the organic layer upon the addition of hexanes and filtered. The orange solid was dried in vacuo to provide the desired acid (204.9 mg, 70%).

To a solution of the acid (98.3 mg, 0.12 mmol) in DMF (0.625 mL) was added HATU (51.5 mg, 0.13 mmol) and diisopropylethylamine (0.026 mL, 0.15 mmol). The solution was stirred at room temperature for 2 h before additional HATU (50.2 mg, 0.13 mmol) was added. After an additional 2 h 15 min, sulfamic acid phenyl ester (86.1 mg, 0.50) and DBU (0.074 mL, 0.50 mmol) were added, and the reaction mixture was stirred at room temperature for 19 h. The resulting solution was diluted with EtOAc, and washed with aqueous HCl (0.5 N, 2×). The aqueous layer was back-extracted with EtOAc, dried over sodium sulfate, and concentrated to an orange oil. The crude product was combined with a second batch of material run on the same scale and purified by column chromatography (0→10% MeOH/CH$_2$Cl$_2$) to provide the acyl sulfamate (Compound 14, 68.6 mg, 29%). Impure fractions were combined and repurified by reverse phase HPLC (30→90% MeCN/H$_2$O-1% TFA) to provide additional acyl sulfamate (39.3 mg, 17%): $^1$H NMR (d$_3$-MeOD, 300 MHz) δ 8.04 (d, 1H), 7.80 (s, 1H), 7.44 (s, 1H), 7.20-7.41 (m, 5H), 6.74 (d, 1H), 5.85 (m, 1H), 5.40 (s, 1H), 5.23 (d, 1H), 5.04 (d, 1H), 4.56 (m, 2H), 4.45 (m, 1H), 4.21 (m, 1H), 4.04 (s, 3H), 3.92-4.04 (m, 4H), 2.62 (m, 2H), 2.10 (m, 1H), 1.85 (m, 1H), 1.30-1.61 (m, 10H), 1.35 (s, 3H), 1.33 (s, 3H), 1.00 (s, 9H); LCMS found 952.00 [M+H]$^+$.

Example 15

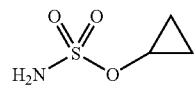

Compound 15

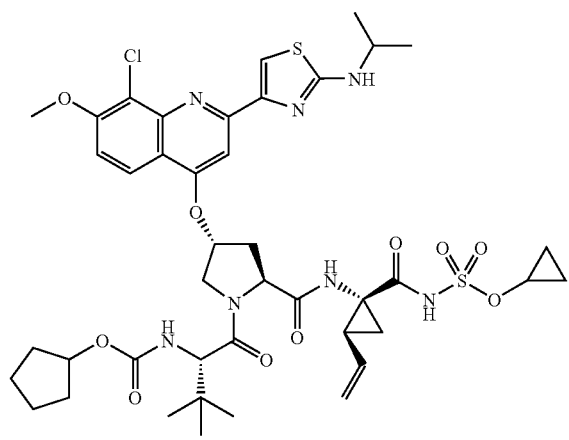

Compound 15 was prepared according to the method presented in the synthesis of Compound 16. Treatment of 1-{[4-[8-chloro-2-(2-isopropylamino-thiazol-4-yl)-7-methoxy-quinolin-4-yloxy]-1-(2-cyclopentyloxycarbonylamino-3,3-dimethyl-butyryl)-pyrrolidine-2-carbonyl]-amino}-2-vinyl-cyclopropanecarboxylic acid (101.1 mg, 0.13 mmol) occurred under the same conditions, adjusted for scale and with the exception of utilizing sulfamic acid cyclopropyl ester (70.8 mg, 0.52 mmol). Purification of the crude product was accomplished by reverse phase HPLC (30→90% MeCN/H$_2$O-1% TFA) to provide the acyl sulfamate (Compound 15, 66.3 mg, 57%): $^1$H NMR (d$_3$-MeOD, 300 MHz) δ 8.33 (d, 1H), 8.30 (s, 1H), 7.84 (s, 1H), 7.65 (d, 1H), 5.81 (s, 1H), 5.74 (m, 1H), 5.34 (d, 1H), 5.17 (d, 1H), 4.64 (m, 2H), 4.34 (m, 1H), 4.25 (m, 1H), 4.17 (s, 3H), 4.01-4.16 (m, 5H), 2.80 (m, 1H), 2.45 (m, 1H), 2.29 (m, 1H), 1.91 (m, 1H), 1.30-1.61 (m, 12H), 1.38 (s, 3H), 1.36 (s, 3H), 1.02 (s, 9H); LCMS found 916.15 [M+H]$^+$.

Example 16

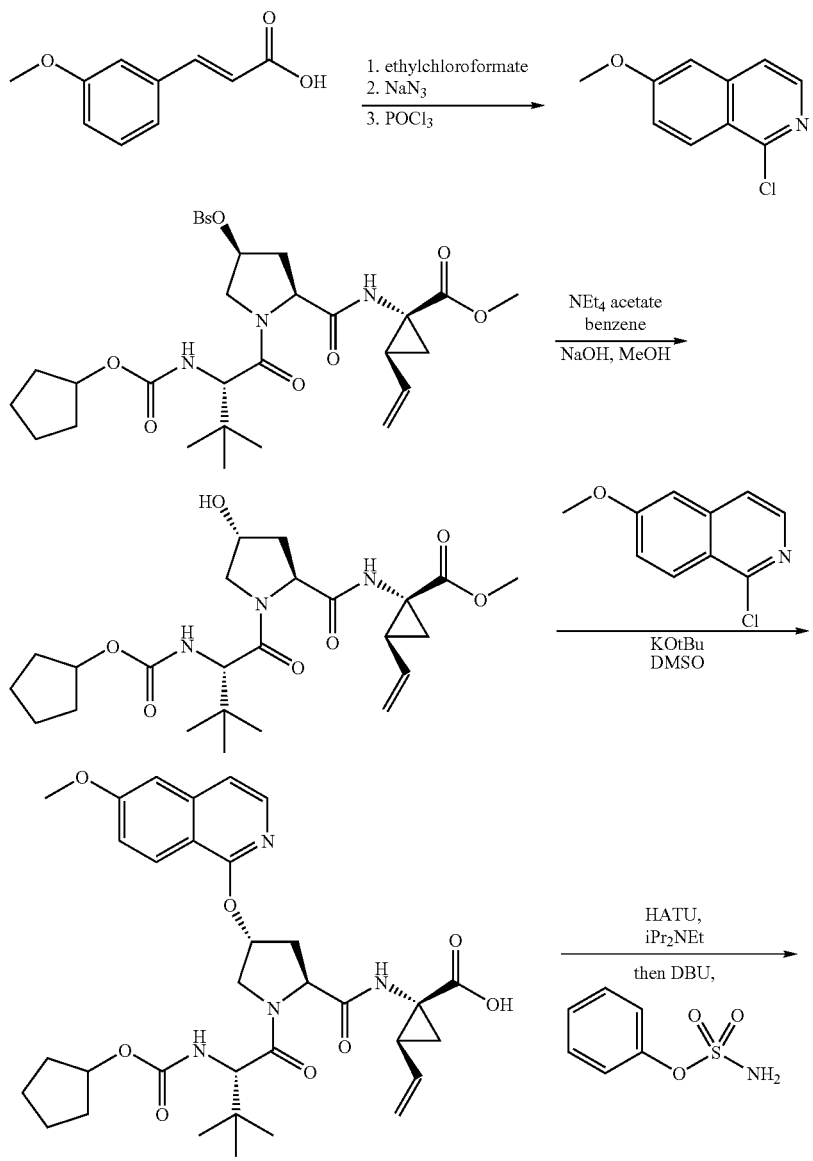

-continued

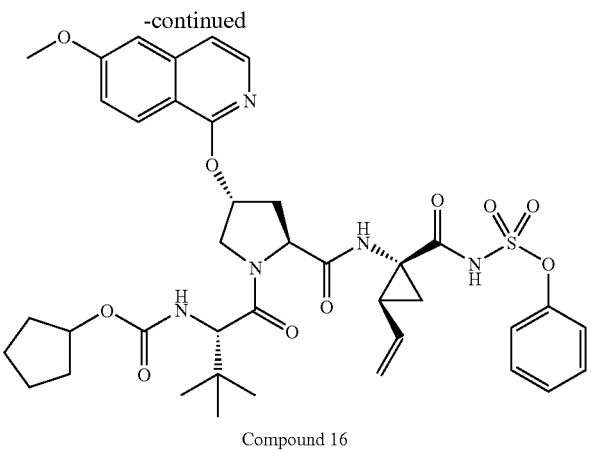

Compound 16

1-Chloro-6-methoxy-isoquinoline was prepared according to the following procedure. To a solution of 3-methoxy cinnamic acid (25 g, 140.3 mmol) and triethylamine (39.1 mL, 280.6 mmol) in THF (200 mL) was added ethyl chloroformate (20 ml, 210 mmol) dropwise at 0° C. After stirring at this temperature for 1 hour, aqueous $NaN_3$ (14.7 g, 226 mmol in 80 mL $H_2O$) was added dropwise and the reaction mixture was stirred for 16 hours at ambient temperature. Water (220 mL) was added to the mixture and the volatiles were removed in vacuo. The resulting slurry was extracted with toluene (3×110 mL) and the combined organic layers were dried over $MgSO_4$, filtered and concentrated. The dried solution was added dropwise to a heated solution of diphenylmethane (120 mL) and tributylamine (68 mL) at 190° C. The toluene was distilled off during the addition. After complete addition, the reaction temperature was raised to 210° C. for 2 hours. Upon cooling via an ice bath, the precipitated product was collected by filtration, washed with hexanes, and dried to yield the desired product as an off-white solid (14.04 g, 57%): LCMS found 176.1 $[M+H]^+$. 6-Methoxy-2H-isoquinolin-1-one (14.04 g, 80.15 mmol) in $POCl_3$ (30.5 ml) was heated to gentle reflux for 1 hour and the mixture was then concentrated in vacuo. The residue was poured into ice water and brought to pH 10 by the addition of 10 M NaOH. The resulting mixture was extracted with $CH_2Cl_2$. The organic layer was washed with brine, dried over $MgSO_4$, filtered and concentrated. The residue was purified by flash chromatography (0-20% EtOAc/hexane) to afford 13.31 g (86%) of the desired 1-chloro-6-methoxy-isoquinoline intermediate as a white solid. LCMS found 194.19 $[M+H]^+$.

Tetraethylammonium acetate tetrahydrate was dissolved in benzene (17 mL), equipped with a Dean-Stark trap and heated to reflux for 14 h. 1-{[4-(4-Bromo-benzenesulfonyloxy)-1-(2-cyclopentyloxycarbonylamino-3,3-dimethyl-butyryl)-pyrrolidine-2-carbonyl]-amino}-2-vinyl-cyclopropanecarboxylic acid methyl ester (2.60 g, 3.72 mmol) in benzene (20 mL) was added to above tetraethylammonium acetate solution. After heating at reflux for 1.5 h, the reaction was allowed to cool to room temperature. Solids were filtered and rinsed. The resultant solids were dissolved in MeOH (7 mL) and cooled to 0° C. to which aqueous 1N sodium hydroxide (6 mL) was added slowly. After 2 h at 0° C., the reaction was neutralized with 2N aqueous HCl and extracted with $CH_2Cl_2$. The organics were washed with saturated aqueous NaCl and dried over sodium sulfate. After removal of solvent, the crude product was purified by column chromatography on silica to provide the desired alcohol (0.90 g, 49%).

1-{[1-(2-Cyclopentyloxycarbonylamino-3,3-dimethyl-butyryl)-4-hydroxy-pyrrolidine-2-carbonyl]-amino}-2-vinyl-cyclopropanecarboxylic acid methyl ester (860 mg, 1.79 mmol) was dissolved in anhydrous DMSO (12 mL) and treated with solid KOtBu (300 mg, 2.69 mmol). After 1 h at room temperature, 1-chloro-6-methoxy-isoquinoline (380 mg, 1.97 mmol) was added to the reaction flask. After 14 h additional stirring, the reaction was quenched with cold 5% aqueous citric acid and extracted with EtOAc. The organics were washed with saturated aqueous NaCl and dried over sodium sulfate. After removal of solvent, the crude product was purified by column chromatography (5-11% MeOH/$CH_2Cl_2$) on silica to provide the desired ether (190 mg, 17%).

The acid (130 mg, 0.21 mmol) and HATU (87 mg, 0.23 mmol) were combined in DMF (2.11 mL) to which $iPr_2NEt$ (46 µL, 0.25 mmol) was added. After stirring 30 min at room temperature, sulfamic acid phenyl ester (145 mg, 0.84 mmol) and DBU (126 µL, 0.84 mmol) was added and reacted for 14 h at room temperature. The crude reaction mixture was treated with $H_2O$ to reconvert any remaining oxazolone intermediate to the corresponding acid. The reaction was neutralized with 1N aqueous HCl and extracted with EtOAc. The organics were washed with saturated aqueous NaCl and dried over sodium sulfate. After removal of solvent, the crude product was purified by column chromatography on silica (0-8% MeOH/$CH_2Cl_2$) to provide Compound 16 (38 mg, 23%): $^1H$ NMR ($CD_3OD$, 300 MHz) δ 8.05 (d, 1H), 7.88 (d, 1H), 7.21-7.39 (m, 6H), 7.15 (s, 1H), 7.09 (d, 1H), 6.74 (d, 1H), 5.80-5.89 (m, 1H), 5.76 (bs, 1H), 5.26 (d, 1H), 5.08 (d, 1H), 4.66 (bs, 1H), 4.53 (m, 1H), 4.38 (d, 1H), 4.25 (d, 1H), 4.07 (m, 1H), 3.91 (s, 3H), 2.53 (m, 1H), 2.35 (m, 1H), 2.16 (m, 1H), 1.88 (m, 1H), 1.35-1.70 (m, 10H), 0.99 (s, 9H); LCMS found 778.0 $[M+H]^+$.

Example 17

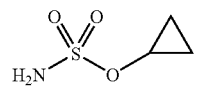

-continued

Compound 17

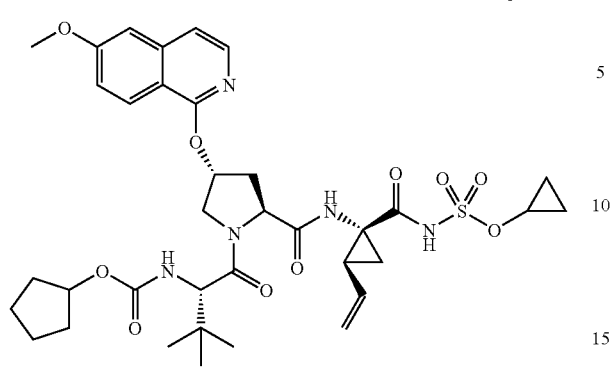

Compound 17 was prepared according to the method presented in the final synthetic step of Example 16. Treatment of 1-{[1-(2-cyclopentyloxycarbonylamino-3,3-dimethyl-butyryl)-4-(6-methoxy-isoquinolin-1-yloxy)-pyrrolidine-2-carbonyl]-amino}-2-vinyl-cyclopropanecarboxylic acid under the same conditions adjusted for scale and with the exception of utilizing sulfamic acid cyclopropyl ester provided the desired product (43 mg, 31%): $^1$H NMR (CD$_3$OD, 300 MHz diagnostic peaks) δ 4.24 (m, 1H), 0.93 (m, 2H), 0.75 (m, 2H); LCMS found 742.0 [M+H]$^+$.

Example 18 due was dissolved in MeOH and passed over a C-18 RP SPE column (Phenomenex Strata, 1 g) and eluted with MeOH to provide the desired Compound 18 (42 mg, 84%): $^1$H NMR (CD$_3$OD, 300 MHz) δ 9.11 (s, 1H), 8.10 (d, 1H), 7.89 (d, 1H), 7.28 (d, 1H), 7.21 (s, 1H), 7.12 (d, 1H), 5.84 (m, 1H), 4.70 (m, 1H), 4.59 (m, 1H), 4.43 (m, 1H), 4.29 (m, 2H), 4.04 (m, 1H), 3.93 (s, 3H), 2.62 (m, 1H), 2.26 (m, 1H), 1.26-1.72 (m, 16H), 1.03 (s, 9H), 0.96 (m, 2H), 0.77 (m, 2H); LCMS found 744.1 [M+H]$^+$.

Example 19

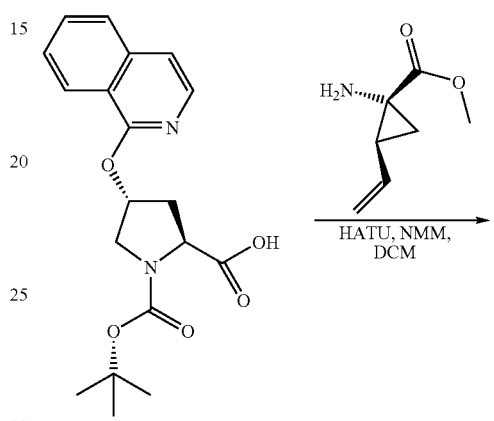

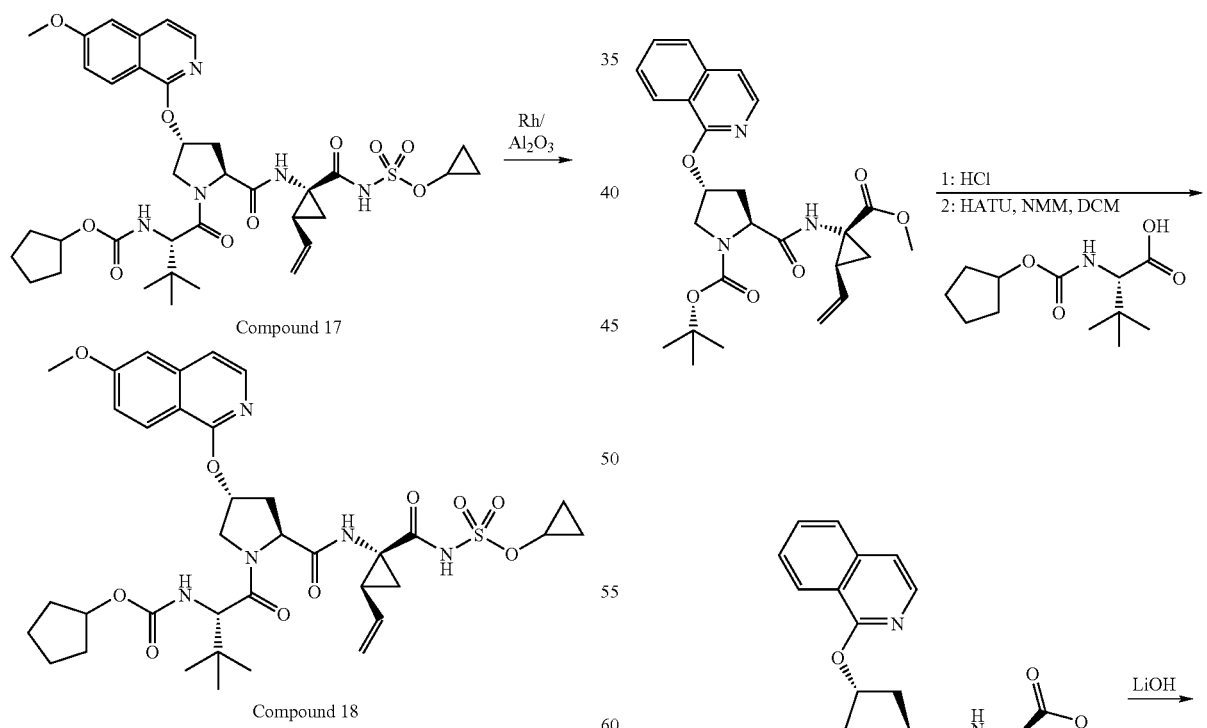

To Compound 17 (50 mg, 0.07 mmol) in EtOAc (0.7 mL) was added Rh/Al$_2$O$_3$ (10 mg, 20 wt %). The reaction atmosphere was flushed with H$_2$ gas and flask equipped with a H$_2$ filled balloon. After stirring at room temperature for 2 h, the reaction was filtered via a syringe tip filter (Nylon, 0.45 μM) and washed with CH$_2$Cl$_2$. After removal of solvent the resi-

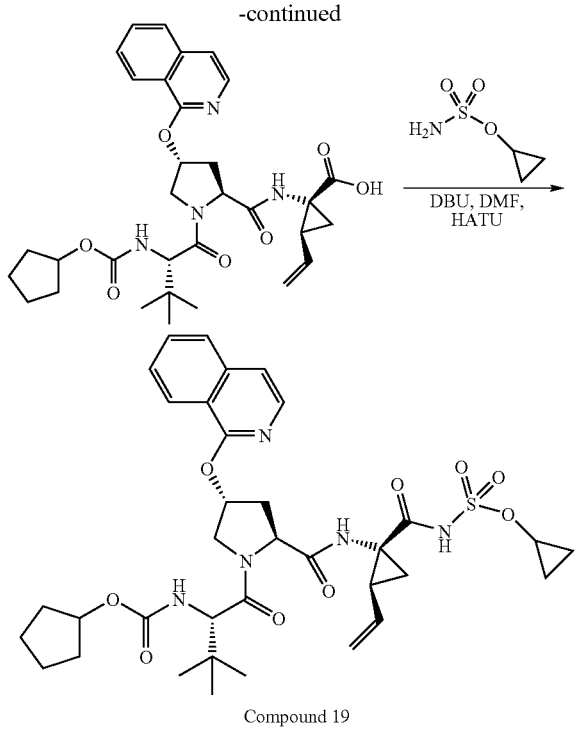

Compound 19

A round bottom flask was charged with 4-(isoquinolin-1-yloxy)-pyrrolidine-1,2-dicarboxylic acid 1-tert-butyl ester (400 mg, 1.11 mmol), DCM (10 ml), HATU (632.7 mg, 1.66 mmol), and NMM (0.37 ml, 3.36 mmol). The mixture was stirred for 15 minutes, and then 1-amino-2-vinyl-cyclopropanecarboxylic acid methyl ester added in 2 ml DCM. The mixture was stirred overnight. The reaction was quenched with water and extracted 2× with ethyl acetate, dried over sodium sulfate, and concentrated. The reaction provided the dipeptide intermediate which was used crude in the next reaction. LCMS found 481.88 [M+H]$^+$.

A round bottom flask was charged with 4-(isoquinolin-1-yloxy)-2-(1-methoxycarbonyl-2-vinyl-cyclopropylcarbamoyl)-pyrrolidine-1-carboxylic acid tert-butyl ester (700 mg, 1.45 mmol), and 2 ml 4N HCl/dioxane. The reaction was stirred 1 hour then concentrated. The resulting solid was used crude in the next reaction.

A round bottom flask was charged with 2-cyclopentyloxy-carbonylamino-3,3-dimethyl-butyric acid (243.3 mg, 1 mmol), DCM (10 ml), HATU (380 mg, 1 mmol), NMM (0.37 ml, 3.36 mmol), and stirred for 15 minutes. Then the acid treated product of 4-(isoquinolin-1-yloxy)-2-(1-methoxycarbonyl-2-vinyl-cyclopropylcarbamoyl)-pyrrolidine-1-carboxylic acid tert-butyl ester was dissolved in 2 ml DCM and added to the reaction and stirred overnight. The reaction was quenched with water and extracted 2× ethyl acetate, dried organic over sodium sulfate, and concentrated. The crude mixture was purified by silica gel column to provide the tripeptide intermediate (350 mg, 58%): LCMS found 606.93 [M+H]$^+$.

A round bottom flask was charged with 1-{[1-(2-cyclopentyloxycarbonylamino-3,3-dimethyl-butyryl)-4-(isoquinolin-1-yloxy)-pyrrolidine-2-carbonyl]-amino}-2-vinyl-cyclopropanecarboxylic acid methyl ester (350 mg, 0.58 mmol), 3.5 ml THF, 1 ml methanol, 1 ml water, and lithium hydroxide (20 mg, 0.84 mmol). The reaction was stirred 3 hours at 95° C. The reaction was diluted with water and extracted 1× ethyl acetate. The aqueous layer was acidified with 1 N HCl and extracted 2× ethyl acetate. The organic layer was dried over sodium sulfate, filtered and concentrated. The mixture was purified by reverse phase HPLC to provide the acid (53 mg, 15%): LCMS found 593.13 [M+H]$^+$.

A round bottom flask was charged with 1-{[1-(2-cyclopentyloxycarbonylamino-3,3-dimethyl-butyryl)-4-(isoquinolin-1-yloxy)-pyrrolidine-2-carbonyl]-amino}-2-vinyl-cyclopropanecarboxylic acid (50 mg, 0.084 mmol), 2.5 ml DMF, HATU (50 mg, 0.13 mmol), DIEA (25 uL, 0.14 mmol), sulfamic acid cyclopropyl ester (25 mg, 0.18 mmol) and allowed to stir 15 minutes. To the mixture DBU (50 uL, 0.33 mmol) was added and allowed to stir 3 hours. The reaction was quenched with water and extract 2× ethyl acetate. The organic layer was dried over sodium sulfate, filtered, and concentrated. The mixture was purified by reverse phase HPLC to provide Compound 19 (12 mg, 20%): $^1$H NMR (CD$_3$OD, 300 MHz) δ 9.21 (s, 1H), 8.22 (d, 1H), 7.98 (d, 1H), 7.83 (d, 1H), 7.73 (t, 1H), 7.55 (t, 1H), 7.35 (d, 1H), 5.89 (s, 1H), 5.74 (m, 1H), 5.33 (d, 1H), 5.16 (d, 1H), 4.71 (m, 1H), 4.59 (m, 1H), 4.46 (m, 1H), 4.31 (s, 1H), 4.26 (m, 1H), 4.10 (dd, 2H), 2.64 (m, 1H), 2.26-2.31 (m, 2H), 1.88 (t, 1H), 1.30-1.70 (m, 8H), 1.24 (t, 2H), 1.04 (s, 8H), 0.94 (d, 2H), 0.75 (m, 2H); LCMS found 712.03 [M+H]$^+$.

Example 20

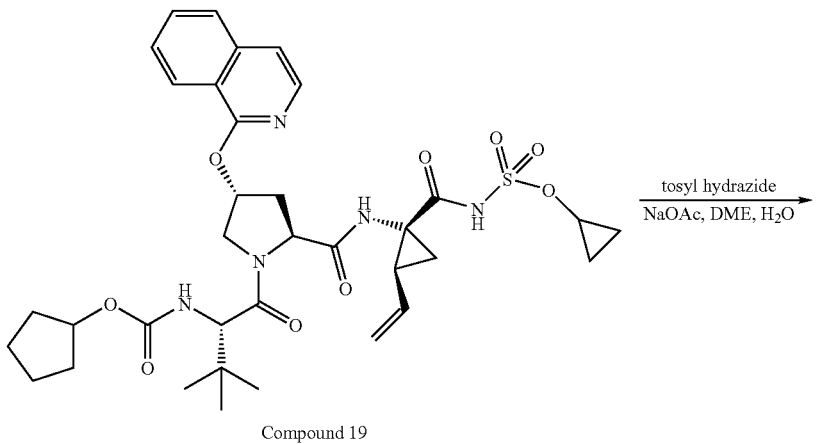

Compound 19

-continued

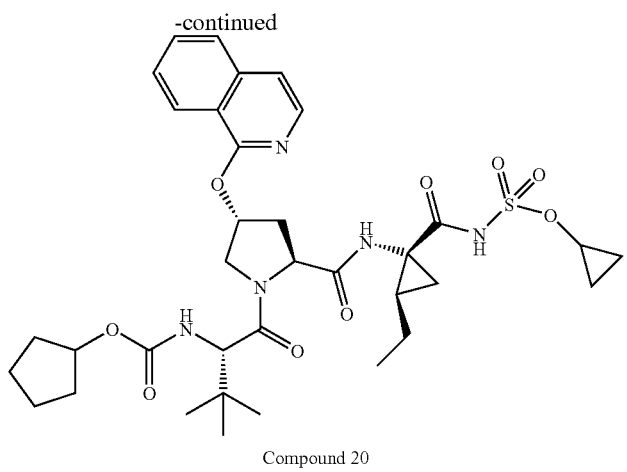

Compound 20

A round bottom flask was charged with Compound 19 (12 mg, 0.017 mmol), 1 ml DME, 1 ml water, tosyl hydrazide (11.17 mg, 0.06 mmol), and sodium acetate (9.83 mg, 0.12 mmol). The reaction was heated to 95° C. and allowed to stir 1 hour. The reaction was diluted with water and extracted 2× ethyl acetate. The organic layer was dried over sodium sulfate, filtered, and concentrated. The mixture was purified by reverse phase HPLC to provide Compound 20 (6.53 mg, 53%): $^1$H NMR (CD$_3$OD, 300 MHz, diagnostic peaks) δ 9.12 (s, 1H), 8.22 (d, 1H), 7.97 (d, 1H), 7.83 (d, 1H), 7.72 (t, 1H), 7.56 (t, 1H), 7.35 (d, 1H), 5.88 (s, 1H); LCMS found 713.99 [M+H]$^+$.

Example 21

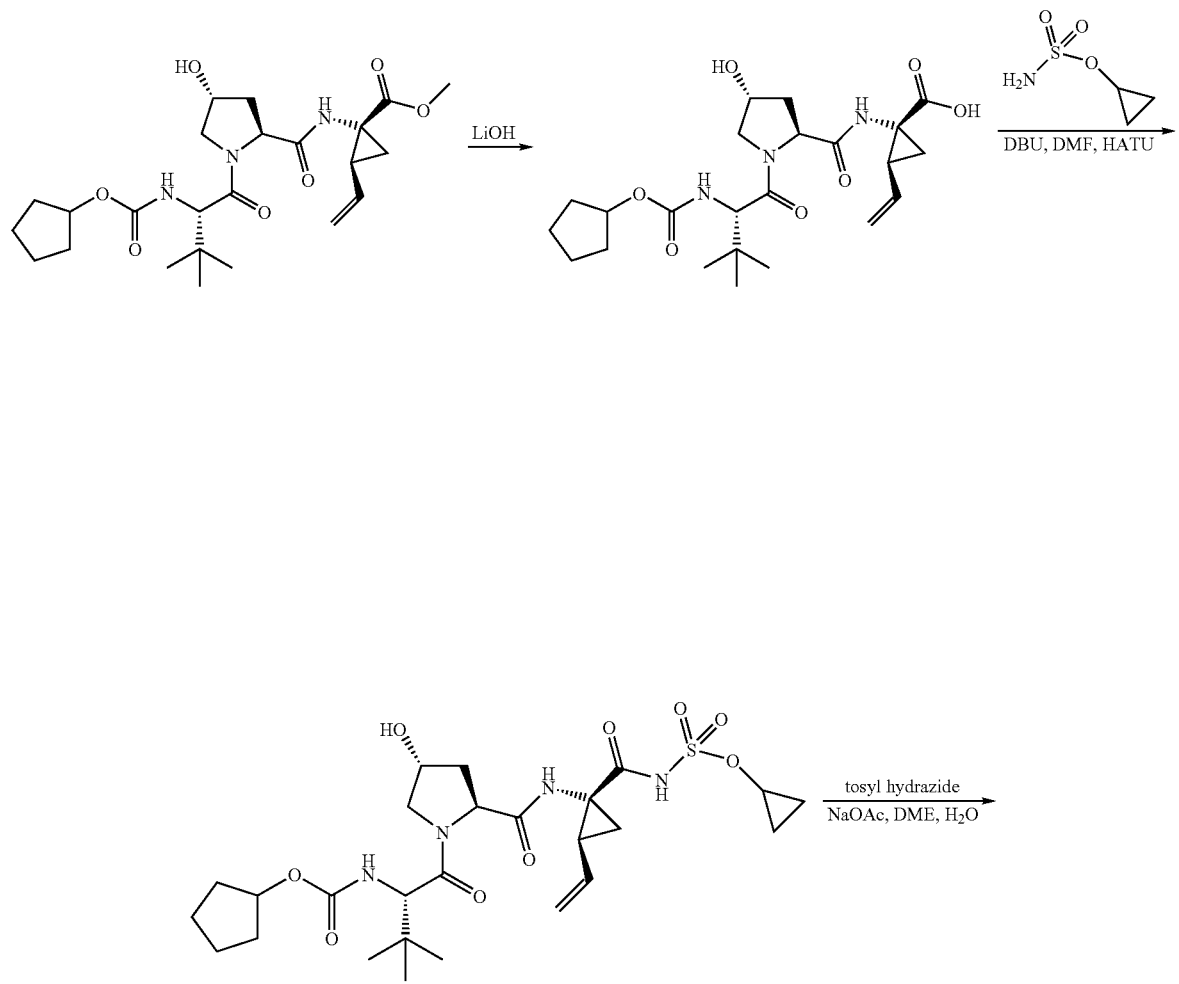

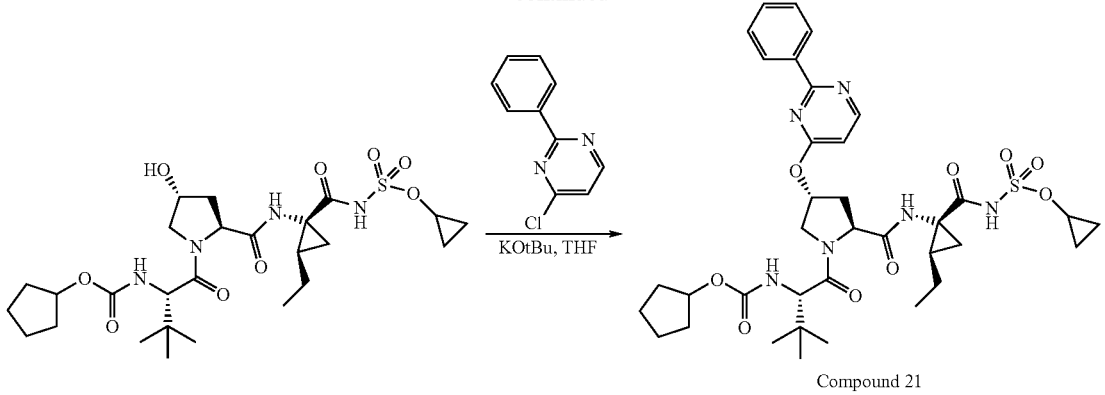

Compound 21

A round bottom was charged with 1-{[1-(2-cyclopentyloxycarbonylamino-3,3-dimethyl-butyryl)-4-hydroxy-pyrrolidine-2-carbonyl]-amino}-2-vinyl-cyclopropanecarboxylic acid methyl ester (2 g, 4.17 mmol), 25 ml THF, 8 ml methanol, 8 ml water, and lithium hydroxide (200 mg, 8.35 mmol). The mixture was stirred overnight. The reaction was quenched with 1 N HCl and extracted 3× ethyl acetate. The organic layer was dried over sodium sulfate, filtered, and concentrated to give the desired acid which was used crude in the next reaction: LCMS found 465.97 [M+H]$^+$.

A round bottom flask was charged with 1-{[1-(2-cyclopentyloxycarbonylamino-3,3-dimethyl-butyryl)-4-hydroxy-pyrrolidine-2-carbonyl]-amino}-2-vinyl-cyclopropanecarboxylic acid (2 g, 4.30 mmol), 50 ml DMF, HATU (2.45 g, 6.45 mmol), and sulfamic acid cyclopropyl ester (883 mg, 6.44 mmol) and allowed to stir 15 minutes. To the mixture DBU (1.8 ml 13.10 mmol) was added and the reaction allowed to stir overnight, followed by more DBU (1.8 ml, 13.10 mmol) and stirred overnight. The mixture was diluted with water and extracted 2× ethyl acetate. The organic layer was dried over sodium sulfate, filtered, and concentrated. The mixture was purified by reverse phase HPLC to give the acylsulfamate (900 mg, 37% two steps): LCMS found 584.94 [M+H]$^+$.

A round bottom was charged with {1-[2-(1-cyclopropoxysulfonylaminocarbonyl-2-vinyl-cyclopropylcarbamoyl)-4-hydroxy-pyrrolidine-1-carbonyl]-2,2-dimethyl-propyl}-carbamic acid cyclopentyl ester (800 mg, 1.37 mmol), 10 ml DME, 10 ml water, tosyl hydrizide (760 mg, 4.08 mmol), and sodium acetate (669 mg, 8.16 mmol). The mixture was heated at 95° C. for 1 hour. The reaction was diluted with water and extracted 2× dichloromethane. The organic layer was dried over sodium sulfate, filtered, and concentrated to give the reduced compound which was used crude in the next reaction: LCMS found 586.94 [M+H]$^+$.

A round bottom flask was charged with {1-[2-(1-cyclopropoxysulfonylaminocarbonyl-2-ethyl-cyclopropylcarbamoyl)-4-hydroxy-pyrrolidine-1-carbonyl]-2,2-dimethyl-propyl}-carbamic acid cyclopentyl ester (100 mg crude, 0.17 mmol), 10 ml THF, 4-chloro-2-phenyl-pyrimidine (40 mg, 0.21 mmol), and potassium t-butoxide (100 mg, 0.89 mmol). The mixture was stirred overnight. The mixture was diluted with water and extracted 2× ethyl acetate. The organic layer was dried over sodium sulfate, filtered, and concentrated. The mixture was purified by reverse phase HPLC giving product Compound 21 (7.5 mg, 3.9% two combined reactions): $^1$H NMR (CDCl$_3$, 300 MHz, diagnostic peaks) δ 8.77 (m, 1H), 8.33 (m, 2H), 7.57 (m, 3H), 7.46 (s, 1H), 7.18 (m, 1H), 6.75-6.81 (m, 1H); LCMS found 741.02 [M+H]$^+$.

Example 22

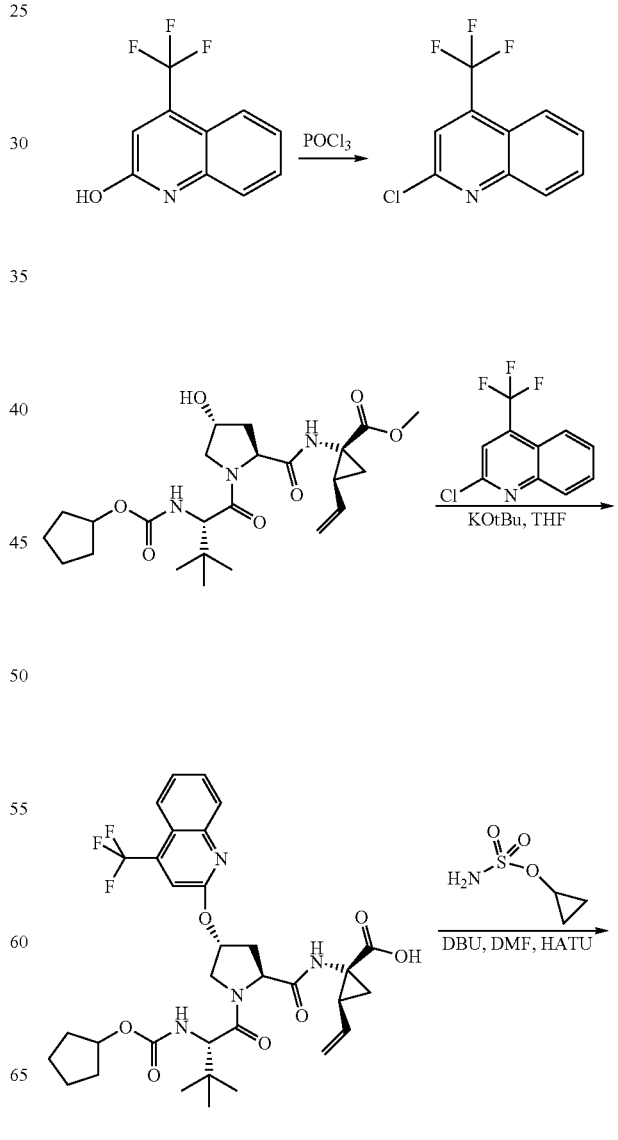

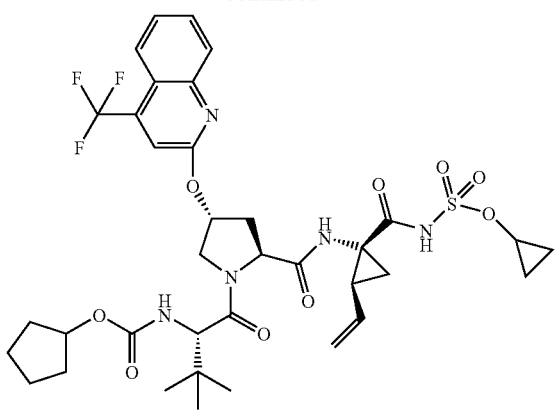

Compound 22

A round bottom was charged with 4-trifluoromethyl-quinolin-2-ol (1 g, 4.69 mmol) and POCl₃ (10 ml, 107.28 mmol). The mixture was heated to reflux for 3 hours, and then concentrated to remove excess POCl₃. The mixture was based with 5 N NaOH and extracted with DCM. The mixture was purified by flash chromatography to give intermediate 2-chloro-4-trifluoromethyl-quinoline (845 mg, 78%): LCMS found 232.22 [M+H]⁺.

A round bottom flask was charged with 1-{[1-(2-cyclopentyloxycarbonylamino-3,3-dimethyl-butyryl)-4-hydroxy-pyrrolidine-2-carbonyl]-amino}-2-vinyl-cyclopropanecarboxylic acid methyl ester (479.6 mg, 0.62 mmol), 20 ml THF, 2-chloro-4-trifluoromethyl-quinoline (142 mg, 0.61 mmol), and potassium t-butoxide (276.1 mg, 2.46 mmol). The mixture was stirred overnight. The mixture was diluted with water and extracted 2× ethyl acetate. The organic layer was dried over sodium sulfate, filtered, and concentrated. The mixture was purified by reverse phase HPLC giving the aryl ether (100 mg, 24%): LCMS found 660.93 [M+H]⁺.

Compound 22 was prepared according to the method presented in the final step in Example 2. Treatment of 1-{[1-(2-cyclopentyloxycarbonylamino-3,3-dimethyl-butyryl)-4-(4-trifluoromethyl-quinolin-2-yloxy)-pyrrolidine-2-carbonyl]-amino}-2-vinyl-cyclopropanecarboxylic acid (100 mg, 0.15 mmol) under the same conditions adjusted for scale and utilizing sulfamic acid cyclopropyl ester provided desired product Compound 22 (4 mg, 3.4%): ¹H NMR (CD₃OD, 300 MHz, diagnostic peaks) δ 9.23 (m, 1H), 9.00 (m, 1H), 8.03 (m, 1H), 7.19-7.35 (m, 2H), 6.67 (s, 1H), 4.15 (m, 1H), 0.93 (m, 2H), 0.75 (m, 2H); LCMS found 779.94 [M+H]⁺.

Example 23

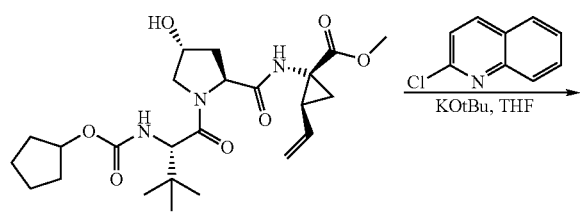

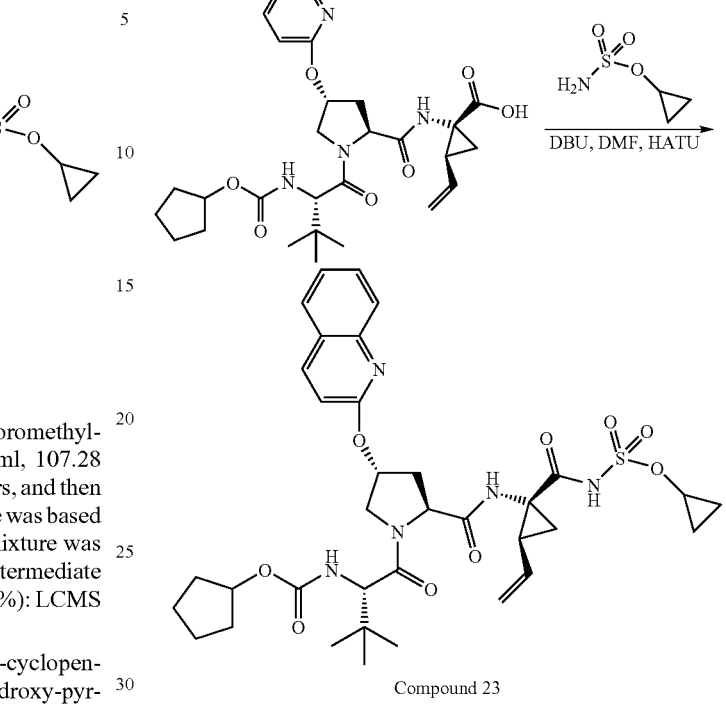

Compound 23

1-{[1-(2-Cyclopentyloxycarbonylamino-3,3-dimethyl-butyryl)-4-(quinolin-2-yloxy)-pyrrolidine-2-carbonyl]-amino}-2-vinyl-cyclopropanecarboxylic acid was prepared according to the method presented in Example 16. Treatment of 2-chloro-quinoline (102.3 mg, 0.63 mmol) under the same conditions provided desired aryl ether (105.8 mg, 29%): LCMS found 593.03 [M+H]⁺.

Compound 23 was prepared according to the method presented in the final step in Example 2. Treatment of 1-{[1-(2-cyclopentyloxycarbonylamino-3,3-dimethyl-butyryl)-4-(quinolin-2-yloxy)-pyrrolidine-2-carbonyl]-amino}-2-vinyl-cyclopropanecarboxylic acid (100 mg, 0.17 mmol) under the same conditions adjusted for scale and utilizing sulfamic acid cyclopropyl ester provided desired product Compound 23 (17.1 mg, 14%): ¹H NMR (CDCl₃, 300 MHz, diagnostic peaks) δ 8.08 (d, 1H), 7.85 (d, 1H), 7.84 (d, 1H), 7.68 (m, 1H), 7.27 (m, 1H, blocked by solvent peak), 6.88-6.92 (2, 1H), 4.15 (m, 1H), 1.02 (m, 2H), 0.73 (m, 2H); LCMS found 712.03 [M+H]⁺.

Example 24

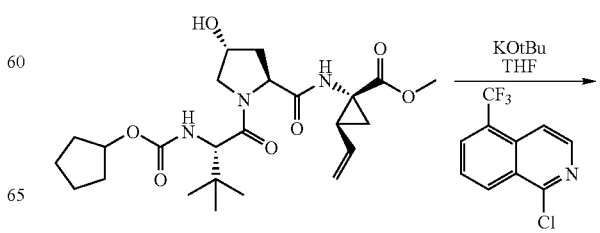

-continued

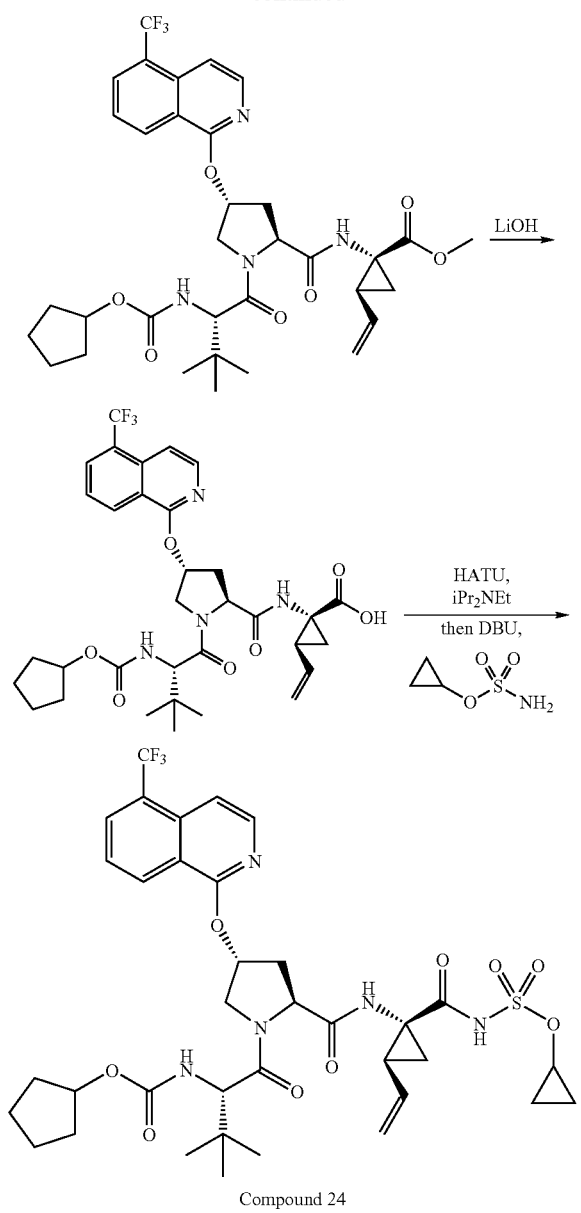

Compound 24

1-Chloro-5-trifluoromethoxy-isoquinoline was synthesized according to the method presented in Example 16 with the exception of utilizing 2-(trifluoromethoxy)cinnamic acid.

1-{[1-(2-Cyclopentyloxycarbonylamino-3,3-dimethyl-butyryl)-4-hydroxy-pyrrolidine-2-carbonyl]-amino}-2-vinyl-cyclopropanecarboxylic acid methyl ester (203 mg, 0.423 mmol) was dissolved in anhydrous THF (2 mL) and treated with solid KOtBu (1.4 ml, 1.40 mmol) at −78 C. After 4 min. stirring, 1-chloro-5-trifluoromethyl-isoquinoline (118 mg, 0.508 mmol) in 1.2 ml of THF was added to the reaction flask. After 60 min. stirring at r.t., the reaction was quenched with saturated $NH_4Cl$ and extracted with EtOAc. The organics were dried over sodium sulfate. After removal of solvent, the crude product was purified by column chromatography (30-80% EtOAc/Hexane) on silica to provide the aryl ether (135 mg, 47%), LCMS found 675.0 $[M+H]^+$.

1-{[1-(2-Cyclopentyloxycarbonylamino-3,3-dimethyl-butyryl)-4-(5-trifluoromethyl-isoquinolin-1-yloxy)-pyrrolidine-2-carbonyl]-amino}-2-vinyl-cyclopropanecarboxylic acid methyl ester (135 mg, 0.200 mmol) was dissolved in anhydrous THF (1.2 mL) and treated with 1 M $LiOH/H_2O$ (0.8 ml, 0.801 mmol). After 8.25 h stirring, the reaction was quenched with 2 N HCl and extracted with EtOAc. The organics were dried over sodium sulfate. Removal of solvent provided the acid (125 mg, 94%), LCMS found 661.1 $[M+H]^+$.

1-{[1-(2-Cyclopentyloxycarbonylamino-3,3-dimethyl-butyryl)-4-(5-trifluoromethyl-isoquinolin-1-yloxy)-pyrrolidine-2-carbonyl]-amino}-2-vinyl-cyclopropanecarboxylic acid (125 mg, 0.189 mmol) and HATU (91 mg, 0.284 mmol) were combined in DMF (0.8 mL) to which $iPr_2NEt$ (42 mL, 0.284 mmol) was added. After stirring 30 min at room temperature, sulfamic acid cyclopropyl ester (44 mg, 0.378 mmol) and DBU (96 mL, 0.756 mmol) was added and reacted for 14 h at room temperature. The crude reaction mixture was quenched with saturated $NaHCO_3$ and extracted with EtOAc. The organics were washed with 1N aqueous HCl and dried over sodium sulfate. After removal of solvent, the crude product was purified by column chromatography (60-100% EtOAc/Hexane and 0-10% $MeOH/CH_2Cl_2$) on silica and prep HPLC to provide Compound 24 (40.4 mg, 27%): $^1H$ NMR ($CDCl_3$, 300 MHz) 10.18 (bs, 1H), 8.41 (d, 1H), 8.12 (d, 1H), 8.04 (d, 1H), 7.57 (bs, 1H), 7.21 (bs, 1H), 5.80-5.89 (m, 1H), 5.76 (bs, 1H), 5.26 (d, 1H), 5.08 (d, 1H), 4.66 (bs, 1H), 4.53 (m, 1H), 4.38 (d, 1H), 4.25 (d, 1H), 4.24 (m, 1H), 4.07 (m, 1H), 3.91 (s, 3H), 2.53 (m, 1H), 2.35 (m, 1H), 2.16 (m, 1H), 1.97 (m, 1H), 1.62-1.48 (m, 10H), 1.02 (s, 9H), 0.96 (m, 2H), 0.70 (m, 2H); LCMS found 780.1 $[M+H]^+$.

Example 25

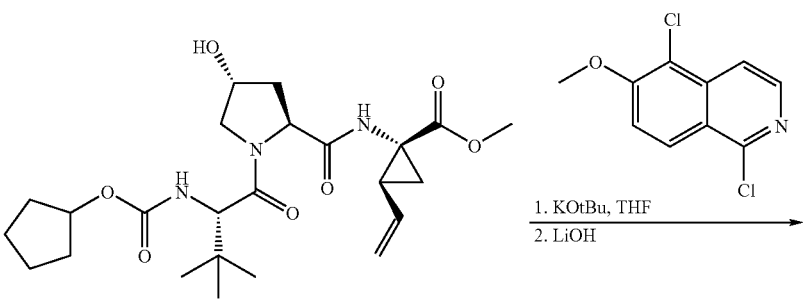

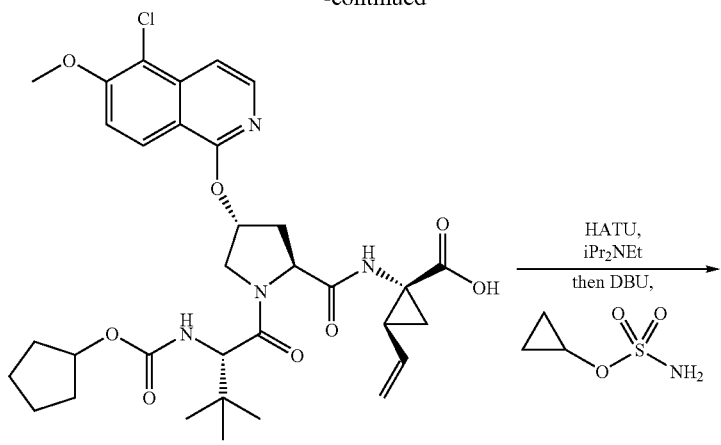

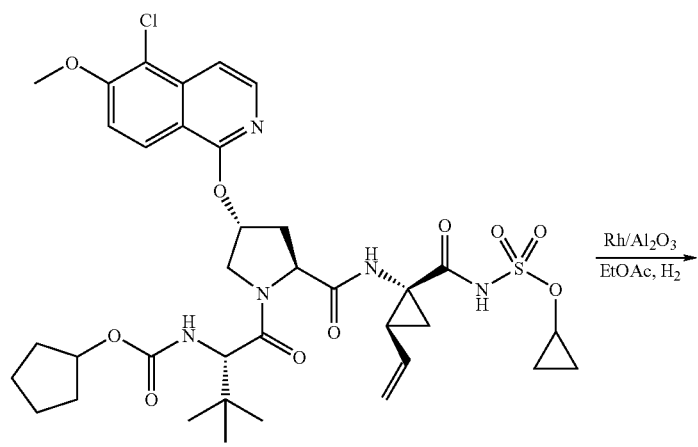

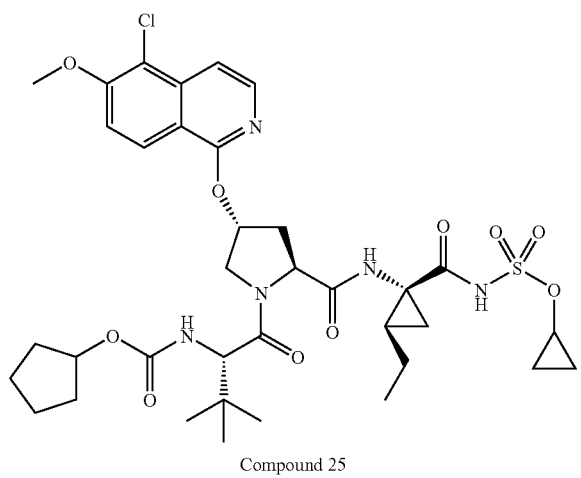

Compound 25

1,7-Dichloro-6-methoxy-isoquinoline was synthesized according to the method presented in Example 16 with the exception of utilizing 2-chloro-3-methoxycinnamic acid.

1-{[1-(2-cyclopentyloxycarbonylamino-3,3-dimethyl-butyryl)-4-hydroxy-pyrrolidine-2-carbonyl]-amino}-2-vinyl-cyclopropanecarboxylic acid methyl ester (250 mg, 0.521 mmol) was dissolved in anhydrous THF (4 mL) and treated with solid KOtBu (1.8 ml, 1.80 mmol) at −78 C. After 4 min. stirring, 1,5-dichloro-6-methoxy-isoquinoline (178 mg, 0.782 mmol) was added to the reaction flask. After 60 min. stirring at r.t., the reaction was treated with 1 M LiOH/H$_2$O (6 ml, 6.0 mmol) and 2 ml of MeOH. After 14 h stirring, the reaction was quenched with 2 N HCl and extracted with EtOAc. The organics were dried over sodium sulfate. After removal of solvent, the crude product was purified by column chromatography (0-10% MeOH/CH$_2$Cl$_2$) on silica to provide the aryl ether (113 mg, 33% O), LCMS found 657.1 [M+H]$^+$.

1-{[4-(5-chloro-6-methoxy-isoquinolin-1-yloxy)-1-(2-cyclopentyloxycarbonylamino-3,3-dimethyl-butyryl)-pyrrolidine-2-carbonyl]-amino}-2-vinyl-cyclopropanecarboxylic acid (113 mg, 0.172 mmol), sulfamic acid cyclopropyl ester (36 mg, 0.259 mmol) and HATU (98 mg, 0.259 mmol) were combined in DMF (2 mL) to which DBU (77 uL, 0.517 mmol) was added. After stirring 3 h at room temperature, the crude reaction mixture was quenched with 1N aqueous HCl and extracted with EtOAc. The organics were dried over sodium sulfate. After removal of solvent, the crude product was purified by perp HPLC to provide the acylsulfamate (70 mg, 50%), LCMS found 776.1 [M+H]$^+$.

To {1-[4-(5-chloro-6-methoxy-isoquinolin-1-yloxy)-2-(1-cyclopropoxysulfonylaminocarbonyl-2-vinyl-cyclopropyl-carbamoyl)-pyrrolidine-1-carbonyl]-2,2-dimethyl-propyl}-carbamic acid cyclopentyl ester (70 mg, 0.086 mmol) in EtOAc (2.5 mL) was added Rh/Al$_2$O$_3$ (14 mg, 20 wt %). The reaction atmosphere was flushed with H$_2$ gas and flask equipped with a H$_2$ filled balloon. After stirring at room temperature for 1.5 h, the reaction was filtered and washed with CH$_2$Cl$_2$. After removal of solvent, the crude product was purified by preperatory TLC (3% MeOH/CH$_2$Cl$_2$) and reverse phase HPLC to provide the Compound 25 (15 mg, 20%): $^1$H NMR (CDCl$_3$, 300 MHz) 8.11 (d, 1H), 8.01 (d, 1H), 7.63 (d, 1H), 7.24 (d, 1H), 7.14 (bs, 1H), 5.88 (bs, 1H), 5.34 (d, 1H), 4.69 (bs, 1H), 4.53 (m, 1H), 4.43 (d, 1H), 4.29 (d, 2H), 4.19 (m, 1H), 4.05 (s, 3H), 2.60 (m, 1H), 2.47 (m, 1H), 1.62-1.48 (m, 10H), 1.02 (s, 9H), 0.96 (m, 2H), 0.70 (m, 2H); LCMS found 778.1 [M+H]$^+$.

Example 26

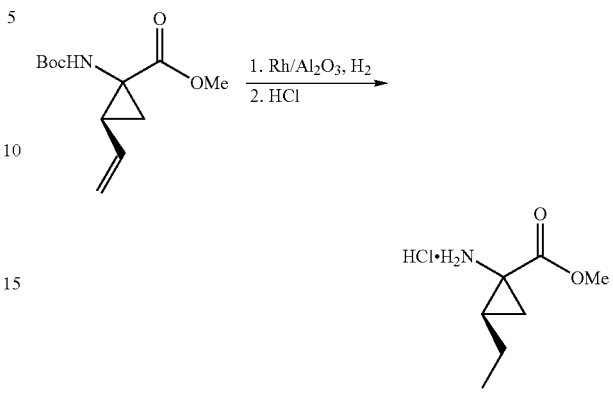

Reduction of 1-tert-Butoxycarbonylamino-2-ethyl-cyclopropanecarboxylic acid methyl ester was performed according to the method presented in Example 18. Treatment of 1-tert-butoxycarbonylamino-2-vinyl-cyclopropanecarboxylic acid methyl ester under the same conditions adjusted for scale provided the desired reduced compound after purification on silica gel. Treatment of this material with 4N HCl in dioxanes, followed by removal of solvents provided the desired intermediate 1-amino-2-ethyl-cyclopropanecarboxylic acid methyl ester as the HCl salt: $^1$H NMR (300 MHz, CD$_3$OD): δ 3.80 (s, 3H), 1.39-1.63 (m, 5H), 0.94 (t, 3H).

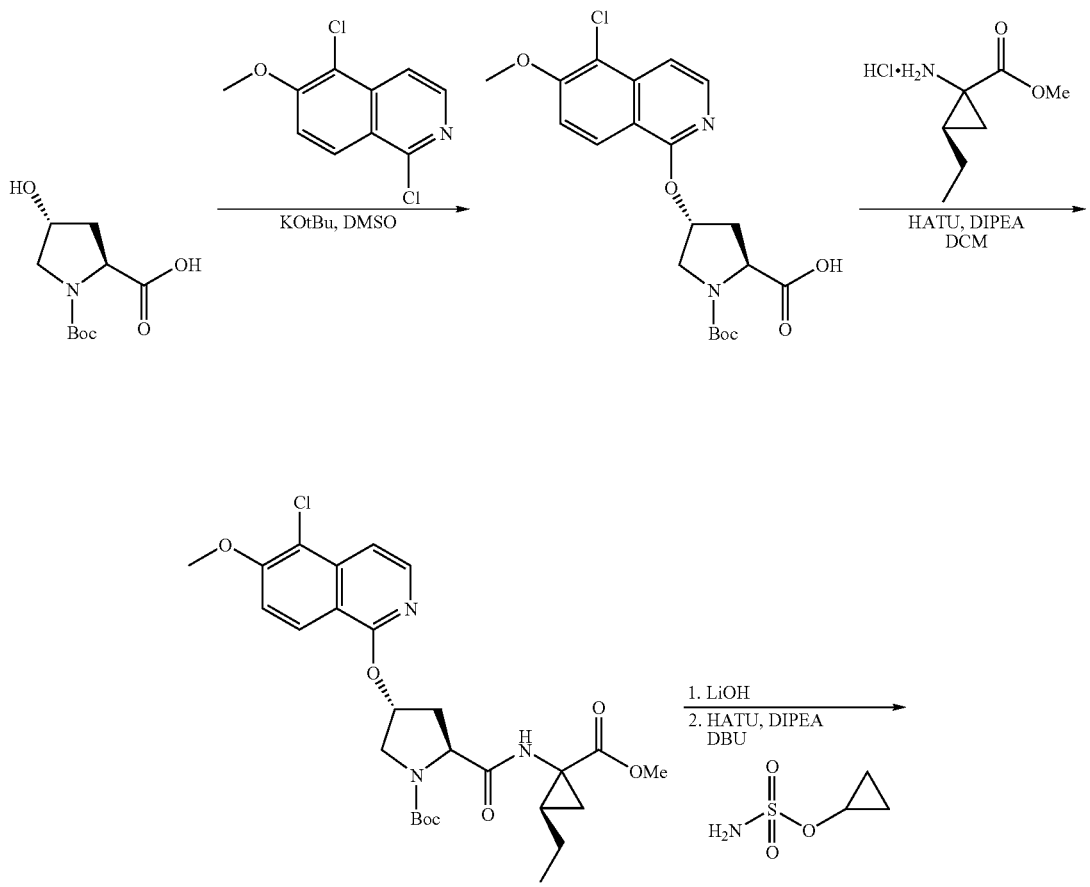

-continued

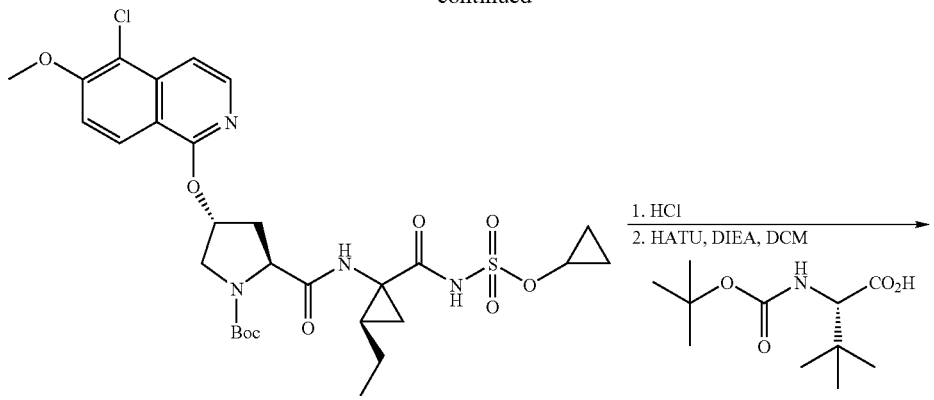

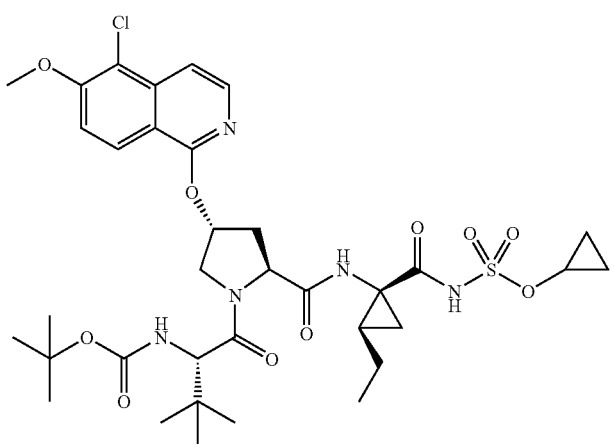

Compound 26

4-Hydroxy-pyrrolidine-1,2-dicarboxylic acid 1-tert-butyl ester (1.01 g, 4.38 mmol) was dissolved in anhydrous DMSO (11 mL) and THF (22 mL), then treated with 1M KOtBu/THF (11 mL, 11.0 mmol). After 10 min. at room temperature, 1,5-dichloro-6-methoxy-isoquinoline (1.0 g, 4.38 mmol) was added to the reaction flask. After 1.5 h additional stirring, the reaction was quenched with 2N HCl and extracted with EtOAc. The organics were dried over sodium sulfate. After removal of solvent, the tan foam crude product was used in the next reaction without further purification.

4-(6-Methoxy-isoquinolin-1-yloxy)-pyrrolidine-1,2-dicarboxylic acid 1-tert-butyl ester (1.38 mmol) was combined with the HCl salt of 1-amino-2-ethyl-cyclopropanecarboxylic acid methyl ester (4.38 mmol) in $CH_2Cl_2$ (10 mL) to which HATU (2.5 g, 6.58 mmol) and $iPr_2NEt$ (3.06 mL, 17.5 mmol) were added. After stirring for 100 min. at room temperature, the reaction was purified by column chromatography on silica (0-10% $MeOH/CH_2Cl_2$) to provide the desired ester: LCMS found 548.0 $[M+H]^+$. The product was used in the next reaction without quantitative analysis.

4-(5-Chloro-6-methoxy-isoquinolin-1-yloxy)-2-(2-ethyl-1-methoxycarbonyl-cyclopropylcarbamoyl)-pyrrolidine-1-carboxylic acid tert-butyl ester (4.38 mmol) was dissolved in anhydrous THF (30 mL) and MeOH (10 mL), then treated with 1 M $LiOH/H_2O$ (10 ml, 10.0 mmol). After 18 h stirring, the reaction was quenched with 2 N HCl and extracted with EtOAc. The organics were dried over sodium sulfate. Removal of solvent provided the acid (1.34 g, 54% over 3 steps, LCMS found 532.0 (M−H)). The acid (211 mg, 0.370 mmol) and HATU (183 mg, 0.481 mmol) were combined in DMF (4 mL) to which DBU (276 uL, 0.185 mmol) and sulfamic acid cyclopropyl ester was added. After stirring 3 h at room temperature, the crude reaction mixture was quenched with 1N aqueous HCl and extracted with EtOAc. The organics were dried over sodium sulfate. After removal of solvent, the crude product was purified by column chromatography (30-100% EtOAc/Hexane) on silica to provide the acylsulfamate (127 mg, 53%), LCMS found 653.0 $[M+H]^+$.

4-(5-Chloro-6-methoxy-isoquinolin-1-yloxy)-2-(1-cyclopropoxysulfonylaminocarbonyl-2-ethyl-cyclopropylcarbamoyl)-pyrrolidine-1-carboxylic acid tert-butyl ester (127 mg, 0.194 mmol) was stirred in 4N HCl in dioxanes (3.5 mL) for 30 min. Solvents were removed and the crude residue dried. The resultant crude amine was combined with HATU (111 mg, 0.292 mmol) and Boc-L-tert-leucine, dissolved in $CH_2Cl_2$ (3 mL), and treated with DIEA (169 uL, 0.972 mmol). After stirring for 2 h at room temperature, the reaction was purified by column chromatography on silica (0-8% $MeOH/CH_2Cl_2$ and 30-100% EtOAc/Hexane) and reverse phase HPLC to provide Compound 26 (145 mg, 85%): $^1$H NMR (CDCl$_3$, 300 MHz) 10.33 (s, 1H), 8.13 (d, 1H), 8.02 (d, 1H), 7.63 (d, 1H), 7.24 (d, 1H), 6.91 (bs, 1H), 5.94 (bs, 1H), 5.19 (d, 1H), 4.51 (d, 2H), 4.33 (m, 1H), 4.23 (d, 1H), 4.07 (s, 3H), 3.97 (m, 3H), 2.55 (m, 2H), 1.73-1.60 (m, 3H), 1.44 (s, 1H), 1.28 (s, 9H), 1.03 (m, 15H), 0.74 (m, 2H); LCMS found 766.0 [M+H]$^+$.

Example 27

4-Hydroxy-pyrrolidine-1,2-dicarboxylic acid 1-tert-butyl ester (512 mg, 2.21 mmol) was dissolved in anhydrous DMSO (22 mL) and treated with solid KOtBu (745 mg, 6.64 mmol). After 1 h at room temperature, the solution was cooled to 0° C. and 1-chloro-6-methoxy-isoquinoline (450 mg, 2.32 mmol) was added to the reaction flask. After warming to room temperature and 14 h additional stirring, the reaction was

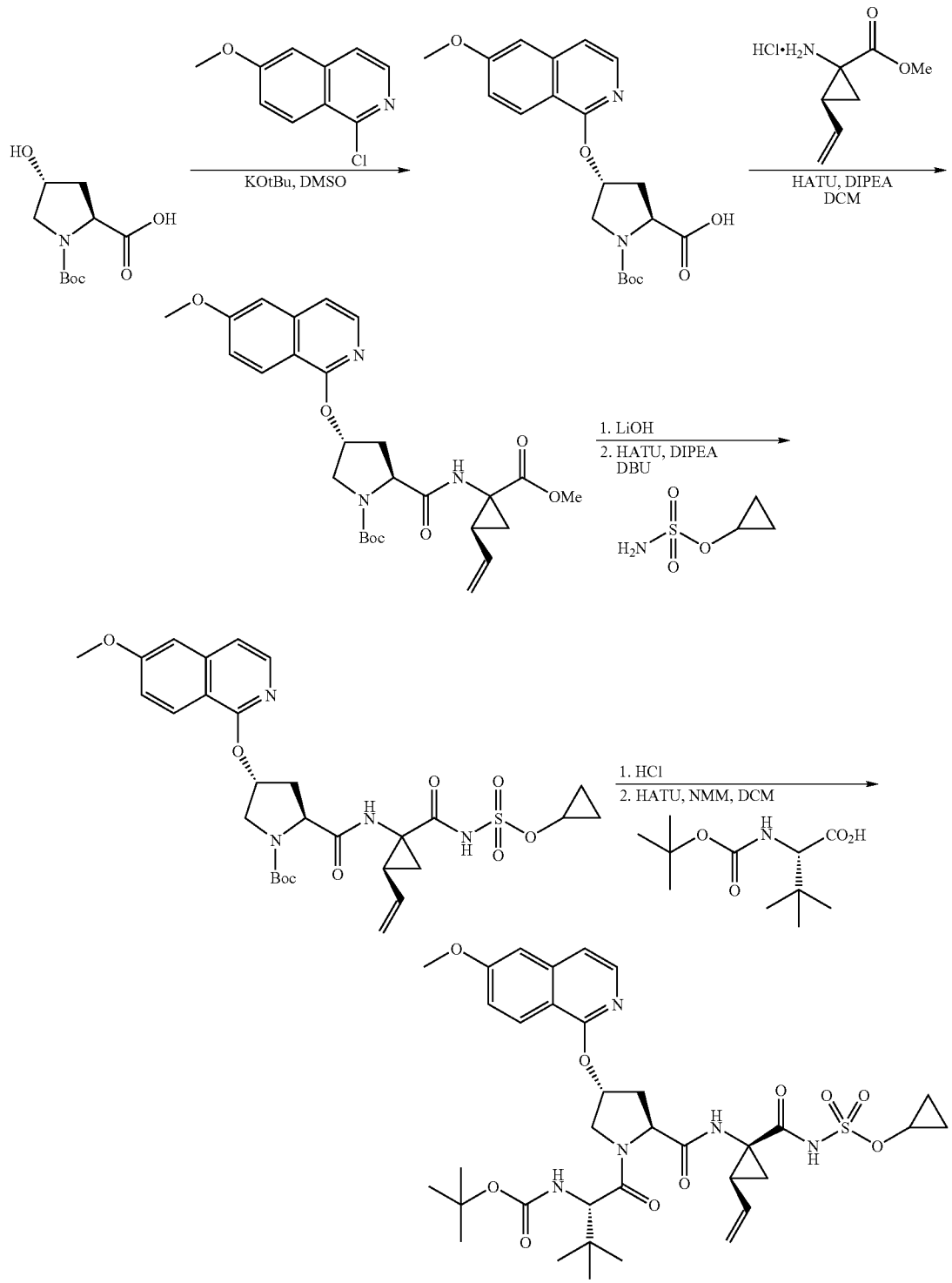

Compound 27 quenched with cold 5% aqueous citric acid and extracted with EtOAc. The organics were washed with saturated aqueous NaCl and dried over sodium sulfate. After removal of solvent, the tan foam crude product was used in the next reaction without further purification (940 mg, 99%).

The acid 4-(6-methoxy-isoquinolin-1-yloxy)-pyrrolidine-1,2-dicarboxylic acid 1-tert-butyl ester (2.21 mmol) was combined with 1-amino-2-vinyl-cyclopropanecarboxylic acid methyl ester (2.54 mmol) in $CH_2Cl_2$ (22 mL) to which HATU (1.26 g, 3.32 mmol) and $iPr_2NEt$ (1.15 mL, 6.64 mmol) were added. After stirring for 2 h at room temperature, the reaction was acidified with 1N aqueous HCl and extracted with EtOAc. The organics were washed 5% aqueous citric acid, saturated aqueous NaCl and dried over sodium sulfate. After removal of solvent, the crude product was purified by column chromatography on silica (40-60% EtOAc/hexanes) to provide the desired ester (978 mg, 87%):

2-(1-Methoxycarbonyl-2-vinyl-cyclopropylcarbamoyl)-4-(6-methoxy-isoquinolin-1-yloxy)-pyrrolidine-1-carboxylic acid tert-butyl ester (1.44 g, 2.93 mmol) was dissolved in THF/MeOH (3:1, 24 mL) to which a solution of LiOH (352 mg, 14.68 mmol) in $H_2O$ (6 mL) was added and stirred at room temperature for 12 h. The reaction was diluted with $H_2O$ and acidified with 1N aqueous HCl. The solution was extracted with EtOAc, washed with saturated aqueous NaCl, and dried over sodium sulfate. After removal of solvent, the crude product was used directly in the next reaction.

The resultant acid (440 mg, 0.89 mmol) and HATU (506 mg, 1.33 mmol) were combined in DMF (8.9 mL) and treated with $iPr_2NEt$ (0.24 mL, 1.33 mmol). After 15 min stirring at room temperature, sulfamic acid cyclopropyl ester (304 mg, 2.22 mmol) and DBU (0.53 mL, 3.55 mmol) were then added to the reaction mixture. After stirring for 3 h at room temperature, the reaction was diluted with $H_2O$. The solution was extracted with EtOAc, washed with saturated aqueous $NaHCO_3$, and dried over sodium sulfate. After removal of solvent, the crude product was purified by column chromatography on silica (60-90% EtOAc/hexanes) to provide the acylsulfamate (400 mg, 73%).

2-(1-Cyclopropoxysulfonylaminocarbonyl-2-vinyl-cyclopropylcarbamoyl)-4-(6-methoxy-isoquinolin-1-yloxy)-pyrrolidine-1-carboxylic acid tert-butyl ester (400 mg, 0.65 mmol) was dissolved in $CH_2Cl_2$ (2 mL), treated with 4N HCl in dioxanes (2 mL) and reacted at room temperature for 1 h. Solvents were removed and the crude residue dried. The resultant crude amine was combined with HATU (370 mg, 0.97 mmol), dissolved in $CH_2Cl_2$ (6.5 mL), and treated with Boc-L-tert-leucine (0.65 mmol) and NMM (0.21 mL, 1.95 mmol). After stirring for 14 h at room temperature, the reaction was acidified with 1N aqueous HCl and extracted with $CH_2Cl_2$. The organics were washed with 1N aqueous HCl, saturated aqueous NaCl and dried over sodium sulfate. After removal of solvent, the crude product was purified by reverse phase column chromatography on C18 (30-95% $ACN/H_2O$-1% TFA) to provide Compound 27 (222 mg, 47%): $^1H$ NMR ($CD_3OD$, 300 MHz) δ 9.22 (s, 1H), 8.14 (d, 1H), 7.89 (d, 1H), 7.28 (d, 1H), 7.21 (s, 1H), 7.12 (d, 1H), 5.84 (m, 1H), 5.77 (m, 1H), 5.32 (d, 1H), 5.15 (d, 1H), 4.58 (m, 1H), 4.49 (m, 1H), 4.25 (m, 2H), 4.10 (m, 1H), 3.94 (s, 3H), 2.62 (m, 1H), 2.29 (m, 2H), 1.91 (m, 1H), 1.46 (m, 1H), 1.28 (s, 9H), 1.03 (s, 9H), 0.94 (m, 2H), 0.75 (m, 2H); LCMS found 730.0 $[M+H]^+$.

Example 28

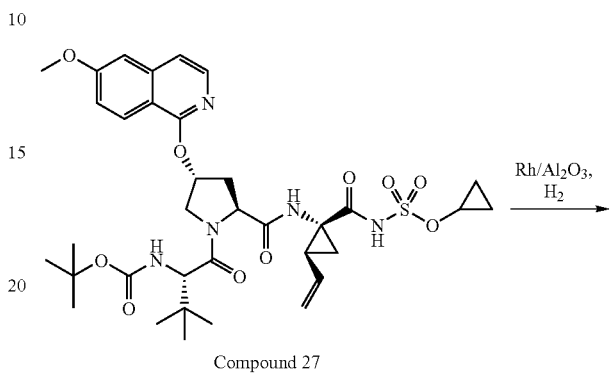

Compound 27

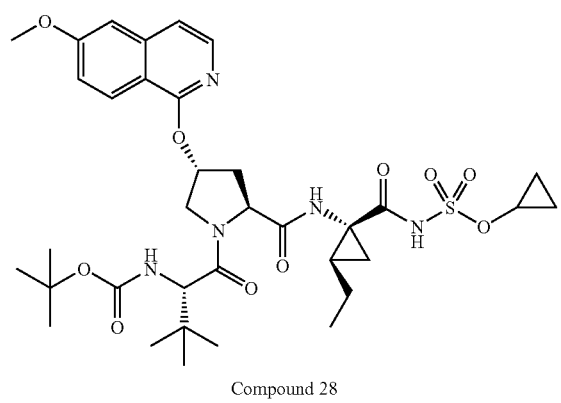

Compound 28

To Compound 27 (50 mg, 0.07 mmol) in EtOAc (0.7 mL) was added $Rh/Al_2O_3$ (10 mg, 20 wt %). The reaction atmosphere was flushed with $H_2$ gas and flask equipped with a $H_2$ filled balloon. After stirring at room temperature for 2 h, the reaction was filtered via a syringe tip filter (Nylon, 0.45 μM) and washed with $CH_2Cl_2$. After removal of solvent the residue was dissolved in MeOH and passed over a C-18 RP SPE column (Phenomenex Strata, 1 g) and eluted with MeOH to provide the desired Compound 28 (42 mg, 84%): $^1H$ NMR ($CD_3OD$, 300 MHz) δ 9.09 (s, 1H), 8.12 (d, 1H), 7.89 (d, 1H), 7.28 (d, 1H), 7.21 (s, 1H), 7.12 (d, 1H), 5.83 (m, 1H), 4.56 (m, 1H), 4.47 (m, 1H), 4.25 (m, 2H), 4.06 (m, 1H), 3.93 (s, 3H), 2.60 (m, 1H), 2.27 (m, 1H), 1.60 (m, 4H), 1.27 (s, 9H), 1.16-1.27 (m, 3H), 1.03 (s, 9H), 0.96 (m, 2H), 0.75 (m, 2H); LCMS found 732.0 $[M+H]^+$.

Example 29

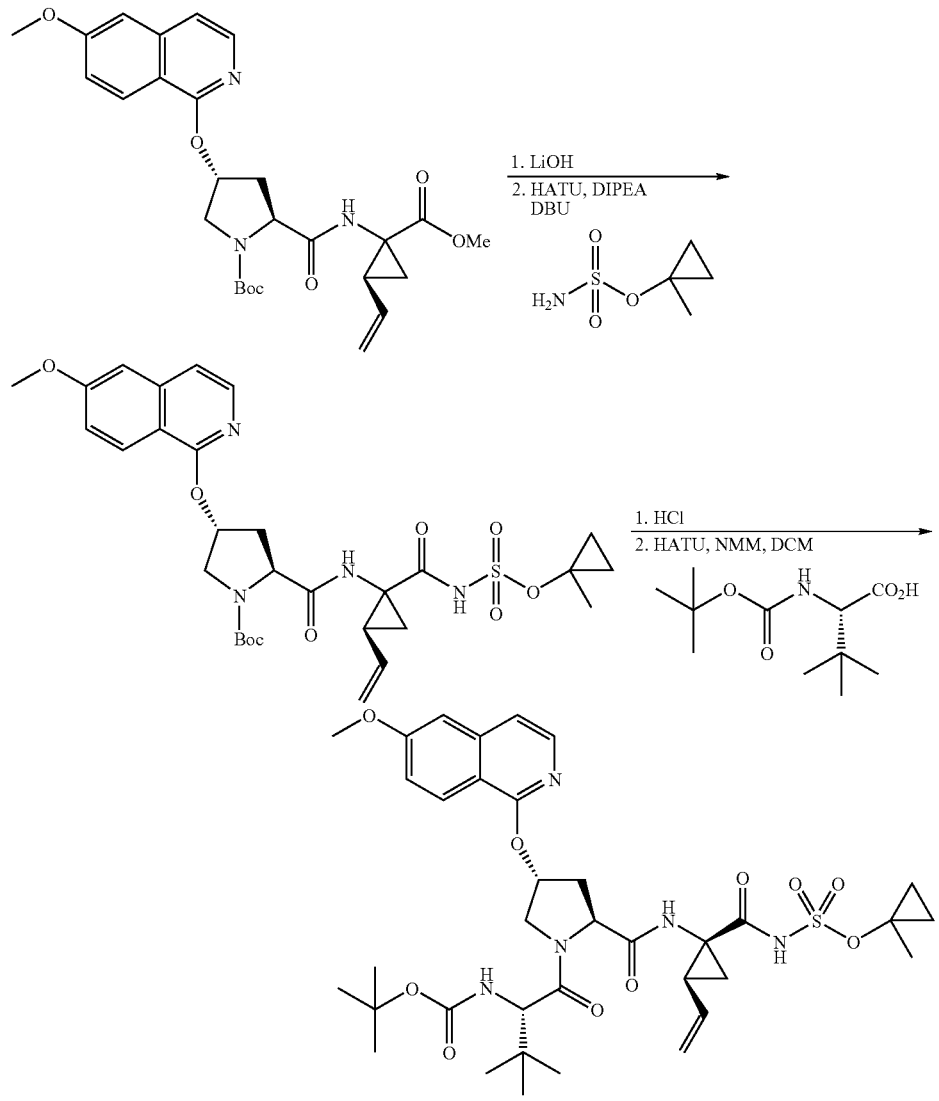

Compound 29

Sulfamic acid 1-methyl-cyclopropyl ester was synthesized according to the method presented in the synthesis of sulfamic acid phenyl ester in Example 1 with the exception of utilizing 1-methylcyclopropanol (synthesized by methods reported in *Synthesis* 1991, 234) to obtain sulfamic acid 1-methyl-cyclopropyl ester.

2-(1-Methoxycarbonyl-2-vinyl-cyclopropylcarbamoyl)-4-(6-methoxy-isoquinolin-1-yloxy)-pyrrolidine-1-carboxylic acid tert-butyl ester (550 mg, 1.08 mmol) from Example 40 was dissolved in THF/MeOH (3:1, 8 mL) to which a solution of LiOH (129 mg, 5.38 mmol) in H$_2$O (2 mL) was added and stirred at room temperature for 3 h. The reaction was diluted with H$_2$O and acidified with 1N aqueous HCl. The solution was extracted with EtOAc, washed with saturated aqueous NaCl, and dried over sodium sulfate. After removal of solvent, the crude product was used directly in the next reaction.

The resultant acid and HATU (600 mg, 1.58 mmol) were combined in DMF (10.8 mL) and treated with iPr$_2$NEt (1.58 mmol). After 15 min stirring at room temperature, sulfamic acid 1-methyl-cyclopropyl ester (238 mg, 1.58 mmol) and DBU (0.31 mL, 2.10 mmol) were then added to the reaction mixture. After stirring for 12 h at room temperature, the reaction was diluted with H$_2$O. The solution was extracted with EtOAc, washed with saturated aqueous NaHCO$_3$, and dried over sodium sulfate. After removal of solvent, the crude product was purified by column chromatography on silica (60-90% EtOAc/hexanes) to provide the acylsulfamate (260 mg, 39%).

4-(6-Methoxy-isoquinolin-1-yloxy)-2-[1-(1-methyl-cyclopropoxysulfonylaminocarbonyl)-2-vinyl-cyclopropylcarbamoyl]-pyrrolidine-1-carboxylic acid tert-butyl ester (400 mg, 0.65 mmol) was dissolved in CH$_2$Cl$_2$ (2 mL), treated with 4N HCl in dioxanes (2 mL) and reacted at room temperature for 1 h. Solvents were removed and the crude residue dried. The resultant crude amine was combined with HATU (370 mg, 0.97 mmol), dissolved in CH$_2$Cl$_2$ (6.5 mL), and treated with NMM (0.21 mL, 1.95 mmol). After stirring for 14 h at room temperature, the reaction was acidified with 1N aqueous HCl and extracted with CH$_2$Cl$_2$. The organics were washed with 1N aqueous HCl, saturated aqueous NaCl and dried over sodium sulfate. After removal of solvent, the crude product was purified by reverse phase column chromatography on C18 (30-95% ACN/H$_2$O-1% TFA) to provide Compound 29 (213 mg, 47%): $^1$H NMR (CD$_3$OD, 300 MHz) δ 9.22 (s, 1H), 8.13 (d, 1H), 7.90 (d, 1H), 7.31 (d, 1H), 7.22 (s, 1H), 7.14 (d, 1H), 5.85 (m, 1H), 5.75 (m, 1H), 5.32 (d, 1H), 5.15 (d, 1H), 4.55 (m, 1H), 4.50 (m, 1H), 4.24 (m, 1H), 4.09 (m, 1H), 3.94 (s, 3H), 2.63 (m, 1H), 2.27 (m, 2H), 1.88 (m, 1H), 1.67 (s, 3H), 1.46 (m, 1H), 1.28 (m, 11H), 1.05 (s, 9H), 0.68 (m, 2H); LCMS found 744.0 [M+H]$^+$.

Example 30

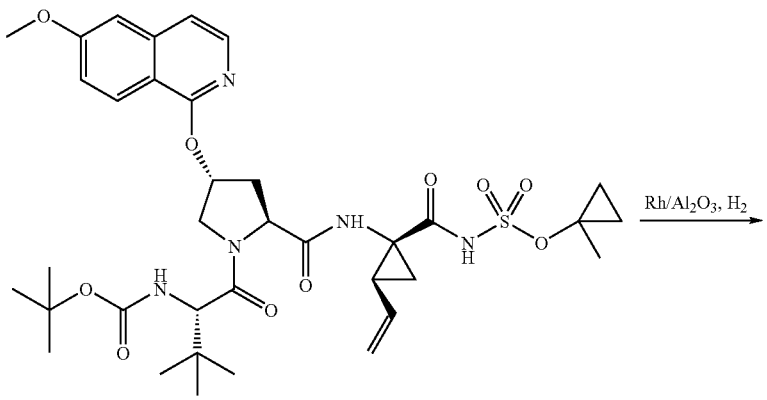

Compound 29

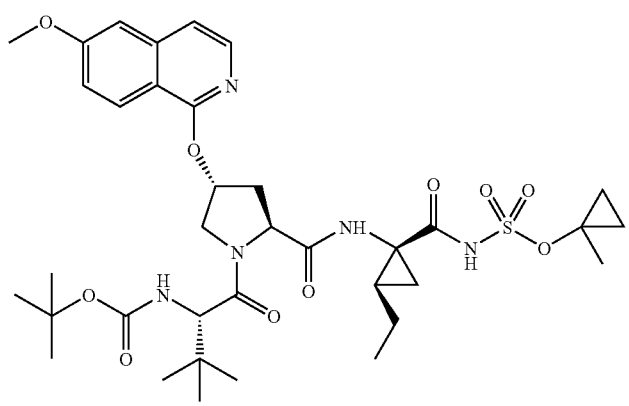

Compound 30

Compound 30 was prepared according to the method presented for the synthesis of Compound 28. Treatment of Compound 29 from Example 29 under the same conditions adjusted for scale provided the desired product (45 mg, 90%): %): $^1$H NMR (CD$_3$OD, 300 MHz) δ 8.11 (d, 1H), 7.89 (d, 1H), 7.26 (d, 1H), 7.20 (s, 1H), 7.11 (d, 1H), 5.55 (d, 1H), 5.84 (m, 1H), 4.54 (m, 1H), 4.46 (m, 1H), 4.27 (m, 2H), 4.06 (m, 1H), 3.93 (s, 3H), 2.59 (m, 1H), 2.26 (m, 1H), 1.69 (s, 3H), 1.60 (m, 4H), 1.27 (s, 9H), 1.20-1.31 (m, 3H), 1.02 (s, 9H), 0.97 (m, 3H), 0.69 (m, 2H); LCMS found 746.0 [M+H]$^+$.

Example 31

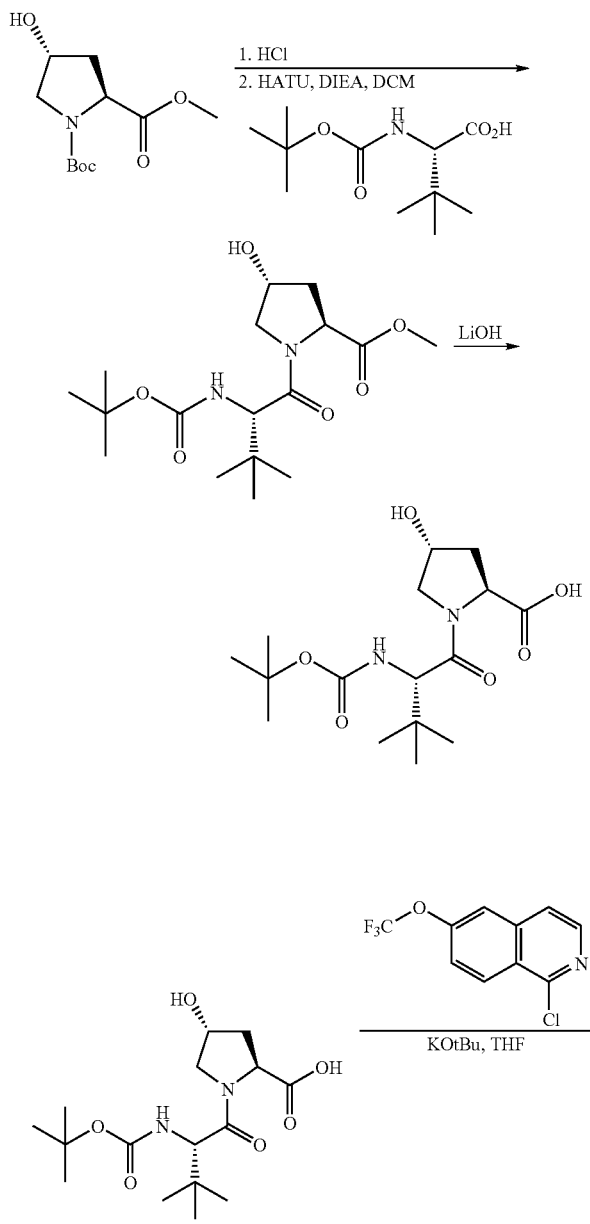

4-Hydroxy-pyrrolidine-1,2-dicarboxylic acid 1-tert-butyl ester 2-methyl ester (10.0 g, 40.8 mmol) was stirred in 4N HCl in dioxanes (60 mL) for 210 min. Solvents were removed and the crude residue was dried. The resultant crude amine was combined with HATU (18.6 g, 48.9 mmol) and Boc-L-tert-leucine (10.8 g, 46.9 mmol), dissolved in $CH_2Cl_2$ (450 mL), and treated with DIEA (24.9 mL, 148 mmol). After stirring for 4 hr at room temperature, the reaction was purified by column chromatography on silica (0-10% MeOH/$CH_2Cl_2$ and 40-100% EtOAc/Hexane) to provide 13.2 g (90%) of the desired product as white foam. LCMS found 359.0 $[M+H]^+$.

To a solution of 1-(2-tert-butoxycarbonylamino-3,3-dimethyl-butyryl)-4-hydroxy-pyrrolidine-2-carboxylic acid methyl ester (2.74 g, 7.64 mmol) in tetrahydrofuran (45 mL) was added 2M lithium hydroxide (15 mL, 30.0 mmol). The reaction was stirred at ambient temperature for 18 hr. The solution was diluted with EtOAc and acidified with 2 M HCl. The layers were separated and the organic layer was dried over $Na_2SO_4$ and concentrated to give 2.57 g (98%) of the product. LCMS found 345.0 $[M+H]^+$.

Compound 31

1-Chloro-6-trifluoromethoxy-isoquinoline was synthesized according to the method presented in Example 16 with the exception of utilizing 3-(trifluoromethoxy)cinnamic acid.

1-(2-tert-butoxycarbonylamino-3,3-dimethyl-butyryl)-4-hydroxy-pyrrolidine-2-carboxylic acid (1.38 g, 4.01 mmol) was dissolved in anhydrous THF (20 mL), then treated with 1M KOtBu/THF (20 mL, 20 mmol). After 10 min. at room temperature, 1-chloro-6-trifluoromethoxy-isoquinoline (1.49 g, 6.01 mmol) in 10 mL of THF was added to the reaction flask. After 50 min. additional stirring, the reaction was quenched with 2N HCl and extracted with EtOAc. The organics were dried over sodium sulfate and purified by column chromatography on silica (0-20% MeOH/CH$_2$Cl$_2$) to conditions, adjusted for scale, and purified by reverse phase HPLC to afford Compound 31 (441 mg, 29%): $^1$H NMR (CDCl$_3$, 300 MHz) δ 10.31 (s, 1H), 8.21 (d, 1H), 8.03 (d, 1H), 7.55 (s, 1H), 7.32-7.25 (m, 2H), 6.89 (s, 1H), 5.89 (s, 1H), 5.21 (d, 1H), 4.52-4.45 (m, 2H), 4.25 (d, 1H), 4.04 (d, 1H), 2.57-2.49 (m, 2H), 1.72 (s, 3H), 1.68 (m, 2H), 1.58 (m, 2H), 1.44-1.29 (m, 12H), 1.04 (s, 9H), 0.96 (m, 3H), 0.65 (m, 2H); LCMS found 800.4 [M+H]$^+$.

Example 32

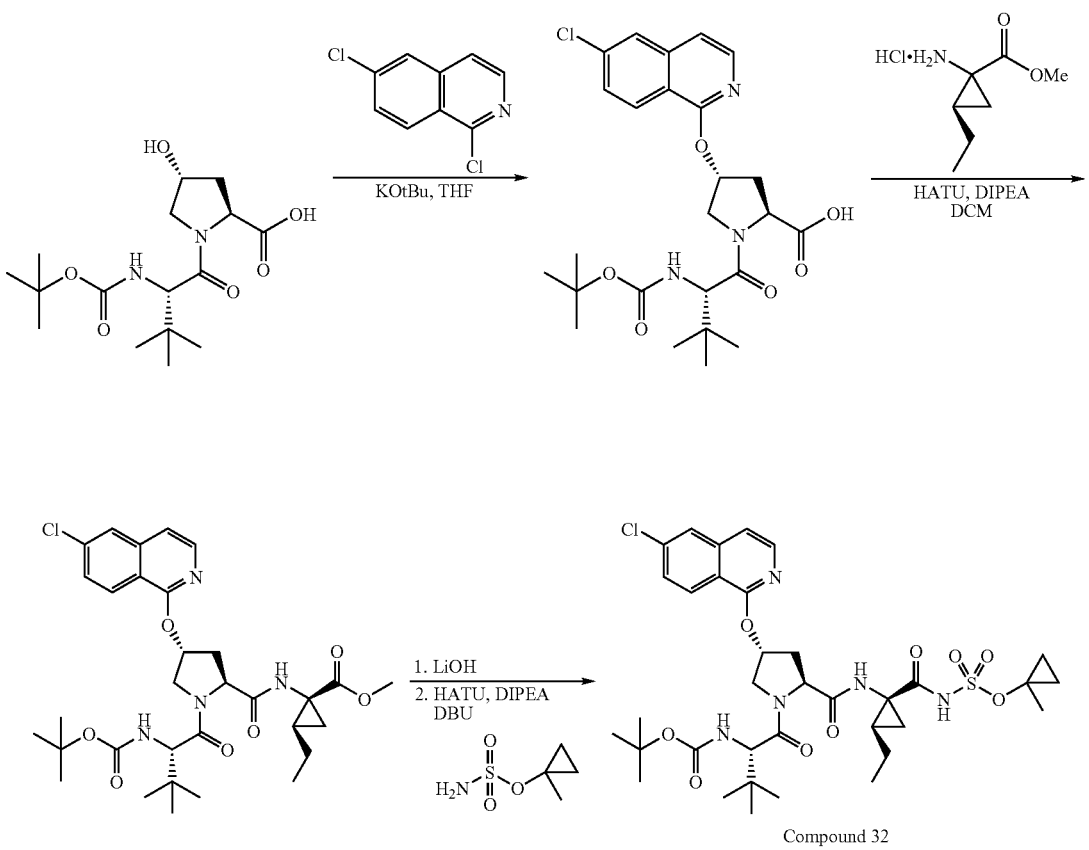

Compound 32 provide 2.37 g (98%) of the desired product as yellow-brown foam. LCMS found 554.0 [M–H]$^-$.

1-{[1-(2-tert-Butoxycarbonylamino-3,3-dimethyl-butyryl)-4-(6-trifluoromethoxy-isoquinoline-4-yloxy)-pyrrolidine-2-carbonyl]-amino}-2-ethyl-cyclopropanecarboxylic acid methyl ester was prepared according to the method presented in the synthesis of Compound 26. Treatment of 1-(2-tert-butoxycarbonylamino-3,3-dimethyl-butyryl)-4-(6-trifluoromethoxy-isoquinoline-4-yloxy)-pyrrolidine-2-carboxylic acid (2.37 g, 4.00 mmol) occurred under the same conditions, adjusted for scale, to afford the desired methyl ester (1.90 g, 70%). LCMS found 681.0 [M+H]$^+$.

Compound 31 was prepared according to the method presented in the synthesis of Compound 29. Treatment of 1-{[1-(2-tert-butoxycarbonylamino-3,3-dimethyl-butyryl)-4-(6-trifluoromethoxy-isoquinoline-4-yloxy)-pyrrolidine-2-carbonyl]-amino}-2-ethyl-cyclopropanecarboxylic acid methyl ester (1.29 g, 1.88 mmol) occurred under the same 1,6-Dichloroisoquinoline was synthesized according to the method presented in Example 16 with the exception of utilizing 3-chlorocinnamic acid.

Compound 32 was prepared according to the method presented in the synthesis of Compound 31 with the exception of utilizing 1,6-dichloroisoquinoline. For the final step, treatment of 1-(2-tert-butoxycarbonylamino-3,3-dimethyl-butyryl)-4-hydroxy-pyrrolidine-2-carboxylic acid (532 mg, 1.54 mmol) occurred under the same conditions, adjusted for scale, to afford Compound 32 (107 mg, 28%): $^1$H NMR (CDCl$_3$, 300 MHz) δ 10.34 (s, 1H), 8.08 (d, 1H), 8.01 (d, 1H), 7.73 (s, 1H), 7.42 (d, 1H), 7.18 (d, 1H), 6.86 (s, 1H), 5.89 (s, 1H), 5.22 (d, 1H), 4.53-4.42 (m, 2H), 4.25 (d, 1H), 4.04 (d, 1H), 2.59-2.52 (m, 2H), 1.72 (s, 3H), 1.68 (m, 2H), 1.58 (m, 2H), 1.44-1.22 (m, 12H), 1.04 (s, 9H), 0.94 (m, 3H), 0.65 (m, 2H); LCMS found 750.4 [M+H]$^+$.

Example 33

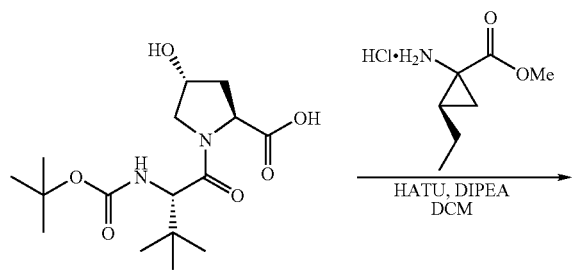

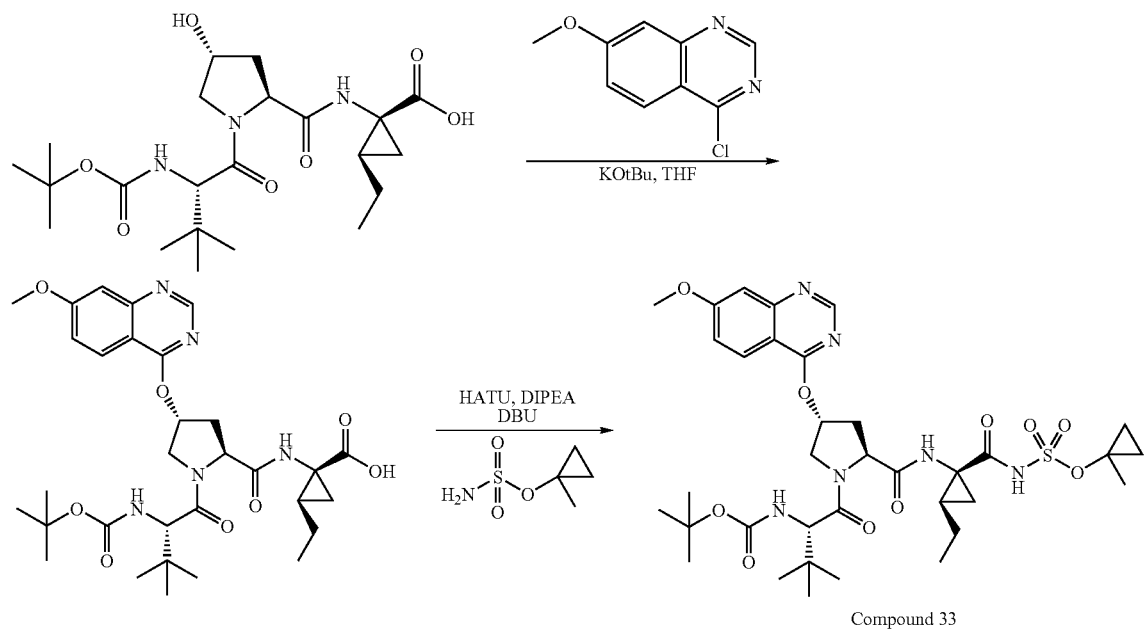

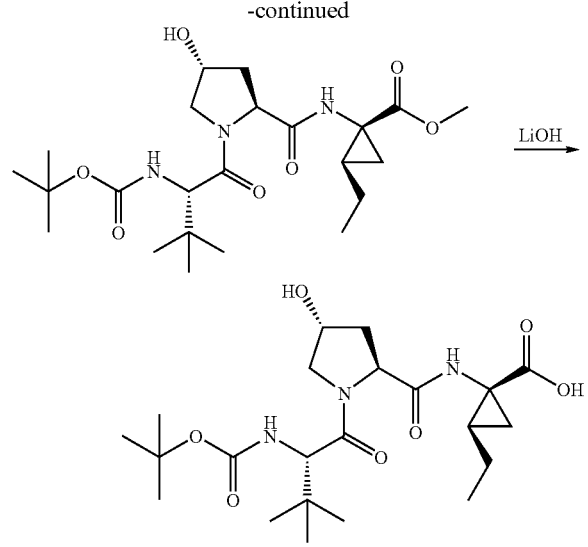

Treatment of 1-(2-tert-butoxycarbonylamino-3,3-dimethyl-butyryl)-4-hydroxy-pyrrolidine-2-carboxylic acid (738 mg, 2.14 mmol) under peptide coupling conditions presented in Example 26 occurred under the same conditions, adjusted for scale, to afford the ester which was subsequently hydrolyzed to −1-{[1-(2-tert-butoxycarbonylamino-3,3-dimethyl-butyryl)-4-hydroxy-pyrrolidine-2-carbonyl]-amino}-2-ethyl-cyclopropanecarboxylic acid (565 mg, 64%): LCMS found 456.0 [M+H]$^+$.

Compound 33 was prepared according to the method presented in the synthesis of Compound 31. Treatment of 1-{[1-(2-tert-Butoxycarbonylamino-3,3-dimethyl-butyryl)-4-hydroxy-pyrrolidine-2-carbonyl]-amino}-2-ethyl-cyclopropanecarboxylic acid (300 mg, 0.659 mmol) and 6-methoxy-quinazoline, synthesized by methods reported in *J. Chem. Soc.* 1947, 890-894 occurred under the same conditions, adjusted for scale, to afford Compound 33 (220 mg, 45%): $^1$H NMR (CDCl$_3$, 300 MHz) δ 8.96 (s, 1H), 8.08 (d, 1H), 7.59 (s, 1H), 7.47 (s, 1H), 7.22 (d, 1H), 5.99 (s, 1H), 5.21 (d, 1H), 4.57 (m, 2H), 4.18 (d, 1H), 4.06 (s, 1H), 4.01 (s, 3H), 2.65-2.57 (m, 2H), 1.65 (s, 3H), 1.63 (m, 2H), 1.50 (m, 2H), 1.26 (m, 2H), 1.27 (s, 9H), 1.26 (m, 1H), 1.03 (s, 9H), 0.93 (m, 3H), 0.63 (m, 2H); LCMS found 747.0 [M+H]$^+$.

Example 34

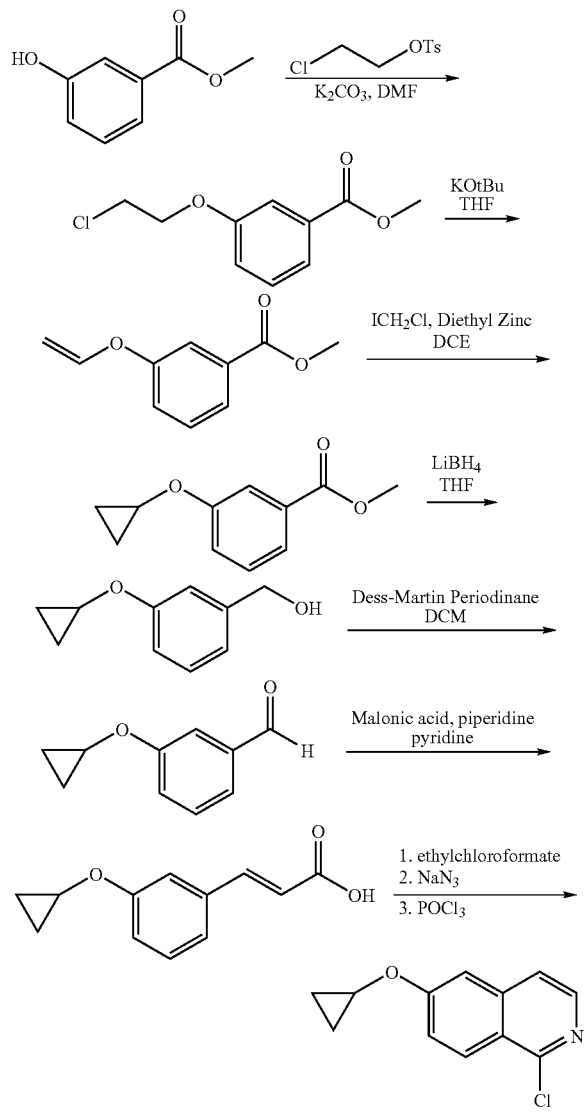

To a solution of methyl-3-hydroxybenzoate (25.0 g, 164 mmol) in DMF (250 mL) were added K₂CO₃ (45.4 g, 328 mmol) and 2-chloroethyl p-toluenesulfonate (39.3 g, 167 mmol). The reaction was stirred at 65° C. for 12 hr then diluted with EtOAc and H₂O. The layers were separated and the organic layer was dried over Na₂SO₄, concentrated, and purified by column chromatography on silica (0-100% CH₂Cl₂/Hexane) to provide 25.0 g (71%) of the desired product as a clear oil.

The chloride (25.0 g, 116 mmol) was dissolved in THF (220 mL) then KOtBu (16.3 g, 145 mmol) was added. The reaction was stirred at ambient temperature for 18 hr then diluted with EtOAc and H₂O. The layers were separated and the organic layer was dried over Na₂SO₄, concentrated, and purified by column chromatography on silica (0-25% EtOAc/Hexane and 0-70% CH₂Cl₂/Hexane) to provide 11.2 g (54%) of the desired ester.

To a solution of the ester (11.2 g, 62.6 mmol) in dichloroethane (310 mL) was added chloroiodomethane (17.0 mL, 235 mmol), then cooled to 0° C. added IM Et₂Zn/Hexane (117 mL, 117 mmol) slowly. The reaction was stirred at ambient temperature for 100 min then diluted with 1N HCl and DCM. The layers were separated and the organic layer was dried over Na₂SO₄, concentrated, and purified by column chromatography on silica (30-100% CH₂Cl₂/Hexane) to provide 9.77 g (81%) of methyl-3-cyclopropoxybenzoate as clear oil.

Methyl-3-cyclopropoxybenzoate (7.49 g, 39.0 mmol) was dissolved in THF (135 mL) then 2M LiBH₄/THF (58.5 mL, 117 mmol) was added. The reaction was stirred at 50° C. for 1 hr then 1.6 mL of MeOH was added. After 30 min of stirring, the reaction mixture was cooled to r.t. and quenched with excess MeOH. The solution was concentrated and diluted with EtOAc and H₂O. The layers were separated and the organic layer was dried over Na₂SO₄ and concentrated to provide 6.37 g (98%) of the desired alcohol.

To a solution of the alcohol (6.37 g, 38.8 mmol) in dichloromethane (194 mL) was added Dess-Martin Periodinane (18.1 g, 42.7 mmol). The reaction was stirred at ambient temperature for 15 min. The solution was purified by column chromatography on silica (0-40% EtOAc/Hexane) to provide 6.00 g (93%) of the aldehyde as yellow oil.

3-cyclopropoxybenzaldehyde (7.51 g, 46.3 mmol) was dissolved in pyridine (195 mL) then malonic acid (19.3 g, 185 mmol) and piperidine (6.86 mL, 69.5 mmol) were added. The reaction was stirred at reflux for 2 hr then concentrated. The residue was poured on to ice cold 6N HCl and decanted to collect the solution. The solution was diluted with DCM and extracted with DCM. The extract and the solid from the water layer were combined and basified with 2N NaOH. The basic solution was washed with DCM, acidified and filtered to give 3-(3-cyclopropoxy-phenyl)-acrylic acid as white solid: ¹H NMR (CDCl₃, 300 MHz) δ 7.77 (d, 1H), 7.36-7.09 (m, 4H), 6.44 (d, 1H), 3.77 (m, 1H), 0.81 (m, 4H).

1-Chloro-6-cyclopropoxy-isoquinoline was synthesized according to the method presented in Example 16. Treatment of 3-(3-cyclopropoxy-phenyl)-acrylic acid under the same occurred under the same conditions, adjusted for scale, to afford 1-chloro-6-cyclopropoxy-isoquinoline: LCMS found 220.1 [M+H]⁺.

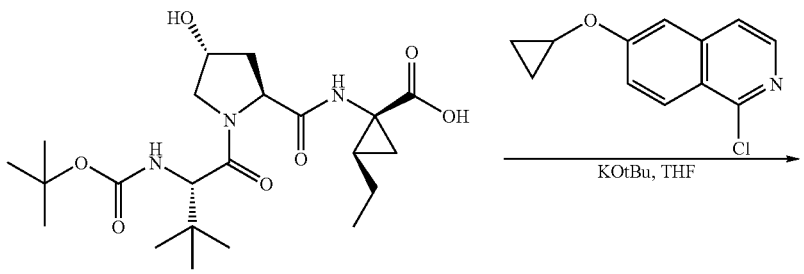

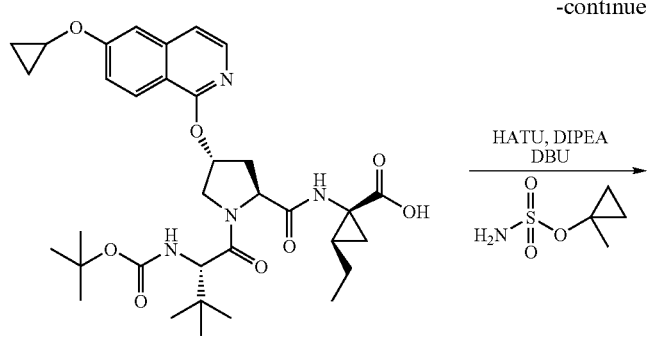
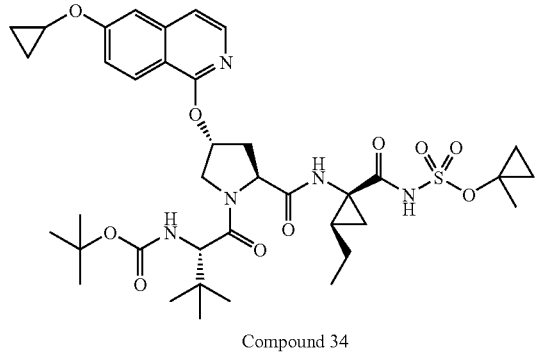

Compound 34

Compound 34 was prepared according to the method presented in the synthesis of Compound 31 with the exception of utilizing 1-chloro-6-cyclopropoxy-isoquinoline. For the final step, treatment of 1-{[1-(2-tert-Butoxycarbonylamino-3,3-dimethyl-butyryl)-4-hydroxy-pyrrolidine-2-carbonyl]-amino}-2-ethyl-cyclopropanecarboxylic acid (200 mg, 0.439 mmol) and 1-chloro-6-cyclopropoxy-isoquinoline occurred under the same conditions, adjusted for scale, to afford Compound 34 (220 mg, 45%): $^1$H NMR (CDCl$_3$, 300 MHz) δ 9.89 (s, 1H), 8.35 (d, 1H), 7.22-7.12 (m, 3H), 6.52 (d, 1H), 5.88 (s, 1H), 5.22 (d, 1H), 4.62 (m, 2H), 4.15 (d, 1H), 4.05 (s, 4H), 3.88-3.82 (m, 1H), 2.74 (m, 1H), 2.52 (m, 1H), 1.63 (m, 2H), 1.50 (m, 2H), 1.26 (m, 3H), 1.18 (s, 9H), 1.05 (s, 9H), 0.92 (m, 3H), 0.90-0.80 (m, 4H), 0.61 (m, 2H); LCMS found 772.0 [M+H]$^+$.

Example 35

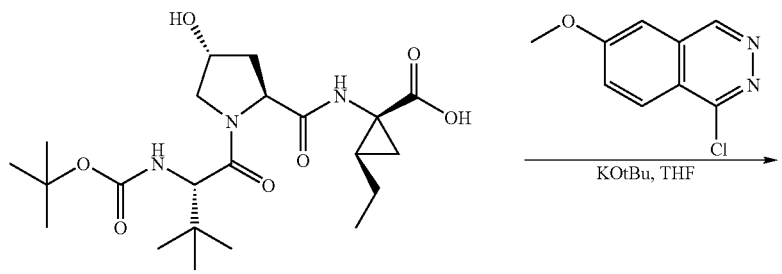

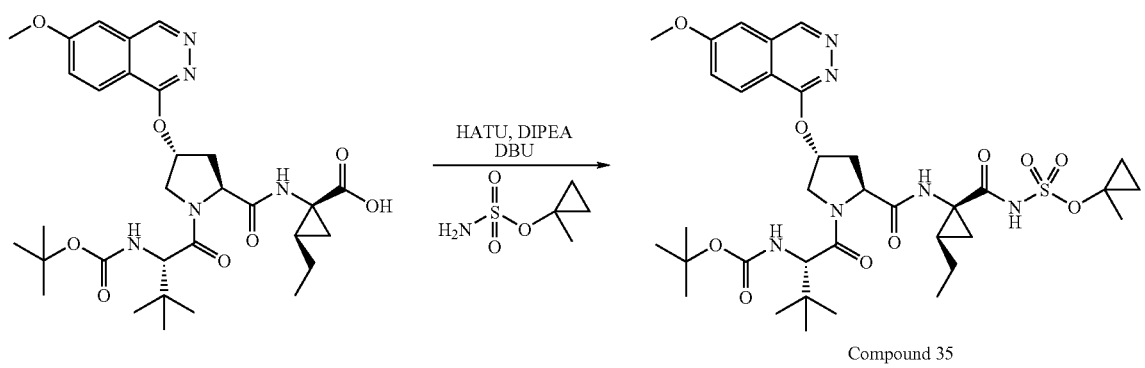

Compound 35

Compound 35 was prepared according to the method presented in the synthesis of Compound 31. Treatment of 1-{[1-(2-tert-Butoxycarbonylamino-3,3-dimethyl-butyryl)-4-hydroxy-pyrrolidine-2-carbonyl]-amino}-2-ethyl-cyclopropanecarboxylic acid (400 mg, 0.878 mmol) and 1-Chloro-6-methoxy-phthalazine, synthesized by methods reported in *Bioorg. Med. Chem. Lett.* 2002, 12, 5-8, occurred under the same conditions, adjusted for scale, to afford Compound 35 (107 mg, 16%): $^1$H NMR (CDCl$_3$, 300 MHz) δ 9.89 (s, 1H), 8.35 (d, 1H), 8.03 (s, 1H), 7.71 (m, 2H), 5.88 (s, 1H), 5.22 (d, 1H), 4.62 (m, 2H), 4.15 (d, 1H), 4.05 (s, 4H), 2.74 (m, 1H), 2.52 (m, 1H), 1.65 (s, 3H), 1.63 (m, 2H), 1.50 (m, 2H), 1.26 (m, 3H), 1.18 (s, 9H), 1.05 (s, 9H), 0.92 (m, 3H), 0.61 (m, 2H); LCMS found 747.3 [M+H]$^+$.

Example 36

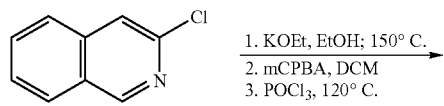

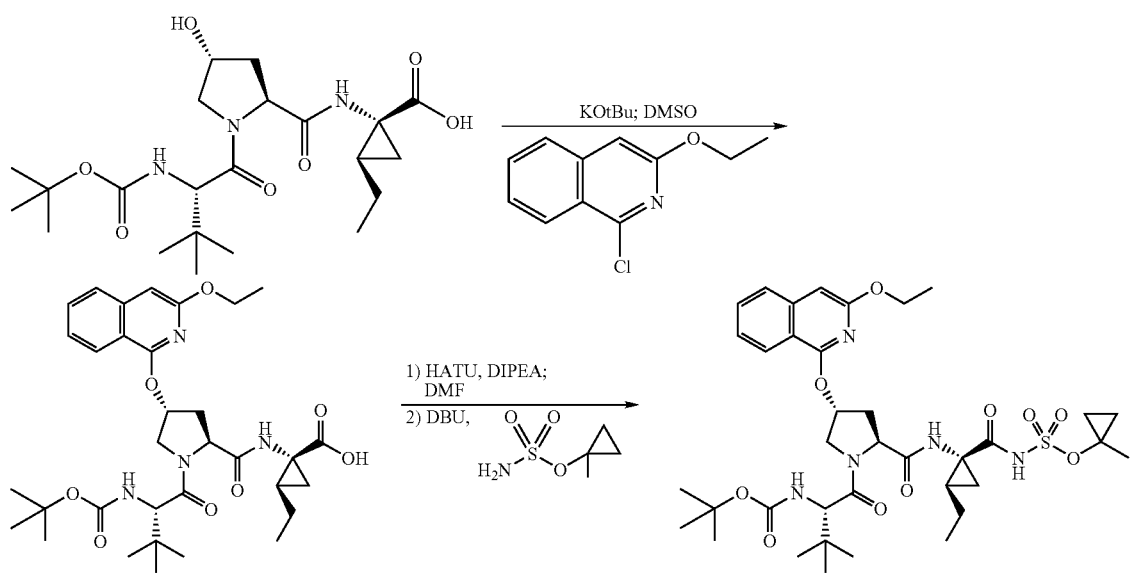

-continued

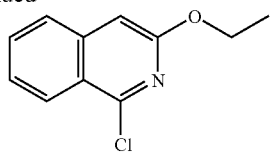

3-Chloroisoquinoline (3.0, 18 mmol) was dissolved in potassium ethoxide (24% in EtOH, 10.6 mL, 27 mmol) and heated to 150° C. in a sealed tube for 24 h. After cooling, the solvent was removed in vacuo and the residue treated with 1M HCl until the solution reaches a pH 3. Saturated NaHCO$_3$ solution then added slowly to return the solution to pH 8 followed by extraction with CHCl$_3$. The combined organics were washed with brine, dried over anhydrous MgSO$_4$. The residue obtained from concentration in vacuo was purified by column chromatography on SiO$_2$ (0-15% EtOAc, hex) to afford 1.5 g (48%) of 3-ethoxyisoquinoline. LCMS found 174.11 [M+H]$^+$.

3-Ethoxyisoquinoline (1.5 g, 8.7 mmol) was taken up in DCM (45 mL) at 0° C. mCPBA (77%, 4.1 g, 18.3 mmol) was added slowly and the resulting solution allowed to warm to rt overnight. The reaction volume was doubled with additional DCM and washed with 1M NaOH. Following separation and extraction with DCM, the combined organics were washed with brine, dried over anhydrous MgSO$_4$ and concentrated in vacuo to afford 3-ethoxyisoquinoline N-oxide (1.15 g, 69%) as a white low melting solid that was used without further purification. LCMS found 190.05 [M+H]$^+$.

3-Ethoxyisoquinoline N-oxide (1.15 g, 6.1 mmol) was taken up in POCl$_3$ (5 mL) at rt and then heated to 120° C. under an atmosphere of Ar for 2 h. Following cooling to rt, the reaction was diluted with CHCl$_3$ and poured into icewater (20 mL) and the resulting solution was placed in an ice bath and treated with 10M NaOH until pH 10 with vigorous stirring. Following extraction with CHCl$_3$, the combined organics were washed with brine and dried over anhydrous MgSO$_4$. Following concentration in vacuo, purification on SiO$_2$ (3-15% EtOAc/hex) afforded 0.51 g (40%) of 1-chloro-3-ethoxyisoquinoline. LCMS found 208.1 [M+H]$^+$.

1-{[1-(2-tert-Butoxycarbonylamino-3,3-dimethylbutyryl)-4-hydroxypyrrolidine-2-carbonyl]-amino}-2-ethyl-cyclopropanecarboxylic acid (See Example 33), 0.21 g, 0.46 mmol) was diluted in DMSO (4 mL) and treated with potassium tert-butoxide (0.26 g, 2.3 mmol) at rt for 30 min. 1-Chloro-3-ethoxyisoquinoline (0.100 g, 0.48 mmol) was added and the solution allowed to age overnight. Icewater was added, followed by 1M HCl until the solution reaches pH 3. Extraction with EtOAc was followed by washing of the combined organics with brine and drying over anhydrous Na$_2$SO$_4$ prior to concentration in vacuo. The resulting residue was purified by preparatory HPLC to produce 0.127 g (42%) of 1-{[1-(2-tert-Butoxycarbonylamino-3,3-dimethyl-butyryl)-4-(3-ethoxy-isoquinolin-1-yloxy)-pyrrolidine-2-carbonyl]-amino}-2-ethyl-cyclopropanecarboxylic acid as a white solid. LCMS found 626.90 [M+].

Compound 36 was produced analogously to Compound 33 from Example 33 by treating 1-{[1-(2-tert-Butoxycarbonylamino-3,3-dimethyl-butyryl)-4-(3-ethoxy-isoquinolin-1-yloxy)-pyrrolidine-2-carbonyl]-amino}-2-ethyl-cyclopropanecarboxylic acid (0.13 g, 0.20 mmol) and sulfamic acid 1-methyl-cyclopropyl ester (0.061 g, 0.41 mmol) under similar conditions with appropriate adjustments for scale to produce Compound 36 (0.114 g, 74%) as white powder. ¹H NMR (CD₃OD, 400 MHz) δ 8.06 (d, 1H); 7.63 (d, 1H); 7.55 (t, 1H); 7.26 (t, 1H); 6.60 (s, 1H); 5.86 (s, 1H); 4.54 (m, 1H); 4.45 (d, 1H); 4.38-4.20 (m, 3H); 4.09 (d, 1H); 2.61 (m, 1H); 2.29 (m, 1H); 1.68 (s, 3H); 1.66-1.48 (m, 4H); 1.44 (t, 3H); 1.38-1.16 (m, 2H); 1.23 (s, 9H); 0.97 (t, 3H); 0.68 (m, 2H). LCMS found 760.2 [M+H]⁺.

Example 37

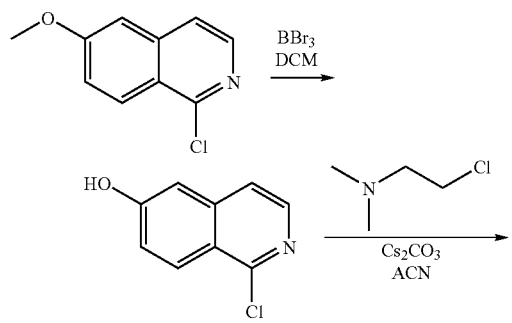

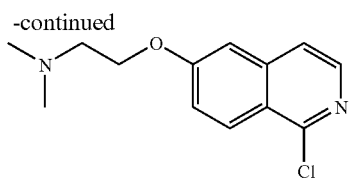

To a solution of 1-chloro-6-methoxy-isoquinoline (2 g, 10.3 mmol) in DCM (60 ml) was added BBr₃ in (4.9 ml, 51.6 mmol) in 10 mL THF and the reaction was heated to 50° C. overnight. The reaction was cooled to 0° C. and 30 volumes of methanol was added as a quench. The solvent was removed to afford 2.87 g (>99%) of 1-chloro-isoquinolin-6-ol as a brown solid. LCMS found 180.36 [M+H]⁺.

To a solution of 1-chloro-isoquinolin-6-ol (300 mg, 1.67 mmol) in acetonitrile (16 ml) was added (2-Chloro-ethyl)-dimethyl-amine (289 mg, 2.0 mmol) and cesium carbonate (1.2 g, 3.67 mmol). The reaction was stirred at 65° C. overnight. The solvent was removed and the residue dissolved in ethyl acetate. The organic solution was washed with saturated sodium bicarbonate, dried over magnesium sulfate and concentrated. The crude product was purified using reverse phase HPLC to afford 505 mg (83%) of [2-(1-chloro-isoquinolin-6-yloxy)-ethyl]-dimethyl-amine as a white amorphous solid. LCMS found 251.04 [M+H]⁺.

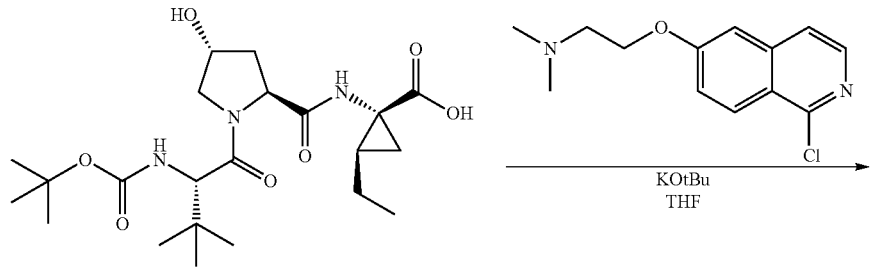

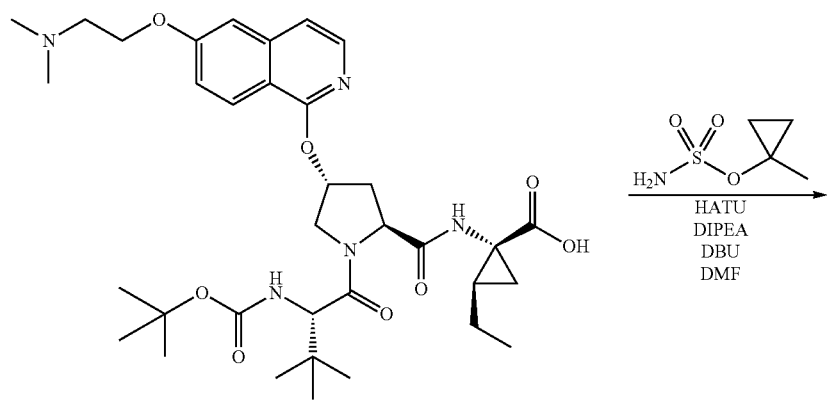

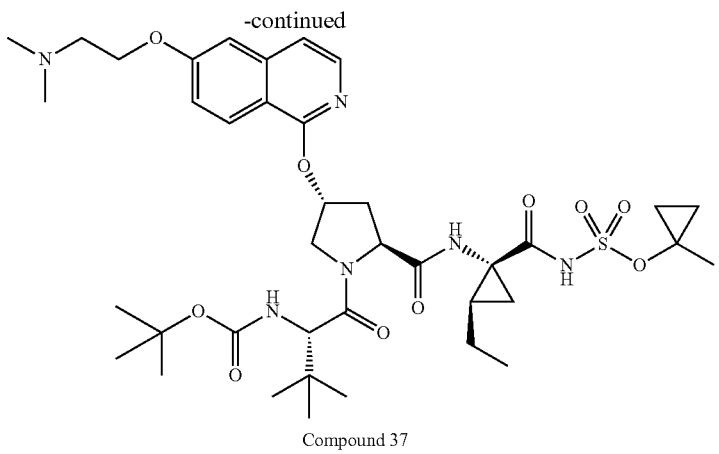

Compound 37

To a solution of 1-{[1-(2-tert-butoxycarbonylamino-3,3-dimethyl-butyryl)-4-hydroxy-pyrrolidine-2-carbonyl]-amino}-2-ethyl-cyclopropanecarboxylic acid (321 mg, 0.71 mmol) in THF (3 mL) was added 1M KOtBu in THF (3.9 ml) and stirred for 15 minutes. [2-(1-chloro-isoquinolin-6-yloxy)-ethyl]-dimethyl-amine (283 mg, 0.78 mmol) was then added in THF (3 ml) and the reaction was heated to 50° C. for approximately three hours. The reaction was cooled to room temp and quenched with 1N HCl and the solvents removed. The crude material was purified by reverse phase HPLC to afford 94.3 mg (17%) of intermediate 1-({1-(2-tert-butoxycarbonylamino-3,3-dimethyl-butyryl)-4-[6-(2-dimethylamino-ethoxy)-isoquinolin-1-yloxy]-pyrrolidine-2-carbonyl}-amino)-2-ethyl-cyclopropanecarboxylic acid as a white solid.

1-({1-(2-tert-butoxycarbonylamino-3,3-dimethyl-butyryl)-4-[6-(2-dimethylamino-ethoxy)-isoquinolin-1-yloxy]-pyrrolidine-2-carbonyl}-amino)-2-ethyl-cyclopropanecarboxylic acid (101 mg, 0.13 mmol) was dissolved in DMF (4 mL) and diisopropylethyl amine (56 µL, 0.32 mmol) to which was added HATU (73 mg, 0.19 mmol). To this reaction mixture was then added DBU (77 mL, 0.52 mmol) and sulfamic acid 1-methyl-cyclopropyl ester (39 mg, 0.26 mmol) and the reaction was stirred at ambient temperature for 16 hrs. The reaction was diluted with water and acetonitrile and purified by reverse phase chromatography to give 61.1 mg (52%) of Compound 37 as an amorphous white solid. $^1$H NMR (CD$_3$OD, 300 MHz) δ 8.11 (m, 1H); 7.90 (d, J=6 Hz, 1H); 7.23 (m, 3H); 5.81 (2, 1H); 4.47 (m, 2H); 4.40 (m, 1H); 4.22 (s, 1H); 4.08 (m, 1H); 3.64 (m, 2H); 3.27 (s, 3H); 2.98 (s, 6H); 2.58 (m, 1H); 2.20 (m, 1H); 1.64 (s, 3H); 1.53 (m, 4H); 1.26 (s, 9H); 1.67 (m, 9H); 0.96 (m, 12H); 0.64 (s, 2H). LCMS found 803.14 [M+H]$^+$.

Example 38

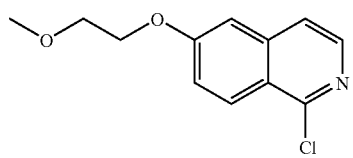

Compound 38

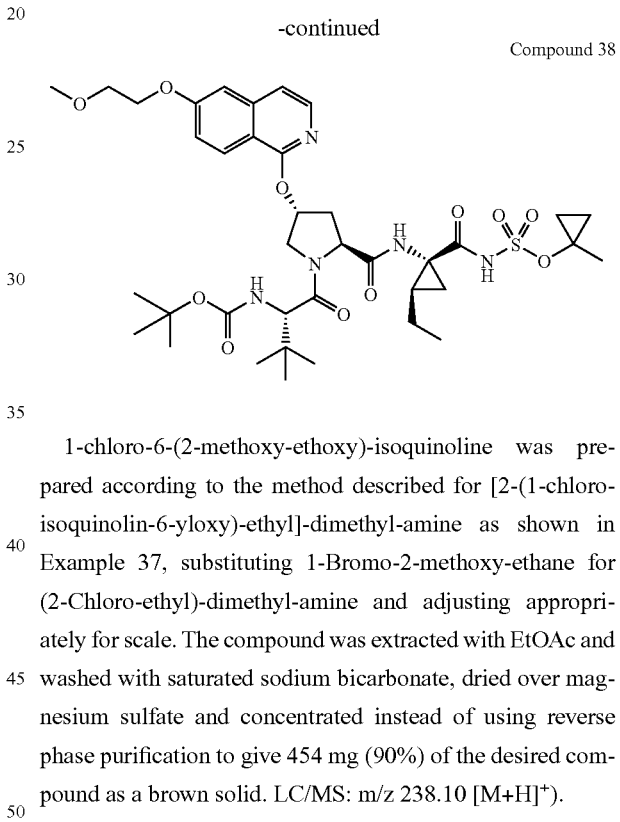

1-chloro-6-(2-methoxy-ethoxy)-isoquinoline was prepared according to the method described for [2-(1-chloro-isoquinolin-6-yloxy)-ethyl]-dimethyl-amine as shown in Example 37, substituting 1-Bromo-2-methoxy-ethane for (2-Chloro-ethyl)-dimethyl-amine and adjusting appropriately for scale. The compound was extracted with EtOAc and washed with saturated sodium bicarbonate, dried over magnesium sulfate and concentrated instead of using reverse phase purification to give 454 mg (90%) of the desired compound as a brown solid. LC/MS: m/z 238.10 [M+H]$^+$).

Compound 38 was prepared according to the method described as shown in Example 37, substituting 1-chloro-6-(2-methoxy-ethoxy)-isoquinoline for [2-(1-chloro-isoquinolin-6-yloxy)-ethyl]-dimethyl-amine and adjusting appropriately for scale. The compound was purified using reverse phase HPLC to give 89.6 mg (69%) of the desired compound Compound 38 as a white amorphous solid. $^1$H NMR (CD$_3$OD, 300 MHz) δ 8.07 (d, 1H); 7.85 (d, 1H); 7.19 (m, 2H); 7.11 (m, 1H); 5.78 (s, 1H); 4.45 (m, 2H); 4.21 (m, 3H); 4.08 (m, 1H); 3.77 (m, 2H); 3.40 (s, 3H); 2.53 (m, 1H); 2.21

(m, 1H) 1.64 (m, 3H); 1.53 (m, 3H); 1.24 (m, 11H); 1.00 (s, 9H); 0.92 (m, 5H); 0.64 (m, 2H). LCMS found 789.94 [M+H]⁺.

Example 39

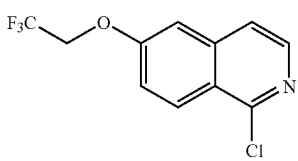

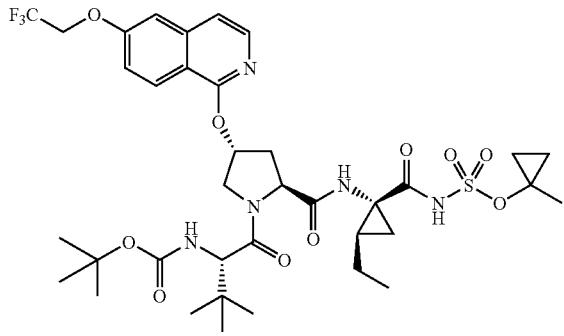

Compound 39

1-chloro-6-(2,2,2-trifluoro-ethoxy)-isoquinoline was prepared according to the method described for [2-(1-chloro-isoquinolin-6-yloxy)-ethyl]-dimethyl-amine as shown in Example 37, substituting Trifluoro-methanesulfonic acid 2,2,2-trifluoro-ethyl ester for (2-Chloro-ethyl)-dimethyl-amine and adjusting appropriately for scale. The compound was extracted with EtOAc, washed with brine, dried over magnesium sulfate and concentrated instead of using reverse phase purification to give 820 mg (56%) of the desired compound 1-chloro-6-(2,2,2-trifluoro-ethoxy)-isoquinoline as a white solid. LCMS found 262.34 [M+H]⁺).

Compound 39 was prepared according to the method described as shown in Example 37, substituting 1-chloro-6-(2,2,2-trifluoro-ethoxy)-isoquinoline for [2-(1-chloro-isoquinolin-6-yloxy)-ethyl]-dimethyl-amine and adjusting appropriately for scale. The compound was purified using reverse phase HPLC to give 104.3 mg (18%) of the desired compound Compound 39 as a white amorphous solid. ¹H NMR (CD₃OD, 300 MHz) δ 8.13 (d, J=9.6 Hz, 1H); 7.90 (d, J=5.7 Hz, 1H); 7.26 (m, 2H); 7.18 (m, 1H); 5.80 (s, 1H); 4.66 (m, 2H); 4.44 (m, 2H); 4.20 (s, 1H); 4.02 (m, 1H); 2.54 (m, 1H); 2.22 (m, 1H); 1.64 (s, 3H); 1.54 (m, 4H); 1.19 (m, 12H); 0.96 (m, 14H); 0.64 (s, 2H). LCMS found 813.84 [M+H]⁺.

Example 40

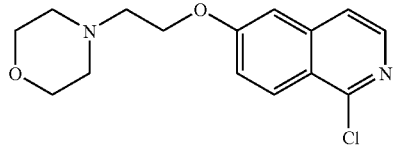

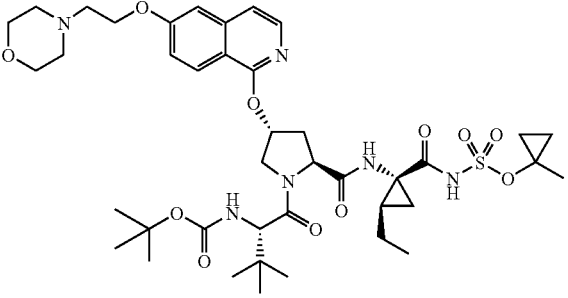

Compound 40

1-chloro-6-(2-morpholin-4-yl-ethoxy)-isoquinoline was prepared according to the method described for [2-(1-chloro-isoquinolin-6-yloxy)-ethyl]-dimethyl-amine as shown in Example 37, substituting 4-(2-chloro-ethyl)-morpholine for (2-chloro-ethyl)-dimethyl-amine and adjusting appropriately for scale to give 459.5 mg (94%) of the desired compound 1-chloro-6-(2-morpholin-4-yl-ethoxy)-isoquinoline as a white solid. LCMS found 293.09 [M+H]⁺.

Compound 40 was prepared according to the method described as shown in Example 37, substituting 1-chloro-6-(2-morpholin-4-yl-ethoxy)-isoquinoline for [2-(1-chloro-isoquinolin-6-yloxy)-ethyl]-dimethyl-amine and adjusting appropriately for scale. The compound was purified using reverse phase HPLC to give 128.5 mg (13%) of the desired compound Compound 40 as a white amorphous solid. ¹H NMR (CD₃OD, 400 MHz) δ 8.17 (d, J=8.4 Hz, 11H); 7.94 (d, J=5.6 Hz, 1H); 7.26 (m, 3H); 5.86 (s, 1H); 4.55 (m, 3H); 4.43 (d, J=10.4 Hz, 1H); 4.26 (s, 1H); 4.10 (m, 2H); 3.8 (m, 2H); 3.73 (m, 2H); 3.61 (m, 2H); 3.36 (m, 1H); 2.60 (m, 1H); 2.28 (m, 1H); 1.68 (s, 3H); 1.55 (m, 5H); 1.31 (s, 9H); 1.19 (m, 2H); 1.05 (m, 12H); 0.98 (m, 2H); 0.68 (s, 2H). LCMS found 845.07 [M+H]⁺.

Example 41

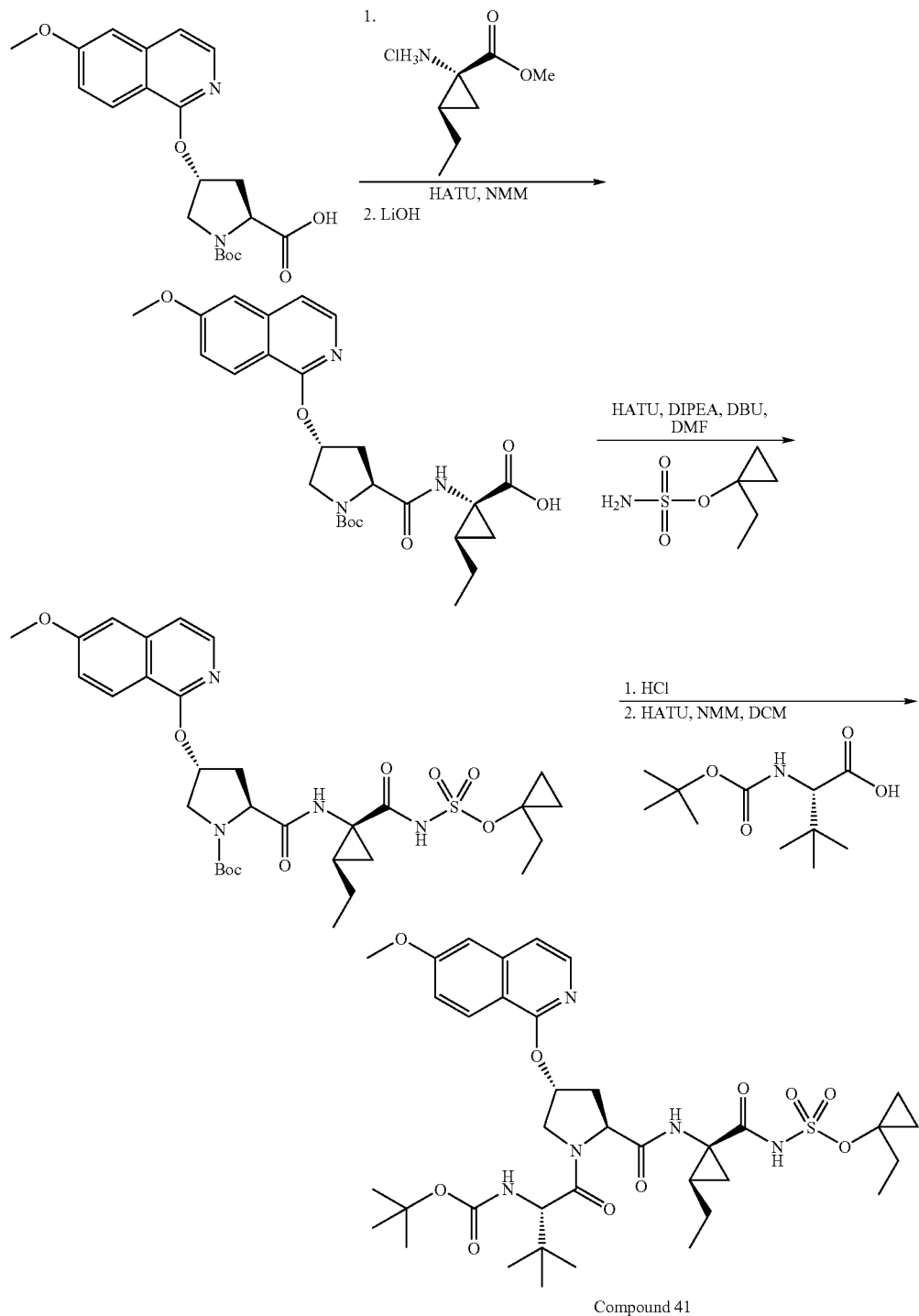

Compound 41

To a solution of 4-(6-methoxy-isoquinolin-1-yloxy)-pyrrolidine-1,2-dicarboxylic acid 1-tert-butyl ester (1.78 g, 4.59 mmol) and the HCl salt of 1-amino-2-ethyl-cyclopropanecarboxylic acid methyl ester (0.605 g, 3.37 mmol) in DMF (17 mL) was added HATU (1.938 g, 5.09 mmol) and NMM (1.9 mL, 17.28 mmol). The reaction mixture was stirred at room temperature for 18 h, and then diluted with EtOAc. The resulting slurry was washed with aqueous HCl (1N) and brine. The aqueous layers were extracted with EtOAc. The resulting organic layers were combined, dried ($Na_2SO_4$) and concentrated. The crude product was purified by column chromatography on silica (15→50% Hex/EtOAc) to provide the desired intermediate (0.647 g, 37%): LCMS found 514.87 [M+H]$^+$.

Hydrolysis of 2-(2-Ethyl-1-methoxycarbonyl-cyclopropylcarbamoyl)-4-(6-methoxy-isoquinolin-1-yloxy)-pyrrolidine-1-carboxylic acid tert-butyl ester according to the method presented in Example 27 provided the acid which was used without further purification.

Sulfamic acid 1-ethyl-cyclopropyl ester was synthesized according to the method presented in the synthesis of sulfamic acid phenyl ester in Example 1 with the exception of utilizing 1-ethylcyclopropanol (synthesized by methods reported in *Synthesis* 1991, 234) to obtain sulfamic acid 1-ethyl-cyclopropyl ester.

2-[2-Ethyl-1-(1-ethyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester was prepared according to the method presented in Example 27. Treatment of 2-(1-carboxy-2-ethyl-cyclopropylcarbamoyl)-4-(6-methoxy-isoquinolin-1-yloxy)-pyrrolidine-1-carboxylic acid tert-butyl ester (0.70 mmol) occurred under the same conditions, adjusted for scale with the exception of utilizing sulfamic acid 1-ethyl-cyclopropyl ester to afford the desired acylsulfamate (230 mg, 51%): LCMS found 647.1 [M+H]$^+$.

Compound 41 was prepared according to the method presented in the synthesis of Compound 27. Treatment of 2-[2-ethyl-1-(1-ethyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (0.36 mmol) occurred under the same conditions, adjusted for scale, and purified by reverse phase HPLC to afford Compound 41 (89 mg, 12%): $^1$H NMR (CD$_3$OD, 300 MHz) δ 9.15 (s, 1H), 8.10 (d, 1H), 7.90 (d, 1H), 7.28 (d, 1H), 7.22 (s, 1H), 7.11 (d, 1H), 5.83 (m, 1H), 4.58 (m, 1H), 4.39 (m, 1H), 4.23 (m, 2H), 4.08 (m, 1H), 3.94 (s, 3H), 2.59 (m, 1H), 2.27 (m, 1H), 1.90 (q, 2H), 1.60 (m, 4H), 1.48 (s, 3H), 1.26 (s, 9H), 1.20-1.31 (m, 3H), 1.09 (t, 3H), 1.05 (s, 9H), 0.98 (m, 3H), 0.70 (m, 2H); LCMS found 760.4 [M+H]$^+$.

Example 42

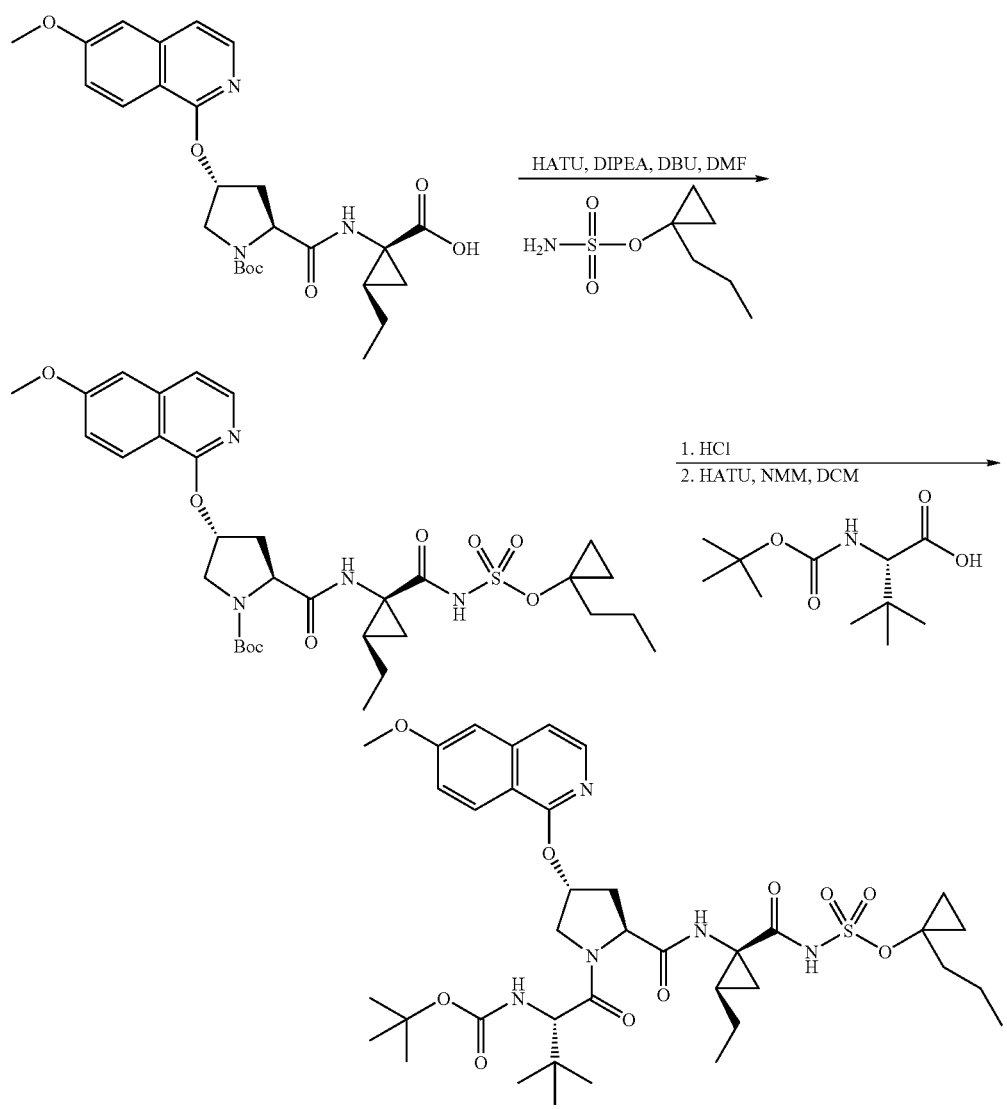

Compound 42

Sulfamic acid 1-propyl-cyclopropyl ester was synthesized according to the method presented in the synthesis of sulfamic acid phenyl ester in Example 1 with the exception of utilizing 1-propylcyclopropanol (synthesized by methods reported in *Synthesis* 1991, 234) to obtain sulfamic acid 1-propyl-cyclopropyl ester.

2-[2-Ethyl-1-(1-propyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester was prepared according to the method presented in Example 27. Treatment of 2-(1-carboxy-2-ethyl-1-cyclopropylcarbamoyl)-4-(6-methoxy-isoquinolin-1-yloxy)-pyrrolidine-1-carboxylic acid tert-1-butyl ester (0.50 mmol) occurred under the same conditions, adjusted for scale with the exception of utilizing sulfamic acid 1-propyl-cyclopropyl ester to afford acylsulfamate (200 mg, 61%): LCMS found 660.9 [M+H]$^+$.

Compound 42 was prepared according to the method presented in the synthesis of Compound 27. Treatment of 2-[2-ethyl-1-(1-propyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (0.30 mmol) occurred under the same conditions, adjusted for scale, and purified by reverse phase HPLC to afford Compound 42 (26 mg, 11%): $^1$H NMR (CD$_3$OD, 300 MHz) δ 9.12 (s, 1H), 8.11 (d, 1H), 7.89 (d, 1H), 7.29 (d, 1H), 7.22 (s, 1H), 7.13 (d, 1H), 5.84 (m, 1H), 4.55 (m, 1H), 4.44 (m, 1H), 4.24 (m, 2H), 4.09 (m, 1H), 3.94 (s, 3H), 2.59 (m, 1H), 2.28 (m, 1H), 1.83 (t, 2H), 1.58 (m, 4H), 1.48 (q, 2H), 1.27 (s, 9H), 1.20-1.31 (m, 3H), 1.05 (s, 9H), 0.98 (m, 3H), 0.70 (m, 2H); LCMS found 774.0 [M+H]$^+$.

Example 43

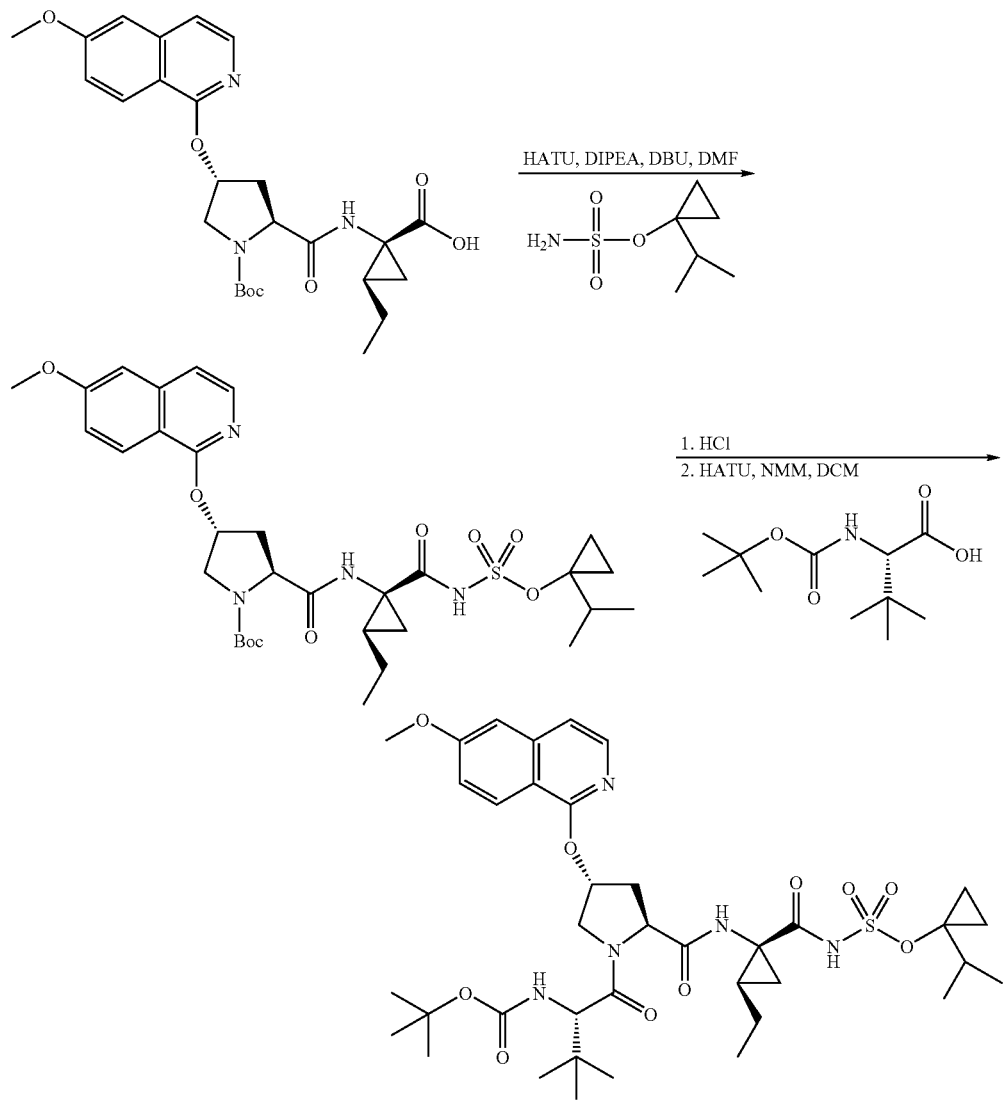

Compound 43

Sulfamic acid 1-isopropyl-cyclopropyl ester was synthesized according to the method presented in the synthesis of sulfamic acid phenyl ester in Example 1 with the exception of utilizing 1-isopropylcyclopropanol (synthesized by methods reported in *Synthesis* 1991, 234.) to obtain sulfamic acid 1-isopropyl-cyclopropyl ester.

2-[2-Ethyl-1-(1-isopropyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester was prepared according to the method presented in Example 27. Treatment of 2-(1-carboxy-2-ethyl-cyclopropylcarbamoyl)-4-(6-methoxy-isoquinolin-1-yloxy)-pyrrolidine-1-carboxylic acid tert-butyl ester (0.50 mmol) occurred under the same conditions, adjusted for scale with the exception of utilizing sulfamic acid 1-isopropyl-cyclopropyl ester to afford acylsulfamate (185 mg, 56%): LCMS found 660.9 [M+H]$^+$.

Compound 43 was prepared according to the method presented in the synthesis of Compound 27. Treatment of 2-[2-ethyl-1-(1-isopropyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (0.19 mmol) occurred under the same conditions, adjusted for scale, and purified by reverse phase HPLC to afford Compound 43 (57.8 mg, 7%): $^1$H NMR (CD$_3$OD, 300 MHz) δ 9.12 (s, 1H), 8.11 (d, 1H), 7.89 (d, 1H), 7.27 (d, 1H), 7.20 (s, 1H), 7.11 (d, 1H), 5.84 (m, 1H), 4.54 (m, 1H), 4.44 (m, 1H), 4.25 (m, 2H), 4.09 (m, 1H), 3.94 (s, 3H), 2.58 (m, 1H), 2.27 (m, 1H), 2.16 (m, 1H), 1.57 (m, 4H), 1.27 (s, 9H), 1.20-1.31 (m, 3H), 1.05 (s, 9H), 1.00 (m, 6H), 0.98 (m, 3H), 0.78 (m, 2H); LCMS found 774.0 [M+H]$^+$.

Example 44

Sulfamic acid 2,2,2-trifluoro-1,1-dimethyl-ethyl ester was synthesized according to the method presented in the synthesis of sulfamic acid phenyl ester in Example 1 with the exception of utilizing 1,1,1-trifluoro-2-methyl-propan-2-ol to obtain sulfamic acid 2,2,2-trifluoro-1,1-dimethyl-ethyl ester.

2-[2-Ethyl-1-(2,2,2-trifluoro-1,1-dimethyl-ethoxysulfonylaminocarbonyl)-cyclopropylcarbamoyl]-4-(6-methoxy-isoquinolin-1-yloxy)-pyrrolidine-1-carboxylic acid tert-butyl ester was prepared according to the method presented in Example 27. Treatment of 2-(1-carboxy-2-ethyl-cyclopropylcarbamoyl)-4-(6-methoxy-isoquinolin-1-yloxy)-pyrrolidine-1-carboxylic acid tert-butyl ester (2.01 mmol) occurred under the same conditions, adjusted for scale with the exception of utilizing sulfamic acid 2,2,2-trifluoro-1,1-dimethyl-ethyl ester to afford acylsulfamate (450 mg, 65%): LCMS found 688.9 [M+H]$^+$.

Compound 44 was prepared according to the method presented in the synthesis of Compound 27. Treatment of 2-[2-Ethyl-1-(2,2,2-trifluoro-1,1-dimethyl-ethoxysulfonylaminocarbonyl)-cyclopropylcarbamoyl]-4-(6-methoxy-isoquinolin-1-yloxy)-pyrrolidine-1-carboxylic acid tert-butyl ester (0.15 mmol) occurred under the same conditions,

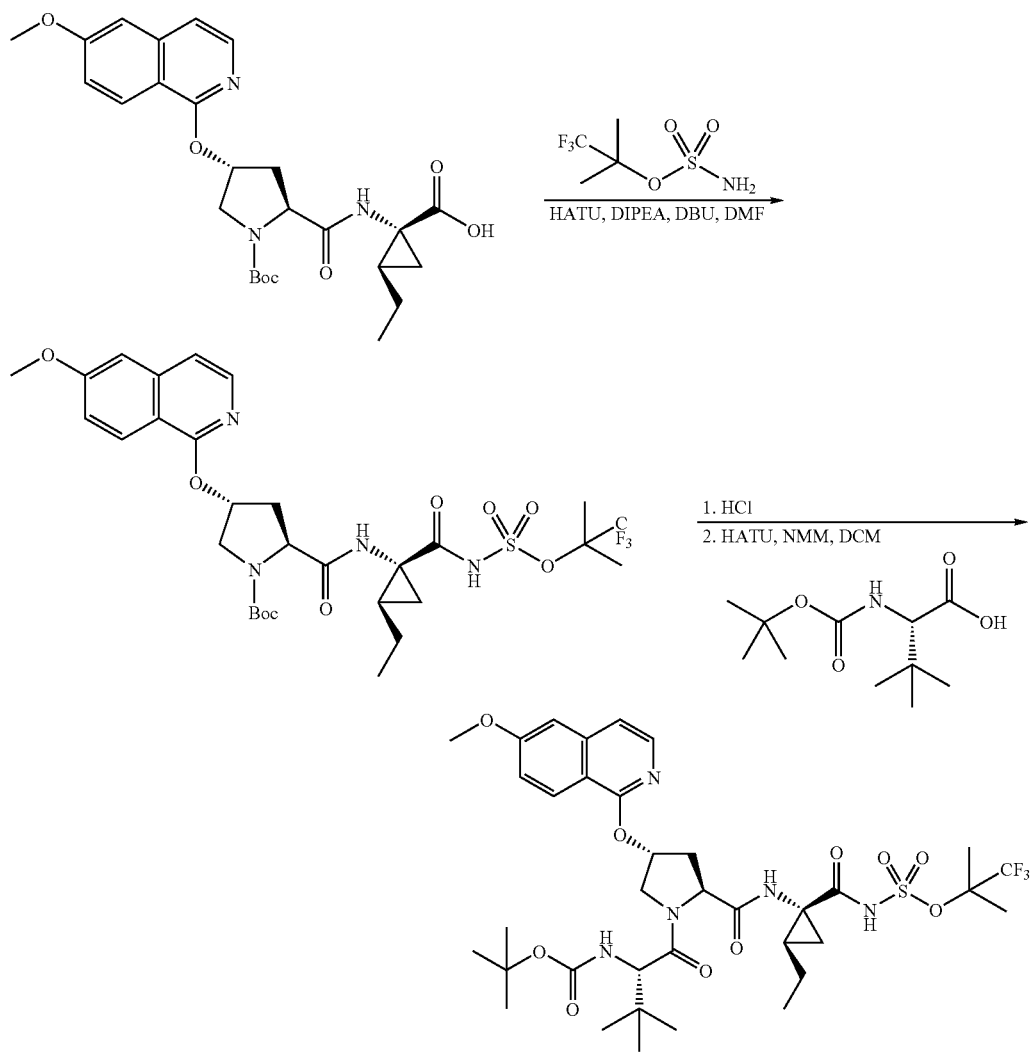

Compound 44 adjusted for scale, and purified by reverse phase HPLC to afford Compound 44 (55 mg, 46%): ¹H NMR (CD₃OD, 300 MHz) diagnostic δ 1.81 (s, 3H), 1.80 (s, 3H); LCMS found 801.9 [M+H]⁺.

Example 45 lcarbamoyl)-4-(6-methoxy-isoquinolin-1-yloxy)-pyrrolidine-1-carboxylic acid tert-butyl ester (0.10 mmol) occurred under the same conditions, adjusted for scale with the exception of utilizing sulfamic acid 1-sulfamoyloxy-cyclopropanecarboxylic acid methyl ester (40 mg, 60%): LCMS found 676.2 [M+H]⁺.

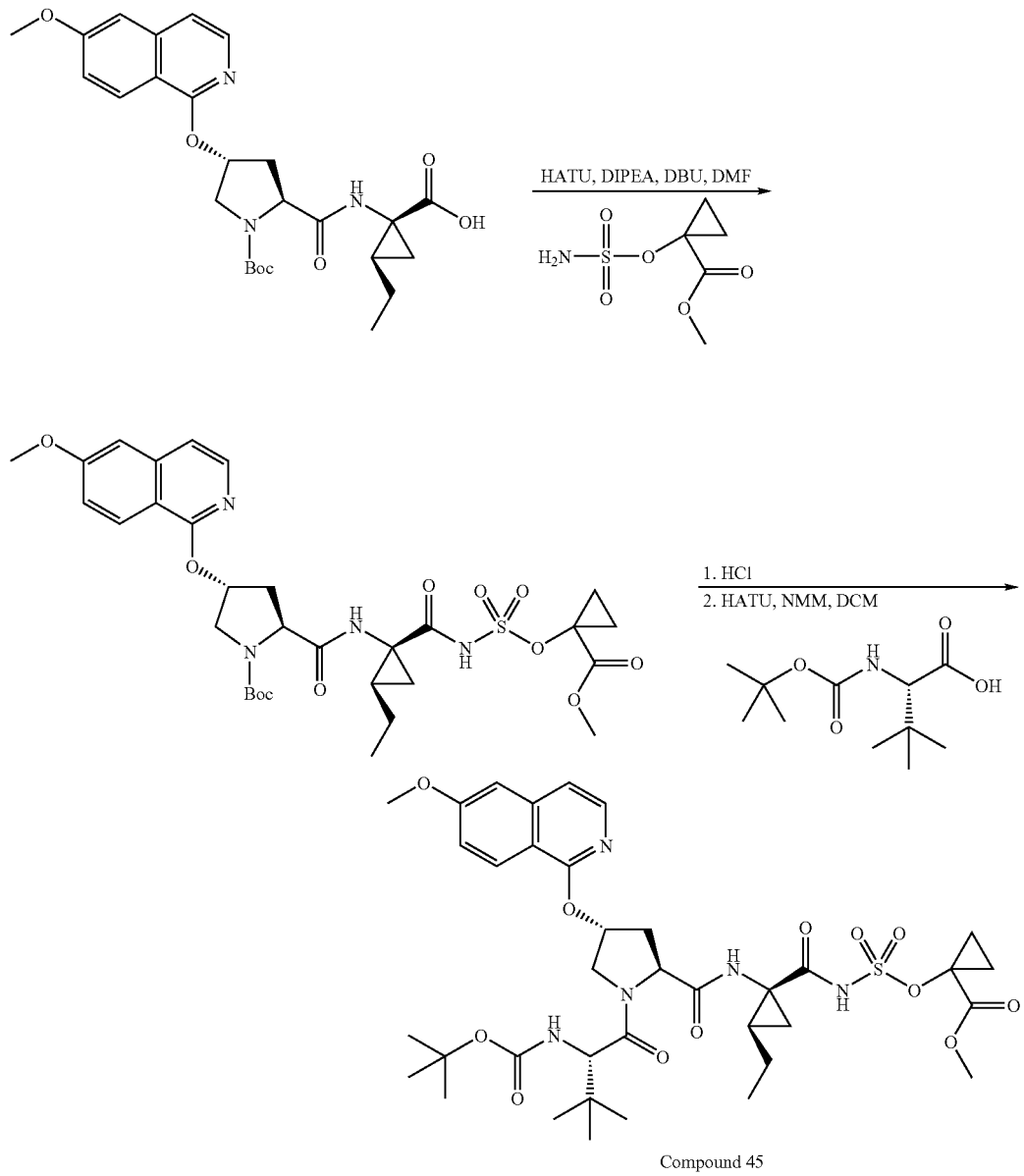

Compound 45

1-Sulfamoyloxy-cyclopropanecarboxylic acid methyl ester was synthesized according to the method presented in the synthesis of sulfamic acid phenyl ester in Example 1 with the exception of utilizing 1-hydroxy-cyclopropanecarboxylic acid methyl ester to obtain 1-Sulfamoyloxy-cyclopropanecarboxylic acid methyl ester.

2-[2-Ethyl-1-(1-methoxycarbonyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester was prepared according to the method presented in Example 27. Treatment of 2-(1-carboxy-2-ethyl-cyclopropy- Compound 45 was prepared according to the method presented in the synthesis of Compound 27. Treatment of 2-[2-ethyl-1-(1-methoxycarbonyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (0.06 mmol) occurred under the same conditions, adjusted for scale, and purified by reverse phase HPLC to afford Compound 45 (16.3 mg, 34%): ¹H NMR (CD₃OD, 300 MHz) diagnostic δ 3.79 (s, 3H), 1.77 (m, 2H), 1.72 (m, 2H); LCMS found 789.3 [M+H]⁺.

Example 46

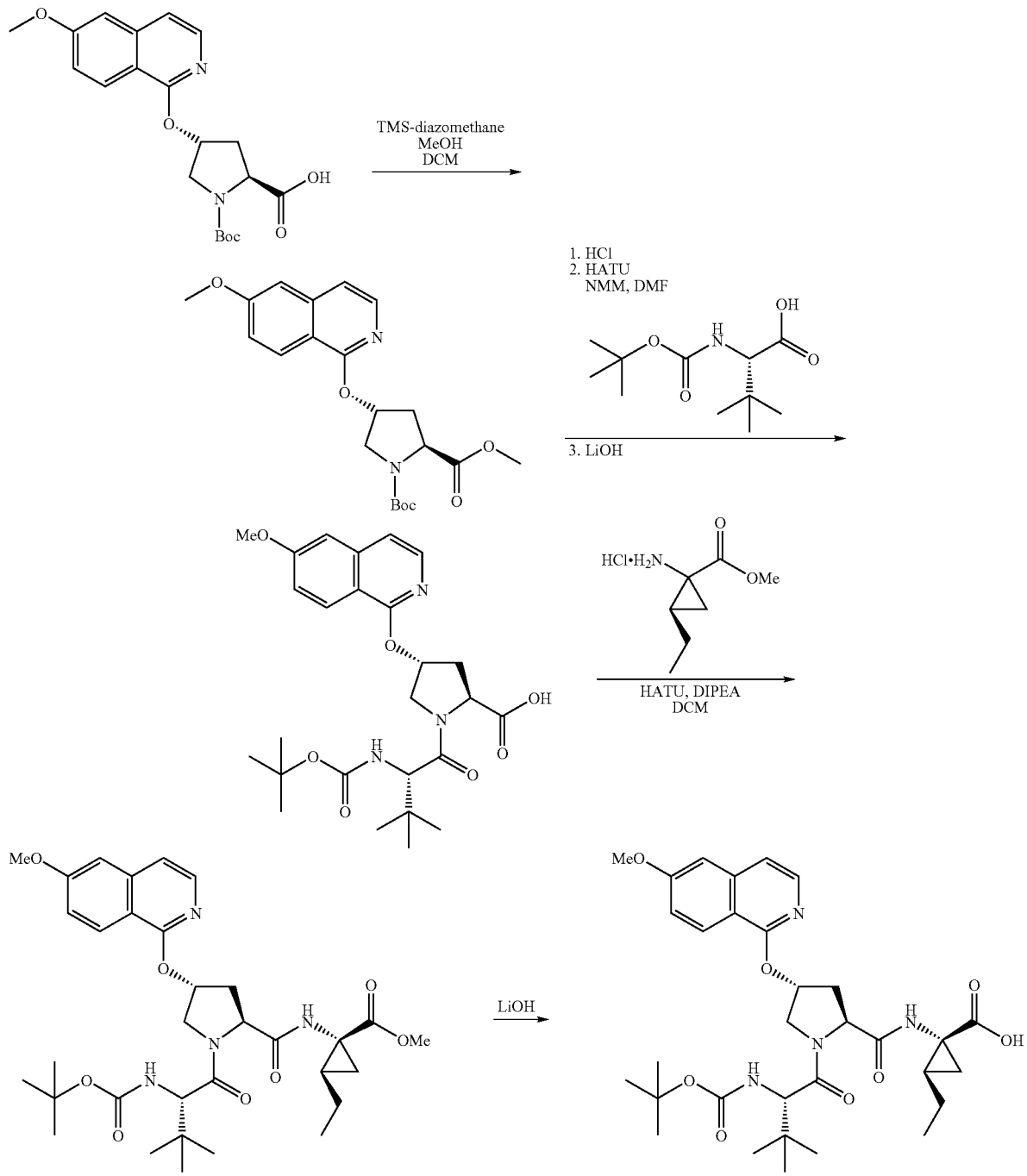

To a solution of 2 M (trimethylsilyl)diazomethane in hexanes (6.44 mL, 12.875 mmol) and methanol (6.44 mL) was added a solution of 4-(6-methoxy-isoquinolin-1-yloxy)-pyrrolidine-1,2-dicarboxylic acid 1-tert-butyl ester (5 g, 12.875 mmol) in dichloromethane (125 mL) and stirred at ambient temperature overnight. The solvent was removed under vacuum and the residue was purified by flash chromatography (0-30% EtOAc/hexane) to afford 3.94 g (76%) of the desired product as a white foam. LCMS found 403.0 [M+H]$^+$.

4-(6-Methoxy-isoquinolin-1-yloxy)-pyrrolidine-1,2-dicarboxylic acid 1-tert-butyl ester 2-methyl ester (4.16 g, 10.34 mmol) was dissolved in HCl in dioxanes (20 mL) and stirred at room temperature for 1 h. Solvent removed under vacuum. The residue was dissolved in dimethyl formamide followed by addition of 4-methylmorpholine (5.7 mL, 51.7 mmol), boc-L-tert-leucine (2.63 g, 11.37 mmol) and HATU (5.9 g, 15.51 mmol) and stirred at ambient temperature for 16 h. The solvent was removed under vacuum, the residue was diluted with EtOAc and washed with saturated sodium bicarbonate and brine. The organic layer was dried over MgSO$_4$ and concentrated. The residue was purified by flash chromatography (0-40% EtOAC/hexane) to afford 4.7 g (88%) of the desired product as a white solid. LCMS found 516.0 [M+H]+.

To a solution of 1-(2-tert-butoxycarbonylamino-3,3-dimethyl-butyryl)-4-(6-methoxy-isoquinolin-1-yloxy)-pyrrolidine-2-carboxylic acid methyl ester (4.7 g, 9.12 mmol) in tetrahydrofuran and methanol (1:1, 100 mL) was added a solution of lithium hydroxide (800 mg, 33.4 mmol) in water (25 ml). The reaction was stirred at ambient temperature for 1 hr. The volatiles were removed under vacuum and the solution was diluted with EtOAc and acidified with 1 M HCl. The layers were separated and the organic layer was dried over MgSO$_4$ and concentrated to give 4.63 g (>99%) of the product as a white foam. LCMS found 502.1 [M+H]+.

1-{[1-(2-tert-Butoxycarbonylamino-3,3-dimethyl-butyryl)-4-(6-methoxy-isoquinolin-1-yloxy)-pyrrolidine-2-carbonyl]-amino}-ethyl-cyclopropanecarboxylic acid was prepared according to the method presented in the synthesis of Compound 26. Treatment of 1-(2-tert-butoxycarbonylamino-3,3-dimethyl-butyryl)-4-(6-methoxy-isoquinolin-1-yloxy)-pyrrolidine-2-carboxylic acid (2.31 g, 4.29 mmol) occurred under the same conditions, adjusted for scale, to afford the desired carboxylic acid (2.57 g, 92%). LCMS found 613.0 [M+H]+.

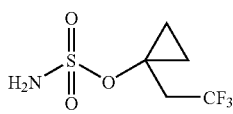

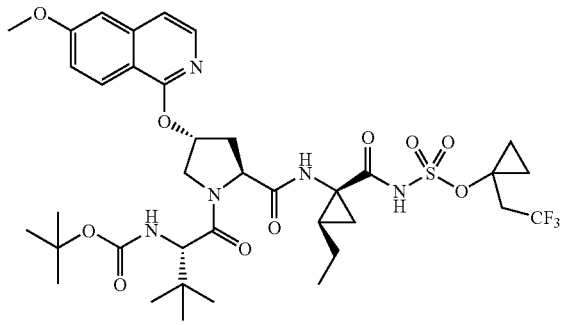

Compound 46

Sulfamic acid 1-trifluoroethyl-cyclopropyl ester was synthesized according to the method presented in the synthesis of sulfamic acid phenyl ester in Example 1 with the exception of utilizing 1-trifluoroethylcyclopropanol (synthesized by methods reported in *Synthesis* 1991, 234.) to obtain sulfamic acid 1-trifluoroethyl-cyclopropyl ester.

Compound 46 was prepared according to the method presented in the synthesis of Compound 27. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid (200 mg, 0.308 mmol) and sulfamic acid 1-trifluoroethyl-cyclopropyl ester occurred under the same conditions, adjusted for scale, and purified by reverse phase HPLC to afford Compound 46 (99.1 mg, 40%): $^1$H NMR (CDCl$_3$, 300 MHz) δ 8.19 (d, 1H), 7.97 (d, 1H), 7.36 (d, 1H), 7.21 (d, 1H), 7.15 (s, 1H), 7.11 (s, 1H), 6.01 (s, 1H), 5.21 (d, 1H), 4.57 (m, 2H), 4.15 (m, 2H), 3.98 (s, 3H), 2.87 (m, 1H), 2.71 (m, 2H), 2.57 (m, 1H), 1.64-1.43 (m, 6H), 1.26 (s, 9H), 1.19 (m, 1H), 1.02 (s, 9H), 0.96-0.91 (m, 5H); LCMS found [M+H]+.

Example 47

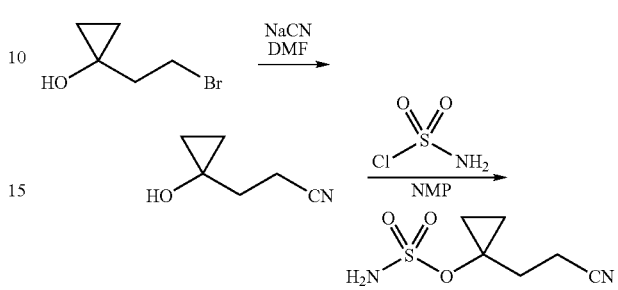

To 1-(2-Bromo-ethyl)-cyclopropanol (synthesized according to the method presented in *Eur. J. Org. Chem.* 2003, 551) in DMF was added NaCN. The mixture was then stirred at 70° C. for 4 hr. After cooling to room temperature, the reaction mixture was diluted with 140 mL of 0.5 M NaOH and EtOAc. The layers were separated and the organic layer was dried over Na$_2$SO$_4$ and purified by column chromatography on silica (40-70% EtOAc/Hexane) to provide 436 mg (32%) of 1-(2-cyanoethyl)-cyclopropanol.

The cyclopropylsulfamate was synthesized according to the method presented in the synthesis of sulfamic acid phenyl ester in Example 1 with the exception of utilizing 1-(2-cyanoethyl)-cyclopropanol (synthesized by methods reported in *JOC* 1980, 45, 4129-35) to obtain the sulfamic acid 1-(2-cyanoethyl)-cyclopropyl ester.

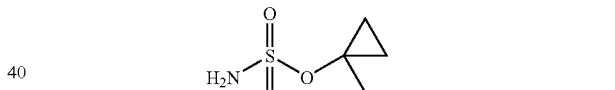

Compound 47

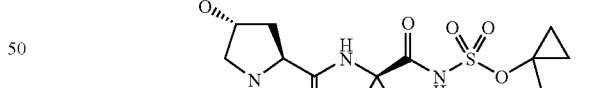
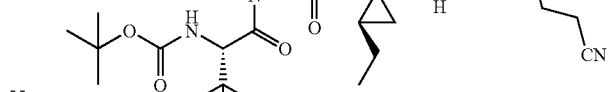
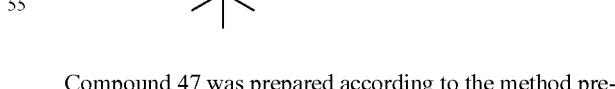
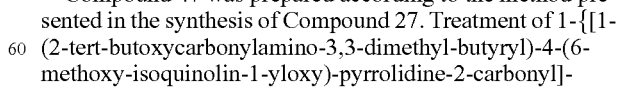
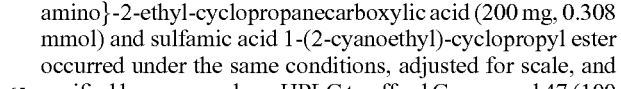
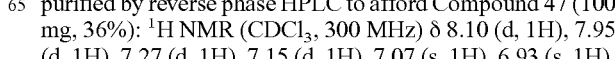

Compound 47 was prepared according to the method presented in the synthesis of Compound 27. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid (200 mg, 0.308 mmol) and sulfamic acid 1-(2-cyanoethyl)-cyclopropyl ester occurred under the same conditions, adjusted for scale, and purified by reverse phase HPLC to afford Compound 47 (100 mg, 36%): $^1$H NMR (CDCl$_3$, 300 MHz) δ 8.10 (d, 1H), 7.95 (d, 1H), 7.27 (d, 1H), 7.15 (d, 1H), 7.07 (s, 1H), 6.93 (s, 1H), 6.00 (s, 1H), 5.19 (d, 1H), 4.51 (m, 1H), 4.22 (d, 1H), 4.12 (m, 1H), 4.06 (s, 1H), 3.97 (s, 3H), 2.74 (m, 2H), 2.55 (m, 1H), 2.52 (m, 1H), 2.27 (m, 1H), 2.18 (m, 1H), 1.69 (m, 2H), 1.60 (m, 2H), 1.42 (m, 2H), 1.31 (s, 9H), 1.30 (m, 1H), 1.03 (s, 9H), 0.95 (m, 3H), 0.85 (m, 2H); LCMS found 784.9 [M+H]$^+$.

Example 48

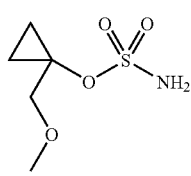

Compound 48

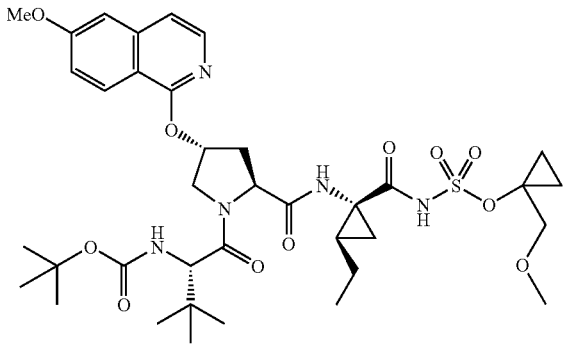

Sulfamic acid 1-methoxymethyl-cyclopropyl ester was synthesized according to the method presented in the synthesis of sulfamic acid phenyl ester in Example 1 with the exception of utilizing 1-methoxymethyl cyclopropanol (synthesized by methods reported in *European Journal of Chemistry* 2006, 5069) to obtain sulfamic acid 1-methoxymethyl-cyclopropyl ester.

Compound 48 was prepared according to the method presented in the synthesis of Compound 27. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid (0.49 mmol) occurred under the same conditions, adjusted for scale, and purified by reverse phase HPLC to afford Compound 48 (70 mg, 18%): $^1$H NMR (CD$_3$OD, 300 MHz) δ 9.12 (s, 1H), 8.10 (d, 1H), 7.89 (d, 1H), 7.26 (d, 1H), 7.19 (s, 1H), 7.10 (d, 1H), 5.84 (m, 1H), 4.54 (m, 1H), 4.44 (m, 1H), 4.25 (m, 2H), 4.08 (m, 1H), 3.94 (s, 3H), 3.41 (s, 3H), 3.32 (s, 2H), 2.58 (m, 1H), 2.27 (m, 1H), 1.57 (m, 4H), 1.29 (s, 9H), 1.20-1.31 (m, 3H), 1.04 (s, 9H), 0.98 (m, 3H), 0.89 (m, 2H); LCMS found 775.6 [M+H]$^+$.

Example 49

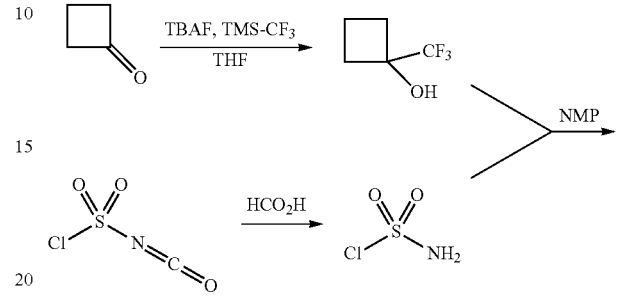

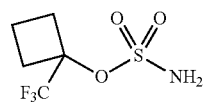

Compound 49

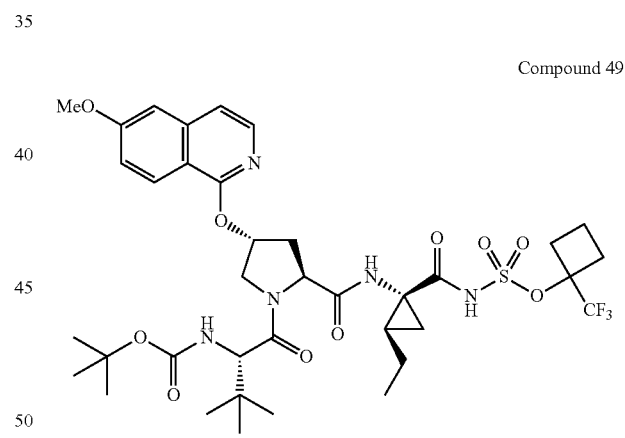

A round bottom flask was charged with 20 ml THF, cyclobutanone (5 g, 71 mmol), and TMS-CF$_3$ (42.8 ml, 86 mmol, 2 M in THF). The stirring mixture was cooled to 0° C. and TBAF (0.68 ml, 0.68 mmol, 1 M in THF) was slowly added. Stir 2 hours, quench with water and extract with ether. Wash organic layer with brine, dry over sodium sulfate, and concentrate. Use resulting oil crude in the next reaction.

Sulfamic acid 1-trifluoromethyl-cyclobutyl ester was synthesized according to the method presented in the synthesis of sulfamic acid phenyl ester in Example 1 with the exception of utilizing 1-trifluoromethyl-cyclobutanol to obtain sulfamic acid 1-trifluoromethyl-cyclobutyl ester: $^1$H NMR (CDCl$_3$, 300 MHz) δ 5.85 (s, 2H), 3.40 (t, 1H), 3.01 (m, 1H), 2.56 (m, 1H), 2.42 (t, 1H), 2.04 (m, 1H), 1.85 (m, 1H).

Compound 49 was prepared according to the method presented in the synthesis of Compound 27. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid (0.33 mmol) occurred under the same conditions, adjusted for scale, and purified by reverse phase HPLC to afford Compound 49 (95 mg, 12%): ¹H NMR (CD₃OD, 300 MHz) diagnostic δ 3.14 (m, 2H), 2.54 (m, 2H), 2.05 (m, 1H), 1.88 (m, 1H); LCMS found 813.9 [M+H]⁺.

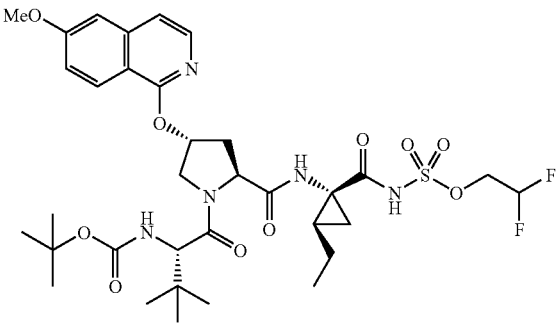

Compound 50

Compound 50 was prepared according to the method presented in the synthesis of Compound 27. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid (0.33 mmol) occurred under the same conditions, adjusted for scale, and purified by reverse phase HPLC to afford Compound 50 (120 mg, 48%): ¹H NMR (CD₃OD, 300 MHz) diagnostic δ 6.11 (t, 1H), 4.51 (m, 2H); LCMS found 756.0 [M+H]⁺.

Example 50

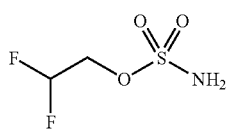

Example 51

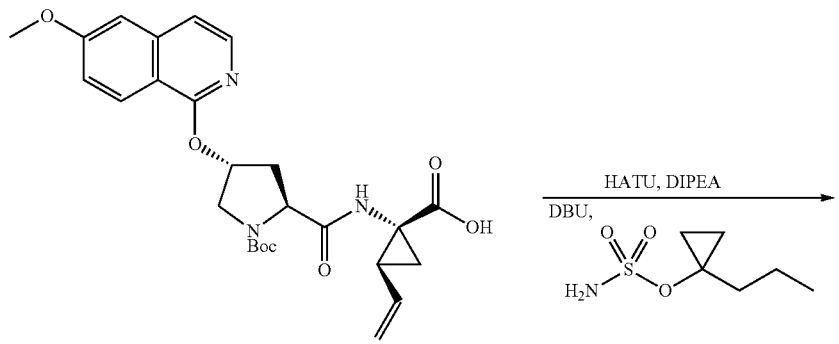

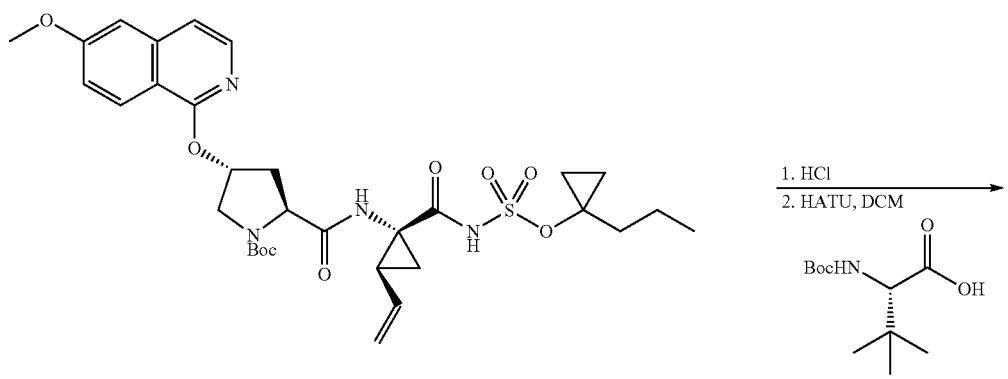

-continued

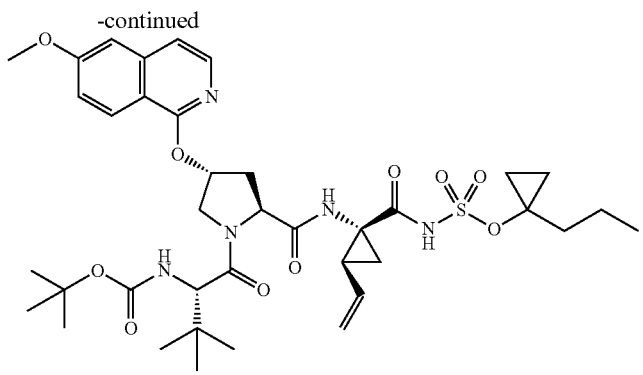

Compound 51

To a solution of 2-(1-carbonyl-2-vinyl-cyclopropylcarbamoyl)-4-(6-methoxy-isoquinolin-1-yloxy)-pyrrolidine-1-carboxylic acid tert-butyl ester (1.00 g, 2.01 mmol) in DMF (10 mL) was added HATU (1.14 g, 3.02 mmol, 1.5 equiv.) and DIPEA (0.52 mL, 2.98 mmol, 1.5 equiv.). The solution was stirred at room temperature for 15 min before sulfamic acid 1-propyl-cyclopropyl ester (0.71 mg, 4.00 mmol, 2 equiv.) and DBU (1.2 mL, 8.02 mmol, 4 equiv.) were added. The reaction was then stirred for an additional 15 h. The solution was diluted with EtOAc and washed twice with 1M aqueous HCl and Brine. The organic layer was dried over $MgSO_4$ and concentrated in vacuo. The desired sulfamate was precipitated from $EtOH/H_2O$ to provide 4-(6-methoxy-isoquinolin-1-yloxy)-2-[1-(1-propyl-cyclopropoxysulfonylaminocarbonyl)-2-vinyl-cyclopropylcarbamoyl]-pyrrolidine-1-carboxylic acid tert-butyl ester (520 mg, 39%). The mother liquor was concentrated in vacuo and further purified by column chromatography (50→100% EtOAc/hexanes) to provide additional sulfamate. Precipitation from $EtOH/H_2O$ provided 4-(6-methoxy-isoquinolin-1-yloxy)-2-[1-(1-propyl-cyclopropoxysulfonylaminocarbonyl)-2-vinyl-cyclopropylcarbamoyl]-pyrrolidine-1-carboxylic acid tert-butyl ester (244 mg, 18%): LCMS found 659.0 $[M+H]^+$.

To a solution of 4-(6-methoxy-isoquinolin-1-yloxy)-2-[1-(1-propyl-cyclopropoxysulfonylaminocarbonyl)-2-vinyl-cyclopropylcarbamoyl]-pyrrolidine-1-carboxylic acid tert-butyl ester in $CH_2Cl_2$ (0.9 mL) was added 4M HCl in dioxane (4.5 mL). The solution was stirred at room temperature for 2 h before concentration in vacuo. The crude amine was redissolved in $CH_2Cl_2$ (2.3 mL), to which was added HATU (224 mg, 0.59 mmol, 1.25 equiv.), 2-tert-Butoxycarbonylamino-3,3-dimethyl-butyric acid (134 mg, 0.58 mmol, 1.25 equiv.) and DIPEA (0.4 mL, 2.29 mmol, 5 equiv.). The resulting solution was stirred at room temperature for 14 h before dilution with $CH_2Cl_2$. The organic layer was washed twice with 1M aqueous HCl and Brine, dried over $MgSO_4$, and concentrated in vacuo. The crude product was triterated with $EtOH/H_2O$ to provide Compound 51 (298 mg, 84%): $^1H$ NMR ($CD_3OD$, 300 MHz) δ 8.10 (d, 1H), 7.89 (d, 1H), 7.26 (d, 1H), 7.19 (s, 1H), 7.10 (d, 1H), 6.53 (d, 1H), 5.84 (m, 1H), 5.73 (m, 1H), 5.31 (d, 1H), 5.14 (d, 1H), 4.54 (m, 1H), 4.43 (d, 1H), 4.26 (d, 1H), 4.07 (m, 1H), 3.93 (s, 3H), 2.60 (m, 1H), 2.27 (m, 2H), 1.79-1.89 (m, 4H), 1.59 (m, 2H), 1.47 (m, 2H), 1.29 (s, 9H), 1.18 (m, 2H), 1.04 (s, 9H), 0.97 (t, 3H), 0.69 (m, 2H); LCMS found 772.09 $[M+H]^+$.

Example 52

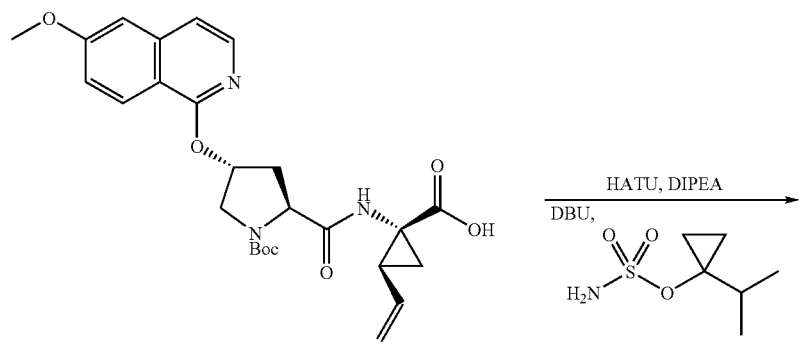

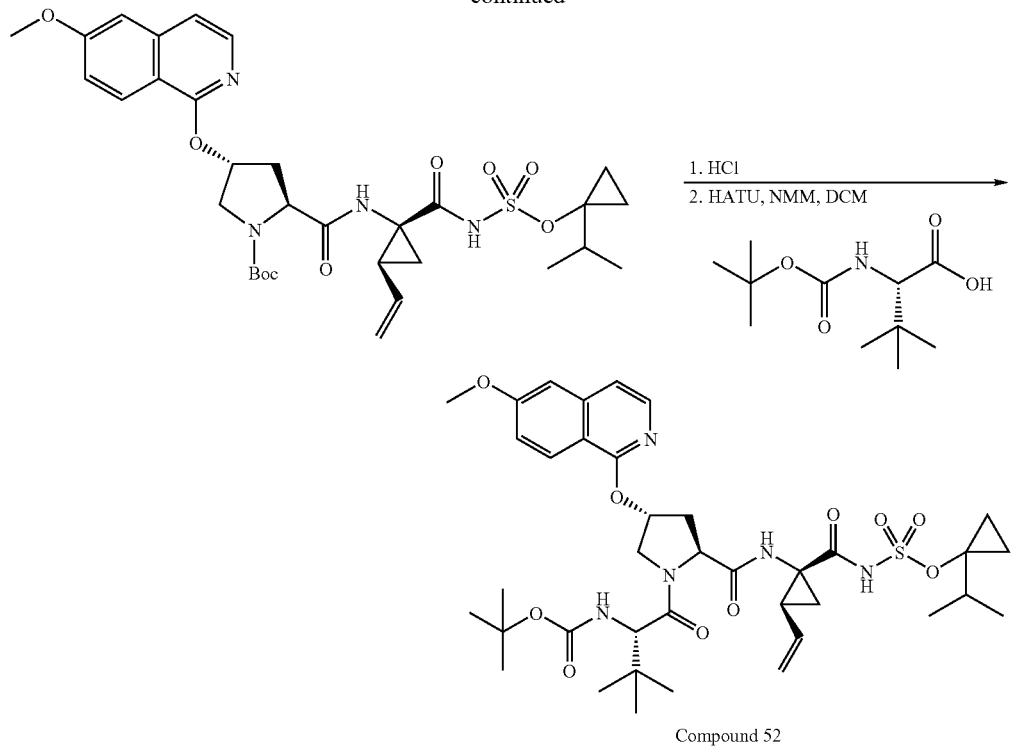

Compound 52

2-[1-(1-Isopropyl-cyclopropoxysulfonylaminocarbonyl)-2-vinyl-cyclopropylcarbamoyl]-4-(6-methoxy-isoquinolin-1-yloxy)-pyrrolidine-1-carboxylic acid tert-butyl ester was prepared according the method presented in the synthesis of Compound 51. Treatment of 2-(1-carboxy-2-vinyl-cyclopropylcarbamoyl)-4-(6-methoxy-isoquinolin-1-yloxy)-pyrrolidine-1-carboxylic acid tert-butyl ester with sulfamic acid 1-isopropyl-cyclopropyl ester, synthesized according to the method presented in the synthesis of sulfamic acid phenyl ester in Example 1 utilizing 1-isopropyl cyclopropanol, yielded the desired sulfamic ester.

Compound 52 was prepared according to the method presented in the synthesis of Compound 51. Treatment of the 2-[1-(1-Isopropyl-cyclopropoxysulfonylaminocarbonyl)-2-vinyl-cyclopropylcarbamoyl]-4-(6-methoxy-isoquinolin-1-yloxy)-pyrrolidine-1-carboxylic acid tert-butyl ester (320 mg, 0.49 mmol) occurred under the same conditions, adjusted for scale and with the exception of utilizing 2-tert-Butoxycarbonylamino-3,3-dimethyl-butyric acid to provide compound 52 as a white solid (150 mg), $^1$H NMR (300 MHz, CD$_3$OD): δ 9.25 (s, 1H), 8.11 (d, 1H), 57.89 (d, 1H), 57.30 (d, 1H), 7.23 (s, 1H), 7.15 (d, 1H), 5.84 (m, 1H), 5.72 (m, 1H), 5.29 (m, 1H), 5.12 (m, 1H), 4.53-4.09 (m, 4H), 3.94 (s, 3H), 3.91 (m, 1H), 2.27-1.85 (m, 4H), 1.481.27-1.59 (m, 10H), 1.07-0.93 (m, 15H), 0.77-0.71 (m, 5H). LCMS found 773 [M+H]$^+$.

Example 53

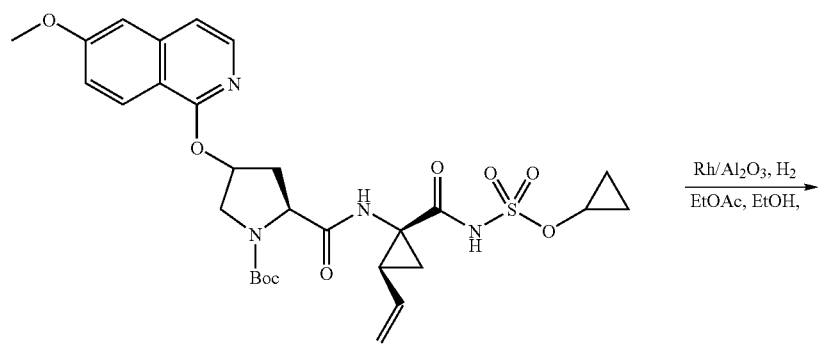

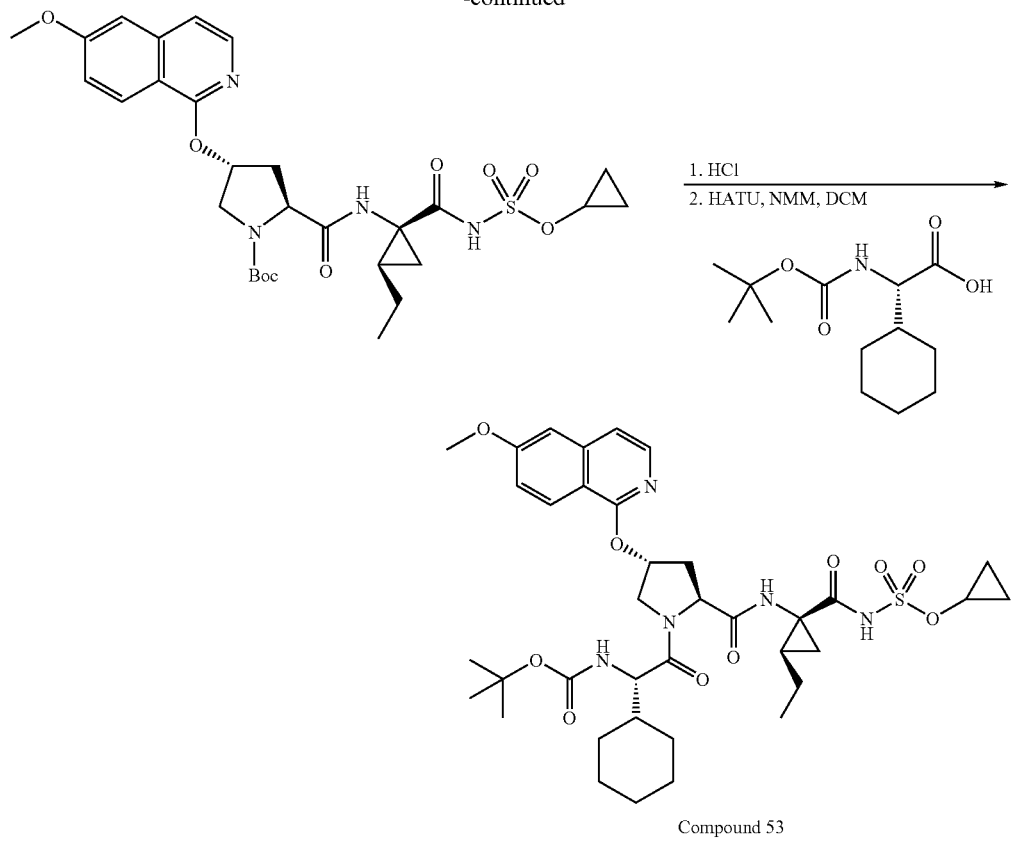

Compound 53

To the trifluoroacetate salt of 2-(1-cyclopropoxysulfonylaminocarbonyl-2-vinyl-cyclopropylcarbamoyl)-4-(6-methoxy-isoquinolin-1-yloxy)-pyrrolidine-1-carboxylic acid tert-butyl ester (181 mg, 0.253 mmol) Rh/AlO$_3$ (37.2 mg, 5 wt %) was added and the mixture was suspended in EtOAc (4.5 mL) and EtOH (1.0 mL). The reaction flask was flushed with H$_2$ gas and the reaction was allowed to stir at room temperature under a hydrogen atmosphere for 3 h. The reaction was filtered through a syringe tip filter (0.45 µM) and washed with ethanol. The filtrate was concentrated and then filtered through a C-18 RP SPE column (Phenomenex Strata, 1 g) and washed with methanol. The filtrate was concentrated and purified on silica (12 g, 0-7% MeOH/CH$_2$Cl$_2$) to give 2-(1-cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (151 mg, 83%). LCMS found 619.1 [M+H]$^+$.

2-(1-Cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (50 mg, 0.08 mmol) was dissolved in DCM (0.2 mL) and HCl in dioxane (4N, 0.2 mL) was added. The reaction was allowed to stir at room temperature for 2 h before it was concentrated. The solid residue was dissolved in DCM (0.8 mL) and tert-butoxycarbonylamino-cyclohexyl-acetic acid (23 mg, 0.1 mmol) was added followed by HATU (46 mg, 0.12 mmol) and NMM (0.027 mL, 0.24 mmol). The reaction was allowed to stir at room temperature for 16 h. The reaction was neutralized with HCl (1N) and partitioned between H$_2$O (3 mL) and DCM (5 mL). The aqueous layer was extracted with DCM (2×5 mL) and the combined organic layers were washed with brine and dried over Na$_2$SO$_4$ and concentrated. The crude residue was purified by reverse phase HPLC (25-100% CH$_3$CN/H$_2$O+0.1% TFA) to give Compound 53 as a white solid (44 mg, 70%). $^1$H NMR (300 MHz, CD$_3$OD): δ 9.24 (s, 1H), 8.15 (d, 1H), 7.89 (d, 1H), 7.31 (d, 1H), 7.23 (s, 1H), 7.14 (d, 1H), 5.84 (m, 1H), 4.54 (m, 2H), 4.31 (m, 1H), 4.06 (m, 2H), 3.94 (s, 3H), 2.60 (m, 1H), 2.34 (m, 1H), 2.05 (m, 1H), 1.83-1.62 (m, 10H), 1.24 (s, 9H), 1.06 (s, 6H), 1.10-0.96 (m, 6H), 0.77 (m, 2H). LCMS found 759 [M+H]$^+$.

Example 54

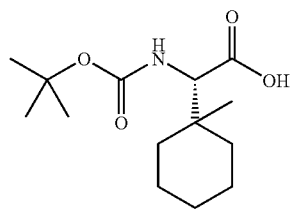

Compound 54

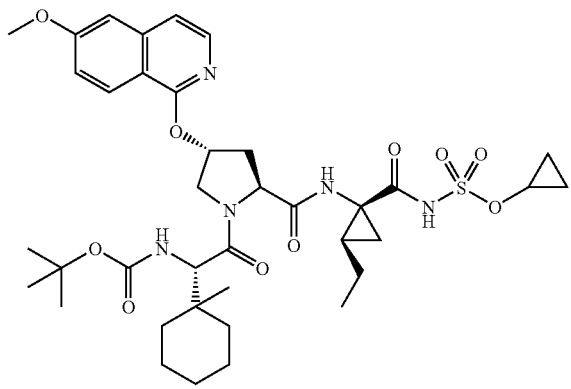

Compound 54 was prepared according to the method presented in the synthesis of Compound 53. Treatment of the trifluoroacetate salt of 2-(1-cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (50 mg, 0.08 mmol) occurred under the same conditions, adjusted for scale and with the exception of utilizing 3 tert-butoxycarbonylamino-(1-methyl-cyclohexyl)-acetic acid to provide Compound 54 as a white solid (40 mg, 65%). $^1$H NMR (300 MHz, CD$_3$OD): δ 9.11 (s, 1H), 8.13 (d, 1H), 7.90 (d, 1H), 7.32 (d, 1H), 7.23 (s, 1H), 7.14 (d, 1H), 5.85 (m, 1H), 4.51 (m, 2H), 4.29 (m, 2H), 4.07 (m, 1H), 3.95 (s, 3H), 2.61 (m, 1H), 2.28 (m, 1H), 2.05 (m, 1H), 1.61-1.13 (m, 15H), 1.25 (s, 9H), 1.06 (s, 6H), 0.97 (m, 3H), 0.76 (m, 2H). LCMS found 773 [M+H]$^+$.

Example 55 and 56

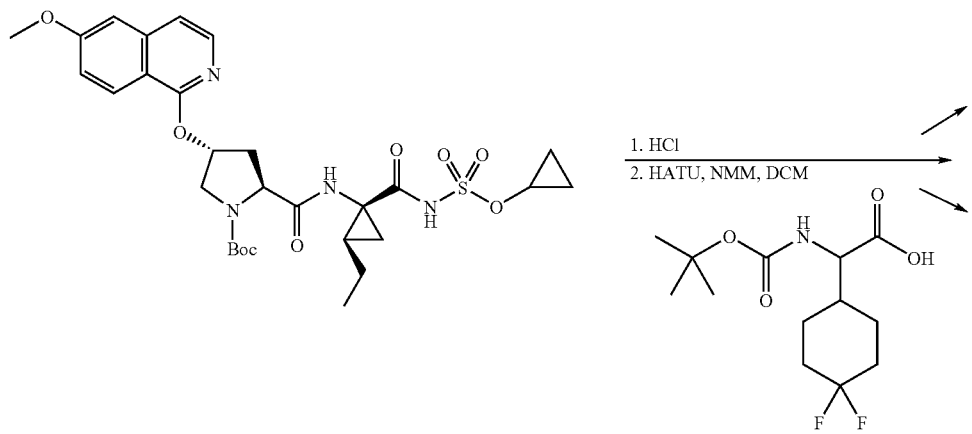

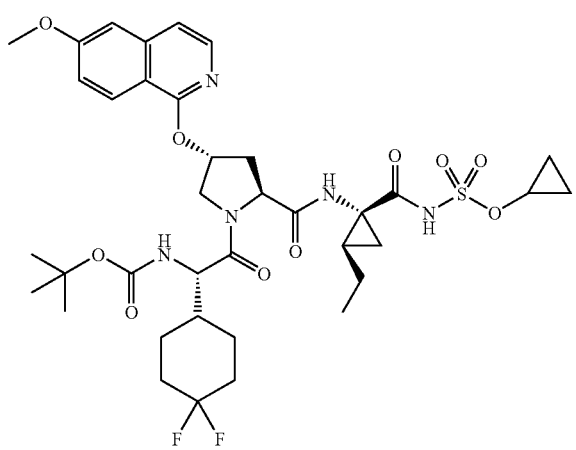

Compound 55

Compound 56

Compound 55 and 56 were prepared according to the method presented in the synthesis of Compound 53 Treatment of the trifluoroacetate salt of 2-(1-cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (50 mg, 0.08 mmol) occurred under the same conditions, adjusted for scale and with the exception of utilizing tert-butoxycarbonylamino-(4,4-difluoro-cyclohexyl)-acetic acid to provide Compound 55 and Compound 56 (purified by chiral HPLC (Chiralpak AS-H, Heptane:Ethanol 80:20)) both as a white solid. $^1$H NMR (300 MHz, CDCl$_3$) for Compound 55: δ 8.80 (m, 1H), 8.23 (d, 1H), 7.96 (d, 1H), 7.42 (d, 1H), 7.25 (m, 1H), 7.15 (s, 1H), 6.04 (s, 1H), 5.30 (m, 1H), 4.67 (m, 1H), 4.52 (m, 1H), 4.35 (m, 1H), 4.13 (m, 2H), 4.01 (s, 3H), 2.71 (m, 1H), 2.59 (m, 1H), 2.07 (m, 2H), 1.87-1.34 (m, 13H), 1.25 (s, 9H), 0.99-0.92 (m, 6H), 0.76 (s, 2H). $^1$H NMR (300 MHz, CDCl$_3$) for Compound 56: δ 9.90 (m, 1H), 8.07 (d, 1H), 7.93 (d, 1H), 7.52 (d, 1H), 7.43 (m, 1H), 7.31 (m, 1H), 7.17 (s, 1H), 7.17 (s, 1H), 6.05 (s, 1H), 5.51 (m, 1H), 4.76 (m, 1H), 4.25 (m, 2H), 4.01 (s, 3H), 2.87 (m, 1H), 2.43 (m, 1H), 1.98 (m, 2H), 1.85-1.51 (m, 13H), 1.41 (s, 9H), 1.01 (m, 6H), 0.75 (s, 2H). LCMS found 795 [M+H]$^+$.

Example 57

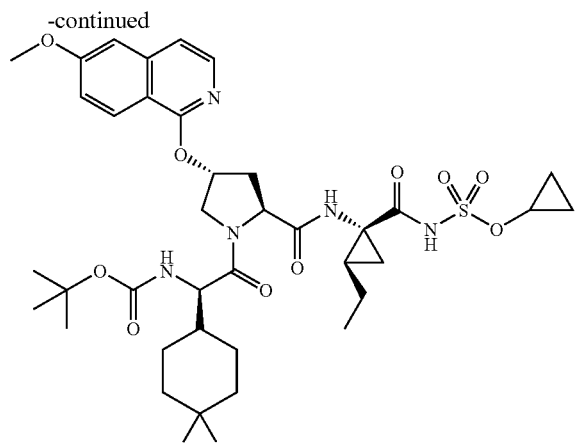

Compound 57

Compound 57 was prepared according to the method presented in the synthesis of Compound 53. Treatment of the trifluoroacetate salt of 2-(1-cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (100 mg, 0.16 mmol) occurred under the same conditions, adjusted for scale and with the exception of utilizing 2-tert-butoxycarbonylamino-4,4,4-trifluoro-3-trifluoromethyl-butyric acid to provide Compound 57 as a white solid (80 mg, 60%). $^1$H NMR (300 MHz, CDCl$_3$): δ 10.1 (s, 1H), 8.01 (d, 1H), 7.94 (d, 1H), 7.22 (d, 1H), 7.13 (d, 1H), 7.05 (s, 1H), 6.99-6.82 (m, 2H), 5.95 (m, 1H), 5.42 (m, 1H), 5.15 (m, 1H), 4.53-4.10 (m, 3H), 3.95 (s, 3H), 3.86 (m, 1H), 2.68-2.46 (m, 2H), 1.71-1.46 (m, 4H), 1.21 (s, 9H), 0.99-0.92 (m, 6H), 0.73 (m, 2H). LCMS found 827 [M+H]$^+$.

Example 58

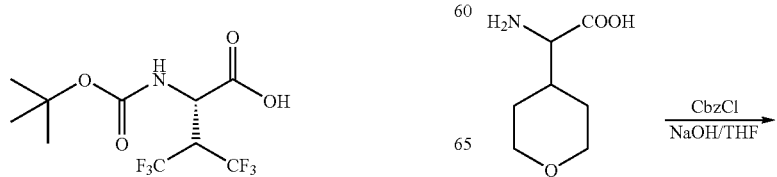

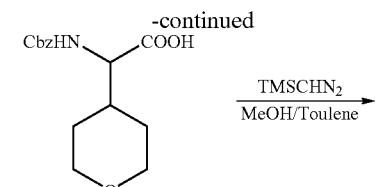

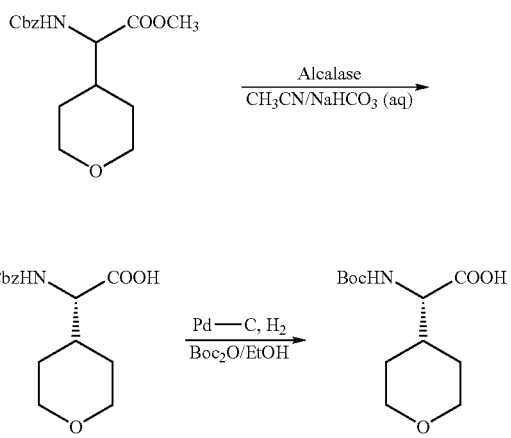

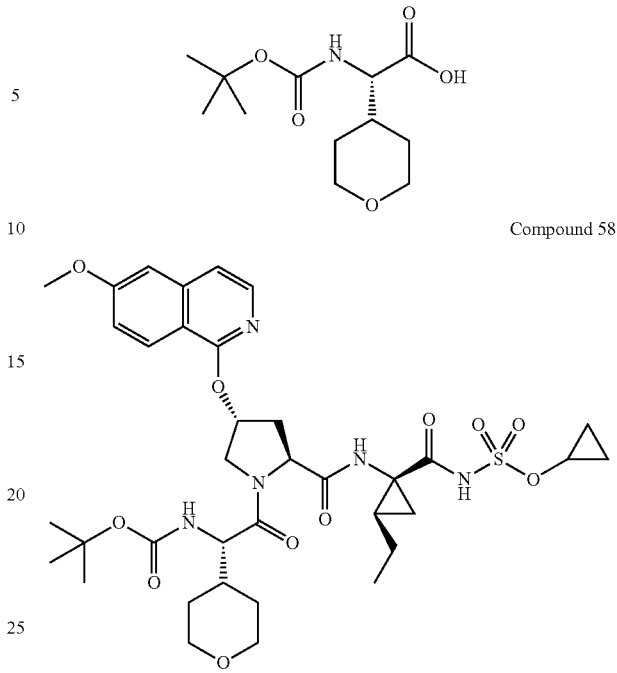

Compound 58

Amino-(4-tetrahydropyranyl)acetic acid (3.18 g, 20 mmol) was dissolved in 2N NaOH (20 mL) and THF (5 mL), benzyl chloroformate (3.6 mL, 25 mmol) was added. The reaction was allowed to stir at room temperature for 16 h. The reaction was extracted with EtOAc (2×30 mL), the aqueous layer was acidified with HCl (6N) to pH 3 and the aqueous layer was extracted with EtOAc (5×30 mL) and the combined organic layers were washed with brine and dried over $Na_2SO_4$ and concentrated to give the crude carbamate as a white solid (5.8 g, 99%).

Benzyloxycarbonylamino-(tetrahydro-pyran-4-yl)-acetic acid (5 g, 17 mmol) was dissolved in MeOH (77 mL) and toluene (8.5 mL), trimethylsilyldiazomethane (2.0M in Hexane) (35 mL) was added slowly. The reaction was allowed to stir at room temperature for 2 h. After concentrated, the crude product was purified on silica (40 g, 25-75% EtOAc/hexanes) to give the methyl ester as white solid (4 g, 77%).

Benzyloxycarbonylamino-(tetrahydro-pyran-4-yl)-acetic acid methyl ester (4 g, 13 mmol) was dissolved in acetonitrile (45 mL) and 0.2 M $NaHCO_3$ (90 mL). The resulting solution was treated with Alcalase (1 mL) and the reaction mixture was allowed to stir at room temperature for 24 h. until about 47% of methyl ester has been consumed as determined by HPLC. After concentrated to remove acetonitrile, the reaction mixture was extracted with hexane (2×100 mL), the aqueous phase was acidified with 6N HCl to pH 3 and the solution was extracted with EtOAc (3×100 mL). The combined organic phase were dried over $Na_2SO_4$ and concentrated to give the desired chiral acid (1.5 g, 40%).

Benzyloxycarbonylamino-(tetrahydro-pyran-4-yl)-acetic acid (900 mg, 3.1 mmol) was dissolved in EtOH (60 mL) 10% Pd—C (300 mg) and $Boc_2O$ (810 mg, 3.7 mmol) were added. The resulting solution was allowed to stir at room temperature under $H_2$ balloon for 24 h. After filtration through celite, and washed with ethanol and water, concentrated to remove all solvents to give the intermediate tert-butoxycarbonylamino-(tetrahydro-pyran-4-yl)-acetic acid (640 mg, 81%).

Compound 58 was prepared according to the method presented in the synthesis of Compound 53. Treatment of the trifluoroacetate salt of 2-(1-cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (50 mg, 0.08 mmol) occurred under the same conditions, adjusted for scale and with the exception of utilizing tert-butoxycarbonylamino-(tetrahydro-pyran-4-yl)-acetic acid to provide Compound 58 as a white solid (41 mg, 66%). $^1$H NMR (300 MHz, $CD_3OD$): δ 9.30 (s, 1H), 8.13 (d, 1H), 7.89 (d, 1H), 7.27 (d, 1H), 7.20 (s, 1H), 7.14 (d, 1H), 5.86 (m, 1H), 4.54 (m, 2H), 4.33 (m, 1H), 4.13 (m, 2H), 3.94 (s, 3H), 3.41 (m, 2H), 2.61 (m, 1H), 2.38 (m, 1H), 2.05 (m, 1H), 1.68-1.30 (m, 12H), 1.24 (s, 9H), 0.98 (m, 6H), 0.76 (m, 2H). LCMS found 761 $[M+H]^+$.

Example 59

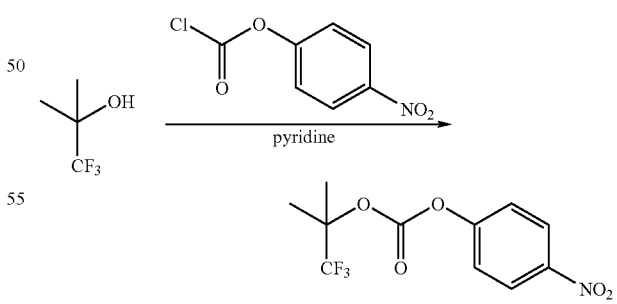

To a cooled solution of 4-nitrophenyl chloroformate (94.4 g, 0.468 mol) in $CH_2Cl_2$ (800 mL) was added 1,1,1-trifluoro-2-methyl-propan-2-ol (50 g, 0.39 mol) in one portion. Pyridine (75.7 mL, 0.936 mol) was added dropwise while the solution was maintained at 0° C. After the addition was complete, the solution was let warm to room temperature. After 12 h stirring, the solution was acidified with aqueous 1N HCl, washed with water and saturated aqueous NaHCO$_3$, dried over Na2SO4. After removal of solvent, the residue was crystallized from a mixture EtOAc/hexanes (1:1). The solid was mixed with 2× silica gel and eluted by column chromatography (CH$_2$Cl$_2$/hexanes, 1:3) to provide the desired carbonate as a white solid (25 g, 22%).

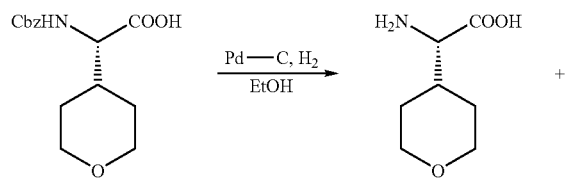

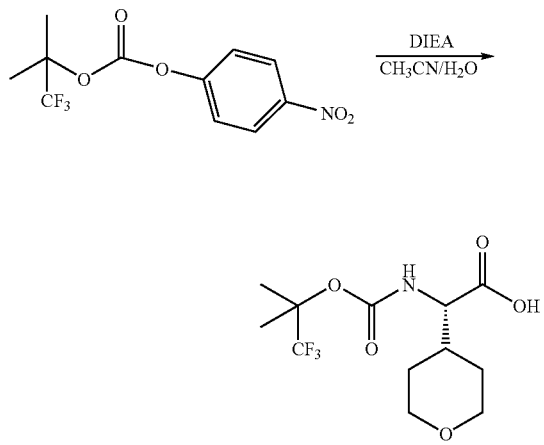

Benzyloxycarbonylamino-(tetrahydro-pyran-4-yl)-acetic acid (500 mg, 1.7 mmol) was dissolved in EtOH (5 mL) 10% Pd—C (90 mg) was added. The resulting solution was allowed to stir at room temperature under H$_2$ balloon for 2 h. After filtration through celite, and washed with ethanol and water, concentrated to remove all solvents to give the amino acid (244 mg, 90%).

Amino-(tetrahydro-pyran-4-yl)-acetic acid (80 mg, 0.5 mmol) was dissolved in CH$_3$CN (5 mL) and H$_2$O (1 mL), carbonic acid 4-nitro-phenyl ester 2,2,2-trifluoro-1,1-dimethyl-ethyl ester (175 mg, 0.6 mmol) and DIEA (88 µL, 0.5 mmol) were added slowly. The reaction was allowed to stir at room temperature for 16 h. After concentrated, diluted with EtOAc, washed with brine and H$_2$O, dried over Na2SO4, the crude product was purified on silica (12 g, 25-75% EtOAc/hexanes) to give intermediate (tetrahydro-pyran-4-yl)-(2,2,2-trifluoro-1,1-dimethyl-ethoxycarbonylamino)-acetic acid as light yellow solid (110 mg, 70%).

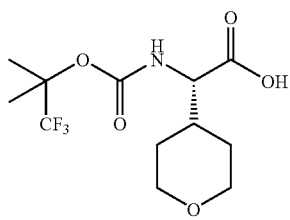

Compound 59

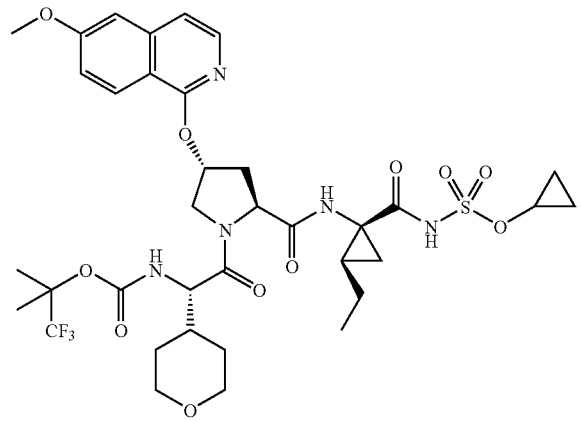

Compound 59 was prepared according to the method presented in the synthesis of Compound 53. Treatment of the trifluoroacetate salt of 2-(1-cyclopropoxysulfonylaminocarbonyl-2-ethyl-cyclopropylcarbamoyl)-4-(6-methoxy-isoquinolin-1-yloxy)-pyrrolidine-1-carboxylic acid tert-butyl ester (100 mg, 0.16 mmol) occurred under the same conditions, adjusted for scale and with the exception of utilizing (tetrahydro-pyran-4-yl)-(2,2,2-trifluoro-1,1-dimethyl-ethoxycarbonylamino)-acetic acid to provide Compound 59 as a white solid (85 mg, 65%). $^1$H NMR (300 MHz, CDCl$_3$): δ 10.2 (m, 1H), 8.10 (m, 1H), 7.99 (m, 1H), 7.32 (m, 1H), 7.21 (m, 1H), 7.11 (m, 1H), 6.86 (m, 1H), 5.99 (m, 1H), 5.52 (m, 1H), 4.77 (m, 4H), 4.51 (m, 2H), 4.38 (m, 1H), 4.14 (m, 1H), 3.98 (s, 3H), 3.40 (m, 2H), 2.64 (m, 1H), 2.55 (m, 1H), 2.13 (m, 1H), 1.77-1.28 (m, 13H), 0.98 (m, 6H), 0.76 (m, 2H). LCMS found 815 [M+H]$^+$.

Example 60

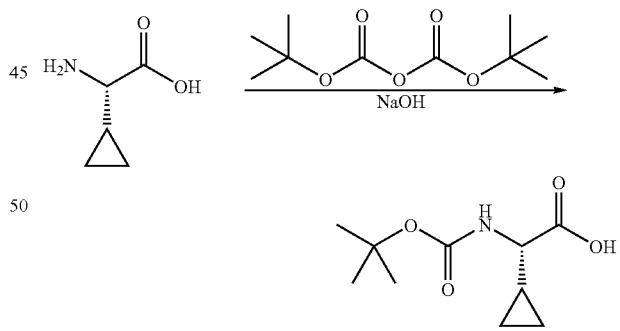

L-cyclopropyl glycine (500 mg, 4.34 mmol) was dissolved in aqueous NaOH solution (2N, 4.4 mL) and the reaction was cooled to 0° C. Di-tert-butyl dicarbonate (1.14 g, 5.2 mmol) was added portion wise and the reaction was allowed to stir for 0.5 h at 0° C. and then for 2 h at room temperature. The reaction was acidified using concentrated HCl and extracted with EtOAc (3×10 mL). The organic layers were dried over Na$_2$SO$_4$ and concentrated. The crude white solid was recrystallized in EtOAc and Hexane and the resulting white solid tert-butoxycarbonylamino-cyclopropyl-acetic acid was dried under-vacuum. LCMS found 213.8 [M−H]$^-$.

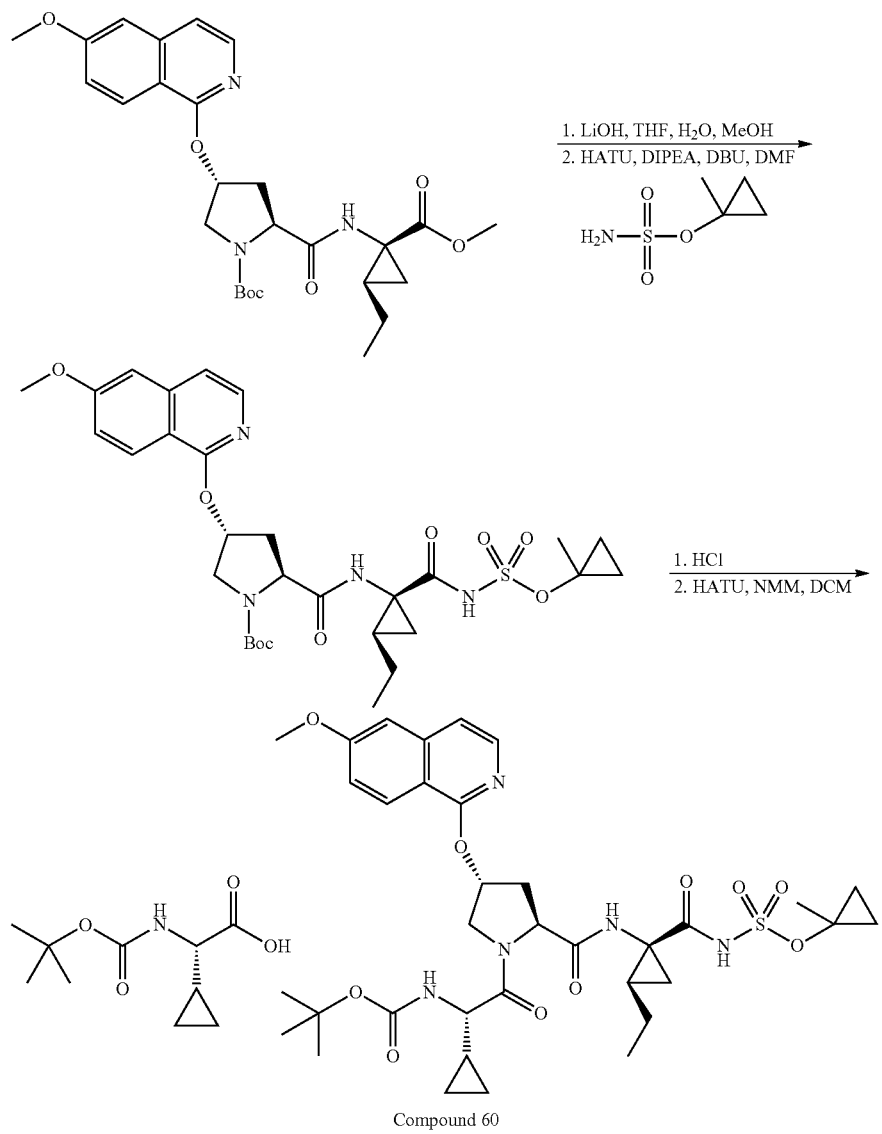

Compound 60

2-(2-Ethyl-1-methoxycarbonyl-cyclopropylcarbamoyl)-4-(6-methoxy-isoquinolin-1-yloxy)-pyrrolidine-1-carboxylic acid tert-butyl ester (3.1 g, 6.1 mmol) was dissolved in THF (36 mL) and MeOH (12 mL). LiOH (730 mg, 30.5 mmol) was dissolved in H₂O (12 mL) and the resulting solution was added to the reaction flask. The reaction was allowed to stir at room temperature for 16 h. The reaction solution was acidified with HCl (1N) and extracted with EtOAc (3×250 mL). The combined organic layers were washed with H₂O (100 mL), and brine (100 mL) and dried over Na₂SO₄, before being concentrated and dried on high vacuum. The crude residue was dissolved in DMF (61 mL) and HATU (3.5 g, 9.2 mmol) was added followed by diisoproylethylamine (1.6 mL, 9.2 mmol) and the reaction mixture was allowed to stir for 30 min at room temperature. Sulfamic acid 1-methyl-cyclopropyl ester was added followed by DBU (3.65 mL, 24.4 mmol) and the reaction was allowed to stir for 16 h at room temperature. The reaction was acidified with HCl (1N) and then extracted with EtOAc (3×250 mL) and the combined organic layers were washed with brine (1×100 mL), dried over Na₂SO₄ and concentrated. The crude residue was purified on silica (330 g, 50-80% EtOAc/Hexanes) and then triturated with DCM (5 mL) and hexanes (20 mL) to give the acylsulfamate as a white solid (2.3 g, 60%). LCMS found 633.1 [M+H]⁺.

2-[2-Ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (109 mg, 0.17 mmol) was dissolved in DCM (0.53 mL) and HCl in dioxane (4N, 0.53 mL) was added. The reaction was allowed to stir at room temperature for 2.5 h before it was concentrated. The solid residue was dissolved in DCM (1.7 mL) and tert-butoxycarbonylamino-cyclopropyl-acetic acid (41 mg, 0.19 mmol) was added followed by HATU (98.7 mg, 0.26 mmol) and n-methylmorpholine (0.057 mL, 0.52 mmol). The reaction was allowed to stir at room temperature for 2 h. The reaction was neutralized with HCl (1N) and partitioned between H₂O (3 mL) and DCM (5 mL). The aqueous layer was extracted with DCM (2×5 mL) and the combined organic layers were washed with brine and dried over Na₂SO₄ and concentrated. The crude residue was purified on silica (12 g, 50-100% EtOAc/hexanes), and then by reverse phase HPLC (25-100% CH$_3$CN/H$_2$O+0.1% TFA) to give Compound 60 as a white solid (115.7 mg, 81%). $^1$H NMR (300 MHz, CD$_3$OD): δ 9.17 (m, 1H), 8.12 (d, 1H), 7.84 (d, 1H), 7.25 (d, 1H), 7.17 (s, 1H), 7.11 (d, 1H), 5.81 (m, 1H), 4.54 (m, 1H), 4.35 (m, 1H), 4.02 (m, 1H), 3.89 (s, 3H), 3.81 (m, 1H), 2.54 (m, 1H), 2.29 (m, 1H), 1.54-1.63 (m, 7H), 1.16-1.63 (m, 13H), 0.93-0.95 (m, 3H), 0.63 (s, 2H), 0.40-0.51 (m, 4H). LCMS found 730.8 [M+H]$^+$.

Example 61

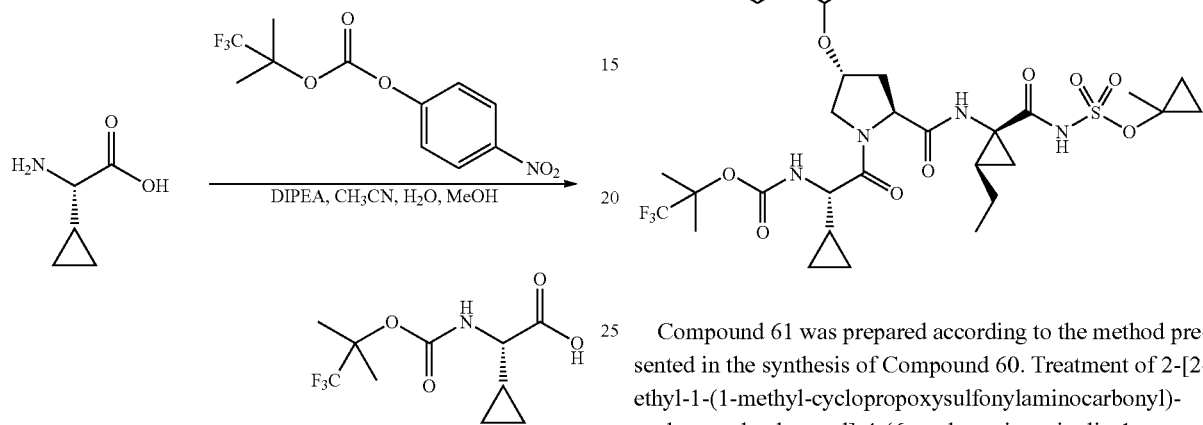

Compound 61

Commercially available L-cyclopropyl glycine (500.8 mg, 4.35 mmol) was dissolved in CH$_3$CN (30 mL), H$_2$O (4 mL), and MeOH (4 mL). Carbonic acid 4-nitro-phenyl ester 2,2,2-trifluoro-1,1-dimethyl-ethyl ester (1.91 g, 6.52 mmol) was added followed by DIPEA (1.89 mL, 10.9 mmol). The reaction was allowed to stir at room temperature for three days. The reaction was acidified and extracted with EtOAc (3×50 mL). The organic layer was mixed with saturated NaHCO$_3$ solution (100 mL) and the layers were separated. The aqueous layer was extracted with EtOAc (30 mL) and the organic was discarded. The aqueous layer was acidified with HCl (1N) and extracted with EtOAc (3×50 mL). The organic layer was washed with brine (30 mL), dried over Na$_2$SO$_4$, and concentrated to produce cyclopropyl-(2,2,2-trifluoro-1,1-dimethyl-ethoxycarbonylamino)-acetic acid (797.6 mg, 68%). LCMS found 267.7 [M–H]$^-$.

Compound 61 was prepared according to the method presented in the synthesis of Compound 60. Treatment of 2-[2-ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester occurred under the same conditions, adjusted for scale and with the exception of utilizing cyclopropyl-(2,2,2-trifluoro-1,1-dimethyl-ethoxycarbonylamino)-acetic acid, to provide Compound 61 as a white solid (98.0 mg, 69%): $^1$H NMR (300 MHz, CD$_3$OD): δ 9.19 (m, 1H), 8.11 (d, 1H), 7.84 (d, 1H), 7.23 (d, 1H), 7.17 (m, 1H), 7.09 (d, 1H), 5.79 (m, 1H), 4.55 (m, 1H), 4.37 (m, 1H), 3.99 (m, 1H), 3.89 (s, 3H), 3.72 (m, 1H), 2.53 (m, 1H), 2.29 (m, 1H), 1.42-1.62 (m, 10H), 1.16-1.29 (m, 7H), 0.93 (m, 3H), 0.38-0.62 (m, 6H). $^{19}$F NMR (300 MHz, CD$_3$OD): 6-78.14, –88.53. %). LCMS found 784.1 [M+H]$^+$.

Example 62

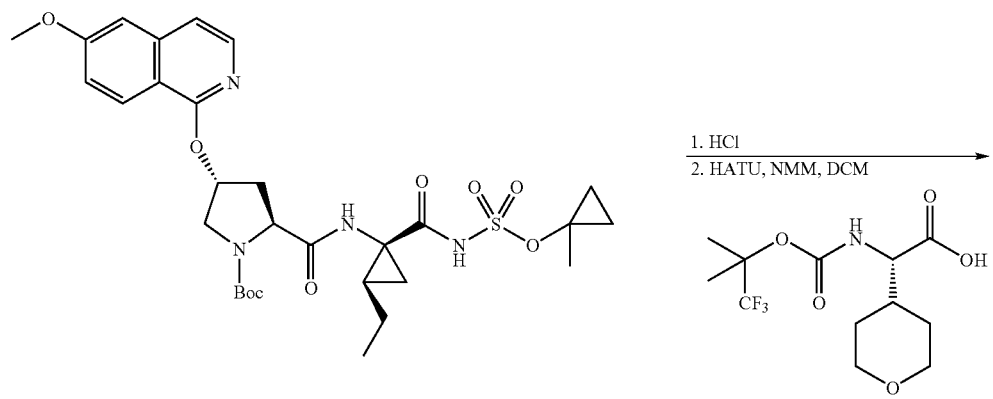

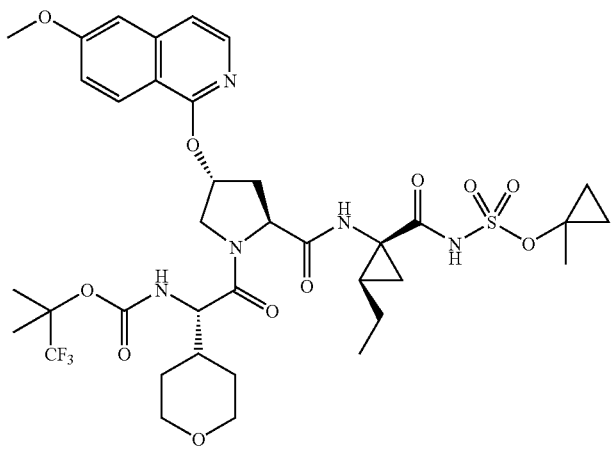

Compound 62

Compound 62 was prepared according to the method presented in the synthesis of Compound 60. Treatment of 2-[2-ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester occurred under the same conditions, adjusted for scale and with the exception of utilizing (tetrahydro-pyran-4-yl)-(2,2,2-trifluoro-1,1-dimethyl-ethoxycarbonylamino)-acetic acid, to provide Compound 62 as a white solid (79 mg, 70%). $^1$H NMR (300 MHz, CD$_3$OD): δ 9.34 (s, 1H), 8.13 (d, 1H), 7.90 (d, 1H), 7.31 (d, 1H), 7.23 (s, 1H), 7.16 (d, 1H), 5.85 (m, 1H), 4.60 (m, 2H), 4.08 (m, 2H), 3.94 (s, 3H), 3.90 (m, 1H), 3.42-3.32 (m, 3H), 2.60 (m, 1H), 2.29 (m, 1H), 2.05 (m, 1H), 1.70-1.59 (m, 10H), 1.42 (m, 3H), 1.33 (m, 4H), 1.16 (s, 6H), 0.98 (m, 3H), 0.71 (m, 2H). LCMS found 829 [M+H]$^+$.

Example 63

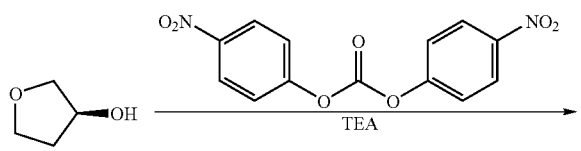

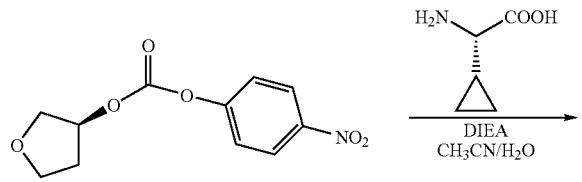

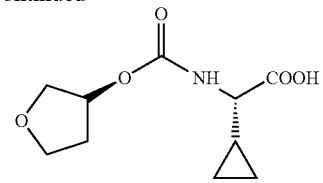

(S)-(+)-3-Hydroxy-tetrahydrofuran (0.88 mL, 13 mmol) was dissolved in DCM (5 mL) and H$_2$O (40 mL), carbonic acid bis-(4-nitro-phenyl) ester (5.8 g 19 mmol) and TEA (2.8 mL, 20 mmol) were added slowly. The reaction was allowed to stir at room temperature for 24 h. After concentrated, diluted with EtOAc, washed with brine and H$_2$O, dried over Na$_2$SO$_4$, the crude product was purified on silica (12 g, 25-75% EtOAc/hexanes) to give carbonic acid 4-nitro-phenyl ester tetrahydro-furan-3-yl ester as light yellow solid (2.3 g, 71%).

Cyclopropyl-[(tetrahydro-furan-3-yloxycarbonylamino)]-acetic acid was prepared according to the method presented in the synthesis of the intermediate 3,3-dimethyl-2-(tetrahydro-furan-3-yloxycarbonylamino)-butyric acid in Example 62. Treatment of amino-cyclopropyl-acetic acid with carbonic acid 4-nitro-phenyl ester tetrahydro-furan-3-yl ester occurred under the same conditions, adjusted for scale, to provide the desired cyclopropyl-[(tetrahydro-furan-3-yloxycarbonylamino)]-acetic acid.

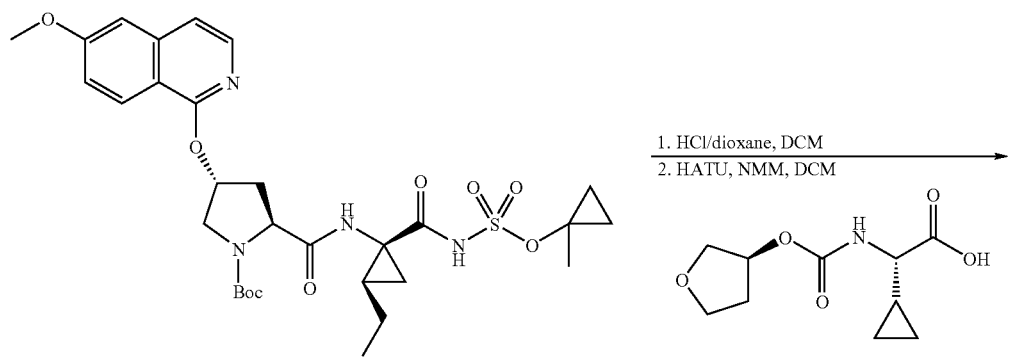

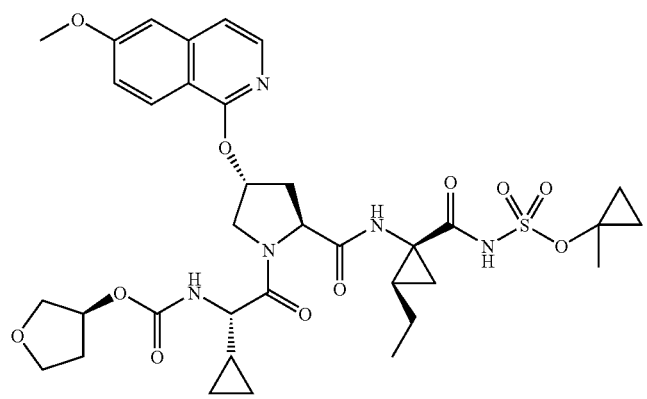

Compound 63

Compound 63 was prepared according to the method presented in the synthesis of Compound 60. Treatment of 2-[2-ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester occurred under the same conditions, adjusted for scale and with the exception of utilizing cyclopropyl-[(tetrahydro-furan-3-yloxycarbonylamino)]-acetic acid, to provide Compound 63 as a white solid (79 mg, 75%). $^1$H NMR (300 MHz, CD$_3$OD): δ 9.22 (s, 1H), 8.14 (d, 1H), 7.89 (d, 1H), 7.30 (d, 1H), 7.22 (s, 1H), 7.18 (d, 1H), 5.86 (m, 1H), 4.80 (m, 1H), 4.60 (m, 1H), 4.38 (m, 1H), 4.06 (m, 1H), 3.94 (s, 3H), 3.85 (m, 1H), 3.70 (m, 4H), 2.60 (m, 1H), 2.38 (m, 1H), 1.92 (m, 1H), 1.77-1.59 (m, 10H), 1.31-1.21 (m, 4H), 1.01-0.96 (m, 3H), 0.67 (s, 2H), 0.57-0.45 (m, 4H). LCMS found 745 [M+H]$^+$.

Example 64

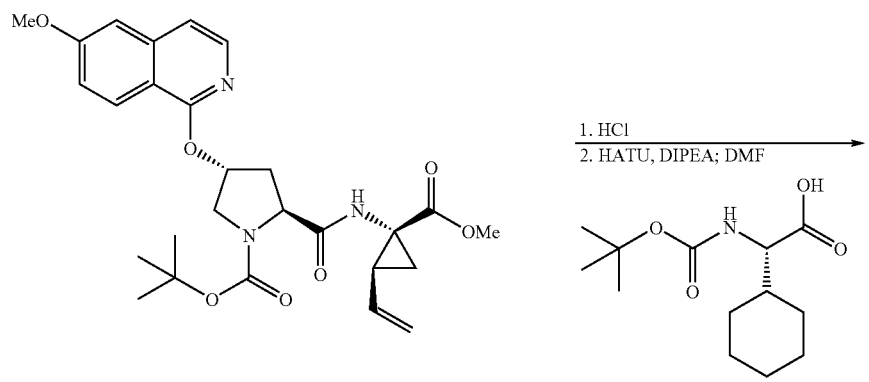

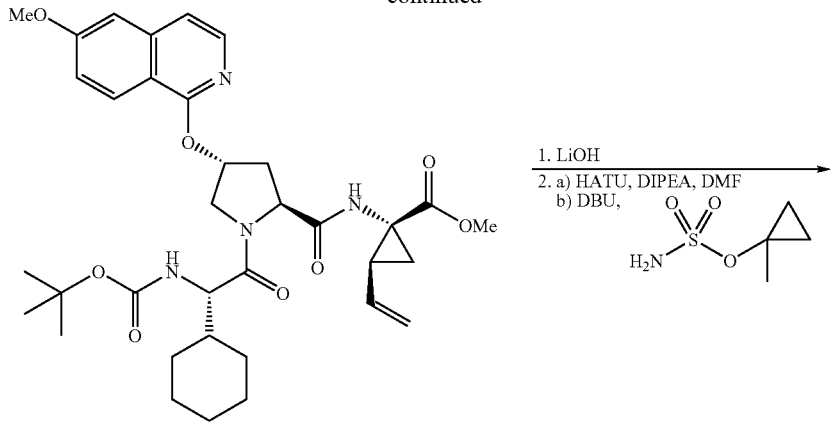

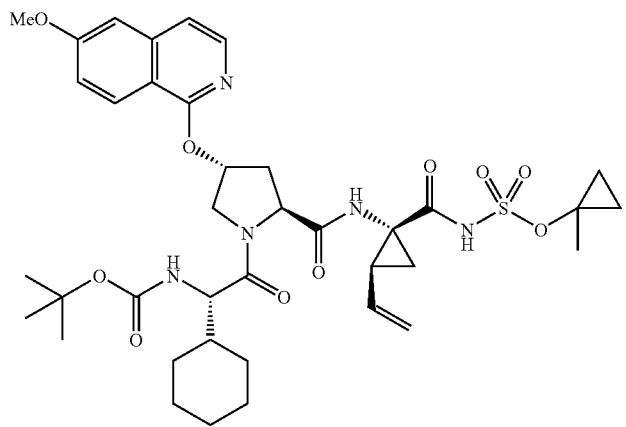

Compound 64

A solution of 2-(1-methoxycarbonyl-2-vinyl-cyclopropylcarbamoyl)-4-(6-methoxy-isoquinolin-1-yloxy)-pyrrolidine-1-carboxylic acid tert-butyl ester (prepared as described in Example 27; 0.50 g, 0.98 mmol) in THF (3 mL) was treated with 4M HCl in dioxanes (1.2 mL, 4.9 mmol) at rt. After 4 h, additional 2-(1-methoxycarbonyl-2-vinyl-cyclopropylcarbamoyl)-4-(6-methoxy-isoquinolin-1-yloxy)-pyrrolidine-1-carboxylic acid tert-butyl ester (0.30 g, 0.58 mmol) and 4M HCl/dioxane solution (5 mL) were added. After an additional 4 h, the solvent was removed in vacuo and the resulting foamy white solid was taken up in DMF (3 mL) and treated with tert-Butoxycarbonylamino-cyclohexyl-acetic acid (0.55 g, 2.1 mmol), HATU (1.0 g, 2.7 mmol) and DIPEA (0.78 mL, 4.5 mmol) at rt and allowed to age overnight. The reaction mixture was diluted in EtOAc and washed consecutively with saturated NaHCO₃, brine and then dried over anhydrous Na₂SO₄. After concentration in vacuo, the residue was purified via column chromatography on SiO₂ (0-75% EtOAc/hex) to produce 1.0 g (89% over two steps) of 1-{[1-(2-tert-butoxycarbonylamino-2-cyclohexyl-acetyl)-4-(6-methoxy-isoquinolin-1-yloxy)-pyrrolidine-2-carbonyl]-amino}-2-vinyl-cyclopropanecarboxylic acid methyl ester as an off-white solid. LCMS found 651.1 [M+H]$^+$.

Compound 64 was produced analogously to the conversion of 2-(1-methoxycarbonyl-2-vinyl-cyclopropylcarbamoyl)-4-(6-methoxy-isoquinolin-1-yloxy)-pyrrolidine-1-carboxylic acid tert-butyl ester to 4-(6-methoxy-isoquinolin-1-yloxy)-2-[1-(1-methyl-cyclopropoxysulfonylaminocarbonyl)-2-vinyl-cyclopropylcarbamoyl]-pyrrolidine-1-carboxylic acid tert-butyl ester detailed in Example 29 with appropriate adjustment of reagent quantities for scale. Utilizing this sequence, 1-{[1-(2-tert-butoxycarbonylamino-2-cyclohexyl-acetyl)-4-(6-methoxy-isoquinolin-1-yloxy)-pyrrolidine-2-carbonyl]-amino}-2-vinyl-cyclopropanecarboxylic acid methyl ester (0.80 g, 1.8 mmol) was converted to Compound 64. The crude product was taken up in MeOH (~320 mg/mL) and 1 mL of this solution was subjected to purification via preparatory HPLC to afford 0.11 g of Compound 64. The remainder of the material was purified via SiO₂ chromatography (0-5% MeOH/DCM) to afford an additional 0.596 g (57% total over two steps). ¹H-NMR (300 MHz, CD₃OD): δ 9.38 (s, 1H); 8.14 (d, 1H); 7.88 (d, 1H); 7.33 (d, 1H); 7.23 (s, 1H); 7.15 (d, 1H); 5.84 (s, 1H); 5.75 (dd, 1H); 5.31 (d, 1H); 5.13 (d, 1H); 4.53 (m, 2H); 4.05 (m, 2H); 3.94 (s, 3H); 2.60 (m, 1H); 2.35 (m, 1H); 2.24 (m, 1H); 1.92-1.60 (m, 6H); 1.67 (s, 3H); 1.41 (m, 1H); 1.38-0.91 (m, 8H); 1.21 (s, 9H); 0.67 (m, 2H). LCMS found 770.0 [M+H]$^+$.

Example 65

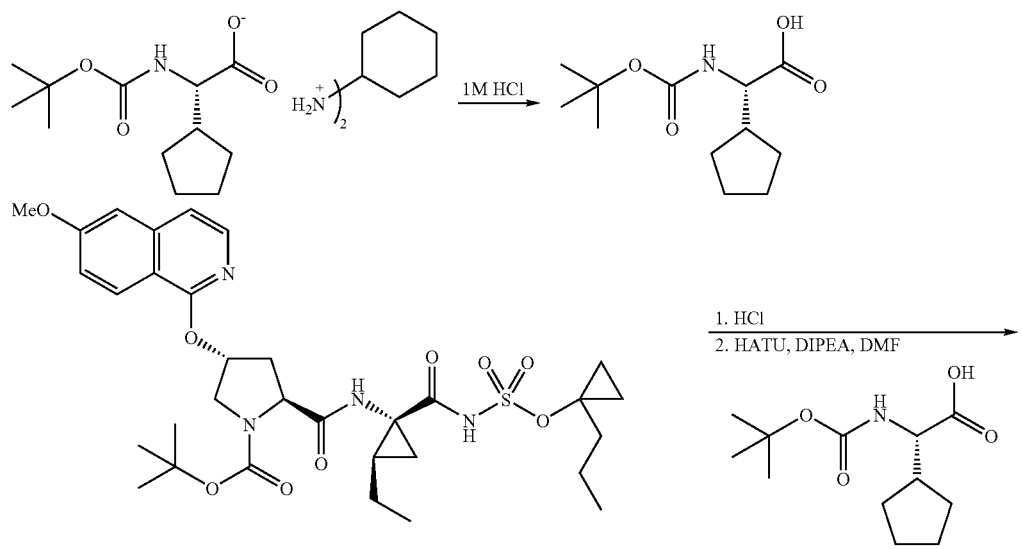

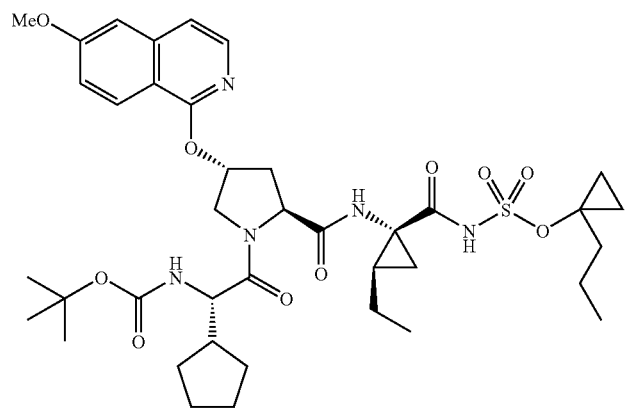

Compound 65 tert-Butoxycarbonylamino-cyclopentyl-acetate dicyclohexylammonium salt (2.85 g, 6.6 mmol; commercially available from Bachem) was dissolved in 1M HCl. Immediate EtOAc extractions were washed with brine and dried over anhydrous $Na_2SO_4$. Following concentration in vacuo, tert-Butoxycarbonylamino-cyclopentyl-acetic acid was isolated as a white foamy solid (1.6 g, quant) and was used without further purification. LCMS found 241.9 [M−H]⁻.

Compound 65 was prepared analogously to the method described for Compound 51. Following HCl/dioxane deprotection of 2-[2-ethyl-1-(1-propyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester, (2-ethyl-1-{[4-(6-methoxy-isoquinolin-1-yloxy)-pyrrolidine-2-carbonyl]-amino}-cyclopropanecarbonyl)-sulfamic acid 1-propyl-cyclopropyl ester (HCl salt, 0.50 g, 0.84 mmol) was immediately taken up in DMF (5 mL) and treated with tert-butoxycarbonylamino-cyclopentyl-acetic acid (0.243 g, 1.0 mmol), HATU (0.48 g, 1.3 mmol) and DIPEA (0.73 mL, 4.2 mmol). Following workup and purification by preparatory HPLC, 0.10 g (16%) of Compound 65 was isolated as a white powder. ¹H-NMR (300 MHz, CDCl₃): δ 10.22 (br s, 1H); 8.19 (d, 1H); 7.92 (d, 1H); 7.36 (d, 1H); 7.22 (m, 1H); 7.25-7.00 (m, 2H); 6.16, br s, 1H); 5.11 (m, 1H); 4.66 (br d, 1H); 4.53 (m, 1H); 4.17 (br d, 1H); 4.05-3.90 (br s, 1H); 3.96 (s, 3H); 2.65 (m, 2H); 2.23 (m, 1H); 1.94-1.43 (m, 11H); 1.43-1.10 (m, 6H); 1.12 (s, 9H); 0.90 (m, 7H); 0.61 (m, 3H). LCMS found 786.1 [M+H]⁺.

Example 66

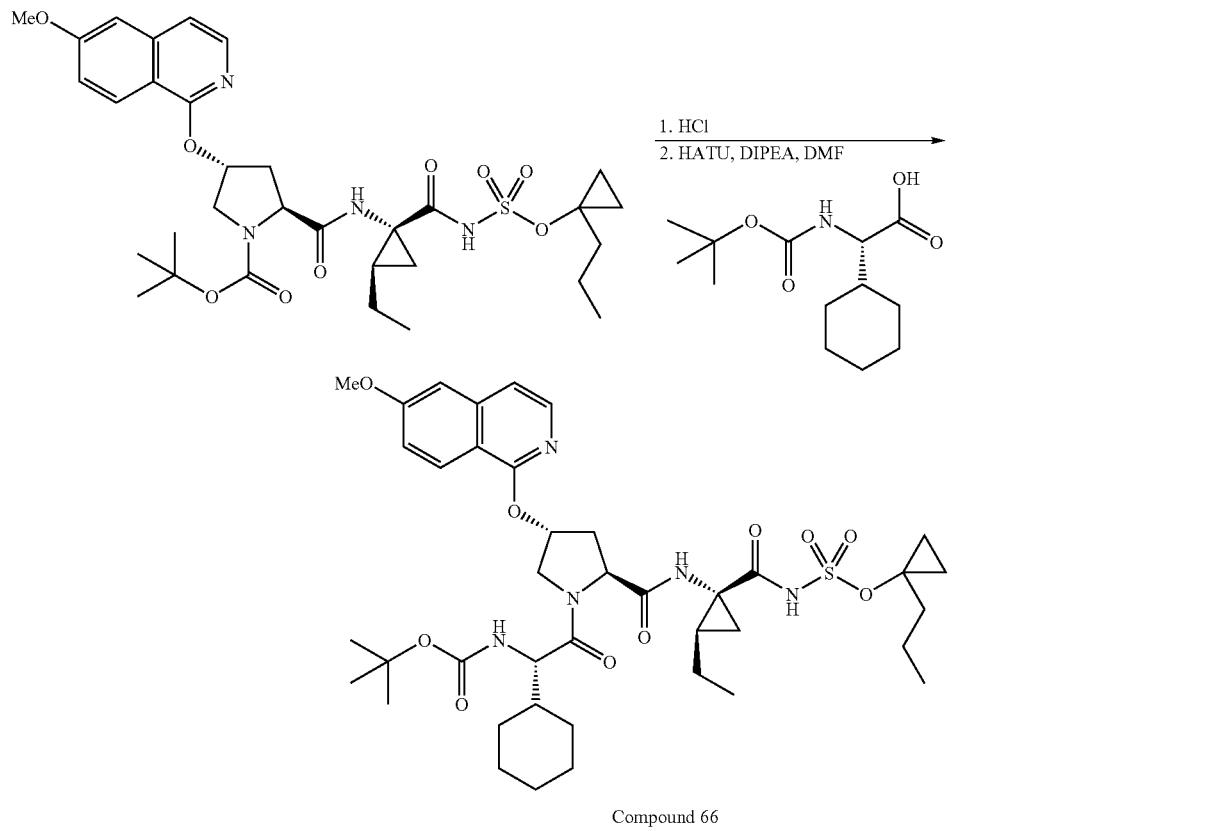

Compound 66

Compound 66 was prepared analogously to the method described for Compound 65, substituting tert-butoxycarbonylamino-cyclohexyl-acetic acid and with appropriate adjustments for scale. Compound 66 (3.5 mg, 0.2%) was recovered after preparatory HPLC purification as a white solid. $^1$H-NMR (300 MHz, CDCl$_3$): δ 10.39 (br s, 1H); 8.14 (d, 1H); 7.92 (d, 1H); 7.12 (d, 1H); 7.18 (m, 1H); 7.08 (m, 2H); 6.11 (s, 1H); 5.20 (m, 1H); 4.51 (m, 2H); 4.14 (m, 1H); 4.03 (m, 1H); 3.94 (s, 3H); 2.62 (m, 2H); 1.96-1.44 (m, 11H); 1.42-0.96 (m, 9H); 1.19 (s, 9H); 0.90 (m, 6H); 0.62 (m, 2H). LCMS found 800.5 [M]$^+$.

Example 67

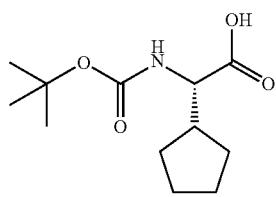

-continued

Compound 67

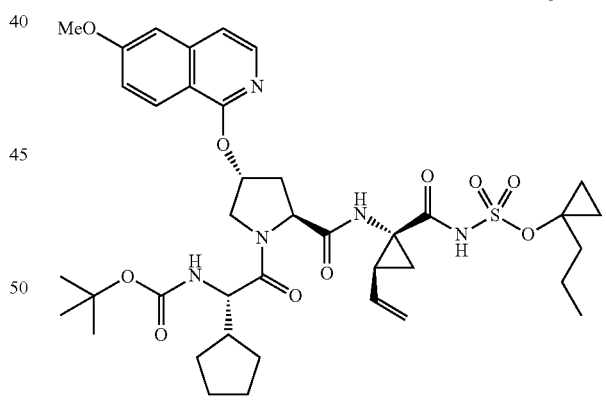

Compound 67 was prepared analogously to the method described for Compound 51. Treatment of (1-cyclopentyl-2-{4-(6-methoxy-isoquinolin-1-yloxy)-2-[1-(1-propyl-cyclopropoxysulfonylaminocarbonyl)-2-vinyl-cyclopropylcarbamoyl]-pyrrolidin-1-yl}-2-oxo-ethyl)-carbamic acid tert-butyl ester with tert-butoxycarbonylamino-cyclopentyl-acetic acid under the same conditions, adjusted for scale, following purification via preparatory HPLC provided 0.150 g (32% over three steps) of Compound 67. $^1$H-NMR (400 MHz, CD$_3$OD): δ 8.17 (d, 1H); 7.88 (d, 1H); 7.34 (d, 1H); 7.24 (s, 1H); 7.16 (m, 1H); 5.38 (br s, 1H); 5.74 (m, 1H); 5.31 (d, 1H); 5.13 (d, 1H); 4.68-4.51 (m, 2H); 4.05 (m, 2H); 3.94

(s, 3H); 2.62 (m, 1H); 2.36 (m, 2H); 2.24 (m, 1H); 1.87 (m, 2H); 1.76 (m, 2H); 1.57 (m, 6H); 1.46-1.08 (m, 6H); 1.18 (s, 9H); 0.96 (t, 3H); 0.68 (m, 2H). LCMS found 782.15 [M−H]⁻.

2.00-1.50 (m, 11H); 1.46-1.00 (m, 8H); 1.24 (s, 9H); 0.96 (t, 3H); 0.68 (m, 2H). LCMS found 798.5 [M+H]⁺.

Example 68

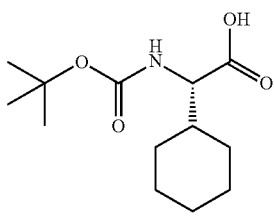

Compound 68

Example 69

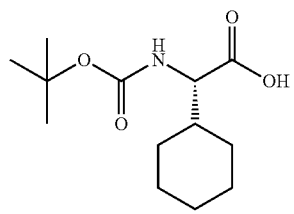

Compound 69

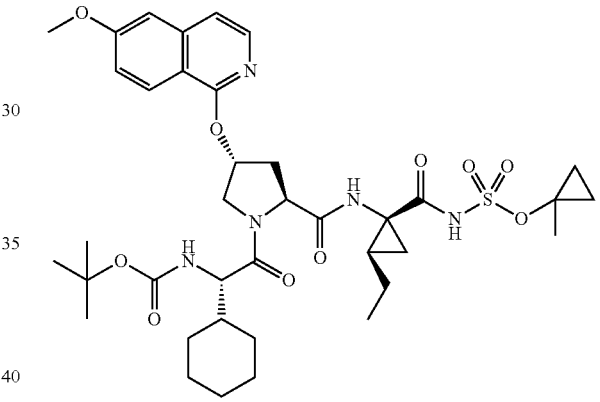

2-[2-Ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (100 mg, 0.15 mmol) was dissolved in DCM (0.4 mL) and HCl in dioxane (4N, 0.4 mL) was added. The reaction was allowed to stir at room temperature for 2 h before it was concentrated. The solid residue was dissolved in DCM (1 mL) and tert-butoxycarbonylamino-cyclohexyl-acetic acid (52 mg, 0.2 mmol) was added followed by HATU reagent (92 mg, 0.24 mmol) and n-methylmorpholine (0.053 mL, 0.48 mmol). The reaction was allowed to stir at room temperature for 16 h. The reaction was neutralized with HCl (1N) and partitioned between H₂O (3 mL) and DCM (5 mL). The aqueous layer was extracted with DCM (2×5 mL) and the combined organic layers were washed with brine and dried over Na₂SO₄ and concentrated. The crude residue was purified on silica (12 g, 50-100% EtOAc/hexanes), and then by reverse phase HPLC (25-100% CH₃CN/H₂O+0.1% TFA) to give Compound 69 as a white solid (55 mg, 45%). ¹H MNR (300 MHz, CD₃OD): δ 9.25 (s, 1H), δ 8.15 (d, 1H), δ 7.89 (d, 1H), δ 7.32 (d, 1H), δ 7.22 (s, 1H), δ 7.15 (d, 1H), δ 5.83 (m, 1H), δ 4.89 (m, 1H), δ 4.54 (m, 2H), δ 4.06 (m, 2H), δ 3.93 (m, 3H), δ 2.60 (m, 1H), δ 2.37 (m, 1H), δ1.87-1.53 (m, 13H), δ 1.32-1.10 (m, 15H), δ 0.97-0.69 (m, 7H). LCMS found 772 [M+H]⁺.

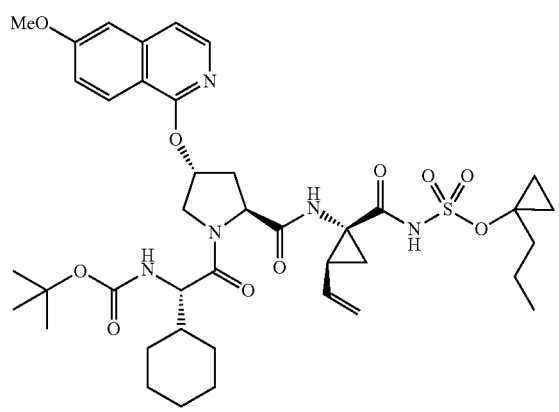

Compound 68 was prepared analogously to the method described for Compound 51. Treatment of (1-cyclopentyl-2-{4-(6-methoxy-isoquinolin-1-yloxy)-2-[1-(1-propyl-cyclopropoxysulfonylaminocarbonyl)-2-vinyl-cyclopropylcarbamoyl]-pyrrolidin-1-yl}-2-oxo-ethyl)-carbamic acid tert-butyl ester with tert-butoxycarbonylaminocyclohexylacetic acid under the same conditions, adjusted for scale, following purification via preparatory HPLC provided 0.200 g (58% over three steps) of Compound 68. ¹H-NMR (400 MHz, CD₃OD): δ 9.34 (s, 1H); 8.12 (d, 1H); 7.87 (d, 1H); 7.27 (d, 1H); 7.19 (s, 1H); 7.12 (d, 1H); 5.83 (m, 1H); 5.75 (m, 1H); 5.30 (d, 1H); 5.13 (d, 1H); 4.58-4.44 (m, 2H); 4.12-4.00 (m, 2H); 3.92 (s, 3H); 2.59 (m, 1H); 2.34 (m, 1H); 2.23 (m, 1H);

Example 70 and 71

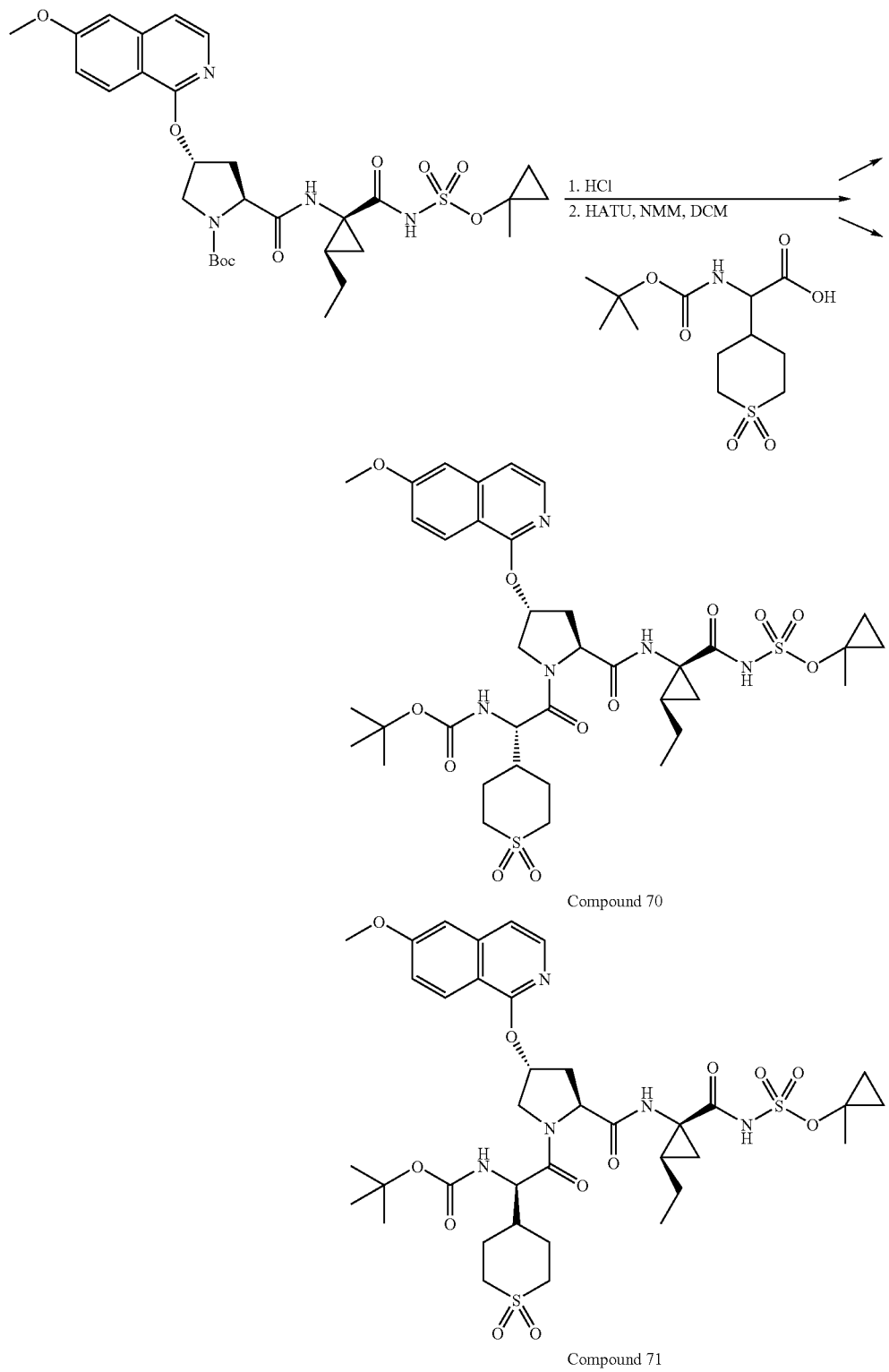

Compound 70

Compound 71

2-[2-Ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (50 mg, 0.0.08 mmol) was dissolved in DCM (0.2 mL) and HCl in dioxane (4N, 0.2 mL) was added. The reaction was allowed to stir at room temperature for 2.5 h before it was concentrated. The solid residue was dissolved in DCM (0.8 mL) and tert-Butoxycarbonylamino-(1,1-dioxo-hexahydro-1l6-thiopyran-4-yl)-acetic acid (31 mg, 0.1 mmol) was added followed by HATU reagent (46 mg, 0.2 mmol) and n-methylmorpholine (0.027 mL, 0.24 mmol). The reaction was allowed to stir at room temperature for 2 h. The reaction was neutralized with HCl (1N) and partitioned between H₂O (3 mL) and DCM (5 mL). The aqueous layer was extracted with DCM (2×5 mL) and the combined organic layers were washed with brine and dried over Na₂SO₄ and concentrated. The crude residue was purified by chiral HPLC (Chiralpak AS-H, Heptane:Ethanol 80:20) to give two compounds 70 and 71, both as white solids: ¹H MNR (300 MHz, CD₃OD) for Compound 70: δ 9.37 (s, 1H), δ 8.14 (d, 1H), δ 7.89 (d, 1H), δ 7.31 (d, 1H), δ 7.23 (s, 1H), δ 7.15 (m, 1H), δ 5.87 (m, 1H), δ 4.55 (m, 2H), δ 4.20 (m, 1H), δ 4.09 (m, 1H), δ 3.94 (s, 3H), δ 3.16-2.99 (m, 4H), δ 2.61 (m, 1H), δ 2.36 (m, 1H), δ 2.13 (m, 3H), δ1.86-1.55 (m, 10H), δ 1.36-1.10 (m, 13H), δ1.02-0.96 (m, 3H), δ0.72 (m, 2H).

¹H MNR (300 MHz, CD₃OD 3) for Compound 71: δ 9.15 (s, 1H), δ 8.06 (d, 1H), δ 7.94 (d, 1H), δ 7.32 (d, 1H), δ 7.25 (s, 1H), δ 7.21 (m, 1H), δ 5.86 (m, 1H), δ 4.65 (m, 1H), δ 4.35-4.03 (m, 3H), δ 3.95 (s, 3H), δ 2.68-2.25 (m, 5H), δ 2.06 (m, 1H), δ1.86-1.26 (m, 26H), δ1.01-0.96 (m, 3H), δ0.72 (m, 2H). LCMS-found 823 [M+H]⁺.

Example 72

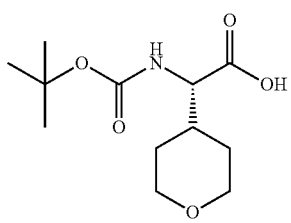

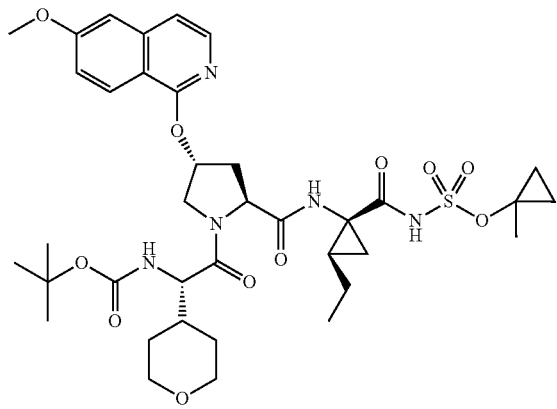

Compound 72

Compound 72 was prepared according to the method presented in the synthesis of Compound 69. Treatment of the 2-[2-ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (150 mg, 0.24 mmol) occurred under the same conditions, adjusted for scale and with the exception of utilizing tert-butoxycarbonylamino-(tetrahydro-pyran-4-yl)-acetic acid to provide Compound 72 as a white solid (128 mg), 1H MNR (300 MHz, CD₃OD): δ 9.30 (s, 1H), δ 8.13 (d, 1H), δ 7.89 (d, 1H), δ 7.30 (d, 1H), δ 7.22 (s, 1H), δ 7.14 (d, 1H), δ 5.85 (m, 1H), δ 4.56 (m, 2H), δ 4.11 (m, 2H), δ 3.94 (s, 3H), δ 3.88 (m, 2H), δ 3.40 (m, 2H), δ 2.61 (m, 1H), δ 2.37 (m, 1H), δ 2.15 (m, 1H), δ1.71-1.17 (m, 2H),), δ 0.98 (m, 3H), δ 0.70 (m, 2H). LCMS found 775 [M+H]⁺.

Example 73

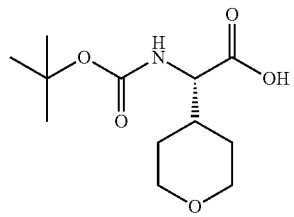

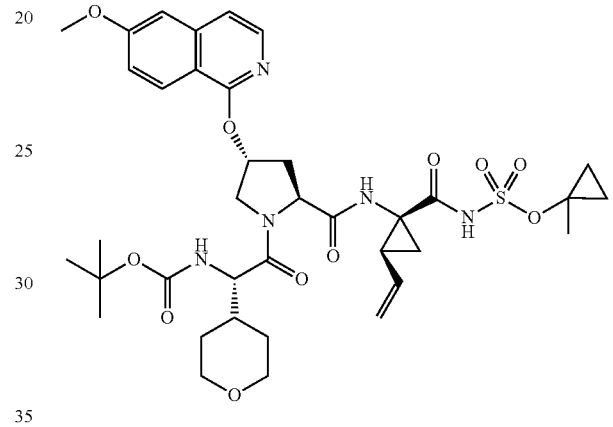

Compound 73

Compound 73 was prepared according to the method presented in the synthesis of Compound 69. Treatment of the 4-(6-methoxy-isoquinolin-1-yloxy)-2-[1-(1-methyl-cyclopropoxysulfonylaminocarbonyl)-2-vinyl-cyclopropylcarbamoyl]-pyrrolidine-1-carboxylic acid tert-butyl ester (158 mg, 0.25 mmol) occurred under the same conditions, adjusted for scale and with the exception of utilizing tert-butoxycarbonylamino-(tetrahydro-pyran-4-yl)-acetic acid to provide Compound 73 as a white solid (50 mg), 1H MNR (300 MHz, CD₃OD): δ 9.45 (s, 1H), δ 8.14 (d, 1H), δ 7.90 (d, 1H), δ 7.31 (d, 1H), δ 7.23 (s, 1H), δ 7.14 (d, 1H), δ 5.86 (m, 1H), δ 5.74 (m, 1H), 5.36 (d, 1H), 5.15 (d, 1H), δ 4.58 (m, 2H), δ 4.10 (m, 2H), δ 3.94 (s, 3H), δ 3.87 (m, 2H), δ 3.39 (m, 2H), δ 2.62 (m, 1H), δ 2.30 (m, 2H), δ 2.22 (m, 1H), δ 1.90 (m, 1H), δ1.68-1.13 (m, 2H), δ 0.69 (m, 2H). LCMS found 772 [M+H]⁺.

Example 74

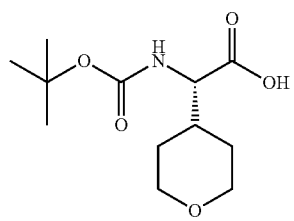

-continued

Compound 74

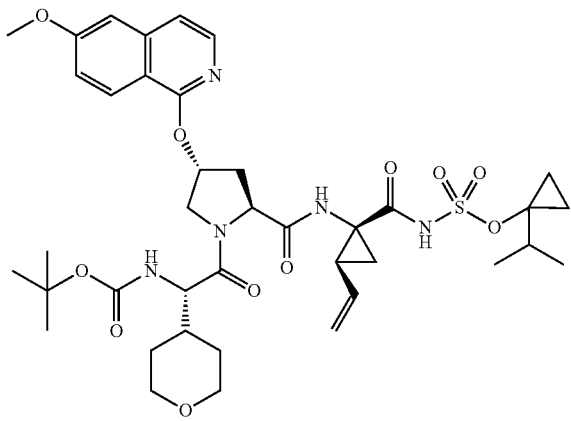

Compound 74 was prepared according to the method presented in the synthesis of Compound 69. Treatment of the 2-[1-(1-isopropyl-cyclopropoxysulfonylaminocarbonyl)-2-vinyl-cyclopropylcarbamoyl]-4-(6-methoxy-isoquinolin-1-yloxy)-pyrrolidine-1-carboxylic acid tert-butyl ester (160 mg, 0.25 mmol) occurred under the same conditions, adjusted for scale and with the exception of utilizing tert-butoxycarbonylamino-(tetrahydro-pyran-4-yl)-acetic acid to provide Compound 74 as a white solid (60 mg), 1H MNR (300 MHz, CD$_3$OD): δ 9.42 (s, 1H), δ 8.13 (d, 1H), δ 7.89 (d, 1H), δ 7.30 (d, 1H), δ 7.23 (s, 1H), δ 7.15 (d, 1H), δ 5.86 (m, 1H), δ 5.74 (m, 1H), LCMS found 801[M+H]$^+$.

Example 75

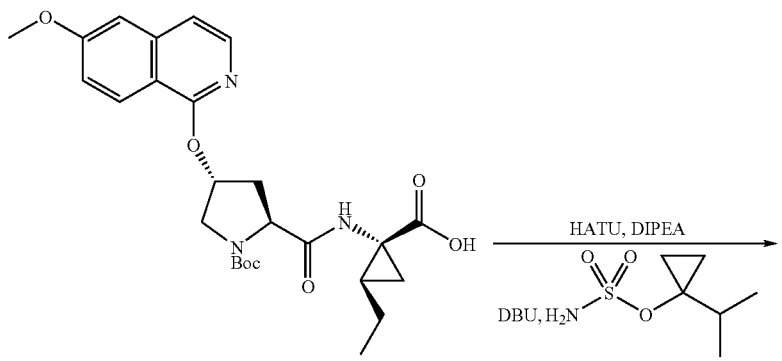

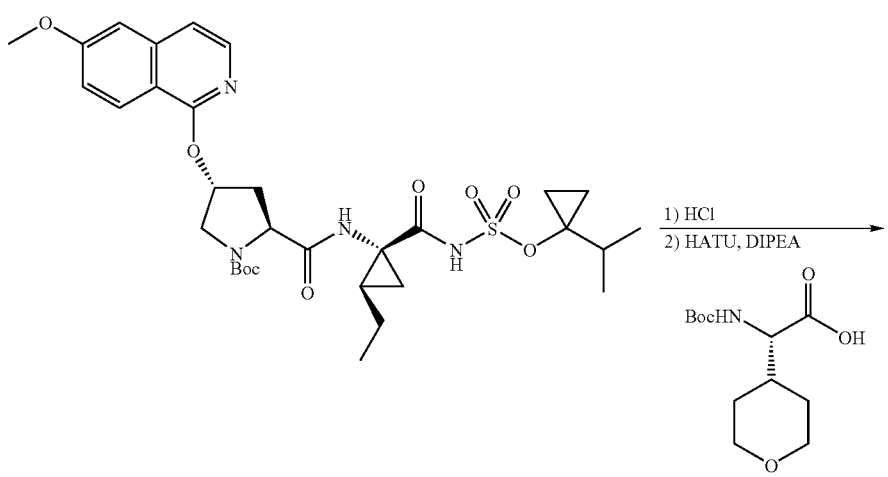

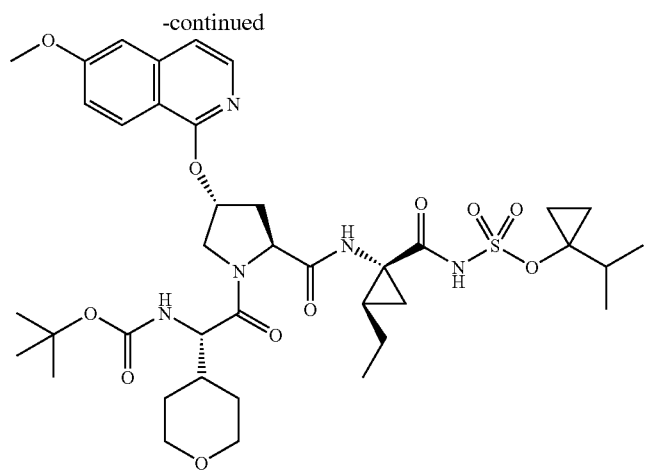

Compound 75

Compound 75 was prepared according to the method presented Example 42. Treatment of 2-(1-Carboxy-2-ethyl-cyclopropylcarbamoyl)-4-(6-methoxy-isoquinolin-1-yloxy)-pyrrolidine-1-carboxylic acid tert-butyl ester (744 mg, 1.49 mmol) under the same conditions adjusted for scale and with the exceptions of utilizing sulfamic acid 1-isopropyl-cyclopropyl ester (547 mg, 3.05 mmol) and tert-Butoxycarbonylamino-(tetrahydro-pyran-4-yl)-acetic acid (86 mg, 0.33 mmol) provided Compound 75 (146 mg, 47%): $^1$H NMR (d$_3$-MeOD, 300 MHz) δ 8.11 (d, 1H), 7.89 (d, 1H), 7.25 (d, 1H), 7.19 (s, 1H), 7.11 (d, 1H), 6.70 (d, 1H), 5.86 (s, 1H), 4.49-4.53 (m, 2H), 4.05-4.17 (m, 2H), 3.93 (s, 3H), 3.88 (m, 2H), 3.43 (m, 2H), 2.56 (m, 1H), 2.18 (m, 1H), 2.13-2.16 (m, 2H), 1.59-1.67 (m, 5H), 1.28-1.37 (m, 3H), 1.24 (s, 9H), 1.17 (m, 2H), 1.03 (d, 6H), 0.98 (m, 3H), 0.79 (m, 2H); LCMS found 801.98 [M+H]$^+$.

Example 76

Compound 76

Compound 76 was prepared by the same method as for Compound 60. Treatment of 2-[2-ethyl-1-(1-methyl-cyclo-propoxysulfonylaminocarbonyl)-cyclopropylcarbamoyl]-4-(6-methoxy-isoquinolin-1-yloxy)-pyrrolidine-1-carboxylic acid tert-butyl ester occurred under the same conditions, adjusted for scale and with the exception of utilizing tert-butoxycarbonylamino-cyclopentyl-acetic acid and subsequent purification produced Compound 76 as a white solid (63.7 mg, 76%) as a free base: 1H MNR (300 MHz, CD$_3$OD): δ 8.06 (d, 1H), δ 7.84 (d, 1H), δ 7.20 (d, 1H), δ 7.14 (s, 1H), δ 7.05 (d, 1H), δ 6.63 (m, 1H), δ 5.79 (m, 1H), δ 4.50 (m, 1H), δ 3.98-4.10 (m, 2H), 63.88 (s, 3H), 682.51 (m, 1H), 62.28 (m, 2H), δ1.40-1.73 (m, 13H), δ 1.08-1.27 (m, 14H), δ 0.94 (m, 3H), δ 0.62 (m, 2H). LCMS found 758.1 [M+H]$^+$.

Example 77

Compound 26 was (102 mg, 0.116 mmol) was stirred in 4N HCl in dioxanes (2 mL) for 40 min. Solvents were removed and the crude residue dried. The resultant residue was dissolved in THF (3 mL) to which carbonic acid 4-nitro-phenyl ester 2,2,2-trifluoro-1,1-dimethyl-ethyl ester (51 mg, 0.174 mmol) and TEA (97 μL, 0.348 mmol) were added sequentially. After 1.5 h at room temperature, the reaction was heated to 50° C. for 1 h. The reaction was purified by reverse phase HPLC to provide Compound 77 (42 mg, 39%): $^1$H NMR (CDCl$_3$, 300 MHz) 10.33 (s, 1H), 8.13 (d, 1H), 8.02 (d, 1H), 7.63 (d, 1H), 7.24 (d, 1H), 6.91 (bs, 1H), 5.94 (bs, 1H), 5.19 (d, 1H), 4.51 (d, 2H), 4.33 (m, 1H), 4.23 (d, 1H), 4.07 (s, 3H), 3.97 (m, 3H), 2.55 (m, 2H), 1.72 (m, 1H), 1.60 (m, 3H), 1.50 (m, 4H), 1.31 (s, 3H), 1.04 (m, 15H), 0.74 (m, 2H); LCMS found 820.1 [M+H]$^+$.

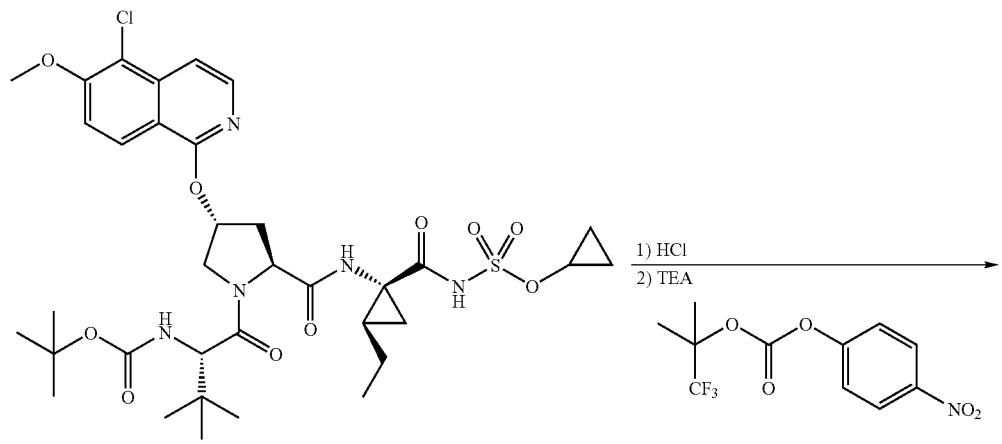

Compound 26

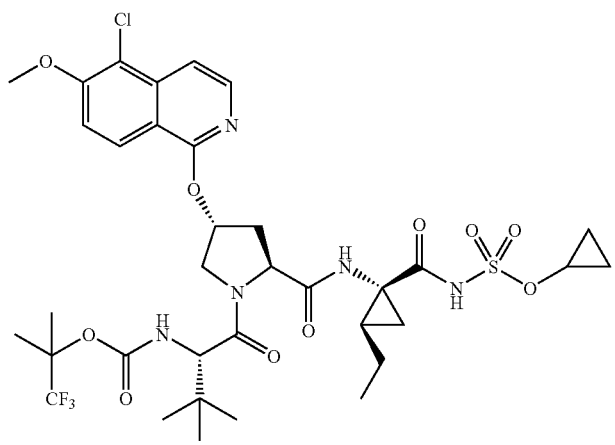

Compound 77

Example 78

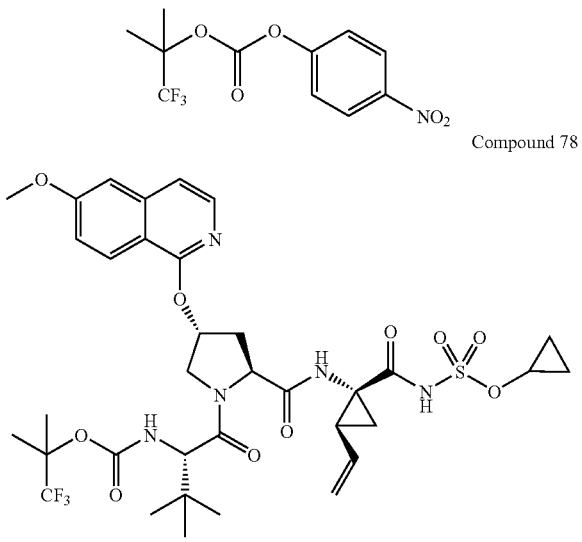

Compound 27 (175 mg, 0.24 mmol) was dissolved in CH$_2$Cl$_2$ (1 mL) and treated with 4N HCl in dioxanes (1 mL). After stirring for 45 min at room temperature, solvents were removed in vacuo. The resultant residue was dissolved in THF/H$_2$O (6:1, 1.2 mL) to which carbonic acid 4-nitro-phenyl ester 2,2,2-trifluoro-1,1-dimethyl-ethyl ester (77 mg, 0.26 mmol) and TEA (74 µL, 0.52 mmol) were added sequentially. After 24 h at room temperature, the reaction was heated to 40° C. for 12 h. The reaction was diluted with H$_2$O and acidified with 1N aqueous HCl. The solution was extracted with EtOAc, washed with saturated aqueous NaCl, and dried over sodium sulfate. After removal of solvent, the crude product was purified by reverse phase column chromatography on C18 (30-95% ACN/H$_2$O-1% TFA) to provide the desired product Compound 78 (135 mg, 72%): $^1$H NMR (CD$_3$OD, 300 MHz) δ 9.23 (s, 1H), 8.11 (d, 1H), 7.90 (d, 1H), 7.29 (d, 1H), 7.21 (s, 1H), 7.13 (d, 1H), 5.83 (m, 1H), 5.75 (m, 1H), 5.32 (d, 1H), 5.15 (d, 1H), 4.58 (m, 1H), 4.52 (m, 1H), 4.22 (m, 2H), 4.05 (m, 1H), 3.94 (s, 3H), 2.61 (m, 1H), 2.29 (m, 2H), 1.91 (m, 1H), 1.47 (m, 4H), 1.25 (s, 3H), 1.03 (s, 9H), 0.94 (m, 2H), 0.75 (m, 2H); LCMS found 784.1 [M+H]$^+$.

Example 79

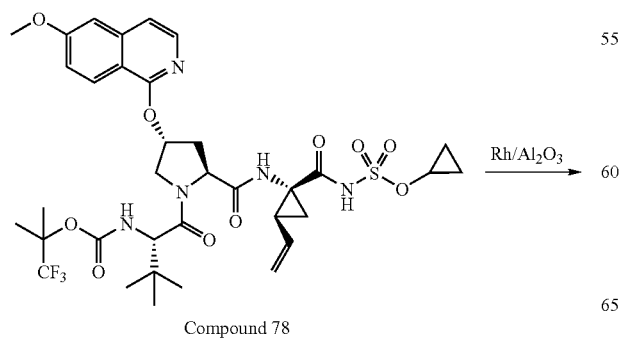

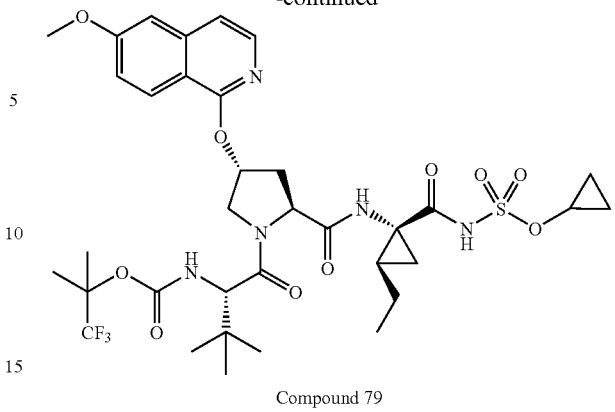

Compound 79 was prepared according to the method presented for the synthesis of Compound 28. Treatment of Compound 78 under the same conditions adjusted for scale provided the desired product (40 mg, 85%): $^1$H NMR (CD$_3$OD, 300 MHz) δ 9.11 (s, 1H), 8.11 (d, 1H), 7.89 (d, 1H), 7.28 (d, 1H), 7.21 (s, 1H), 7.12 (d, 1H), 5.81 (m, 1H), 4.59 (m, 1H), 4.47 (m, 1H), 4.22-4.30 (m, 2H), 4.04 (m, 1H), 3.93 (s, 3H), 2.62 (m, 1H), 2.30 (m, 1H), 1.50-1.66 (m, 4H), 1.47 (s, 3H), 1.25 (s, 3H), 1.15-1.25 (m, 3H), 1.03 (s, 9H), 0.96 (m, 2H), 0.77 (m, 2H); LCMS found 786.0 [M+H]$^+$.

Example 80

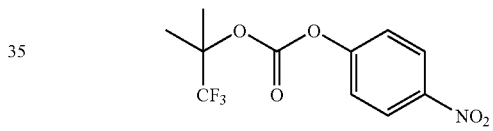

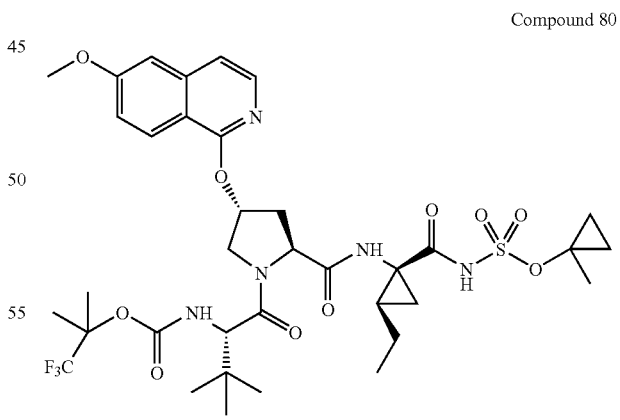

Compound 80 was prepared according to the method presented for the synthesis of Compound 77. Treatment of Compound 30 under the same conditions adjusted for scale provided the desired product (165 mg, 35%): $^1$H NMR (CD$_3$OD, 300 MHz) δ 9.15 (s, 1H), 8.13 (d, 1H), 7.90 (d, 1H), 7.33 (d, 1H), 7.24 (s, 1H), 7.15 (d, 1H), 5.84 (m, 1H), 4.58 (m, 1H), 4.48 (d, 1H), 4.22 (s, 1H), 4.06 (m, 1H), 3.95 (s, 3H), 2.63 (m, 1H), 2.29 (m, 1H), 1.68 (s, 3H), 1.43-1.62 (m, 7H), 1.20-1.34 (m, 6H), 1.05 (s, 9H), 0.98 (m, 3H), 0.69 (m, 2H); LCMS found 800.0 [M+H]⁺.

Example 81

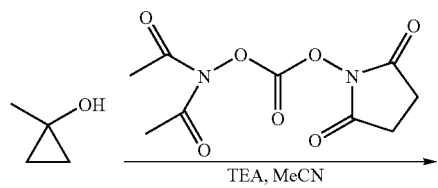

To a solution of 1-methyl-cyclopropanol (1.25 g, 17.4 mmol) in acetonitrile (44 mL) was added carbonic acid bis-(2,5-dioxo-pyrrolidin-1-yl) ester (6.68 g, 26.1 mmol) and triethylamine (7.3 mL, 52.3 mmol). The reaction was stirred at room temperature for 21 h. The reaction mixture was diluted with EtOAc and washed with saturated aqueous NaHCO₃ (2×) and brine. The organic layer was dried over MgSO₄ and concentrated. The crude product was purified by column chromatography on silica (15→50%→100% Hex/EtOAc) to provide carbonic acid 2,5-dioxo-pyrrolidin-1-yl ester 1-methyl-cyclopropyl ester (722.8 mg, 19%): ¹H NMR (CDCl₃, 300 MHz) δ 2.83 (s, 4H), 1.63 (s, 3H), 1.10 (m, 2H), 0.73 (m, 2H).

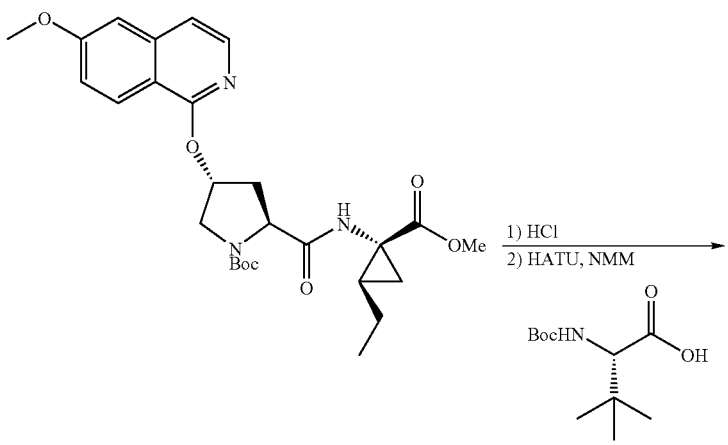

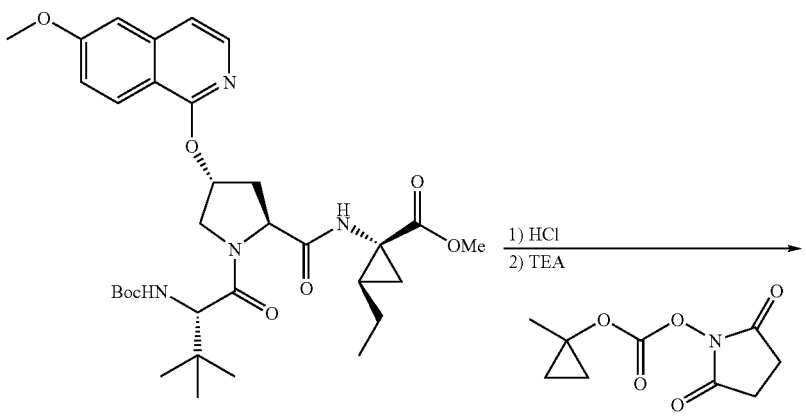

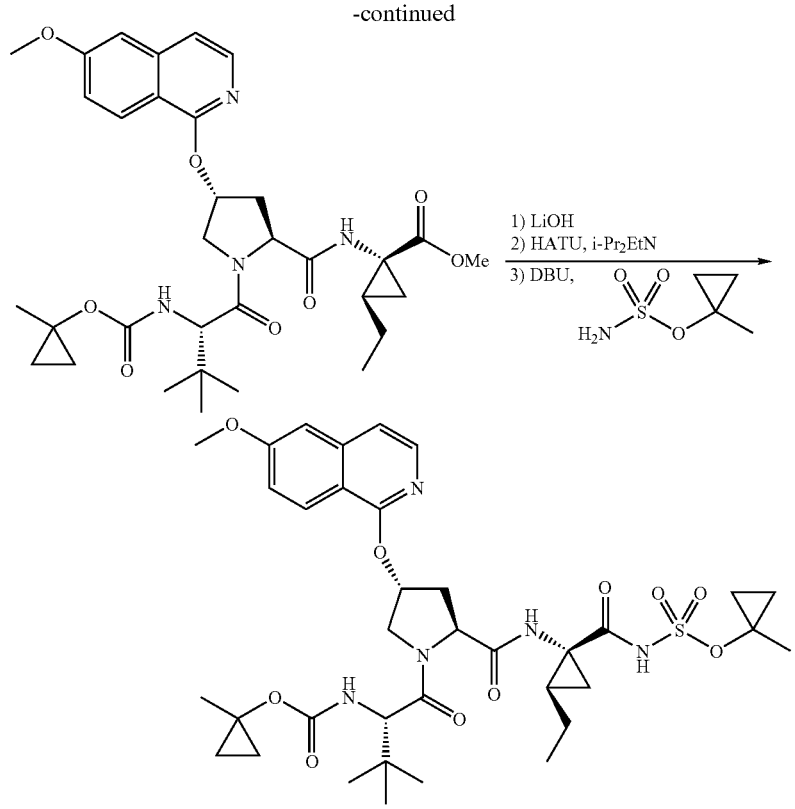

Compound 81

To a solution of 2-(2-ethyl-1-methoxycarbonyl-cyclopropylcarbamoyl)-4-(6-methoxy-isoquinolin-1-yloxy)-pyrrolidine-1-carboxylic acid tert-butyl ester (647 mg, 1.26 mmol) was added HCl (12.5 mL, 4M in dioxanes). The reaction was stirred at room temperature for 2 h and the concentrated in vacuo. The resulting amine was dissolved in DMF (6.3 mL), to which was added Boc-tert-Leu-OH (367 mg, 1.58 mmol), HATU (958 mg, 2.52 mmol) and NMM (0.7 mL, 6.29 mmol). The resulting solution was stirred at room temperature for 17 h, and then diluted with EtOAc. The subsequent slurry was washed with aqueous HCl (1N) and brine. The aqueous layers were extracted with EtOAc. The resulting organic layers were combined, dried ($Na_2SO_4$) and concentrated. The crude product was purified by column chromatography on silica (15→50→100% Hex/EtOAc) to provide the desired intermediate (0.332 g, 42%): LCMS found 626.96 ([M+H]$^+$.

To a solution of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid methyl ester (153 mg, 0.24 mmol) was added HCl (2.5 mL, 4M in dioxanes). The reaction was stirred at room temperature for 2 h and the concentrated in vacuo. The resulting amine was dissolved in THF (2.5 mL) and $H_2O$ (0.4 mL), to which was added triethylamine (0.08 mL, 0.57 mmol) and carbonic acid 2,5-dioxo-pyrrolidin-1-yl ester 1-methyl-cyclopropyl ester (66 mg, 0.31 mmol). The solution was stirred at room temperature for 90 min, and then diluted with EtOAc. The subsequent slurry was washed the $H_2O$ and Brine, and the aqueous layers were backextracted with EtOAc. The combined organic layers were dried over $Na_2SO_4$ and concentrated to provide the methyl ester which was taken directly into the next reaction.

To a solution of 1-{[1-[3,3-dimethyl-2-(1-methyl-cyclopropoxycarbonylamino)-butyryl]-4-(6-methoxy-isoquinolin-1-yloxy)-pyrrolidine-2-carbonyl]-amino}-2-ethyl-cyclopropanecarboxylic acid methyl ester in a THF:MeOH:$H_2O$ mixture (3:1:1, 2.5 mL) was added LiOH (57 mg, 1.36 mmol). The heterogenous mixture was stirred at room temperature for 72 h, and then diluted with EtOAc. The solution was washed with aqueous HCl (1N) and Brine, and the aqueous layers were backextracted with EtOAc. The combined organic layers were dried over $Na_2SO_4$ and concentrated. The crude acid was dissolved in DMF (1.2 mL), to which was added HATU (140 mg, 0.38 mmol) and DIPEA (0.06 mL, 0.38 mmol). The resulting yellow solution was sturred at room temperature for 45 min before sulfamic acid 1-methyl-cyclopropyl ester (81 mg, 0.54 mmol) and DBU (0.15 mL, 1.00 mmol) were added. The solution was stirred for an additional 24 h, and then diluted with EtOAc. The resulting slurry was washed with aqueous HCl (1N) and brine. The organic layer was then dried over $Na_2SO_4$ and concentrated. The crude product was purified by reverse phase HPLC (30→90% MeCN/$H_2O$/0.1% TFA) to provide Compound 81 (146 mg, 80%): $^1$H NMR ($d_3$-MeOD, 300 MHz) δ 9.11 (s, 1H), 8.15 (d, 1H), 7.90 (d, 1H), 7.33 (d, 1H), 7.23 (s, 1H), 7.17 (d, 1H), 5.85 (s, 1H), 4.55 (m, 1H), 4.45 (d, 1H), 4.29 (s, 1H), 4.13 (d, 1H), 3.94 (s, 3H), 2.61 (m, 1H), 2.30 (m, 1H), 1.68 (s, 3H), 1.58 (m, 5H), 1.32 (s, 3H), 1.25 (m, 5H), 1.05 (s, 9H), 0.98 (m, 2H), 0.68 (m, 4H), 0.50 (m, 2H); LCMS found 744.03 [M+H]$^+$.

Example 82

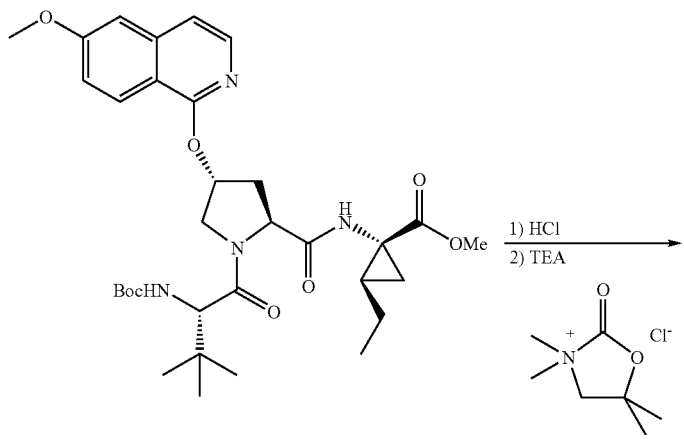

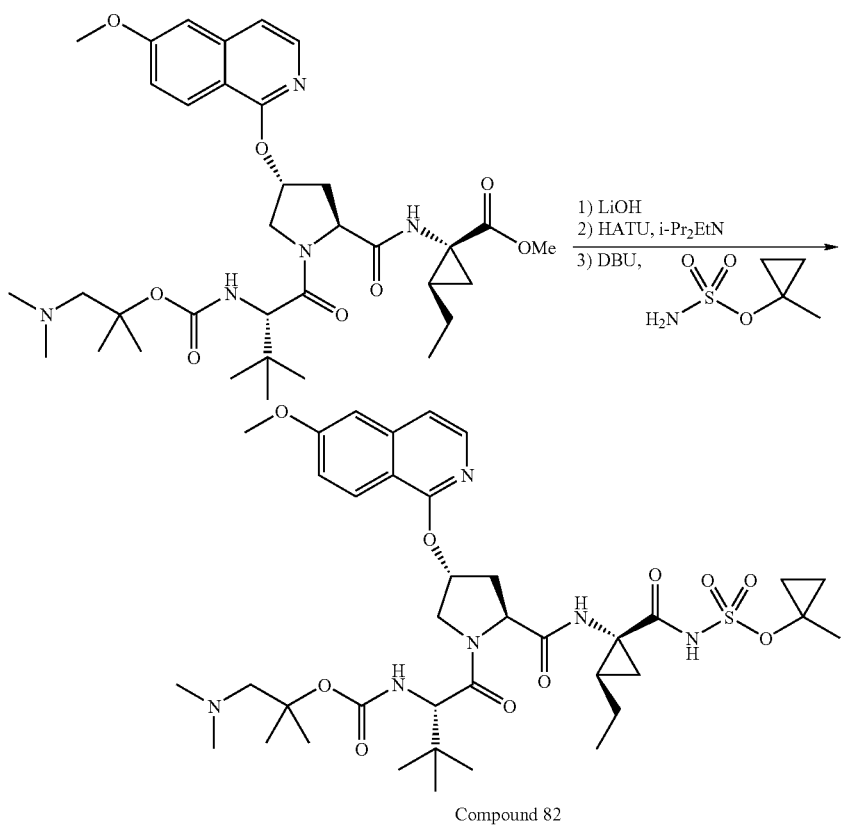

Compound 82

Compound 82 was prepared according to the method presented in the synthesis of Compound 81. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid methyl ester (178 mg, 0.25 mmol) occurred under the same conditions, adjusted for scale and with the exception of utilizing 3,3,5,5-tetramethyl-2-oxo-oxazolidin-3-ium chloride (*JOC* 1968, 33, 1367, 28 mg, 0.15 mmol) in a solution of THF (1.25 mL) and DMF (0.5 mL). Purification of the crude product was accomplished by reverse phase HPLC (30→90% MeCN/H$_2$O/0.1% TFA) to provide Compound 82 (31 mg, 32%): $^1$H NMR (d$_3$-MeOD, 300 MHz) δ 69.15 (s, 1H), 8.13 (d, 1H), 7.91 (d, 1H), 7.30 (d, 1H), 7.23 (s, 1H), 7.15 (d, 1H), 5.82 (s, 1H), 4.59 (m, 1H), 4.50 (d, 1H), 4.21 (s, 1H), 4.07 (d, 1H), 3.94 (s, 3H), 2.85 (s, 6H), 2.63 (m, 1H), 2.31 (m, 1H), 1.68 (s, 3H), 1.58 (m, 5H), 1.33 (s, 6H), 1.25 (m, 7H), 1.07 (s, 9H), 0.98 (m, 2H), 0.68 (m, 2H), LCMS found 789.37 [M+H]$^+$.

Example 83

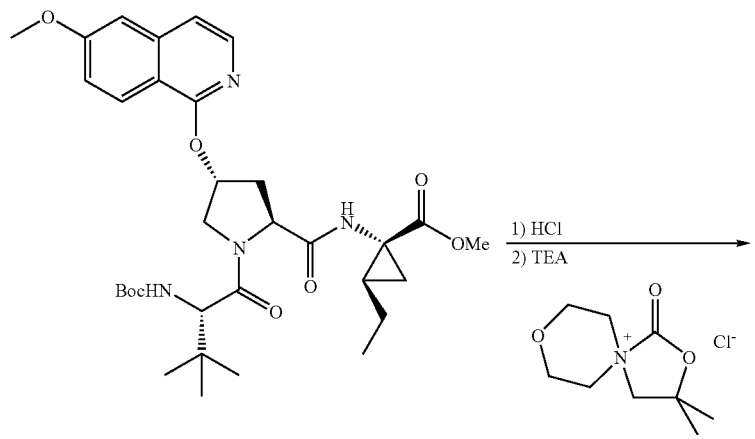

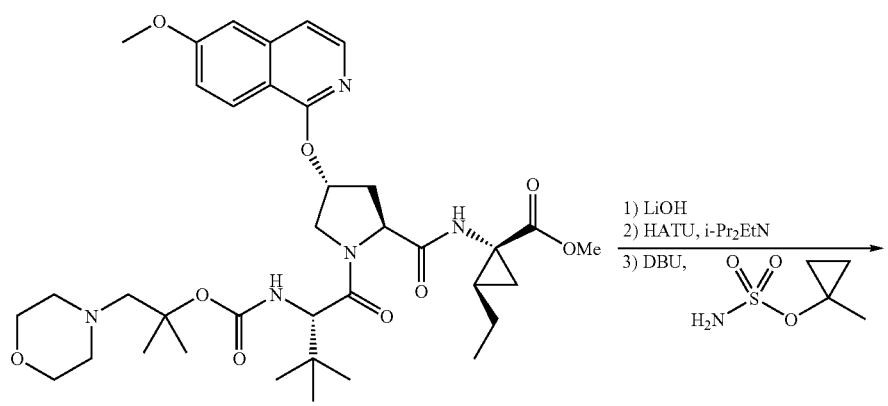

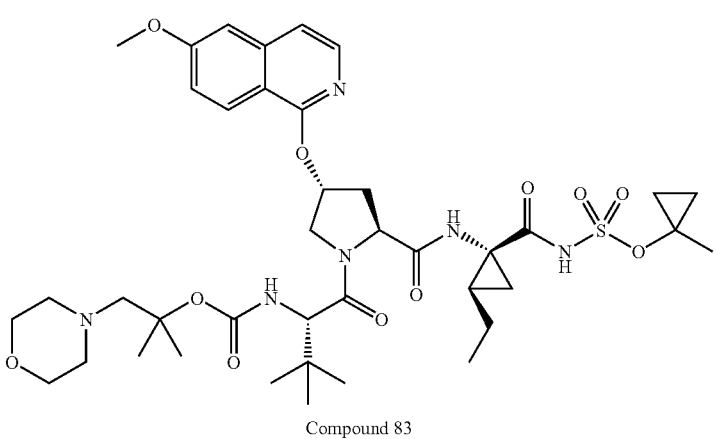
Compound 83

Compound 83 was prepared according to the method presented in the synthesis of Compound 81. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-ethyl-cyclopropanecarboxylic acid methyl ester (178 mg, 0.25 mmol) occurred under the same conditions, adjusted for scale and with the exception of utilizing 3,3-dimethyl-1-oxo-2,8-dioxa-5-azonia-spiro[4.5]decane chloride (32 mg, 0.15 mmol) in a solution of THF (1.25 mL) and DMF (0.5 mL). Purification of the crude product was accomplished by reverse phase HPLC (30→90% MeCN/H$_2$O/0.1% TFA) to provide Compound 83 (31 mg, 30%): $^1$H NMR (d$_3$-MeOD, 300 MHz) δ 9.18 (s, 1H), 8.17 (d, 1H), 7.92 (d, 1H), 7.31 (d, 1H), 7.23 (s, 1H), 7.18 (d, 1H), 5.82 (s, 1H), 4.60 (m, 1H), 4.51 (d, 1H), 4.21 (s, 1H), 4.08 (d, 1H), 3.94 (s, 3H), 3.85 (m, 4H), 3.42 (m, 4H), 2.62 (m, 1H), 2.32 (m, 1H), 1.71 (s, 3H), 1.58 (m, 5H), 1.33 (s, 6H), 1.25 (m, 5H), 1.08 (s, 9H), 1.01 (m, 2H), 0.70 (m, 2H); LCMS found 832.18 [M+H]$^+$.

Example 84

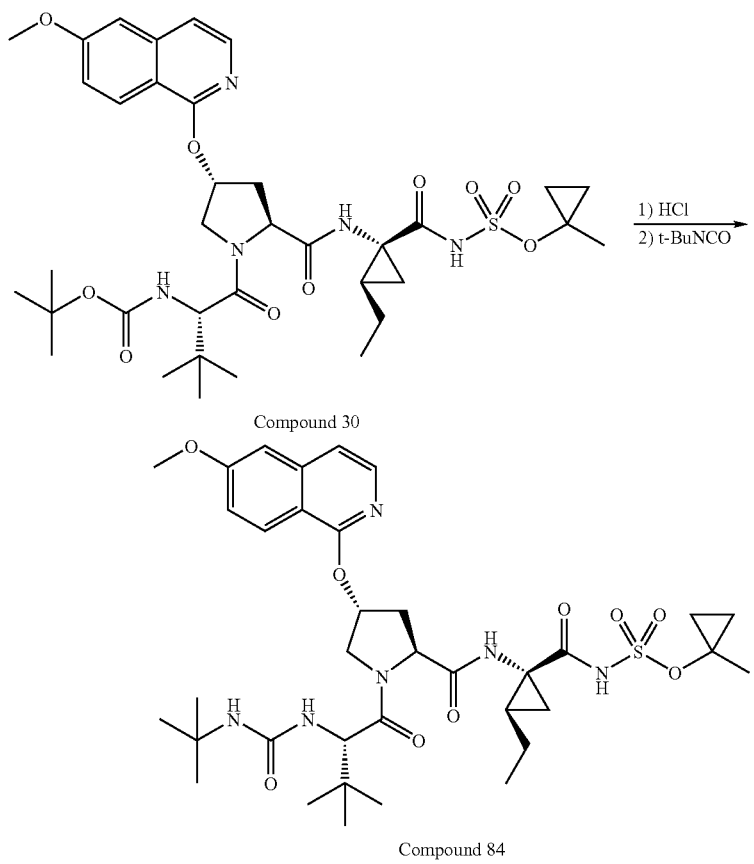

Compound 30

Compound 84

To a solution of Compound 30 (214 mg, 0.28 mmol) was added HCl (3.0 mL, 4M in dioxanes). The reaction was stirred at room temperature for 1.5 h and the concentrated in vacuo. A portion of the resulting amine (52 mg) was dissolved in CH$_2$Cl$_2$ (0.75 mL, to which was added triethylamine (0.05 mL, 0.36 mmol) and tert-butyl isocyanate-(0.025 mL, 0.21 mmol). The solution was stirred at room temperature for 90 min, and concentrated in vacuo. The crude product was purified by reverse phase HPLC (30→90% MeCN/H$_2$O/0.1% TFA) to provide Compound 84 (31 mg, 54%): $^1$H NMR (d$_3$-MeOD, 300 MHz) δ 9.05 (s, 11H), 8.15 (d, 1H), 7.88 (d, 1H), 7.29 (d, 1H), 7.21 (s, 1H), 7.13 (d, 1H), 5.84 (s, 1H), 4.52 (m, 2H), 4.35 (s, 1H), 4.09 (d, 1H), 3.93 (s, 3H), 2.61 (m, 1H), 2.24 (m, 1H), 1.68 (s, 3H), 1.58 (m, 5H), 1.28 (m, 3H), 1.19 (s, 9H), 1.05 (s, 9H), 0.98 (m, 4H), 0.67 (m, 2H); LCMS found 744.93 [M+H]$^+$.

Example 85

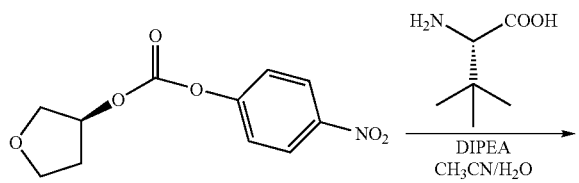

-continued

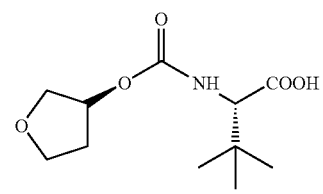

2-Amino-3,3-dimethyl-butyric acid (551 mg, 4.2 mmol) was dissolved in CH$_3$CN (15 mL), H$_2$O (3 mL) and MeOH (3 mL). Carbonic acid 4-nitro-phenyl ester tetrahydro-furan-3-yl ester (1.6 g, 6.3 mmol) and DIEA (1.46 mL, 8.4 mmol) were added. This reaction mixture was allowed to stir at room temperature for 16 h. After concentrated, diluted with EtOAc, washed with brine and H$_2$O, dried over Na$_2$SO$_4$, the crude product was purified on silica (12 g, 25-75% EtOAc/hexanes) to give intermediate 3,3-dimethyl-2-(tetrahydro-furan-3-yloxycarbonylamino)-butyric acid as a white solid (670 mg, 65%).

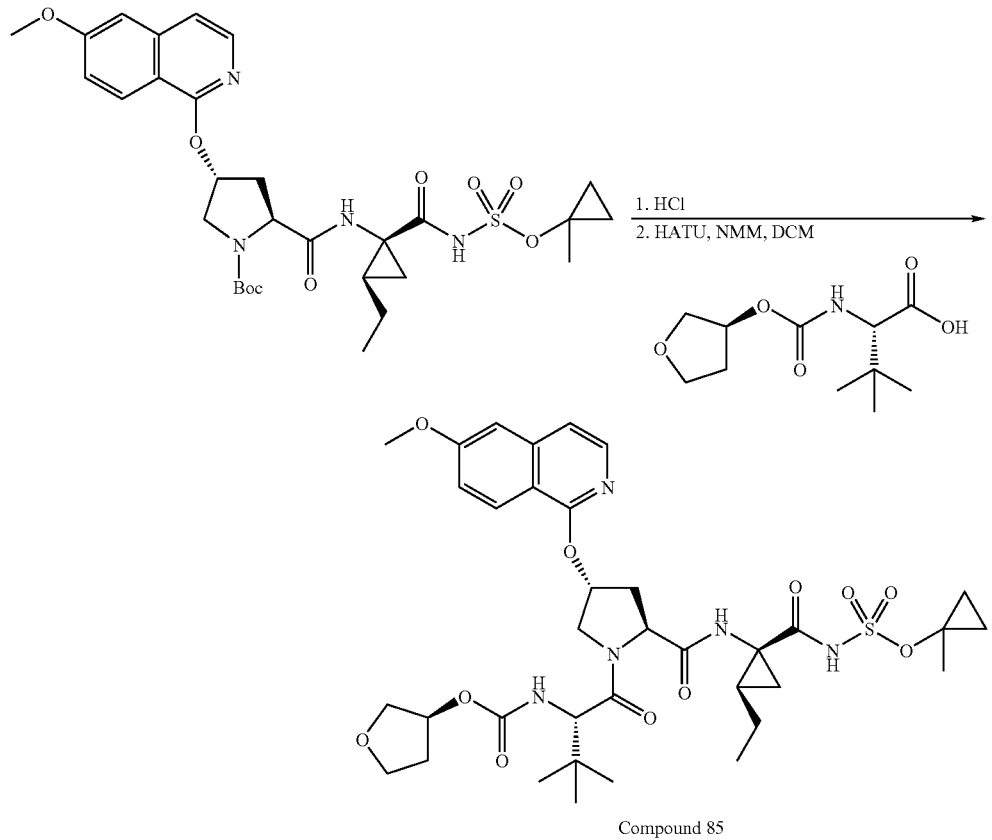

Compound 85

Compound 85 was prepared according to the method presented in the synthesis of Compound 63. Treatment of 2-[2-ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tent-butyl ester occurred under the same conditions, adjusted for scale and with the exception of utilizing 3,3-dimethyl-2-(tetrahydrofuran-3-yloxycarbonylamino)-butyric acid, to provide Compound 85 as a white solid (84 mg, 78%). $^1$H NMR (300 MHz, CD$_3$OD): δ 9.12 (s, 1H), 8.10 (d, 1H), 7.90 (d, 1H), 7.30 (d, 1H), 7.23 (s, 1H), 7.16 (d, 1H), 5.84 (m, 1H), 4.73 (m, 1H), 4.58 (m, 1H), 4.44-4.05 (m, 3H), 3.94 (s, 3H), 3.74-3.62 (m, 4H), 3.70 (m, 4H), 2.60 (m, 1H), 2.29 (m, 1H), 1.86 (m, 1H), 1.68 (s, 3H), 1.63-1.55 (m, 2H), 1.35-1.21 (m, 4H), 1.04 (s, 9H), 0.99 (m, 3H), 0.68 (m, 2H). LCMS found 761 [M+H]$^+$.

Example 86

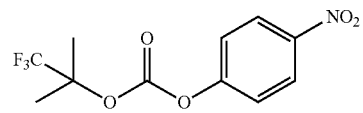

-continued

Compound 86

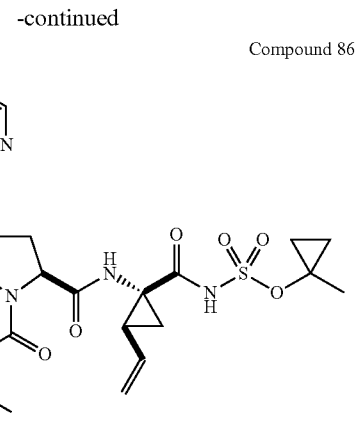

Compound 86 was prepared according to the methods described in Example 84. Treatment of Compound 29 (200 mg, 0.27 mmol) under the same conditions adjusted for scale and with the exception of using carbonic acid 4-nitro-phenyl ester 2,2,2-trifluoro-1,1-dimethyl-ethyl ester (157 mg, 0.54 mmol, 2 equiv.) and triethylamine (0.19 mL, 1.34 mmol, 5 equiv.) provided Compound 86 (102 mg, 51%): $^1$H NMR (d$_3$-MeOD, 300 MHz) δ 8.11 (d, 1H), 7.92 (s, 1H), 7.09-7.28 (m, 3H), 5.84 (s, 1H), 5.33 (d, 1H), 5.18 (d, 1H) 4.43-4.65 (m, 2H), 4.22 (s, 1H), 4.07 (d, 1H), 3.93 (s, 3H), 2.57-2.70 (m, 1H), 2.21-2.38 (m, 2H) 1.91 (d, 1H), 1.68 (s, 3H), 1.44 (s, 4H), 1.22 (s, 9H), 1.07 (s, 6H), 0.68 (s, 2H); LCMS found 798.00 [M+H]+.

Example 87

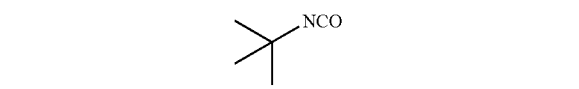

Compound 87

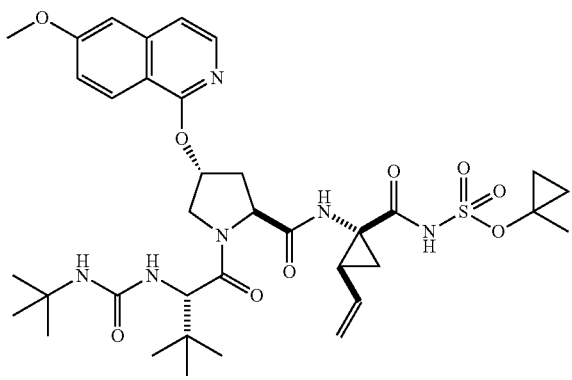

Compound 87 was prepared according to the methods described in Example 84. Treatment of Compound 29 (150 mg, 0.20 mmol) under the same conditions adjusted for scale and with the exception of using tert-butyl isocyanate (0.07 mL, 0.60 mmol, 3 equiv.) and triethylamine (0.14 mL, 1.0 mmol, 5 equiv.) provided Compound 87 (80 mg, 54%): $^1$H NMR (d$_3$-MeOD, 300 MHz) ☐ 8.17 (d, 1H), 7.86 (s, 1H), 7.05-7.29 (m, 3H), 5.87 (s, 1H), 5.31 (d, 1H), 5.12 (d, 1H), 4.41-4.57 (m, 2H), 4.37 (s, 1H), 4.10 (d, 1H), 3.92 (s, 3H), 2.51-2.67 (m, 1H), 2.16-2.33 (m, 1H), 1.81-1.91 (m, 1H), 1.69 (s, 4H), 1.38-1.50 (m, 1H), 1.19 (s, 11H), 1.03 (s, 9H), 0.67 (s, 2H); LCMS found 742.95 [M+H]+.

Example 88

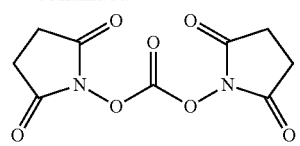

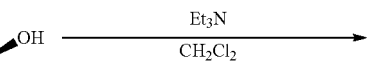

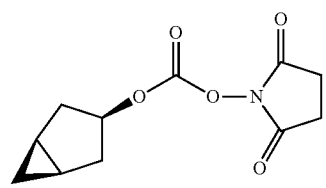

To a dry, argon purged three-neck round bottom flask (1000 mL) were added anhydrous dichloromethane (100 mL) and Et$_2$Zn (28 mL, 273 mmol) at 0° C. (CAUTION: Source of argon can not be from needle. Use appropriate glass adapter only. A second bubbler can also be attached to the flask to prevent excessive pressure build up.) Cyclopenten-3-ol (10.0 mL, 119 mmol) was then added dropwise (large quantity of ethane gas was produced) to the flask and the reaction mixture was allowed to stir until the evolution of gas had ceased. Diiodomethane (22 mL, 242 mmol) was then added dropwise over a period of 30 min. The reaction was allowed to warm to room temperature and continued to stir overnight under a positive flow of argon, at which point TLC analysis had indicated complete disappearance of the starting alcohol. The reaction was then diluted with CH$_2$Cl$_2$ and quenched with 2M HCl (white precipitate should be completely dissolved). The biphasic mixture was poured into a separatory funnel and the organic layer was collected. The solvent was removed under reduced pressure until 100 mL of material remained.

Anhydrous dichloromethane (525 mL) was added to the flask followed by the dropwise addition of triethylamine (34 mL, 245 mmol). The reaction continued to stir at room temperature under a positive flow of nitrogen at which point, disuccinimidylcarbonate (40.7 g, 159 mmol) was added to the flask portion wise. The reaction was allowed to stir until TLC analysis indicated complete disappearance of the starting material (2-3 days). Reaction rate can be accelerated by increasing the reaction temperature to 45° C. Upon completion, the reaction mixture was quenched with 1M HCl (200 mL) and washed with H$_2$O (200 mL). The desired material was extracted using CH$_2$Cl$_2$ and the combined organic layers were dried using anhydrous MgSO$_4$ and passed through a silica plug. The solvent was removed under reduced pressure and the crude material was purified using flash chromatography (1:1 Hex/EtOAc) to provide carbonic acid bicyclo[3.1.0]hex-3-yl ester 2,5-dioxo-pyrrolidin-1-yl ester (22 g, 75%): $^1$H NMR (300 MHz, CDCl$_3$): δ 5.24 (t, 1H), 3.82 (s, 4H), 2.24 (m, 2H), 2.03 (d, 2H), 1.38 (m, 2H), 0.48 (m, 1H), 0.40 (m, 1H).

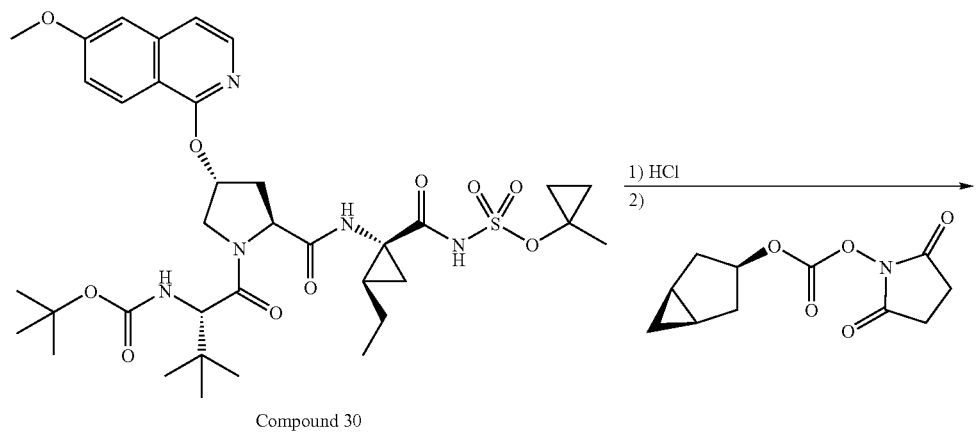

Compound 30

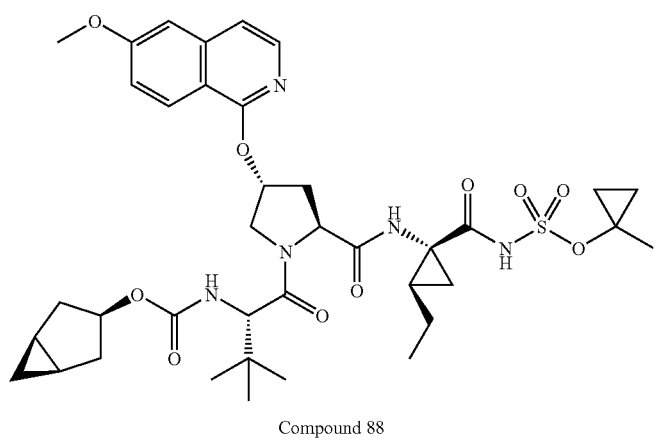

Compound 88

Compound 88 was prepared according to the methods described in Example 84. Treatment of Compound 30 (53 mg, 0.072 mmol) under the same conditions adjusted for scale and with the exception of using carbonic acid bicyclo[3.1.0]hex-3-yl ester 2,5-dioxo-pyrrolidin-1-yl ester (35 mg, 0.15 mmol, 2 equiv.) provided Compound 88 (48 mg, 87%): $^1$H NMR (CD$_3$OD, 300 MHz) ☐ 9.11 (s, 1H), 8.14 (d, 1H), 7.89 (d, 1H), 7.36 (d, 1H), 7.27 (s, 1H), 7.20 (dd, 1H), 5.83 (m, 1H), 4.67 (m, 1H), 4.57 (m, 1H), 4.46 (d, 1H), 4.25 (s, 1H), 4.07 (m, 1H), 3.96 (s, 3H), 2.62 (m, 1H), 2.31 (m, 1H), 1.90 (m, 1H), 1.68 (s, 3H), 1.47-1.59 (m, 6H), 1.20-1.35 (m, 6H), 1.03 (s, 9H), 0.97 (m, 3H), 0.68 (m, 2H), 0.38 (m, 2H); LCMS found 770.03 [M+H]$^+$.

Example 89

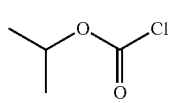

-continued

Compound 89

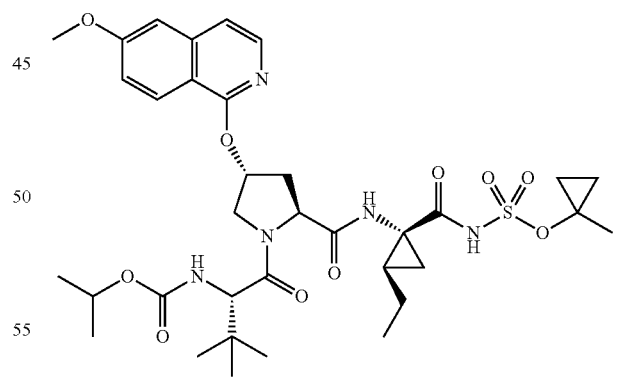

Compound 89 was prepared according to the methods described in Example 84. Treatment of Compound 30 (75 mg, 0.10 mmol) under the same conditions adjusted for scale and with the exception of using isopropylchloroformate (1 M in toluene, 0.2 mL, 0.20 mmol, 2 equiv.) provided Compound 89 (51 mg, 69%): $^1$H NMR (CD$_3$OD, 300 MHz) δ 9.11 (s, 1H), 8.12 (d, 1H), 7.89 (d, 1H), 7.30 (d, 1H), 7.22 (s, 1H), 7.14 (d, 1H), 5.84 (m, 1H), 4.54 (m, 2H), 4.44 (d, 1H), 4.29 (s, 1H), 4.07 (m, 1H), 3.94 (s, 3H), 2.95 (m, 1H), 2.28 (m, 1H), 1.68

(s, 3H), 1.54-1.68 (m, 5H), 1.13-1.35 (m, 8H), 1.05 (s, 9H), 0.98 (m, 3H), 0.66 (m, 2H); LCMS found 732.01 [M+H]⁺.

Example 90

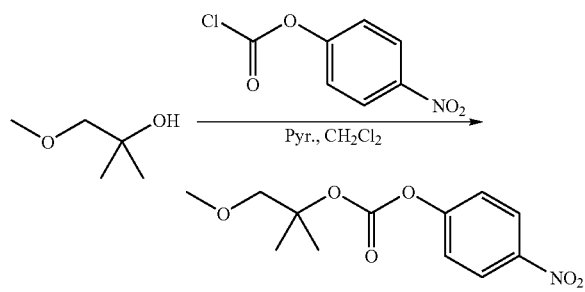

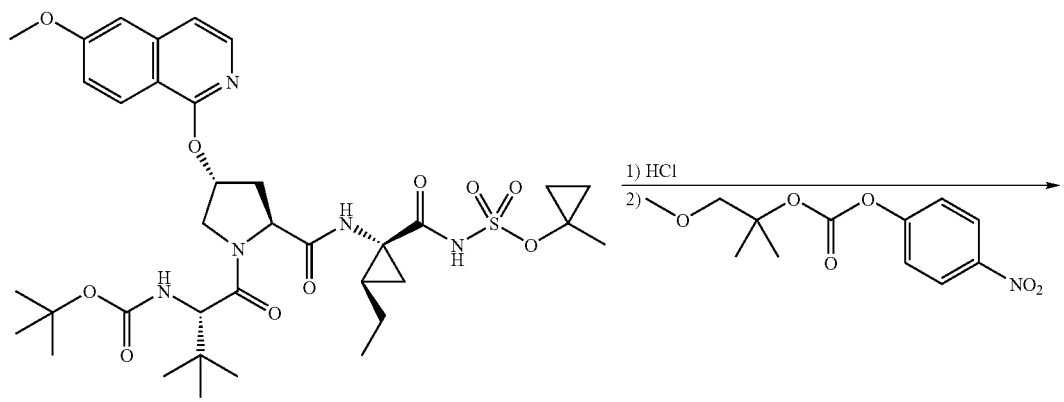

Compound 30

To a solution of 1-methoxy-2-methyl-2-propanol (2.8 mL, 24.0 mmol) in $CH_2Cl_2$ (80 mL) at 0° C. was added pyridine (2.0 mL, 24.8 mmol, 1.05 equiv.) and 4-nitrophenyl chloroformate (4.84 g, 24.0 mmol). The resulting slurry was stirred at room temperature for 20 h over which time the reaction becomes homogenous. The solution was diluted with $CH_2Cl_2$ and washed with 1M aqueous HCl, saturated aqueous $NaHCO_3$ and brine. The aqueous layers were extracted with $CH_2Cl_2$, dried over $Na_2SO_4$, and concentrated in vacuo. The crude product was purified by column chromatography (10-30% EtOAc/hexanes) to provide the desired carbonate (5.72 g, 89%): ¹H NMR ($CDCl_3$, 300 MHz) δ 8.71 (d, 2H), 7.71 (d, 2H), 3.57 (s, 2H), 3.44 (s, 3H), 1.57 (s, 6H).

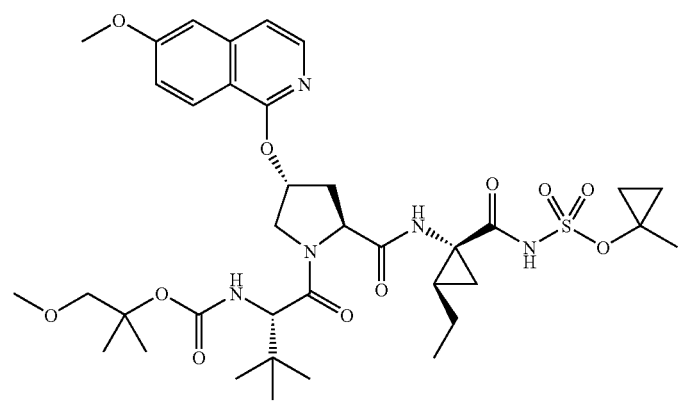

Compound 90

Compound 90 was prepared according to the methods described in Example 84. Treatment of Compound 30 (117 mg, 0.16 mmol) under the same conditions adjusted for scale and with the exception of using carbonic acid 2-methoxy-1,1-dimethyl-ethyl ester 4-nitro-phenyl ester (0.17 mg, 0.63 mmol) and triethylamine (0.22 mL, 1.58 mmol) and stirring at room temp for 18 h provided Compound 90 (91 mg, 75%): $^1$H NMR (CD$_3$OD, 300 MHz) δ 9.11 (s, 1H), 8.13 (d, 1H), 7.90 (d, 1H), 7.31 (d, 1H), 7.23 (s, 1H), 7.15 (d, 1H), 5.83 (m, 1H), 4.55 (m, 1H), 4.48 (d, 1H), 4.22 (s, 1H), 4.06 (m, 1H), 3.94 (s, 3H), 3.12 (s, 3H), 3.26 (s, 3H), 2.61 (m, 1H), 2.27 (m, 1H), 1.68 (s, 3H), 1.52-1.68 (m, 5H), 1.28-1.39 (m, 3H), 1.22 (d, 6H), 1.05 (s, 9H), 0.98 (m, 5H), 0.68 (m, 2H); LCMS found 775.99 [M+H]$^+$.

Example 91

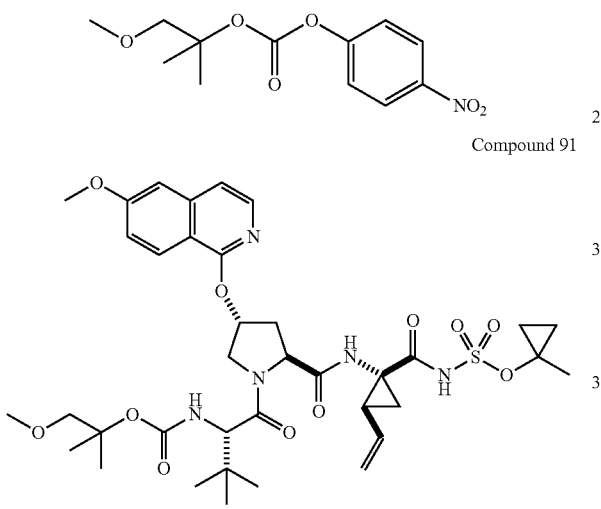

Compound 91

Compound 91 was prepared according to the methods described in Example 84. Treatment of Compound 29 (200 mg, 0.27 mmol) under the same conditions adjusted for scale and with the exception of using carbonic acid 2-methoxy-1,1-dimethyl-ethyl ester 4-nitro-phenyl ester (290 mg, 1.08 mmol) and triethylamine (0.28 mL, 1.69 mmol) and stirring at room temp for 18 h provided Compound 91 (88 mg, 42%); $^1$H NMR (d$_3$-MeOD, 400 MHz) δ 8.16 (d, 1H), 7.90 (d, 1H), 7.29 (d, 1H), 7.21 (d, 1H), 7.12 (d, 1H), 5.69-5.87 (m, 2H), 5.30 (d, 1H), 5.14 (d, 1H), 4.52-4.57 (m, 1H), 4.46 (d, 1H), 4.24 (s, 1H), 4.07 (dd, 1H), 3.91 (s, 3H), 3.38 (d, 2H), 3.26 (s, 3H), 2.62 (dd, 1H), 2.20-2.33 (m, 1H), 1.85-1.90 (m, 3H), 1.41-1.47 (m, 1H), 1.18-1.31 (m, 7H), 0.91-1.16 (m, 11H), 0.66 (t, 2H); LCMS found 772.4 [M+H]$^+$.

Example 92

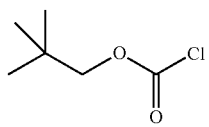

Compound 92

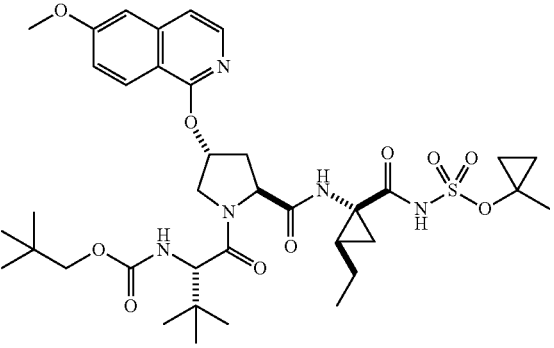

Compound 92 was prepared according to the methods described in Example 84. Treatment of Compound 30 (150 mg, 0.20 mmol) under the same conditions adjusted for scale and with the exception of using neopentyl chloroformate (0.12 mL, 0.80 mmol) and triethylamine (0.28 mL, 2.01 mmol) provided Compound 92 (33 mg, 22%): $^1$H NMR (d$_3$-MeOD, 400 MHz) "====" 8.10 (d, 1H), 7.90 (d, 1H), 7.28 (d, 1H), 7.20 (s, 1H), 7.12 (d, 1H), 5.85 (s, 1H), 4.55 (m, 1H), 4.43 (d, 1H), 4.30 (s, 1H), 3.95 (s, 3H), 3.56 (d, 1H), 3.40 (d, 1H), 2.60 (m, 1H), 2.25 (m, 1H), 1.70 (s, 3H), 1.48-1.68 (m, 4H), 1.30 (m, 3H), 1.15 (s, 9H), 0.85 (s, 9H), 0.60-0.75 (m, 3H); LCMS found 760.08 [M+H]$^+$.

Example 93

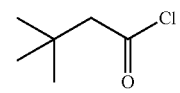

Compound 93

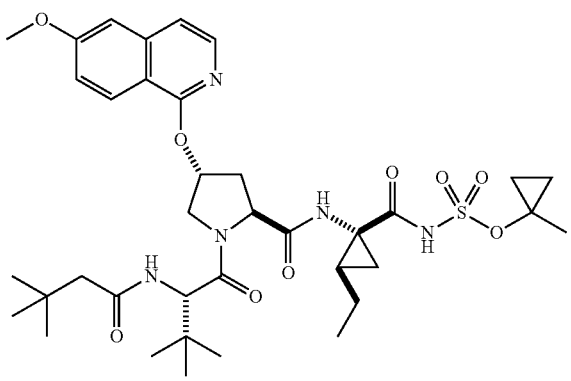

Compound 93 was prepared according to the methods described in Example 84. Treatment of Compound 30 (150 mg, 0.20 mmol) under the same conditions adjusted for scale and with the exception of using 3,3-dimethylbutyryl chloride (0.11 mL, 0.8 mmol) and triethylamine (0.28 mL, 2.01 mmol) provided Compound 93 (86 mg, 58%): $^1$H NMR (d$_3$-MeOD, 400 MHz) δ 8.05 (d, 1H), 7.90 (d, 1H), 7.29 (d, 1H), 7.20 (s, 1H), 7.12 (d, 1H), 5.84 (s, 1H) 4.64 (s, 1H), 4.53 (q 1H), 4.42 (d, 1H), 4.10 (dd, 1H), 2.58 (dd, 1H), 2.22-2.27 (m, 1H), 2.01 (s, 1H), 2.70 (s, 3H), 1.50-1.64 (m, 4H), 1.31 (q, 2H), 1.18-

1.24 (m, 1H), 1.03 (s, 9H), 0.97 (t, 3H), 0.84 (q, 9H), 0.68-0.72 (m, 2H); LCMS found 744.06 [M+H]$^+$.

Example 94

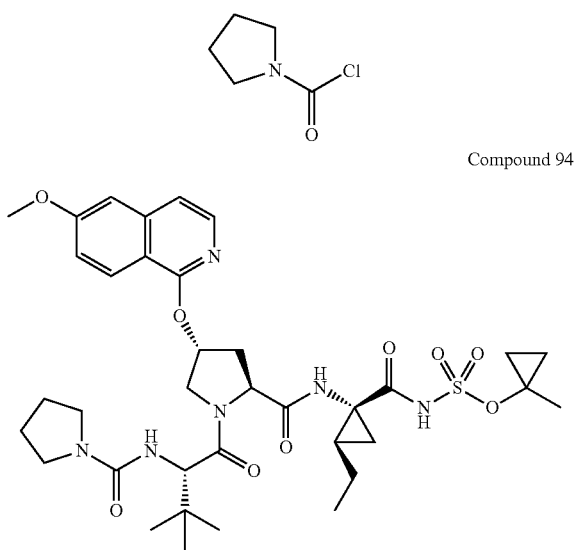

Compound 94 was prepared according to the methods described in Example 84. Treatment of Compound 30 (60 mg, 0.080 mmol) under the same conditions adjusted for scale and with the exception of using 1-pyrrolidinecarbonyl chloride (0.022 mL, 0.20 mmol) provided Compound 94 (53 mg, 89%): $^1$H NMR (CD$_3$OD, 300 MHz) δ 9.12 (s, 1H), 8.13 (d, 1H), 7.89 (d, 1H), 7.32 (d, 1H), 7.24 (s, 1H), 7.17 (dd, 1H), 5.86 (m, 1H), 4.56 (m, 1H), 4.47 (s, 1H), 4.40 (d, 1H), 4.13 (m, 1H), 3.95 (s, 3H), 3.26 (m, 4H), 2.58 (m, 1H), 2.29 (m, 1H), 1.87 (m, 4H), 1.69 (s, 3H), 1.51-1.66 (m, 4H), 1.26-1.29 (m, 3H), 1.07 (s, 9H), 0.97 (m, 3H), 0.69 (m, 2H); LCMS found 743.00 [M+H]$^+$.

Example 95

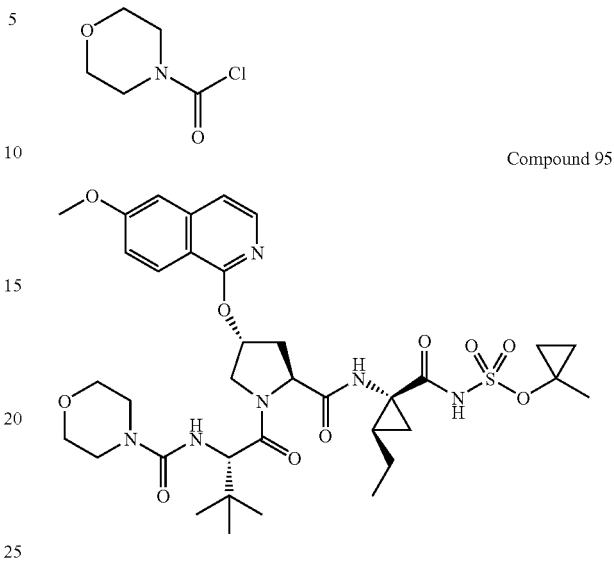

Compound 95 was prepared according to the methods described in Example 84. Treatment of Compound 30 (60 mg, 0.080 mmol) under the same conditions adjusted for scale and with the exception of using 4-morpholinylcarbonyl chloride (0.024 mL, 0.20 mmol) provided Compound 95 (58 mg, 95%): $^1$H NMR (CD$_3$OD, 300 MHz) δ 9.12 (s, 1H), 8.13 (d, 1H), 7.89 (d, 1H), 7.33 (d, 1H), 7.24 (s, 1H), 7.15 (d, 1H), 5.85 (m, 1H), 4.57 (m, 1H), 4.48 (d, 1H), 4.45 (s, 1H), 4.11 (m, 1H), 3.95 (s, 3H), 3.55 (m, 4H), 3.21 (m, 4H), 2.60 (m, 1H), 2.31 (m, 1H), 1.69 (s, 3H), 1.54-1.65 (m, 4H), 1.25-1.34 (m, 3H), 1.06 (s, 9H), 0.98 (m, 3H), 0.69 (m, 2H); LCMS found 758.95 [M+H]$^+$.

Example 96

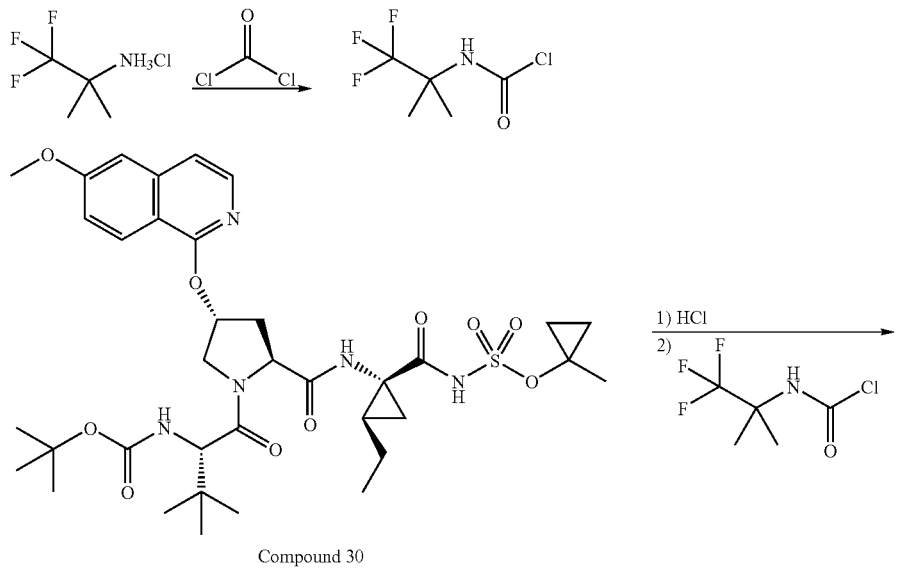

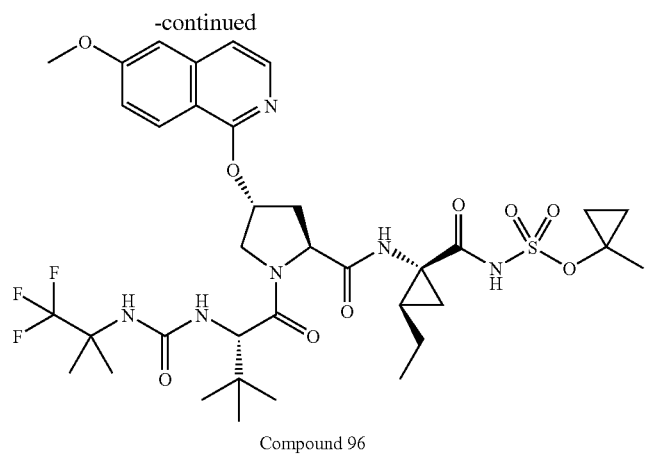

Compound 96

To a solution of phosgene (20% in toluene, 0.089 mL, 0.16 mmol,) and triethylamine (0.12 mL, 0.85 mmol, 5 equiv) in CH$_2$Cl$_2$ (0.8 mL) at 0° C. was slowly added 2,2,2-trifluoro-1,1-dimethyl-ethylamine hydrochloride (31 mg, 0.19 mmol). The resulting solution was stirred at room temperature for 15 min to provide 2,2,2-trifluoro-1,1-dimethyl-ethylaminecarbonyl chloride and used in the subsequent reaction.

To a solution of Compound 30 (62 mg, 0.083 mmol) in CH$_2$Cl$_2$ (0.1 mL) was added HCl (0.8 mL, 4M in dioxanes). The reaction was stirred at room temperature for 1.5 h and the concentrated in vacuo. The resulting amine was dissolved in CH$_2$Cl$_2$ (0.8 mL) to which was added the solution of 2,2,2-trifluoro-1,1-dimethyl-ethylaminecarbonyl chloride (assumed 0.16 mmol, 2 equiv). The reaction was stirred at room temperature for 3 h, and concentrated in vacuo. Analysis of the crude material by LCMS did not show complete conversion so the crude material was redissolved in CH$_2$Cl$_2$ (0.8 mL) and resubjected to a solution of 2,2,2-trifluoro-1,1-dimethyl-ethylaminecarbonyl chloride (assumed 0.084 mmol). The crude product was purified by reverse phase HPLC (30→90% MeCN/H$_2$O/0.1% TFA) to provide Compound 96 (30 mg, 45%): $^1$H NMR (CD$_3$OD, 300 MHz) δ 9.05 (s, 1H), 8.14 (d, 1H), 7.98 (d, 1H), 7.30 (d, 1H), 7.22 (s, 1H), 7.12 (dd, 1H), 5.83 (m, 1H), 4.51 (m, 2H), 4.33 (s, 1H), 4.06 (m, 1H), 3.94 (s, 3H), 2.60 (m, 1H), 2.27 (m, 1H), 1.68 (s, 3H), 1.47-1.63 (m, 4H), 1.36 (s, 3H), 1.35 (s, 3H), 1.18-1.31 (m, 3H), 1.06 (s, 9H), 0.96 (m, 3H), 0.67 (m, 2H); LCMS found 799.00 [M+H]$^+$.

Example 97

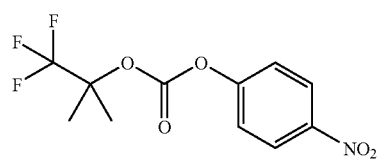

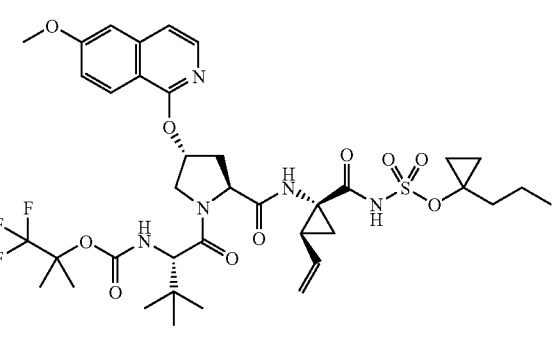

Compound 97

Compound 97 was prepared according to the methods described in Example 84. Treatment of Compound 51 (161 mg, 0.21 mmol) under the same conditions adjusted for scale and with the exception of using carbonic acid 4-nitro-phenyl ester 2,2,2-trifluoro-1,1-dimethyl-ethyl ester (124 mg, 0.63 mmol, 2 equiv.) provided Compound 97 (89 mg, 52%): $^1$H NMR (CD$_3$OD, 300 MHz) δ 9.23 (s, 1H), 8.11 (d, 1H), 7.90 (d, 1H), 7.29 (d, 1H), 7.22 (d, 1H), 7.13 (dd, 1H), 5.84 (m, 1H), 5.75 (m, 1H), 5.31 (d, 1H), 5.14 (d, 1H), 4.57 (m, 1H), 4.46 (d, 1H), 4.23 (s, 1H), 4.06 (m, 1H), 3.94 (s, 3H), 2.63 (m, 1H), 2.27 (m, 2H), 1.79-1.89 (m, 4H), 1.58 (m, 2H), 1.48 (s, 3H), 1.27 (m, 2H), 1.25 (s, 3H), 1.04 (s, 9H), 0.97 (t, 3H), 0.69 (m, 2H), LCMS found 826.1 [M+H]$^+$.

Example 98

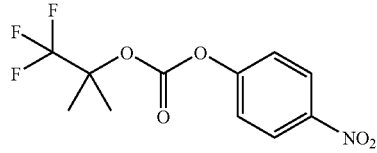

Compound 98

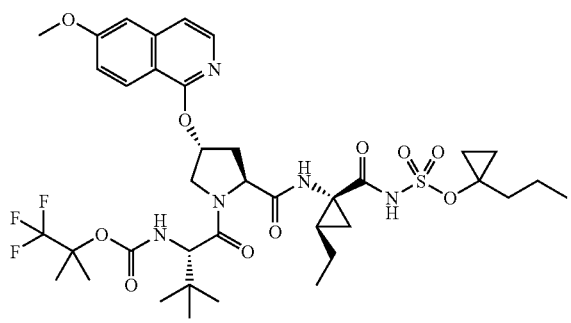

Compound 98 was prepared according to the methods described in Example 84. Treatment of Compound 42 (205 mg, 0.26 mmol) under the same conditions adjusted for scale and with the exception of using carbonic acid 4-nitro-phenyl ester 2,2,2-trifluoro-1,1-dimethyl-ethyl ester (124 mg, 0.63 mmol, 2 equiv.) provided Compound 98 (93 mg, 42%): $^1$H NMR (CD$_3$OD, 300 MHz) δ 9.14 (s, 1H), 8.11 (d, 1H), 7.90 (d, 1H), 7.30 (d, 1H), 7.22 (d, 1H), 7.15 (d, 1H), 5.83 (m, 1H), 4.57 (m, 1H), 4.46 (d, 1H), 4.22 (s, 1H), 4.05 (m, 1H), 3.94 (s, 3H), 2.61 (m, 1H), 2.30 (m, 1H), 1.82 (m, 2H), 1.52-1.64 (m, 6H), 1.48 (s, 3H), 1.29-1.41 (m, 3H), 1.25 (s, 3H), 1.05 (s, 9H), 0.97 (m, 6H), 0.69 (m, 2H); LCMS found 828.1 [M+H]$^+$.

Example 99

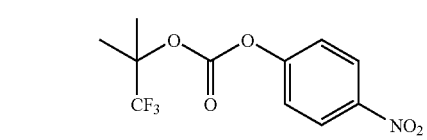

Compound 99

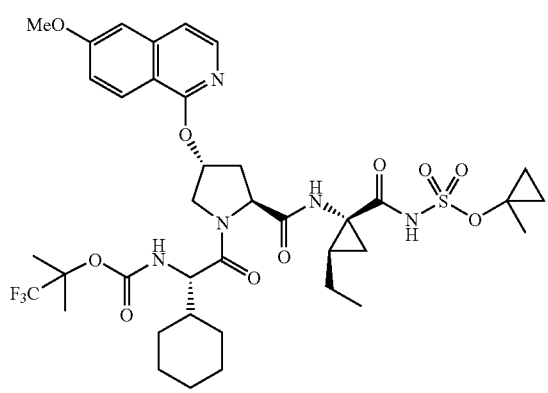

Compound 99 was prepared analogously to the method described in Example 77. Treatment of Compound 69 under appropriate conditions adjusted for scale provided Compound 99 (0.165 g, 42% over two steps). $^1$H-NMR (300 MHz, CDCl$_3$): δ 10.42 (br s, 1H); 8.17 (d, 1H); 7.99 (d, 1H); 7.39 (d, 1H); 7.26 (d, 1H); 7.12 (br d, 1H); 6.19 (m, 1H); 5.47 (m, 1H); 4.58 (m, 1H); 4.50-4.20 (m, 2H); 4.00 (s, 3H); 2.67 (m, 1H); 1.71 (s, 3H); 1.85-0.98 (m, 20H); 1.44 (s, 3H); 1.30 (s, 3H); 0.95 (t, 3H); 0.66 (m, 2H). LCMS found 826.5 [M+H]$^+$.

Example 100

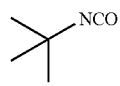

Compound 100

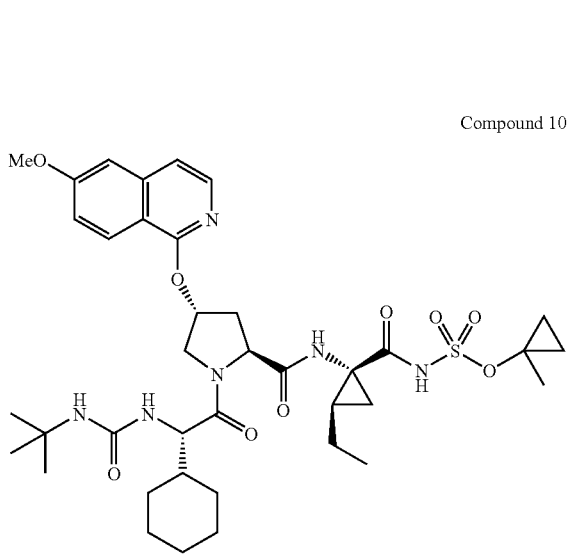

Compound 100 was prepared analogously to the method described in Example 84. Treatment of Compound 69 under similar conditions and with the exception of using tert-butyl isocyanate adjusted for scale provided the desired product (0.070 g, 29% over two steps). $^1$H-NMR (300 MHz, CDCl$_3$): δ 10.69 (br s, 1H); 8.16 (d, 1H); 7.94 (d, 1H); 7.33 (d, 1H); 7.24 (d, 1H); 7.10 (s, 1H); 6.17 (br s, 1H); 4.54 (m, 1H); 4.34 (m, 2H); 4.22 (1H); 3.98 (s, 3H); 2.62 (m, 2H); 1.71 (s, 3H); 1.88-1.54 (m, 10H); 1.54-1.00 (m, 10H); 1.25 (s, 9H); 0.95 (t, 3H); 0.65 (m, 2H). LCMS found 771.5 [M+H]$^+$.

Example 101

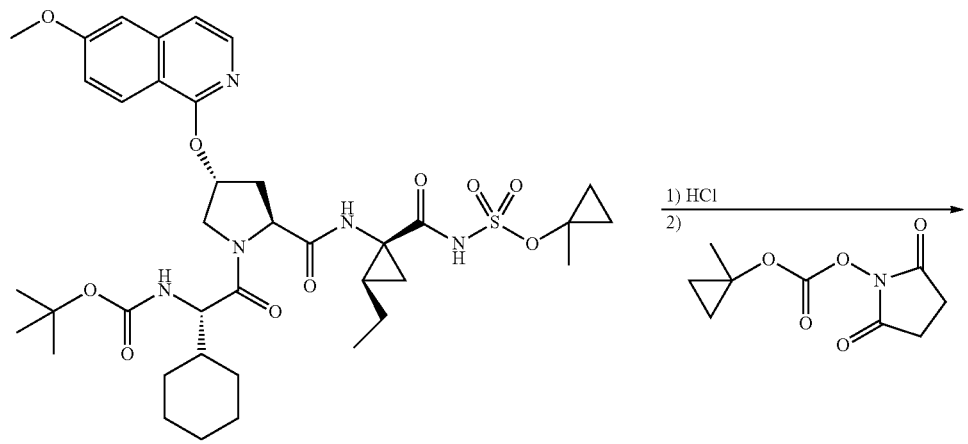

Compound 69

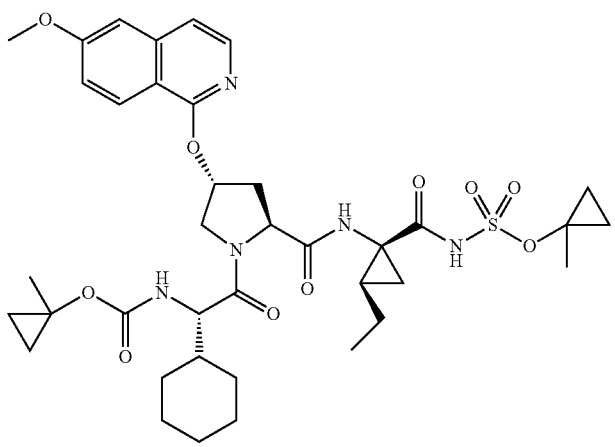

Compound 101

Compound 69 (60 mg, 0.078 mmol) was dissolved in DCM (0.3 mL) then HCl in dioxane (4N, 0.3 mL) was added. The reaction was allowed to stir at room temperature for 2 h before it was concentrated. The solid residue was dissolved in DCM (1 mL) and carbonic acid 2,5-dioxo-pyrrolidin-1-yl ester 1-methyl-cyclopropyl ester (28 mg, 0.13 mmol) was added followed by triethylamine (0.055 mL, 0.39 mmol). The reaction was allowed to stir at room temperature for 16b. The reaction was neutralized with HCl (1N) and partitioned between H$_2$O (3 mL) and DCM (5 mL). The aqueous layer was extracted with DCM (2×5 mL) and the combined organic layers were washed with brine and dried over Na$_2$SO$_4$ and concentrated. The crude residue was purified on silica (12 g, 50-100% EtOAc/hexanes), and then by reverse phase HPLC (25→100% CH$_3$CN/H$_2$O+0.1% TFA) to afford compound 101 as a white solid (51 mg, 85%). 1H MNR (300 MHz, CD$_3$OD): δ 9.26 (s, 1H), δ 8.15 (d, 1H), δ 7.89 (d, 1H), δ 7.33 (d, 1H), δ 7.24 (s, 1H), δ 7.17 (d, 1H), δ 5.86 (m, 1H), δ 4.53 (m, 2H), δ 4.13 (m, 2H), δ 3.94 (s, 3H), δ 2.59 (m, 1H), δ 2.34 (m, 1H), δ 1.82-1.09 (m, 22H), δ 0.97 (m, 6H), δ 0.69 (m, 4H), δ 0.45 (m, 3H). LCMS found 771 [M+H]$^+$.

Example 102

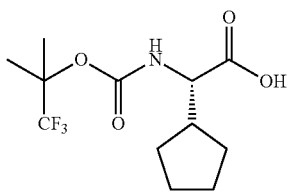

Compound 102

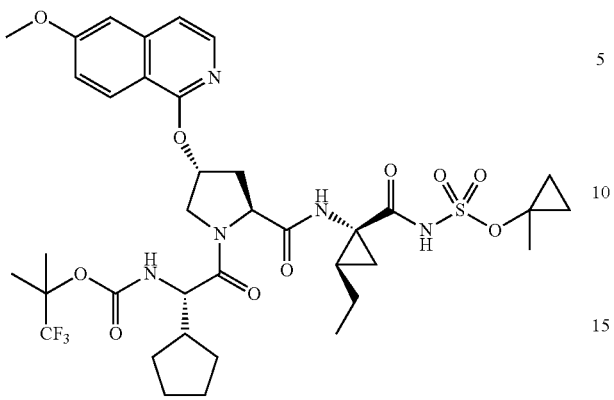

Compound 102 was prepared according to the method presented in the synthesis of compound 60. Treatment of the 2-[2-ethyl-1-(1-methyl-cyclopropoxysulfonylaminocarbonyl)-cyclopropylcarbamoyl]-4-(6-methoxy-isoquinolin-1-yloxy)-pyrrolidine-1-carboxylic acid tert-butyl ester (50 mg, 0.08 mmol) occurred under the same conditions, adjusted for scale and with the exception of utilizing cyclopentyl-(2,2,2-trifluoro-1,1-dimethyl-ethoxycarbonylamino)-acetic acid to provide compound 102 as a white solid (13 mg). 1H MNR (300 MHz, CD$_3$OD): δ 9.28 (s, 1H), δ 8.13 (d, 1H), δ 7.90 (d, 1H), δ 7.28 (d, 1H), δ 7.21 (s, 1H), δ 7.13 (d, 1H), δ 5.84 (m, 1H), δ 4.60 (m, 2H), δ 4.03 (m, 2H), δ 3.94 (s, 3H), δ 2.58 (m, 1H), δ 2.34 (m, 2H), δ 1.90-1.17 (m, 26H),), δ 0.98 (m, 3H), δ 0.69 (m, 2H). LCMS found 813 [M+H]$^+$.

Example 103

Compound 103

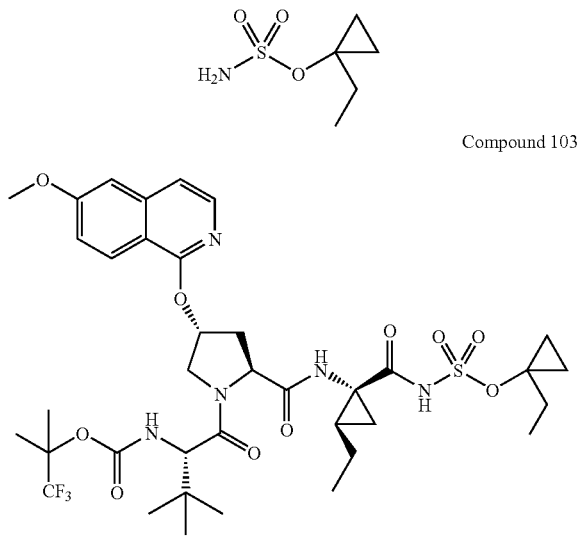

Compound 103 was prepared according to the method presented in the synthesis of compound 29. Treatment of 1-{[1-[3,3-dimethyl-2-(2,2,2-trifluoro-1,1-dimethyl-ethoxycarbonylamino)-butyryl]-4-(6-methoxy-isoquinolin-1-yloxy)-pyrrolidine-2-carbonyl]-amino}-2-ethyl-cyclopropanecarboxylic acid (0.18 mmol) and sulfamic acid 1-ethyl-cyclopropyl ester occurred under the same conditions, adjusted for scale, to afford compound 103 (28.7 mg, 20%): $^1$H NMR (CD$_3$OD, 300 MHz) δ 9.15 (s, 1H), 8.11 (d, 1H), 7.90 (d, 1H), 7.29 (d, 1H), 7.22 (s, 1H), 7.13 (d, 1H), 5.83 (m, 1H), 4.57 (m, 1H), 4.45 (d, 1H), 4.23 (s, 1H), 4.08 (m, 1H), 3.94 (s, 3H), 2.60 (m, 1H), 2.29 (m, 1H), 1.91 (q, 2H), 1.48 (s, 3H), 1.43-1.62 (m, 4H), 1.20-1.34 (m, 6H), 1.09 (t, 3H) 1.05 (s, 9H), 0.98 (m, 3H), 0.70 (m, 2H); LCMS found [M+H]$^+$: 814.3.

Example 104

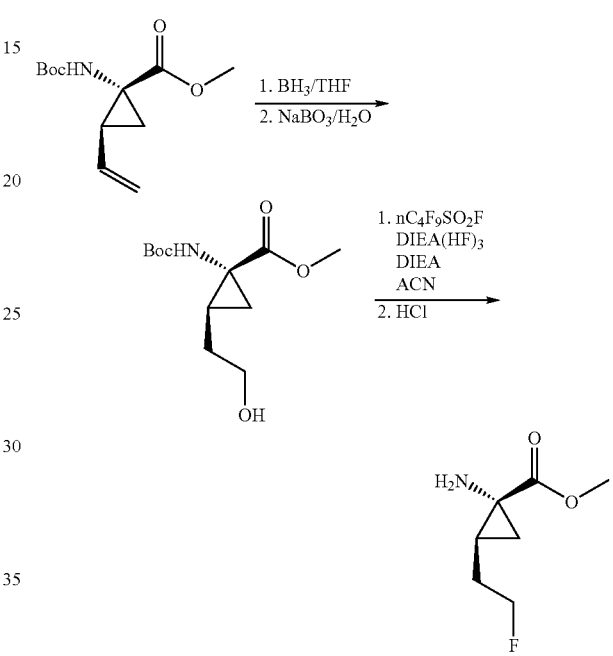

To a solution of 1-tert-butoxycarbonylamino-2-vinyl-cyclopropanecarboxylic acid methyl ester (9.585 g, 39.73 mmol) in THF (40 mL) was added 1 M BH$_3$/THF (19.86 mL) at 0° C. The reaction was stirred at room temperature for three hours. Upon cooling the reaction to 0° C., water (40 mL) was added, followed by NaBO$_3$ (9.17 g, 59.6 mmol) and the reaction was warmed to room temperature for one hour. The solution was diluted with EtOAc and the layers were separated. The organic layer was washed with brine, dried over MgSO$_4$ and concentrated. The residue was purified by flash chromatography (0→40% EtOAc/hexane) to afford 5.67 g (55%) of the desired product as a white solid. $^1$H NMR (CD$_3$OD, 300 MHz) δ 3.64 (s, 3H); 3.55 (m, 2H); 1.86-1.58 (m, 2H); 1.56-1.28 (m, 2H); 1.40 (s, 9H); 1.17 (m, 1H).

To a solution of 1-tert-butoxycarbonylamino-2-(2-hydroxy-ethyl)-cyclopropanecarboxylic acid methyl ester (1.6 g, 6.18 mmol) in acetonitrile (60 mL), diisopropylethylamine (6.45 mL, 37.1 mmol), and nonafluoro-1-butanesulfonyl fluoride (2.175 mL, 12.36 mmol) was added iPr$_2$NEt(HF)$_3$ (3.15 mL) dropwise. After one hour the reaction was cooled to 0° C. and quenched with saturated sodium bicarbonate and diluted with EtOAc. The layers were separated and the organic layer was washed with 0.5 M HCl and brine, dried over MgSO$_4$ and concentrated. The residue was purified by flash chromatography (0-40% EtOAc/hexane) to afford 590 mg (37%) of the intermediate as a clear oil. (520 mg, 1.99 mmol) This intermediate was dissolved in a 1 M solution of HCl in dioxanes (6 mL) and stirred at room temperature for one hour. The solvent was removed in vacuo to afford 379 mg (96%) of the HCl salt of the 1-amino-2-(2-fluoro-ethyl)-cyclopropanecarboxylic acid methyl ester as a white solid. LCMS found 161.9 [M+H]⁺.

To a solution of 1-{[1-(2-tert-butoxycarbonylamino-3,3-dimethyl-butyryl)-4-(6-methoxy-isoquinolin-1-yloxy)-pyrrolidine-2-carbonyl]-amino}-2-(2-fluoro-ethyl)-cyclopropanecarboxylic acid methyl ester (228 mg, 0.35 mmol) in

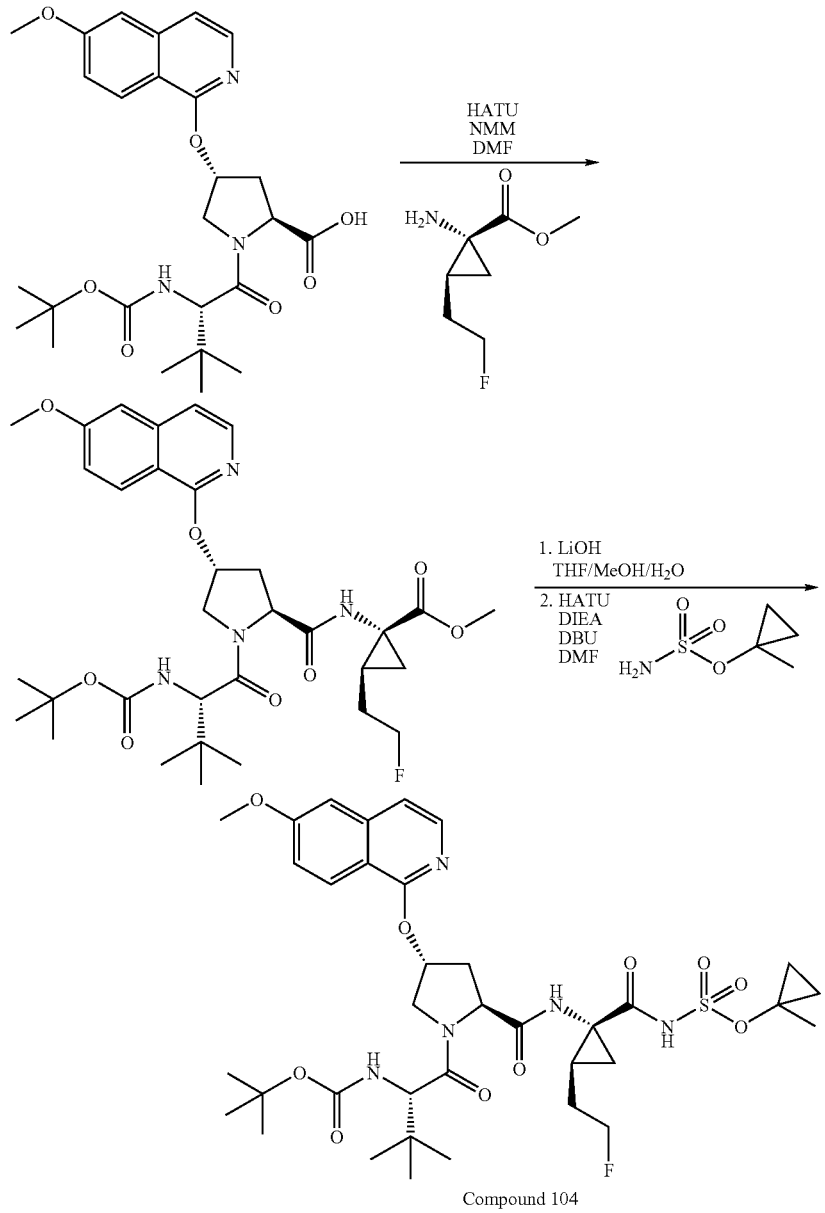

Compound 104

To a solution of 1-(2-tert-butoxycarbonylamino-3,3-dimethyl-butyryl)-4-(6-methoxy-isoquinolin-1-yloxy)-pyrrolidine-2-carboxylic acid (200 mg, 0.4 mmol), 1-amino-2-(2-fluoro-ethyl)-cyclopropanecarboxylic acid methyl ester (87 mg, 0.44 mmol) and 4-methylmorpholine (176 μL, 1.6 mmol) in DMF was added HATU (228 mg, 0.6 mmol). The reaction was stirred at ambient temperature for 1 h and the solvent was removed under vacuum. The residue was diluted with EtOAc and washed with saturated sodium bicarbonate and brine, dried over MgSO₄ and concentrated. The residue was purified by flash chromatography (0→100% EtOAc/hexane) to afford 228 mg (88%) of the product as a white foam. LCMS found 645.1 [M+H]⁺.

tetrahydrofuran and methanol (1:1, 8 mL) was added a solution of lithium hydroxide (42 mg, 1.77 mmol) in water (2 ml). The reaction was stirred at ambient temperature for 4 hr and then heated to 40° C. for several hours. The solvent was removed under vacuum and the solution was diluted with EtOAc and acidified with 1 M HCl. The layers were separated and the organic layer was dried over MgSO₄ and concentrated to give 183 mg (83%) of the acid intermediate as a white solid. LC/MS: m/z 631.1 [M+H]⁺). The acid was then dissolved in DMF (3 mL) and DIPEA (75 L, 0.44 mmol) to which was added HATU (165 mg, 0.44 mmol). To this reaction mixture was then added DBU (170 L, 1.16 mmol) and sulfamic acid 1-methyl-cyclopropyl ester (88 mg, 0.58 mmol) and the reac- Example 105

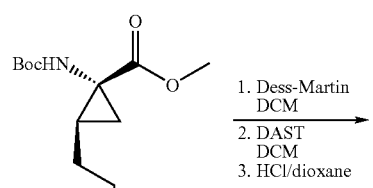

1. Dess-Martin DCM
2. DAST DCM
3. HCl/dioxane

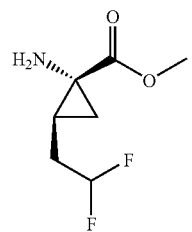

To a solution of 1-tert-butoxycarbonylamino-2-(2-hydroxy-ethyl)-cyclopropanecarboxylic acid methyl ester (2.9 g, 11.18 mmol) in dichloromethane was added Dess-Martin Periodinane (7.1 g, 16.8 mmol) and the reaction was stirred at ambient temperature for 4 h. The reaction was diluted with EtOAc (350 mL) and quenched with saturated sodium bicarbonate and sodium thiosulfate (1:1). The layers were separated and the organic layer was washed with brine, dried over MgSO$_4$ and concentrated. The residue was purified by flash chromatography on silica (0-80% EtOAc/hexane) to afford 2.2 g (76%) of the aldehyde intermediate as a light yellow oil, which was used immediately. To a solution of the aldehyde intermediate (2.2 g, 8.55 mmol) in dichloromethane (80 mL) at 0° C. was added diethylaminosulfur trifluoride (2.8 mL, 21.4 mmol) dropwise. The reaction was warmed to ambient temperature and stirred for 6 hours. The reaction was quenched at 0° C. by the addition of saturated sodium bicarbonate and diluted with EtOAc (300 mL). The layers were separated, and the organic layer was washed with brine, dried over MgSO$_4$ and concentrated. The residue was purified by flash chromatography (0-30% EtOAc/hexane) to afford 690 mg (29%) of the intermediate as a light yellow oil. The intermediate (660 mg, 2.37 mmol) was dissolved in a 1 M solution of HCl in dioxanes (6 mL) and stirred at room temperature for one hour. The solvent was removed in vacuo to afford 519 mg (>99%) of the HCl salt of the desired 1-amino-2-(2,2-difluoro-ethyl)-cyclopropanecarboxylic acid methyl ester as a yellow solid. LCMS found 180.0 [M+H]$^+$.

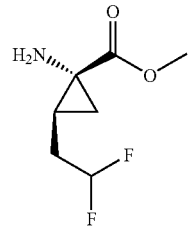

Compound 105

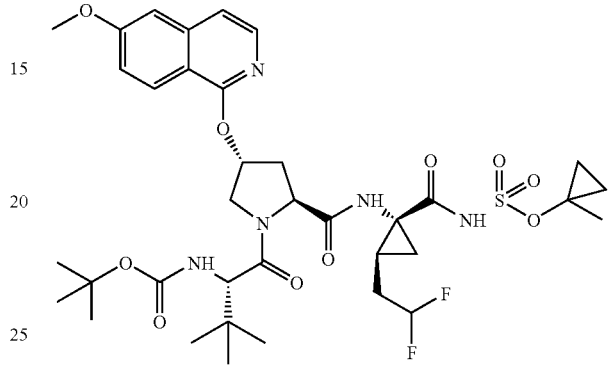

Compound 105 was prepared according to the method described for compound 104, substituting for intermediate 1-amino-2-(2,2-difluoro-ethyl)-cyclopropanecarboxylic acid methyl ester and adjusting appropriately for scale. 155 mg (57%) of the desired compound 105 was obtained as a white amorphous solid. $^1$H NMR (CD$_3$OD, 300 MHz) δ 9.13 (s, 1H); 8.06 (d, 1H); 7.84 (d, 1H); 7.22 (d, 1H); 7.15 (s, 1H); 7.07 (d, 1H); 6.11-5.61 (m, 1H); 5.79 (s, 1H); 4.50 (m, 1H); 4.40 (d, 1H); 4.20 (s, 1H); 4.02 (d, 1H); 3.88 (s, 3H); 2.61-2.52 (m, 1H); 2.30-2.00 (m, 2H); 1.70-1.54 (m, 2H); 1.64 (s, 3H); 1.38-1:14 (m, 2H); 1.23 (s, 9H); 1.80-0.88 (m, 2H); 0.99 (s, 9H); 0.64 (m, 2H). LCMS found 782.1 [M+H]$^+$.

Example 106

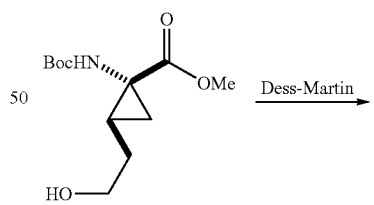

Dess-Martin

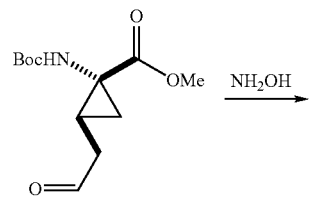

NH$_2$OH

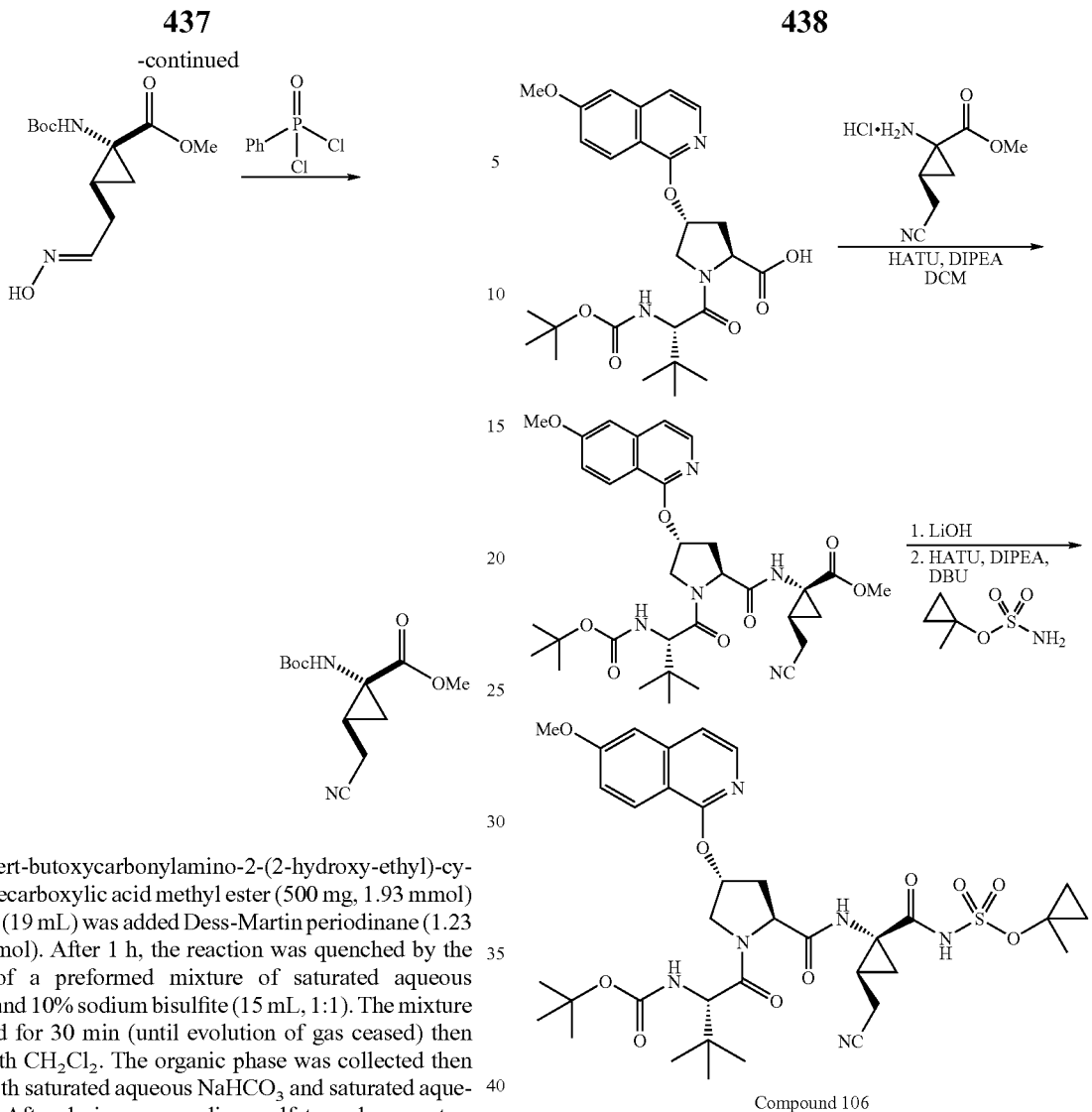

Compound 106

To 1-tert-butoxycarbonylamino-2-(2-hydroxy-ethyl)-cyclopropanecarboxylic acid methyl ester (500 mg, 1.93 mmol) in CH$_2$Cl$_2$ (19 mL) was added Dess-Martin periodinane (1.23 g, 2.89 mmol). After 1 h, the reaction was quenched by the addition of a preformed mixture of saturated aqueous NaHCO$_3$ and 10% sodium bisulfite (15 mL, 1:1). The mixture was stirred for 30 min (until evolution of gas ceased) then diluted with CH$_2$Cl$_2$. The organic phase was collected then washed with saturated aqueous NaHCO$_3$ and saturated aqueous NaCl. After drying over sodium sulfate and concentration, the crude residue was purified by column chromatography on silica (20→50% EtOAc/hexane) to provide the aldehyde (496 mg, 100%). LCMS found 257.7 [M+H]$^+$.

To 1-tert-butoxycarbonylamino-2-(2-oxo-ethyl)-cyclopropanecarboxylic acid methyl ester (496 mg, 1.93 mmol) in CH$_2$Cl$_2$ (10 mL) and methanol (2 mL) was added pyridine (311 μL, 3.86 mmol) and hydroxylamine hydrochloride (134 mg, 1.93 mmol). After stirring for 1 h, the reaction mixture was concentrated then placed on the high-vac for 2 h to afford the crude oxime, which was used in the next step without further purification. LCMS found 272.7 [M+H]$^+$.

To a suspension of the crude oxime 1-tert-butoxycarbonylamino-2-(2-hydroxyimino-ethyl)-cyclopropanecarboxylic acid methyl ester in CH$_2$Cl$_2$ (13 mL) and pyridine (311 μL, 3.86 mmol) at 0° C. was added phenylphosphonic dichloride (540 μL, 3.86 mmol) dropwise. After 1.5 h, the reaction was quenched with saturated aqueous NaHCO$_3$ then extracted with CH$_2$Cl$_2$. After being washed with 10% sodium sulfate and saturated aqueous NH$_4$Cl, the organic phase was dried over sodium sulfate and concentrated. The crude residue was purified by column chromatography on silica (20→50% EtOAc/hexane) to provide the nitrile 1-tert-butoxycarbonylamino-2-cyanomethyl-cyclopropanecarboxylic acid methyl ester (270 mg, 55%). LCMS found 254.7 [M+H]$^+$.

1-{[1-(2-tert-Butoxycarbonylamino-3,3-dimethyl-butyryl)-4-(6-methoxy-isoquinolin-1-yloxy)-pyrrolidine-2-carbonyl]-amino}-2-cyanomethyl-cyclopropanecarboxylic acid methyl ester was prepared according to the method presented in the synthesis of compound 31. Treatment of 1-(2-tert-butoxycarbonylamino-3,3-dimethyl-butyryl)-4-(6-methoxy-isoquinolin-1-yloxy)-pyrrolidine-2-carboxylic acid (387 mg, 0.69 mmol) and 1-amino-2-cyanomethyl-cyclopropanecarboxylic acid methyl ester occurred under the same conditions, adjusted for scale, to afford the desired methyl ester (349 mg, 74%). LCMS found 638.0 [M+H]$^+$.

Compound 106 was prepared according to the method presented in the synthesis of compound 31. Treatment of 1-{[1-(2-tert-butoxycarbonylamino-3,3-dimethyl-butyryl)-4-(6-methoxy-isoquinolin-1-yloxy)-pyrrolidine-2-carbonyl]-amino}-2-cyanomethyl-cyclopropanecarboxylic acid methyl ester (560 mg, 0.88 mmol) occurred under the same conditions, adjusted for scale, to afford compound 106 (201 mg, 30%). $^1$H NMR (CD$_3$OD, 300 MHz) δ 9.25 (s, 1H), 8.13 (d, 1H), 7.88 (d, 1H), 7.31 (d, 1H), 7.22 (s, 1H), 7.14 (d, 1H), 5.82 (s, 1H), 4.45-4.53 (m, 2H), 4.22 (s, 1H), 4.07 (d, 1H), 3.93 (s, 3H), 2.88 (dd, 1H), 2.74 (dd, 1H), 2.58-2.62 (m, 1H), 2.26-2.31 (m, 1H), 1.88-1.93 (m, 1H), 1.68 (s, 3H), 1.44-1.48

(m, 1H), 1.20-1.32 (m, 11H), 1.03 (s, 9H), 0.86-0.89 (m, 1H), 0.67 (s, 2H); LCMS found 757.0 [M+H]+.

Example 107

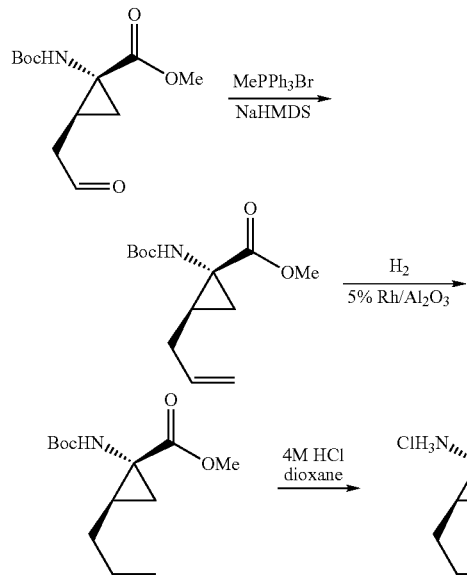

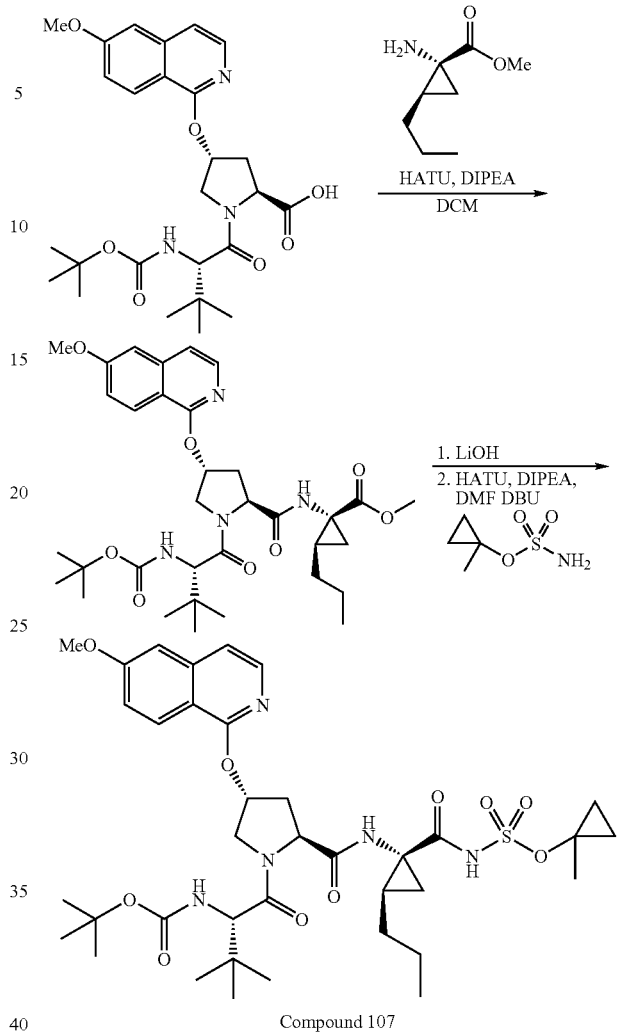

Compound 107

Methyltriphenylphosphonium bromide (4.6 mmol) was suspended in THF (10 mL) at room temperature. NaHMDS (1.0 M in THF, 4.1 mmol) was added dropwise at room temperature to produce a dark yellow turbid solution which was allowed to stir for 30 min. A THF (6 mL) solution of 1-tert-butoxycarbonylamino-2-(2-oxo-ethyl)-cyclopropanecarboxylic acid methyl ester was added dropwise to the ylide solution and allowed to age at room temperature for 30 min. The reaction was partitioned between EtOAc and saturated NH4Cl. The aqueous layer was extracted with EtOAc (3×10 mL) and the combined organics washed with brine, dried over anhydrous Na2SO4, and concentrated in vacuo. Purification by column chromatography on SiO2 (0→10% EtOAc/hex) afforded 2-allyl-1-tert-butoxycarbonylamino-cyclopropanecarboxylic acid methyl ester as a colorless film (0.070 g, 15%). (1H-NMR (300 MHz, CDCl3): δ 5.90-5.72 (m, 1H); 5.14 (br s, 1H); 5.08-4.94 (m, 2H); 3.71 (s, 3H); 2.34 (m, 2H); 1.55 (m, 2H); 1.45 (s, 9H), 1.37 (m, 1H)).

A solution of 2-allyl-1-tert-butoxycarbonylamino-cyclopropanecarboxylic acid methyl ester (0.27 mmol) in EtOAc (3 mL) was treated with 5% Rh/Al2O3 (0.014 mmol Rh). The atmosphere over the reaction was replaced with a H2 balloon and the reaction allowed to stir vigorously for 45 min. The H2 was removed and the catalyst removed by filtration through a pad of celite. Volatiles were removed in vacuo to afford 1-tert-butoxycarbonylamino-2-propyl-cyclopropanecarboxylic acid methyl ester as a colorless film that was used without further purification (0.069 g, quant). LCMS found 257.8 [M+H]+

A solution of 1-tert-butoxycarbonylamino-2-propyl-cyclopropanecarboxylic acid methyl ester (0.27 mmol) in THF (0.5 mL) was treated with 4M HCl in dioxane (2.4 mmol HCl). After 2 h, the volatiles are removed in vacuo to afford 1-amino-2-propyl-cyclopropanecarboxylic acid methyl ester hydrochloride salt as an amorphous white solid that was used without further purification (0.053 g, quant). LCMS found 157.9 ([M+H]+.

1-(2-tert-butoxycarbonylamino-3,3-dimethyl-butyryl)-4-(6-methoxy-isoquinolin-1-yloxy)-pyrrolidine-2-carboxylic acid (0.33 mmol) and 1-amino-2-propyl-cyclopropanecarboxylic acid methyl ester (0.27 mmol) are taken up in DCM (3 mL) and treated subsequently with DIPEA (0.68 mmol) and HATU (0.36 mmol). The resulting clear yellow solution was allowed to age at rt overnight. The volatiles are removed in vacuo and the residue purified by column chromatography on silica (5-50% EtOAc/Hex) to produce 0.163 g (78%) of the methyl ester as a colorless film. LCMS found 641.1 [M+H]+.

1-{[1-(2-tert-Butoxycarbonylamino-3,3-dimethyl-butyryl)-4-(6-methoxy-isoquinolin-1-yloxy)-pyrrolidine-2-carbonyl]-amino}-2-propyl-cyclopropanecarboxylic acid methyl ester (0.25 mmol) was dissolved in a mixture of THF (3 mL) and MeOH (1 mL) and treated with a freshly prepared solution of LiOH (1.6 mmol/1.5 mL H2O). The resulting solution was heated to 40° C. for 3 h. After the solution has cooled to rt, the volatiles are removed in vacuo and the residue diluted with H2O (5 mL). The resulting turbid solution was extracted once with EtOAc (5 mL), then acidified by dropwise addition of conc. HCl until pH~3. The resulting aqueous suspension was extracted with EtOAc until no turbidity remains (3×5 mL). The combined organics are washed with brine, dried over anhydrous Na2SO4 and concentrated in vacuo to produce 0.127 g (80%) of the desired acid as a white foam that was used without further purification. LCMS found 627.1 [M+H]⁺.

The resultant acid (0.20 mmol) was taken up in DMF (1 mL) and treated at rt with DIPEA (0.30 mmol) and HATU (0.30 mmol). After 30 min, sulfamic acid 1-methyl-cyclopropyl ester (0.41 mmol) and DBU (1.0 mmol) are added and the reaction allowed to age at rt for 24 h. The volatiles are removed in vacuo and the residue was partitioned between EtOAc and 1M HCl (5 mL each). The aqueous phase was extracted with EtOAc (3×5 mL) and the combined organics are washed with brine, dried over anhydrous Na₂SO₄ and concentrated in vacuo. The residue was purified by preparatory HPLC to afford 0.037 g (24%) of compound 107 as a foamy white solid; ¹H-NMR (300 MHz, CD₃OD): δ 9.09 (s, 1H); 8.10 (d, J=9 Hz, 1H); 7.88 (d, J=6 Hz, 1H); 7.27 (d, J=6 Hz, 1H); 7.19 (s, 1H); 7.10 (d, J=9 Hz, 1H); 5.82 (br s, 1H); 4.54 (m, 1H); 4.44 (br d, J=11 Hz, 1H); 4.23 (s, 1H); 4.06 (br d, J=10 Hz, 1H); 3.92 (s, 3H); 2.64-2.52 (m, 1H); 2.32-2.18 (m, 1H); 1.67 (s, 3H); 1.64-1.32 (m, 5H); 1.32-1.16 (m, 4H); 1.27 (s, 9H); 1.03 (s, 9H); 0.93 (t, J=7 Hz,); 0.67 (m, 2H). LCMS found 760.1 [M+H]⁺

Example 108

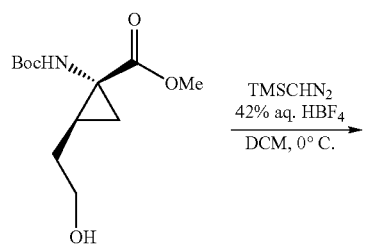

1-tert-Butoxycarbonylamino-2-(2-hydroxyethyl)-cyclopropanecarboxylic acid methyl ester (0.456 g, 1.76 mmol, from Example 104) was treated with conditions described in Aoyama and Shioiri; *Tetrahedron Lett.* 1990, 31, 5507 to produce 1-tert-butoxycarbonylamino-2-(2-methoxyethyl)-cyclopropanecarboxylic acid methyl ester (0.150 g, 31%): LCMS found 273.9 [M+H]⁺.

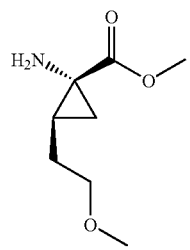

-continued

Compound 108

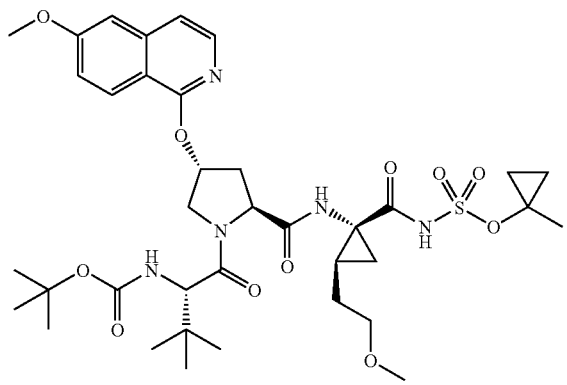

Compound 108 was prepared according to the method described for compound 104, substituting intermediate 1-amino-2-(2-methoxy-ethyl)-cyclopropanecarboxylic acid methyl ester for 1-amino-2-(2-fluoro-ethyl)-cyclopropanecarboxylic acid methyl ester and adjusting appropriately for scale. 29.9 mg (28%) of the desired compound 108 was obtained as a white amorphous solid ¹H NMR (CD₃OD, 300 MHz) δ 8.07 (d, 1H); 7.84 (d, 1H); 7.25 (d, 1H); 7.17 (m, 1H); 7.08 (d, 1H); 5.78 (s, 1H); 4.50 (m, 1H); 4.41 (d, 1H); 4.19 (s, 1H); 4.02 (d, 1H); 3.89 (s, 3H); 3.63 (m, 2H); 3.28 (s, 3H); 2.55 (m, 1H); 2.22 (m, 1H); 1.77 (m, 1H); 1.64 (s, 3H); 1.57 (m, 1H); 1.22 (m, 11H); 0.99 (s, 11H); 0.63 (m, 1H). LCMS found 776.2 [M+H]⁺.

Example 109

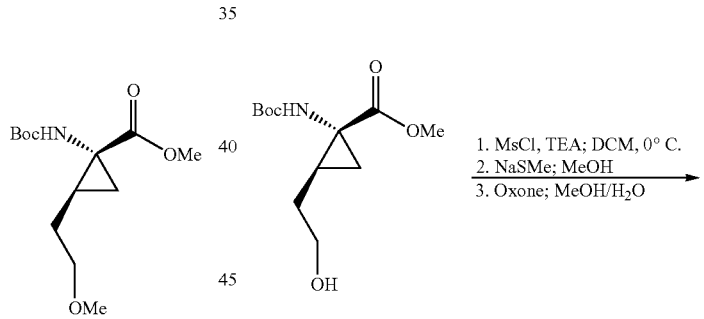

1-tert-Butoxycarbonylamino-2-(2-hydroxyethyl)-cyclopropanecarboxylic acid methyl ester (0.500 g, 1.93 mmol, from Example 104) was diluted in 8 mL DCM and cooled to 0° C. under an Ar atmosphere. TEA (0.54 mL, 3.9 mmol) and methanesulfonyl chloride (0.30 mL, 3.9 mmol) were added sequentially. After 2.5 h, the solvent was removed in vacuo and the residue taken up in EtOAc and H₂O (15 mL each). The aqueous layer was extracted with 3×10 mL EtOAc. The combined organics were washed with brine and dried over anhydrous MgSO₄. Following concentration in vacuo, the residue was purified by column chromatography on SiO$_2$ (0 to 50% Hex/EA) to produce 1-tert-butoxycarbonylamino-2-(2-methanesulfonyloxyethyl)cyclopropanecarboxylic acid methyl ester (0.55 g, 84%). LCMS found 360.1 [M+Na]$^+$.

A solution of 1-tert-butoxycarbonylamino-2-(2-methanesulfonyloxyethyl)cyclopropanecarboxylic acid methyl ester (0.52 g, 1.53 mmol) in 5 mL MeOH was added dropwise to a rt solution of sodium thiomethoxide in 3 mL MeOH. After 4.75 h, the solvent was removed in vacuo and the residue was taken up in EtOAc and H$_2$O (15 mL each). The aqueous layer was extracted with 3×10 mL EtOAc. The combined organics were washed with brine and dried over anhydrous MgSO$_4$. Following concentration in vacuo, 1-tert-butoxycarbonylamino-2-(2-methylsulfanylethyl)cyclopropanecarboxylic acid methyl ester (0.350 g, 79%) was obtained as a colorless oil that was used without further purification. LCMS found 312.0 [M+Na]$^+$.

A solution of 1-tert-butoxycarbonylamino-2-(2-methylsulfanylethyl)-cyclopropanecarboxylic acid methyl ester (0.63 g, 2.2 mmol) in 10 mL MeOH was added slowly to a suspension of Oxone (2.0 g, 3.3 mmol) in 10 mL H$_2$O at rt. After 2 h at rt, the solvent was removed in vacuo and the residue was taken up in EtOAc and H$_2$O (15 mL each). The aqueous layer was extracted with 3×10 mL EtOAc. The combined organics were washed with brine and dried over anhydrous MgSO$_4$. Following concentration in vacuo, the residue was purified by column chromatography on SiO$_2$ (0→65% EtOAc/hexanes) to produce 1-tert-butoxycarbonylamino-2-(2-methanesulfonylethyl)-cyclopropanecarboxylic acid methyl ester (0.50 g, 71%) as a colorless film. LCMS found 222.0 [(M-Boc)+H]$^+$.

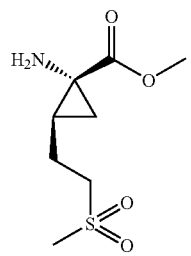

Compound 109

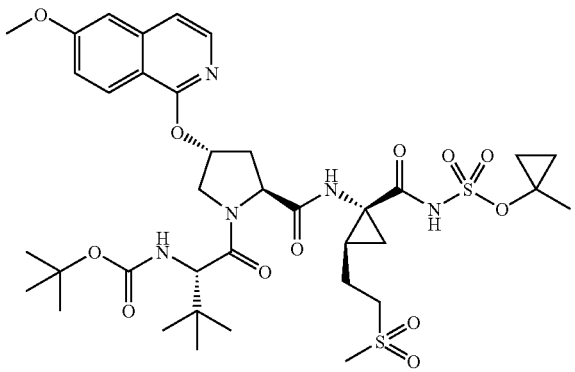

Compound 109 was prepared according to the method described for compound 104, substituting intermediate 1-amino-2-(2-methanesulfonyl-ethyl)-cyclopropanecarboxylic acid methyl ester for 1-amino-2-(2-fluoro-ethyl)-cyclopropanecarboxylic acid methyl ester and adjusting appropriately for scale. 150 mg (17%) of the desired compound compound 109 was obtained as a white amorphous solid. $^1$H NMR (CD$_3$OD, 300 MHz) δ 8.08 (d, 1H); 7.85 (d, 1H); 7.24 (d, 1H); 7.17 (s, 1H); 7.08 (d, 1H); 5.79 (s, 1H); 4.44 (m, 2H); 4.19 (s, 1H); 4.02 (m, 1H); 3.89 (s, 3H); 3.27 (s, 3H); 3.06 (m, 2H); 2.89 (s, 3H); 2.56 (m, 1H); 2.23 (m, 1H); 2.02 (m, 1H); 1.64 (s, 2H); 1.25 (m, 11H); 1.00 (s, 11H); 0.64 (m, 2H). LCMS found 824.1 [M+H]$^+$.

Example 110

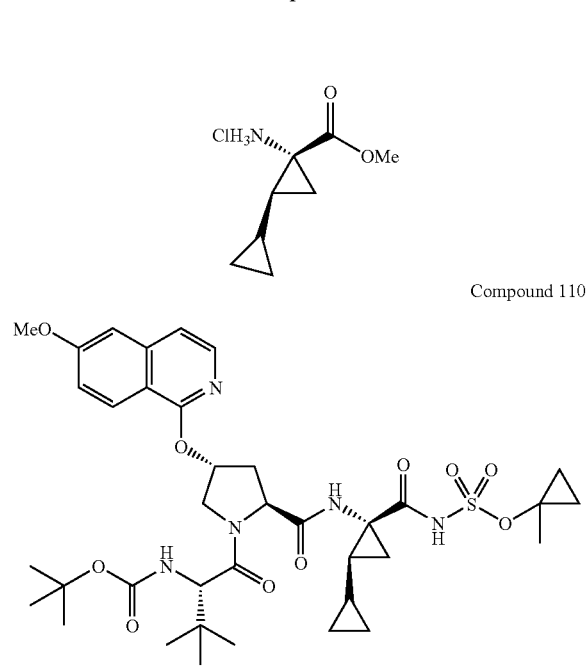

Compound 110

Compound 110 was prepared analogously to the method described for compound 104, utilizing intermediate 2-aminobicyclopropyl-2-carboxylic acid methyl ester (prepared as detailed in Ripka, A.; et al. WO 2004/032827, p. 142) and adjusting appropriately for scale. 428 mg (44%) of compound 110 was obtained as a crystalline white solid after column chromatography on silica (0→10% MeOH/DCM) followed by crystallization from hot MeOH. $^1$H-NMR (300 MHz, CDCl$_3$): δ 10.39 (s, 1H); 8.01 (d, 1H); 7.90 (d, 1H); 7.16 (d, 1H); 7.07 (d, 1H); 7.01 (s, 1H); 6.92 (s, 1H); 5.86 (s, 1H); 5.21 (br d, 1H); 4.51 (br t, 1H); 4.33 (dd, 1H); 4.02 (m, 1H); 3.93 (s, 3H); 2.68-2.42 (m, 2H); 1.87-1.65 (m, 2H); 1.72 (s, 3H); 1.45-0.80 (m, 5H); 1.33 (s, 9H); 1.02 (s, 9H); 0.65 (br t, 2H); 0.58 (m, 2H); 0.27 (m, 2H). LCMS found 758.1 [M+H]$^+$.

Example 111

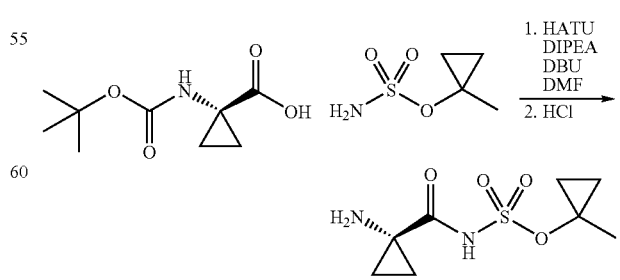

1-tert-butoxycarbonylamino-cyclopropanecarboxylic acid was dissolved in DMF (3 mL) and DIPEA (130 μL, 0.75 mmol) to which was added N,N,N',N'-tetramethyl-O-(7-aza-benzotriazol-1-yl)uronium hexafluorophosphate (285 mg, 0.75 mmol). To this reaction mixture was then added 1,8-Diazabicyclo[5.4.0]undec-7-ene (300 µL, 2 mmol) and sulfamic acid 1-methyl-cyclopropyl ester (150 mg, 0.99 mmol) and the reaction was stirred at ambient temperature for 16 h. The solvent was removed; the residue was diluted with EtOAc and washed with 1 M HCl, dried over MgSO₄ and concentrated. The residue was purified by chromatography (10→100% EtOAc/hexanes) to give 144 mg (86%). The intermediate was then dissolved in 4M HCl in dioxanes (5 mL) and stirred at room temperature for 1 hour. The solvent was removed to give 143 mg of the HCl salt of intermediate (1-amino-cyclopropanecarbonyl)-sulfamic acid 1-methyl-cyclopropyl ester as a pink oil.

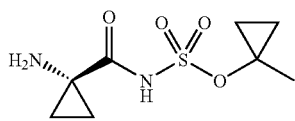

Compound 111

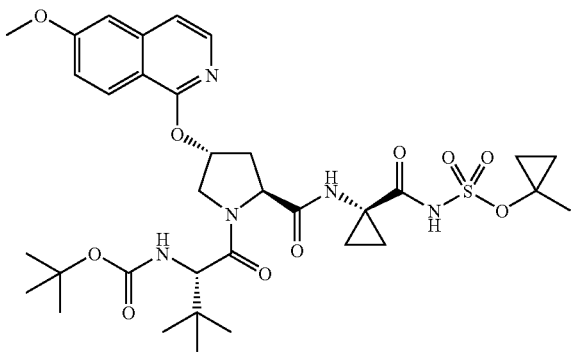

Compound 111 was prepared according to the method described for compound 104, substituting intermediate (1-amino-cyclopropanecarbonyl)-sulfamic acid 1-methyl-cyclopropyl ester for sulfamic acid 1-methyl-cyclopropyl ester and adjusting appropriately for scale. The compound was purified using reverse phase HPLC to afford compound 111 as a white amorphous solid (42.3 mg, 12%). ¹H NMR (CD₃OD, 300 MHz) δ 8.09 (m, 1H); 7.85 (d, 1H); 7.25 (d, 1H); 7.17 (s, 1H); 7.09 (m, 1H); 5.78 (m, 1H); 4.59 (m, 1H); 4.45 (m, 1H); 4.18 (d, 1H); 4.00 (m, 1H); 3.89 (s, 3H); 2.70 (m, 1H); 2.57 (m, 1H); 2.29 (m, 1H); 1.64 (m, 3H); 1.59 (m, 1H); 1.44 (m, 1H); 1.18 (m, 11H); 1.00 (s, 11H); 0.64 (m, 1H). LCMS found 718.0 [M+H]⁺.

Example 112

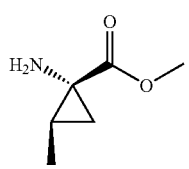

Compound 112

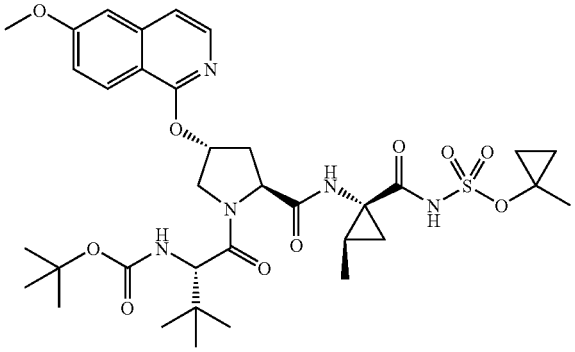

1-Amino-2-methyl-cyclopropanecarboxylic acid methyl ester was prepared according to methods described in LLinas-Brunet et al, WO 00/09543 pgs 56-61.

Compound 112 was prepared according to the method described for compound 104, substituting 1-amino-2-methyl-cyclopropanecarboxylic acid methyl ester for 1-amino-2-(2-fluoro-ethyl)-cyclopropanecarboxylic acid methyl ester and adjusting appropriately for scale. The compound was purified using reverse phase HPLC to afford compound 112 as a white amorphous solid (268.4 mg, 53%). ¹H NMR (CD₃OD, 400 MHz) δ 8.13 (d, J=9.2 Hz, 1H); 7.89 (d, J=6.4 Hz, 1H); 7.30 (d, J=6 Hz, 1H); 7.22 (m, 1H); 7.13 (d, J=9.6 Hz, 1H); 5.84 (s, 1H); 4.49 (m, 2H); 4.24 (s, 1H); 4.07 (m, 1H); 3.94 (s, 3H); 2.61 (m, 1H); 2.28 (m, 1H); 1.68 (s, 3H); 1.56 (m, 2H); 1.25 (m, 15H); 1.04 (s, 10H); 0.69 (m, 2H). LCMS found 731.93 [M+H]⁺.

Example 113

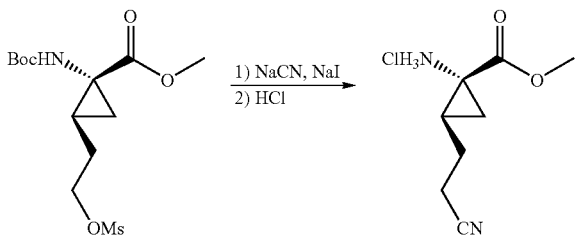

To 1-tert-butoxycarbonylamino-2 (2-methanesulfonyloxy-1-ethyl)-cyclopropanecarboxylic acid methyl ester (400 mg, 1.19 mmol) from example 109 in DMF (6 mL) was added NaCN (350 mg, 7.14 mmol) and NaI (178 mg, 1.19 mmol). The reaction mixture was heated at 80° C. for 2 h then diluted with EtOAc and washed with water and brine. The organic layer was dried over sodium sulfate, filtered, and concentrated. The crude product was purified by column chromatography on silica (20→50% EtOAc/Hexanes) to afford 1-tert-butoxycarbonylamino-2-(2-cyano-ethyl)-cyclopropanecarboxylic acid methyl ester (297 mg, 93%). ¹H NMR (300 MHz, CDCl₃): δ 5.13 (br s, 1H), 2.44 (m, 2H), 2.05 (m, 2H), 1.70-1.53 (m, 1H), 1.53-1.37 (m, 4H) 1.45 (s, 9H). LCMS found 290.9 [M+Na]⁺. To this intermediate (297 mg, 1.10 mmol) in CH₂Cl₂ (2 mL) was added 4N HCl in dioxanes (2 mL). Ater stirring at room temperature for 2 h the reaction was concentrated to afford 225 mg (100%) of the HCl salt of 1-amino-2-(2-cyano-ethyl)-cyclopropanecarboxylic acid methyl ester, which was used in the next step without further purification.

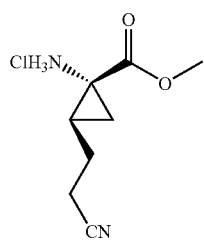

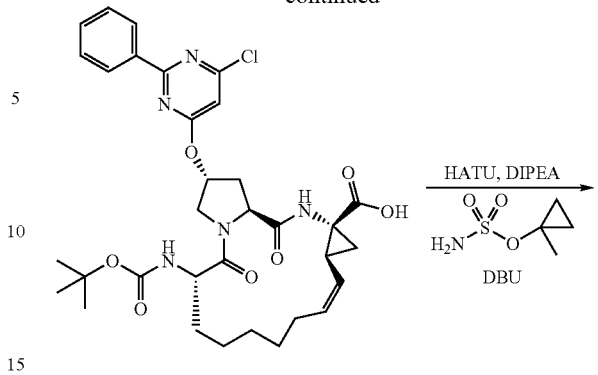

Compound 113

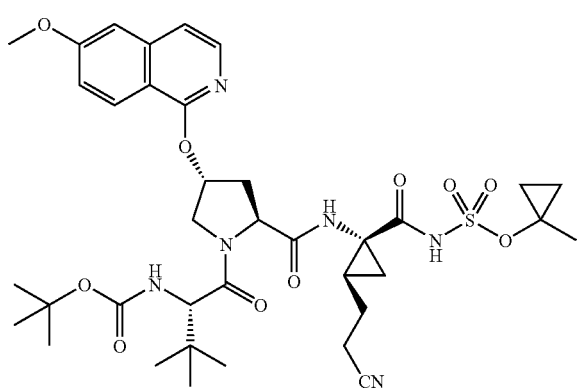

Compound 113 was prepared according to the method presented in the synthesis of compound 104. Treatment of 1-(2-tert-butoxycarbonylamino-3,3-dimethyl-butyryl)-4-(6-methoxy-isoquinolin-1-yloxy)-pyrrolidine-2-carboxylic acid (552 mg, 1.10 mmol) with the HCl salt of 1-amino-2-(2-cyano-ethyl)-cyclopropanecarboxylic acid methyl ester (225 mg, 1.10 mmol) under the same conditions, adjusted for scale, afforded the desired methyl ester (553 mg, 77%). The methyl ester was then converted into compound 113 under the same conditions described in example 104 (88 mg, 47%). $^1$H NMR (300 MHz, CDCl$_3$): δ 8.65 (s, 1H), 8.01 (d, 1H), 7.81 (d, 1H), 7.15 (d, 1H), 7.04 (d, 1H), 6.99 (s, 1H), 5.83 (s, 1H), 4.38 (m, 1H), 4.17 (s, 1H), 4.04-4.00 (m, 1H), 3.87 (s, 3H), 2.51 (m, 1H), 2.34-2.24 (m, 3H), 1.96-1.90 (m, 2H), 1.63-1.17 (m, 5H), 1.25 (s, 9H), 0.96 (s, 9H), 0.58 (m, 2H). LCMS found 789.8 [M+H]$^+$.

Example 114

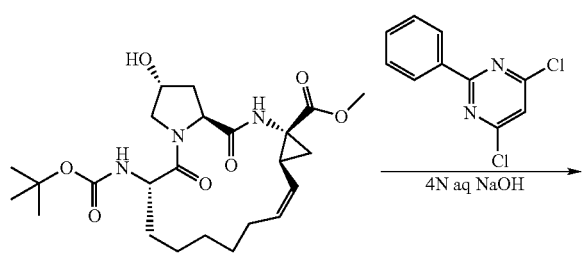

Compound 114

To a solution of cyclopropa[e]pyrrolo[1,2-a][1,4]diazacyclopentadecine-14a(5H)-carboxylic acid, 6-[[(1,1-dimethylethoxy)carbonyl]amino]-1,2,3,6,7,8,9,10,11,13a,14,15,16,16a-tetradecahydro-2-hydroxy-5,16-dioxo-methyl ester, which was synthesized by methods presented in WO2004/094452 for the preparation of the corresponding ethyl ester, (500 mg, 1.0 mmol) in THF (4.7 mL) was added 4N aqueous sodium hydroxide (1.6 mL) and stirred at room temperature for 5 min. 4,6-dichloro-2-phenylpyrimidine (700 mg, 3.1 mmol) was added to the mixture and stirred at room temperature for 40 h. The mixture was diluted with ethyl acetate (40 mL), washed with brine, and concentrated. The residue was purified by silica gel column chromatography using ethyl acetate/hexanes as eluents, which afforded acid (900 mg, 55%). LCMS found 652.0 (M$^+$−1).

To a solution of the acid (50 mg, 0.076 mmol) were added HATU (44 mg, 0.114 mmol) and DIPEA (0.020 mL, 0.114 mmol) and stirred for 0.5 h at room temperature. Sulfamic acid 1-methyl-cyclopropyl ester (23 mg, 0.153 mmol) and DBU (0.046 mL, 0.30 mmol) were then added. The resulting mixture was stirred at room temperature for 2 days. After diluting the mixture with ethyl acetate (30 mL), 1N HCl (~0.5 mL) was added to neutralize it to pH ~4. The mixture was then washed with brine (2×30 mL) and concentrated. The residue was purified by reverse phase HPLC, affording compound 114 (30 mg, 50%) as a white solid: $^1$H NMR (300 MHz, CD$_3$OD): δ 8.92 (brs, 1H), 8.41 (d, 2H), 7.53 (brs, 3H), 6.78 (s, 1H), 6.60 (s, 1H), 5.95 (m, 1H), 5.67 (q, 1H), 5.14 (t, 1H), 4.77 (d, 1H), 4.63 (t, 1H), 4.08 (m, 2H), 2.62 (m, 3H), 2.40 (q, 1H), 1.7-1.9 (m, 3H), 1.65 (s, 3H), 1.3-1.6 (m, 7H), 1.27 (s, 9H), 1.18 (m, 2H), 0.66 (m, 2H). LCMS found 785.4 (M$^+$−1).

1H), 2.46 (m, 1H), 1.77 (m, 1H), 1.68 (s, 3H), 1.3-1.7 (m, 16H), 1.29 (s, 9H), 1.20 (m, 2H), 0.71 (m, 2H). LCMS found 787.4 (M$^+$−1).

Example 115

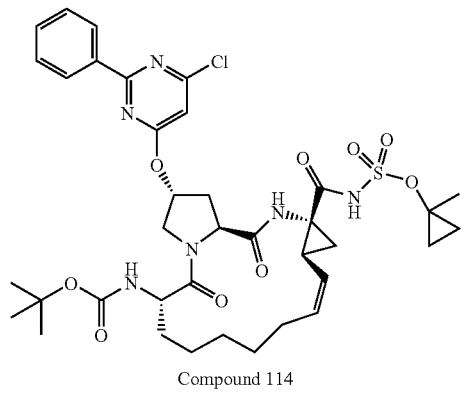

Compound 114

Example 116

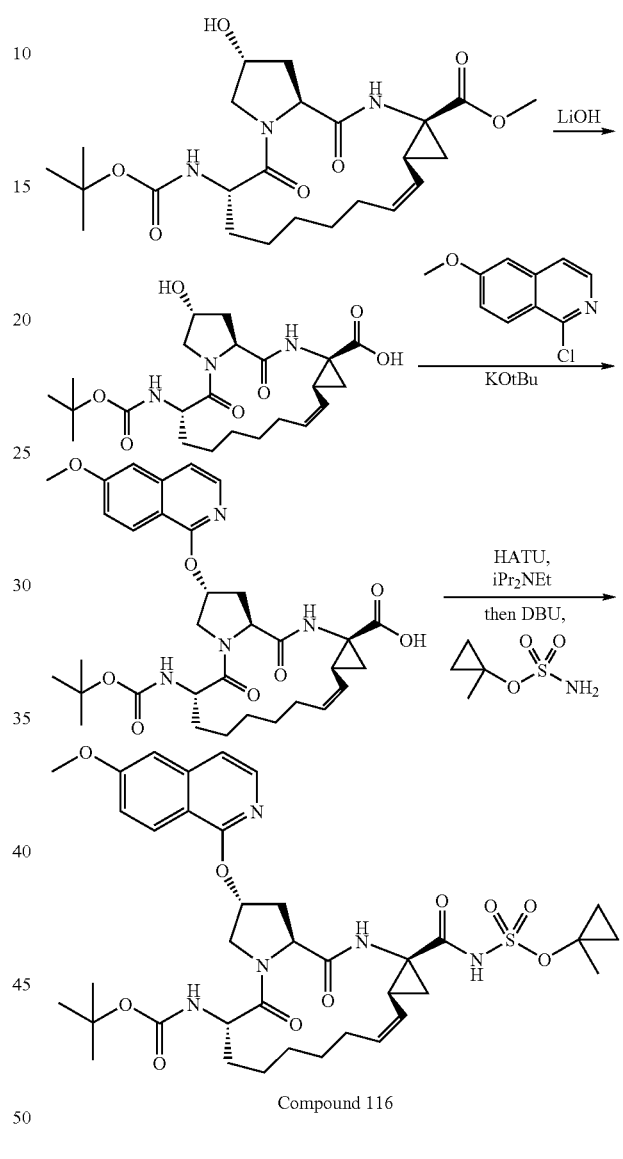

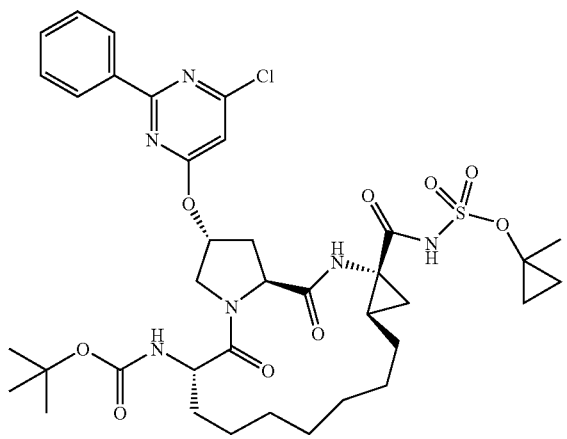

Compound 115

A solution of compound 114 (100 mg, 0.13 mmol), tosyl hydrazide (177 mg, 0.95 mmol) and sodium acetate (157 mg, 1.91 mmol) in DME (1.8 mL) and water (0.2 mL) was stirred at 95° C. for 75 min. Additional sodium acetate (80 mg) and tosyl hydrazide (90 mg) were added and stirred at the same temperature for 45 min. The mixture was partitioned between ethyl acetate (80 mL) and saturated aqueous sodium bicarbonate (80 mL). The organic layer was washed with diluted HCl and then with brine, and concentrated. The residue was purified by reverse phase HPLC, affording compound 115 (75 mg, 75%) as a white solid: $^1$H NMR (300 MHz, CD$_3$OD): δ 9.02 (brs, 1H), 8.41 (d, 2H), 7.51 (m, 3H), 6.81 (s, 1H), 5.96 (brs, 1H), 4.63 (m, 2H), 4.20 (d, 1H), 4.09 (d, 1H), 2.66 (m, To 14-tert-butoxycarbonylamino-18-hydroxy-2,15-dioxo-3,16-diaza-tricyclo[14.3.0.04,6]nonadec-7-ene-4-carboxylic acid methyl ester (1.2 g, 2.5 mmol) in THF/MeOH (3:1, 20 mL) was added a solution of LiOH (300 mg, 12.5 mmol) in H$_2$O (5 mL). After stirring at room temperature for 12 h, the reaction was diluted with H$_2$O and acidified with 1N aqueous HCl. The solution was extracted with EtOAc, washed with saturated aqueous NaCl, and dried over sodium sulfate. After removal of solvent, the crude acid was used directly in the next reaction.

The resultant acid was coupled to 1-chloro-6-methoxy-isoquinoline under conditions previously described in the synthesis of example 36, adjusted for scale, to provide the aryl ether acid (3.04 g, >95%). LCMS found 623.0 [M+H]$^+$.

Compound 116 was prepared according to the method presented for the synthesis of compound 29. Treatment of the aryl ether acid under the same conditions, adjusted for scale, provided compound 116 (100 mg, 32%). ¹H NMR (300 MHz, CD₃OD): δ 8.87 (s, 1H), 8.22 (d, 1H), 7.90 (d, 1H) 7.32 (d, 1H), 7.23 (d, 1H), 7.13 (d, 1H), 5.86 (brs, 1H), 5.68 (dd, 1H), 5.14 (t, 1H), 4.77 (d, 1H), 4.67 (t, 1H), 4.15 (dd, 1H), 4.02 (dd, 1H), 3.94 (s, 3H), 2.73 (m, 2H), 2.56 (m, 1H), 2.42 (dd, 1H), 1.66-1.82 (m, 5H), 1.65 (s, 3H), 1.31-1.55 (m, 8H), 1.17 (s, 9H), 0.67 (m, 2H). LCMS found 756.0 [M+H]⁺.

Example 117

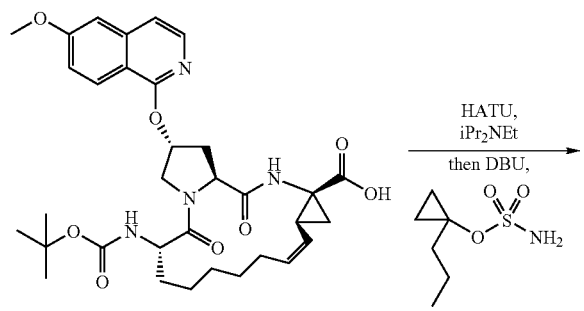

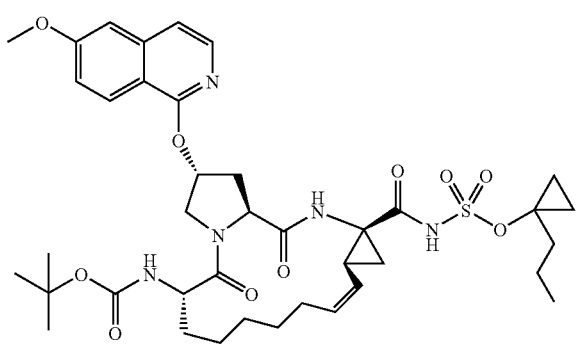

Compound 117

Compound 117 was prepared according to the method presented for the synthesis of compound 29. Treatment of unsaturated macrocycle arylether acid from example 116 and sulfamic acid 1-propyl-cyclopropyl ester under the same conditions, adjusted for scale, and purified by reverse phase HPLC afforded compound 117 (29 mg, 10%): ¹H NMR (300 MHz, CD₃OD): δ 8.87 (s, 1H), 8.21 (d, 1H), 7.90 (d, 1H) 7.29 (d, 1H), 7.21 (d, 1H), 7.12 (d, 1H), 5.86 (brs, 1H), 5.68 (dd, 1H), 5.13 (t, 1H), 4.77 (d, 1H), 4.67 (t, 1H), 4.15 (dd, 1H), 4.01 (dd, 1H), 3.94 (s, 3H), 2.70 (m, 2H), 2.56 (m, 1H), 2.44 (dd, 1H), 1.94 (m, 1H), 1.82 (m, 1H), 1.25-1.75 (m, 13H), 1.18 (s, 9H), 0.99 (t, 3H), 0.97-1.05 (m, 2H), 0.68 (m, 2H). LCMS found 784.0 [M+H]⁺.

Example 118

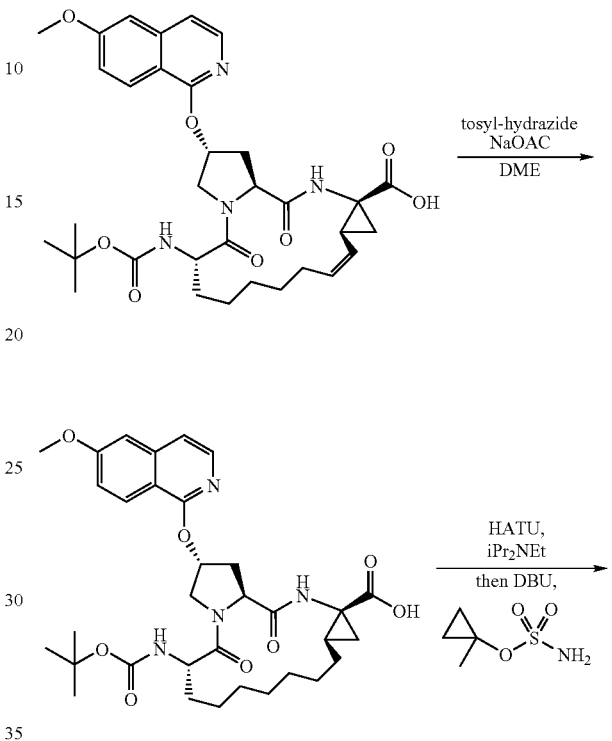

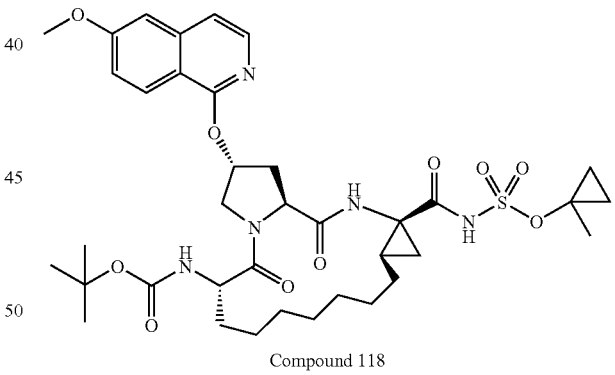

Compound 118

Reduction of the unsaturated macrocycle was accomplished according to the method presented in Example 115, adjusted for scale, to provide the fully saturated macrocyclic acid after purification by column chromatography on silica (2→8% MeOH/CH₂Cl₂) to produce the fully saturated macrocyclic acid (1.97 g, 95%). LCMS found 625.0 [M+H]⁺.

Compound 118 was prepared according to the method presented for the synthesis of compound 29. Treatment of the macrocyclic aryl ether acid under the same conditions, adjusted for scale, and purified by reverse phase HPLC afforded compound 118 (136 mg, 51%). ¹H NMR (300 MHz, CD₃OD): δ 8.97 (s, 1H), 8.22 (d, 1H), 7.90 (d, 1H) 7.35 (d, 1H), 7.25 (d, 1H), 7.16 (d, 1H), 5.87 (brs, 1H), 4.67 (m, 2H), 4.22 (dd, 1H), 4.07 (dd, 1H), 3.95 (s, 3H), 2.75 (m, 1H), 2.49

(m, 1H), 1.28-1.82 (m, 18H), 1.68 (s, 3H), 1.96 (s, 9H), 0.72 (m, 2H). LCMS found 758.1 [M+H]⁺.

Example 119

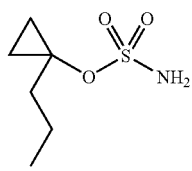

Compound 119 was prepared according to the method presented for the synthesis of Compound 29. Treatment of the saturated macrocycle arylether acid from Example 118 and sulfamic acid 1-propyl-cyclopropyl ester under the same conditions, adjusted for scale, and purified by reverse phase HPLC afforded compound 119 (167 mg, 53%): ¹H NMR (300 MHz, CD₃OD): δ 8.98 (s, 1H), 8.22 (d, 1H), 7.90 (d, 1H) 7.35 (d, 1H), 7.24 (d, 1H), 7.15 (d, 1H), 5.87 (brs, 1H), 4.67 (m, 2H), 4.22 (dd, 1H), 4.07 (dd, 1H), 3.95 (s, 3H), 2.73 (m, 1H), 2.48 (m, 1H), 1.28-1.82 (m, 23H), 1.20 (s, 9H), 0.97 (t, 3H), 0.72 (m, 2H). LCMS found 786.0 [M+H]⁺.

Example 120

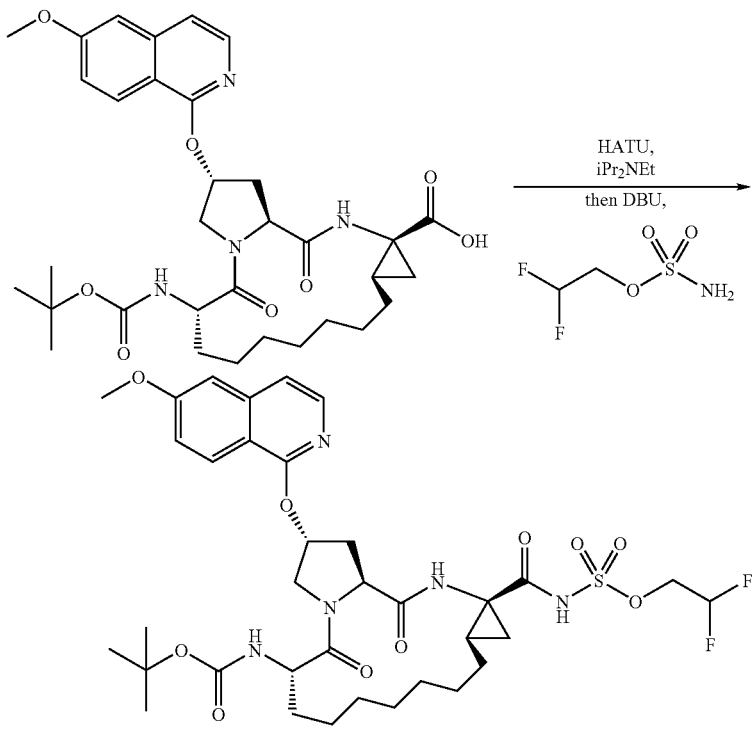

Compound 120

-continued

Compound 119

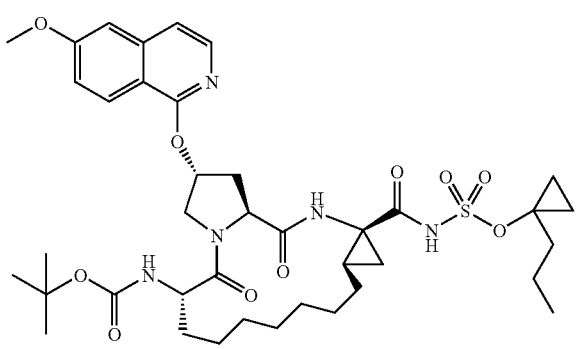

Compound 120 was prepared according to the method presented for the synthesis of compound 29. Treatment of the saturated macrocycle arylether acid from Example 118 and sulfamic acid 2,2-difluoro-ethyl ester under the same conditions, adjusted for scale, and purified by reverse phase HPLC afforded compound 120 (142 mg, 52%): ¹H NMR (300 MHz, CD₃OD): δ 8.93 (s, 1H), 8.21 (d, 1H), 7.90 (d, 1H) 7.33 (d, 1H), 7.24 (d, 1H), 7.15 (d, 1H), 6.12 (dt, 1H), 5.86 (brs, 1H), 4.66 (m, 2H), 4.53 (dt, 2H), 4.23 (dd, 1H), 4.06 (dd, 1H), 3.95

Example 121

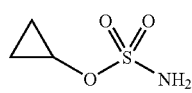

Compound 121

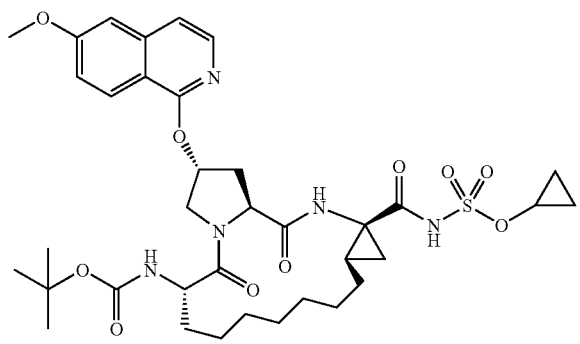

Compound 122

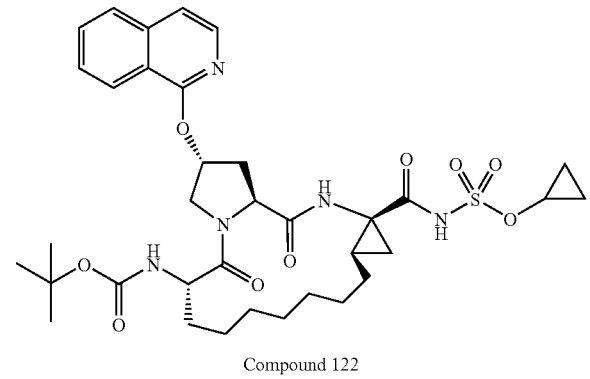

Compound 121 was prepared according to the method presented for the synthesis of compound 27. Treatment of the saturated macrocycle arylether acid from Example 118 under the same conditions, adjusted for scale, and purified by reverse phase HPLC afforded compound 121 (54 mg, 21%): $^1$H NMR (300 MHz, CD$_3$OD): δ 8.95 (s, 1H), 8.22 (d, 1H), 7.90 (d, 1H) 7.34 (d, 1H), 7.25 (d, 1H), 7.15 (d, 1H), 5.86 (brs, 1H), 4.69 (m, 2H), 4.28 (m, 1H), 4.22 (dd, 1H), 4.06 (dd, 1H), 2.75 (m, 1H), 2.48 (m, 1H), 1.3-1.8 (m, 17H), 1.20 (s, 9H), 0.96 (m, 2H), 0.72 (m, 2H). LCMS found 744.1 [M+H]$^+$.

Example 122

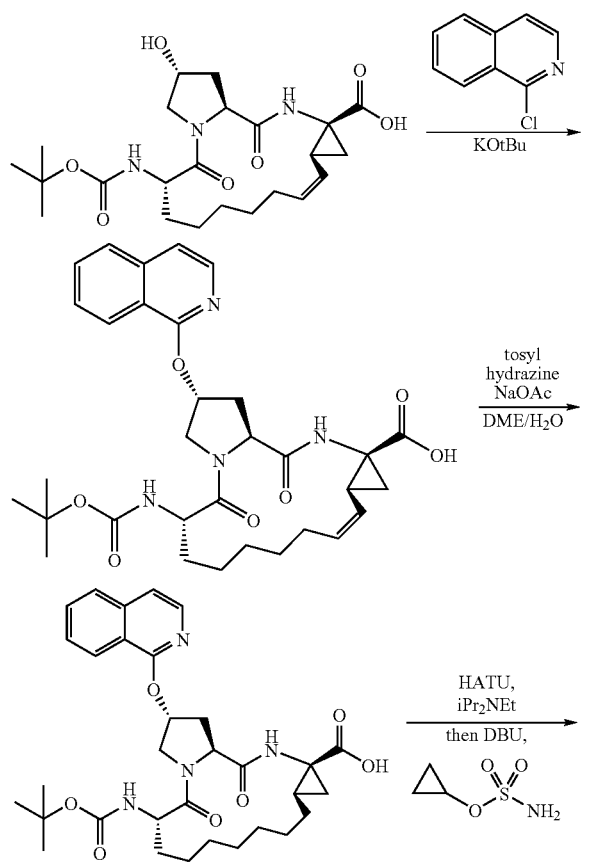

Aryl ether formation was accomplished according to the method presented in example 36, adjusted for scale, to provide the desired aryl ether macrocycle (537 mg, 77%). LCMS found 593.0 [M+H]$^+$.

Reduction of the unsaturated macrocycle was accomplished according to the method presented in Example 115 adjusted for scale to provide the fully saturated macrocyclic acid (196 mg, 42%). LCMS found 595.0 [M+H]$^+$.

Compound 122 was prepared according to the method presented for the synthesis of compound 27. Treatment of the saturated macrocycle arylether acid from Example 118 under the same conditions, adjusted for scale, and purified by reverse phase HPLC, afforded compound 122 (77 mg, 33%): $^1$H NMR (300 MHz, CD$_3$OD): δ 8.95 (s, 1H), 8.29 (d, 1H), 7.97 (d, 1H), 7.82 (d, 1H), 7.73 (t, 1H), 7.54 (t, 1H), 7.35 (d, 1H), 5.91 (brs, 1H), 4.67 (m, 2H), 4.27 (m, 2H), 4.07 (dd, 1H), 2.75 (m, 1H), 2.46 (m, 1H), 1.3-1.8 (m, 17H), 1.20 (s, 9H), 0.95 (m, 2H), 0.78 (m, 2H). LCMS found 714.0 [M+H]$^+$.

Example 123

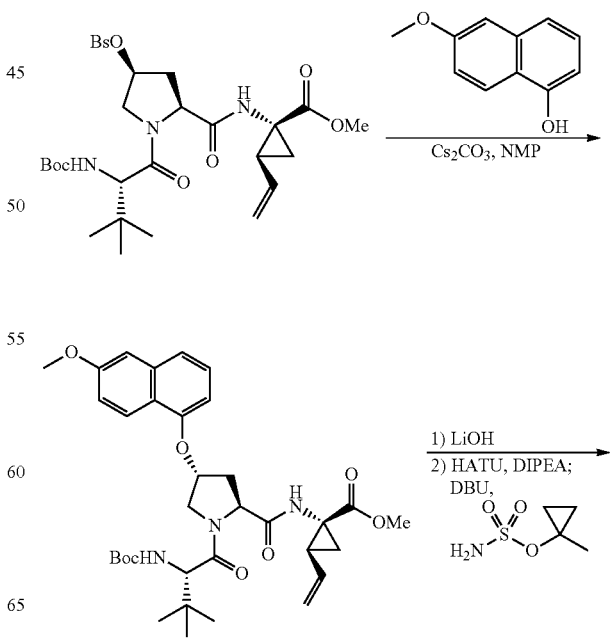

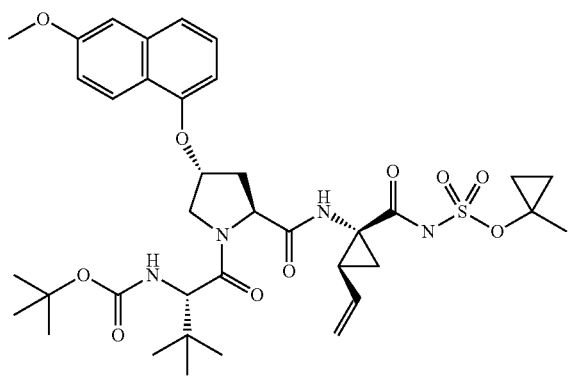

Compound 123

Compound 123 was prepared according to the method presented example 14. Treatment of 1-{[4-(4-Bromo-benzenesulfonyloxy)-1-(2-tert-butoxycarbonylamino-3,3-dimethyl-butyryl)-pyrrolidine-2-carbonyl]-amino}-2-vinyl-cyclopropanecarboxylic acid methyl ester (345 mg, 0.50 mmol) under the same conditions adjusted for scale and with the exceptions of utilizing 6-methoxy-naphthalen-1-ol (97 mg, 0.56 mmol), sulfamic acid 1-methyl-cyclopropyl ester (96 mg, 0.63 mmol), and performing the hydrolysis of the methyl ester at 40° C. for 3 h provided compound 123 (152 mg, 40%): $^1$H NMR (d$_3$-MeOD, 300 MHz) δ 9.24 (s, 1H), 8.06 (d, 1H), 8.31-8.39 (m, 2H), 7.18 (s, 1H), 7.02 (d, 1H), 6.81 (d, 1H), 5.73 (m, 1H), 5.32 (s, 1H), 5.29 (d, 1H), 5.13 (d, 1H), 4.49 (m, 1H), 4.41 (d, 1H), 4.30 (s, 1H), 4.05 (m, 1H), 3.90 (s, 3H), 2.60 (m, 1H), 2.23 (m, 2H), 1.88 (m, 1H), 1.67 (s, 3H), 1.43 (m, 1H), 1.36 (s, 9H), 1.28 (m, 2H), 1.05 (s, 9H), 0.68 (m, 2H). LCMS found 741.1 [M+H]$^+$.

Example 124

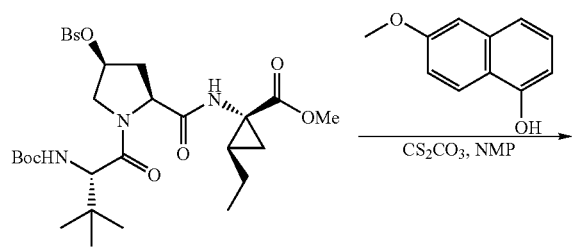

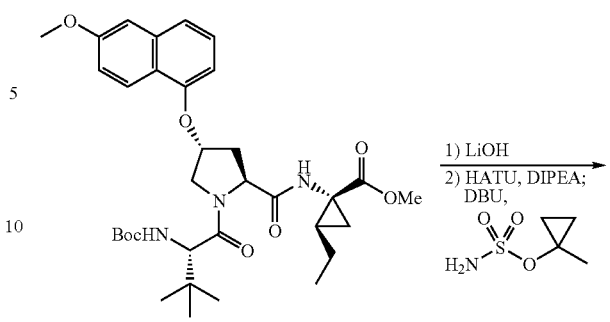

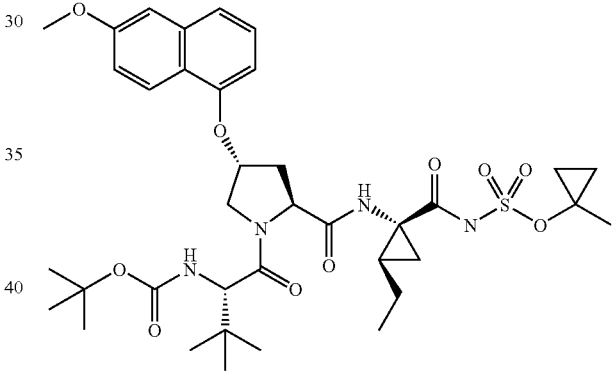

Compound 124

Compound 124 was prepared according to the method presented in example 14. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (344 mg, 0.50 mmol) under the same conditions adjusted for scale and with the exceptions of utilizing 6-methoxy-naphthalen-1-ol (97 mg, 0.56 mmol), sulfamic acid 1-methyl-cyclopropyl ester (114 mg, 0.75 mmol), and performing the hydrolysis of the methyl ester at 40° C. for 3 h provided compound 124 (178 mg, 48%): $^1$H NMR (d$_3$-MeOD, 300 MHz) δ 9.15 (s, 1H), 8.04 (d, 1H), 7.31-7.38 (m, 2H), 7.17 (d, 1H), 7.01 (d, 1H), 6.79 (d, 1H), 5.48 (s, 1H), 4.50 (m, 1H), 4.40 (m, 1H), 4.29 (s, 1H), 4.03 (d, 1H), 3.89 (s, 3H), 2.57 (m, 1H), 2.19 (m, 1H), 1.68 (s, 3H), 1.46-1.64 (m, 3H), 1.34 (s, 9H), 1.24-1.31 (m, 2H), 1.19 (m, 2H), 1.043 (s, 9H), 0.95 (m, 3H), 0.68 (m, 2H). LCMS found 743.2 [M+H]$^+$.

Example 125

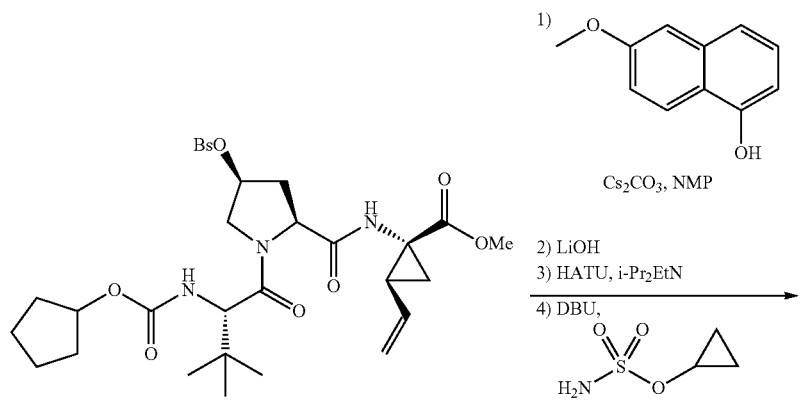

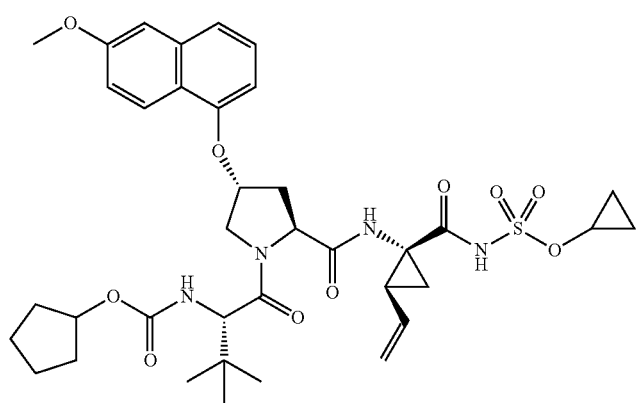

Compound 125

Compound 125 was prepared according to the method presented in the Example 14. Treatment of 1-{[4-(4-bromo-benzenesulfonyloxy)-1-(2-cyclopentyloxycarbonylamino-3,3-dimethyl-butyryl)-pyrrolidine-2-carbonyl]-amino}-2-vinyl-cyclopropanecarboxylic acid methyl ester (355 mg, 0.51 mmol) occurred under the same conditions, adjusted for scale and with the exception of utilizing 6-methoxy-naphthalen-1-ol (100 mg, 0.57 mmol) and sulfamic acid cyclopropyl ester (91 mg, 0.66 mmol). Purification of the crude product was accomplished by column chromatography on silica (0→20% MeOH/CH$_2$Cl$_2$) to afford compound 125 (188 mg, 49%): $^1$H NMR (d$_3$-MeOD, 300 MHz) δ 9.22 (s, 1H), 8.03 (d, 1H), 7.34 (m, 2H), 7.18 (d, 1H), 7.03 (d, 1H), 6.80 (d, 1H), 5.74 (s, 1H), 5.32 (m, 1H), 5.28 (d, 1H), 5.14 (d, 1H), 4.82 (m, 1H), 4.52 (m, 1H), 4.38 (m, 1H), 4.25 (m, 1H), 4.03 (m, 1H), 3.89 (s, 3H), 2.60 (m, 1H), 2.23 (m, 2H), 1.88 (m, 1H), 1.23-1.79 (m, 12H), 1.03 (s, 9H), 0.92 (m, 2H), 0.74 (m, 2H). LCMS found 741.07 [M+H]$^+$.

Example 126

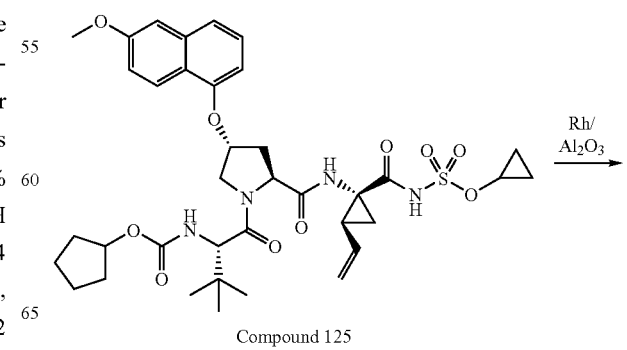

Compound 125

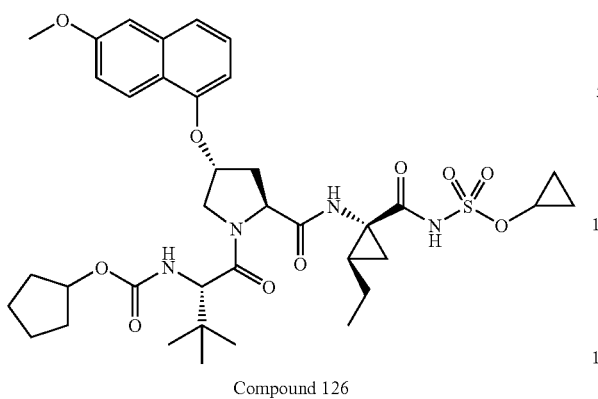

Compound 126

Compound 126 was prepared according to the method presented for the synthesis of example 18. Treatment of compound 125 under the same conditions adjusted for scale provided the desired compound 126 (48 mg, 60%): $^1$H NMR (d$_3$-MeOD, 300 MHz) δ 9.08 (s, 1H), 8.03 (d, 1H), 7.35 (m, 2H), 7.18 (d, 1H), 7.02 (d, 1H), 6.79 (m, 1H), 5.27 (s, 1H), 4.53 (m, 1H), 4.31 (m, 3H), 4.05 (m, 1H), 3.88 (s, 3H), 2.59 (m, 1H), 2.19 (m, 1H), 1.21-1.79 (m, 17H), 1.03 (s, 9H), 0.94 (m, 2H), 0.76 (m, 2H). LCMS found 742.95 [M+H]$^+$.

Example 127

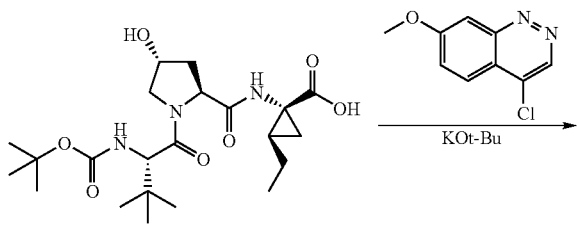

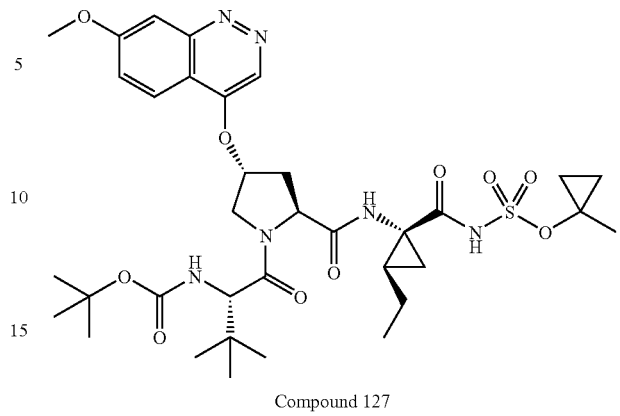

Compound 127

To 1-{[1-(2-tert-butoxycarbonylamino-3,3-dimethyl-butyryl)-4-hydroxy-pyrrolidine-2-carbonyl]-amino}-2-ethyl-cyclopropanecarboxylic acid (210 mmg, 0.46 mmol) at 0° C. (external temperature, ice bath) was added KOt-Bu (1 m in THF, 2.3 mL, 2.3 mmol, 5 equiv.) and 4-chloro-7-methoxy-cinnoline (95 mg, 0.49 mmol, 1.06 equiv.) in THF (3 mL). The reaction was stirred at 0° C. for 2.5 h and diluted with EtOAc. The solution was washed with aqueous HCl (1M), resulting a precipitation of the crude product. The organic layer was dried over Na$_2$SO$_4$ and combined with the precipitate. The crude product was purified by column chromatography (0→15% MeOH/CH$_2$Cl$_2$) to provide 1-{[1-(2-tert-butoxycarbonylamino-3,3-dimethyl-butyryl)-4-(7-methoxy-cinnolin-4-yloxy)-pyrrolidine-2-carbonyl]-amino}-2-ethyl-cyclopropanecarboxylic acid (161 mg, 57%).

To a solution of 1-{[1-(2-tert-butoxycarbonylamino-3,3-dimethyl-butyryl)-4-(7-methoxy-cinnolin-4-yloxy)-pyrrolidine-2-carbonyl]-amino}-2-ethyl-cyclopropanecarboxylic acid (161 mg, 0.26 mmol) in CH$_2$Cl$_2$ (2 mL) was added HATU (139 mg, 0.36 mmol, 1.5 equiv.) and DIPEA (0.09 mL, 0.52 mmol, 2 equiv.). The solution was stirred at room temperature for 30 min before sulfamic acid 1-methyl-cyclopropyl ester (90 mg, 0.60 mmol, 2.4 equiv.) and DBU (0.22 m×L, 1.47 mmol, 5.5 equiv) were added. The reaction was stirred for 60 h then diluted with EtOAc. The solution was washed with aqueous HCl (1M, 3×) and Brine (3×). The organic layer was dried over Na$_2$SO$_4$ and concentrated in vacuo. The crude product was purified by reverse phase HPLC (30→90% MeCN/H$_2$O/0.1% TFA) to provide compound 127 (13 mg, 7%): $^1$H NMR (CD$_3$OD, 300 MHz) δ 9.13 (s, 1H), 8.31 (d, 1H), 7.59 (d, 1H), 7.50 (s, 1H), 4.49 (s, 1H), 4.39 (m, 1H), 4.29 (s, 1H), 4.08 (s, 3H), 3.82 (m, 2H), 2.11 (m, 1H), 1.95 (m, 1H), 1.67 (s, 3H), 1.50-1.62 (m, 3H), 1.45 (s, 9H), 1.29 (m, 2H), 1.03 (s, 9H), 0.98 (m, 3H), 0.69 (m, 2H).

Example 128

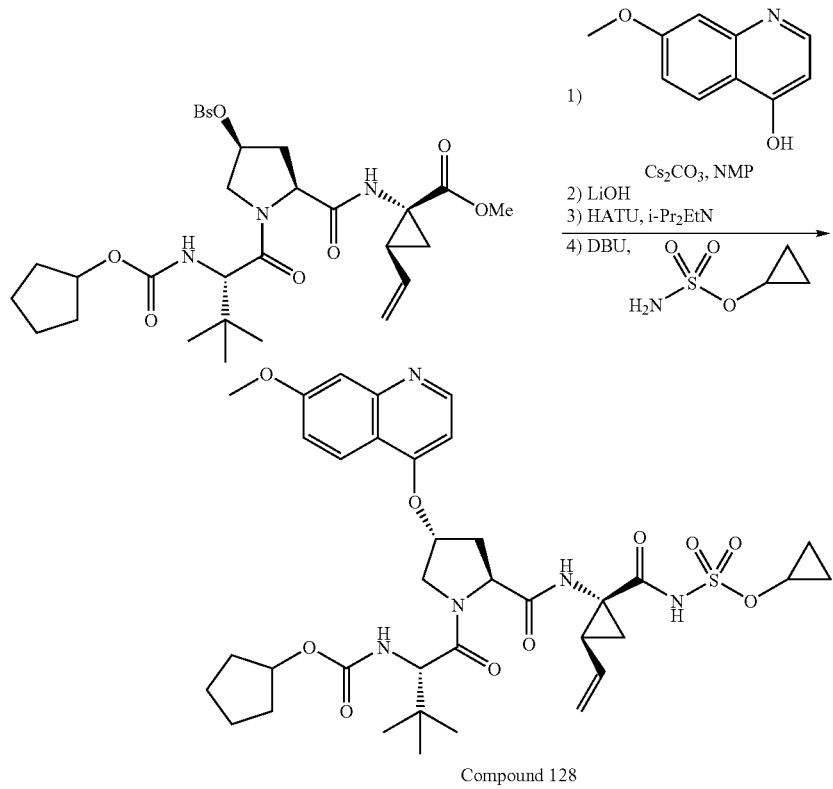

Compound 128

Compound 128 was prepared according to the method presented in the synthesis of compound 14. Treatment of 1-{[4-(4-bromo-benzenesulfonyloxy)-1-(2-cyclopentyloxy-carbonylamino-3,3-dimethyl-butyryl)-pyrrolidine-2-carbonyl]-amino}-2-vinyl-cyclopropanecarboxylic acid methyl ester (178 mg, 0.25 mmol) occurred under the same conditions, adjusted for scale and with the exception of utilizing 7-methoxy-quinolin-4-ol (50 mg, 0.28 mmol) and sulfamic acid cyclopropyl ester (48 mg, 0.35 mmol). Purification of the crude product was accomplished by reverse phase HPLC (30→90% MeCN/H$_2$O/0.1% TFA) to provide compound 128 (41 mg, 22%): $^1$H NMR (d$_3$-MeOD, 300 MHz) δ 9.12 (s, 1H), 8.70 (d, 1H), 8.16 (d, 1H), 7.35 (s, 1H), 7.18 (d, 1H), 7.07 (d, 1H), 5.82 (m, 1H), 5.52 (s, 1H), 5.24 (d, 1H), 5.17 (d, 1H), 4.62 (m, 2H), 4.57 (m, 1H), 4.18 (m, 2H), 3.98 (s, 3H), 2.74 (m, 1H), 2.58 (m, 1H), 2.21 (m, 1H), 1.84 (m, 1H), 1.29-1.59 (m, 12H), 1.02 (s, 9H), 0.93 (m, 2H), 0.75 (m, 2H). LCMS found 742.2 [M+H]$^+$.

Example 129

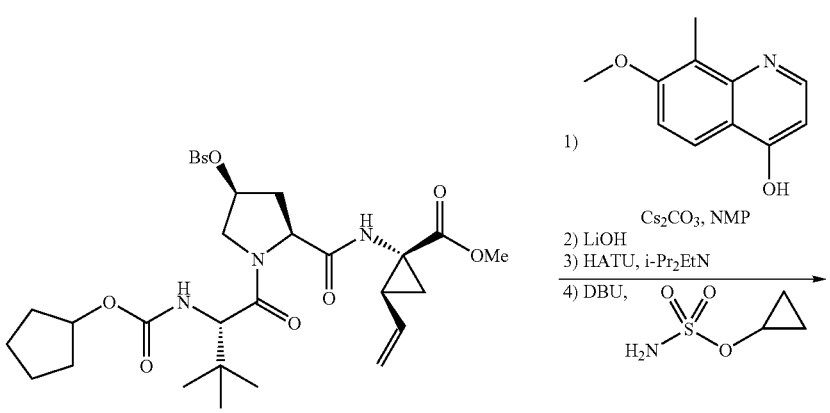

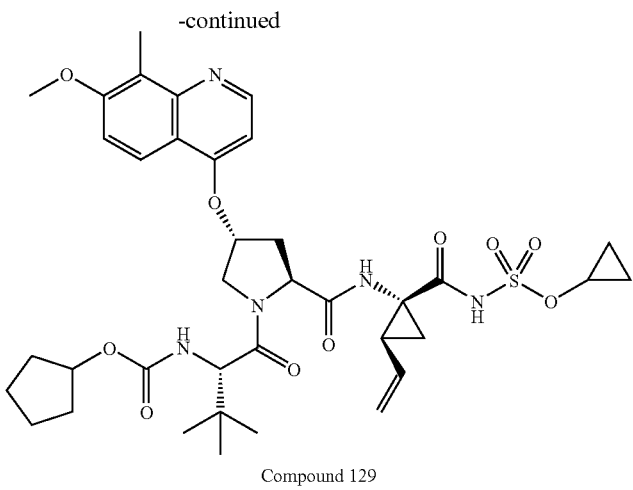

Compound 129

Compound 129 was prepared according to the method presented in the synthesis of compound 14. Treatment of 1-{[4-(4-bromo-benzenesulfonyloxy)-1-(2-cyclopentyloxy-carbonylamino-3,3-dimethyl-butyryl)-pyrrolidine-2-carbonyl]-amino}-2-vinyl-cyclopropanecarboxylic acid methyl ester (356 mg, 0.51 mmol) occurred under the same conditions, adjusted for scale and with the exception of utilizing 7-methoxy-8-methyl-quinolin-4-ol (107 mg, 0.57 mmol) and sulfamic acid cyclopropyl ester (115 mg, 0.84 mmol). Purification of the crude product was accomplished by reverse phase HPLC (30→90% MeCN/H$_2$O/0.1% TFA) to provide compound 129 (225 mg, 57%): $^1$H NMR (d$_3$-MeOD, 300 MHz) δ 9.25 (s, 1H), 8.89 (s, 1H), 8.39 (d, 1H), 7.67 (d, 1H), 7.46 (d, 1H), 5.77 (s, 1H), 5.73 (m, 1H), 5.34 (d, 1H), 5.17 (d, 1H), 4.66 (m, 2H), 4.32 (m, 1H), 4.24 (m, 1H), 4.16 (m, 1H), 4.11 (s, 3H), 2.78 (m, 1H), 2.58 (s, 3H), 2.43 (m, 1H), 2.29 (m, 1H), 1.92 (m, 1H), 1.29-1.59 (m, 12H), 1.02 (s, 9H), 0.93 (m, 2H), 0.75 (m, 2H). LCMS found 756.14 [M+H]$^+$.

Example 130

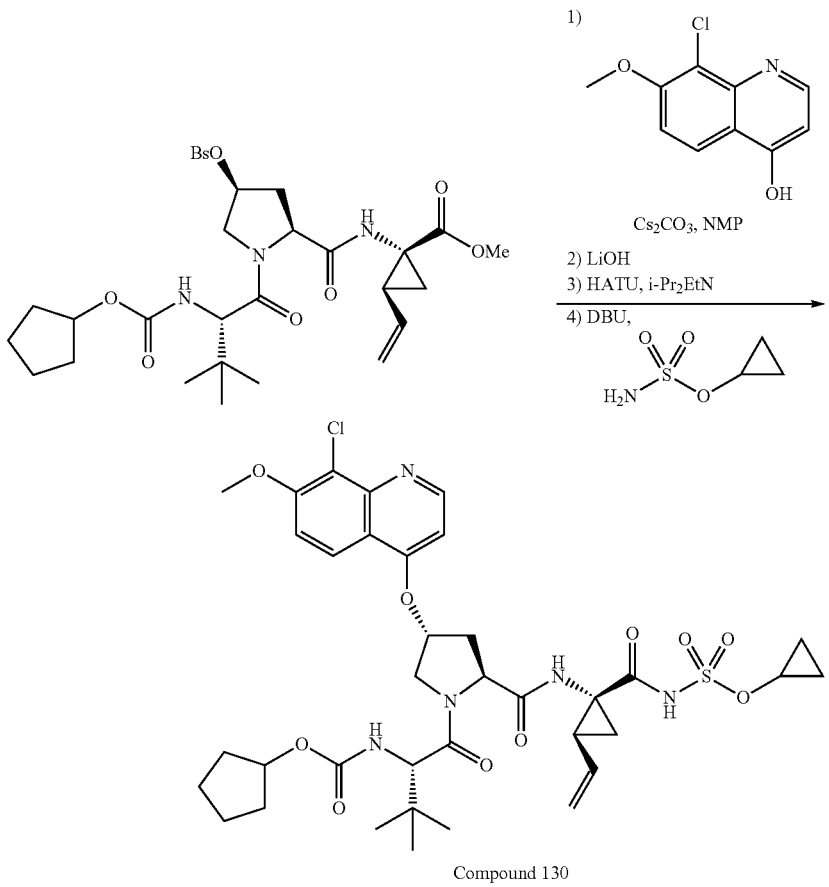

Compound 130

Compound 130 was prepared according to the method presented in the synthesis of compound 14. Treatment of 1-{[4-(4-bromo-benzenesulfonyloxy)-1-(2-cyclopentyloxy-carbonylamino-3,3-dimethyl-butyryl)-pyrrolidine-2-carbonyl]-amino}-2-vinyl-cyclopropanecarboxylic acid methyl ester (355 mg, 0.51 mmol) occurred under the same conditions, adjusted for scale and with the exception of utilizing 7-methoxy-8-chloro-quinolin-4-ol (118 mg, 0.57 mmol) and sulfamic acid cyclopropyl ester (151 mg, 1.10 mmol). Purification of the crude product was accomplished by reverse phase HPLC (30→90% MeCN/H$_2$O/0.1% TFA) to provide compound 130 (204 mg, 48%): $^1$H NMR (d$_3$-MeOD, 300 MHz) δ 9.24 (s, 1H), 8.96 (s, 11H), 8.46 (d, 1H), 7.79 (d, 1H), 7.55 (d, 1H), 5.80 (s, 1H), 5.71 (m, 1H), 5.34 (d, 1H), 5.17 (d, 1H), 4.66 (m, 3H), 4.23 (m, 2H), 4.19 (s, 3H), 2.78 (m, 1H), 2.46 (m, 1H), 2.32 (m, 1H), 1.93 (m, 1H), 1.29-1.57 (m, 12H), 1.01 (s, 9H), 0.93 (m, 2H), 0.75 (m, 2H). LCMS found 776.13 [M+H]$^+$.

Example 131

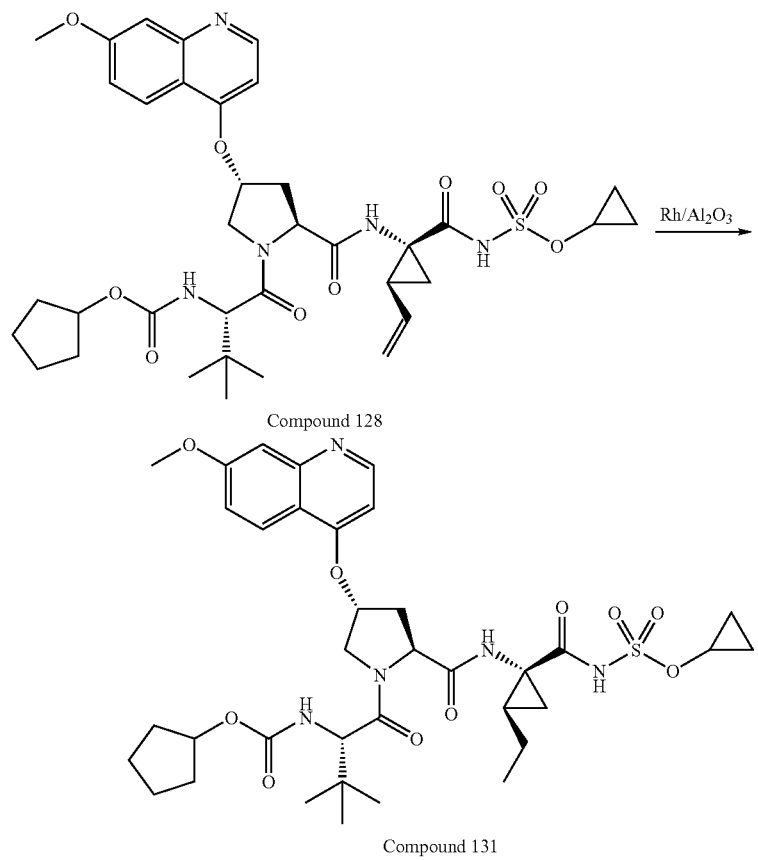

Compound 128

Compound 131

Compound 131 was prepared according to the method presented for the synthesis of compound 18. Treatment of compound 128 under the same conditions adjusted for scale provided compound 131 (12 mg, 58%): $^1$H NMR (d$_3$-MeOD, 300 MHz) δ 9.12 (s, 1H), 8.93 (d, 1H), 8.37 (d, 1H), 7.45 (m, 3H), 5.74 (s, 1H), 4.64 (m, 2H), 4.44 (m, 1H), 4.27 (m, 1H), 4.14 (m, 1H), 4.05 (s, 3H), 2.74 (m, 1H), 2.40 (m, 1H), 1.23-1.62 (m, 17H), 1.03 (s, 9H), 0.97 (m, 2H), 0.76 (m, 2H). LCMS found 744.19 [M+H]$^+$.

Example 132
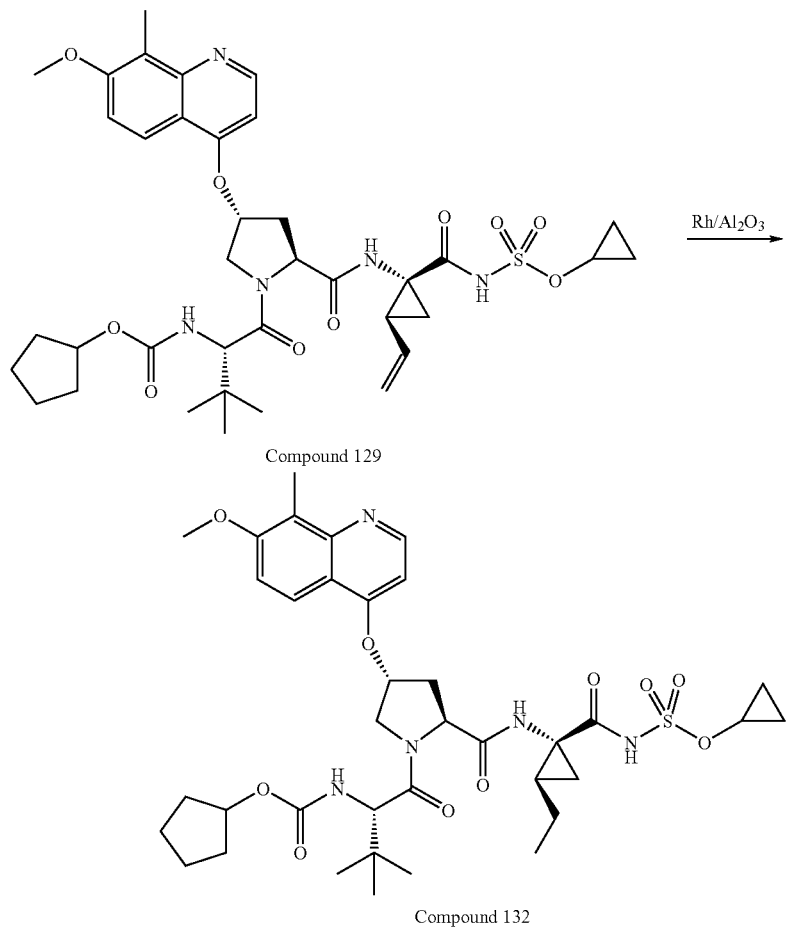
Compound 132 was prepared according to the method presented for the synthesis of compound 18. Treatment of compound 129 under the same conditions adjusted for scale provided compound 132 (34 mg, 43%): $^1$H NMR (d$_3$-MeOD, 300 MHz) δ 9.14 (s, 1H), 8.88 (d, 1H), 8.38 (d, 1H), 7.67 (d, 1H), 7.46 (d, 1H), 5.76 (s, 1H), 4.66 (m, 2H), 4.27 (m, 2H), 4.16 (m, 1H), 4.11 (s, 3H), 2.77 (m, 1H), 2.58 (s, 3H), 2.44 (m, 1H), 1.23-1.62 (m, 17H), 1.02 (s, 9H), 0.96 (m, 2H), 0.76 (m, 2H). LCMS found 758.25 [M+H]$^+$.
Example 133
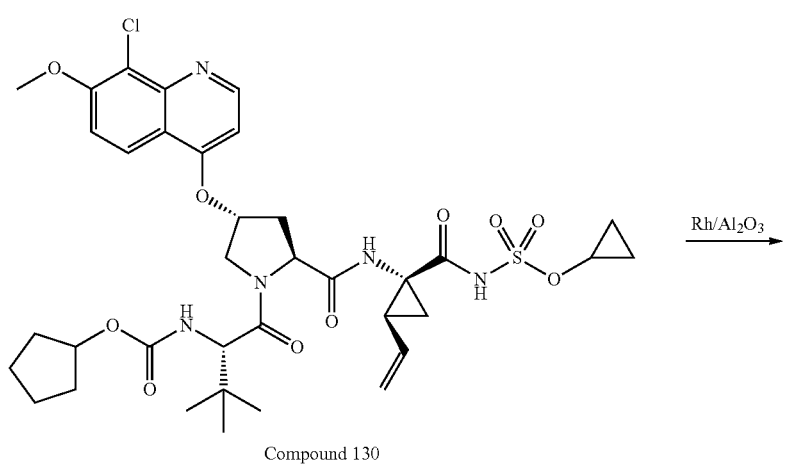

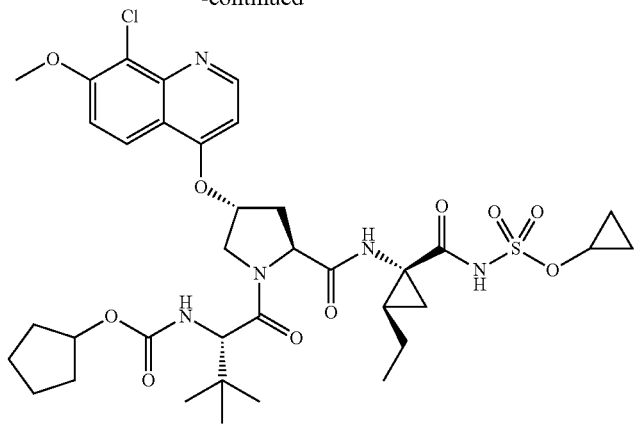

Compound 133

Compound 133 was prepared according to the method presented for the synthesis of compound 18. Treatment of compound 130 under the same conditions adjusted for scale provided compound 133 (35 mg, 43%): $^1$H NMR (d$_3$-MeOD, 300 MHz) δ 9.13 (s, 1H), 8.96 (d, 1H), 8.47 (d, 1H), 7.79 (d, 1H), 7.55 (d, 1H), 5.79 (s, 1H), 4.66 (m, 2H), 4.27 (m, 2H), 4.19 (s, 3H), 4.11 (m, 1H), 2.77 (m, 1H), 2.42 (m, 1H), 1.23-1.63 (m, 17H), 1.01 (s, 9H), 0.94 (m, 2H), 0.76 (m, 2H). LCMS found 778.19 [M+H]$^+$.

Example 134

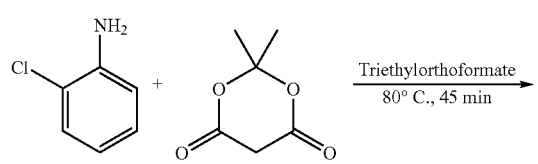

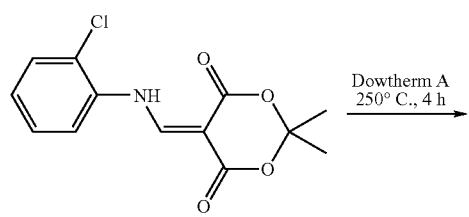

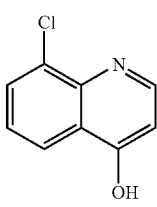

To 2-chloroaniline (8.85 g, 69.4 mmol, 2 equiv) in a round bottom flask was added triethyl orthoformate (30.85 g, 208.2 mmol, 6.0 equiv) and Meldrum's acid (5 g, 34.7 mmol, 1 equiv). The mixture was stirred at 80° C. for 45 minutes, cooled to room temperature, then poured onto ice water. The white color precipitant was filtered, dried on house vacuum, then further dried in a vacuum oven at 40° C. overnight. Yield=6.87 g (70%). $^1$H NMR (CDCl$_3$, 300 MHz) δ 11.70 (d, 1H), 8.7 (d, 1H), 7.51-7.22 (m, 4H), 1.77 (s, 6H). LCMS found 281.60 [M+H]$^+$.

Into the Dowtherm-A (100 mL) in a three-necked round bottom flask at 250° C. was slowly added a hot solution of 5-[(2-chloro-phenylamino)-methylene]-2,2-dimethyl-[1,3]dioxane-4,6-dione (6.87 g, 24.4 mmol, 1 equiv) in Dowtherm-A (50 mL) which was at 80-100° C. The internal temperature of the reaction was kept between 240 and 250° C. during the addition. The reaction content was continuously stirred at this temperature for 4 hours and it was cooled down to room temperature. The crude mixture was then poured onto ice/isopropanol mixture in a beaker (2 L) to precipitate the desired compound. The precipitate was filtered through a glass sintered glass funnel and washed with cold isopropanol (100 mL) and hexanes (100 mL×2). The filter cake was then dissolved in MeOH and 2 equiv of 1N HCl was added. The solvent was removed and the residue was suspended in (1:1) ether/hexanes mixture and the solid was filtered. The filter cake was then washed with ether and dried, first on house vacuum and then on vacuum oven at 40° C. overnight. (4.49 g, 99%) $^1$H NMR (CD$_3$OD, 300 MHz) δ 8.77 (d, 1H), 8.46 (d, 1H), 8.22 (d, 1H), 7.79 (t, 1H), 7.23 (d, 1H). LCMS found 180.44 [M+H]$^+$.

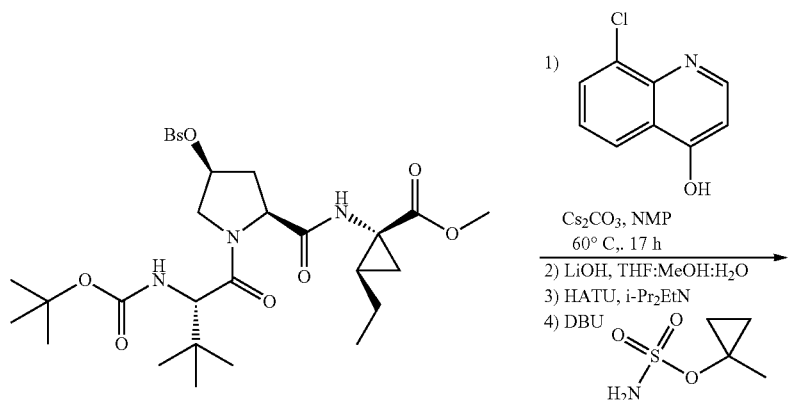

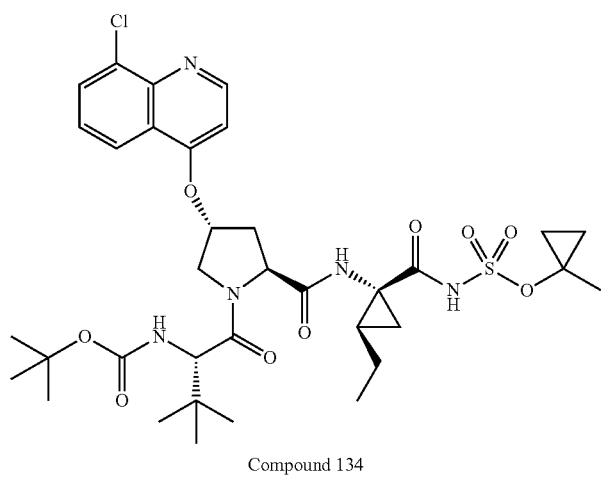

Compound 134

Compound 134 was prepared according to the method presented in the synthesis of compound 14. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (300 mg, 0.436 mmol) occurred under the same conditions, adjusted for scale and with exception of utilizing 8-chloro-quinolin-4-ol (86.2 mg, 0.48 mmol) and sulfamic acid 1-methyl-cyclopropyl ester (113 mg, 0.63 mmol). Purification of the crude product was accomplished by reverse phase HPLC (20%→85%, MeCN/H$_2$O/0.1% TFA) to provide compound 134 (176 mg, 78%): $^1$H NMR (CD$_3$OD, 300 MHz) δ 9.09 (br s, 1H), 9.56 (brs, 1H), 8.35 (m, 1H), 8.12 (brs, 1H), 7.7 (m, 1H), 7.52 (brs, 1H), 5.67 (brs, 1H), 4.56 (m, 2H), 4.07 (brs, 2H), 2.67 (m, 1H), 2.36 (m, 1H), 1.64 (m, 3H), 1.54 (m, 4H), 1.24 (m, 2H), 1.10 (m, 12H), 1.00 (m, 13H), 0.64 (m, 2H). LCMS found 750.53 [M+H]$^+$.

Example 135

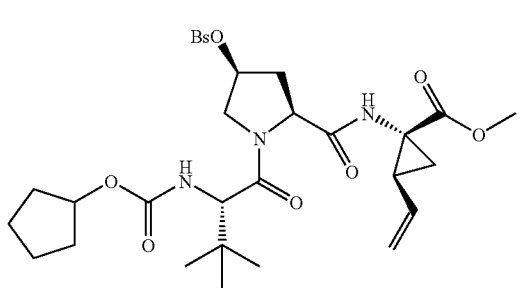 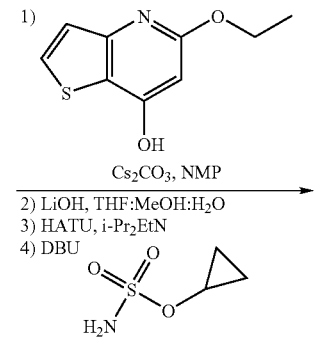

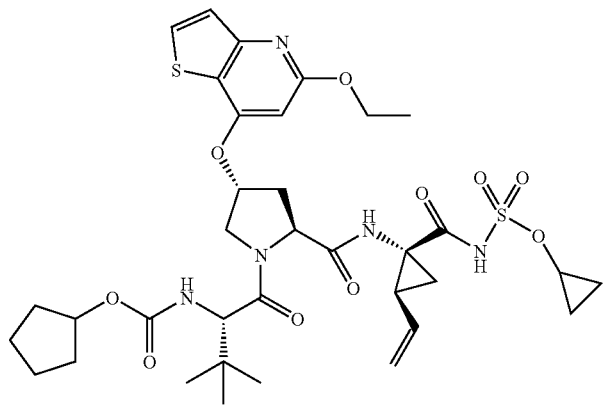

Compound 135

1-{[1-(2-Cyclopentyloxycarbonylamino-3,3-dimethyl-butyryl)-4-(5-ethoxy-thieno[3,2-b]pyridin-7-yloxy)-pyrrolidine-2-carbonyl]-amino}-2-vinyl-cyclopropanecarboxylic acid methyl ester was synthesized according to the method presented in Example 14 with the exception of using 5-ethoxy-thieno[3,2-b]pyridin-7-ol (41 mg, 0.21 mmol) and adjusted for scale to give the desired aryl ether which was used crude in the next reaction. LCMS found 657.03 [M+H]+.

1-{[1-(2-Cyclopentyloxycarbonylamino-3,3-dimethyl-butyryl)-4-(5-ethoxy-thieno[3,2-b]pyridin-7-yloxy)-pyrrolidine-2-carbonyl]-amino}-2-vinyl-cyclopropanecarboxylic acid was prepared according to the method presented in Example 14. Treatment of the methyl ester (100 mg, 0.15 mmol) under the same conditions adjusted for scale provided the desired acid (20 mg, 21%). LCMS found 643.04 [M+H]+.

Compound 135 was prepared according to the method presented in the synthesis of Example 27. Treatment of 1-{[1-(2-cyclopentyloxycarbonylamino-3,3-dimethyl-butyryl)-4-(5-ethoxy-thieno[3,2-b]pyridin-7-yloxy)-pyrrolidine-2-carbonyl]-amino}-2-vinyl-cyclopropanecarboxylic acid (200 mg, 0.31 mmol) under the same conditions adjusted for scale provided compound 135 (71 mg, 30%): $^1$H NMR (CD$_3$OD, 300 MHz, diagnostic peaks) δ 9.29 (s, 1H), 7.94 (d, 1H), 7.34 (d, 1H), 6.58 (s, 1H), 4.08 (m, 1H), 0.93 (m, 2H), 0.74 (m, 2H). LCMS found 762.06 [M+H]+.

Example 136

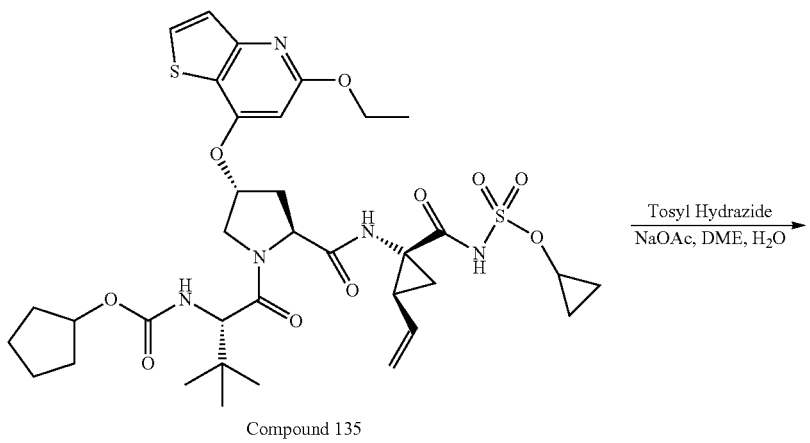

Compound 135

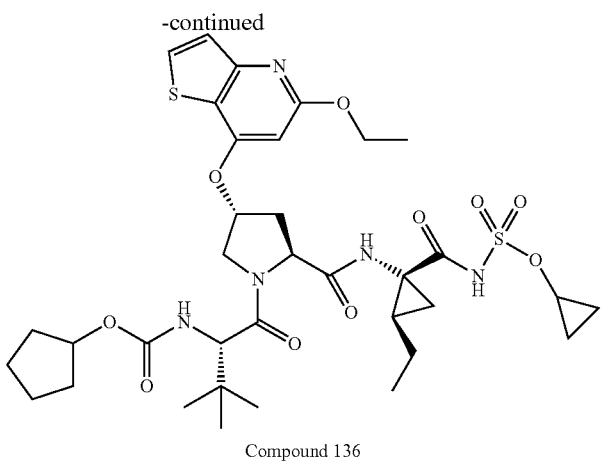

Compound 136

Compound 136 was prepared according to the method presented in example 20. Treatment of compound 135 (56 mg, 0.07 mmol) under the same conditions adjusted for scale provided compound 136 (14.9 mg, 28%): $^1$H NMR (CD$_3$OD, 300 MHz, diagnostic peaks) δ 9.20 (s, 1H), 7.94 (m, 1H), 7.35 (m, 1H), 6.58 (m, 1H), 5.51 (m, 1H). LCMS found 764.08 [M+H]$^+$.

Example 137

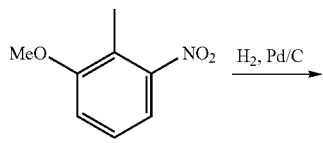

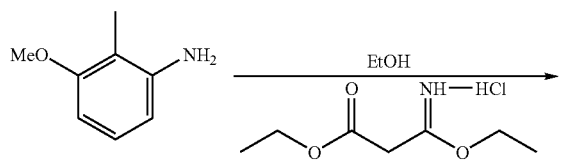

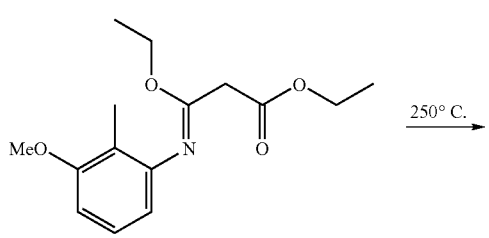

-continued

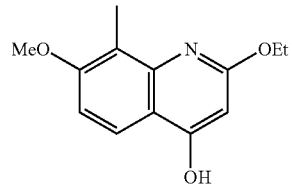

To 2-methyl-3-nitroanisole (5.02 g, 29.9 mmol) in EtOH (300 mL) was added Pd/C (0.50 g). The reaction was stirred under a H$_2$ balloon overnight then filtered through celite to afford 3-methoxy-2-methylaniline (4.00 g, 98%). LCMS found 138.0 [M+H]$^+$.

To 3-methoxy-2-methylaniline (2.15 g, 15.6 mmol) in anhydrous EtOH (30 mL) was added ethyl 3-ethoxy-3-iminopropionate (3.05 g, 15.6 mmol). The reaction was stirred overnight then filtered through celite. The filtrate was concentrated then purified by column chromatography on silica (2→10% EtOAc/hexane) to afford 3-ethoxy-3-(3-methoxy-2-methyl-phenylimino)-propionic acid ethyl ester (3.84 g, 88%). LCMS found 280.2 [M+H]$^+$.

3-Ethoxy-3-(3-methoxy-2-methyl-phenylimino)-propionic acid ethyl ester (1.56 g, 5.57 mmol) was dissolved in diphenyl ether then placed in a 300° C. sand bath. The internal temperature was kept between 240-250° C. for 15 minutes then the reaction was cooled to room temperature. The crude material was directly loaded onto a silica gel column (0→60% EtOAc/hexane) to afford 2-ethoxy-7-methoxy-8-methyl-quinolin-4-ol (882 mg, 68%). LCMS found 234.1 [M+H]$^+$.

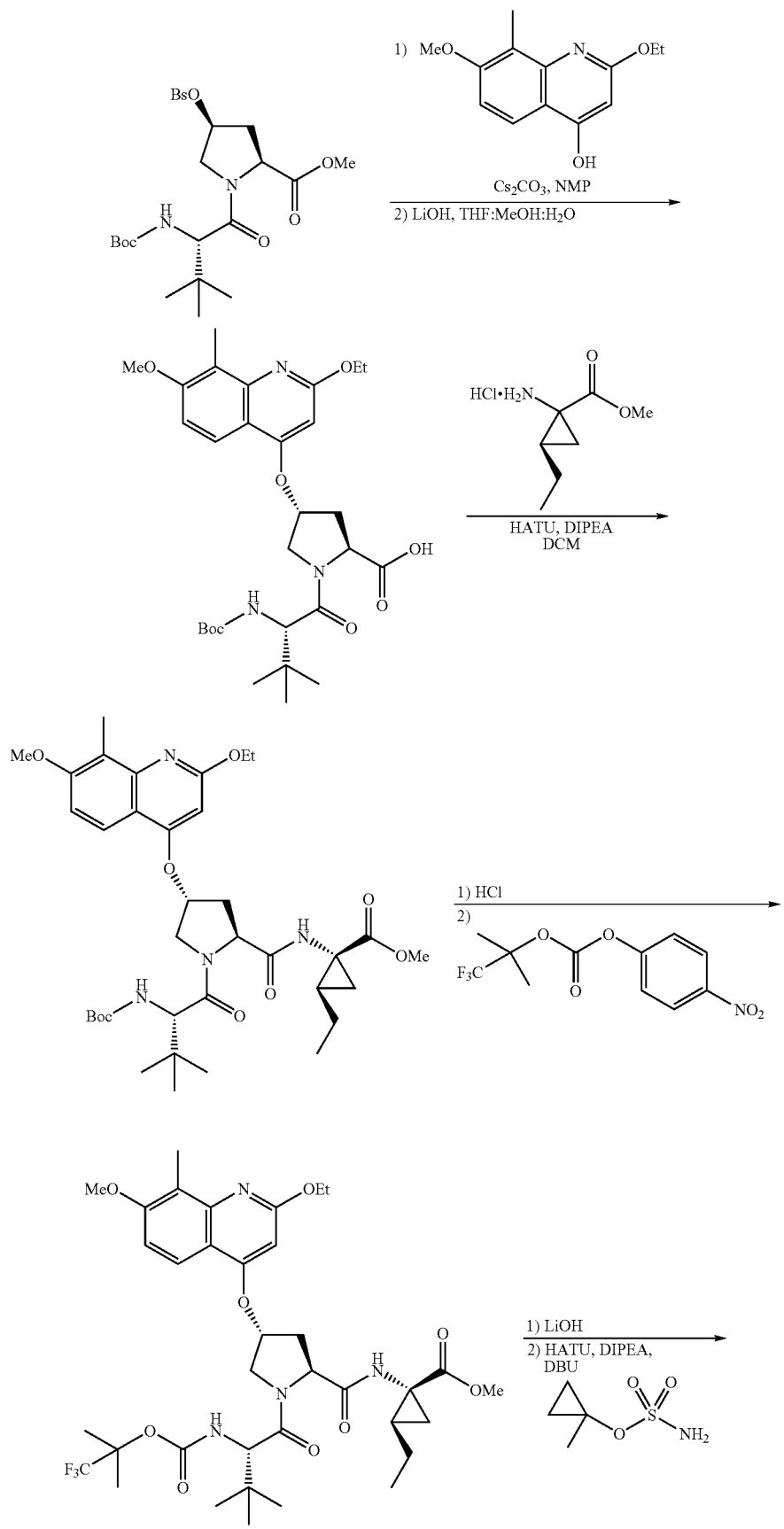

-continued

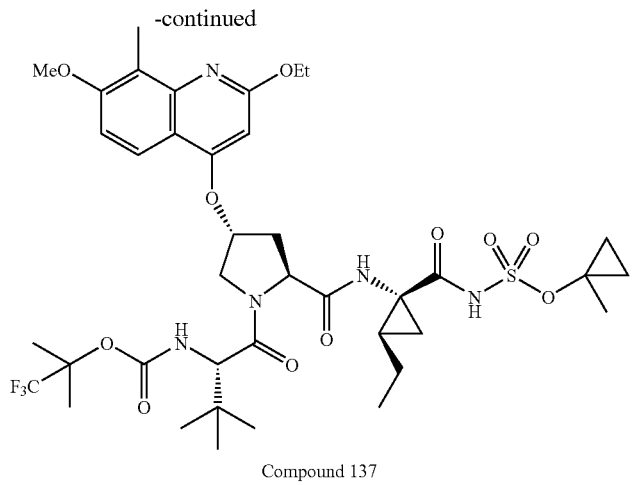

Compound 137

To 4-(4-bromo-benzenesulfonyloxy)-1-(2-tert-butoxycarbonylamino-3,3-dimethyl-butyryl)-pyrrolidine-2-carboxylic acid methyl ester (600 mg, 1.04 mmol) and 2-ethoxy-7-ethoxy-8-methyl-4-hydroxyquinoline (274 mg, 1.18 mmol) in NMP (3.6 mL) was added Cs$_2$CO$_3$ (2.54 g, 7.80 mmol). The reaction mixture was heated to 60° C. overnight then cooled to room temperature. After dilution with EtOAc, the organic phase was washed sequentially with aqueous 5% LiCl, saturated aqueous NH$_4$Cl, and saturated aqueous NaCl. The organic phase was then dried over sodium sulfate, concentrated, and purified by column chromatography on silica (20→50% EtOAc/hexane) to provide the aryl ether (419 mg, 70%). LCMS found 574.2 [M+H]$^+$.

The methyl ester (419 mg, 0.73 mmol) was dissolved in THF:MeOH:H$_2$O (1:1:1, 7.5 mL) and treated with LiOH (153 mg, 3.65 mmol). After 4 h, the reaction was neutralized with 1N HCl then extracted with EtOAc. The organic phase was dried over sodium sulfate then concentrated to afford the crude acid (387 mg), which was used directly in the next reaction. LCMS found 560.2 [M+H]$^+$.

1-{[1-(2-tert-Butoxycarbonylamino-3,3-dimethyl-butyryl)-4-(2-ethoxy-7-methoxy-8-methyl-quinolin-4-yloxy)-pyrrolidine-2-carbonyl]-amino}-2-ethyl-cyclopropanecarboxylic acid methyl ester was prepared according to the method presented in the synthesis of Compound 26. Treatment of 1-(2-tert-butoxycarbonylamino-3,3-dimethyl-butyryl)-4-(2-ethoxy-7-methoxy-8-methyl-quinolin-4-yloxy)-pyrrolidine-2-carboxylic acid (387 mg, 0.69 mmol) occurred under the same conditions, adjusted for scale, to afford the desired methyl ester (349 mg, 74%). LCMS found 685.3 [M+H]$^+$.

1-{[1-[3,3-Dimethyl-2-(2,2,2-trifluoro-1,1-dimethyl-ethoxycarbonylamino)-butyryl]-4-(2-ethoxy-7-methoxy-8-methyl-quinolin-4-yloxy)-pyrrolidine-2-carbonyl]-amino}-2-ethyl-cyclopropanecarboxylic acid methyl ester was prepared according to the method presented in the synthesis of compound 77. Treatment of 1-{[1-(2-tert-butoxycarbonylamino-3,3-dimethyl-butyryl)-4-(2-ethoxy-7-methoxy-8-methyl-quinolin-4-yloxy)-pyrrolidine-2-carbonyl]-amino}-2-ethyl-cyclopropanecarboxylic acid methyl ester (349 mg, 0.51 mmol) occurred under the same conditions, adjusted for scale, and after purification by column chromatography on silica (10→50% EtOAc/hexanes) to afford the fluorinated tert-butylcarbamate (310 mg, 82%). LCMS found 739.2 [M+H]$^+$.

Compound 137 was prepared according to the method presented in the synthesis of compound 29. Treatment of 1-{[1-[3,3-dimethyl-2-(2,2,2-trifluoro-1,1-dimethyl-ethoxycarbonylamino)-butyryl]-4-(2-ethoxy-7-methoxy-8-methyl-quinolin-4-yloxy)-pyrrolidine-2-carbonyl]-amino}-2-ethyl-cyclopropanecarboxylic acid methyl ester (0.42 mmol) occurred under the same conditions, adjusted for scale, and purified by reverse phase HPLC to afford compound 137 (85 mg, 24%): $^1$H NMR (CD$_3$OD, 300 MHz) δ 9.2 (s, 1H), 8.15 (d, 1H), 7.35 (d, 1H), 6.80 (s, 1H), 5.71 (s, 1H), 4.55-4.73 (m, 4H), 4.16 (s, 1H), 3.99-4.11 (m, 1H), 4.03 (s, 3H), 2.72 (dd, 1H), 2.46 (s, 3H), 2.34-2.43 (m, 1H), 1.68 (s, 3H), 1.55-1.63 (m, 7H), 1.41 (s, 3H), 1.21-1.32 (m, 3H), 1.17 (s, 3H), 1.05 (s, 9H), 0.96-1.07 (m, 3H), 0.66-0.71 (m, 2H). LCMS found 858.1 [M+H]$^+$.

Example 138

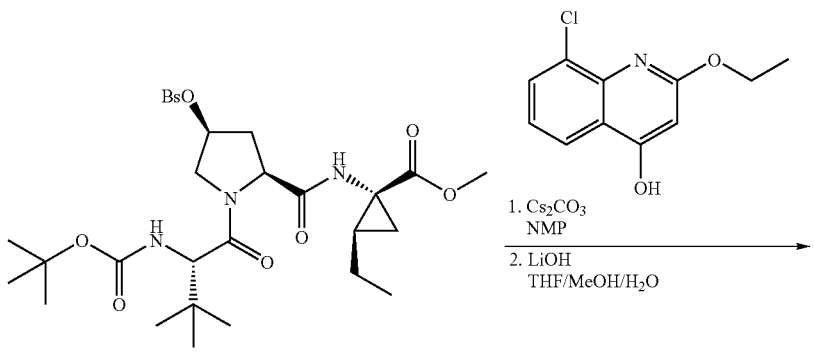

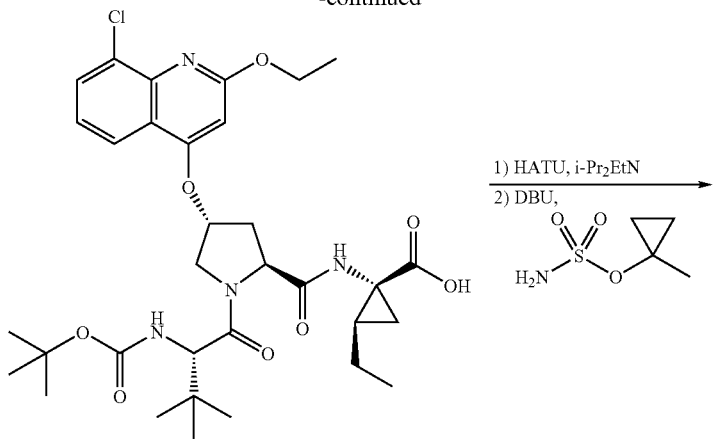

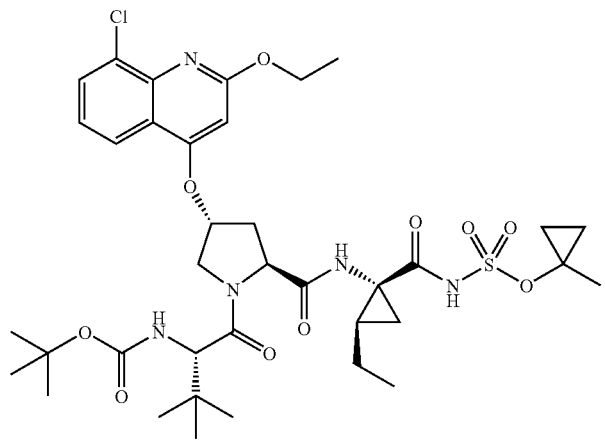

Compound 138

8-Chloro-2-ethoxy-quinolin-4-ol was synthesized according to the method presented in the synthesis of 2-ethoxy-7-methoxy-8-methyl-quinolin-4-ol in Example 137 with the exception of utilizing 2-chloro-aniline.

To a solution of 1-{[4-(4-Bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (800 mg, 1.16 mmol) in NMP (3.9 mL) was added 8-Chloro-2-ethoxy-quinolin-4-ol (285 mg, 0.1.28 mmol) and cesium carbonate (756 mg, 2.32 mmol). The resulting slurry was heated to 65° C. (external temperature, oil bath), and stirred vigorously overnight. Upon cooling to room temperature, the reaction mixture was diluted with EtOAc and washed with saturated ammonium chloride (2×) and then brine. The resulting organic layer was dried over sodium sulfate and concentrated. The crude product was purified by column chromatography (50% EtOAc/hexanes) to provide the aryl ether (627 mg, 80%). LCMS found 675.1 [M+H]$^+$.

To a solution of the aryl ether (627 mg, 0.93 mmol) in a 1:1:1 mixture of THF:MeOH:H$_2$O (9 mL) was added lithium hydroxide (195 mg, 4.64 mmol). The resulting slurry was stirred at 50° C. for 2 h. The reaction mixture was then diluted with EtOAc and washed with 1 N HCl and brine. The resulting organic layer was dried over sodium sulfate and concentrated to provide the crude acid (615 mg, 100%).

To a solution of 1-{[1-(2-tert-Butoxycarbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid (139 mg, 0.21 mmol) in DMF (2 mL) was added HATU (122 mg, 0.32 mmol) and diisopropylethylamine (0.056 mL, 0.32 mmol). The solution was stirred at room temperature for 2 h then sulfamic acid 1-methyl-cyclopropyl ester (64 mg, 0.21 mmol) and DBU (0.126 mL, 0.84 mmol) were added, and the reaction mixture was stirred at room temperature overnight. The resulting solution was diluted with EtOAc then washed with aqueous 1 N HCl and brine. The organic layer was dried over sodium sulfate and concentrated. The crude product was purified by reverse phase HPLC (30→90% MeCN/H$_2$O-1% TFA) to provide compound 138 (102 mg, 61%). $^1$H NMR (300 MHz, CD$_3$OD): δ 9.12 (s, 1H), 8.00 (d, 1H), 7.75 (d, 1H), 7.24 (t, 1H), 6.52 (s, 1H), 5.4 (s, 1H), 4.58 (q, 2H), 4.60-4.50 (m, 2H), 4.23 (s, 1H), 4.08-4.04 (m, 1H), 2.61 (dd, 1H), 2.30-2.22 (m, 1H), 1.68 (s, 3H), 1.62-1.50 (m, 4H), 1.46 (t, 3H), 1.31-1.20 (m, 3H), 1.26 (s, 9H), 1.04 (s, 9H), 0.99-0.94 (m, 3H), 0.68 (m, 2H). LCMS found 794.09 [M+H]$^+$.

Example 139

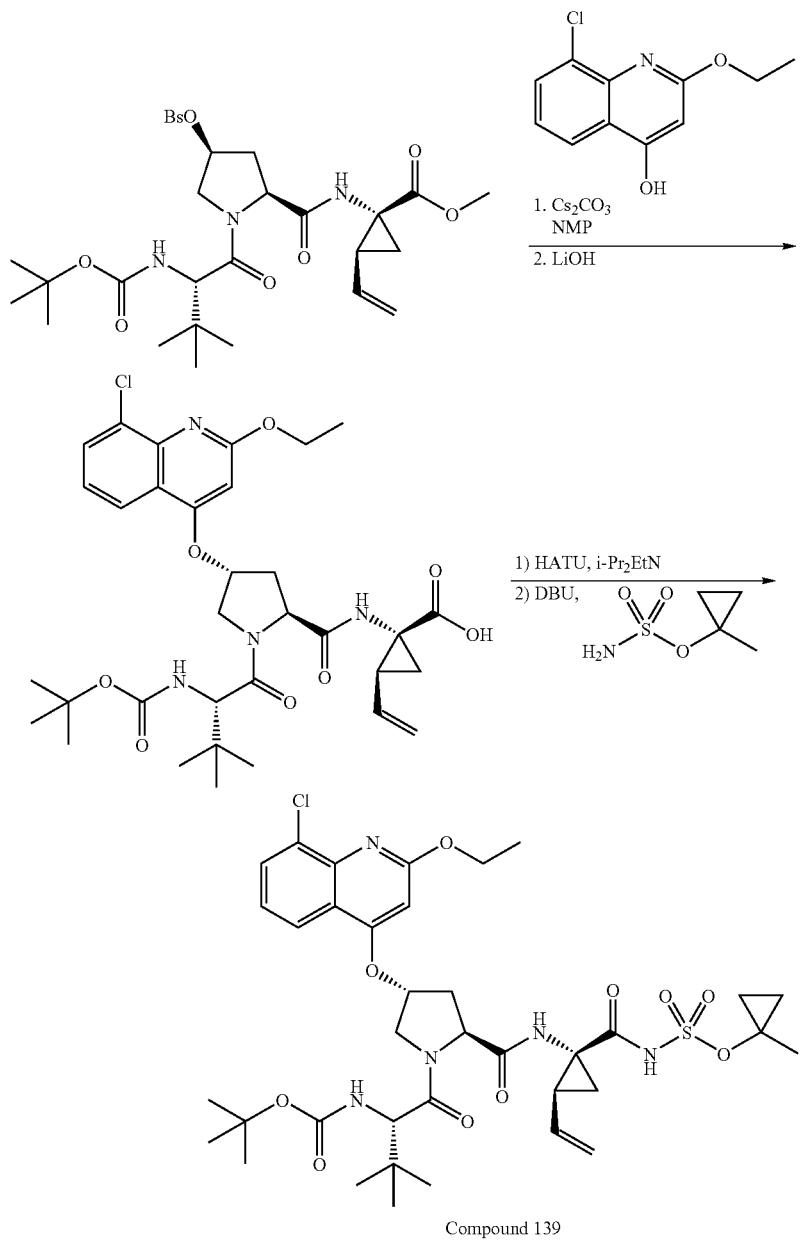

Compound 139

To a solution of 1-{[4-(4-bromo-benzenesulfonyloxy)-1-(2-tert-butoxycarbonylamino-3,3-dimethyl-butyryl)-pyrrolidine-2-carbonyl]-amino}-2-vinyl-cyclopropanecarboxylic acid methyl ester (400 mg, 0.58 mmol) and 8-chloro-2-ethoxy-quinolin-4-ol (143 mg, 0.64 mmol) in DMF (2 mL) was added cesium carbonate (416 mg, 1.28 mmol) and the reaction was heated at 60° C. for 2.5 hours. The solvent was removed under vacuum and the residue was dissolved in ethyl acetate. The solution was washed with saturated ammonium chloride and brine, dried over magnesium sulfate and concentrated. The crude residue was purified via chromatography (0-70% ethyl acetate/hexanes) to give 174 mg (45%) of the desired product as a white solid. LCMS found 673.1 [M+H]⁺. The intermediate was then dissolved in THF and methanol (1:1) and a solution of lithium hydroxide (31 mg, 1.29 mmol) in water (1 ml) was added. The reaction was stirred at room temperature overnight. The solvent was removed, the residue dissolved in ethyl acetate and washed with 1N HCl and brine. The organic layer was then dried over magnesium sulfate and concentrated to give 133.4 mg (81%) of intermediate 1-{[1-(2-tert-butoxycarbonylamino-3,3-dimethyl-butyryl)-4-(8-chloro-2-ethoxy-quinolin-4-yloxy)-pyrrolidine-2-carbonyl]-amino}-2-vinyl-cyclopropanecarboxylic acid as a white solid. LCMS found 659.1 [M+H]⁺.

1-{[1-(2-tert-butoxycarbonylamino-3,3-dimethyl-butyryl)-4-(8-chloro-2-ethoxy-quinolin-4-yloxy)-pyrrolidine-2-carbonyl]-amino}-2-vinyl-cyclopropanecarboxylic acid (130 mg, 0.20 mmol) was dissolved in DMF (5 µL) and diisopropylethyl amine (52 µL, 0.296 mmol) to which was added HATU (113 mg, 0.30 mmol). To this reaction mixture was then added DBU (118 µL, 0.79 mmol) and sulfamic acid 1-methyl-cyclopropyl ester (60 mg, 0.39 mmol) and the reaction was stirred at ambient temperature for 16 h. The solvent was removed; the residue was diluted with EtOAc and washed with 1 M HCl, dried over MgSO$_4$ and concentrated. The residue was purified reverse phase chromatography to give 63.9 mg (41%) of compound 139 as an amorphous white solid. $^1$H NMR (CD$_3$OD, 300 MHz) δ 7.93 (d, 1H); 7.67 (d, 1H); 7.17 (m, 1H); 6.44 (s, 1H); 5.69 (m, 1H); 5.35 (s, 1H); 5.26 (d, 1H); 5.09 (d, 1H); 4.51 (m, 4H); 4.19 (s, 1H); 4.01 (m, 1H); 2.58 (m, 1H); 2.21 (m, 1H); 1.83 (m, 1H); 1.62 (s, 3H); 1.40 (t, 3H); 1.22 (s, 11H); 0.99 (s, 11H); 0.63 (m, 2H). LCMS found 792.1 [M+H]$^+$.

Example 140

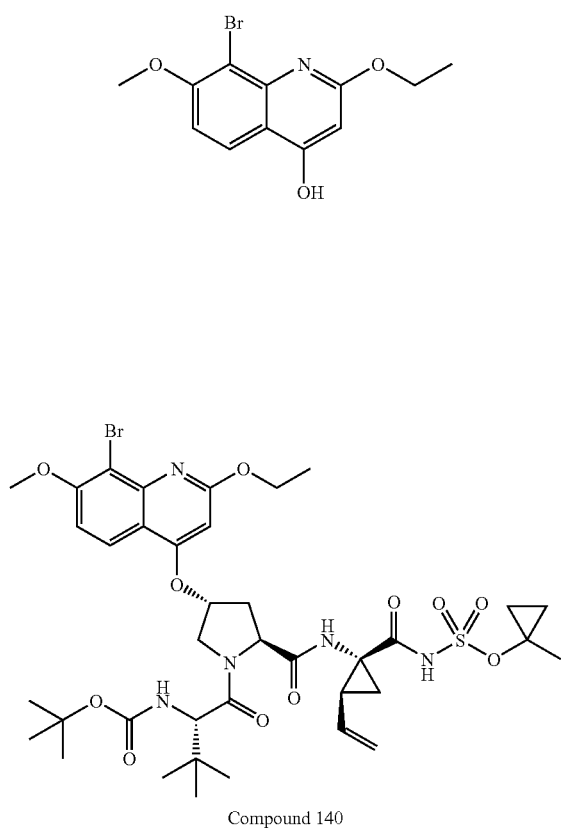

Compound 140

8-Bromo-2-ethoxy-7-methoxy-quinolin-4-ol was synthesized according to the method presented in the synthesis of 2-ethoxy-7-methoxy-8-methyl-quinolin-4-ol in example 132 with the exception of utilizing 2-bromo-3-methoxy-aniline.

Compound 140 was prepared according to the method described in example 139, substituting intermediate 8-bromo-2-ethoxy-7-methoxy-quinolin-4-ol for 8-chloro-2-ethoxy-quinolin-4-ol and adjusting appropriately for scale. The material was purified using reverse phase HPLC to give 92.9 mg (47%) of the desired compound compound 140 as a white amorphous solid. $^1$H NMR (CD$_3$OD, 300 MHz) δ 7.99 (d, 1H); 7.09 (d, 1H); 6.33 (s, 1H); 5.69 (m, 1H) 5.36 (s, 1H); 5.26 (d, 1H); 5.10 (d, 1H); 4.51 (m, 4H); 4.17 (s, 1H); 4.04 (m, 1H); 3.95 (s, 3H); 2.58 (m, 1H); 2.21 (m, 1H); 1.83 (m, 1H); 1.62 (s, 3H); 1.42 (m, 3H); 1.21 (s, 11H); 0.99 (s, 11H); 0.63 (m, 2H). LCMS found 866.2 [M+H]$^+$.

Example 141

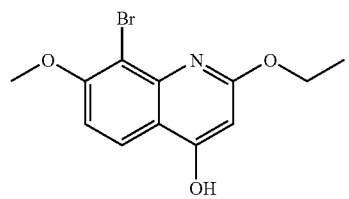

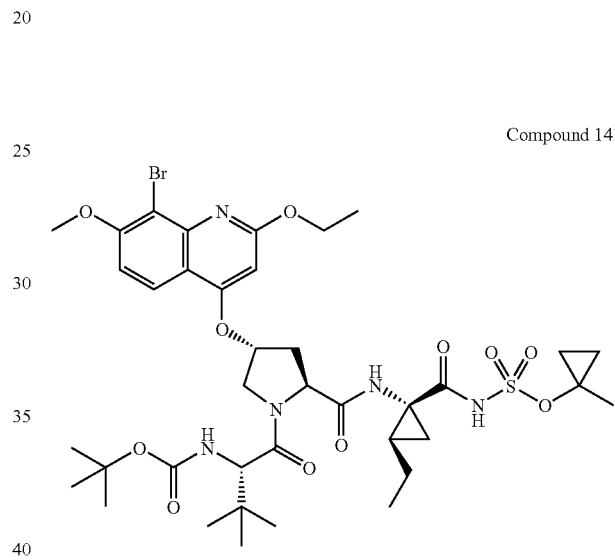

Compound 141

Compound 141 was prepared according to the method presented in example 138, substituting 8-bromo-2-ethoxy-7-methoxy-quinolin-4-ol for 8-chloro-2-ethoxy-quinolin-4-ol and adjusting for scale. The material was purified using reverse phase HPLC to afford compound 141 (250 mg, 65%). $^1$H NMR (300 MHz, CD$_3$OD): δ 9.08 (s, 1H), 7.97 (d, 1H), 7.08 (d, 1H), 6.31 (s, 1H), 5.34 (s, 1H), 4.53 (q, 2H), 4.50-4.42 (m, 2H), 4.17 (s, 1H), 4.12 (m, 1H), 3.92 (s, 3H), 2.55 (dd, 1H), 2.25-2.18 (m, 1H), 1.63 (s, 3H), 1.61-1.46 (m, 4H), 1.41 (t, 3H), 1.26-1.15 (m, 3H), 1.21 (s, 9H), 0.99 (s, 9H), 0.96-0.92 (m, 3H), 0.63 (m, 2H). LCMS found 768.1 [M+H]$^+$.

Example 142

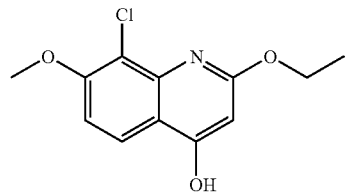

Compound 142

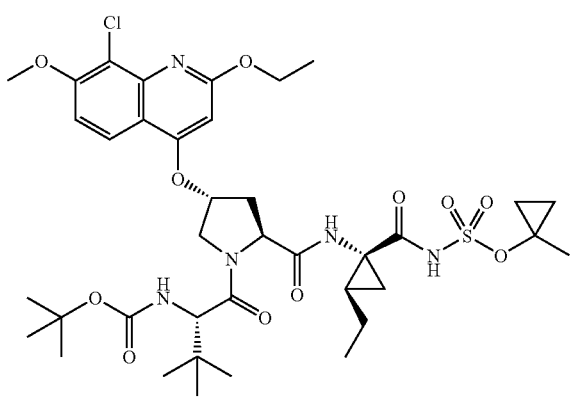

8-Chloro-2-ethoxy-7-methoxy-quinolin-4-ol was synthesized according to the method presented in the synthesis of 2-Ethoxy-7-methoxy-8-methyl-quinolin-4-ol in Example 132 with the exception of utilizing 2-Chloro-3-methoxy-aniline.

Compound 142 was prepared according to the method presented in example 138, substituting intermediate 8-chloro-2-ethoxy-7-methoxy-quinolin-4-ol for 8-chloro-2-ethoxy-quinolin-4-ol and adjusting appropriately for scale. The material was purified using reverse phase HPLC to give compound 142 (205 mg, 57%). $^1$H NMR (300 MHz, CD$_3$OD): δ 9.14 (s, 1H), 8.05 (d, 1H), 7.23 (d, 1H), 6.40 (s, 1H), 5.48 (s, 1H), 4.62 (q, 2H), 4.59-4.50 (m, 2H), 4.20 (s, 1H), 4.07 (m, 1H), 4.02 (s, 3H), 2.63 (dd, 1H), 2.34-2.25 (m, 1H), 1.68 (s, 3H), 1.58 (m, 4H), 1.50 (t, 3H), 1.32-1.29 (m, 3H), 1.23 (s, 9H), 1.04 (s, 9H), 1.00-0.95 (m, 3H), 0.68 (m, 2H). LCMS found 824.1 [M+H]$^+$.

Example 143

Compound 143

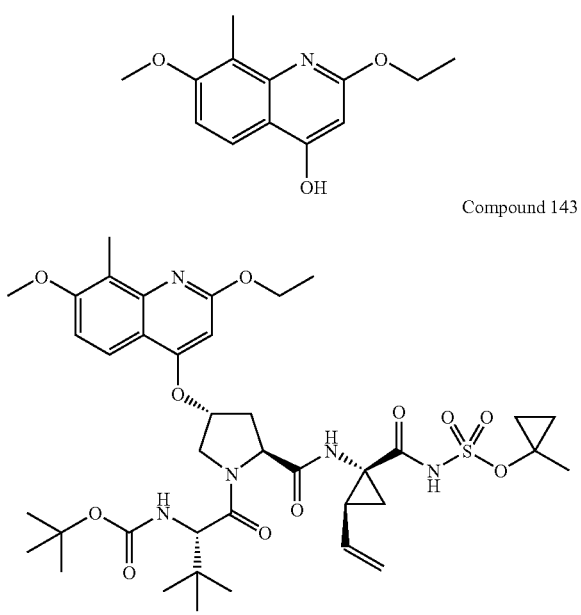

Compound 143 was prepared according to the method described for example 139, substituting intermediate 2-ethoxy-7-methoxy-8-methyl-quinolin-4-ol for 8-chloro-2-ethoxy-quinolin-4-ol and adjusting appropriately for scale. The material was purified using reverse phase HPLC to give 40.1 mg (25%) of compound 143 as a white amorphous solid. $^1$H NMR (CD$_3$OD, 300 MHz) δ 7.94 (d, 1H); 7.12 (d, 1H); 6.42 (s, 1H); 5.71 (m, 1H); 5.45 (s, 1H); 5.27 (d, 1H); 5.11 (d, 1H); 4.51 (m, 4H); 4.16 (s, 1H); 4.02 (m, 1H); 3.92 (s, 3H); 2.61 (m, 1H); 2.42 (s, 3H); 2.23 (m, 1H) 1.84 (m, 1H); 1.62 (s, 3H); 1.44 (m, 3H); 1.21 (m, 11H); 0.99 (s, 9H); 0.63 (m, 2H). LCMS found 802.2 [M+H]$^+$.

Example 144

Compound 144

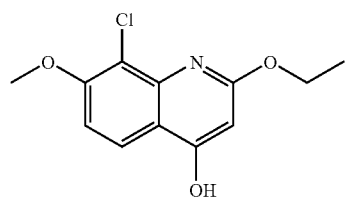

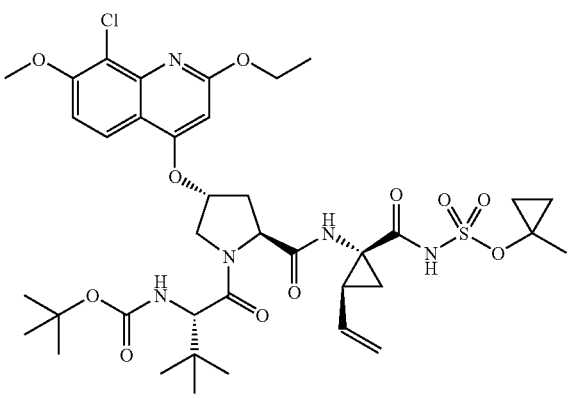

Compound 144 was prepared according to the method presented in example 139, substituting intermediate 8-chloro-2-ethoxy-7-methoxy-quinolin-4-ol for 8-chloro-2-ethoxy-quinolin-4-ol and adjusting appropriately for scale. The material was purified using reverse phase HPLC to give 62.3 mg (38%) of the desired compound 144 as a white amorphous solid. $^1$H NMR (CD$_3$OD, 300 MHz) δ 7.96 (d, 1H); 7.14 (d, 1H); 6.37 (s, 1H); 5.69 (m, 1H); 5.39 (s, 1H); 5.27 (d, 1H); 5.10 (d, 1H); 4.51 (m, 4H); 4.17 (s, 1H); 4.02 (m, 1H); 3.96 (s, 3H); 2.59 (m, 1H); 2.22 (m, 1H); 1.83 (m, 1H); 1.62 (s, 3H); 1.42 (m, 3H); 1.21 (m, 1H); 0.99 (s, 11H); 0.63 (m, 2H). LCMS found 822.2 [M+H]$^+$.

Example 145

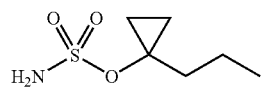

Compound 145

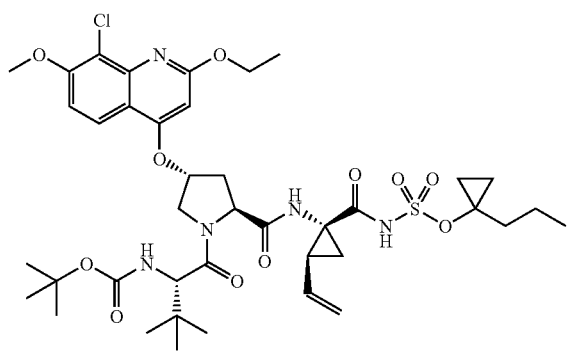

Compound 145 was prepared according to the method presented in example 139, substituting intermediate 8-chloro-2-ethoxy-7-methoxy-quinolin-4-ol for 8-chloro-2-ethoxy-quinolin-4-ol, substituting sulfamic acid 1-propyl-cyclopropyl ester for sulfamic acid 1-methyl-cyclopropyl ester, and adjusting appropriately for scale. The compound was purified using reverse phase HPLC to give 34.9 mg (68%) of the desired compound 145 as a white amorphous solid. $^1$H NMR (CD$_3$OD, 300 MHz) δ 7.94 (d, 1H); 7.12 (d, 1H); 6.37 (s, 1H); 5.67 (m, 1H); 5.37 (m, 1H); 5.26 (d, 1H); 5.09 (d, 1H); 4.50 (m, 4H); 4.18 (m, 1H); 4.03 (m, 1H); 3.95 (s, 3H); 2.58 (m, 1H); 2.22 (m, 1H); 1.79 (m, 2H); 1.54 (m, 1H); 1.41 (m, 5H); 1.23 (m, 11H); 0.99 (m, 11H); 0.93 (m, 3H); 0.64 (m, 2H). LCMS found 850.2 [M+H]$^+$.

Example 146

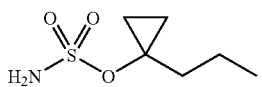

Compound 146

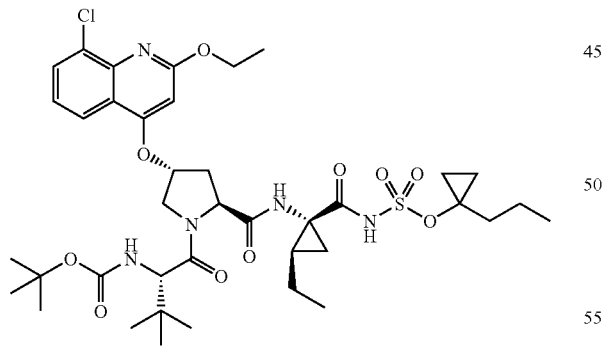

Compound 146 was prepared according to the method presented in example 138, substituting sulfamic acid 1-propyl-cyclopropyl ester for sulfamic acid 1-methyl-cyclopropyl ester, and adjusting appropriately for scale. The compound was purified using reverse phase HPLC to afford compound 146 (141 mg, 71%). $^1$H NMR (300 MHz, CD$_3$OD): δ 9.12 (s, 1H), 7.98 (d, 1H), 7.72 (d, 1H), 7.23 (t, 1H), 6.51 (s, 1H), 5.41 (s, 1H), 4.57 (q, 2H), 4.55-4.48 (m, 2H), 4.23 (s, 1H), 4.08-4.04 (m, 1H), 2.60 (dd, 1H), 2.27 (m, 1H), 1.87-1.80 (m, 2H), 1.65-1.40 (m, 6H), 1.46 (t, 3H), 1.31 (m, 3H), 1.26 (s, 9H), 1.04 (s, 9H), 1.00-0.95 (m, 6H), 0.69 (m, 2H). LCMS found 823.2 [M+H]$^+$.

Example 147

Compound 147

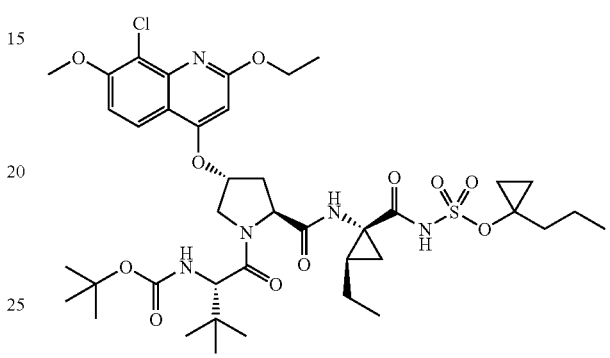

Compound 147 was prepared according to the method presented in example 138, substituting intermediate 8-chloro-2-ethoxy-7-methoxy-quinolin-4-ol for 8-chloro-2-ethoxy-quinolin-4-ol, substituting sulfamic acid 1-propyl-cyclopropyl ester for sulfamic acid 1-methyl-cyclopropyl ester, and adjusting appropriately for scale. The compound was purified using reverse phase HPLC to afford compound 146 (174 mg, 82%). $^1$H NMR (300 MHz, CD$_3$OD): δ 9.10 (s, 1H), 8.01 (d, 1H), 7.21 (d, 1H), 6.48 (s, 1H), 5.45 (s, 1H), 4.57 (q, 2H), 4.48 (m, 2H), 4.15 (s, 1H), 4.04 (m, 1H), 3.98 (s, 3H), 2.57 (dd, 1H), 2.31-2.22 (m, 1H), 1.82-1.77 (m, 2H), 1.60-1.44 (m, 9H), 1.26 (m, 3H), 1.18 (s, 9H), 0.99 (s, 9H), 0.95-0.90 (m, 6H), 0.65 (m, 2H). LCMS found 852.4 [M+H]$^+$.

Example 148

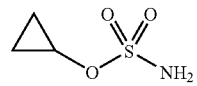

Compound 148

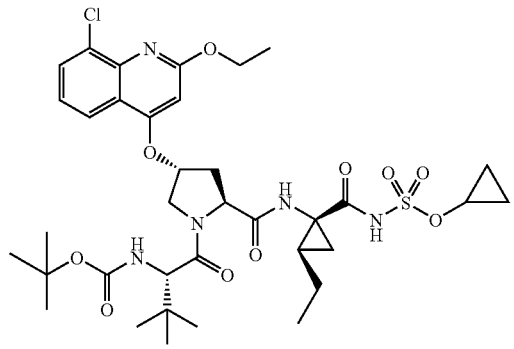

Compound 148 was prepared according to the method presented for the synthesis of compound 138, substituting sulfamic acid cyclopropyl ester for sulfamic acid 1-methyl-cyclopropyl ester, and adjusting appropriately for scale. The material was purified using reverse phase HPLC to afford compound 148 (174 mg, 82%). (105 mg, 56%): $^1$H NMR (300 MHz, CD$_3$OD): δ 9.13 (s, 1H), 8.01 (d, 1H), 7.74 (d, 1H) 7.24 (t, 1H), 6.52 (d, 1H), 5.42 (brs, 1H), 4.52-4.62 (m, 4H), 4.28 (m, 2H), 4.05 (dd, 1H), 2.62 (m, 1H), 2.27 (m, 1H), 1.60 (m, 6H), 1.46 (t, 3H), 1.26 (s, 9H), 1.03 (s, 9H), 0.97 (m, 4H), 0.76 (m, 2H). LCMS found 780.0 [M+H]$^+$.

Example 149

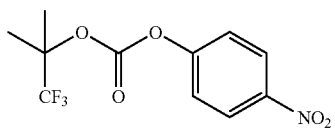

Compound 149

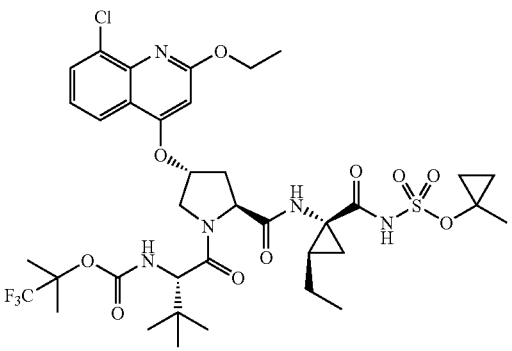

Compound 149 was prepared according to the method presented in the synthesis of example 77. Treatment of compound 138 (150 mg, 0.19 mmol) under the same conditions, adjusted for scale, afforded compound 149 (145 mg, 90%). $^1$H NMR (400 MHz, CD$_3$OD): δ 9.12 (s, 1H), 7.96 (d, 1H), 7.71 (d, 1H), 7.21 (t, 1H), 6.48 (s, 1H), 5.38 (s, 1H), 4.59-4.49 (m, 4H), 4.21 (s, 1H), 4.03-4.01 (m, 1H), 2.60 (dd, 1H), 2.30-2.23 (m, 1H), 1.67 (s, 3H), 1.63-0.43 (m, 10H), 1.33-1.25 (m, 3H), 1.20 (s, 3H), 1.04 (s, 9H), 0.96 (m, 3H), 0.67 (m, 2H). LCMS found 848.1 [M+H]$^+$.

Example 150

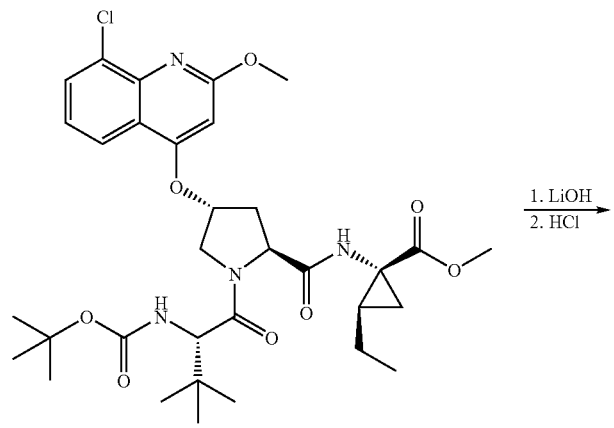

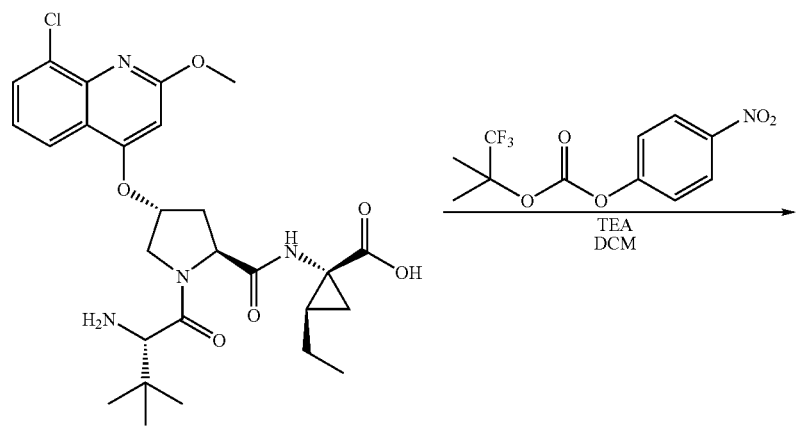

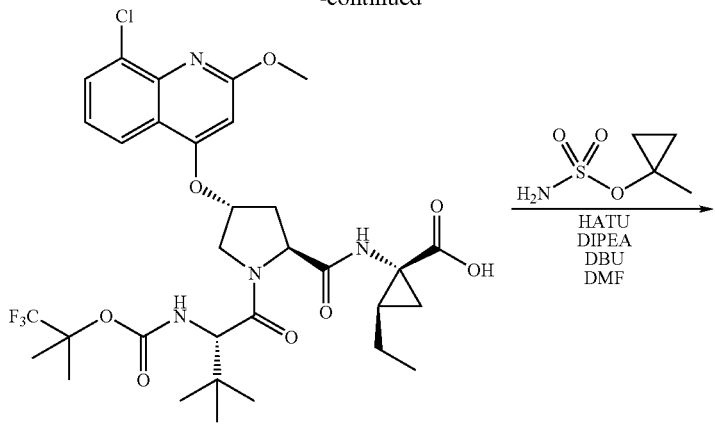

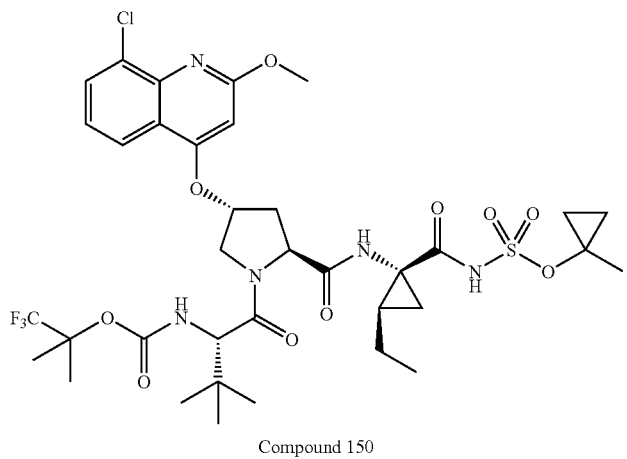

Compound 150

Intermediate 1-{[1-(2-tert-butoxycarbonylamino-3,3-dimethyl-butyryl)-4-(8-chloro-2-methoxy-quinolin-4-yloxy)-pyrrolidine-2-carbonyl]-amino}-2-ethyl-cyclopropanecarboxylic acid methyl ester was prepared as shown in Example 138 substituting 8-chloro-2-methoxy-quinolin-4-ol for 8-chloro-2-ethoxy-quinolin-4-ol and adjusting appropriately for scale.

To a solution of 1-{[1-(2-tert-butoxycarbonylamino-3,3-dimethyl-butyryl)-4-(8-chloro-2-methoxy-quinolin-4-yloxy)-pyrrolidine-2-carbonyl]-amino}-2-ethyl-cyclopropanecarboxylic acid methyl ester (325 mg, 0.49 mmol) in THF and methanol (1:1, 5 ml) was added a solution of lithium hydroxide (59 mg, 2.46 mmol) in water and the reaction was stirred at room temperature overnight. The reaction was acidified with 1N HCl and extracted with ethyl acetate, dried over magnesium sulfate and concentrated to afford 324 mg (99%) of a white solid. This crude material was then dissolved in DCM (10 ml), 4N HCl in dioxanes was added (2.5 ml) and the reaction was stirred at room temp for 2.5 hours. The solvent was removed and then taken up again in dichloromethane (12 ml). To this solution was added carbonic acid 4-nitro-phenyl ester 2,2,2-trifluoro-1,1-dimethyl-ethyl ester (733 mg, 2.5 mmol) and triethylamine (1.05 mL, 7.5 mmol), and the reaction was stirred at room temperature for two days. The solution was then washed with 1N HCl and brine, dried over magnesium sulfate and concentrated to give 1.008 g of the crude acid as a yellow oil. LCMS found 700.92 [M+H]$^+$.

1-({4-(8-chloro-2-methoxy-quinolin-4-yloxy)-1-[3,3-dimethyl-2(2,2,2-trifluoro-1,1-dimethyl-ethoxycarbonylamino)-butyryl]-pyrrolidine-2-carbonyl}-amino)-2-ethyl-cyclopropanecarboxylic acid (284 mg, 0.41 mmol) was dissolved in dimethyl formamide (4 mL) and diisopropylethyl amine (177 µL, 1.01 mmol) to which was added N,N,N',N'-Tetramethyl-O-(7-azabenzotriazol-1-yl)uronium hexafluorophosphate (234 mg, 0.62 mmol). To this reaction mixture was then added 1,8-Diazabicyclo[5.4.0]undec-7-ene (245 µL, 1.64 mmol) and sulfamic acid 1-methyl cyclopropyl ester (124 mg, 0.82 mmol) and the reaction was stirred at ambient temperature for 16 hours. The reaction was diluted with water and acetonitrile and purified reverse phase chromatography to give 199.9 mg (58%) of compound 150 as an amorphous white solid. $^1$H NMR (CD$_3$OD, 400 MHz) δ 7.95 (d, 3 6.8 Hz, 1H, 7.71 (d, J=8.8 Hz, 1H); 7.20 (m, 1H); 6.48 (s, 1H); 5.37 (s, 1H); 4.50 (m, 2H); 4.19 (m, 1H); 4.06 (s, 3H); 4.00 (m, 1H); 2.59 (m, 1H); 2.25 (m, 1H); 1.66 (s, 2H); 1.56 (m, 6H); 1.45 (s, 3H); 1.28 (m, 2H); 1.20 (m, 4H); 1.02 (s, 9H); 0.94 (m, 2H); 0.66 (m, 2H). LCMS found 833.98 [M+H]$^+$.

Example 151

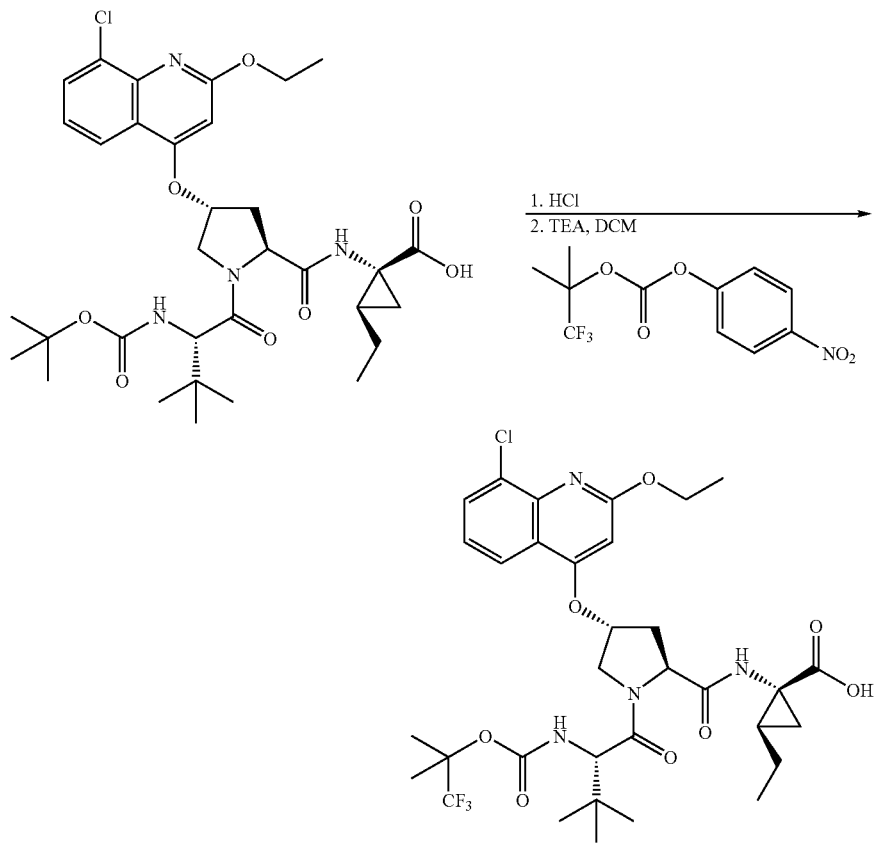

1-{[1-(2-tert-Butoxycarbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid (0.80 g, 1.2 mmol) was taken up in DCM (3 mL) and treated with 4M HCl/dioxane solution (3 mL, 12 mmol) at rt. After 2 h, the volatiles were removed in vacuo to produce 0.71 g (98%) of the HCl salt. LCMS found 561.0 [M+H]$^+$. The HCl salt (0.71 g, 1.2 mmol) was taken up in DCM (5 mL) and treated with TEA (0.84 mL, 6 mmol) and carbonic acid 4-nitro-phenyl ester 2,2,2-trifluoro-1,1-dimethyl-ethyl ester (0.70 g, 2.4 mmol) at rt. After 24 h, the solution was diluted with DCM and water (5 mL). The stirred solution was then acidified with 12 M HCl until pH=3 was obtained. The aqueous layer was extracted with DCM and EtOAc, and the combined organics are washed with brine followed by drying over anhydrous Na$_2$SO$_4$. Following concentration in vacuo, the resulting residue was subjected to column chromatography on SiO$_2$ (0-17% MeOH/DCM) to provide 0.69 g (86% yield) of 1-({4-(8-chloro-2-ethoxy-quinolin-4-yloxy)-1-[3,3-dimethyl-2-(2,2,2-trifluoro-1,1-dimethyl-ethoxycarbonylamino)-butyryl]-pyrrolidine-2-carbonyl}-amino)-2-ethyl-cyclopropanecarboxylic acid as a pale yellow solid that was used without further purification. LCMS found 716.0 [M+H]$^+$.

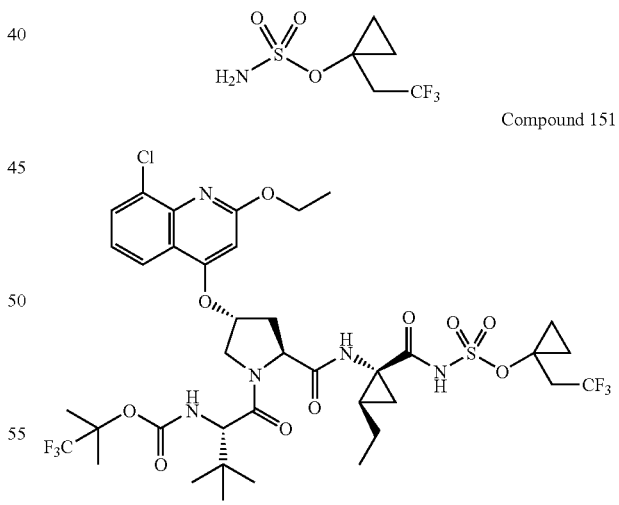

Compound 151

Compound 151 was prepared according to the methods presented in Example 138 using 1-({4-(8-chloro-2-ethoxy-quinolin-4-yloxy)-1-[3,3-dimethyl-2-(2,2,2-trifluoro-1,1-dimethyl-ethoxycarbonylamino)-butyryl]-pyrrolidine-2-carbonyl}-amino)-2-ethyl-cyclopropanecarboxylic acid, replacing sulfamic acid cyclopropyl ester with sulfamic acid 1-(2,2,2-trifluoroethyl)cyclopropyl ester (0.12 g, 0.56 mmol and 0.19 g, 0.87 mmol) with appropriate adjustments for scale to produce 0.207 g (30% yield overall from the P2 alkylated tripeptide) of Compound 151 as a white powder following purification by reverse phase HPLC. $^1$H NMR (CD$_3$OD, 400 MHz) δ 7.97 (d, 1H); 7.71 (d, 1H); 7.21 (t, 1H); 7.15 (d, 1H); 6.48 (s, 1H); 5.39 (m, 1H); 4.62-4.48 (m, 4H); 4.20 (d, 1H); 4.01 (m, 1H); 2.87 (qd, 2H); 2.61 (m, 1H); 2.26 (m, 1H); 1.68-1.50 (m, 4H); 1.50-1.38 (m, 8H); 1.24-1.16 (m, 4H); 1.12 (s, 9H); 1.00-0.90 (5H). LCMS found 917.9 [M+H]$^+$.

Example 152

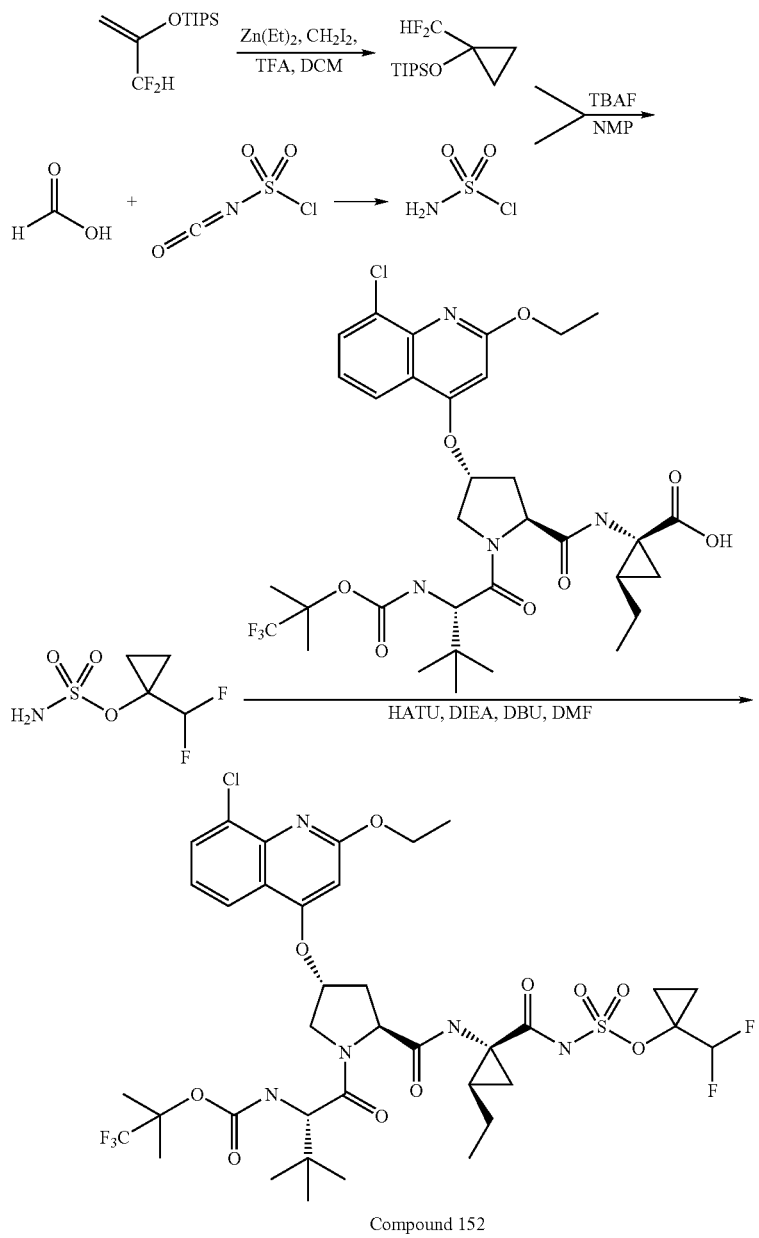

Compound 152

(1-Difluoromethyl-cyclopropoxy)-triisopropyl-silane synthesized by methods reported in *Journal of Fluorine Chemistry* 2002, 207.

A round bottom flask (fitted with glass inlet and outlet) was charged with 60 ml DCM followed by Et$_2$Zn (60 mmol, 60 ml, 1 M in hexane) and cooled to 0° C. TFA (60 mmol, 4.62 ml dissolved in 30 ml DCM) was slowly added to the stirring solution. The reaction was stirred for 20 minutes, followed by addition of CH$_2$I$_2$ (60 mmol, 4.83 ml dissolved in 20 ml DCM) and 20 minutes further stirring. At this point, (1-Difluoromethyl-vinyloxy)-triisopropyl-silane DCM (11.98 mmol, 3 g dissolved in 30 mL) was added and the mixture warmed to rt and stirred for 1 hour. The reaction was then quenched with 1 N HCl and water and extracted two times with hexane. The combined organics were washed with saturated NaHCO$_3$ and dried over sodium sulfate and concentrated, providing (1-difluoromethyl-cyclopropoxy)-triisopropyl-silane which was used crude in the next reaction.

A three-neck round bottom flask equipped with a reflux condenser was charged with chlorosulfonyl isocyanate (2.6 ml, 29.9 mol) and cooled to 0° C. Formic acid (1.13 mL, 29.9 mol) was added dropwise with rapid stirring and with rapid gas evolution observed. Upon complete addition of formic acid, the reaction was allowed to warm to room temperature. After 2 h, the reaction vessel was cooled to 0° C. and (1-difluoromethyl-cyclopropoxy)-triisopropyl-silane (500 mg, 1.89 mol) dissolved in NMP (5 mL) was added dropwise via an addition funnel. The mixture was warmed to RT and TBAF (7 ml, 7 mmol) was added. Stir mixture four days. The reaction mixture was poured into cold saturated aqueous NaCl and extracted with EtOAc two times. After removal of the separated organic solvent, the crude product was, purified by column chromatography on silica to provide sulfamic acid 1-difluoromethyl-cyclopropyl ester (10 mg, 2.8% yield): $^1$H NMR (CDCl$_3$, 300 MHz) δ 6.24 (t, 1H), 5.18 (s, 2H), 1.49 (m, 2H), 1.19 (m, 2H).

Compound 152 was prepared according to the method presented in example 138. Treatment of 1-({4-(8-chloro-2-ethoxy-quinolin-4-yloxy)-1-[3,3-dimethyl-2-(2,2,2-trifluoro-1,1-dimethyl-ethoxycarbonylamino)-butyryl]-pyrrolidine-2-carbonyl}-amino)-2-ethyl-cyclopropanecarboxylic acid (0.28 mmol) occurred under the same conditions, substituting sulfamic acid 1-difluoromethyl-cyclopropyl ester for sulfamic acid 1-methyl-cyclopropyl and adjusting for scale, to afford Compound 152 (87.1 mg, 35% yield): $^1$H NMR (CD$_3$OD, 300 MHz) diagnostic δ 6.39 (t, 1H); 1.44 (m, 2H), 1.17 (m, 2H); $^{19}$F NMR (CD$_3$OD, 282.2 MHz) –128.16 (d, 2F). LCMS found 884.0 [M+H]$^+$.

Example 153

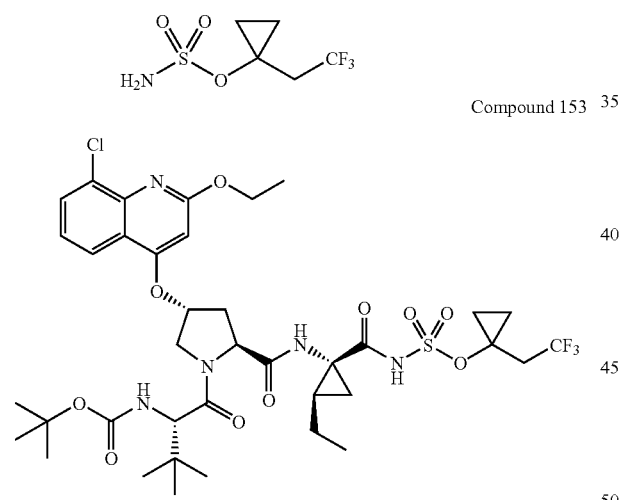

Compound 153

[1-(4-(8-Chloro-2-ethoxy-quinolin-4-yloxy)-2-{2-ethyl-1-[1-(2,2,2-trifluoro-ethyl)-cyclopropoxysulfonylaminocarbonyl]-cyclopropylcarbamoyl}-pyrrolidine-1-carbonyl)-2,2-dimethyl-propyl]-carbamic acid tert-butyl ester was prepared according to the method described in Example 138, substituting sulfamic acid 1-(2,2,2-trifluoro-ethyl)-cyclopropyl ester for sulfamic acid 1-methyl-cyclopropyl and using 1-{[4-(4-Bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester, adjusting appropriately for scale. The compound was purified using reverse phase HPLC to give 157.5 mg (15% yield) of the desired Compound 153 as an off-white amorphous solid. $^1$H NMR (CD$_3$OD, 400 MHz). δ 7.95 (d, J=8.4 Hz, 1H); 7.69 (d, J=7.2 Hz, 1H); 7.18 (m, 1H); 6.45 (s, 1H); 5.36 (s, 1H); 4.54 (m, 4H); 4.21 (s, 1H); 4.03 (d, J=12 Hz, 1H); 2.85 (m, 2H); 2.58 (m, 1H); 2.24 (m, 1H); 1.54 (m, 4H); 1.42 (m, 5H); 1.24 (s, 8H); 1.186 (m, 1H); 1.01 (s, 9H); 0.94 (m, 6H). LCMS found 861.94 [M+H]$^+$.

Example 154

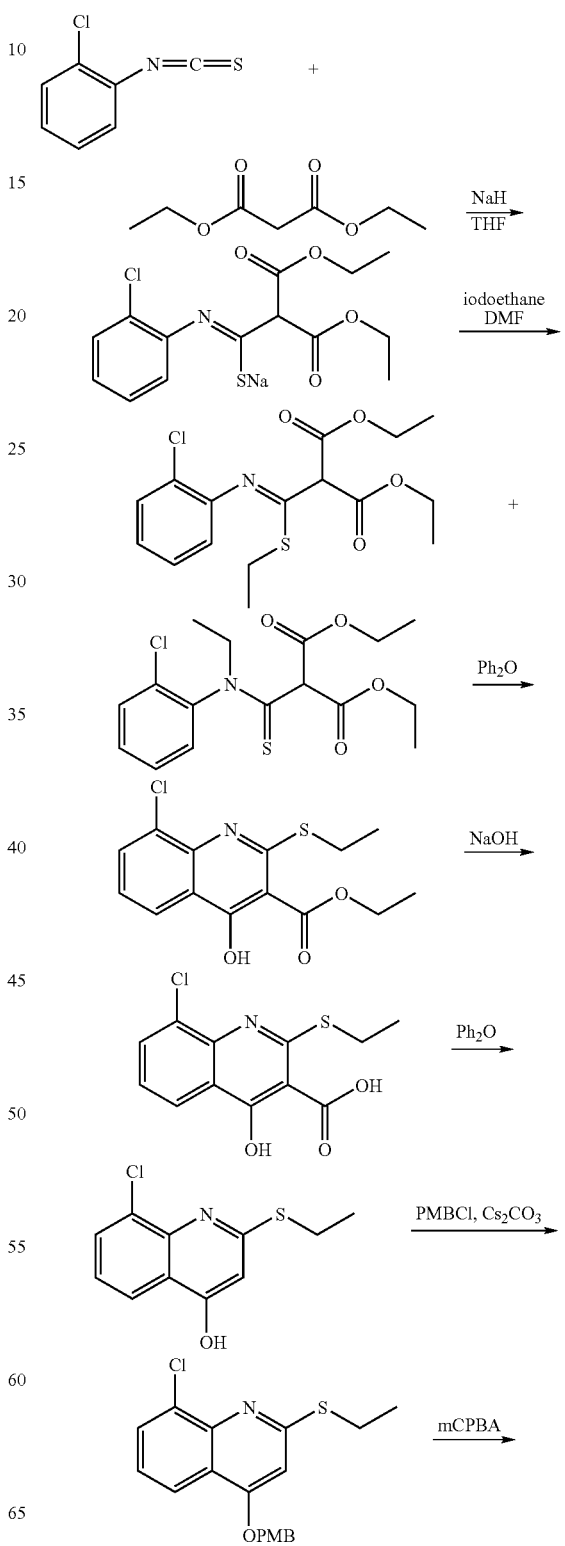

-continued

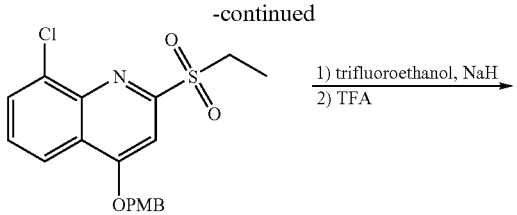

1) trifluoroethanol, NaH
2) TFA

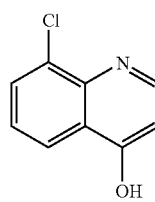

To a pre-dried 3-necked round bottom flask (1 L) equipped with an additional funnel, J-Kem temperature probe and nitrogen inlet and outlet was added anhydrous tetrahydrofuran (200 mL) under nitrogen atmosphere. Sodium hydride (60% in mineral oil, 4.53 g, 113.2 mmol) was then added in portions at 0° C. Diethyl malonate (15.1 g, 94.3 mmol) was dropwise added to the mixture keeping the internal temperature below 10° C. in an ice bath. The mixture was stirred at room temperature for 2 hours. The reaction content was cooled down to 0° C. again and 2-chloro-phenylisothiocyanate (16 g, 94.3 mmol) was added to the mixture. The resulting mixture was then allowed to warm-up to room temperature and stirred for 3 hours. The volatiles were removed in vacuo to afford the sodium salt adduct (33 g, 100% yield).

To a solution of the sodium adduct (33.2 g, 94.3 mmol) in anhydrous dimethylformamide (277 mL) at 45° C. was slowly added iodoethane (17.65 g, 113.16 mmol) over 20 min and the mixture was stirred at −45° C. for 2 hours and warmed up to room temperature and stirred overnight. The reaction mixture was quenched with water and extracted twice into a mixture of ether/hexanes (1:1). The combined organic extracts were washed with water, brine and dried over MgSO$_4$. The mixture was concentrated in vacuo to obtain an approximately 1:1 mixture of two different alkylated products as a yellow oil. This mixture was carried onward without further purification. LCMS found 358.14 [M+H]$^+$.

In a pre-heated sand bath at 350° C., a solution of the alkylated products (33.7 g, 94.3 mmol) in diphenyl ether (330 mL) was heated until the internal temperature reached 220° C. and then stirred for 15 minutes at this temperature. The solution was cooled to room temperature and the mixture loaded directly on a silica gel cartridge and purified by flash chromatography to afford 8-Chloro-2-ethylsulfanyl-4-hydroxy-quinoline-3-carboxylic acid ethyl ester (19.81 g, 67.4% yield). $^1$H NMR (CDCl$_3$, 300 MHz) δ 8.14 (d, 1H), 7.82 (d, 1H), 7.31 (t, 1H), 4.60-4.53 (m, 2H), 3.38-3.31 (m, 2H), 1.60-1.44 (m, 6H). LCMS found 312.12 [M+H]$^+$.

To a solution of 8-chloro-2-ethylsulfanyl-4-hydroxy-quinoline-3-carboxylic acid ethyl ester (19.81 g, 63.5 mmol) in THF:MeOH (1:1, 150 mL) at room temperature was added 1N NaOH. The reaction was allowed to stir at reflux for 24 hours, monitoring by HPLC. Upon the completion of the reaction, the mixture was acidified with 4N HCl and extracted 3 times with dichloromethane. The organic phases were combined, dried over Mg$_2$SO$_4$, and concentrated in vacuo to afford 8-chloro-2-ethylsulfanyl-4-hydroxy-quinoline-3-carboxylic acid (17.17 g, 95% yield). LCMS found 383.88 [M+H]$^+$.

8-Chloro-2-ethylsulfanyl-4-hydroxy-quinoline-3-carboxylic acid (17.17 g, 60.52 mmol) was suspended in diphenyl ether (250 mL) and heated to 250° C. for 30 minutes and the mixture was then cooled down to room temperature. The mixture was directly transferred onto a load cartridge and purified by column chromatography to afford 8-chloro-2-ethylsulfanyl-quinolin-4-ol (12.36 g, 85% yield). $^1$H NMR (CDCl$_3$, 300 MHz) δ 8.25 (d, 1H), 7.70 (d, 1H), 7.32 (t, 1H), 6.52 (s, 1H), 3.18-3.11 (m, 2H), 1.54-1.44 (m, 3H). LCMS found 240.17 [M+H]$^+$.

8-Chloro-2-ethylsulfanyl-quinolin-4-ol (10.26 g, 42.8 mmol) was dissolved in anhydrous dimethylformamide (100 mL). Cesium carbonate (27.9 g, 85.6 mmol) was added, followed by p-methoxybenzyl chloride (8.0 g, 51.36 mmol). The mixture was then heated at 65° C. for 2 hours and then cooled to room temperature and diluted with ethyl acetate. The diluted reaction mixture was washed with brine 2 times, dried over Mg$_2$SO$_4$ and concentrated in vacuo. The residue was recrystallized from EtOAc/Hexanes to afford 8-chloro-2-ethylsulfanyl-4-(4-methoxy-benzyloxy)-quinoline (11.14 g, 67% yield). LCMS found 360.21 [M+H]$^+$.

To a solution of 8-chloro-2-ethylsulfanyl-4-(4-methoxybenzyloxy)-quinoline (11.14 g, 30.96 mmol) in chloroform (300 mL) was added m-chloroperbenzoic acid (13.9 g, 61.9 mmol) in three portions at 0° C. (exotherm). The reaction mixture was then stirred overnight at room temperature. Upon confirming completion of the reaction by LCMS and HPLC, the mixture was quenched with a saturated solution of sodium bicarbonate and stirred approximately 10 min at room temperature. The mixture was diluted with dichloromethane and the phases separated. The organic layer was washed with 1N NaOH and brine, dried over MgSO$_4$, and concentrated in vacuo. The residue was recrystallized from a mixture of ethyl acetate and hexanes to afford 8-chloro-2-ethanesulfonyl-4-(4-methoxy-benzyloxy)-quinoline (11.28 g, 93% yield) of white bright crystals. $^1$H NMR (CDCl$_3$, 400 MHz) δ 8.18 (d, 1H), 7.89 (d, 1H), 7.59 (s, 1H), 7.51 (t, 1H), 7.43 (d, 2H), 6.97 (d, 2H), 5.29 (s, 2H), 3.83 (s, 3H), 3.68 (q, 2H), 1.45 (t, 3H). LCMS found 391.88 [M+H]$^+$.

To a solution of sodium hydride (60 wt %, 177 mg, 7.7 mmol) in THF (3 mL) was added trifluoroethanol and 8-chloro-2-ethanesulfonyl-4-(4-methoxy-benzyloxy)-quinoline (300 mg, 0.77 mmol). The reaction was stirred at room temperature for 1 h, quenched with H$_2$O, then diluted with EtOAc and washed with brine. The resulting organic layer was dried over sodium sulfate and concentrated to provide crude 8-Chloro-4-(4-methoxy-benzyloxy)-2-(2,2,2-trifluoro-ethoxy)-quinoline. LCMS found 397.9 [M+H]$^+$. The crude quinoline was then dissolved in CH$_2$Cl$_2$ (4 mL) and trifluoroacetic acid (4 mL). After stirring for 15 min the reaction was concentrated. The crude product was purified by column chromatography (10-30% EtOAc/hexanes) to provide 8-chloro-2-(2,2,2-trifluoro-ethoxy)-quinolin-4-ol (220 mg, 100% yield). LCMS found 278.3 [M+M]$^+$.

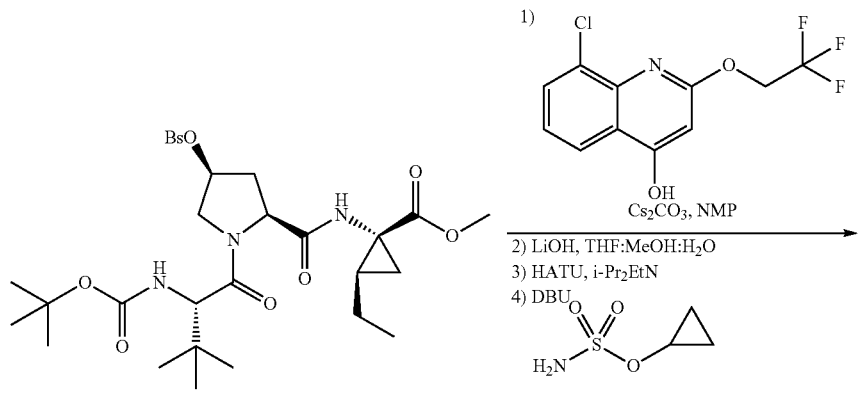

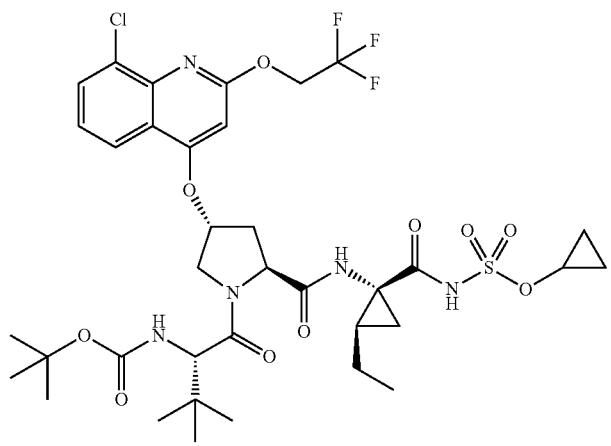

Compound 154

1-({1-(2-tert-butoxycarbonylamino-3,3-dimethyl-butyryl)-4-[8-chloro-2-(2,2,2-trifluoro-ethoxy)-quinolin-4-yloxy]-pyrrolidine-2-carbonyl}-amino)-2-ethyl-cyclopropanecarboxylic acid was prepared according to the method presented in Example 138. Treatment of 1-{[1-(2-tert-butoxycarbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid methyl ester (566 mg, 0.82 mmol) occurred under the same conditions, adjusted for scale and with the exception of utilizing 8-chloro-2-(2,2,2-trifluoro-ethoxy)-quinolin-4-ol (228 mg, 0.82 mmol). Purification of the crude product was accomplished by column chromatography on silica (30→50% EtOAc/hexanes) to provide 1-({1-(2-tert-Butoxycarbonylamino-3,3-dimethyl-butyryl)-4-[8-chloro-2-(2,2,2-trifluoro-ethoxy)-quinolin-4-yloxy]-pyrrolidine-2-carbonyl}-amino)-2-ethyl-cyclopropanecarboxylic acid methyl ester (376 mg, 63% yield). LCMS found 729.3 [M+H]$^+$. To a solution of the methyl ester (376 mg, 0.52 mmol) in a 1:1:1 mixture of THF:MeOH:H$_2$O (6 mL) was added lithium hydroxide (109 mg, 2.60 mmol). The resulting slurry was stirred at room temperature overnight. The reaction mixture was then diluted with EtOAc and washed with 1 N HCl and brine. The resulting organic layer was dried over sodium sulfate and concentrated to provide the crude acid (369 mg, 100% yield). LCMS found 714.8 [M+H]$^+$.

To a solution of the acid (369 mg, 0.52 mmol) in DMF (5 mL) was added HATU (294 mg, 0.77 mmol) and diisopropylethylamine (0.134 mL, 0.77 mmol). The solution was stirred at room temperature for 1 h then sulfamic acid cyclopropyl ester (126 mg, 1.04 mmol) and DBU (0.311 mL, 2.08 mmol) were added, and the reaction mixture was stirred at room temperature overnight. The resulting solution was diluted with EtOAc then washed with aqueous 1 N HCl and brine. The organic layer was dried over sodium sulfate and concentrated. The crude product was purified by reverse phase HPLC (30→90% ACN/H$_2$O-1% TFA) to provide Compound 154 (326 mg, 75% yield). $^1$H NMR (400 MHz, CD$_3$OD): δ 9.09 (s, 1H), 8.03 (d, 1H), 7.77 (d, 1H), 7.29 (t, 1H), 6.67 (s, 1H), 5.43 (s, 1H), 5.08-5.04 (m, 2H), 4.55-4.50 (m, 2H), 4.28-4.25 (m, 1H), 4.22 (s, 1H), 4.06-4.03 (m, 1H), 2.62 (dd, 1H), 2.29-2.24 (m, 1H), 1.68-1.50 (m, 4H), 1.23 (m, 10H), 1.02 (s, 9H), 1.00-0.94 (m, 5H), 0.74 (s, 2H). LCMS found 888.3 [M+H]$^+$.

Example 155

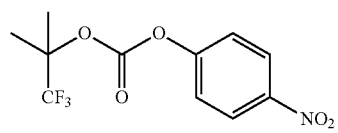

Compound 155

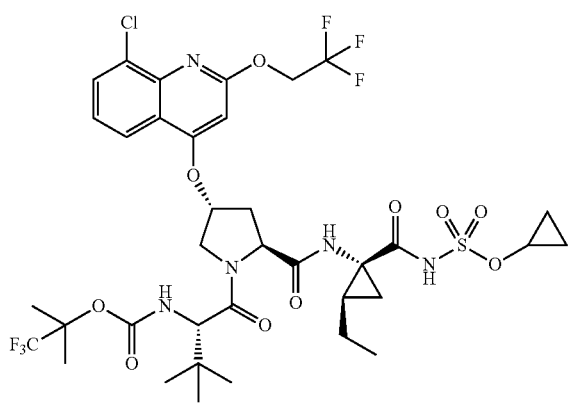

Compound 155 was prepared according to the method presented in the synthesis of example 77. Treatment of compound 154 (163 mg, 0.19 mmol) and carbonic acid 4-nitrophenyl ester 2,2,2-trifluoro-1,1-dimethyl-ethyl ester (112 mg, 0.20 mmol) under the same conditions adjusted for scale afforded the desired product (124 mg, 70% yield). $^1$H NMR (400 MHz, CD$_3$OD): d 9.12 (s, 1H), 8.02 (d, 1H), 7.77 (d, 1H), 7.29 (t, 1H), 6.68 (s, 1H), 5.43 (s, 1H), 5.07 (q, 2H), 4.56-4.53 (m, 2H), 4.27 (m, 1H), 4.20 (s, 1H), 4.04-4.01 (m, 1H), 2.64 (dd, 1H), 2.30-2.25 (m, 1H), 1.62-1.50 (m, 4H), 1.44 (s, 3H), 1.22 (m, 1H), 1.18 (s, 3H), 1.03 (s, 9H), 0.99-0.94 (m, 5H), 0.76-0.74 (m, 2H). LCMS found 888.9 [M+H]$^+$.

Example 156

Compound 156

Intermediate 8-Chloro-2-(2-morpholin-4-yl-ethoxy)-quinolin-4-ol was prepared according to the method presented in Example 154. Treatment of 8-chloro-2-ethanesulfonyl-4-(4-methoxy-benzyloxy)-quinoline (500 mg, 1.28 mmol) and with the exception of using 2-morpholin-4-yl-ethanol (0.468 mL, 3.83 mmol) under the same conditions adjusted for scale followed by deprotection with TFA (5 mL) afforded the desired quinoline (328 mg, 83% yield). LCMS found 308.8 [M+H]$^+$.

Compound 156 was prepared according to the method presented in example 138. Treatment of 1-{[1-(2-tert-butoxy-carbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid methyl ester (731 mg, 1.06 mmol) occurred under the same conditions, adjusted for scale and with the exception of utilizing 8-chloro-2-(2-morpholin-4-yl-ethoxy)-quinolin-4-ol (328 mg, 1.06 mmol) and sulfamic acid 1-methyl-cyclopropyl ester (65 mg, 0.54 mmol). Purification of the crude product was accomplished by reverse phase HPLC (30→90% MeCN/H$_2$O/0.1% TFA) to provide Compound 156 (104 mg, 22% yield over 4 steps). $^1$H NMR (400 MHz, CD$_3$OD): δ 8.00 (d, 1H), 7.74 (d, 1H), 7.26 (t, 1H), 6.61 (s, 1H), 5.40 (s, 1H), 4.98-4.90 (m, 2H), 4.58-4.47 (m, 2H), 4.17 (s, 1H), 4.06-4.03 (m, 1H), 3.93 (m, 4H), 3.68 (m, 2H), 3.46 (m, 4H), 2.61 (dd, 1H), 2.29 (m, 1H), 1.65 (s, 3H), 1.61-1.40 (m, 4H), 1.30-1.27 (m, 3H), 1.23 (s, 9H), 1.02 (s, 9H), 0.97 (t, 3H), 0.65 (m, 2H). LCMS found 878.9 [M+H]$^+$.

Example 157

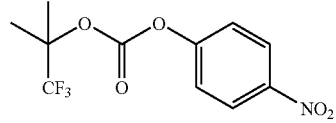

Compound 157

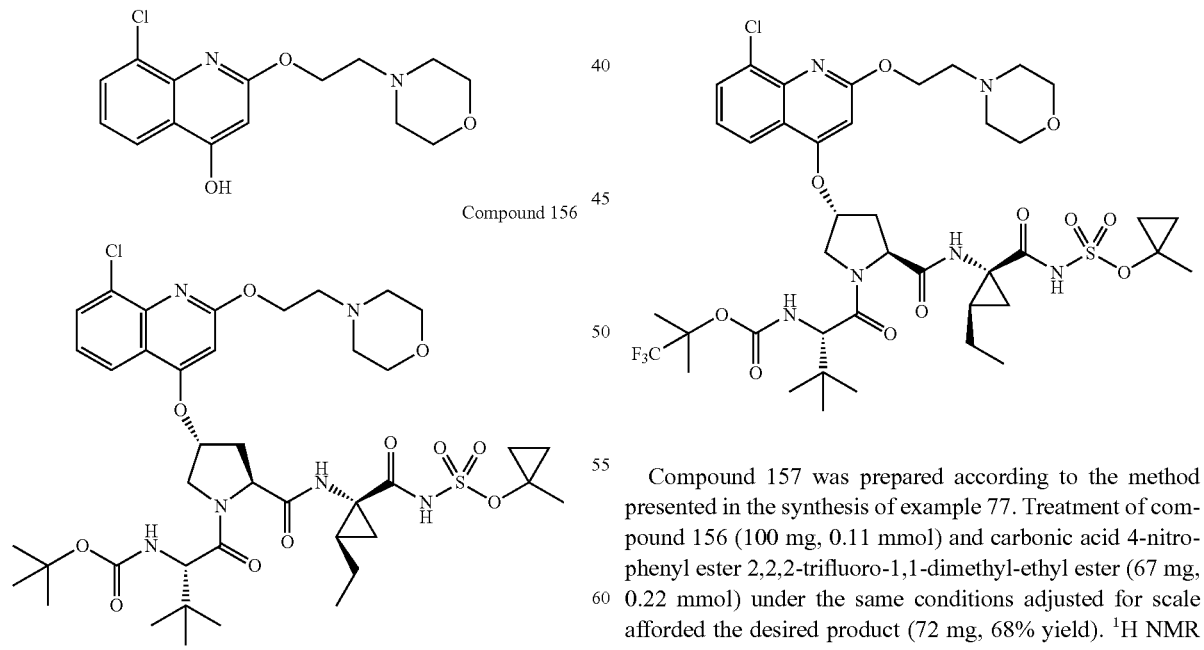

Compound 157 was prepared according to the method presented in the synthesis of example 77. Treatment of compound 156 (100 mg, 0.11 mmol) and carbonic acid 4-nitrophenyl ester 2,2,2-trifluoro-1,1-dimethyl-ethyl ester (67 mg, 0.22 mmol) under the same conditions adjusted for scale afforded the desired product (72 mg, 68% yield). $^1$H NMR (400 MHz, CD$_3$OD): δ 9.21 (s, 1H), 8.05 (dd, 1H), 7.81 (dd, 1H), 7.33 (t, 1H), 6.64 (s, 1H), 5.45 (m, 1H), 5.01 (m, 2H), 4.59 (dd, 1H), 4.53 (d, 1H), 4.21 (s, 1H), 4.15-4.06 (m, 3H), 3.92-3.77 (m, 6H), 3.35 (m, 2H), 2.68 (dd, 1H), 2.37-2.30 (m, 1H), 1.71 (s, 3H), 1.67-1.52 (m, 4H), 1.47 (s, 3H), 1.32 (q, 2H), 1.25-1.21 (m, 1H), 1.21 (s, 3H), 1.08 (s, 9H), 1.00 (t, 3H), 0.72-071 (m, 2H). LCMS found 932.91 [M+H]+.

Example 158

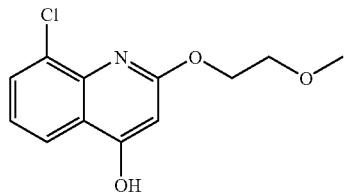

Compound 158

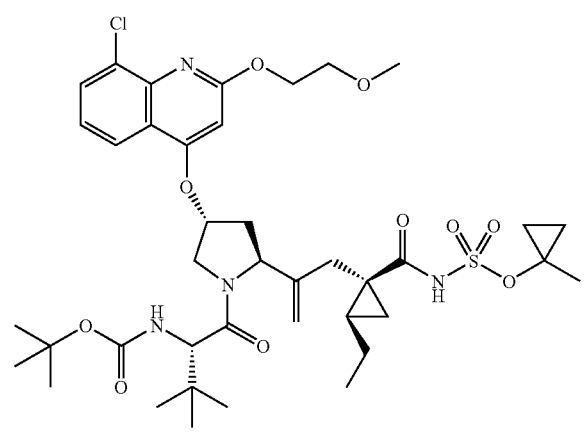

Intermediate 8-chloro-2-(2-methoxy-ethoxy)-quinolin-4-ol was prepared according to the method presented in Example 154. Treatment of 8-Chloro-2-ethanesulfonyl-4-(4-methoxy-benzyloxy)-quinoline (400 mg, 1.02 mmol) and with the exception of using 2-methoxyethanol (0.403 mL, 5.10 mmol) under the same conditions adjusted for scale followed by deprotection with TFA (4 mL) afforded the desired quinoline (260 mg, 99% yield). LCMS found 254.0 [M+H]+.

Compound 158 was prepared according to the method presented in example 138. Treatment of 1-{[1-(2-tert-Butoxycarbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid methyl ester (673 mg, 0.98 mmol) occurred under the same conditions, adjusted for scale and with the exception of utilizing 8-chloro-2-(2-methoxy-ethoxy)-quinolin-4-ol (248 mg, 0.98 mmol) and sulfamic acid 1-methyl-cyclopropyl ester (70 mg, 0.58 mmol) to afford the crude product, which was purified by reverse phase HPLC (30→90% MeCN/H₂O/0.1% TFA) to provide compound 158 (158 mg, 55% overall yield). ¹H NMR (400 MHz, CD₃OD): δ 9.04 (s, 1H), 7.93 (d, 1H), 7.68 (d, 1H), 7.18 (t, 1H), 6.45 (s, 1H), 5.33 (m, 1H), 4.64-4.62 (m, 2H), 4.48-4.46 (m, 2H), 4.21 (s, 1H), 4.02-4.00 (m, 1H), 3.80 (t, 2H), 3.41 (s, 3H), 2.56 (dd, 1H), 2.26-2.19 (m, 1H), 1.65 (s, 3H), 1.60-1.44 (m, 4H), 1.26 (m, 2H), 1.24 (s, 9H), 1.19-1.15 (m, 1H), 1.02 (s, 9H), 0.93 (t, 3H), 0.64 (m, 2H). LCMS found 823.99 [M+H]+.

Example 159

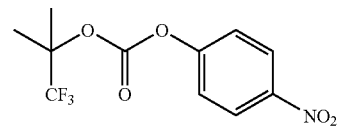

Compound 159

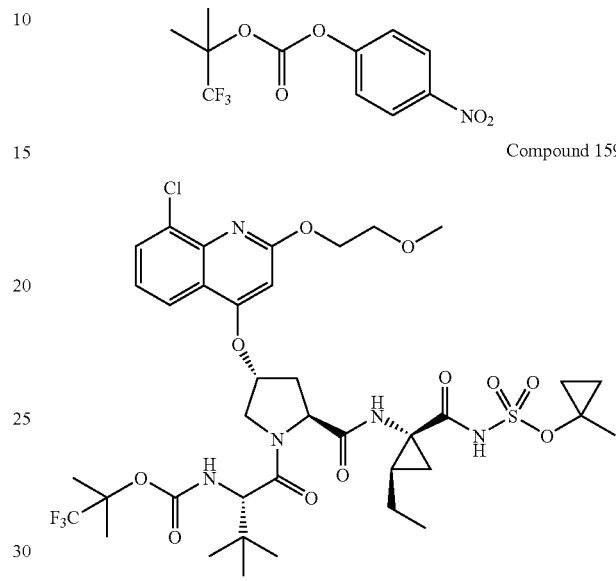

Compound 158 was prepared according to the method presented in the synthesis of Example 77. Treatment of Compound 158 (153 mg, 0.19 mmol) and carbonic acid 4-nitrophenyl ester 2,2,2-trifluoro-1,1-dimethyl-ethyl ester (109 mg, 0.38 mmol) under the same conditions adjusted for scale afforded the desired product (133 mg, 81% yield). ¹H NMR (400 MHz, CD₃OD): δ 9.10 (s, 1H), 7.95 (dd, 1H), 7.71 (dd, 1H), 7.21 (t, 1H), 6.50 (s, 1H), 5.36 (m, 1H), 4.65 (t, 2H), 4.53-4.48 (m, 2H), 4.18 (s, 1H), 4.00 (dd, 1H), 3.81 (t, 2H), 3.42 (s, 3H), 2.59 (dd, 1H), 2.28-2.21 (m, 1H), 1.65 (s, 3H), 1.61-1.48 (m, 4H), 1.46 (s, 3H), 1.27 (q, 2H), 1.19 (s, 3H), 1.20 (m, 1H), 1.02 (s, 9H), 0.96 (t, 3H), 0.66 (m, 2H). LCMS found 877.98 [M+H]+.

Example 160

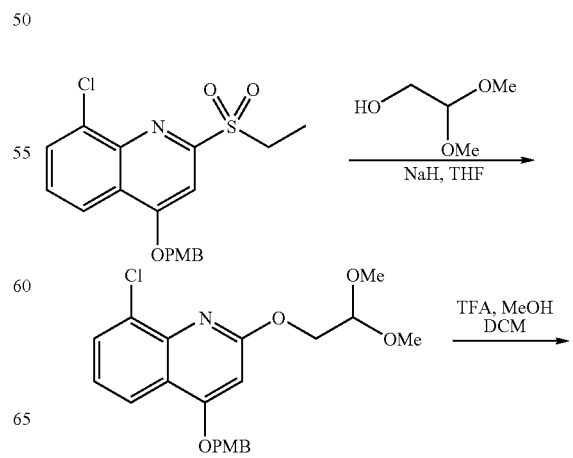

-continued

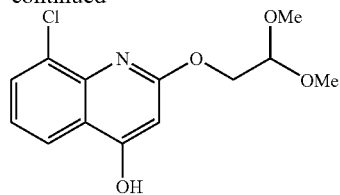

To a solution of glycoaldehydedimethylacetal (704 mg, 6.63 mmol) and NaH (60 wt %, 265 mg, 6.63 mmol) in THF (51 mL) was added 8-chloro-2-ethanesulfonyl-4-(4-methoxy-benzyloxy)-quinoline (2.00 g, 5.10 mmol). The reaction was stirred at ambient-temperature for 25 min. The reaction mixture was partitioned with H$_2$O and EtOAc. The layers were separated and the organic layer was dried over Na$_2$SO$_4$ and purified by column chromatography on silica (13-35% EtOAc/Hexane) to provide the acetal as white solid (1.93 g, 94% yield). LCMS found 403.8 [M+H]$^+$.

The acetal (2.05 g, 5.09 mmol) was dissolved in DCM (23.9 mL) and MeOH (1.93 mL, 47.8 mmol) and to which TFA (23.9 mL) was added. The reaction was stirred at ambient temperature for 15 min. The reaction was diluted with MeOH (47 mL) and concentrated. The crude mixture was partitioned with sat. NaHCO$_3$ and DCM. The layers were separated and the organic layer was purified by column chromatography on silica (20-60% EtOAc/Hexane) to provide the phenol as a white solid (1.41 g, 98% yield). LCMS found 283.8 [M+H]$^+$.

Intermediate (1-{4-[8-chloro-2-(2,2-dimethoxy-ethoxy)-quinolin-4-yloxy]-2-[2-ethyl-1-(1-methyl-cyclopropoxysulfonylaminocarbonyl)-cyclopropylcarbamoyl]-pyrrolidine-1-carbonyl}-2,2-dimethyl-propyl)-carbamic acid tert-butyl ester was prepared according to the method presented in the synthesis of compound 138. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (2.01 g, 2.92 mmol) occurred under the same conditions, adjusted for scale and with the exception of utilizing 2-(2,2-dimethoxy)-ethyl-8-chloro-quinolin-4-ol (720 mg, 2.54 mmol) and sulfamic acid 1-methyl-cyclopropyl ester (735 mg, 4.86 mmol) to provide the acyl sulfamate (1.64 g, 76% yield). LCMS found 854.0 [M+H]$^+$.

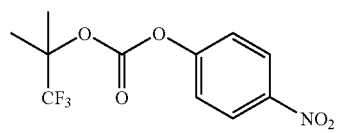

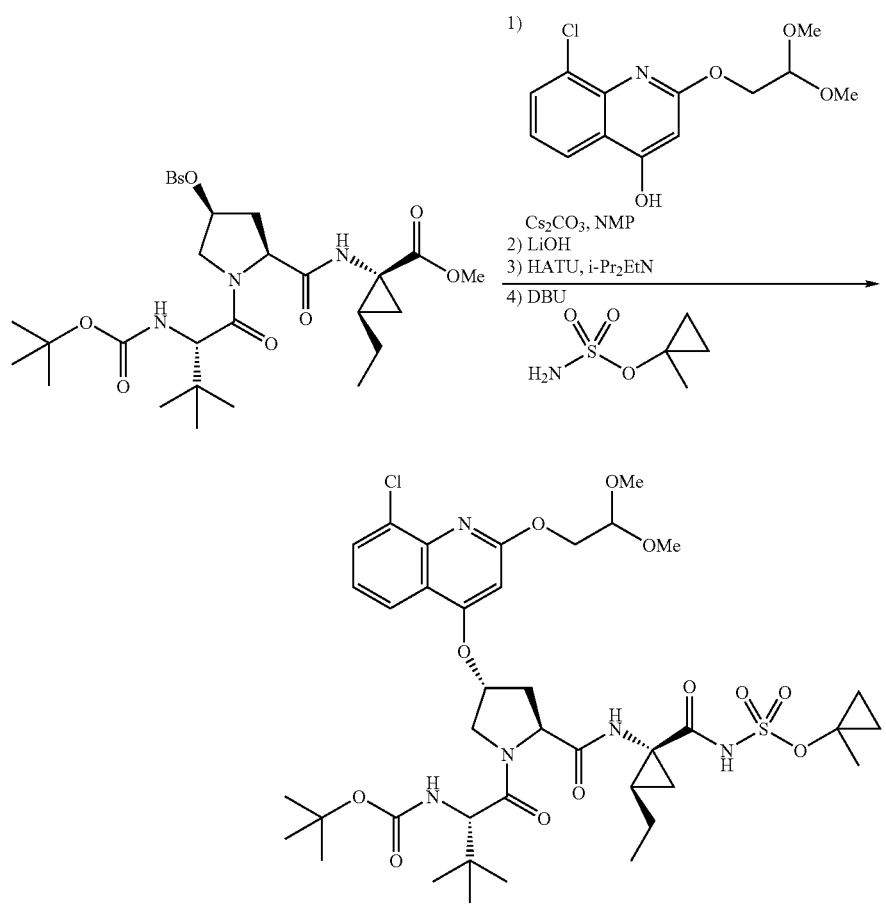

513

-continued

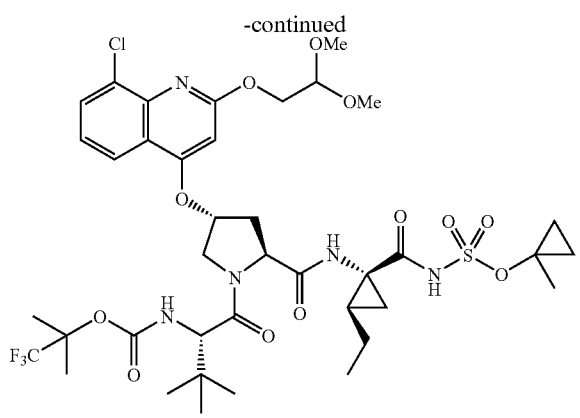

(1-{4-[8-chloro-2-(2,2-dimethoxy-ethoxy)-quinolin-4-yloxy]-2-[2-ethyl-1-(1-methyl-cyclopropoxysulfonylaminocarbonyl)-cyclopropylcarbamoyl]-pyrrolidine-1-carbo-

514 nyl}-2,2-dimethyl-propyl)-carbamic acid tert-butyl ester (444 mg, 0.520 mmol) was dissolved in CH$_2$Cl$_2$ (2.6 mL) and MeOH (0.21 mL, 5.20 mmol), and treated with TFA (2.6 mL). After stirring for 25 min at room temperature, MeOH (7 mL) was added and the solvents were removed in vacuo. The crude mixture was partitioned with saturated NaHCO$_3$ and DCM. The layers were separated and the organic layer was dried over Na$_2$SO$_4$ and concentrated. The resultant residue was dissolved in DCM (5.2 mL) to which carbonic acid 4-nitro-phenyl ester 2,2,2-trifluoro-1,1-dimethyl-ethyl ester (183 mg, 0.624 mmol) and diisopropylethylamine (362 µL, 2.08 mmol) were added sequentially. After stirring for 24 h at 35° C., the reaction was purified by column chromatography on silica (3-7% MeOH/DCM) to provide (1-{4-[8-chloro-2-(2,2-dimethoxy-ethoxy)-quinolin-4-yloxy]-2-[2-ethyl-1-(1-methyl-cyclopropoxysulfonylaminocarbonyl)-cyclopropyl-carbamoyl]-pyrrolidine-1-carbonyl}-2,2-dimethyl-propyl)-carbamic acid 2,2,2-trifluoro-1,1-dimethyl-ethyl ester (222 mg, 47% yield). LCMS found 908.0 [M+H]$^+$.

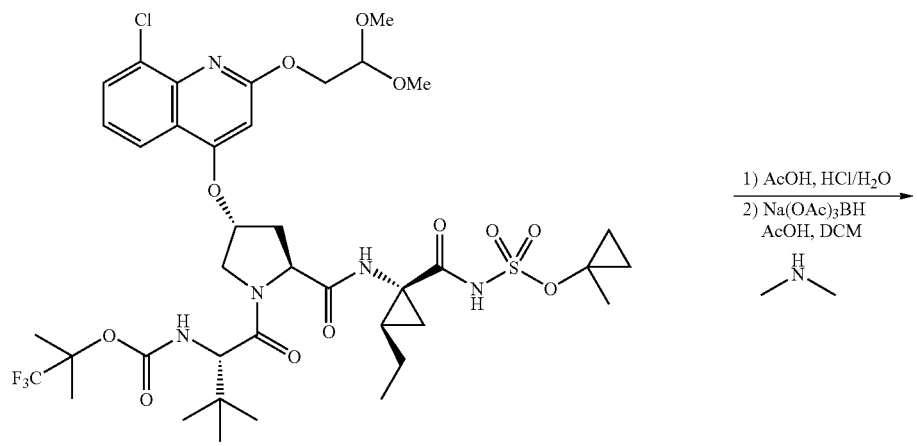

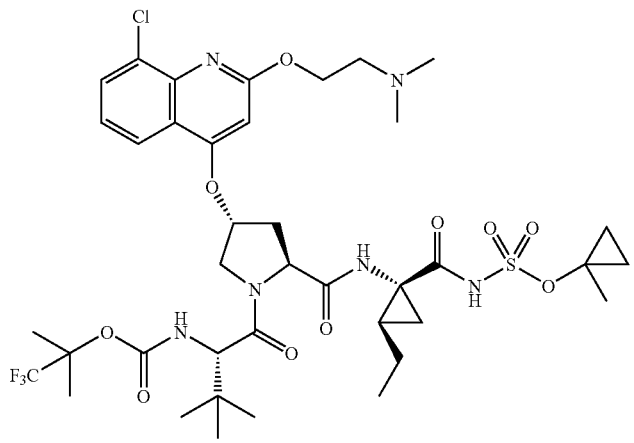

Example 160

To a solution of (1-{4-[8-chloro-2-(2,2-dimethoxy-ethoxy)-quinolin-4-yloxy]-2-[2-ethyl-1-(1-methyl-cyclo-propoxysulfonylaminocarbonyl)-cyclopropylcarbamoyl]-pyrrolidine-1-carbonyl}-2,2-dimethyl-propyl)-carbamic acid 2,2,2-trifluoro-1,1-dimethyl-ethyl ester (285 mg, 0.314 mmol) in AcOH (2.9 mL) was added 1.4 N HCl (1.1 mL). The reaction was stirred at 60° C. for 30 min. The solvents were removed in vacuo. The crude mixture was partitioned with sat. NaHCO$_3$ and EtOAc. The layers were separated and the organic layer was washed with brine and dried over Na$_2$SO$_4$, and then concentrated and dried under high-vac. for 10 min. The resultant residue was dissolved in 2M dimethylamine/THF (4.0 µL) to which NaBH(OAc)$_3$ (113 mg, 0.628 mmol) and AcOH (2.0 mL) were added sequentially. After stirring for 24 h at room temperature, the reaction was directly purified by column chromatography on silica (5-12% MeOH/DCM) and subsequently by reverse phase HPLC (30-95% ACN/H$_2$O-0.1% formic acid) to provide 51.6 mg (18% yield) of Compound 160. $^1$H NMR (CDCl$_3$, 400 MHz) δ 8.18 (s, 1H), 7.78 (m, 1H), 7.59 (m, 1H), 7.07 (m, 1H), 6.36 (s, 1H), 5.22 (s, 1H), 4.79-4.67 (m, 2H), 4.24-3.98 (m, 2H), 3.30 (s, 1H), 3.05 (m, 1H), 2.86 (m, 2H), 2.75 (s, 6H), 2.69 (m, 1H), 2.35 (m, 1H), 1.63-1.38 (m, 10H), 1.23-0.83 (m, 18H), 0.43 (m, 2H). LCMS found 891.0 [M+H]$^+$.

Example 161

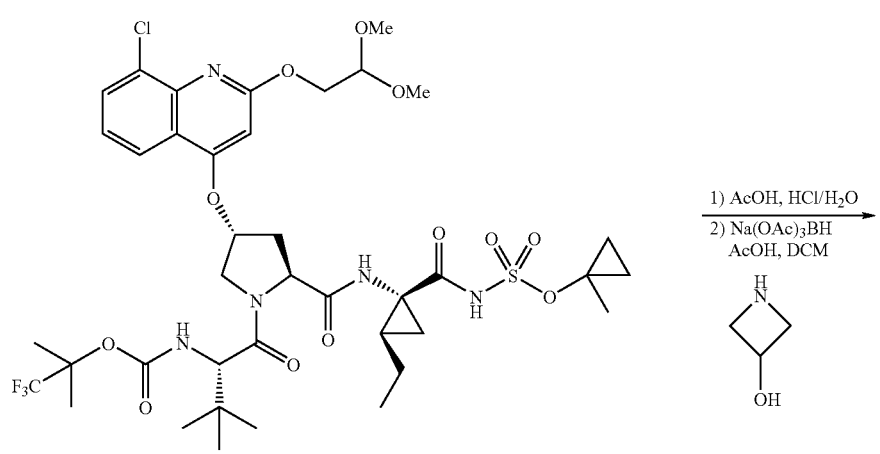

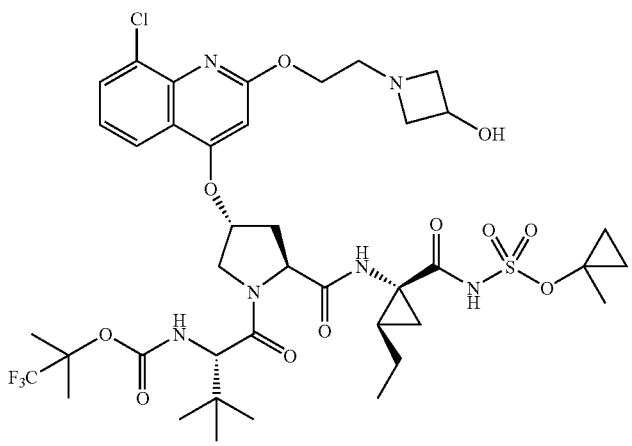

Compound 161

Compound 161 was prepared according to the method presented in example 160. Treatment of (1-{4-[8-chloro-2-(2,2-dimethoxy-ethoxy)-quinolin-4-yloxy]-2-[2-ethyl-1-(1-methyl-cyclopropoxysulfonylaminocarbonyl)-cyclopropyl-carbamoyl]-pyrrolidine-1-carbonyl}-2,2-dimethyl-propyl)-carbamic acid 2,2,2-trifluoro-1,1-dimethyl-ethyl ester (285 mg, 0.314 mmol) and with the exception of using 3-azetidinol occurred under the same conditions, adjusted for scale, to afford compound 161 (78.1 mg, 27% yield). $^1$H NMR (CDCl$_3$, 400 MHz) δ 8.29 (s, 1H), 7.77 (m, 1H), 7.60 (m, 1H), 7.08 (m, 1H), 6.35 (s, 1H), 5.49 (s, 1H), 5.19-5.14 (m, 2H), 4.75 (m, 1H), 4.64-4.57 (m, 2H), 4.37 (m, 2H), 4.20-3.90 (m, 4H), 3.63-3.50 (m, 2H), 2.61 (m, 1H), 2.40 (m, 1H), 1.63-1.38 (m, 10H), 1.23-0.83 (m, 18H), 0.43 (m, 2H). LCMS found 919.0 [M+H]$^+$.

Example 162

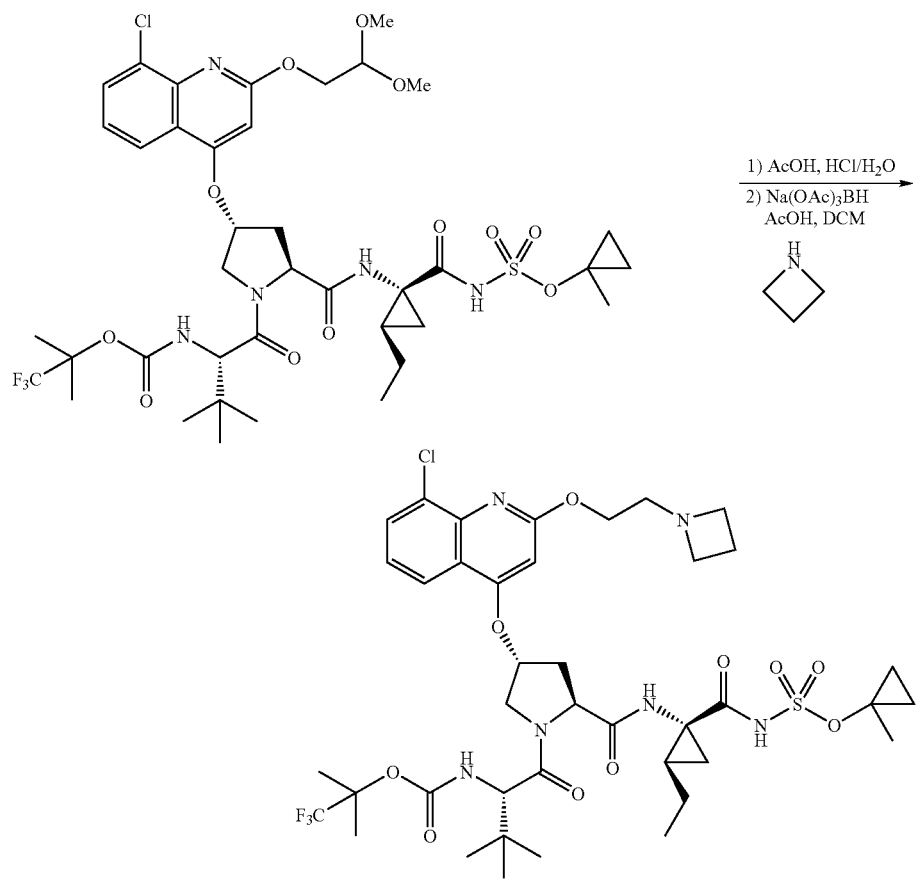

Compound 162

Compound 162 was prepared according to the method presented in example 160. Treatment of (1-{4-[8-chloro-2-(2,2-dimethoxy-ethoxy)-quinolin-4-yloxy]-2-[2-ethyl-1-(1-methyl-cyclopropoxysulfonylaminocarbonyl)-cyclopropyl-carbamoyl]-pyrrolidine-1-carbonyl}-2,2-dimethyl-propyl)-carbamic acid 2,2,2-trifluoro-1,1-dimethyl-ethyl ester (352 mg, 0.388 mmol) and with the exception of using azetidine occurred under the same conditions, adjusted for scale, to afford Compound 162 (113 mg, 32% yield). $^1$H NMR (CDCl$_3$, 400 MHz) δ 8.38 (s, 1H), 7.75 (m, 1H), 7.59 (m, 1H), 7.06 (m, 1H), 6.34 (s, 1H), 5.21 (s, 1H), 4.74-4.55 (m, 2H), 4.40-4.21 (m, 2H), 4.13 (m, 4H), 4.02-3.92 (m, 2H), 3.50-3.41 (m, 2H), 2.43 (m, 3H), 2.09 (m, 1H), 1.63-1.38 (m, 10H), 1.23-0.83 (m, 18H), 0.43 (m, 2H); LCMS found 903.0 [M+H]$^+$.

Example 163

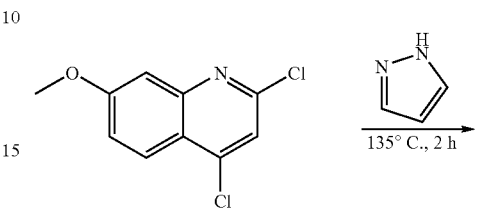

-continued

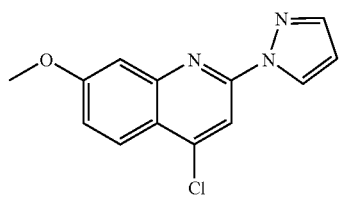

Pyrazole (3.32 g, 48.7 mmol, 3 equiv) was weighed out in a small round bottom flask (50 mL) and melted in an oil bath at 80° C. 2,4-Dichloro-7-methoxy-quinoline (3.7 g, 16.2 mmol, 1 equiv) was added and the melt was heated to 135° C. for 2 hours with continuous stirring. LCMS showed the complete consumption of dichloride reactant but the majority of the product was 7-methoxy-2,4-di-pyrazol-1-yl-quinoline. The desired mono-pyrazole product, 4-chloro-7-methoxy-2-pyrazol-1-yl-quinoline, was separated by normal column chromatography (20% EtOAc/Hexanes) (343 mg, 8% yield). LCMS found 260.29 [M+H]$^+$.

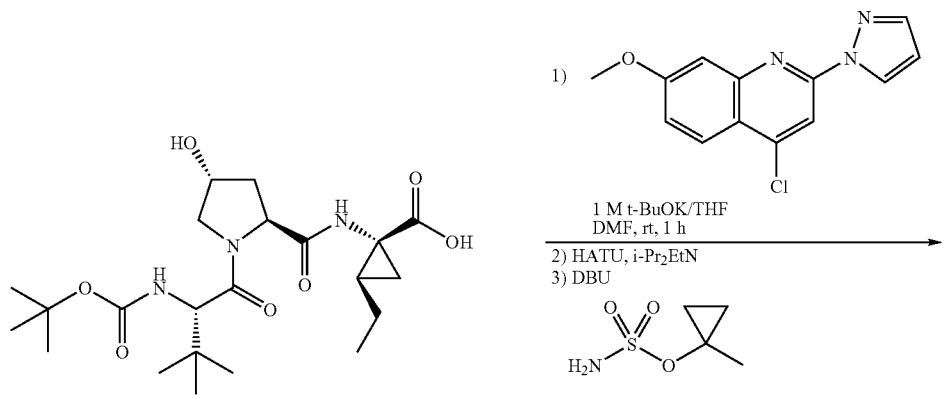

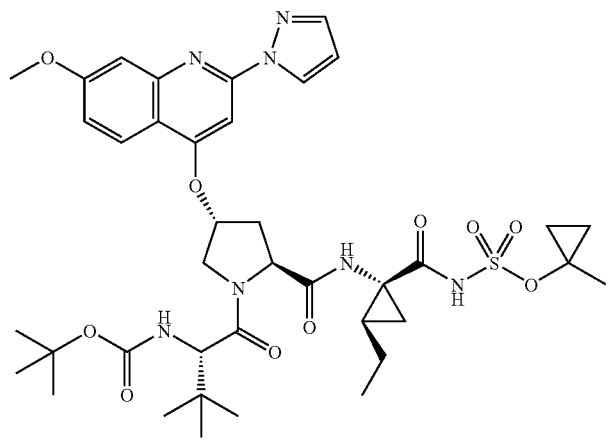

Compound 163

Compound 163 was prepared according to the method presented in example 16. Treatment of 1-{[1-(2-tert-butoxy-carbonylamino-3,3-dimethyl-butyryl)-4-hydroxy-pyrrolidine-2-carbonyl]-amino}-2-ethyl-cyclopropanecarboxylic acid (250 mg, 0.55 mmol) under the same conditions adjusted for scale and with the exception of utilizing 4-chloro-7-methoxy-2-pyrazol-1-yl-quinoline (143 mg, 0.55 mmol) and sulfamic acid 1-methyl-cyclopropyl ester (94 mg, 0.525 mmol) provided compound 163 (146 mg, 72% yield): $^1$H NMR (CD$_3$OD, 300 MHz) δ 8.81 (s, 1H), 8.11 (d, 1H), 7.89 (s, 1H), 7.54 (s, 1H), 7.38 (s, 1H), 7.12 (d, 1H), 6.65 (s, 1H), 5.58 (s, 1H), 4.56 (m, 2H), 4.24 (s, 1H), 4.15 (m, 1H), 3.97 (s, 3H), 2.68 (m, 1H), 2.35 (m, 1H), 1.69 (s, 3H), 1.59 (m, 4H), 1.28 (m, 11H), 1.05-0.97 (m, 13H), 0.69 (s, 2H). LCMS found 812.03 [M+H]$^+$.

Example 164

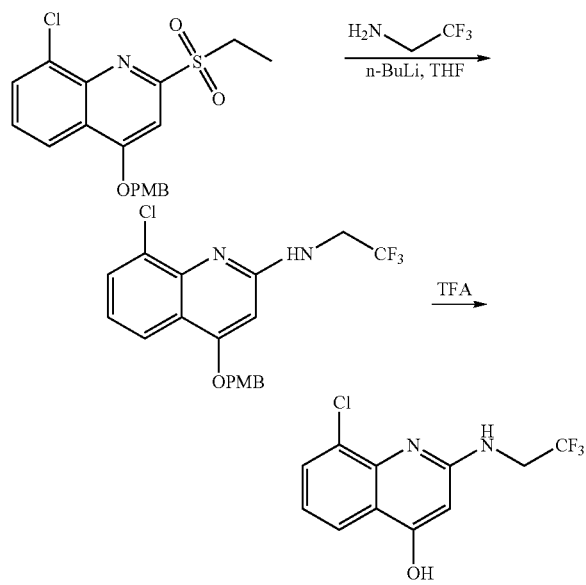

In a pre-dried 3-necked round bottom flask was dissolved 2,2,2-trifluoro-ethylamine (91 mg, 0.92 mmol, 1.2 equiv) in dry tetrahydrofuran (0.5 mL), under a nitrogen atmosphere. The flask was cooled down to −78° C. and 2.5M n-BuLi in hexanes (428 μL, 1.07 mmol, 1.4 equiv) was added via syringe. The mixture was stirred for 5 minutes then gradually warmed to 0° C. At this point, 8-chloro-2-ethanesulfonyl-4-(4-methoxy-benzyloxy)-quinoline (300 mg, 0.766 mmol, 1 equiv) in a solution of THF was slowly added. The mixture was stirred for 17 h at room temperature then quenched with brine and extracted into dichloromethane. The organic layer was dried over $MgSO_4$ and concentrated down in vacuo to afford [8-chloro-4-(4-methoxy-benzyloxy)-quinolin-2-yl]-(2,2,2-trifluoro-ethyl)-amine (203 mg, 67% yield). LCMS found 397.11 $[M+H]^+$.

[8-Chloro-4-(4-methoxy-benzyloxy)-quinolin-2-yl]-(2,2,2-trifluoro-ethyl)-amine (200 mg, 0.504 mmol, 1 equiv) was stirred in (1:1) mixture of TFA:Dichloromethane (110 mL) at room temperature for about 1 hour. The volatiles were subsequently removed on rotovap and used without further purification as a TFA salt. LCMS found 277.42 $[M+H]^+$.

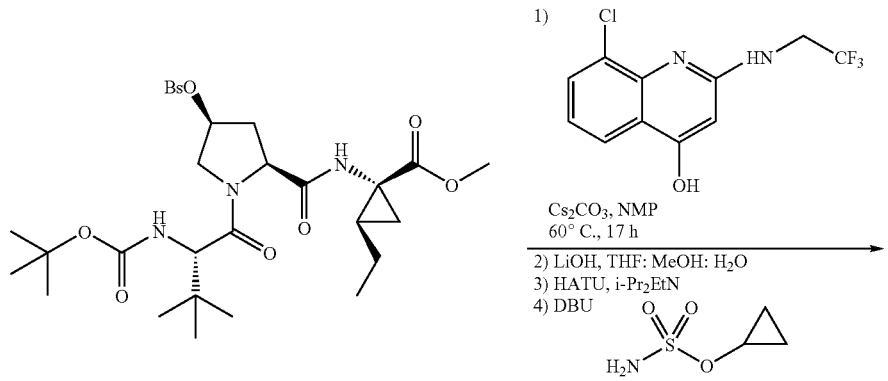

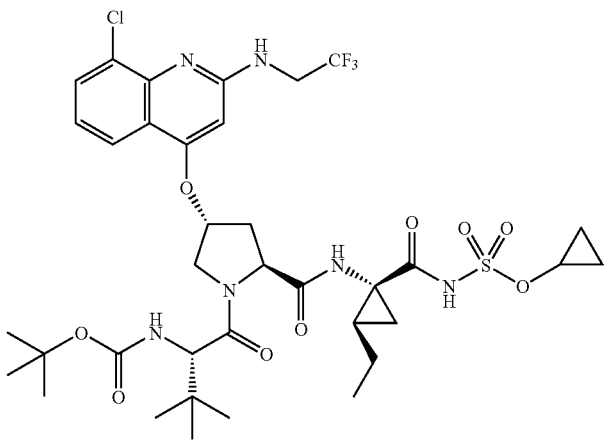

Compound 164

Compound 164 was prepared according to the method presented in example 138. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (344 mg, 0.5 mmol) occurred under the same conditions, adjusted for scale and with exception of utilizing 8-chloro-2-(2,2,2-trifluoro-ethylamino)-quinolin-4-ol (138 mg, 0.5 mmol) and sulfamic acid cyclopropyl ester (158 mg, 1.15 mmol). Purification of the crude product was accomplished by reverse phase HPLC (20%→85%, MeCN/H$_2$O/0.1% TFA) to provide compound 164 (388 mg, 85% yield): $^1$H NMR (CD$_3$OD, 300 MHz) δ 8.11 (d, 1H), 7.92 (d, 1H), 7.40 (t, 1H), 6.77 (br s, 1H), 5.57 (br s, 1H), 4.66-4.51 (m, 4H), 4.28-4.25 (m, 1H), 4.14 (br s, 1H), 4.09-4.05 (m, 1H), 2.73-2.66 (m, 1H), 2.4-2.32 (m, 1H), 1.61-1.58 (m, 4H), 1.45 (s, 1H), 1.19 (s, 9H), 1.04 (s, 9H), 1.02-0.94 (m, 6H), 0.77 (d, 2H). LCMS found 833.05 [M+H]$^+$.

Example 165

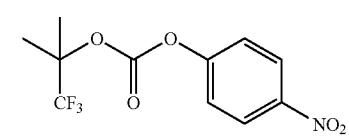

Compound 165

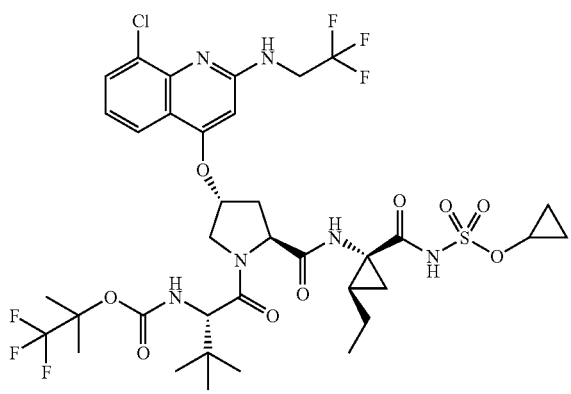

Compound 165 was prepared according to the method presented in Example 77 adjusted for scale and with the exception of starting from compound 164. Purification of the crude product was accomplished by reverse phase HPLC (20%→85%, MeCN/H$_2$O/0.1% TFA) to afford Compound 165 (30.6 mg, 57% yield): $^1$H NMR (CHCl$_3$, 400 MHz) δ 7.75 (d, 1H), 7.63 (d, 11H), 7.22 (br s, 1H), 7.05 (t, 1H), 6.07 (br s, 1H), 4.63 (m, 1H), 4.51 (m, 1H), 4.38 (m, 2H), 4.28 (m, 2H), 4.05-3.95 (m, 1H), 2.53 (m, 1H), 2.44 (m, 1H), 1.68-1.56 (m, 5H), 1.51-1.42 (m, 4H), 1.26-1.15 (m, 2H), 1.04-0.97 (m, 10H), 0.92 (m, 3H), 0.72 (br s, 2H). LCMS found 887.02 [M+H]$^+$.

Example 166

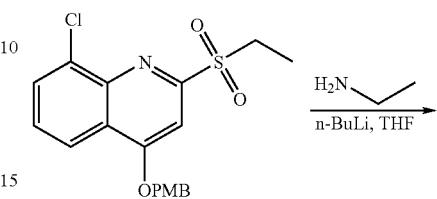

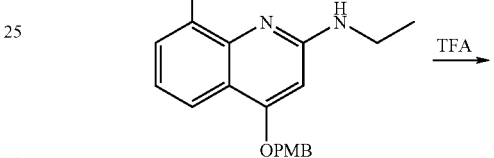

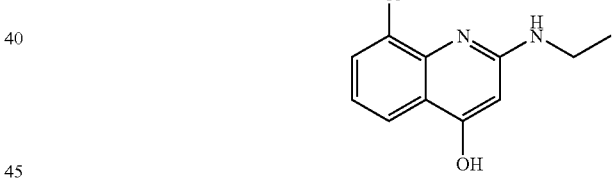

In a pre-dried 3-necked round bottom flask was added 2M ethylamine solution in THF (960 μL, 1.92 mmol), under nitrogen atmosphere. The flask was cooled to −78° C. and 2.5M n-BuLi in hexanes (768 μL, 1.92 mmol) was added via syringe. The mixture was stirred for 5 minutes and then allowed to warm up to room temperature. As the temperature was warming up, at approximately 0° C., 8-chloro-2-ethane-sulfonyl-4-(4-methoxy-benzyloxy)-quinoline (500 mg, 1.28 mmol) in a solution in THF was slowly added from a syringe. The mixture was stirred for 17 h at room temperature. The mixture was quenched with brine and extracted into dichloromethane. The organic layer was dried over MgSO$_4$ and concentrated in vacuo to provide the desired compound (373 mg, 85% yield). LCMS found 343.10 [M+H]$^+$.

[8-Chloro-4-(4-methoxy-benzyloxy)-quinolin-2-yl]-ethyl-amine (373 mg, 1.09 mmol) was stirred in TFA:Dichloromethane (1:1, 10 mL) at room temperature for about 1 hour. The volatiles were subsequently removed on rotovap and the crude residue was used directly as a TFA salt. LCMS found 223.29 [M+H]$^+$.

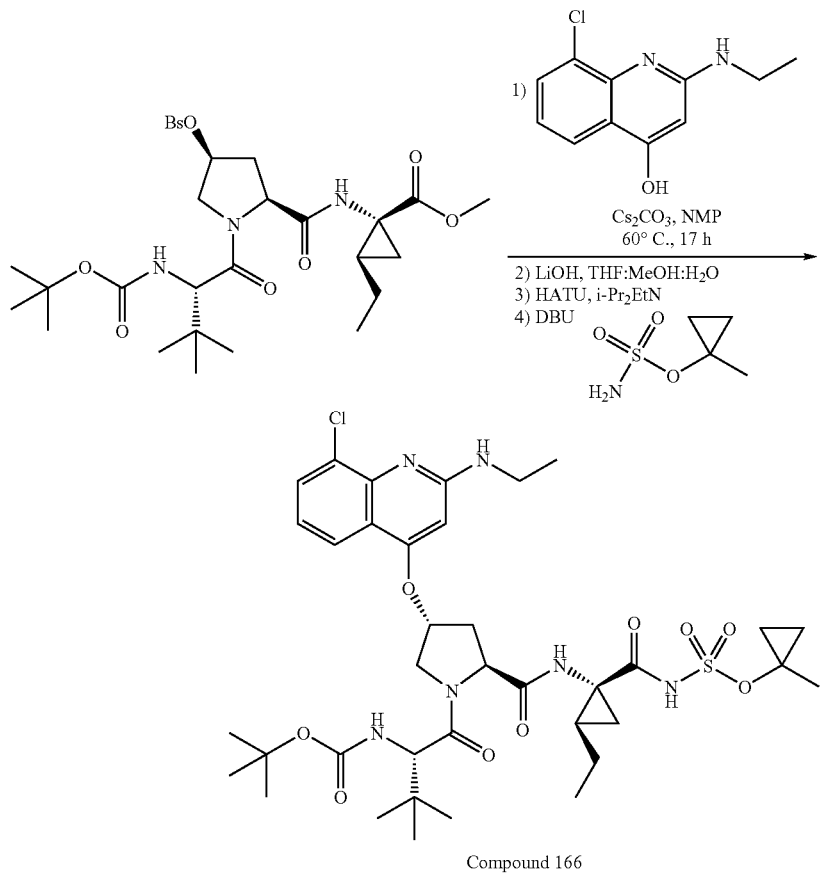

Compound 166

Compound 166 was prepared according to the method presented in example 138. Treatment of 1-{[4-(4-Bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (764 mg, 1.11 mmol) occurred under the same conditions, adjusted for scale and with exception of utilizing 8-chloro-2-ethylamino-quinolin-4-ol (373 mg, 1.11 mmol) as TFA salt and sulfamic acid 1-methyl-cyclopropyl ester (365 mg, 2.04 mmol). Purification of the crude product was accomplished by reverse phase HPLC (20%→85%, MeCN/H$_2$O/0.1% TFA) to provide Compound 166 (680 mg, 88% yield): $^1$H NMR (CHCl$_3$, 400 MHz) δ 9.55 (br s, 1H), 7.86 (d, 1H), 7.62 (m, 1H), 7.34 (br s, 1H), 7.11 (s, 1H), 6.02 (br s, 1H), 5.31-5.12 (m, 3H), 4.53-4.34 (m, 3H), 4.12-3.97 (m, 3H), 3.62 (d, 1H), 3.41 (br s, 2H), 1.61 (s, 3H), 1.57-1.42 (m, 2H), 1.33 (s, 6H), 1.25 (s, 9H), 0.96 (s, 6H), 0.93 (s, 3H), 0.89-0.83 (m, 4H), 0.56 (s, 2H). LCMS found 793.01 [M+H]$^+$.

Example 167

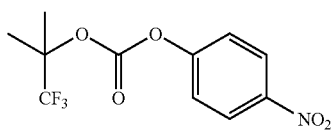

-continued

Compound 167

Compound 167 was prepared according to the method presented in Example 77 adjusted for scale and with the exception of starting from compound 166. Purification of the crude product was accomplished by reverse phase HPLC (20%→85%, MeCN/H$_2$O/0.1% TFA) to provide Compound 167 (200 mg, 29% yield): $^1$H NMR (CHCl$_3$, 400 MHz) δ 9.01 (br s, 1H), 7.99 (s, 1H), 7.89 (d, 1H), 7.65 (d, 1H), 7.22 (t, 1H), 6.20 (s, 1H), 5.52-5.47 (m, 2H), 4.57-4.53 (m, 1H), 4.44-4.42 (m, 1H), 4.21-4.19 (m, 2H), 3.49 (br s, 2H), 2.66 (m, 1H), 2.49 (m, 1H), 2.18-2.05 (m, 1H), 1.64 (m, 5H), 1.52 (s, 3H), 1.45 (m, 3H), 1.38 (s, 2H), 1.35 (m, 2H), 1.25 (m, 2H), 1.17 (m, 1H), 1.01 (s, 6H), 0.98 (s, 3H), 0.91 (m, 3H), 0.60 (s, 2H). LCMS found 846.95 [M+H]⁺.

Example 168

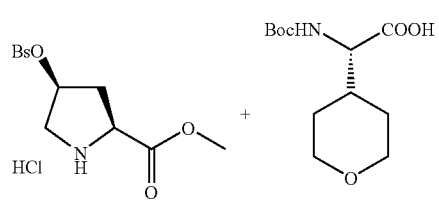 + 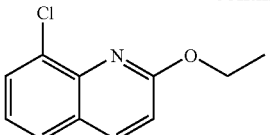 →(DIPEA, HATU/DCM)

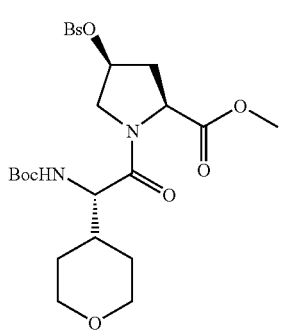

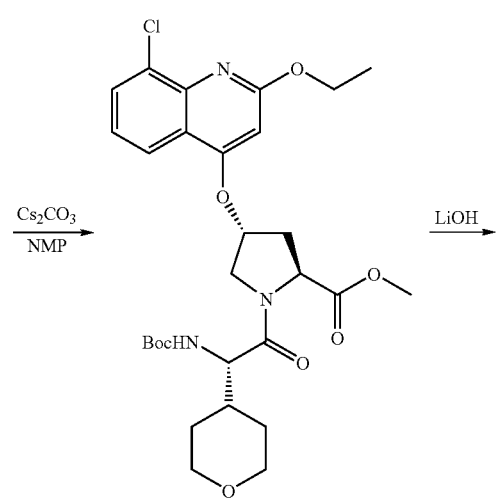 →(Cs₂CO₃, NMP)

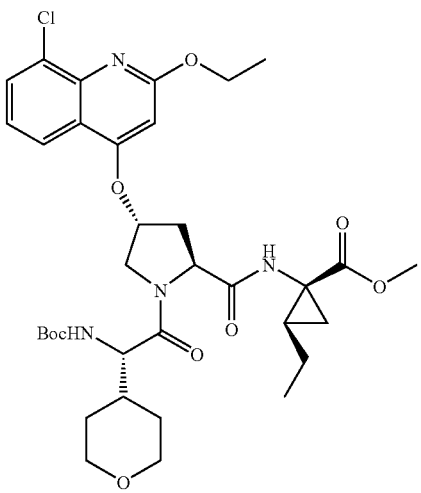 →(LiOH)

To a solution of 4-(4-bromo-benzenesulfonyloxy)-pyrrolidine-2-carboxylic acid methyl ester HCl salt (4 g, 10 mmol) in DCM (50 mL) was added tert-butoxycarbonylamino-(tetrahydro-pyran-4-yl)-acetic acid (2.86 g, 11 mmol), HATU (5.7 g, 15 mmol) and DIPEA (7 mL, 40 mmol). The solution was stirred at room temperature for 16 h. The solution was diluted with DCM and washed twice with aq NH₄Cl and brine. The organic layer was dried over MgSO₄ and concentrated in vacuo. The desired product was purified by silica gel column chromatography from hexane/EtOAc to provide 4-(4-bromo-benzenesulfonyloxy)-1-[2-tert-butoxycarbonylamino-2-(tetrahydro-pyran-4-yl)-acetyl]-pyrrolidine-2-carboxylic acid methyl ester (4.25 g 70% yield). LCMS found 606 ([M+H]⁺.

Treatment of 4-(4-bromo-benzenesulfonyloxy)-1-[2-tert-butoxycarbonylamino-2-(tetrahydro-pyran-4-yl)-acetyl]-pyrrolidine-2-carboxylic acid methyl ester under the same conditions as presented in example 137 adjusted for scale and with the exception of using 8-chloro-2-ethoxy-quinolin-4-ol provided 1-{[1-[2-tert-Butoxycarbonylamino-2-(tetrahydro-pyran-4-yl)-acetyl]-4-(8-chloro-2-ethoxy-quinolin-4-yloxy)-pyrrolidine-2-carbonyl]-amino}-2-ethyl-cyclopropanecarboxylic acid. LCMS found 690 ([M+H]⁺.

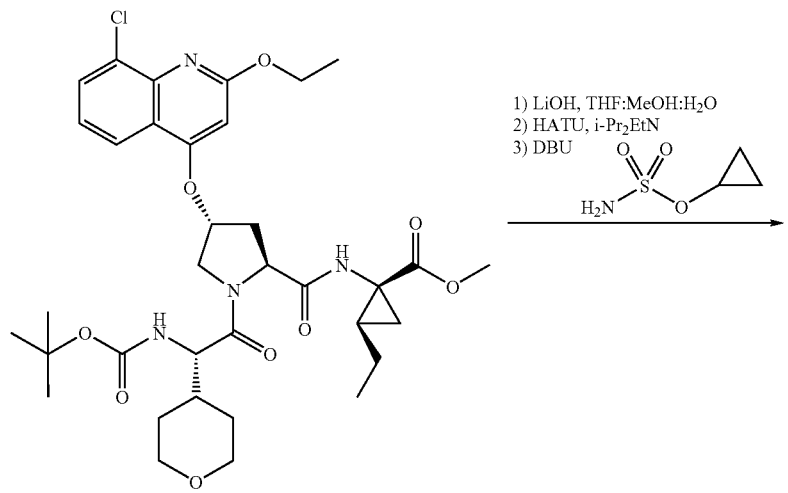

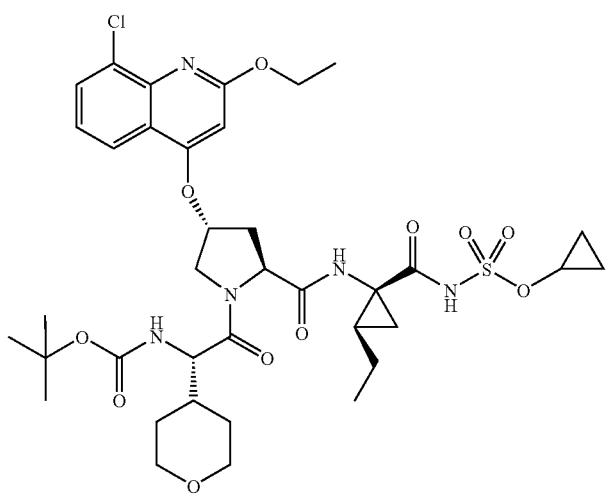

Compound 168

The 1-{[1-[2-tert-butoxycarbonylamino-2-(tetrahydro-pyran-4-yl)-acetyl]-4-(8-chloro-2-ethoxy-quinolin-4-yloxy)-pyrrolidine-2-carbonyl]-amino}-2-ethyl-cyclopropanecarboxylic acid methyl ester (0.76 g, 1.1 mmol) was dissolved in THF/MeOH/H₂O (3:3:1) (7 mL) and lithium hydroxide (143 mg, 5.5 mmol) was added. The reaction was stirred at room temperature for approximately 1 hour and the solvent was then removed. The residue was diluted with 1M HCl and then extracted with EtOAc twice. The combined organic layers were washed with brine, dried over magnesium sulfate and concentrated to give 0.7 g (95% yield) of the desired carboxylic acid as a white solid compound. LCMS found 690 [M+H]⁺.

To a solution of 1-{[1-[2-tert-butoxycarbonylamino-2-(tetrahydro-pyran-4-yl)-acetyl]-4-(8-chloro-2-ethoxy-quinolin-4-yloxy)-pyrrolidine-2-carbonyl]-amino}-2-ethyl-cyclopropanecarboxylic acid (200 mg, 0.29 mmol) in DCM (2 mL) was added HATU (167 mg, 0.44 mmol) and DIPEA (0.077 mL, 0.44 mmol). The solution was stirred at room temperature for 15 min before sulfamic acid cyclopropyl ester (80 mg, 0.58 mmol) and DBU (0.17 mL, 1.16 mmol) were added. The reaction was then stirred for an additional 16 h. The solution was diluted with EtOAc and washed twice with 1M aqueous HCl and Brine. The organic layer was dried over MgSO₄ and concentrated in vacuo. The desired sulfamate was precipitated from EtOH/H₂O to afford compound 168 (118 mg, 50% yield). ¹H NMR (300 MHz, CD₃OD): δ 9.32 (s, 1H), 8.01 (d, 1H), 7.73 (d, 1H), 7.24 (m, 1H), 6.51 (s, 1H), 5.43 (s, 1H), 4.59 (m, 4H), 4.32 (m, 1H), 4.10-3.85 (m, 4H), 3.32 (m, 2H), 2.60 (m, 1H), 2.35 (m, 1H), 2.14 (m, 1H), 1.61-1.21 (m, 1H), 1.19 (m, 11H), 0.98 (m, 6H), 0.77 (m, 2H). LCMS found 809 [M+H]⁺.

Example 169

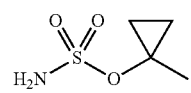

Compound 169

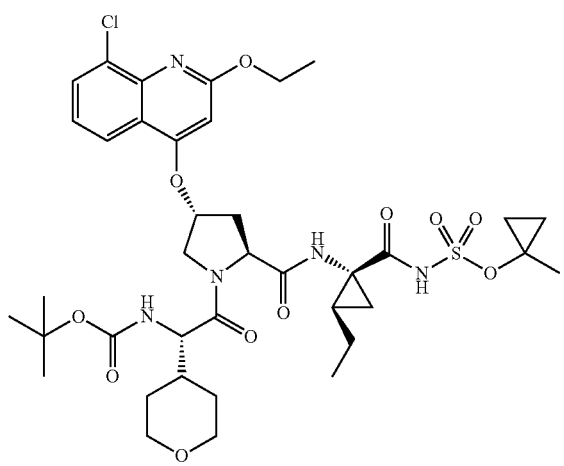

Compound 169 was prepared according to the method presented in example 138. Treatment of 1-{[1-[2-tert-butoxy-carbonylamino-2-(tetrahydro-pyran-4-yl)-acetyl]-4-(8-chloro-2-ethoxy-quinolin-4-yloxy)-pyrrolidine-2-carbonyl]-amino}-2-ethyl-cyclopropanecarboxylic acid (200 mg, 0.29 mmol) occurred under the same conditions, adjusted for scale to provide compound 169 as a white solid (107 mg). $^1$H MNR (300 MHz, CD$_3$OD): δ 9.34 (s, 1H), 8.00 (d, 1H), 7.71 (d, 1H), 7.24 (m, 1H), 6.49 (s, 1H), 5.42 (s, 1H), 4.57 (m, 4H), 4.11-3.85 (m, 4H), 3.41 (m, 2H), 2.60 (m, 1H), 2.35 (m, 1H), 2.14 (m, 1H), 1.71-1.32 (m, 16H), 1.20 (m, 11H), 0.98 (m, 4H), 0.70 (m, 2H). LCMS found 823 [M+H]$^+$.

Example 170

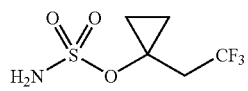

Compound 170

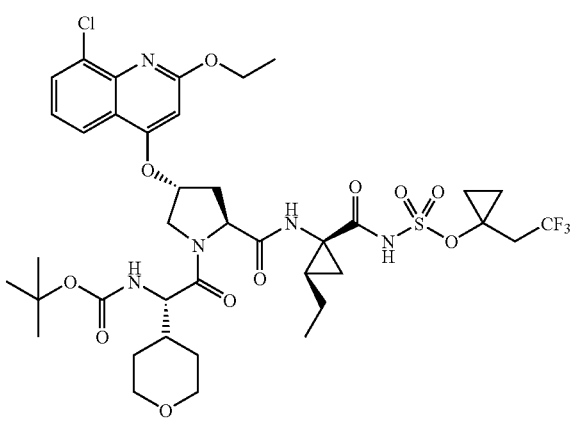

Compound 170 was prepared according to the method presented in Example 138, substituting sulfamic acid 1-(2,2,2-trifluoro-ethyl)-cyclopropyl ester for sulfamic acid 1-methyl-cyclopropyl and using 1-{[1-[2-tert-butoxycarbony-lamino-2-(tetrahydro-pyran-4-yl)-acetyl]-4-(8-chloro-2-ethoxy-quinolin-4-yloxy)-pyrrolidine-2-carbonyl]-amino}-2-ethyl-cyclopropanecarboxylic acid (200 mg, 0.29 mmol) occurred under the same conditions, adjusted for scale to afford Compound 170 as a white solid (103 mg). $^1$H MNR (300 MHz, CD$_3$OD): δ9.31 (s, 1H), 8.00 (d, 1H), 7.73 (d, 1H), 7.25 (d, 1H), 6.50 (s, 1H), 5.42 (m, 1H), 4.57 (m, 4H), 4.10-3.87 (m, 4H), 3.39 (m, 2H), 2.90 (m, 2H), 2.60 (m, 1H), 2.35 (m, 1H), 2.10 (m, 1H), 1.74-1.31 (m, 15H), 1.19 (m, 11H), 0.97 (m, 4H). LCMS found 891 [M+H]$^+$.

Example 171

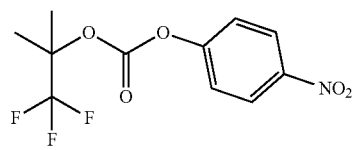

Compound 171

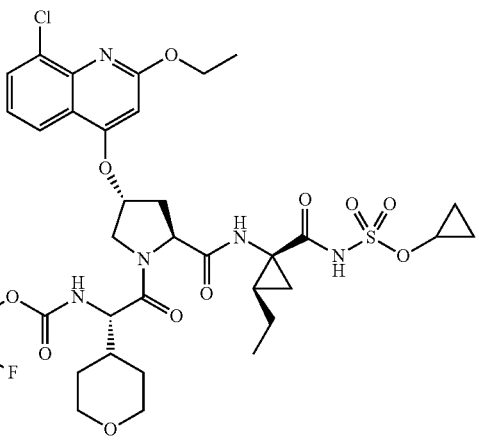

Compound 171 was prepared according to the methods described in Example 77. Treatment of Compound 168 (100 mg, 0.12 mmol) under the same conditions, adjusted for scale, provided Compound 171 (82 mg, 77% yield). $^1$H MNR (300 MHz, CD$_3$OD): δ 9.34 (s, 1H), 8.00 (d, 1H), 7.72 (d, 1H), 7.23 (m, 1H), 6.50 (s, 1H), 5.42 (s, 1H), 4.71-4.54 (m, 4H), 4.32 (m, 1H), 4.06-3.88 (m, 4H), 3.37 (m, 2H), 2.60 (m, 1H), 2.35 (m, 1H), 2.14 (m, 1H), 1.78-1.43 (m, 9H), 1.40 (S, 3H), 1.34-1.20 (m, 4H), 1.01 (S, 3H), 0.95 (m, 6H), 0.77 (m, 2H). LCMS found 863 [M+H]$^+$.

Example 172

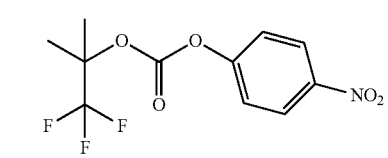

Compound 172

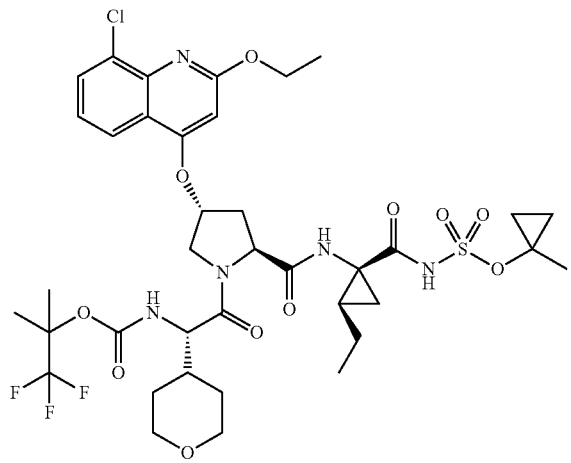

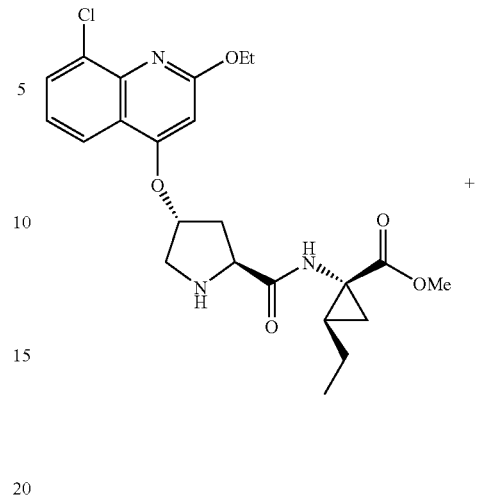

Compound 172 was prepared according to the methods described in Example 77. Treatment of Compound 167 (200 mg, 0.24 mmol) under the same conditions adjusted for scale and with the exception of using carbonic acid 4-nitro-phenyl ester 2,2,2-trifluoro-1,1-dimethyl-ethyl ester (141 mg, 0.48 mmol) provided Compound 172 (120 mg, 56% yield). $^1$H MNR (300 MHz, CD$_3$OD): δ 9.34 (s, 1H), 8.00 (d, 1H), 7.73 (d, 1H), 7.24 (m, 1H), 6.50 (s, 1H), 5.43 (s, 1H), 4.59 (m, 4H), 4.06-3.85 (m, 4H), 3.41 (m, 2H), 2.60 (m, 1H), 2.35 (m, 1H), 2.14 (m, 1H), 1.71-1.09 (m, 24H), 0.98 (m, 4H), 0.70 (m, 2H). LCMS found 877 [M+H]$^+$.

Examples 173 and 174

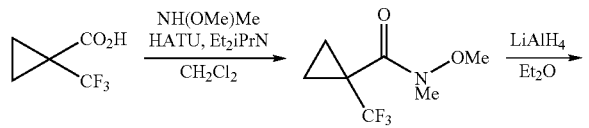

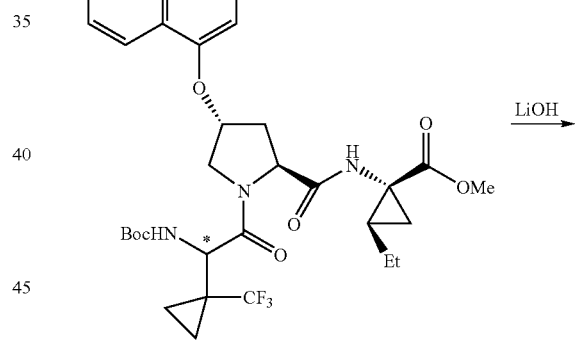

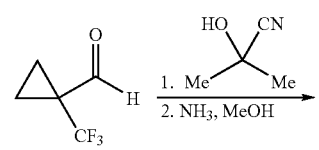

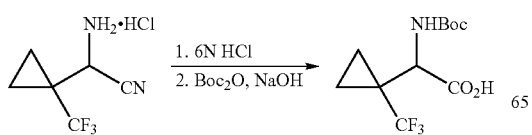

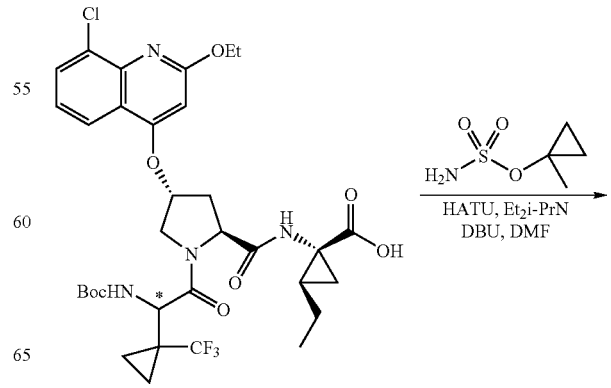

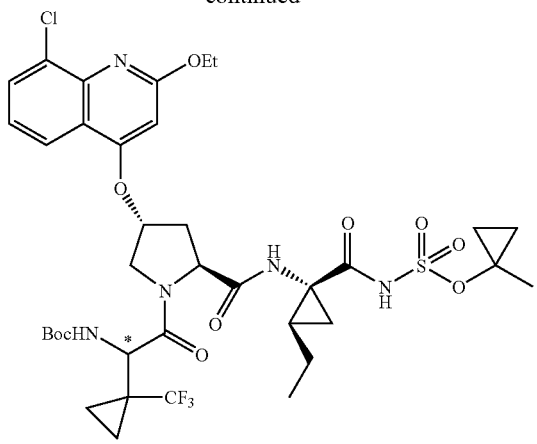

* = (R), Compound 173
* = (R/S), Compound 174

In a 500 mL rbf at rt were added (in order) 1-trifluoromethyl-cyclopropanecarboxylic acid (5 g, 32 mmol), CH$_2$Cl$_2$ (150 mL), Et$_2$iPrN (12.3 mL), and NH(OMe)Me (4.7 g) with stirring. The solution was cooled to 0° C. and HATU (13.4 g) was added. The ice bath was removed and the reaction was warmed to room temperature and stirred for 15 hours. The reaction was then poured onto 1N HCl/ice and extracted with Et$_2$O (3×100 mL). The combined organic extracts were washed successively with 1N HCl, 1M NaOH, water, and brine, and then dried over sodium sulfate. After filtration, concentration in vacuo (80 Torr) gave sufficiently pure material to carry forward without further purification (17.2 mmol, 54% yield). LCMS found 198.02 [M+H]$^+$.

Powdered LiAlH$_4$ was added to anhydrous Et$_2$O and cooled to 0° C. in a flame-dried 3-neck round-bottom flask under inert atmosphere. To the cloudy solution was dropwise added 1-trifluoromethyl-cyclopropanecarboxylic acid methoxy-methyl-amide (3.4 g, 17.2 mmol) over 5 minutes with vigorous stirring. The reaction was continued to stir at 0° C. until complete consumption of starting material was observed by TLC. All 3-necks were then opened to air, and water (0.65 mL) was added dropwise at 0° C. NaOH (15 wt % in water, 0.65 mL) was then carefully added at 0° C. Water (0.65 mL) was again added dropwise at 0° C. The reaction slurry was filtered through celite, and washed 2×50 mL with Et$_2$O. The aldehyde was provided as a clear pale yellow solution in Et$_2$O, and was carried onward without concentration or purification due to its volatility (100% yield assumed; product not characterized).

To 1-trifluoromethyl-cyclopropanecarbaldehyde (17.2 mmol) in Et$_2$O (150 mL) was added acetone cyanohydrin (3.15 mL) and Et$_3$N (4.8 mL). The reaction was stirred for 17 h at rt, and then concentrated in vacuo. NH$_3$ in MeOH (30 mL, 4M) was then added and stirred for an additional 17 h at room temperature. All volatiles were subsequently removed in vacuo. The crude residue was carried onward without purification. The residue was then dissolved in Et$_2$O, cooled to 0° C., and 2M HCl in dioxanes was slowly added and the solid collected by filtration to give the desired product (100% yield assumed, product not characterized).

To tert-butoxycarbonylamino-(1-trifluoromethyl-cyclopropyl)-acetic acid (17.2 mmol) at room temperature was added 6N HCl(aq) (50 mL). The reaction mixture was refluxed for 17 h, then cooled to 0° C. and carefully basified with 30% aq NaOH (47 mL). Boc$_2$O (15.8 g) was added and stirred for 18 h. The reaction was then brought to pH 4 with 1M HCl and extracted with EtOAc (3×200 mL). The combined organics were washed successively with 1M HCl and brine, and then dried over sodium sulfate. Concentration in vacuo gave the crude reside. Purification via flash column chromatography, using MeOH and CH$_2$Cl$_2$, gave the desired product as a clear liquid (1.7 g, 35% yield from 1-trifluoromethyl-cyclopropanecarboxylic acid methoxy-methyl-amide). $^1$H NMR (CDCl$_3$, 400 MHz) δ 8.9 (br s, 1H), 4.0 (d, 1H), 1.5 (s, 9H), 1.38-1.0 (m, 4H).

To 1-{[4-(8-chloro-2-ethoxy-quinolin-4-yloxy)-pyrrolidine-2-carbonyl]-amino}-2-ethyl-cyclopropanecarboxylic acid methyl ester (56 mg, 0.12 mmol) in DMF (5 mL) was added iPr$_2$EtN (90 µL) and HATU (143 mg). After stirring for 15 min at room temperature, tert-butoxycarbonylamino-(1-trifluoromethyl-cyclopropyl)-acetic acid was added (117 mg) and stirred for 16 hours. The reaction mixture was then added to saturated sodium bicarbonate and extracted with EtOAc. The combined organic extracts were washed with 1N HCl, water, and brine, and then dried over magnesium sulfate. Purification by flash column chromatography separated two diastereomeric products (configuration assigned by activity of final product). (R)-diastereomer (29 mg, 33% yield) and (S)-diastereomer (44 mg, 50% yield). LCMS found 726.99 [M+H]$^+$.

A solution of 1-{[1-[2-tert-Butoxycarbonylamino-2-(1-trifluoromethyl-cyclopropyl)-acetyl]-4-(8-chloro-2-ethoxy-quinolin-4-yloxy)-pyrrolidine-2-carbonyl]-amino}-2-ethyl-cyclopropanecarboxylic acid methyl ester (45 mg, 0.06 mmol) in THF/MeOH/H$_2$O (1:1:1, 3 mL) was stirred at room temperature. To the solution was added LiOH (10 mg) and the reaction mixture was heated to 50° C. for 3 hours. Complete conversion was observed by LCMS, as well as complete epimerization. In one instance of running this reaction, purification by HPLC was attempted, and provided a small amount of pure diastereomer (5% yield, 9 mg) (R)-configuration assigned based on final product's activity). In a separate instance of running this reaction, the diastereomeric mixture (1:1 at P3) was carried on crude. LCMS found 712.96 [M+H]$^+$.

To a room temperature solution of 1-{[1-[2-tert-butoxycarbonylamino-2-(1-trifluoromethyl-cyclopropyl)-acetyl]-4-(8-chloro-2-ethoxy-quinolin-4-yloxy)-pyrrolidine-2-carbonyl]-amino}-2-ethyl-cyclopropanecarboxylic acid (40 mg, 0.06 mmol, procedure was for (R/S)-diastereomeric mixture at P3) in DMF (5 mL) was added i-Pr$_2$EtN (31 µL) and HATU (34 mg). The mixture was stirred for 30 minutes, and then DBU (36 µL) and sulfamic acid 1-methyl-cyclopropyl ester (18 mg). The reaction was stirred for 18 h at room temperature, then added to 5% aq. citric acid. The mixture was extracted with EtOAc, and the combined organics were washed with brine and dried over magnesium sulfate. Concentration in vacuo followed by purification by reverse phase HPLC gave the desired product Compound 174 (13 mg, 26% yield, 1:1 diastereomeric mixture at P3). Same procedure as above for (R)-diastereomer at P3, provided desired product Compound 173 in 44% yield (4:5 mg). $^1$H NMR (CD$_3$OD, 500 MHz, diagnostic peaks) δ 8.9 (s, 0.5H), 7.9 (d, 0.5H), 7.8 (d, 0.5H), 7.65 (m, 1H), 7.42 (s, 1H), 7.17 (m, 1H), 6.27 (s, 0.5H), 6.24 (s, 0.5H), 5.29 (br s, 1H), 5.11 (s, 0.5H), 4.98 (s, 0.5H), 4.58 (q, 2H), 4.48-4.3 (m, 2H), 4.28-4.1 (m, 2H), 2.6 (m, 0.5H), 2.5

(m, 0.5H), 2.32 (m, 1H), 1.65 (s, 1.5H), 1.60 (s, 1.5H), 1.48-1.62 (m, 7H). LCMS found 845.94 [M+H]⁺.

Example 175

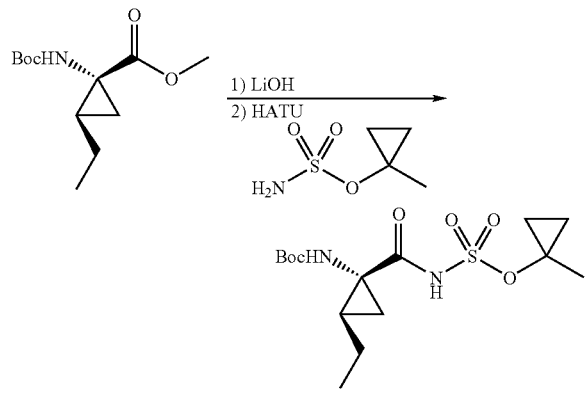

To a solution of 1-tert-butoxycarbonylamino-2-ethyl-cyclopropanecarboxylic acid methyl ester (4.95 g, 20.3 mmol) in a mixture of THF (40 mL) and MeOH (40 mL) was added aqueous LiOH (2.5M, 40 mL, 100 mmol, 5 equiv.). The solution was heated to 45° C. (external temperature) for 5 h before cooling to room temperature. To the reaction was added aqueous HCl (6M, 20 mL) and the volatiles were removed in vacuo. The residue was diluted with EtOAc and the aqueous layer was separated. The organic layer was washed with Brine, dried over Na₂SO₄ and concentrated to give the crude acid.

To a portion of the crude acid (2.02 g, 8.8 mmol) in CH₂Cl₂ (45 mL) was added sulfamic acid 1-methyl-cyclopropyl ester (2.0 g, 13.26 mmol), HATU (3.68 g, 9.7 mmol) and diisopropylethylamine (8.0 mL, 45.9 mmol). The reaction mixture was stirred at room temperature for 3 days before dilution with CH₂Cl₂. The solution was washed twice with aqueous HCl (1M) and once with Brine. The aqueous layers were backextracted with CH₂Cl₂. The organic layers were combined, dried over Na₂SO₄, and concentrated in vacuo. The crude sulfamate was purified by column chromatography (20→100% EtOAc/hexanes) to provide [2-ethyl-1-(1-methyl-cyclopropoxysulfonylaminocarbonyl)-cyclopropyl]-carbamic acid tert-butyl ester (2.8 g, 89%): ¹H NMR (d₃-MeOD, 300 MHz) δ 10.05 (s, 1H), 1.69 (s, 3H), 1.47-1.52 (m, 2H), 1.45 (s, 9H), 1.29-1.41 (m, 4H), 1.06 (m, 1H), 0.975 (t, 3H), 0.65 (m, 2H).

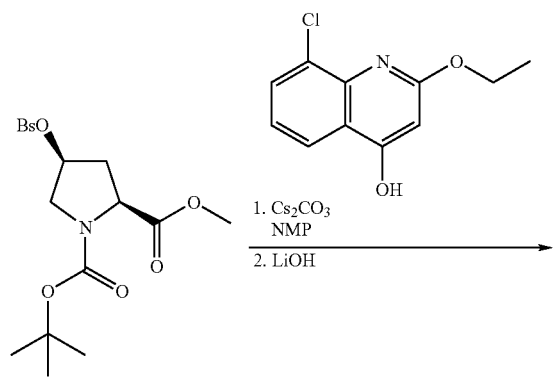

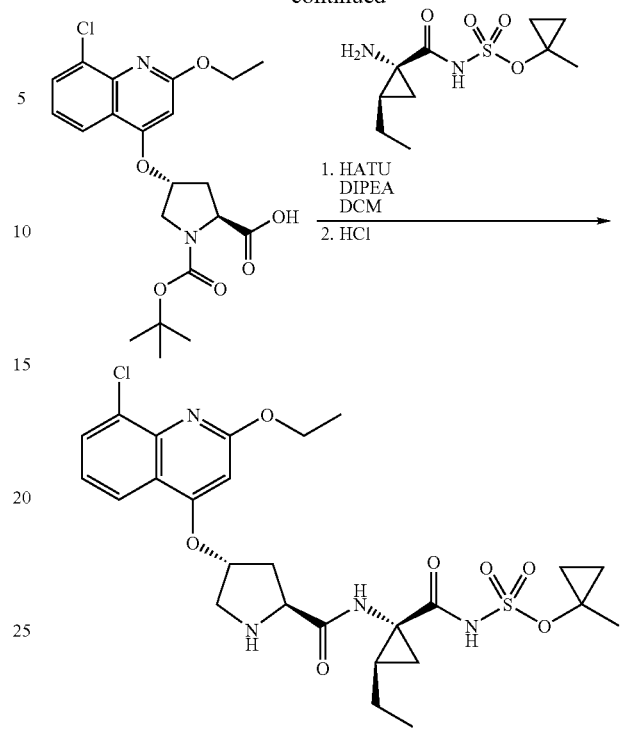

4-(4-Bromo-benzenesulfonyloxy)-pyrrolidine-1,2-dicarboxylic acid 1-tert-butyl ester 2-methyl ester (5.68 g, 12.23 mmol) was dissolved in NMP (40 mL) and 8-chloro-2-ethoxy-quinolin-4-ol (3.0 g, 13.4 mmol) was added followed by cesium carbonate (12.01 g, 36.86 mmol). The reaction was heated to 65° C. for three hours and then cooled to room temperature. The reaction was then diluted with EtOAc and washed with water, saturated ammonium chloride and brine. The organic layer was dried over sodium sulfate and concentrated. The crude residue was then triturated with methanol to give 3.98 g (72% yield) of the intermediate as a solid. The intermediate (2.94 g, 6.52 mmol) was then dissolved in THF/MeOH (1:1, 52 mL) and lithium hydroxide (781 mg, 32.6 mmol) was added as a solution in water (13 mL). The reaction was stirred at room temperature for approximately 1 hour and the solvent was then removed. The residue was diluted with 1M HCl and then extracted with EtOAc twice. The combined organic extracts were washed with brine, dried over magnesium sulfate and concentrated to give 2.74 g (96% yield) of the desired carboxylic acid as a white solid. LCMS found 436.92 [M+H]⁺.

[2-ethyl-1-(1-methyl-cyclopropoxysulfonylaminocarbonyl)-cyclopropyl]-carbamic acid tert-butyl ester was treated with HCl in dioxanes to afford the HCl salt of (1-amino-2-ethyl-cyclopropanecarbonyl)-sulfamic acid 1-methyl-cyclopropyl ester (1.81 g, 6.91 mmol). To this amine was added a solution of 4-(8-chloro-2-ethoxy-quinolin-4-yloxy)-pyrrolidine-1,2-dicarboxylic acid 1-tert-butyl ester (2.74 g, 6.27 mmol), diisopropylethyl amine (5.4 mL, 31.35 mmol) and HATU (3.71 g, 9.78 mmol). The reaction was stirred at room temperature overnight. The solution was transferred to a seperatory funnel and the organic layer was washed with 1M HCl and brine, dried over magnesium sulfate and concentrated. The crude residue was triturated with DCM and filtered to get 1.83 g (43% yield) of the coupled intermediate as a solid. This intermediate (1.83 g, 2.69 mmol) was then dissolved in DCM (30 mL) and HCl in dioxanes (6.7 mL) was added. The reaction was stirred at room temperature two hours and then the solvent was removed to give 1.71 g of the desired product (1-{[4-(8-chloro-2-ethoxy-quinolin-4-yloxy)-pyrrolidine-2-carbonyl]-amino}-2-ethyl-cyclopropanecarbonyl)-sulfamic acid 1-methyl-cyclopropyl ester as the HCl salt. LCMS found 850.88 [M+H]⁺.

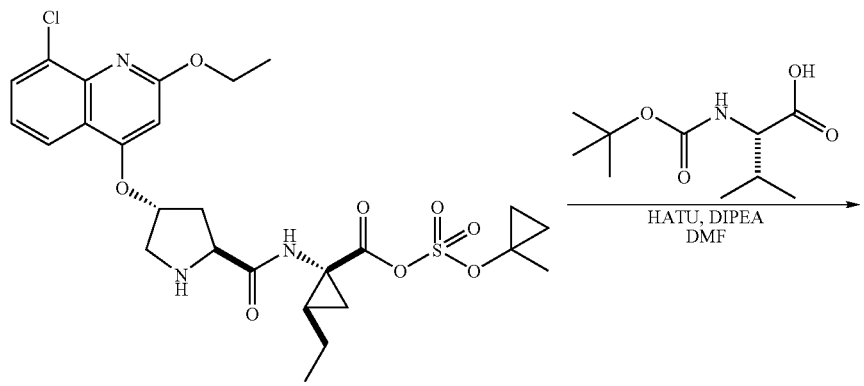

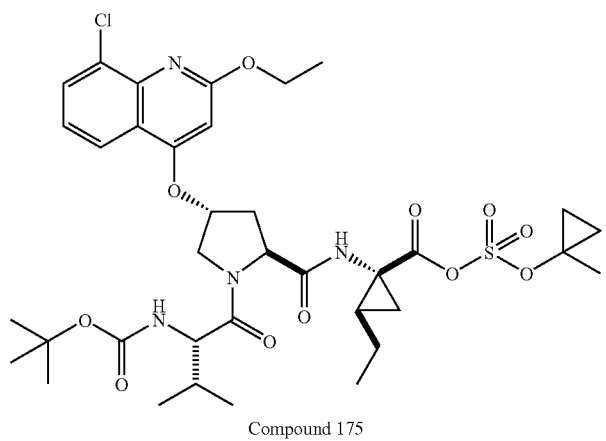

Compound 175

Compound 175 was prepared according to the methods described in Example 27. Treatment of (1-{[4-(8-chloro-2-ethoxy-quinolin-4-yloxy)-pyrrolidine-2-carbonyl]-amino}-2-ethyl-cyclopropanecarbonyl)-sulfamic acid 1-methyl-cyclopropyl ester (250 mg, 0.43 mmol) under the same conditions adjusted for scale and with the exception of using Boc-protected valine (117 mg, 0.54 mmol, 25 equiv.) and diisopropylethylamine (0.37 mL 2.15 mmol, 5 eq) provided Compound 175 (65 mg, 19%): $^1$H NMR (CD$_3$OD, 400 MHz) δ 7.98 (d, 1H), 7.73 (d, 1H), 7.24 (t, 1H), 6.48 (s, 1H), 5.43 (s, 1H), 4.47-4.64 (m, 4H), 3.95-4.09 (m, 2H), 2.58 (dd, 1H), 2.27-2.38 (m, 1H), 2.10 (q, 1H), 1.48-1.70 (m, 7H), 1.45 (t, 3H), 1.12-1.41 (m, 12H), 0.88-1.01 (m, 9H), 0.65-0.71 (m, 2H). LCMS found 779.91 [M+H]$^+$.

Example 176

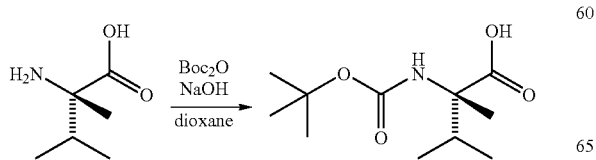

Alpha-methyl-valine (500 mg, 3.8 mmol) was dissolved in dioxane (6 mL) and treated with di-tert-butyl dicarbonate (998 mg, 4.6 mmol, 1.2 eq) and NaOH (3 mmol). The reaction mixture was stirred at room temperature for 8 days after which the reaction was concentrated in vacuo, diluted with EtOAc and washed with 1N HCl, dried over sodium sulfate. After removal of solvent, the crude (811 mg) product was used directly in the next reaction. $^1$H NMR (DMSO, 400 MHz) δ 1.36 (s, 9H), 1.24 (s, 3H), 0.83 (dd, 1H).

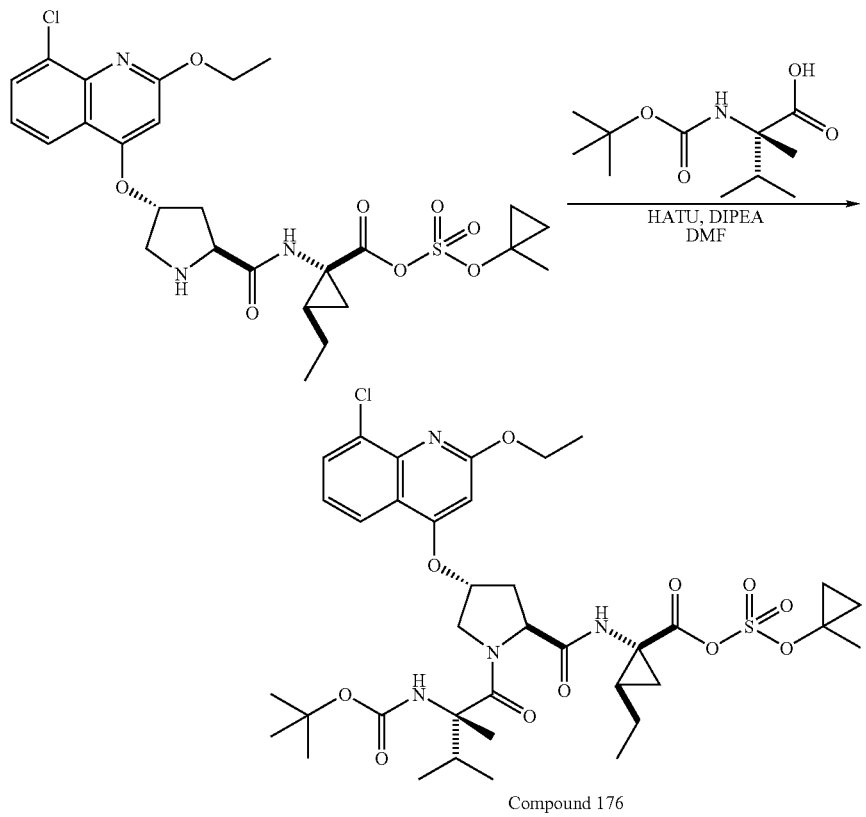

Compound 176

Compound 176 was prepared according to the methods described in Example 60. Treatment of (1-{[4-(8-chloro-2-ethoxy-quinolin-4-yloxy)-pyrrolidine-2-carbonyl]-amino}-2-ethyl-cyclopropanecarbonyl)-sulfamic acid 1-methyl-cyclopropyl ester (170 mg, 0.292 mmol) under the same conditions adjusted for scale and with the exception of using N-Boc-alpha-methyl-valine (203 mg, 0.88 mmol, 3 equiv.), and diisopropylethylamine (0.25 mL 1.46 mmol, 5 eq) provided Compound 176 (6.9 mg, 3%): $^1$H NMR (CD$_3$OD, 400 MHz) δ 7.88 (d, 1H), 7.73 (d, 1H), 7.26 (t, 1H), 6.51 (s, 1H), 5.38 (s, 1H), 4.65 (t, 1H), 4.52-4.60 (m, 4H), 3.72-3.83 (m, 1H), 2.67-2.76 (m, 1H), 1.75-1.83 (m, 1H), 1.66 (s, 5H), 1.517 (s, 9H) 1.43-1.48 (m, 4H), 1.29-1.32 (m, 7H), 1.03 (t, 3H), 0.82 (d, 3H), 0.61 (m, 5H). LCMS found 794.37 [M+H]$^+$.

Example 177

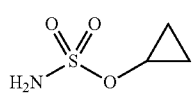

-continued

Compound 177

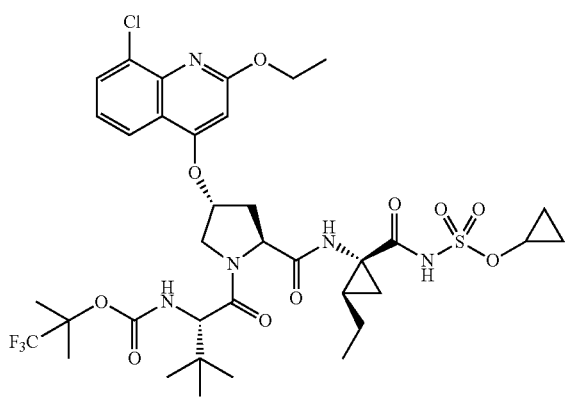

Compound 177 was prepared analogously to the procedure presented in Example 151, starting from 1-{[1-(2-tert-butoxycarbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid, substituting sulfamic acid cyclopropyl ester with sulfamic acid 1-(2,2,2-trifluoro-ethyl)cyclopropyl ester, and adjusting for scale to produce 0.134 g (45%) of Compound 177 as a white powder following purification by reverse phase HPLC. $^1$H NMR (CD$_3$OD, 400 MHz) δ 9.13 (s, 1H); 7.99 (d, 1H); 7.73 (s, 1H); 7.24 (t, 1H); 6.51 (s, 1H); 5.41 (m, 1H); 4.64-4.50 (m, 4H); 4.27 (m, 1H); 4.21 (s, 1H); 4.02 (m, 1H); 2.63 (m, 1H); 2.28 (m, 1H); 1.66-1.50 (m, 4H); 1.46 (s, 3H); 1.46 (t, 3H); 1.21 (s, 3H); 1.21 (m, 1H); 1.03 (s, 9H); 1.02-0.92 (m, 5H); 0.75 (m, 2H). LCMS found 834.03 [M+H]$^+$.
Example 178
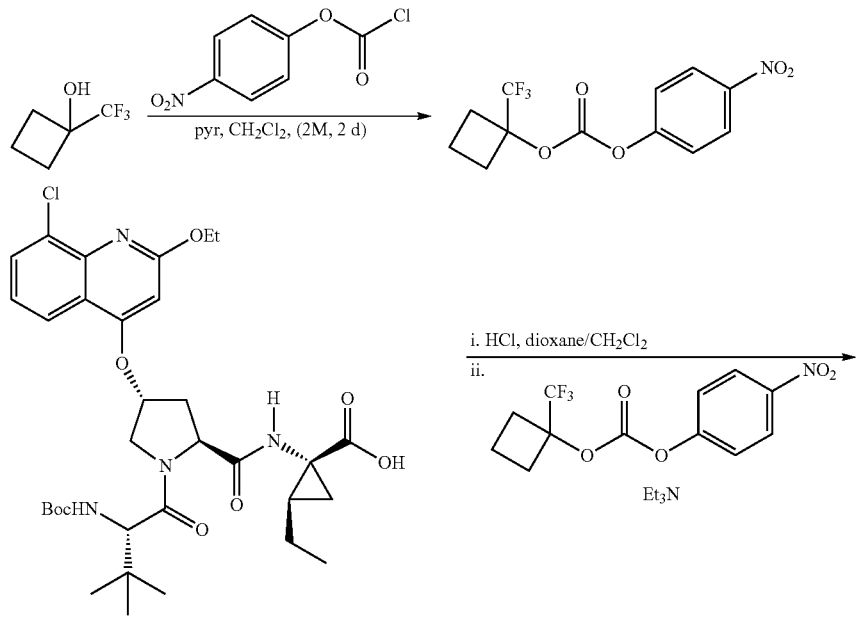
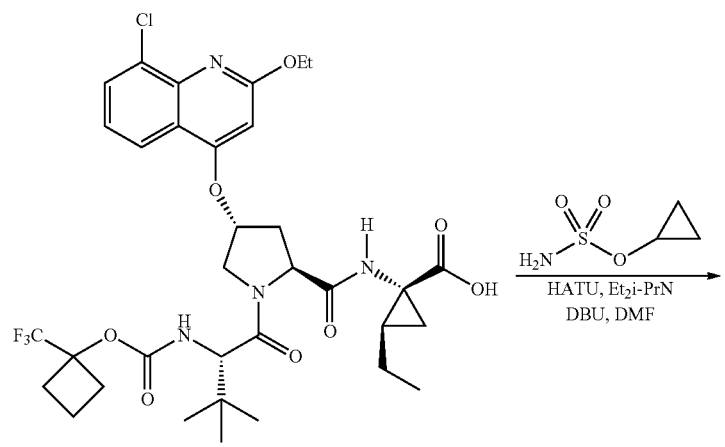

-continued

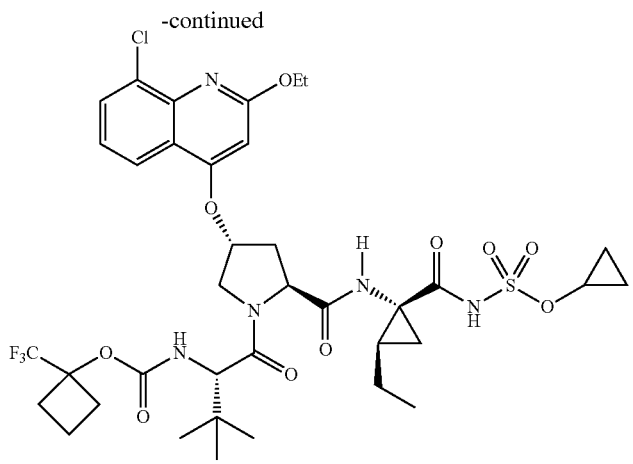

Compound 178

To 1-trifluoromethyl-cyclobutanol (2.2 g, 15 mmol) in dichloromethane (7.5 mL, 2M) was added pyridine (3 mL) and 4-nitrophenyl chloroformate (4 g, 18.3 mmol). The flask was sealed and stirred at room temperature for 2 days. The reaction was diluted with dichloromethane (50 mL) and washed with 1M $KHSO_{4(aq)}$, saturated sodium bicarbonate, water, and brine. The organic layer was dried over sodium sulfate and concentrated in vacuo. Purification by flash column chromatography (gradient elution with 10% to 40% EtOAc in hexane) gave 2.2 g (48% yield) of carbonic acid 4-nitro-phenyl ester 1-trifluoromethyl-cyclobutyl ester as a colorless oil. $^1$H NMR ($CDCl_3$, 400 MHz) δ 8.35 (d, 2H), 7.50 (d, 1H), 2.78-2.85 (m, 2H), 2.58-2.70 (m, 2H), 1.9-2.1 (m, 2H).

To 1-{[1-(2-tert-butoxycarbonylamino-3,3-dimethyl-butyryl)-4-(8-chloro-2-ethoxy-quinolin-4-yloxy)-pyrrolidine-2-carbonyl]-amino}-2-ethyl-cyclopropanecarboxylic acid (200 mg, 0.3 mmol) in dichloromethane (4 mL) was added HCl (4N in dioxane) at room temperature. After 2 h, analysis of the reaction mixture by LC-MS showed complete conversion of starting material. At this point, the reaction was cooled to 0° C. and triethylamine (2 mL) was added dropwise, followed by carbonic acid 4-nitro-phenyl ester 1-trifluoromethyl-cyclobutyl ester (300 mg, 1 mmol). The reaction was allowed to warm to room temperature and stirred 14 h. The reaction mixture was then poured into a 1N solution of $KHSO_{4(aq)}$ and extracted with ethyl acetate. The combined organic extracts were washed with 1N $KHSO_{4(aq)}$, water, and brine, and subsequently dried over magnesium sulfate. Concentration, followed by purification by reverse phase HPLC and lyophilization gave 110 mg (50% yield) of 1-({4-(8-chloro-2-ethoxy-quinolin-4-yloxy)-1-[3,3-dimethyl-2-(1-trifluoromethyl-cyclobutoxycarbonylamino)-butyryl]-pyrrolidine-2-carbonyl}-amino)-2-ethyl-cyclopropanecarboxylic acid as a white powder. LCMS found 727.03 [M+H]$^+$.

To 1-({4-(8-chloro-2-ethoxy-quinolin-4-yloxy)-1-[3,3-dimethyl-2-(1-trifluoromethyl-cyclobutoxycarbonylamino)-butyryl]-pyrrolidine-2-carbonyl}-amino)-2-ethyl-cyclopropanecarboxylic acid (110 mg, 0.15 mmol) in DMF (3 mL, 0.05 M) was added i-$Pr_2EtN$ (90 μL, 0.38 mmol) and HATU (86 mg, 0.23 mmol) and stirred 1 h at rt. To the reaction mixture at rt was added sulfamic acid cyclopropyl ester (46 mg, 0.30 mmol) and DBU (90 μL, 0.60 mmol). The reaction was stirred 17 h at rt, and then added to 5% aq citric acid and extracted with ethyl acetate. The combined organic extracts were washed water, and brine, and subsequently dried over magnesium sulfate. Concentration, followed by purification by reverse phase HPLC and lyophilization gave {1-[4-(8-chloro-2-ethoxy-quinolin-4-yloxy)-2-(1-cyclopropoxysulfonylaminocarbonyl-2-ethyl-cyclopropylcarbamoyl)-pyrrolidine-1-carbonyl]-2,2-dimethyl-propyl}-carbamic acid 1-trifluoromethyl-cyclobutyl ester (20 mg, 16% yield) as a white powder. $^1$H NMR ($CD_3OD$, 500 MHz) δ 9.18 (s, 1H), 7.95 (d, 1H), 7.70 (d, 1H), 7.20 (dd, 1H), 6.48 (s, 1H), 5.4 (br s, 1H), 4.45-4.6 (m, 4H), 4.2-4.3 (m, 2H), 2.58-2.62 (m, 1H), 2.2-2.4 (m, 4H), 1.5-1.7 (m, 4H), 1.43 (t, 3H), 1.2-1.3 (m, 3H) 1.2 (dd, 2H), 1.1-0.9 (m, 13H), 0.85 (m, 2H). LCMS found 846.00 [M+H]$^+$.

Example 179

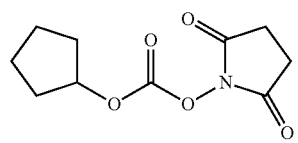

Compound 179

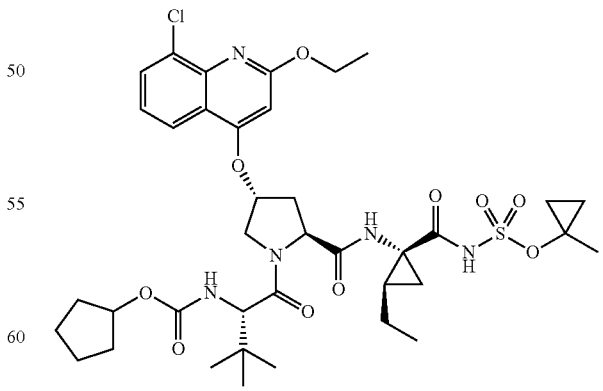

To a solution of Compound 138 in DCM (50 mL) was added 4N HCl in dioxanes (30.7 mL) and the reaction was stirred at room temperature for 1.5 hrs. The solvent was removed in vacuo. A portion of the residue (350 mg, 0.48 mmol) was dissolved in dichloromethane (5 mL), to which was added triethylamine (335 μl, 2.4 mmol) and carbonic acid cyclopentyl ester 2,5-dioxo-pyrrolidin-1-yl ester (131 mg, 0.57 mmol). After two hours the solvent was removed and the crude product was purified using reverse phase HPLC to give 100.9 mg (26% yield) of the desired Compound 179 as a white amorphous solid. ¹H NMR (CD₃OD, 400 MHz) δ 7.94 (d, 1H); 7.69 (d, 1H); 7.20 (m, 1H); 6.81 (d, 1H); 6.45 (s, 1H); 5.37 (s, 1H); 4.64 (m, 1H); 4.51 (m, 4H); 4.26 (m, 1H); 4.02 (m, 1H); 2.59 (m, 1H); 2.25 (m, 1H); 1.70 (m, 1H); 1.66 (s, 3H); 1.55 (m, 7H); 1.43 (m, 4H); 1.27 (m, 5H); 1.01 (s, 9H); 0.95 (m, 3H); 0.65 (m, 2H). LCMS found 805.97 [M+H]⁺.

Example 180

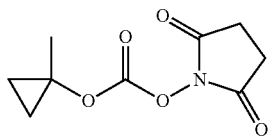

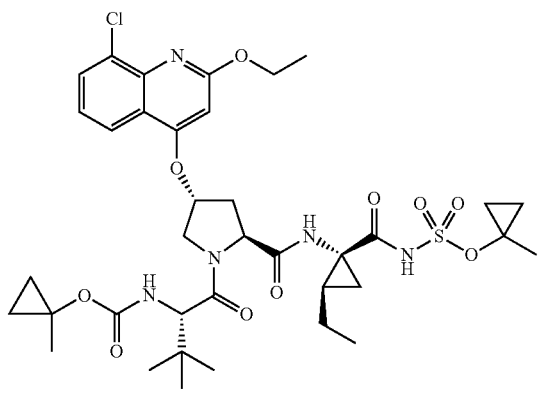

Compound 180

Compound 180 was prepared according to the method presented in Example 179, substituting carbonic acid 2,5-dioxo-pyrrolidin-1-yl ester 1-methyl-cyclopropyl ester for carbonic acid cyclopentyl ester 2,5-dioxo-pyrrolidin-1-yl ester and adjusting appropriately for scale. The compound was purified using reverse phase HPLC to give 45.6 mg (27% yield) of the desired compound 180 as a white amorphous solid. ¹H NMR (CD₃OD, 400 MHz) δ 7.82 (d, 1H); 7.69 (d, 1H); 7.21 (m, 1H); 6.84 (d, 1H); 6.47 (s, 1H); 5.38 (m, 1H); 4.55 (m, 2H); 4.46 (m, 2H); 4.27 (d, 1H); 4.06 (m, 1H); 2.58 (m, 1H); 2.25 (m, 1H); 1.65 (s, 3H); 1.54 (m, 4H); 1.43 (m, 3H); 1.28 (m, 2H); 1.02 (s, 9H); 094 (m, 3H); 0.70 (m, 1H); 0.64 (m, 2H); 0.47 (m, 2H). LCMS found 791.99 [M+H]⁺.

Example 181

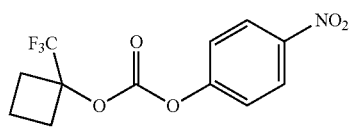

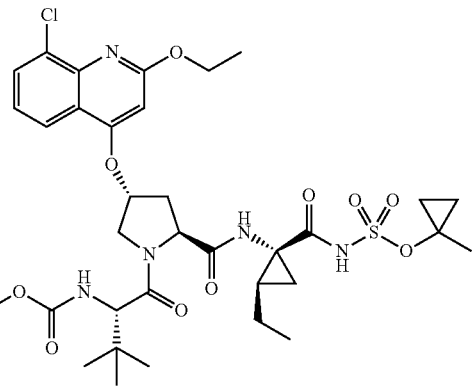

Compound 181

Compound 181 was prepared according to the method presented in Example 179, substituting carbonic acid 4-nitro-phenyl ester 1-trifluoromethyl-cyclobutyl ester 2,5-dioxo-pyrrolidin-1-yl ester for carbonic acid cyclopentyl ester 2,5-dioxo-pyrrolidin-1-yl ester and adjusting appropriately for scale. The compound was purified using reverse phase HPLC to give 144.6 mg (31% yield) of the desired compound 181 as a white amorphous solid. ¹H NMR (CD₃OD, 400 MHz) δ 7.93 (d, 1H); 7.69 (d, 1H); 7.28 (d, 1H); 7.19 (t, 1H); 6.46 (s, 1H); 5.37 (s, 1H); 4.51 (m, 4H); 4.23 (d, 1H); 4.02 (m, 1H); 2.59 (m, 1H); 2.29 (m, 4H); 1.65 (m, 5H); 1.56 (m 4H); 1.42 (m 3H); 1.30 (m, 2H); 1.19 (m, 1H); 1.03 (s, 9H); 095 (m, 2H); 0.65 (m, 2H). LCMS found 859.96 [M+H]⁺.

Example 182

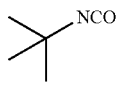

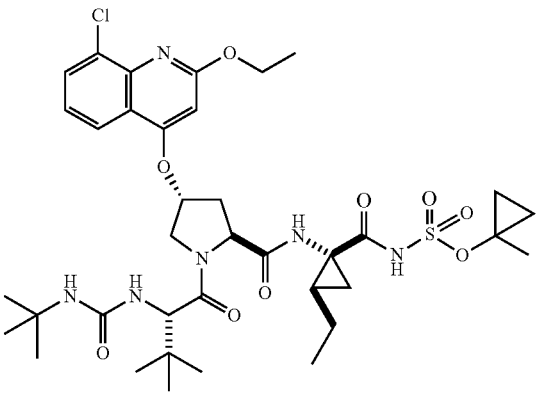

Compound 182

Compound 182 was prepared according to the methods described in Example 179. Treatment of Compound 138 (250 mg, 0.36 mmol) under the same conditions adjusted for scale and with the exception of using tert-butyl isocyanate (0.13 mL, 1.08 mmol, 3 equiv.) and triethylamine (0.25 mL, 1.8 mmol, 5 equiv.) provided Compound 182 (21 mg, 7% yield): ¹H NMR (d₃-MeOD, 400 MHz) δ 7.98 (d, 1H), 7.69 (d, 1H), 7.18 (t, 1H), 6.43 (s, 1H), 5.35-5.39 (m, 1H), 4.42-4.59 (m, 4H), 4.31 (s, 1H), 4.02-4.09 (m, 1H), 1.64 (s, 3H), 1.44-1.62

(m, 4H), 1.25 (d, 3H), 1.17 (s, 12H), 1.02 (s, 9H), 0.94 (t, 3H), 0.62 (m, 2H). LCMS found 792.97 [M+H]+.

Example 183

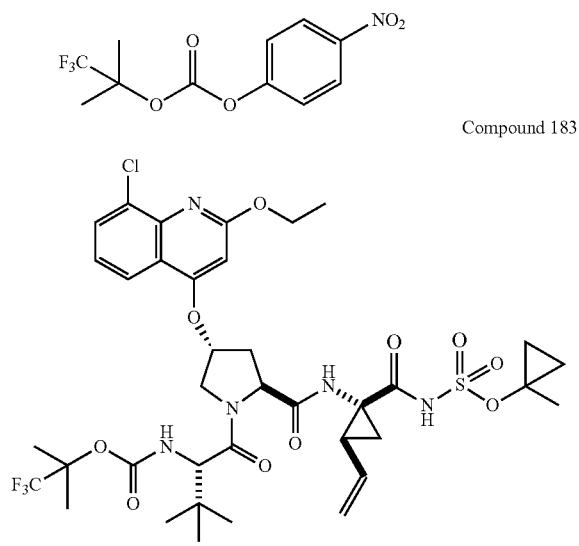

Compound 183

Compound 183 was prepared according to the methods described in Example 179. Treatment of Compound 139 (269 mg, 0.34 mmol) under the same conditions adjusted for scale and with the exception of using carbonic acid 4-nitro-phenyl ester 2,2,2-trifluoro-1,1-dimethyl-ethyl ester (200 mg, 0.68 mmol, 2 equiv.) and triethylamine (0.24 mL, 1.7 mmol, 5 equiv.) provided Compound 183 (42 mg, 15%): $^1$H NMR (d$_3$-MeOD, 400 MHz) δ 7.97 (s, 1H), 7.70 (s, 1H), 7.20 (t, 1H), 6.46 (s, 1H), 5.38 (s, 1H), 5.28 (d, 1H), 5.10 (d, 1H), 4.45-4.59 (m, 4H), 4.20 (d, 1H), 4.02 (d, 1H), 2.97 (s, 1H), 2.83 (s, 1H), 2.80-2.88 (m, 1H), 2.20-2.37 (m, 1H), 1.82-1.89 (m, 1H), 1.63 (s, 3H), 1.40-1.50 (m, 6H), 1.24 (t, 2H), 1.18 (s, 3H), 1.04 (s, 9H), 0.63 (m, 2H). LCMS found 845.92 [M+H]+.

Example 184

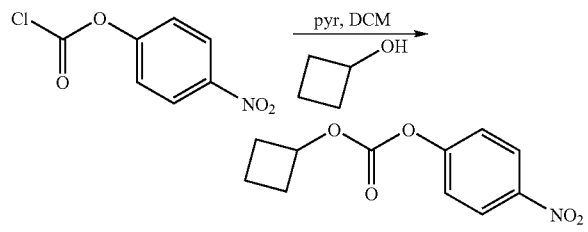

4-Nitrophenylchloroformate (4.2 g, 21 mmol) and cyclobutanol (1 g, 13.9 mmol) were diluted in DCM (25 mL) at 0° C. Pyridine (2.3 mL, 27.8 mmol) was added and the reaction was allowed to warm to rt over 2 h. The reaction volume was doubled with DCM, and washed with 1M HCl. The aqueous layer was extracted with DCM, and the combined organics were washed with sat. NaHCO$_3$ several times. A final wash with water and brine was followed by drying over anhydrous MgSO$_4$ and concentration in vacuo. The resulting residue was purified by column chromatography on SiO$_2$ (2-20% EtOAc/hex) to afford 3.0 g (91%) of carbonic acid cyclobutyl ester 4-nitrophenyl ester as an off-white solid. $^1$H NMR (CDCl$_3$, 400 MHz) δ 8.28 (m, 2H); 7.38 (m 2H); 5.065 (m, 1H); 2.44 (m, 2H); 2.25 (m, 2H); 1.89 (m, 1H); 1.66 (m, 1H).

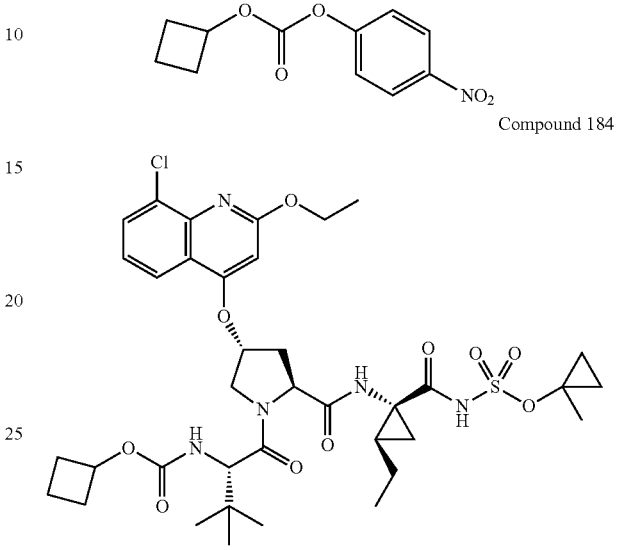

Compound 184

Compound 184 was produced analogously to Example 179 with substitution of DIPEA (0.74 mL, 2.1 mmol) for TEA and carbonic acid cyclobutyl ester 4-nitrophenyl ester (0.195 g, 0.82 mmol) for carbonic acid cyclopentyl ester 2,5-dioxopyrrolidin-1-yl ester to produce compound 184 (0.058 g, 18% yield). $^1$H NMR (CD$_3$OD, 400 MHz) δ 7.95 (d, 1H); 7.72 (d, 1H); 7.23 (t, 1H); 6.88 (d, 1H); 6.47 (s, 1H); 5.39 (m, 1H); 4.66-4.42 (m, 5H); 4.24 (d, 1H); 4.03 (m, 1H); 2.60 (m, 1H); 2.26 (m, 1H); 2.16 (m, 1H); 2.04 (m, 1H); 1.93 (m, 1H); 1.82 (m, 1H); 1.68 (t, 3H); 1.63 (m, 2H); 1.57 (m, 2H); 1.53 (m, 2H); 1.45 (t, 3H); 1.29 (q, 2H); 1.20 (m, 1H); 1.04 (s, 9H); 0.97 (t, 3H); 0.67 (m, 2H). LCMS found 792.0 [M+H]+.

Example 185

Carbonic acid 1-methylcyclopentyl ester 4-nitrophenyl ester was produced analogously to Carbonic acid cyclobutyl ester 4-nitrophenyl ester as described in Example 184 by substituting 1-methylcyclopentanol (1.5 g, 15 mmol) for cyclobutanol and appropriate adjustments for scale and stirring for 24 h to afford the desired product (0.72 g, 18%). $^1$H NMR (CDCl$_3$, 400 MHz) δ 8.27 (m, 2H); 7.37 (m, 2H); 2.24 (m, 2H); 1.88-1.66 (m, 6H); 1.68 (s, 3H).

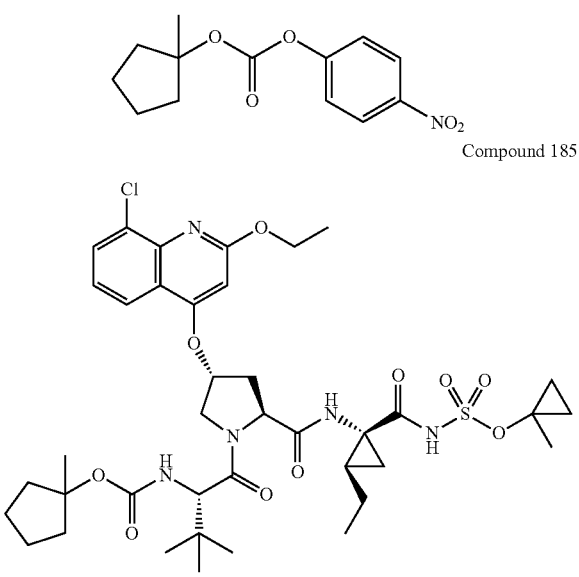

Compound 185

Compound 185 was produced analogously to Example 184 with substitution of carbonic acid 1-methylcyclopentyl ester 4-nitrophenyl ester (0.22 g, 0.82 mmol) for carbonic acid cyclobutyl ester 4-nitrophenyl ester and appropriate adjustments for scale to afford Compound 185 (0.045 g, 13%) after reverse phase HPLC purification. $^1$H NMR (CD$_3$OD, 400 MHz) δ 7.96 (d, 1H); 7.70 (d, 1H); 7.21 (t, 1H); 6.62 (d, 1H); 6.47 (s, 1H); 5.38 (m, 1H); 4.62-4.46 (m, 4H); 4.24 (m, 1H); 4.04 (m, 1H); 2.60 (m, 1H); 2.26 (m, 1H); 1.94 (m, 1H); 1.78 (m, 1H); 1.68 (s, 3H); 1.68-1.48 (m, 10H); 1.45 (t, 3H); 1.31 (s, 3H); 1.29 (m, 2H); 1.04 (s, 9H); 0.96 (t, 3H); 0.67 (m, 2H). LCMS found 821.9 [M+H]$^+$.

Example 186

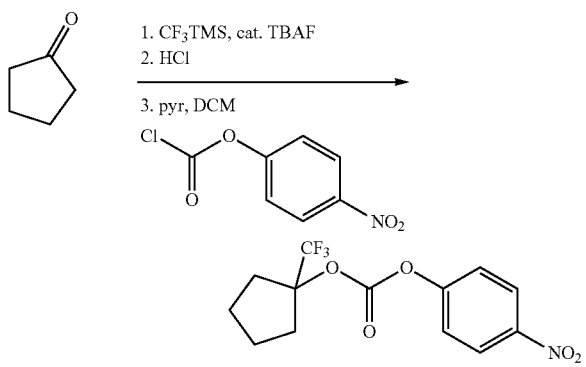

Cyclopentanone (0.89 mL, 10 mmol) was added to a solution of TMSCF$_3$ (0.5M in THF, 25 mL, 12 mmol) at 0° C. TBAF (1M in THF, 0.076 mL, 0.076 mmol) was added and the resulting yellow solution was allowed to warm to rt over 2 h. 1M HCl (30 mL) was added and the resulting solution stirred 1 h at rt. Extraction with Et$_2$O was followed by washing of the combined organics with brine and drying over anhydrous Na$_2$SO$_4$. Following concentration in vacuo, 1-trifluoromethylcyclopentanol (1.4 g, 88%) was isolated as a colorless liquid that was immediately converted to carbonic acid 4-nitrophenyl ester 1-trifluoromethylcyclopentyl ester analogously to carbonic acid cyclobutyl ester 4-nitrophenyl ester as described in Example 184 by substituting 1-trifluoromethylcyclopentanol (1.3 g, 8.4 mmol) for cyclobutanol with appropriate adjustments for scale and performing the reaction in a sealed tube for 40 h. The reaction volume was doubled with DCM and washed with 1M HCl (2×20 mL) followed by washing with 20 ml each of sat. NaHCO$_3$, water, brine and finally dried over anhydrous MgSO$_4$. Following concentration in vacuo, the residue was purified by column chromatography on SiO$_2$ (12-25% EtOAc/hex) to produce 0.59 g (22% yield) of the desired product. $^1$H NMR (CDCl$_3$, 400 MHz) δ 8.29 (m, 2H); 7.40 (m, 2H); 2.38 (m, 2H); 2.26 (m, 2H); 2.04 (m, 2H); 1.78 (m, 2H).

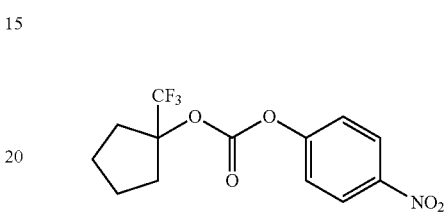

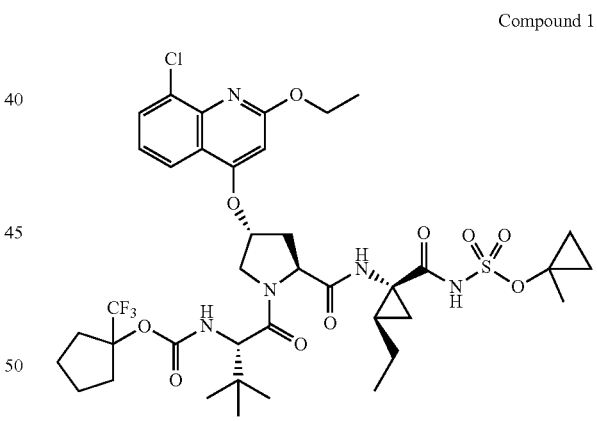

Compound 186

Compound 186 was produced according to the method presented in Example 184 with substitution of carbonic acid 4-nitrophenyl ester 1-trifluoromethylcyclopentyl ester (0.26 g, 0.82 mmol) for carbonic acid cyclobutyl ester 4-nitrophenyl ester and appropriate adjustments for scale to afford Compound 186 (0.056 g, 16% yield) after reverse phase HPLC purification. $^1$H NMR (CD$_3$OD, 400 MHz) δ 7.92 (d, 1H); 7.72 (d, 1H); 7.21 (m, 2H); 6.48 (s, 1H); 5.38 (m, 1H); 4.64-4.45 (m, 4H); 4.24 (d, 1H); 4.04 (m, 1H); 2.61 (m, 1H); 2.28 (m, 1H); 2.03 (m, 1H); 1.93 (m, 1H); 1.74-1.39 (m, 10H); 1.68 (s, 3H); 1.45 (t, 3H); 1.29 (q, 2H); 1.22 (m, 1H); 1.04 (s, 9H); 0.97 (t, 3H); 0.67 (m, 2H). LCMS found 875.99 [M+H]$^+$.

Example 187

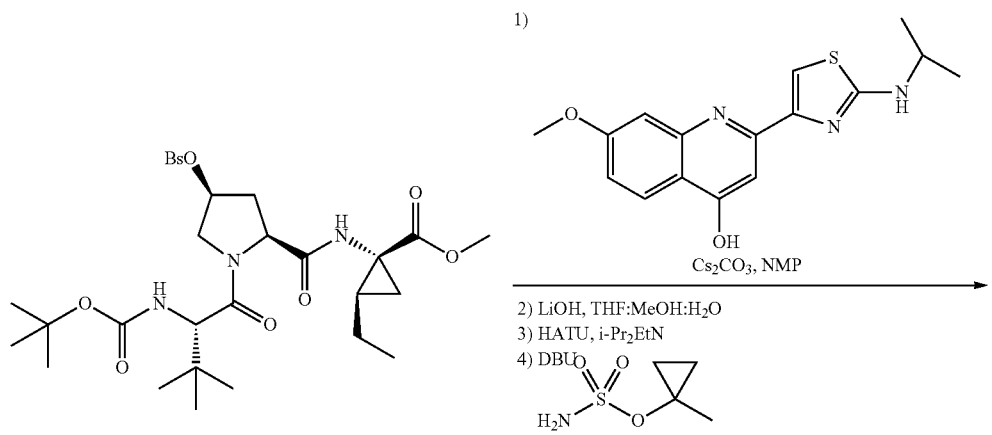

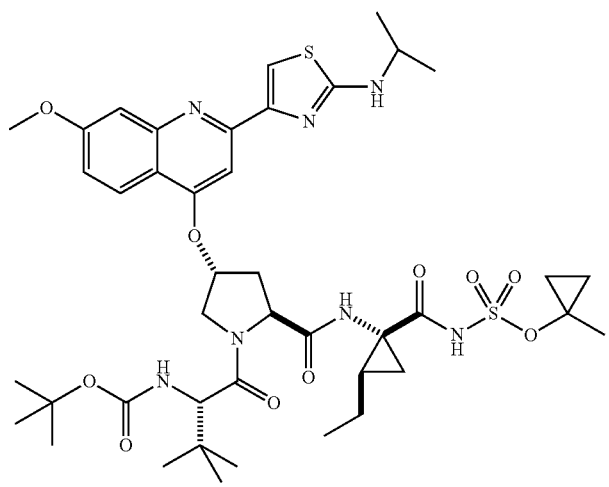

Compound 187

Subjection of 1-{[4-(4-Bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (607 mg, 0.88 mmol) to the reaction conditions employed in example 14, adjusted for scale and with the exception of utilizing 2-(2-Isopropylamino-thiazol-4-yl)-7-methoxy-quinolin-4-ol and sulfamic acid 1-methylcyclopropyl ester (64 mg, 0.42 mmol), followed by purification of the crude product by reverse phase HPLC provided compound 187 (118 mg, 43%). $^1$H NMR (300 MHz, CD$_3$OD): δ 9.2 (s, 1H), 8.24 (d, 1H), 8.19 (s, 1H), 7.75 (s, 1H), 7.72 (s, 1H), 7.31 (d, 1H), 5.78 (s, 1H), 4.66-4.57 (m, 2H), 4.16 (m, 3H), 4.04 (s, 3H), 7.72 (dd, 1H), 2.44-4.37 (m, 1H), 1.68 (s, 3H), 1.59 (m, 4H), 1.33 (d, 6H), 1.35-1.28 (m, 3H), 1.21 (s, 9H), 1.05 (s, 9H), 0.99-0.95 (m, 3H), 0.68 (m, 2H). LCMS found 886.1 [M+H]$^+$.

Example 188

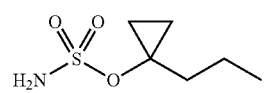

Compound 188

Compound 188

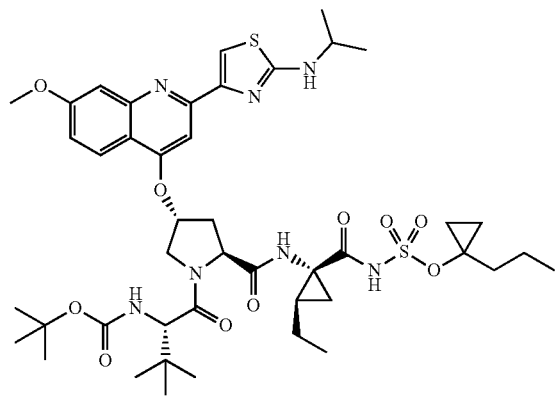

Compound 188 was prepared according to the method presented in example 29, adjusted for scale, starting from 1-({1-(2-tert-butoxycarbonylamino-3,3-dimethyl-butyryl)-4-[2-(2-isopropylamino-thiazol-4-yl)-7-methoxy-quinolin-4-yloxy]-pyrrolidine-2-carbonyl}-amino)-2-ethyl-cyclopropanecarboxylic acid (160 mg, 0.21 mmol), and with the exception of using sulfamic acid 1-propyl-cyclopropyl ester (75 mg, 0.42 mmol) afforded compound 188 (151 mg, 79%). $^1$H NMR (300 MHz, CD$_3$OD): δ 9.14 (s, 1H), 8.25 (d, 1H), 8.18 (s, 1H), 7.75 (s, 1H), 7.73 (s, 1H), 7.31 (d, 1H), 5.79 (s, 1H), 4.65-4.57 (m, 2H), 4.21-4.13 (m, 3H), 4.05 (s, 3H), 2.72 (dd, 1H), 2.46-2.38 (m, 1H), 1.87-1.82 (m, 2H), 1.64-1.55 (m, 6H), 1.33 (d, 6H), 1.31 (m, 3H), 1.21 (s, 9H), 1.05 (s, 9H), 1.00-0.95 (m, 6H), 0.70 (m, 2H). LCMS found 914.1 [M+H]$^+$.

Example 189

Compound 189

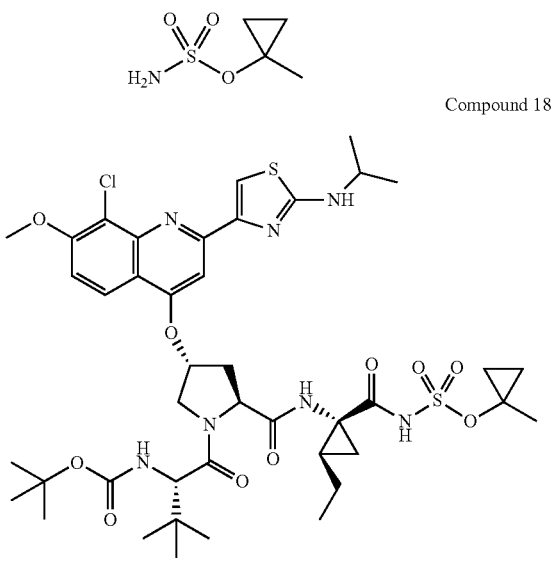

Compound 189 was prepared according to the method presented Example 14. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (0.60 g, 0.88 mmol) under the same conditions adjusted for scale and with the exceptions of utilizing sulfamic acid 1-methylcyclopropyl ester (0.083 g, 0.546 mmol), and performing the hydrolysis of the methyl ester at 40° C. for 3 h. Reverse phase HPLC provided Compound 189 (0.163 g, 33% yield over three steps). $^1$H NMR (CDCl$_3$, 300 MHz) δ 10.58 (br s, 1H); 8.24 (br s, 1H); 8.09 (br d, 1H); 7.86 (br s, 1H); 7.64 (s, 1H); 7.26 (m, 1H); 5.80 (br s, 1H); 5.80-5.20 (m, 2H); 5.17 (m, 1H); 4.61 (m, 1H); 4.33 (s, 1H); 4.09 (m, 1H); 4.04 (s, 3H); 3.68 (m, 1H); 2.60 (m, 1H); 1.64 (s, 3H); 1.62-1.12 (m, 8H); 1.38 (br d, 6H); 1.18 (s, 9H); 0.99 (s, 9H); 0.91 (t, 3H); 0.58 (m, 2H). LCMS found 920.1 [M+H]$^+$.

Example 190

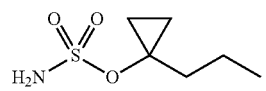

Compound 190

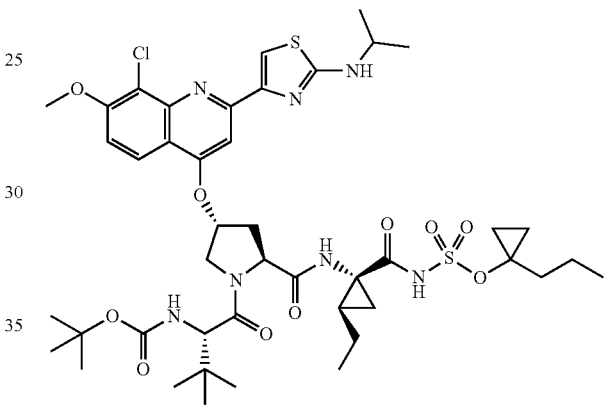

Compound 190 was prepared according to the method presented in example 14, adjusted for scale and with the exceptions of utilizing sulfamic acid 1-propyl-cyclopropyl ester (0.098 g, 0.546 mmol), and performing the hydrolysis of the methyl ester at 40° C. for 3 h. Reverse phase HPLC provided Compound 190 (0.163 g, 25% yield over three steps). $^1$H NMR (CDCl$_3$, 300 MHz) δ 10.59 (br s, 1H); 8.26 (br s, 1H); 8.12 (br s, 1H); 7.89 (m, 1H); 7.66 (m, 1H); 7.78 (m, 1H); 6.00-5.40 (m, 2H); 5.82 (m, 1H); 5.25 (m, 1H); 4.66 (m, 1H); 4.37 (s, 1H); 4.15 (m, 1H); 3.72 (m, 1H); 2.63 (m, 1H); 1.81 (m, 1H); 1.68-1.19 (m, 11H); 1.43 (br d, 6H); 1.23 (s, 9H); 1.04 (s, 9H); 0.93 (m, 6H); 0.64 (m, 2H). LCMS found 948.1 [M+H]$^+$.

Example 191

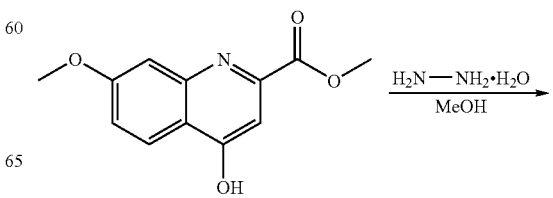

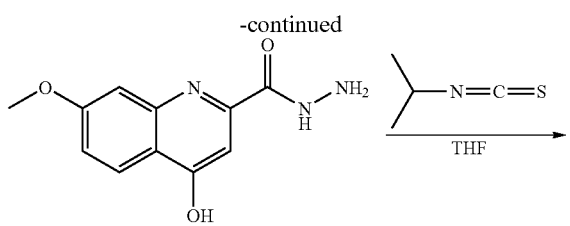

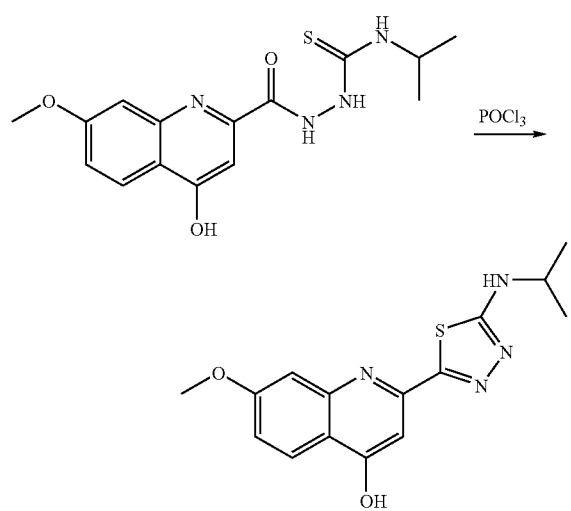

To a solution of 4-hydroxy-7-methoxy-quinoline-2-carboxylic acid methyl ester (2.0 g, 8.58 mmol) in methanol (85 mL) was added hydrazine mono hydrate (1.7 g, 34.3 mmol) and the mixture was refluxed for 6 hours. The crude reaction mixture was concentrated in vacuo and the residue was taken up in methanol and poured onto an ice/water mixture (800 mL). A white precipitate formed, which was collected by filtration and washed with cold water. The filter cake was then dried on house vacuum by passing air through in sintered glass funnel, and then dried on vacuum oven at 45° C. overnight to afford 4-hydroxy-7-methoxy-quinoline-2-carboxylic acid hydrazide (1.6 g, 80% yield). $^1$H NMR (DMSO-$d_6$, 300 MHz) δ 11.57 (s, 1H), 10.28 (s, 1H), 7.95 (d, 1H), 7.43 (d, 1H), 7.01-6.91 (m, 1H), 6.54 (s, 1H), 4.72 (br s, 2H), 3.82 (s, 3H). LCMS found 234.18 [M+H]$^+$.

To a mixture of 4-hydroxy-7-methoxy-quinoline-2-carboxylic acid hydrazide (300 mg, 1.29 mmol) in THF (15 mL) was added isopropyl isothiocyanate. The mixture was stirred overnight at room temperature. HPLC analysis of the reaction mixture showed incomplete reaction after overnight reaction at room temperature. The reaction content was warmed up to 40° C. for 2 hours at which point HPLC analysis indicated a complete reaction. The reaction mixture was concentrated in vacuo and the residue was dissolved in ethyl acetate and washed with brine. The aqueous layer was concentrated in vacuo and the residue was dried on high vacuum pump overnight. The residue was suspended in DMF and the inorganic salts were removed by filtration. The DMF solution was concentrated in vacuo and the residue was purified on reverse phase HPLC (10%→65%, MeCN/H$_2$O/0.1% TFA) to provide 4-hydroxy-7-methoxy-quinoline-2-carboxylic acid-1-(N-Isopropyl-thioformamide) hydrazide (400 mg, 93% yield). LCMS found 334.91 [M+H]$^+$.

4-Hydroxy-7-methoxy-quinoline-2-carboxylic acid-1-(N-Isopropyl-thioformamide) hydrazide (400 mg, 1.19 mmol) was dissolved in phosphorus oxychloride (5 mL) and the mixture was heated at 70° C. for 1 hour. Phosphorus oxychloride was then removed in vacuo and the residue was taken up in EtOAc and washed with 10% sodium carbonate and brine. The organic layers were combined, dried on MgSO$_4$, and concentrated. The residue was then purified via flash column chromatography to afford 2-(5-isopropylamino-[1,3,4]thiadiazol-2-yl)-7-methoxy-quinolin-4-ol (56 mg, 15% yield). LCMS found 317.16 [M+H]$^+$.

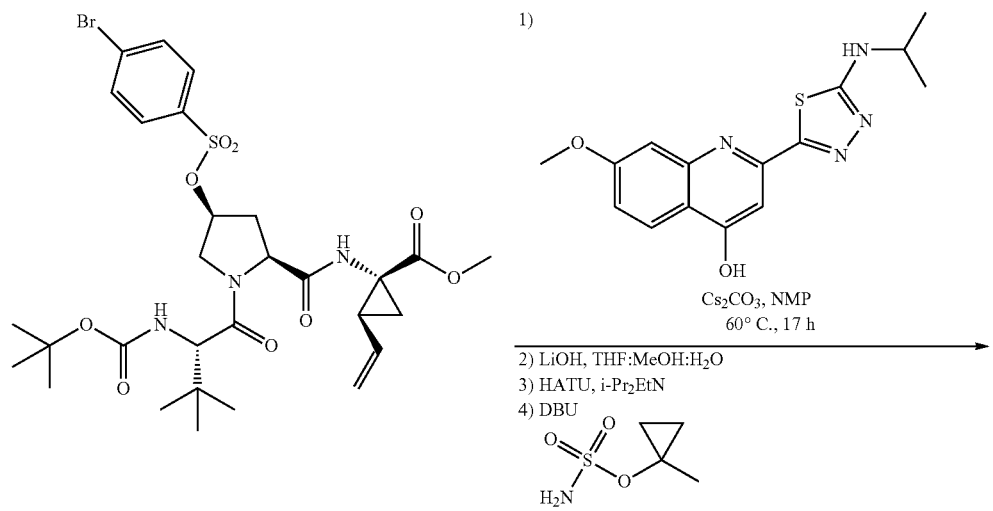

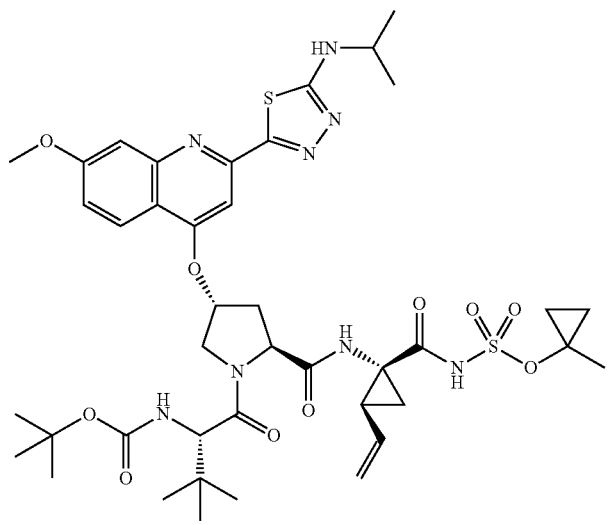

Compound 191

Compound 191 was prepared according to the method presented in example 14. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-vinyl-cyclopropanecarboxylic acid methyl ester (110.5 mg, 0.16 mmol) occurred under the same conditions, adjusted for scale and with exception of utilizing 2-(5-isopropylamino-[1,3,4]thiadiazol-2-yl)-7-methoxy-quinolin-4-ol (56 mg, 0.18 mmol) and sulfamic acid 1-methyl-cyclopropyl ester (47 mg, 0.26 mmol). Purification of the crude product by reverse phase HPLC (20%→85%, MeCN/H$_2$O/0.1% TFA) provided compound 191 (64 mg, 59% yield): $^1$H NMR (CD$_3$OD, 300 MHz) δ 8.14 (d, 1H), 7.57 (s, 1H), 7.39 (s, 1H), 7.15 (d, 1H), 5.71 (m, 1H), 5.60 (br s, 1H), 5.33 (m, 1H), 5.17 (m, 1H), 4.54 (m, 2H), 4.23 (s, 1H), 4.14 (m, 1H), 3.97 (s, 4H), 2.70 (m, 1H), 2.36 (m, 1H), 2.26 (m, 1H), 1.88 (m, 1H), 1.67 (s, 3H), 1.45 (m, 2H), 1.37 (d, 6H), 1.28 (s, 9H), 1.05 (s, 9H), 0.68 (m, 2H). LCMS found 885.04 [M+H]$^+$.

Example 192

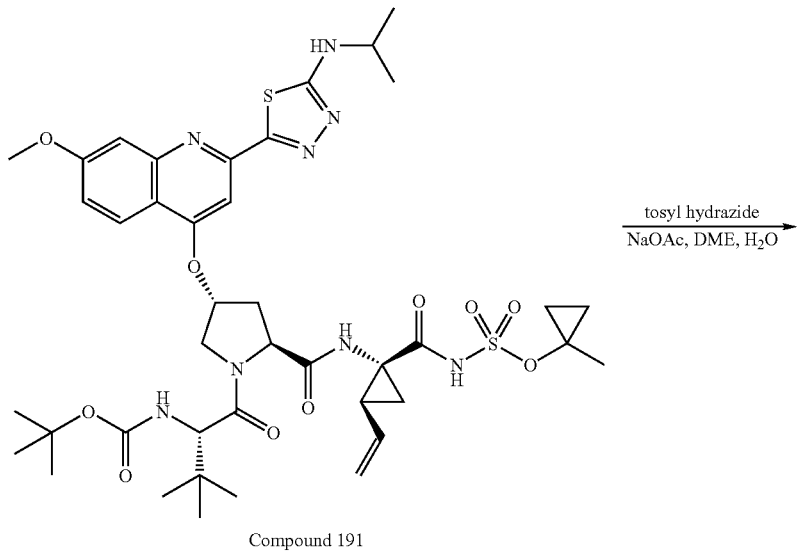

Compound 191

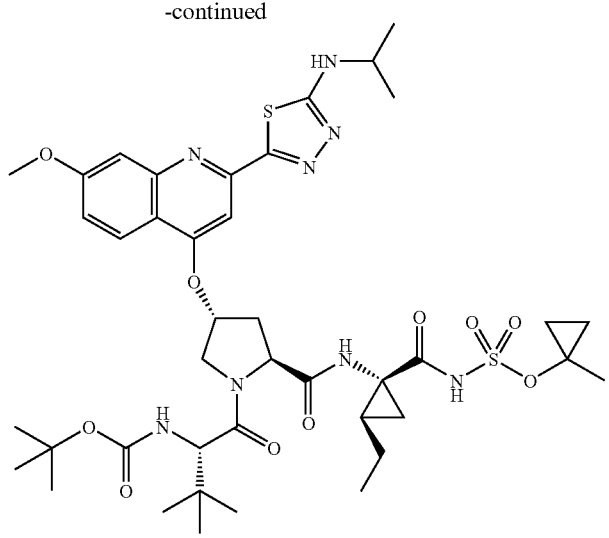

Compound 192

Subjection of compound 191 (58 mg, 0.07 mmol) to the conditions outlined in example 20, with adjustment for scale, provided compound 192 (50 mg, 85%): $^1$H NMR (CD$_3$OD, 300 MHz) δ 9.14 (s, 1H), 8.16 (d, 1H), 7.55 (s, 1H), 7.41 (s, 1H), 7.21 (d, 1H), 5.61 (s, 1H), 4.54 (m, 2H), 4.22 (s, 1H), 4.14 (m, 1H), 3.98 (s, 4H), 2.65 (m, 1H), 2.35 (m, 1H), 1.69 (s, 4H), 1.58 (m, 4H), 1.39 (d, 6H), 1.26 (m, 12H), 1.05 (s, 10H), 0.99 (s, 3H), 0.69 (s, 1H). LCMS found 887.05 [M+H]$^+$.

Example 193

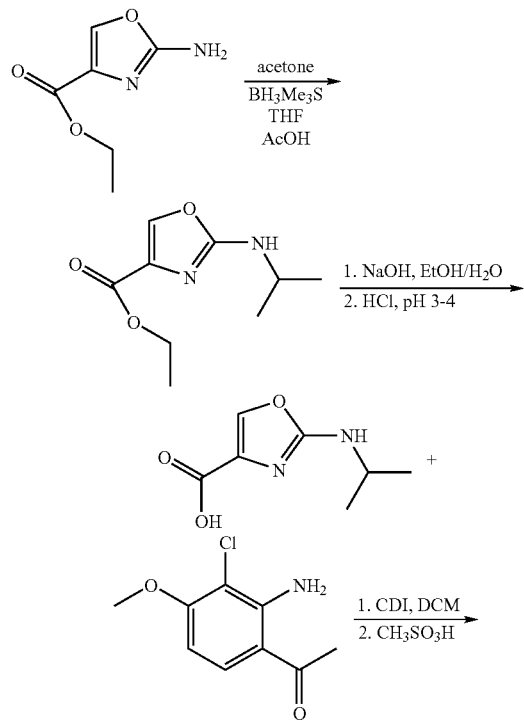

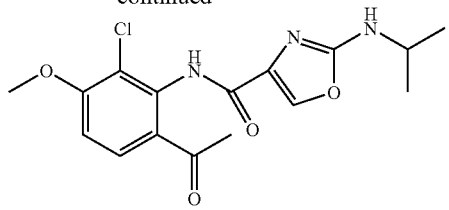

A mixture of 2-aminooxazole-4-carboxylic acid ethyl ester (500 mg, 3.2 mmol) and acetone (2.4 mL, 32 mmol) in THF (6 mL) was stirred at rt. BH$_3$.SMe$_2$ (10M in THF, 0.64 mL, 6.4 mmol) was added slowly via syringe (exotherm and gas evolution were observed). AcOH (0.36 mL, 6.4 mmol) was subsequently added in the same manner. Two additional equivalents of borane and AcOH were added 18 h later. After 3 days at rt, the reaction mixture was concentrated in vacuo. The resulting residue was dissolved in EtOAc (100 mL), washed with saturated NH$_4$Cl solution, 0.1 M NH$_4$OH and brine. The organic phase was dried over Na$_2$SO$_4$ and concentrated in vacuo. The crude product was purified by flash chromatography on silica gel, eluting with EtOAc/hexane to give 2-isopropylamino-oxazole-4-carboxylic acid ethyl ester (0.40 g, 64% yield). LCMS found 199 [M+H]$^+$.

To 2-isopropylamino-oxazole-4-carboxylic acid ethyl ester (2.5 g, 10.9 mmol) in EtOH (42 mL) and water (28 mL) was added NaOH (3.1 g, 77.4 mmol). The mixture was stirred at rt for 16 h, then cooled in an ice-bath and acidified to pH 3 with conc. HCl. The mixture was concentrated in vacuo to remove ethanol. The remaining aqueous phase was extracted with CH$_2$Cl$_2$ (3×200 mL). The organic phases were combined, dried over MgSO$_4$ and concentrated to give 2-isopropylaminooxazole-4-carboxylic acid (1.86 g, 87% yield). LCMS found 171 [M+H]$^+$.

To 2-isopropylaminooxazole-4-carboxylic acid (1.9 g, 10.9 mmol) in DCM (10 ml) was added CDI (1.8 g, 10.9 mmol). The mixture was then stirred at rt for 2 h, followed by addition of 1-(2-Amino-3-chloro-4-methoxyphenyl)ethanone (prepared according to Raboisson, P. J.-M. B., et al., WO2007014926, p 78; 1.4 g, 8.7 mmol) and CH$_3$SO$_3$H (2.1 mL, 32.8 mmol), and then stirred for 18 h at rt. The reaction mixture was diluted with DCM (100 mL) and washed with 1N HCl (2×100 mL). To the collected DCM layer was added K$_2$CO$_3$ (3.02 g, 21.88 mmol) and stirred for 2 h at rt. The solution was filtered and concentrated in vacuo. The resulting residue was purified by flash chromatography on silica gel, eluting with EtOAc/hexane, to give 2-isopropylamino-oxazole-4-carboxylic acid (6-acetyl-2-chloro-3-methoxyphenyl)amide (863 mg, 22% yield). LCMS found 382 [M+H]$^+$.

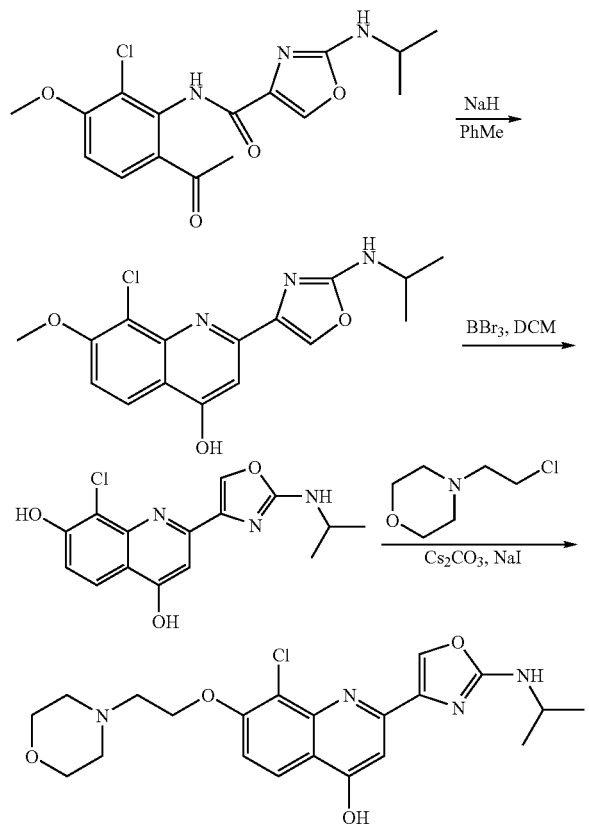

2-Isopropylamino-oxazole-4-carboxylic acid (6-acetyl-2-chloro-3-methoxyphenyl)amide (863 mg, 2.45 mmol) was suspended in toluene (20 ml). NaH (147.3 mg, 3.7 mmol) was added to the vigorously stirred mixture while monitoring H$_2$ evolution. The reaction was refluxed (110° C.) for 3 h. After cooling, additional NaH (approx 80 mg) was carefully added, followed by 20 mL of THF to aid solubility. The mixture was heated for an additional 2 h. After cooling to room temperature, the reaction mixture was acidified to pH 2 with conc. HCl. The slurry was stirred for 1 h at rt, then 10 mL of CH$_3$CN was added, followed by 5 mL H$_2$O and 20 mL of ether. The mixture was stirred for another 30 min, and then the solids were collected by filtration and washed with ether and hexane. The wet cake was dried under high vacuum to a constant weight to provide 8-chloro-2-(2-isopropylaminooxazol-4-yl)-7-methoxy-quinolin-4-ol (840 mg, 100% yield) that was used without further purification. LCMS found 334 [M+H]$^+$.

To a suspension of 8-chloro-2-(2-isopropylaminooxazol-4-yl)-7-methoxy-quinolin-4-ol in DCM (50 mL) was added BBr$_3$ (1 N in DCM) (13.4 ml, 13.4 mmol). The mixture was heated to reflux and stirred for 4 h. The reaction was cooled to rt and poured onto ice. 4N NaOH was used to adjust the pH to 14. The aqueous phase was extracted with DCM twice and the pH was adjusted to about 4 with 2N HCl. Yellow solid precipitated and was collected by filtration. The filter cake was washed with H$_2$O, Et$_2$O, and dried under high vacuum. 8-Chloro-2-(2-isopropylamino-oxazol-4-yl)-quinoline-4,7-diol was collected as a yellow solid (0.41 g, 1.28 mmol, 42%) and used directly in the next reaction. LCMS found 320.3 [M+H]$^+$.

The hydrochloride salt of 4-(2-chloroethyl)morpholine (1.4 g, 7.2 mmol), sodium iodide 0.2 g, 1.3 mmol), and cesium carbonate (5.4 g, 16.4 mmol) were combined in DMF (25 mL) and stirred at rt for 5 min. 8-Chloro-2-(2-isopropylamino-oxazol-4-yl)-quinoline-4,7-diol (2.1 g, 6.6 mmol) was diluted in DMF (25 mL) and added to the reaction solution. After 5 min at rt, the reaction was warmed to 65° C. for 5 h. A small amount of conc. HCl (5-6 pipette drops) was added and the reaction concentrated in vacuo. The residue was taken up in water and MeOH and filtered through a C18 column to remove salts, first eluting with water then with MeOH to elute the desired compound. Following concentration of combined organics in vacuo, the resulting residue was purified by reverse phase HPLC to produce 1.79 g (51% yield) of 8-chloro-2-(2-isopropylamino-oxazol-4-yl)-7-(2-piperidin-1-yl-ethoxy)-quinolin-4-ol. LCMS found 433.3 [M+H]$^+$.

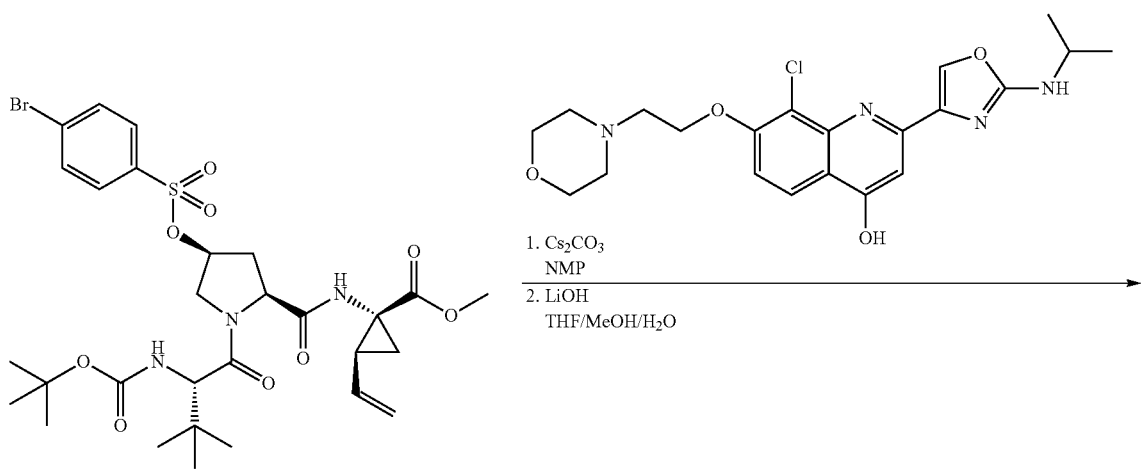

-continued

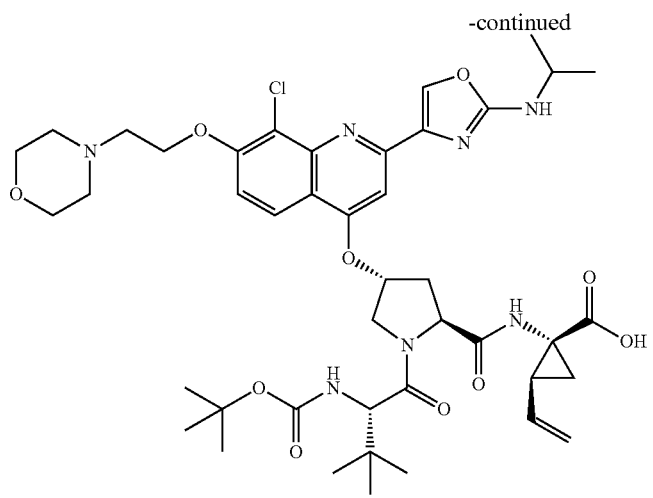

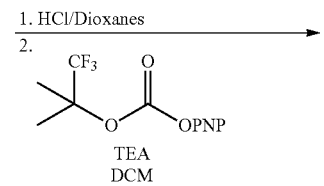

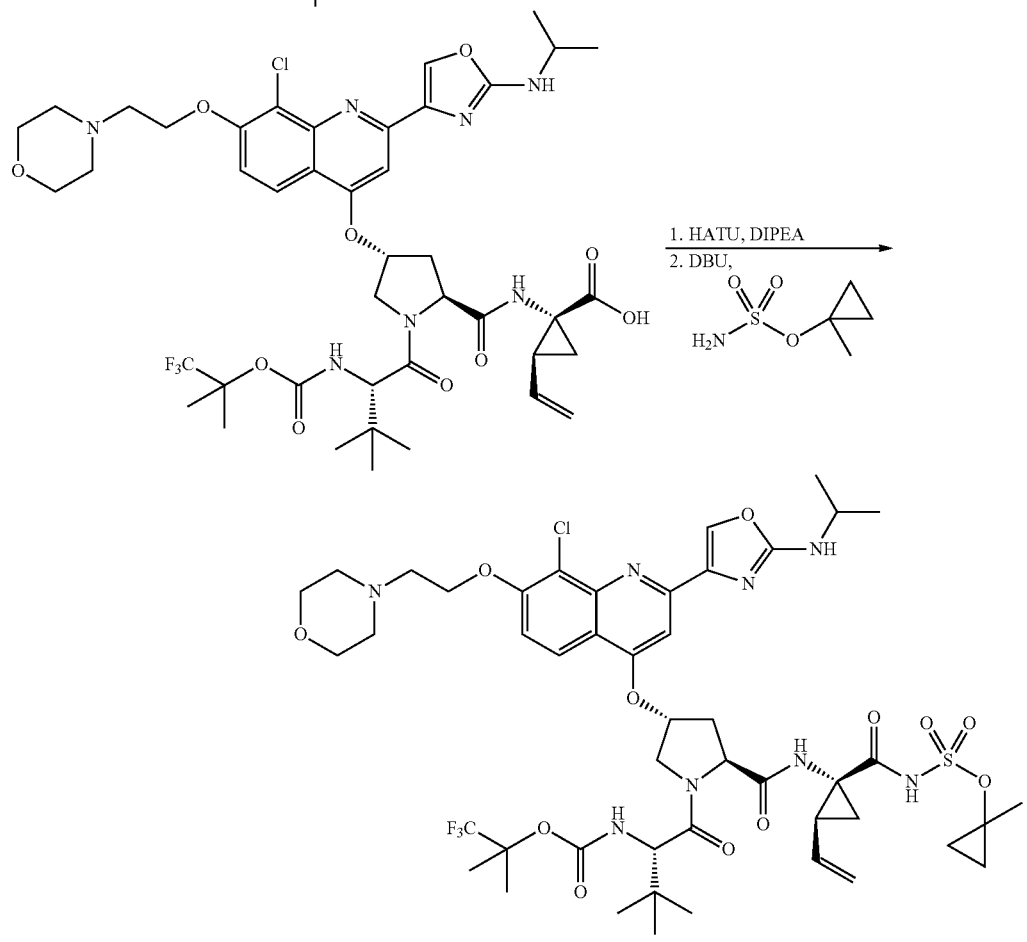

Compound 193

To a solution of 8-chloro-2-(2-isopropylaminooxazol-4-yl)-7-(2-morpholin-4-yl-ethoxy)-quinolin-4-ol (341 mg, 0.63 mmol) and cesium carbonate (1.23 g, 3.78 mmol) in NMP was added 1-{[4-(4-bromobenzenesulfonyloxy)-1-(2-tert-butoxycarbonylamino-3,3-dimethylbutyryl)-pyrrolidine-2-carbonyl]-amino}-2-vinyl-cyclopropanecarboxylic acid methyl ester (432 mg, 0.63 mmol) and the reaction was heated to 65° C. After 2 h an additional 0.5 eq of 1-{[4-(4-bromo-benzenesulfonyloxy)-1-(2-tert-butoxycarbonylamino-3,3-dimethyl-butyryl)-pyrrolidine-2-carbonyl]-amino}-2-vinyl-cyclopropanecarboxylic acid methyl ester was added and stirred an additional hour. The reaction was diluted with EtOAc and 5% lithium chloride with stirring. The reaction was transferred to a separatory funnel and saturated sodium bicarbonate and MeOH (2 ml) was added. The layers were separated and the aqueous extracted again with EtOAc. The combined organic layers were then washed with 5% lithium chloride, dried over magnesium sulfated and concentrated to give 747 mg (99% yield) of 1-({1-(2-tert-butoxycarbonylamino-3,3-dimethylbutyl)-4-[8-chloro-2-(2-isopropylaminooxazol-4-yl)-7-(2-morpholin-4-yl-ethoxy)quinolin-4-yloxy]-pyrrolidine-2-carbonyl}-amino)-2-vinyl-cyclopropanecarboxylic acid methyl ester as a yellow oil. LCMS found 882.11 [M+H]+.

Compound 193 was prepared as shown in Example 150, substituting 1-({1-(2-tert-butoxycarbonylamino-3,3-dimethylbutyryl)-4-[8-chloro-2-(2-isopropylaminooxazol-4-yl)-7-(2-morpholin-4-yl-ethoxy)quinolin-4-yloxy]-pyrrolidine-2-carbonyl}-amino)-2-vinyl-cyclopropanecarboxylic acid methyl ester for 1-{[1-(2-tert-Butoxycarbonylamino-3,3-dimethyl-butyl)-4-(8-chloro-2-methoxyquinolin-4-yloxy)-pyrrolidine-2-carbonyl]-amino}-2-ethyl-cyclopropanecarboxylic acid methyl ester with appropriate adjustments for scale to produce 64 mg, 18% yield over three steps) of Compound 193. $^1$H NMR (CD$_3$OD, 400 MHz) δ 8.04 (m, 1H); 8.00 (s, 1H); 7.34 (d, 1H); 7.26 (m, 1H); 7.11 (d, 1H); 5.80 (m, 1H); 5.31 (m, 1H); 5.27 (d, 1H); 5.10 (d, 1H); 4.58 (m, 1H); 4.51 (m, 2H); 4.16 (d, 1H); 4.06 (d, 1H); 3.94 (q, 2H); 3.87 (m, 3H); 3.36 (m, 2H); 3.20 (m, 4H); 2.52 (m, 1H); 2.32 (m, 1H); 2.19 (m, 1H); 1.85 (m, 1H); 1.65 (m, 1H); 1.65 (s, 3H); 1.52-1.35 (m, 1H); 1.39 (s, 3H); 1.35-1.15 (m, 2H); 1.30 (d, 6H); 1.20 (s, 3H); 1.03 (s, 9H); 0.64 (m, 2H). LCMS found 1056.9 [M+H]+.

Example 194

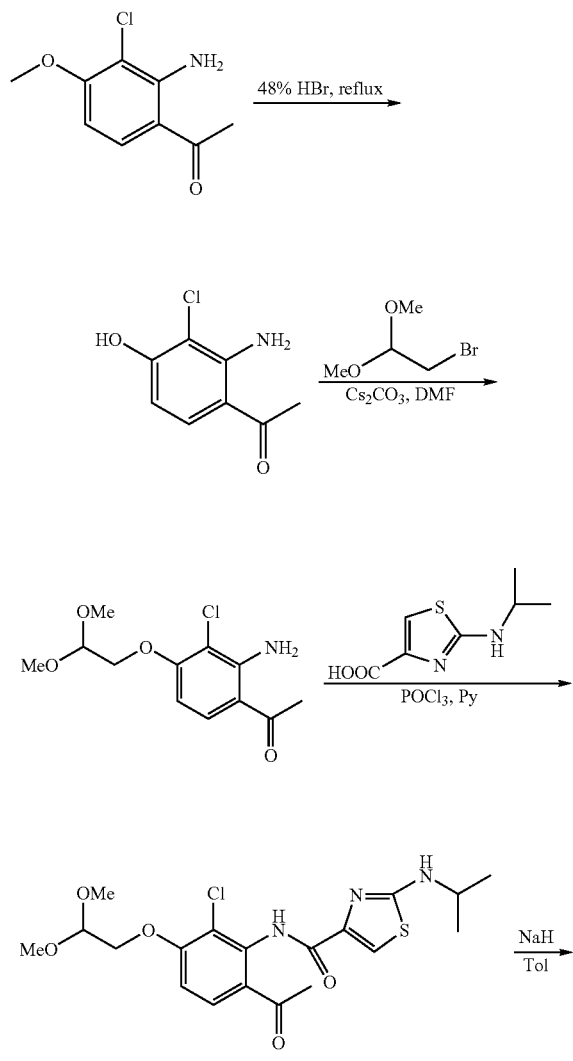

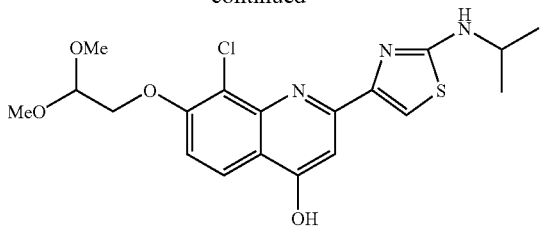

1-(2-Amino-3-chloro-4-methoxyphenyl)ethanone (prepared according to Raboisson, P. J.-M. B., et al., WO2007014926, p 78; 70.7 g, 354 mmol) was stirred in 48% aq. HBr (500 mL) at 110° C. for 72 h. After the mixture was cooled to 0° C. with stirring, the solids were filtered and washed with water. The resulting solids were triturated with a saturated NaHCO$_3$ solution (~350 mL), filtered, washed with water, and dried under vacuum to give 40 g (61% yield) of 1-(2-amino-3-chloro-4-hydroxyphenyl)ethanone as a dark brown solid.

1-(2-Amino-3-chloro-4-hydroxyphenyl)ethanone (40 g, 215 mmol) was dissolved in DMF (360 ml). Cesium carbonate (140 g, 430 mmol) was added, followed by bromoacetaldehyde dimethyl acetal (54.5 g, 323 mmol). The mixture was then vigorously stirred at 65° C. for 24 h. Upon cooling to room temperature, EtOAc (1 L) and H$_2$O (1 L) were added to the mixture. The organic layer was extracted with EtOAc (1×400 ml). The combined organic layer was washed with aqueous 3% LiCl solution (2×1 L), brine, dried (Na$_2$SO$_4$) and concentrated in vacuo. The residue was purified by silica gel chromatography to give 1-[2-amino-3-chloro-4-(2,2-dimethoxyethoxy)phenyl]-ethanone as a white solid (39 g, 67% yield).

To a mixture of 1-[2-amino-3-chloro-4-(2,2-dimethoxyethoxy)phenyl]ethanone (13 g, 47.5 mmol) and isopropylaminothiazole-4-carboxylic acid hydrobromide (prepared as described in Ivanov, V., et. al.; EP1881001A1, p. 62-63; 12.6 g, 47.5 mmol) in pyridine (150 ml) was slowly added phosphorus oxychloride (9.47 g, 61.8 mmol) at −40° C. The mixture was then stirred at 0° C. for 4 h. Upon completion of the reaction, H$_2$O (30 ml) was added dropwise to the mixture. The mixture was then stirred at 0° C. for another 15 min. The mixture was concentrated in vacuo. The residue was diluted with EtOAc, washed with a sat. NaHCO$_3$ aqueous solution. The organic layer was dried (Na$_2$SO$_4$) and concentrated in vacuo. The residue was dissolved in CH$_2$Cl$_2$, hexanes was added slowly to the solution, and a yellow solid started to crash out. More hexanes were added precipitation was complete to afford 2-isopropylaminothiazole-4-carboxylic acid [6-acetyl-2-chloro-3-(2,2-dimethoxyethoxy)phenyl]amide (18 g, 85% yield).

2-Isopropylamino-thiazole-4-carboxylic acid [6-acetyl-2-chloro-3-(2,2-dimethoxy-ethoxy)-phenyl]-amide (18 g, 40.7 mmol) was suspended in toluene (400 ml). NaH (2.4 g, 61 mmol) was added to the vigorously stirred mixture while monitoring H$_2$ evolution. The mixture became a clear solution during heating to reflux. After refluxing for 3 h, the mixture was cooled to room temperature. A solution of AcOH (69.2 mmol) in H$_2$O (3 vol) was added to the mixture. After vigorous agitation for 1 h at 0° C., the solids were collected by filtration and rinsed with H$_2$O. The wet cake was dried under high vacuum to a constant weight to provide 8-chloro-7-(2,2-dimethoxy-ethoxy)-2-(2-isopropylaminothiazol-4-yl)-quinolin-4-ol (15 g, 86% yield).

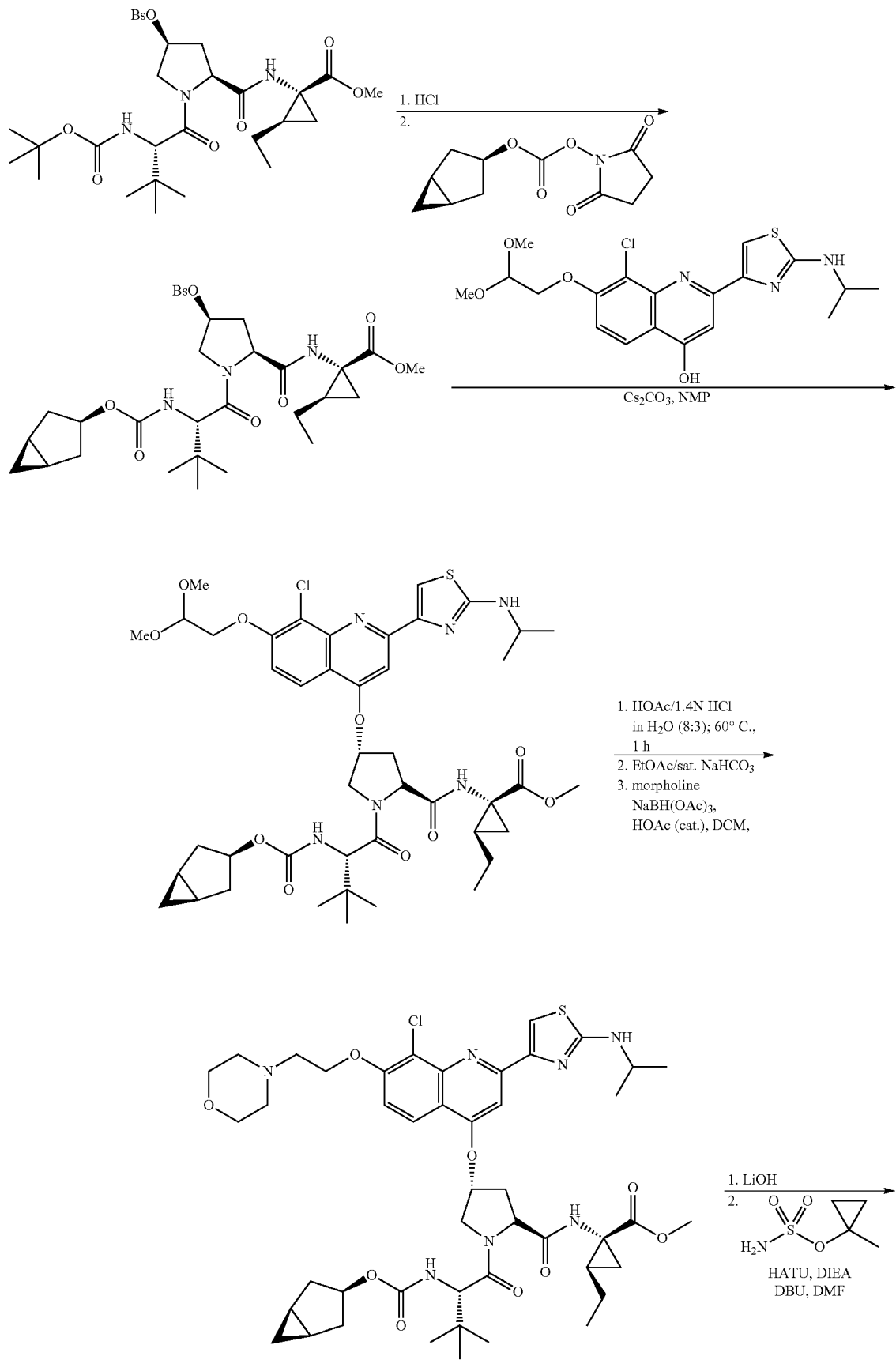

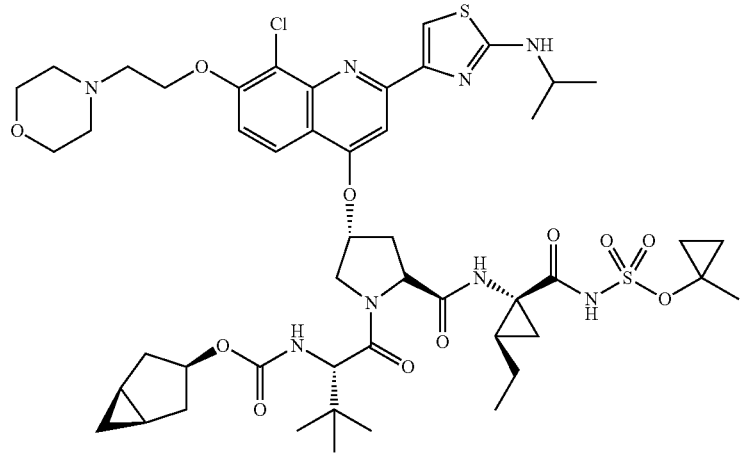

Compound 194

1-{[4-(4-Bromobenzenesulfonyloxy)-1-(2-tert-butoxycarbonylamino-3,3-dimethylbutyryl)-pyrrolidine-2-carbonyl]amino}-2-ethylcyclopropanecarboxylic acid methyl ester was dissolved in 4N HCl in dioxane (300 mL) at room temperature and stirred for 2 h. It was then concentrated under vacuum, and co-evaporated with dichloromethane (2×200 mL) to dryness. The residue was dissolved in EtOAc (600 mL) and sat'd aq. NaHCO$_3$ (1 L). It was stirred vigorously. After 10 min, carbonic acid bicyclo[3.1.0]hex-3-yl ester 2,5-dioxo-pyrrolidin-1-yl ester (41.4 g, 173.1 mmol) was added in one portion. After the resulting mixture was stirred for another 30 min, the organic layer was collect and washed with brine (500 mL), dried over Na$_2$SO$_4$, and concentrated in vacuo. The crude product was purified by flash chromatography on silica gel with ethyl acetate/hexane to afford 94.4 g (92% yield) of 1-{[1-[2-(bicyclo[3.1.0]hex-3-yloxycarbonylamino)-3,3-dimethylbutyryl]-4-(4-bromobenzenesulfonyloxy)-pyrrolidine-2-carbonyl]-amino}-2-ethylcyclopropanecarboxylic acid methyl ester.

To a mixture of 1-{[1-[2-(bicyclo[3.1.0]hex-3-yloxycarbonylamino)-3,3-dimethyl-butyryl]-4-(4-bromobenzenesulfonyloxy)pyrrolidine-2-carbonyl]amino}-2-ethyl-cyclopropanecarboxylic acid methyl ester (15 g, 35 mmol) and 8-chloro-7-(2,2-dimethoxyethoxy)-2-(2-isopropylaminothiazol-4-yl)-quinolin-4-ol (27.5 g, 38.5 mmol) in NMP (200 ml) was added cesium carbonate (25.1 g, 77 mmol). The mixture was stirred at 65° C. for 5 h. The reaction was cooled to room temperature and EtOAc (600 ml) and an aqueous solution of 3% LiCl (600 ml) were added to the mixture. The organic layer was washed with aqueous 3% LiCl (1×600 ml), brine, dried (Na$_2$SO$_4$) and concentrated in vacuo. The residue was purified by silica gel chromatography to produce 1-({1-[2-(bicyclo[3.1.0]hex-3-yloxycarbonylamino)-3,3-dimethylbutyryl]-4-[8-chloro-7-(2,2-dimethoxyethoxy)-2-(2-isopropylaminothiazol-4-yl)-quinolin-4-yloxy]pyrrolidine-2-carbonyl}amino)-2-ethylcyclopropanecarboxylic acid methyl ester as a yellow solid (23.6 g, 75% yield). LCMS found 900.1 [M+H]$^+$.

1-({1-[2-(Bicyclo[3.1.0]hex-3-yloxycarbonylamino)-3,3-dimethylbutyryl]-4-[8-chloro-7-(2,2-dimethoxyethoxy)-2-(2-isopropylaminothiazol-4-yl)-quinolin-4-yloxy]pyrrolidine-2-carbonyl}amino)-2-ethylcyclopropanecarboxylic acid methyl ester (23.6 g, 26 mmol) was dissolved in glacial acetic acid (200 ml) and 1.4N HCl in H$_2$O (75 ml) was added to the solution. The mixture was stirred at 60° C. for 1 h. The mixture was concentrated to remove the solvents, followed by co-evaporation with toluene (×2) to remove residual acetic acid. The residue was then dissolved in EtOAc (500 ml) and sat. NaHCO$_3$ aqueous solution while monitoring CO$_2$ evolution. The organic layer was washed with brine, dried (Na$_2$SO$_4$) and concentrated in vacuo. The residue was further dried under high vacuum for 1 h and used without further purification in the next step. The crude material was dissolved in CH$_2$Cl$_2$ (360 ml) and morpholine (3.4 g, 39 mmol) and sodium triacetoxyborohydride (7.2 g, 34 mmol) were added to the mixture at 0° C. Then glacial acetic acid (0.47 g, 7.8 mmol) was added dropwise to the mixture. The reaction was complete in 10 min at 0° C. Saturated aqueous NaHCO$_3$ solution was added to quench the reaction. After stirring for another 20 min, the organic layer was washed with brine, dried (Na$_2$SO$_4$) and concentrated in vacuo. The residue was purified by silica gel chromatography to give 1-({1-[2-(bicyclo[3.1.0]hex-3-yloxycarbonylamino)-3,3-dimethylbutyryl]-4-[8-chloro-2-(2-isopropylaminothiazol-4-yl)-7-(2-morpholin-4-yl-ethoxy)quinolin-4-yloxy]pyrrolidine-2-carbonyl}-amino)-2-ethyl-cyclopropanecarboxylic acid methyl ester as a yellow solid (12 g, 50% yield). LCMS found 924.63 [M+H]$^+$.

1-({1-[2-(Bicyclo[3.1.0]hex-3-yloxycarbonylamino)-3,3-dimethylbutyryl]-4-[8-chloro-2-(2-isopropylaminothiazol-4-yl)-7-(2-morpholin-4-yl-ethoxy)quinolin-4-yloxy]pyrrolidine-2-carbonyl}-amino)-2-ethyl-cyclopropanecarboxylic acid methyl ester (12 g, 13 mmol) was dissolved in THF (200 ml), LiOH (11 g, 260 mmol) in H$_2$O (200 ml) was added, followed by MeOH (200 ml). The mixture was kept stirring at room temperature for 20 h. Upon completion of the reaction, 4 N HCl in H$_2$O was added to adjust pH to 7 at 0° C. The mixture was extracted with EtOAc (2×400 ml). The combined organic layer was washed with brine, dried (Na$_2$SO$_4$) and concentrated in vacuo to give 1-({1-[2-(bicyclo[3.1.0]hex-3-yloxycarbonylamino)-3,3-dimethyl-butyryl]-4-[8-chloro-2-(2-isopropylamino-thiazol-4-yl)-7-(2-morpholin-4-yl-ethoxy)-quinolin-4-yloxy]-pyrrolidine-2-carbonyl}-amino)-2-ethyl-cyclopropanecarboxylic acid as a yellow solid (11 g, 93% yield). LCMS found 911.52[M+H]$^+$.

Compound 194 was prepared according to the method described in Example 2, starting from 1-({1-[2-(bicyclo [3.1.0]hex-3-yloxycarbonylamino)-3,3-dimethyl-butyryl]-4-[8-chloro-2-(2-isopropylamino-thiazol-4-yl)-7-(2-morpholin-4-yl-ethoxy)-quinolin-4-yloxy]-pyrrolidine-2- carbonyl}-amino)-2-ethyl-cyclopropanecarboxylic acid (0.20 g, 0.22 mmol) and with the exception of using sulfamic acid 1-methyl-cyclopropyl ester (0.066 g, 0.44 mmol) and adjusted for scale to afford 0.86 g (37% yield) of Compound 194. $^1$H NMR (CD$_3$OD, 400 MHz) δ 7.99 (m, 1H); 7.58 (s, 1H); 7.46 (s, 1H); 7.32 (d, 1H); 6.86 (d, 1H); 5.41 (s, 1H); 4.73 (m, 1H); 4.51 (m, 3H); 4.41 (d, 1H); 4.24 (d, 1H); 4.10 (d, 1H); 3.92 (m, 1H); 3.86 (m, 5H); 3.11 (m, 4H); 2.56 (m, 1H); 2.32 (m, 1H); 2.04 (m, 1H); 1.92 (m, 1H); 1.76-1.40 (m, 7H); 1.67 (s, 3H); 1.40-1.14 (m, 5H); 1.32 (m, 6H); 1.02 (m, 9H); 0.97 (t, 3H); 0.66 (s, 2H); 0.36 (m, 2H). LCMS found 1044.9 [M+H]$^+$.

Example 195

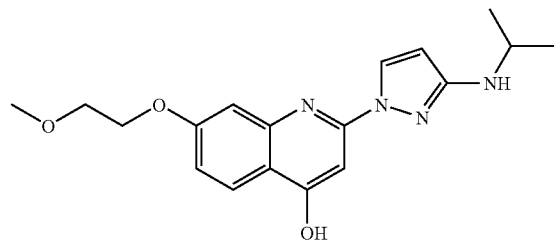

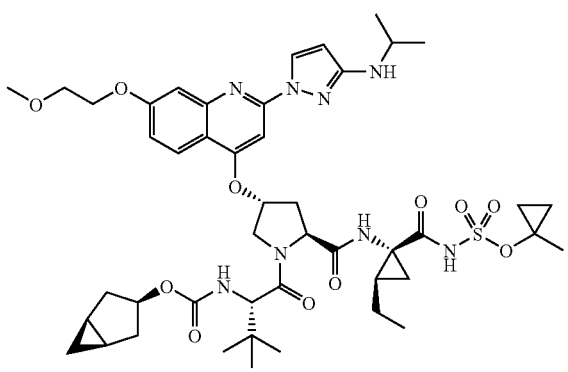

Compound 195

Compound 195 was prepared analogously to Compound 194 with substitution of 2-(3-isopropylaminopyrazol-1-yl)-7-(2-methoxyethoxy)-quinolin-4-ol for 8-chloro-7-(2,2-dimethoxyethoxy)-2-(2-isopropylaminothiazol-4-yl)-quinolin-4-ol and appropriate adjustments for scale to afford 82 mg (35% yield) of Compound 195. $^1$H NMR (CD$_3$OD, 400 MHz) δ 8.46 (m, 1H); 7.94 (d, 1H); 7.25 (s, 2H); 7.02 (m, 1H); 6.89 (m, 1H, exchangeable); 5.98 (m, 1H); 5.48 (s, 1H); 4.77 (t, 1H); 4.55-4.44 (m, 2H); 4.27 (m, 1H); 4.25 (m, 2H); 4.09 (m, 1H); 3.81 (m, 2H); 3.80 (m, 1H); 3.45 (s, 3H); 2.64 (m, 1H); 2.29 (m, 1H); 2.06 (m, 1H); 1.97 (m, 1H); 1.76-1.48 (m, 6H); 1.68 (s, 3H); 1.47-1.15 (m, 5H); 1.29 (m, 6H); 1.03 (s, 9H); 0.96 (t, 3H); 0.68 (m, 2H); 0.41 (m, 2H). LCMS found 938.09 [M+H]$^+$.

Example 196

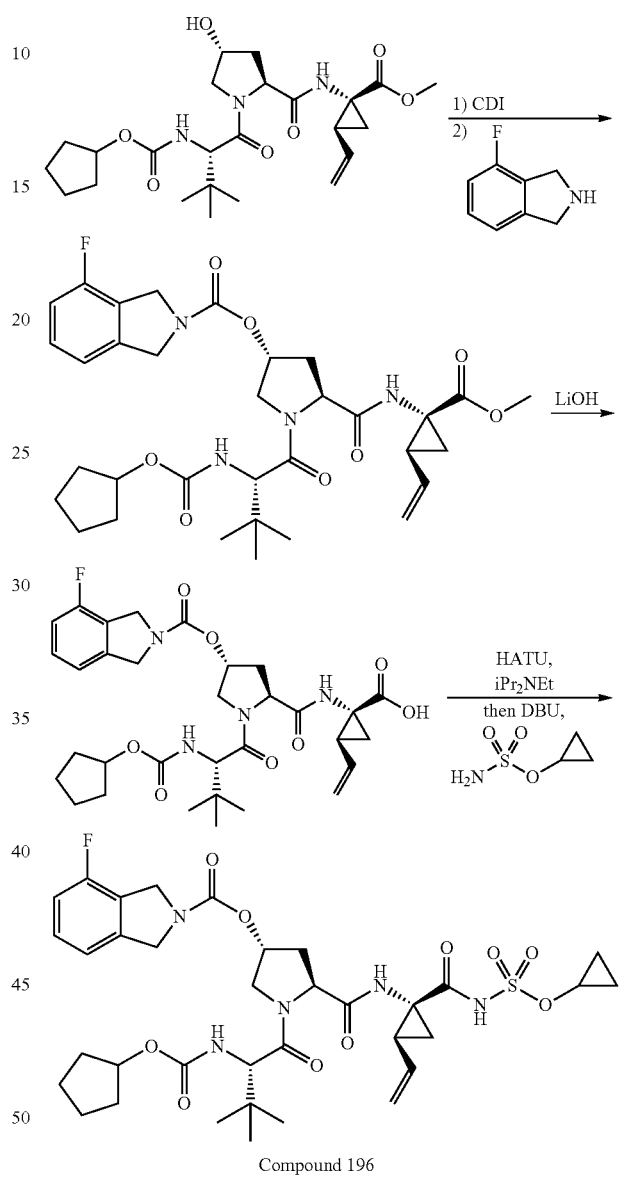

Compound 196

1-{[1-(2-Cyclopentyloxycarbonylamino-3,3-dimethyl-butyryl)-4-hydroxy-pyrrolidine-2-carbonyl]-amino}-2-vinyl-cyclopropanecarboxylic acid methyl ester (530 mg, 1.11 mmol) was dissolved in CH$_2$Cl$_2$ (11 mL) and treated with CDI (234 mg, 1.44 mmol). After stirring overnight at room temperature, 4-fluoro-2,3-dihydro-1H-isoindole (762 mg, 5.56 mmol) was added and the reaction mixture was stirred overnight. The reaction was then diluted with CH$_2$Cl$_2$ and sequentially washed with 1N HCl, saturated aqueous NaHCO$_3$, H$_2$O and saturated aqueous NaCl. The organic phase was then dried over sodium sulfate. After removal of solvent, the crude product was purified by column chromatography on silica (40-60% EtOAc/Hexanes) to provide 4-fluoro-1,3-dihydro-isoindole-2-carboxylic acid 1-(2-cyclopentyloxycarbonylamino-3,3-dimethyl-butyryl)-5-(1-methoxycarbonyl-2-vinyl-cyclopropylcarbamoyl)-pyrrolidin-3-yl ester (563 mg, 79% yield). $^1$H NMR (CDCl$_3$, 300 MHz) δ 7.77 (bd, 1H), 6.92-7.27 (m, 3H), 5.75 (m, 1H), 5.29 (m, 2H), 5.15 (m, 2H), 4.55-4.85 (m, 5H), 4.26 (m, 2H), 3.70 (m, 1H), 3.67 (s, 3H), 2.82 (m, 1H), 2.56 (m, 1H), 2.10 (m, 1H), 1.87 (m, 1H), 1.40-1.65 (m, 5H), 1.02 (s, 9H). LCMS found 643.3 [M+H]$^+$.

4-Fluoro-1,3-dihydro-isoindole-2-carboxylic acid 1-(2-cyclopentyloxycarbonylamino-3,3-dimethyl-butyryl)-5-(1-methoxycarbonyl-2-vinyl-cyclopropylcarbamoyl)-pyrrolidin-3-yl ester (550 mg, 0.86 mmol) was dissolved in THF:MeOH:H$_2$O (1:1:1 8.7 mL) and treated with lithium hydroxide (180 mg, 4.28 mmol). The reaction was judged complete by complete consumption of starting material after approximately 2 h, at which time the reaction was neutralized with 1N aqueous HCl. The organic phase was extracted with EtOAc then washed with saturated aqueous NaCl, and dried over sodium sulfate. After removal of solvent, 4-fluoro-1,3-dihydro-isoindole-2-carboxylic acid 5-(1-carboxy-2-vinyl-cyclopropylcarbamoyl)-1-(2-cyclopentyloxycarbonylamino-3,3-dimethyl-butyryl)-pyrrolidin-3-yl ester was obtained (540 mg, 0.86 mmol), which was used in the next reaction without further purification.

4-Fluoro-1,3-dihydro-isoindole-2-carboxylic acid 5-(1-carboxy-2-vinyl-cyclopropylcarbamoyl)-1-(2-cyclopentyloxycarbonylamino-3,3-dimethyl-butyryl)-pyrrolidin-3-yl ester (160 mg, 0.25 mmol) was dissolved in DMF (3 mL) and HATU (106 mg, 0.28 mmol) and iPr$_2$NEt (53 µL, 0.30 mmol) were added. After stirring for 1.5 h, sulfamic acid cyclopropyl ester (41 mg, 0.24 mmol) and DBU (152 µL, 1.02 mmol) were added and the reaction was stirred overnight. The reaction was then diluted with EtOAc and sequentially washed with 1N HCl, saturated aqueous NR$_4$Cl, and saturated aqueous NaCl. The organic phase was then dried over sodium sulfate and concentrated. Purification via reverse phase HPLC (40-95% ACN/H$_2$O-1% TFA) afforded Compound 196 (147 mg, 77% yield): $^1$H NMR (CD$_3$OD, 300 MHz) δ 9.12 (d, 1H), 6.94-7.32 (m, 3H)), 5.69 (m, 1H), 5.28 (m, 2H), 5.12 (d, 1H), 4.66-4.85 (m, 6H), 4.34 (d, 1H), 4.19 (m, 1H), 4.14 (s, 1H), 3.81 (d, 1H), 2.40 (dd, 1H), 2.24 (q, 1H), 2.11 (m, 1H), 1.85 (dd, 1H), 1.30-1.60 (m, 9H), 0.98 (s, 9H), 0.87 (m, 2H), 0.70 (m, 2H). LCMS found 747.9 [M+H]$^+$.

Example 197

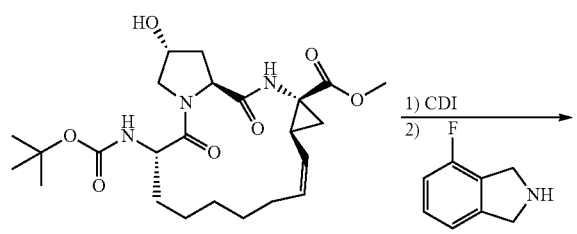

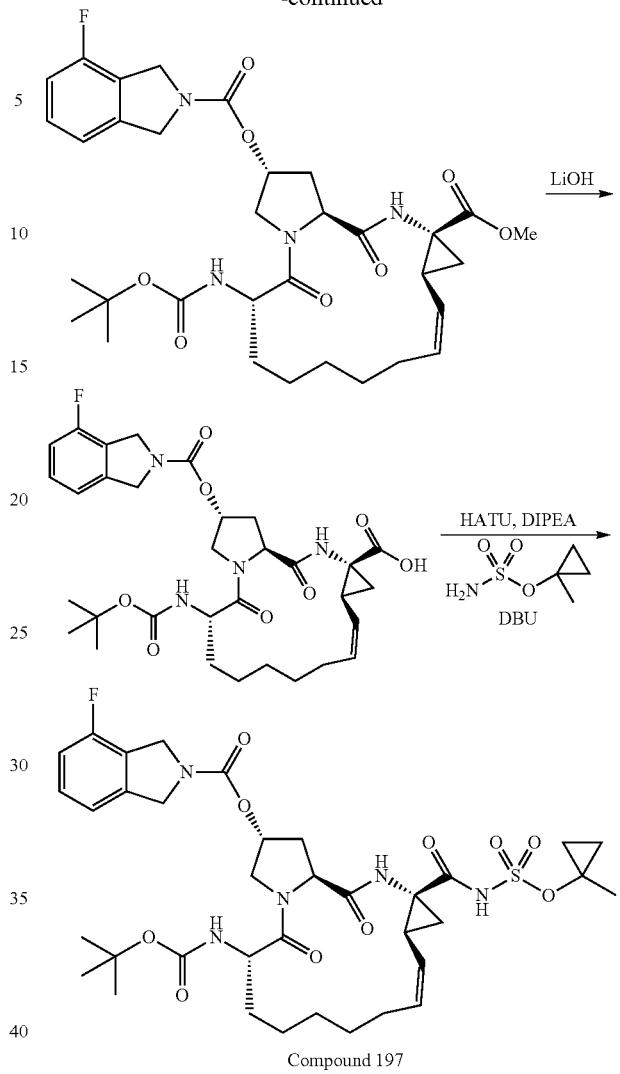

Compound 197

To a solution of cyclopropa[e]pyrrolo[1,2-a][1,4]diazacyclopentadecine-14a(5H)-carboxylicacid, 6-[[(1,1-dimethylethoxy)carbonyl]amino]-1,2,3,6,7,8,9,10,11,13a,14,15,16,16a-tetradecahydro-2-hydroxy-5,16-dioxo-methyl ester (1.00 g, 2.09 mmol) in CH$_2$Cl$_2$ (20 mL) was added CDI (372 mg, 2.29 mmol). After stirring overnight at room temperature, 4-fluoro-2,3-dihydro-1H-isoindole (573 mg, 4.18 mmol) and DBU (0.937 mL, 6.27 mmol) was added and the reaction mixture was stirred for 2 h. The reaction was then diluted with CH$_2$Cl$_2$ and sequentially washed with 1N HCl, saturated aqueous NaHCO$_3$, H$_2$O and saturated aqueous NaCl. The organic phase was then dried over sodium sulfate. After removal of solvent, the crude product was purified by column chromatography on silica (40→60% EtOAc/Hexanes) to provide 14-tert-Butoxycarbonylamino-18-(4-fluoro-1,3-dihydro-isoindole-2-carbonyloxy)-2,15-dioxo-3,16-diaza-tricyclo[14.3.0.04,6]nonadec-7-ene-4-carboxylic acid methyl ester (916 mg, 68% yield). LCMS found 642.8 [M+H]$^+$.

To 14-tert-Butoxycarbonylamino-18-(4-fluoro-1,3-dihydro-isoindole-2-carbonyloxy)-2,15-dioxo-3,16-diaza-tricyclo[14.3.0.04,6]nonadec-7-ene-4-carboxylic acid methyl ester (916 mg, 1.43 mmol) in a 1:1:1 mixture of THF:MeOH:H$_2$O (12 mL) was added lithium hydroxide (299 mg, 41.96 mmol). The resulting slurry was stirred at room temperature overnight then diluted with EtOAc and washed with 1 N HCl and brine. The resulting organic layer was dried over sodium sulfate and concentrated to provide the crude 14-tert-Butoxycarbonylamino-18-(4-fluoro-1,3-dihydro-isoindole-2-carbonyloxy)-2,15-dioxo-3,16-diaza-tricyclo[14.3.0.04,6]nonadec-7-ene-4-carboxylic acid (910 mg, 100% yield). LCMS found 628.8 [M+H]+.

To 14-tert-Butoxycarbonylamino-18-(4-fluoro-1,3-dihydro-isoindole-2-carbonyloxy)-2,15-dioxo-3,16-diaza-tricyclo[14.3.0.04,6]nonadec-7-ene-4-carboxylic acid (150 mg, 0.24 mmol) in CH$_2$Cl$_2$ (2.5 mL) was added HATU (137 mg, 0.36 mmol) and DIPEA (0.063 mL, 0.36 mmol). After stirring for 0.5 h at room temperature, sulfamic acid 1-methyl-cyclopropyl ester (74 mg, 0.48 mmol) and DBU (0.144 mL, 0.96 mmol) were added. The resulting mixture was stirred at room temperature overnight then diluted with EtOAc and washed with saturated NH$_4$Cl and brine. The residue was purified by reverse phase HPLC (30→90% MeCN/H$_2$O/0.1% TFA) to provide Compound 197 (86 mg, 47% yield). $^1$H NMR (300 MHz, CD$_3$OD): δ 8.45 (m, 1H), 7.32 (m, 1H), 7.13 (d, 1H), 7.01 (m, 1H), 5.66 (m, 1H), 5.40 (m, 1H), 5.13 (t, 1H), 4.79-4.52 (m, 6H), 4.06 (m, 1H), 3.82 (d, 1H), 2.68 (m, 1H), 2.51-2.36 (m, 2H), 1.75-1.15 (m, 14H), 1.64 (s, 3H), 1.11 (s, 9H), 0.65 (m, 2H). LCMS found 761.8 [M+H]+.

Example 198

Compound 198

Compound 198 was prepared according to the method presented in example 29, adjusted for scale, starting from 14-tert-butoxycarbonylamino-18-(4-fluoro-1,3-dihydro-isoindole-2-carbonyloxy)-2,15-dioxo-3,16-diaza-tricyclo[14.3.0.04,6]nonadec-7-ene-4-carboxylic acid (150 mg, 0.24 mmol) and with the exception of using sulfamic acid 1-propyl-cyclopropyl ester (86 mg, 0.48 mmol) afforded compound 198 after purification via reverse phase HPLC (95.1 mg, 50% yield). $^1$H NMR (300 MHz, CD$_3$OD): δ 8.65 (m, 1H), 7.32 (m, 1H), 7.13 (d, 1H), 7.01 (m, 1H), 5.66 (q, 1H), 5.40 (s, 1H), 5.12 (t, 1H), 4.79-4.52 (m, 6H), 4.06 (m, 1H), 3.82 (d, 1H), 2.68 (m, 1H), 2.51-2.35 (m, 2H), 2.00-1.94 (m, 1H), 1.77-1.15 (m, 17H), 1.11 (s, 9H), 0.96 (t, 3H), 0.67 (m, 2H). LCMS found 789.8 [M+H]+.

Example 199

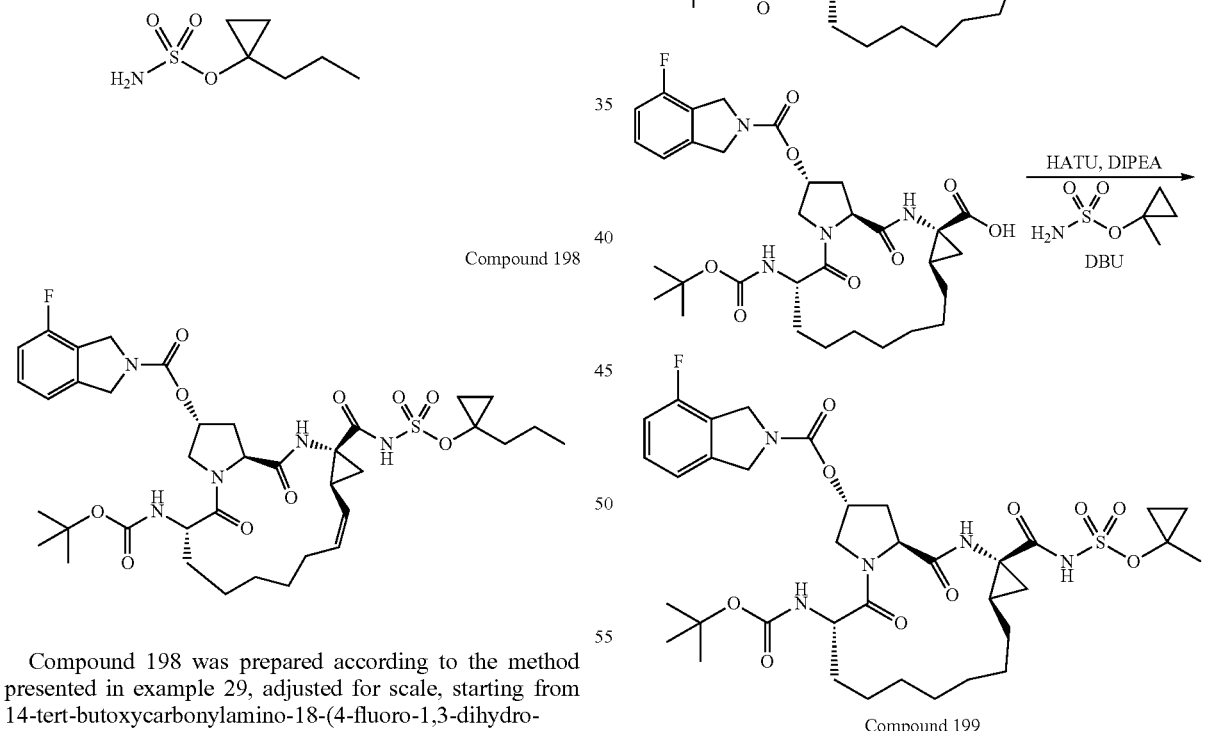

Compound 199

To 14-tert-butoxycarbonylamino-18-(4-fluoro-1,3-dihydro-isoindole-2-carbonyloxy)-2,15-dioxo-3,16-diaza-tricyclo[14.3.0.04,6]nonadec-7-ene-4-carboxylic acid methyl ester (392 mg, 0.61) in DME (3 mL) and water (1 mL) was added tosyl hydrazide (682 mg, 3.66 mmol) and sodium acetate (600 mg, 7.32 mmol). The reaction was heated to 95° C. and allowed to stir 1 hour. The reaction was diluted with water and extracted with ethyl acetate. The organic layer was dried over sodium sulfate, filtered, and concentrated. The crude product was purified by column chromatography on silica (40→60% EtOAc/Hexanes) to provide 14-tert-butoxycarbonylamino-18-(4-fluoro-1,3-dihydro-isoindole-2-carbonyloxy)-2,15-dioxo-3,16-diaza-tricyclo[14.3.0.04,6]nonadecane-4-carboxylic acid methyl ester (319 mg, 81% yield). LCMS found 644.8 [M+H]+.

To 14-tert-butoxycarbonylamino-18-(4-fluoro-1,3-dihydro-isoindole-2-carbonyloxy)-2,15-dioxo-3,16-diaza-tricyclo[14.3.0.04,6]nonadecane-4-carboxylic acid methyl ester (319 mg, 0.49 mmol) in a 1:1:1 mixture of THF:MeOH:H₂O (6 mL) was added lithium hydroxide (104 mg, 2.47 mmol). The resulting slurry was stirred at room temperature overnight then diluted with EtOAc and washed with 1N HCl and brine. The resulting organic layer was dried over sodium sulfate and concentrated to provide the crude 14-tert-butoxycarbonylamino-18-(4-fluoro-1,3-dihydro-isoindole-2-carbonyloxy)-2,15-dioxo-3,16-diaza-tricyclo[14.3.0.04,6]nonadecane-4-carboxylic acid (300 mg, 97% yield). LCMS found 630.8 [M+H]+.

To 14-tert-butoxycarbonylamino-18-(4-fluoro-1,3-dihydro-isoindole-2-carbonyloxy)-2,15-dioxo-3,16-diaza-tricyclo[14.3.0.04,6]nonadecane-4-carboxylic acid (150 mg, 0.24 mmol) in DMF (2.5 mL) was added HATU (137 mg, 0.36 mmol) and DIPEA (0.063 mL, 0.36 mmol). After stirring for 0.5 h at room temperature, sulfamic acid 1-methyl-cyclopropyl ester (74 mg, 0.48 mmol) and DBU (0.144 mL, 0.96 mmol) were added. The resulting mixture was stirred at room temperature overnight then diluted with EtOAc and washed with 1N HCl, aqueous saturated NH₄Cl, and brine. The crude residue was purified by reverse phase HPLC (30→90% MeCN/H₂O/0.1% TFA) to provide compound 199 (79 mg, 45% yield). ¹H NMR (300 MHz, CD₃OD): δ 8.93 (s, 1H), 7.32 (s, 1H), 7.12 (d, 1H), 7.01 (m, 1H), 5.40 (s, 1H), 4.80-4.68 (m, 4H), 4.60 (q, 1H), 4.46 (d, 1H), 4.12 (m, 1H), 3.85 (m, 1H), 2.55-2.50 (m, 1H), 2.34-2.27 (m, 2H), 1.75-1.20 (m, 18H), 1.66 (s, 3H), 1.15 (s, 9H), 0.70 (m, 2H). LCMS found 763.8 [M+H]+.

Example 200

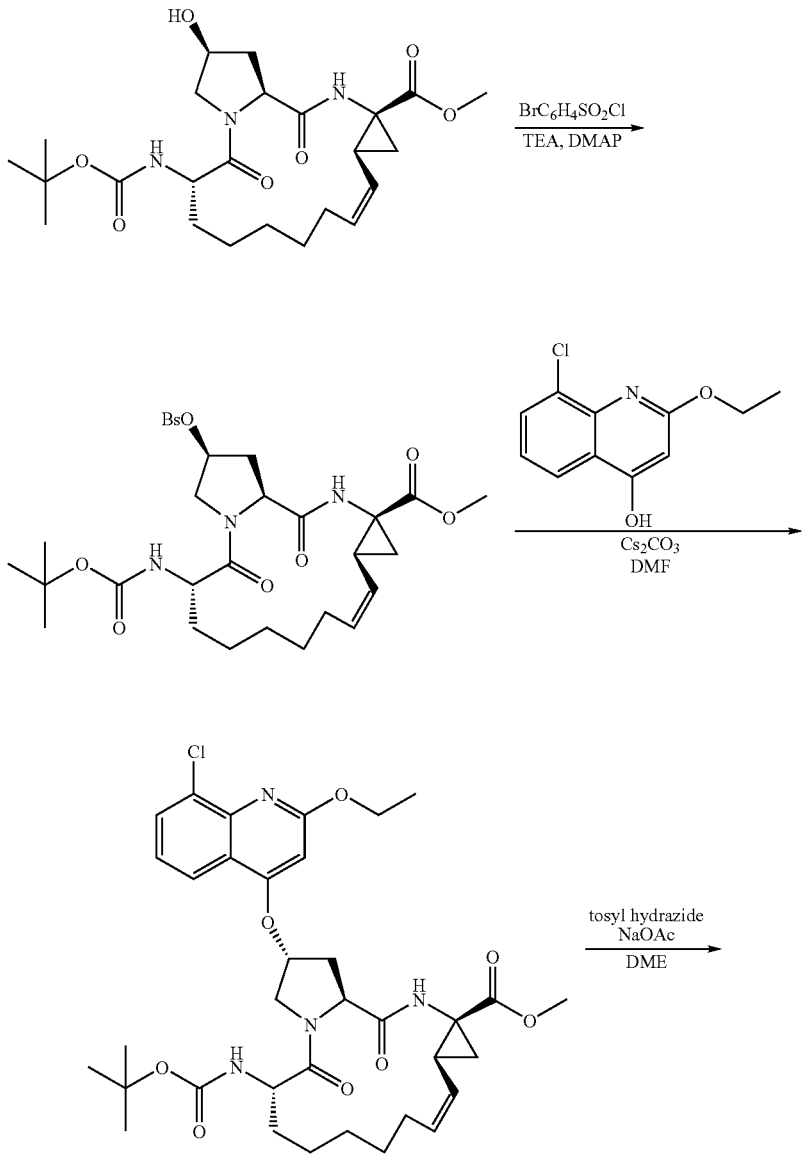

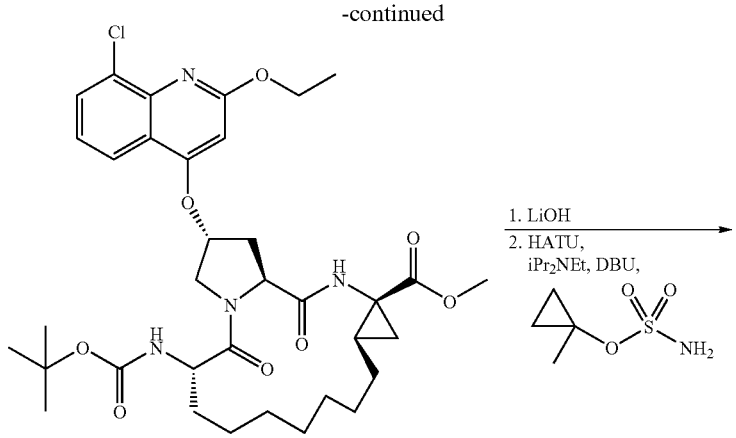

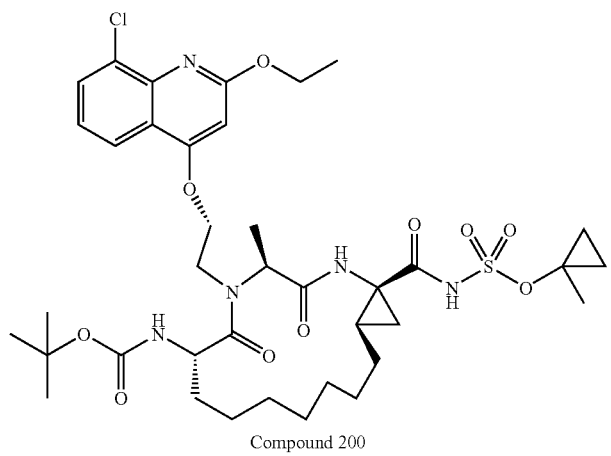

Compound 200

14-tert-Butoxycarbonylamino-18-hydroxy-2,15-dioxo-3,16-diaza-tricyclo[14.3.0.04,6]nonadec-7-ene-4-carboxylic acid methyl ester, synthesized by methods presented in *Org. Lett.* 2004, 6(17), 2901, was converted to the brosylate by methods presented in Example 1 adjusted for scale (570 mg, 54%). LCMS found 697.7 [M+H]$^+$.

14-tert-Butoxycarbonylamino-18-(8-chloro-2-ethoxy-quinolin-4-yloxy)-2,15-dioxo-3,16-diaza-tricyclo[14.3.0.04,6]nonadec-7-ene-4-carboxylic acid methyl ester was synthesized according to the method presented in example 138, adjusting for scale, to provide the desired aryl ether macrocycle (472 mg, 84%). LCMS found 685.1 [M+H]$^+$.

Reduction of the unsaturated macrocycle was accomplished according to the method presented in example 20, adjusting for scale, to provide the fully saturated 14-tert-butoxycarbonylamino-18-(8-chloro-2-ethoxy-quinolin-4-yloxy)-2,15-dioxo-3,16-diaza-tricyclo[14.3.0.04,6]nonadecane-4-carboxylic acid methyl ester. LCMS found 687.1 [M+H]$^+$.

Compound 200 was prepared according to the method presented for the synthesis of compound 29. Treatment of 14-tert-butoxycarbonylamino-18-(8-chloro-2-ethoxy-quinolin-4-yloxy)-2,15-dioxo-3,16-diaza-tricyclo[14.3.0.04,6]nonadecane-4-carboxylic acid methyl ester under the same conditions, adjusted for scale, and after purification by reverse phase HPLC provided compound 200 (150 mg, 58%). $^1$H NMR (300 MHz, CD$_3$OD): δ 8.96 (s, 1H), 8.06 (d, 1H), 7.73 (d, 1H) 7.23 (t, 1H), 6.54 (d, 1H), 5.47 (brs, 1H), 4.77 (dd, 1H), 4.61 (m, 3H), 4.20 (dd, 1H), 4.02 (dd, 1H), 2.74 (m, 1H), 2.44 (m, 1H), 1.2-1.8 (m, 22H), 1.68 (s, 3H), 1.28 (s, 9H), 0.72 (m, 2H). LCMS found 806.0 [M+H]$^+$.

Example 201

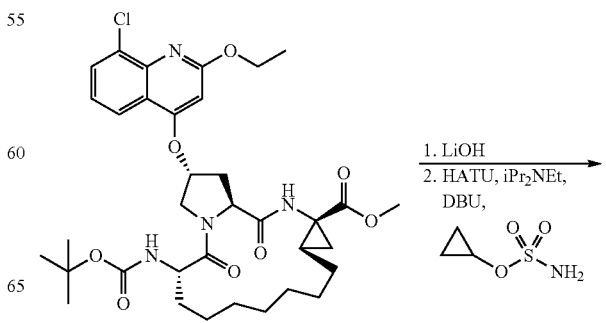

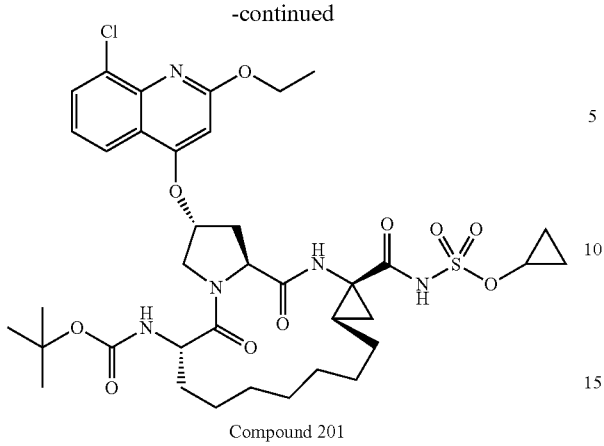

Compound 201

Compound 201 was prepared according to the method presented for the synthesis of compound 27. Treatment of 14-tert-butoxycarbonylamino-18-(8-chloro-2-ethoxy-quinolin-4-yloxy)-2,15-dioxo-3,16-diaza-tricyclo[14.3.0.04,6]nonadecane-4-carboxylic acid methyl ester under the same conditions, adjusted for scale, provided compound 201 (65 mg, 26%): $^1$H NMR (300 MHz, CD$_3$OD): δ 8.94 (s, 1H), 8.07 (d, 1H), 7.73 (d, 1H) 7.25 (t, 1H), 6.54 (d, 1H), 5.46 (brs, 1H), 4.77 (dd, 1H), 4.61 (m, 3H), 4.29 (m, 1H), 4.20 (dd, 1H), 4.03 (dd, 1H), 2.75 (m, 1H), 2.44 (m, 1H), 1.3-1.8 (m, 20H), 1.18 (s, 9H), 0.94 (m, 2H), 0.72 (m, 2H). LCMS found 792.0 [M+H]$^+$.

Example 202

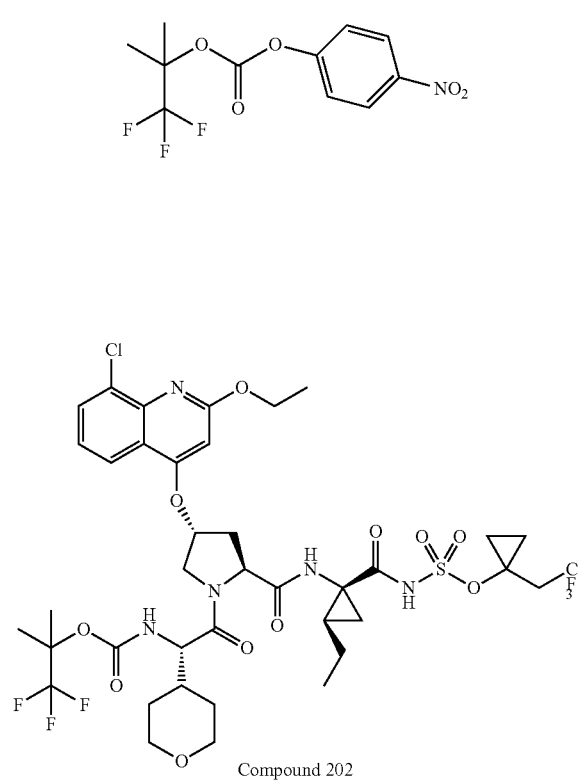

Compound 202

Compound 202 was prepared according to the methods described in Example 77. Treatment of compound 170 (100 mg, 0.11 mmol) under the same conditions, adjusted for scale, provided compound 202 (85 mg, 80%). $^1$H MNR (300 MHz, CD$_3$OD): δ 9.34 (s, 1H), 8.00 (d, 1H), 7.74 (d, 1H), 7.25 (d, 1H), 6.52 (s, 1H), 5.43 (m, 1H), 4.60 (m, 4H), 4.06-3.87 (m, 4H), 3.39 (m, 2H), 2.90 (m, 2H), 2.60 (m, 1H), 2.35 (m, 1H), 2.10 (m, 1H), 1.76-1.18 (m, 18H), 1.10 (m, 3H), 0.95 (m, 6H). LCMS found 945 [M+H]$^+$.

Example 203

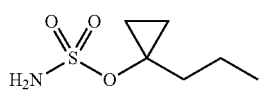

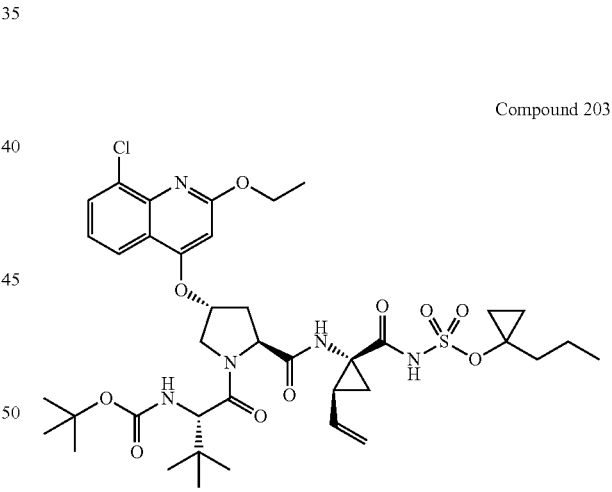

Compound 203

Compound 203 was prepared according to the method presented in example 29, substituting sulfamic acid 1-propyl-cyclopropyl ester for sulfamic acid 1-methyl-cyclopropyl ester, and adjusting appropriately for scale. The compound was purified using reverse phase HPLC to give 142.9 mg (57%) of compound 203 as a white amorphous solid. $^1$H NMR (CD$_3$OD, 300 MHz) δ 7.94 (d, 1H); 7.68 (d, 1H); 7.20 (m, 1H); 6.47 (s, 1H); 5.68 (m, 1H); 5.37 (s, 1H); 5.26 (d, 1H); 5.09 (d, 1H); 4.51 (m, 4H); 4.18 (s, 1H); 4.02 (m, 1H); 2.57 (m, 1H); 2.21 (m, 1H); 1.79 (m, 2H); 1.54 (m, 1H); 1.41 (m, 5H); 1.21 (m, 11H); 0.99 (s, 9H); 0.92 (m, 5H); 0.64 (s, 2H). LCMS found 820.0 [M+H]$^+$.

Example 204

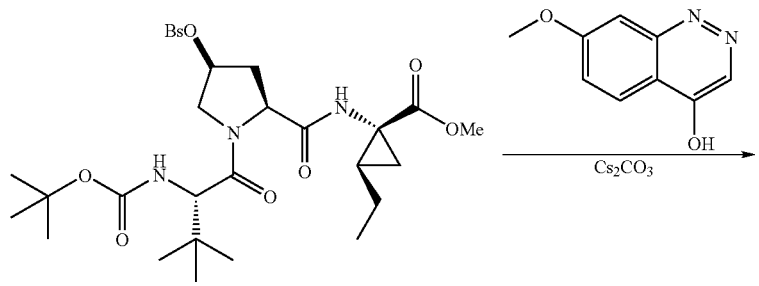

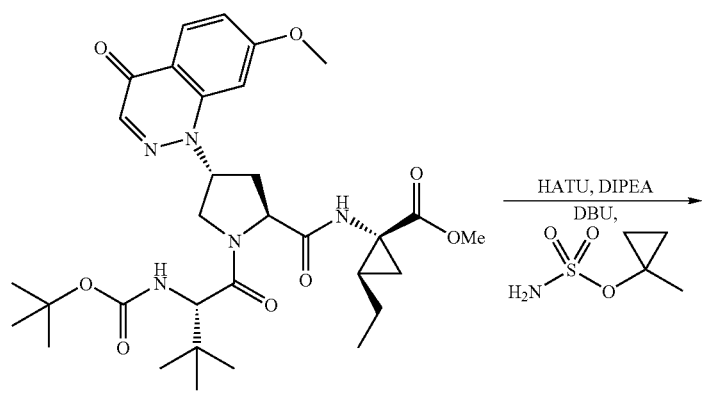

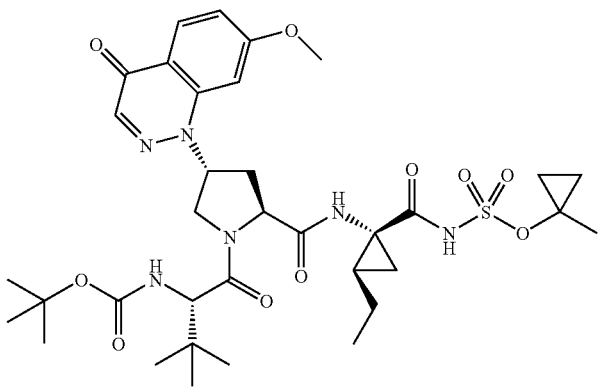

Compound 204

Compound 204 was prepared according to the method presented example 14. Treatment of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (800 mg, 1.16 mmol) under the same conditions adjusted for scale and with the exceptions of utilizing 7-methoxy-cinnolin-4-ol (229 mg, 1.30 mmol), sulfamic acid 1-methyl-cyclopropyl ester (50 mg, 0.33 mmol), and performing the hydrolysis of the methyl ester at 40° C. for 3 h provided compound 204 (50 mg, 8%): $^1$H NMR (CD$_3$OD, 300 MHz) δ 9.12 (s, 1H), 8.13 (d, 1H), 7.68 (s, 1H), 7.15 (s, 1H), 7.07 (s, 1H), 5.66 (s, 1H), 4.62 (m, 1H), 4.51 (d, 1H), 4.22 (m, 2H), 4.02 (s, 3H), 2.77 (m, 1H), 2.49 (m, 1H), 1.67 (s, 3H), 1.50-1.62 (m, 3H), 1.30 (s, 9H), 1.29 (m, 2H), 1.02 (s, 9H), 0.98 (m, 3H), 0.67 (m, 2H).

Example 205
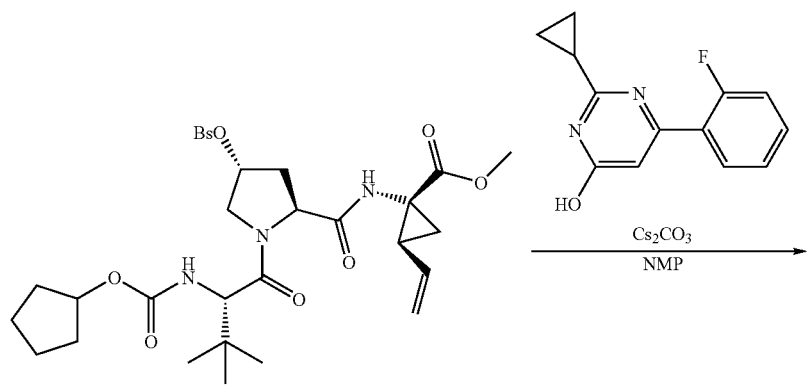
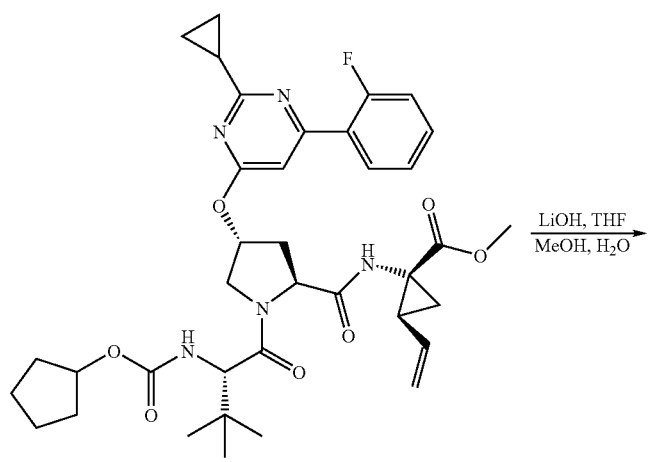
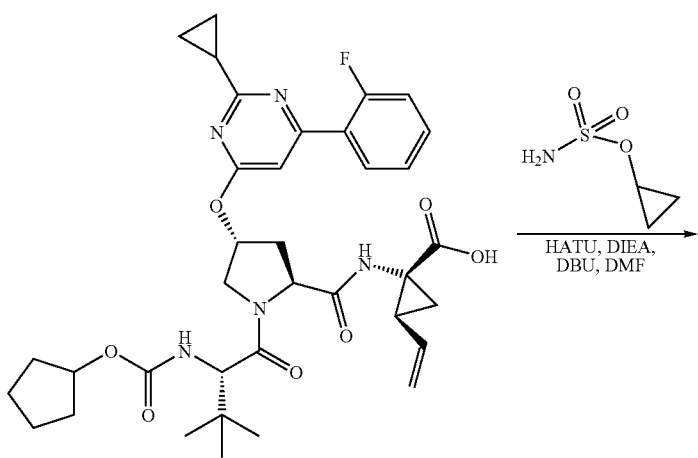

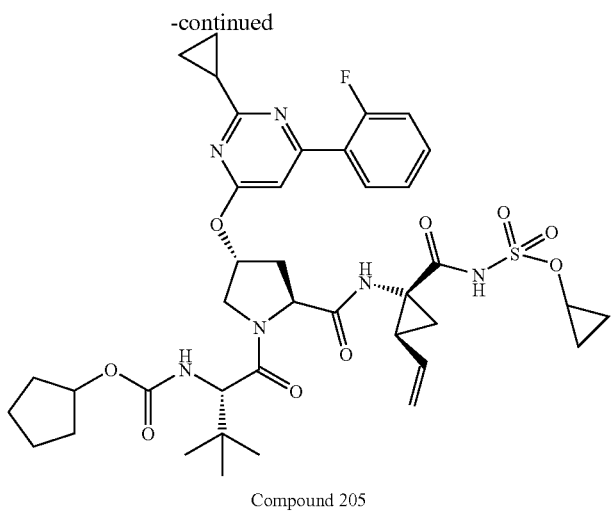

Compound 205

A round bottom flask was charged with 1-{[4-(4-bromo-benzenesulfonyloxy)-1-(2-cyclopentyloxycarbonylamino-3,3-dimethyl-butyryl)-pyrrolidine-2-carbonyl]-amino}-2-vinyl-cyclopropanecarboxylic acid methyl ester (150 mg, 0.21 mmol), 1.5 ml NMP, 2-cyclopropyl-6-(2-fluoro-phenyl)-pyrimidin-4-ol (48 mg, 0.21 mmol), $Cs_2CO_3$ (102.6 mg, 0.31 mmol) and stirred overnight. The reaction was diluted with water and extracted 2× with ethyl acetate. The organic layer was dried over sodium sulfate, filtered, and concentrated to give the aryl ether which was used crude in the next reaction. LCMS found 692.15 [M+H]⁺.

To 1-({1-(2-cyclopentyloxycarbonylamino-3,3-dimethyl-butyryl)-4-[2-cyclopropyl-6-(2-fluoro-phenyl)-pyrimidin-4-yloxy]-pyrrolidine-2-carbonyl}-amino)-2-vinyl-cyclopropanecarboxylic acid methyl ester (100 mg, 0.14 mmol) in 5 ml THF, 2 ml methanol, and 2 ml water, was added lithium hydroxide (10 mg, 0.41 mmol). The mixture was stirred overnight then quenched with 1N HCl and extracted 2× with ethyl acetate. The organic layer was dried over sodium sulfate, filtered, and concentrated. The mixture was purified by reverse phase HPLC to provide the desired acid (71.8 mg, 51%→2 steps): LCMS found 678.10 [M+H]⁺.

Compound 204 was prepared according to the method presented in example 27. Treatment of 1-({1-(2-cyclopentyloxycarbonylamino-3,3-dimethyl-butyryl)-4-[2-cyclopropyl-6-(2-fluoro-phenyl)-pyrimidin-4-yloxy]-pyrrolidine-2-carbonyl}-amino)-2-vinyl-cyclopropanecarboxylic acid under the same conditions adjusted for scale provided the desired product (1.5 mg, 2%): ¹H NMR (CD₃OD, 300 MHz, diagnostic peaks) δ 9.27 (m, 1H), 8.03 (m, 1H), 7.50 (m, 1H), 7.19-7.30 (m, 2H), 6.67 (m, 1H), 4.16 (m, 1H), 0.93 (m, 2H), 0.75 (m, 2H); LCMS found 797.11 [M+H]⁺.

Example 206

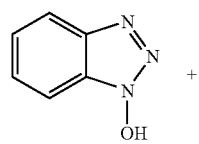

+

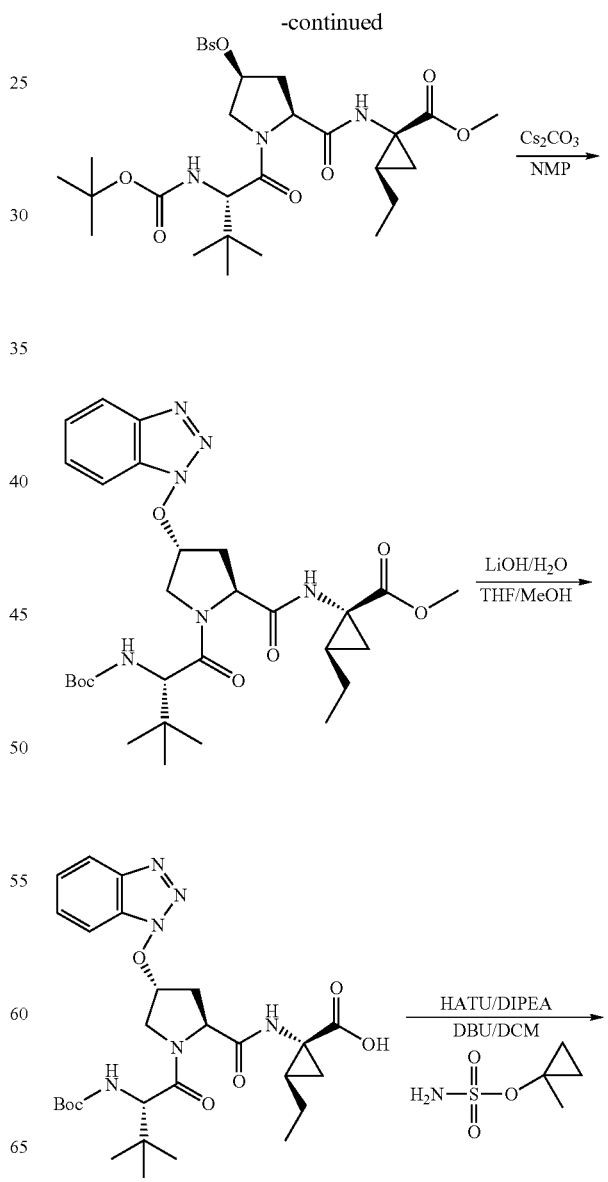

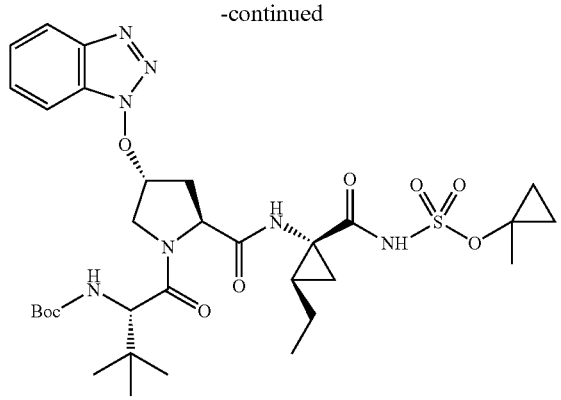

Compound 206

Benzotriazol-1-ol (68 mg, 0.5 mmol) was dissolved in NMP (2.5 mL) and treated with $Cs_2CO_3$ (245 mg, 0.75 mmol) followed by the addition of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (345 mg, 0.5 mmol). The reaction mixture was heated to 60° C. for 16 h after which the reaction was cooled to room temperature and diluted with aqueous 5% LiCl. The solution was extracted with EtOAc, washed with saturated aqueous NaCl, and dried over sodium sulfate. After removal of solvent, the crude product was purified by column chromatography on silica (75-95% EtOAc/hexane) to provide the aryl ether (253 mg, 86%). LCMS found 588 ([M+H]+.

Compound 205 was prepared according to the methods described in example 29. Treatment of 1-{[4-(benzotriazol-1-yloxy)-1-(2-tert-butoxycarbonylamino-3,3-dimethyl-butyryl)-pyrrolidine-2-carbonyl]-amino}-2-ethyl-cyclopropanecarboxylic acid methyl ester under the same conditions, adjusted for scale, and after reverse phase HPLC purification afforded compound 206 (164 mg, 72%). $^1$H MNR (300 MHz, $CD_3OD$): 6.9.36 (s, 1H), δ 8.01 (d, 1H), δ 7.90 (d, 1H), δ 7.65 (m, 1H), δ 7.50 (m, 1H), δ 5.52 (s, 1H), δ 4.67 (m, 1H), δ 4.48 (m, 1H), δ 4.32 (s, 1H), δ 4.08 (m, 1H), δ 2.63 (m, 1H), δ 2.21 (m, 1H), 61.70-0.99 (m, 33H), δ 0.70 (m, 2H). LCMS found 707 [M+H]+.

Example 207

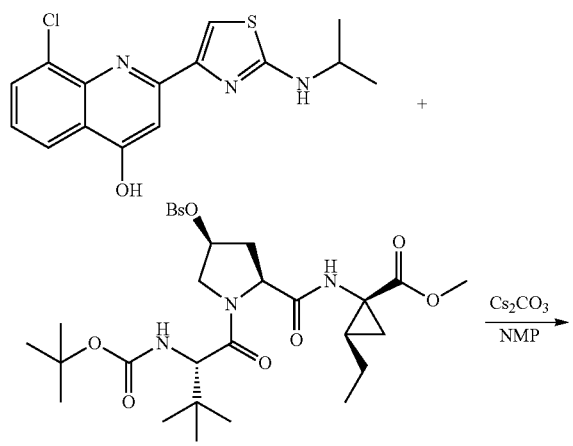

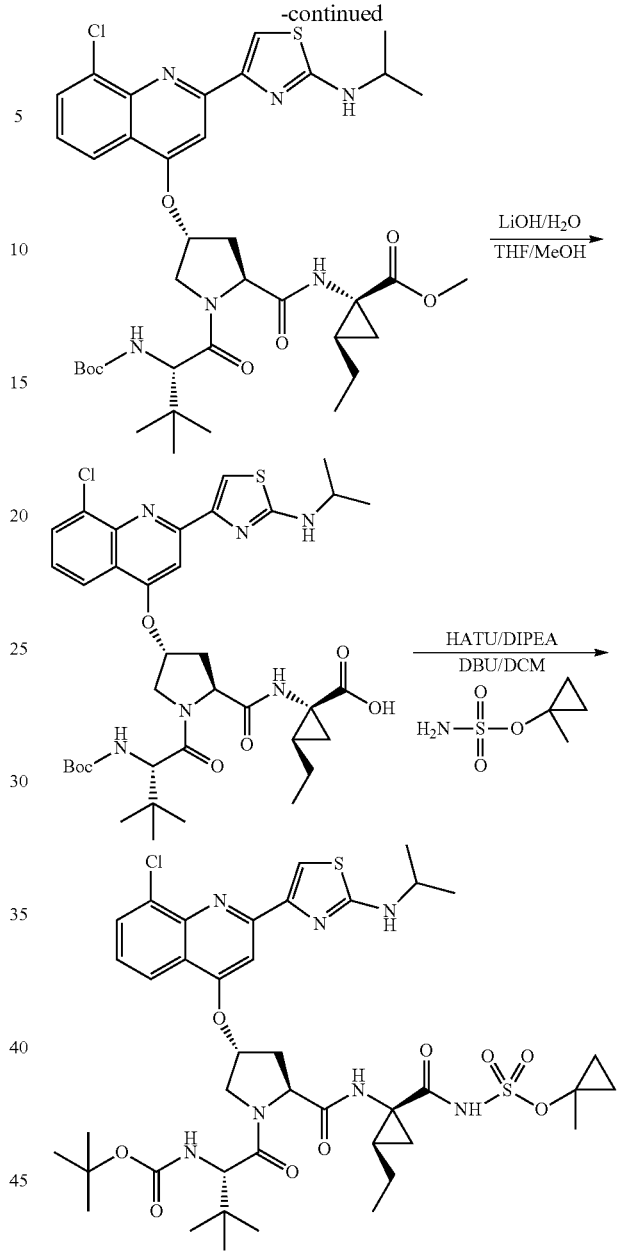

Compound 207

8-Chloro-2-(2-isopropylamino-thiazol-4-yl)-quinolin-4-ol (50 mg, 0.16 mmol) was dissolved in NMP (1 mL) and treated with $Cs_2CO_3$ (76 mg, 0.23 mmol) followed by the addition of 1-{[4-(4-bromo-benzenesulfonyloxy)-1-(2-tert-butoxycarbonylamino-3,3-dimethyl-butyryl)-pyrrolidine-2-carbonyl]-amino}-2-ethyl-cyclopropanecarboxylic acid methyl ester (129 mg, 0.23 mmol). The reaction mixture was heated to 60° C. for 16 h after which the reaction was cooled to room temperature and diluted with aqueous 5% LiCl. The solution was extracted with EtOAc, washed with saturated aqueous NaCl, and dried over sodium sulfate. After removal of solvent, the crude product was purified by column chromatography on silica (75-95% EtOAc/hexane) to provide the aryl ether (97 mg, 81%). LCMS found 772 ([M+H]+.

Compound 207 was prepared according to the methods described in example 29. Treatment of 1-({1-(2-tert-Butoxycarbonylamino-3,3-dimethyl-butyryl)-4-[8-chloro-2-(2-isopropylamino-thiazol-4-yl)-quinolin-4-yloxy]-pyrrolidine-2-carbonyl}-amino)-2-ethyl-cyclopropanecarboxylic acid methyl ester under the same conditions, adjusted for scale, and after reverse phase HPLC purification afforded compound 207 (12 mg, 62%). LCMS found 892 ([M+H]$^+$. $^1$H MNR (300 MHz, CD$_3$OD): δ 9.23 (s, 1H), δ 7.50 (d, 1H), δ 7.31 (d, 1H), δ 7.21 (m, 1H), δ 5.86 (m, 1H), δ 5.47 (m, 2H), δ 4.61-3.84 (m, 5H), δ 2.62 (m, 1H), δ 2.33 (m, 1H), 61.69-0.99 (m, 40H), δ 0.69 (m, 2H).

Biological Assays

NS3 Enzymatic Potency: Purified NS3 protease is complexed with NS4A peptide and then incubated with serial dilutions of compound (DMSO used as solvent). Reactions are started by addition of dual-labeled peptide substrate and the resulting kinetic increase in fluorescence is measured. Non-linear regression of velocity data is performed to calculate IC$_{50}$s. Activity are initially tested against genotype 1b protease. Depending on the potency obtained against genotype 1b, additional genotypes (1a, 2a, 3) and or protease inhibitor resistant enzymes (D168Y, D168V, or A156T mutants) may be tested. BILN-2061 is used as a control during all assays. Representative compounds of the invention were evaluated in this assay and were typically found to have IC$_{50}$ values of less than about 1 μm.

Replicon Potency and Cytotoxicity: Huh-luc cells (stably replicating Bartenschlager's 1389luc-ubi-neo/NS3-3'/ET genotype 1b replicon) is treated with serial dilutions of compound (DMSO is used as solvent) for 72 hours. Replicon copy number is measured by bioluminescence and non-linear regression is performed to calculate EC$_{50}$s. Parallel plates treated with the same drug dilutions are assayed for cytotoxicity using the Promega CellTiter-Glo cell viability assay. Depending on the potency achieved against the 1b replicon, compounds may be tested against a genotype 1a replicon and/or inhibitor resistant replicons encoding D168Y or A156T mutations. BILN-2061 is used as a control during all assays. Representative compounds of the invention were evaluated in this assay and were typically found to have EC$_{50}$ values of less than about 5 μm.

Effect of Serum Proteins on Replicon Potency

Replicon assays are conducted in normal cell culture medium (DMEM+10% FBS) supplemented with physiologic concentrations of human serum albumin (40 mg/mL) or α-acid glycoprotein (1 mg/mL). EC$_{50}$s in the presence of human serum proteins are compared to the EC$_{50}$ in normal medium to determine the fold shift in potency.

Enyzmatic Selectivity: The inhibition of mammalian proteases including Porcine Pancreatic Elastase, Human Leukocyte Elastase, Protease 3, and Cathepsin D are measured at K$_m$ for the respective substrates for each enzyme. IC$_{50}$ for each enzyme is compared to the IC$_{50}$ obtained with NS3 1b protease to calculate selectivity. Representative compounds of the invention have shown activity.

MT-4 Cell Cytotoxicity: MT4 cells are treated with serial dilutions of compounds for a five day period. Cell viability is measured at the end of the treatment period using the Promega CellTiter-Glo assay and non-linear regression is performed to calculate CC$_{50}$.

Compound Concentration Associated with Cells at EC$_{50}$: Huh-luc cultures are incubated with compound at concentrations equal to EC$_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the invention have shown activity.

Solubility and Stability: Solubility is determined by taking an aliquot of 10 mM DMSO stock solution and preparing the compound at a final concentration of 100 μM in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after an 1 hour incubation with PBS at 37° C. will also be determined.

Stability in Cryopreserved Human, Dog, and Rat Hepatocytes: Each compound is incubated for up to 1 hour in hepatocyte suspensions (100 μl, 80,000 cells per well) at 37° C. Cryopreserved hepatocytes are reconstituted in the serum-free incubation medium. The suspension is transferred into 96-well plates (50 μL/well). The compounds are diluted to 2 μM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat: Each compound is incubated for up to 1 hour in S9 suspension (500 μl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability: Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar Transwell® plates. The compounds are dosed on the apical side for forward permeability (A-to-B), and are dosed on the basolateral side for reverse permeability (B-to-A). The cells are incubated at 37° C. with 5% CO2 in a humidified incubator. At the beginning of incubation and at 1 hr and 2 hr after incubation, a 200-μL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 μM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left( \frac{C_f}{C_b + C_f} \right)$$

Where $C_f$ and $C_b$ are free and bound concentrations determined as the post-dialysis buffer and plasma concentrations, respectively.

CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples will be taken from the incubation mixture at the beginning of the incubation and at 5, 15, 30, 45 and 60 min after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds will be incubated for up to 2 hours in plasma (rat, dog, monkey, or human) at 37° C. Compounds are added to the plasma at final concentrations of 1 and 10 ug/mL. Aliquots are taken at 0, 5, 15, 30, 60, and 120 min after adding the compound. Concentration of compounds and major metabolites at each timepoint are measured by LC/MS/MS.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:
1. A compound of formula I:

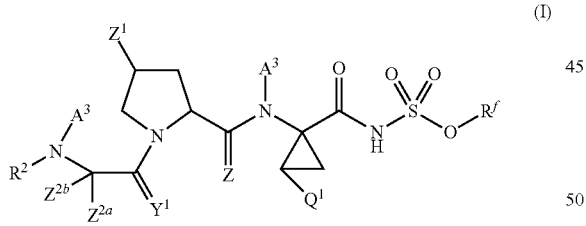

(I)

or a pharmaceutically acceptable salt thereof, wherein:
$Q^1$ is (C1-4)alkyl, (C2-4)alkenyl, or (C2-4)alkynyl which $Q^1$ is optionally substituted with cyano, F, Cl, Br, $S(O)_2R_r$, (C1-4)alkoxy, or cycloalkyl; or $Q^1$ and $Z^{2a}$ taken together with the atoms to which they are attached form a heterocycle, wherein said heterocycle may optionally be substituted with one or more oxo (=O), or $A^3$;
$Z^{2a}$ is H, (C1-6)alkyl, (C2-6)alkenyl, (C2-6)alkynyl, haloalkyl, (C1-10)alkyl-S(=O)$_2$—(C1-10)alkyl, or cycloalkyl, wherein any carbon atom of $Z^{2a}$ may optionally be replaced with O, S, S(=O), S(=O)$_2$, or NH and wherein any cycloalkyl is optionally substituted with one or more (C1-4)alkyl, (C2-4)alkenyl, (C2-4)alkynyl, haloalkyl, F, Cl, Br, or I;

$Z^{2b}$ is H;
$R^f$ is aryl, heteroaryl, or cycloalkyl wherein said aryl, heteroaryl or cycloalkyl is optionally substituted with one to three $A^3$;
$A^2$ is (C1-4)alkyl;
each $A^3$ is independently H, —OH, halo, cyano, alkyl, alkenyl, alkynyl, amino, —C(O)A$^2$, or —C(O)OA$^2$, wherein each $A^3$ may be optionally substituted with up to 4 halogen, cyano, or alkoxy;
$R^2$ is pyrrol-1-ylcarbonyl, morpholinocarbonyl, 3,3-dimethylbutanoyl, tert-butoxycarbonyl, cyclopentoxycarbonyl, 1,1-dimethyl-2,2,2-trifluoroethoxycarbonyl, 1-methylcyclopropyloxycarbonyl, 2-(N,N-dimethylamino)-1,1dimethylethoxycarbonyl, 2-morpholino-1,1dimethylethoxycarbonyl, 3-tetrahydrofuranyloxycarbonyl, isopropoxycarbonyl, 2-methoxy-1,1-dimethylethoxycarbonyl, 2,2-dimethylpropoxycarbonyl, 1-trifluoromethylcyclobutyloxycarbonyl, cyclobutyloxycarbonyl, 1-methylcyclopentyloxycarbonyl, 1-trifluoromethylcyclopentyloxycarbonyl, 1-trifluoromethylcyclobutyloxycarbonyl, or

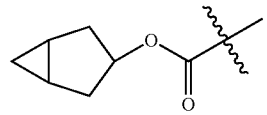 [SMILES: *C(=O)OC1CC2CC2C1]

$Y^1$ is O;
Z is O;
$Z^1$ is selected from the following structures:

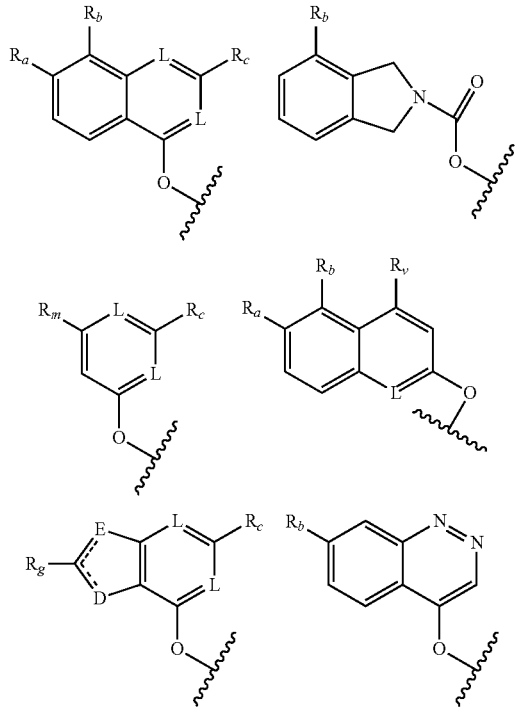

-continued

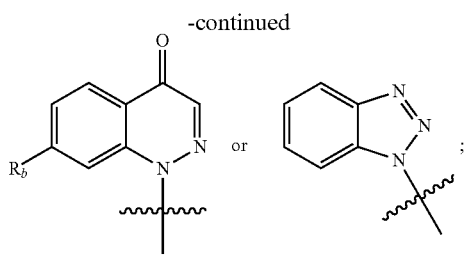

each L is independently CH or N;
one of E or D is O, S, or NR$_y$, and the other E or D is CH or N;
R$_a$ is H, methoxy, trifluoromethoxy, chloro, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, 2-morpholinoethoxy, cyclopropyloxy, 2,2,2-trifluoroethoxy or 2-(N,N-diemthylamino)ethoxy;
R$_b$ is H, F, Cl, methyl or trifluoromethyl;
R$_c$ is a heteroaryl ring selected from:

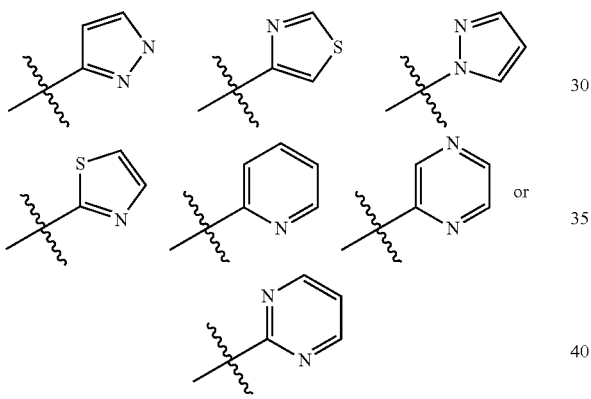

wherein said heteroaryl ring is optionally substituted with one or more (C1-10)alkyl, halo, or NR$_{n1}$R$_{p1}$; wherein each R$_{n1}$ and R$_{p1}$ is independently H or (C1-10)alkyl;
R$_d$ and R$_e$ are each independently H, (C1-10)alkyl, or aryl, wherein each (C1-10)alkyl, or aryl is optionally substituted with one or more halo;
R$_g$ is H, (C1-6)alkyl, (C2-6)alkenyl, (C2-6)alkynyl, halo, hydroxy, cyano, arylthio, (C2-8)cycloalkyl, aryl, heteroaryl, (C1-6)alkoxy, NR$_h$R$_i$, —C(=O)NR$_h$R$_i$, or —C(=O)OR$_d$, wherein each aryl and heteroaryl is optionally substituted with one or more (C1-6)alkyl, halo, hydroxy, cyano, nitro, amino, (C1-6)alkoxy, (C1-6)alkoxycarbonyl, (C1-6)alkanoyloxy, halo-(C1-6)alkyl, or halo(C1-6)alkoxy; wherein each alkyl is optionally substituted with one or more halo, (C1-4)alkoxy, or cyano; and
each R$_h$ and R$_i$ is independently H, alkyl, or haloalkyl;
R$_m$ is H, cyano, F, Cl, Br, I, —C(=O)NR$_d$R$_e$, —C(=O)NR$_d$R$_e$, (C1-10)alkoxy, cycloalkyl, or phenyl that is optionally substituted with one or more F, Cl, Br, I, (C1-10)alkyl, or (C1-10)alkoxy;
each R$_n$ and R$_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, wherein said (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more halo, hydroxy, carboxy, cyano, or (C1-10)alkoxy; or R$_n$ and R$_p$ together with the nitrogen to which they are attached form a pyrrolidine, piperidine, piperazine, morpholino, or thiomorpholino ring;
each R$_r$ is independently H, (C1-10)alkyl, (C2-10)alkenyl, (C2-10)alkynyl, (C1-10)alkanoyl, or (C1-10)alkoxycarbonyl;
R$_v$ is H, F, Cl, Br, I, CF$_3$, or (C1-3)alkyl; and
each R$_y$ is independently H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$, SR$_r$, S(O)R$_r$, or S(O)$_2$R$_r$.

2. The compound of claim 1 wherein Z$^1$ is selected from the following structures:

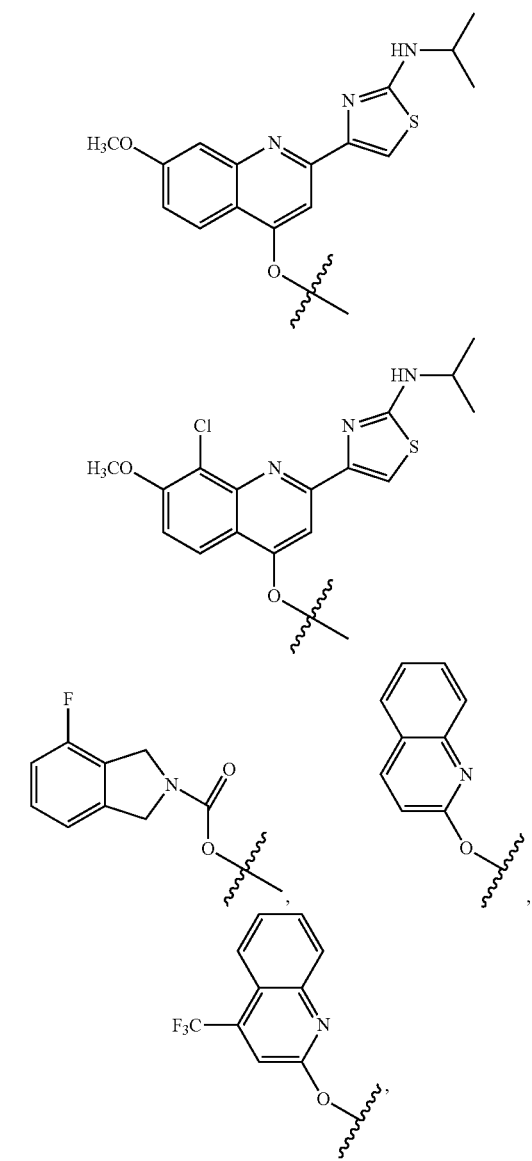

-continued
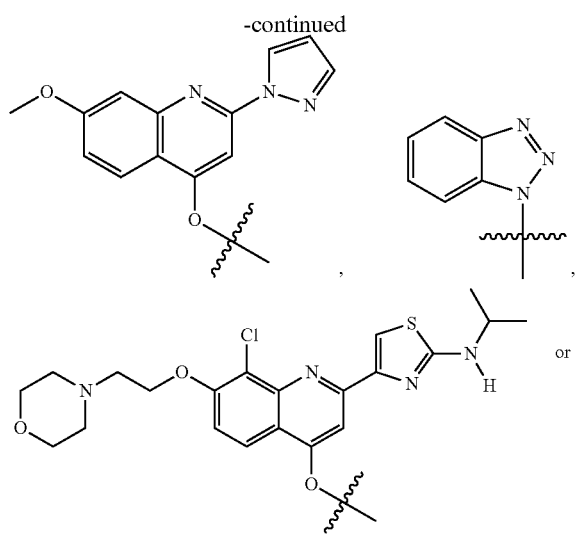
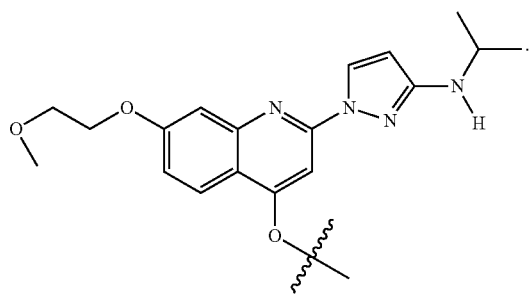
3. The compound of claim 1 wherein $Z^1$ is selected from the following structures:
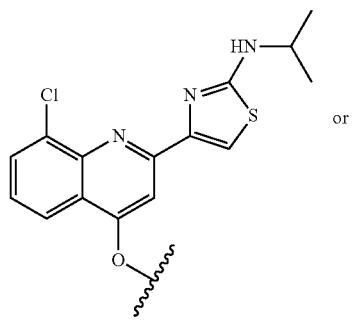
4. The compound of claim 1 which is
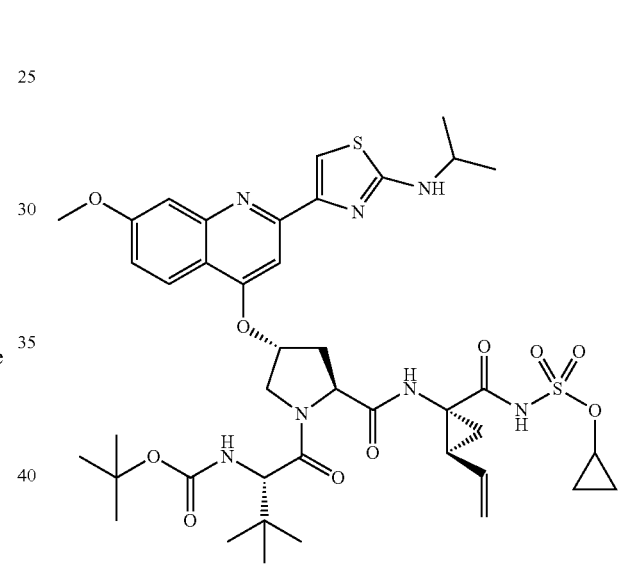
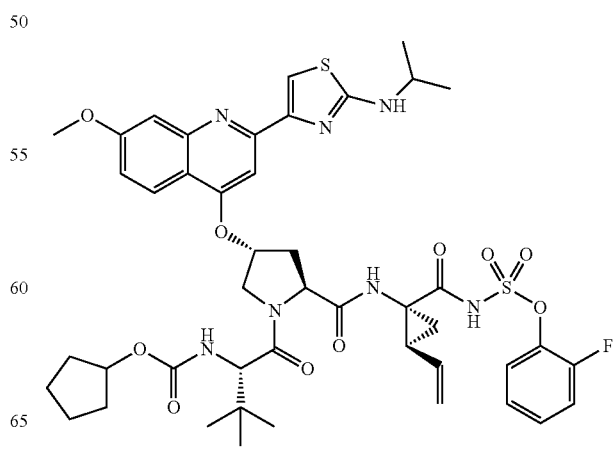

601
-continued
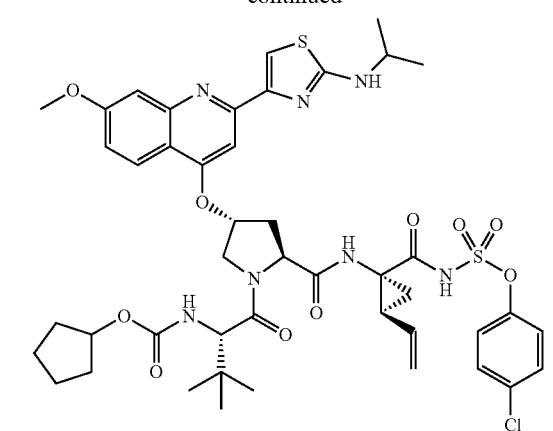
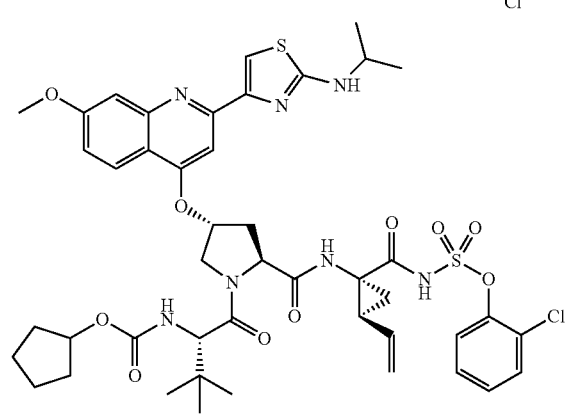
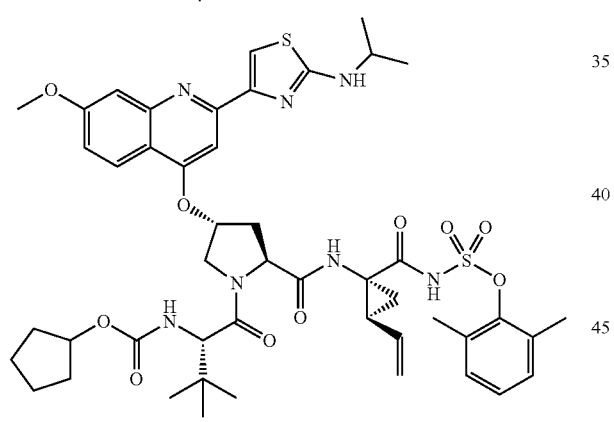
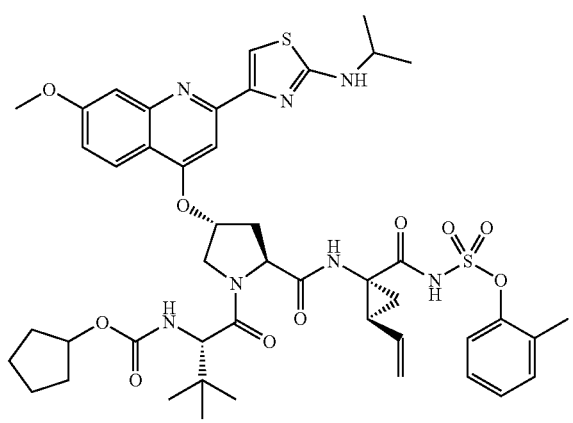
602
-continued
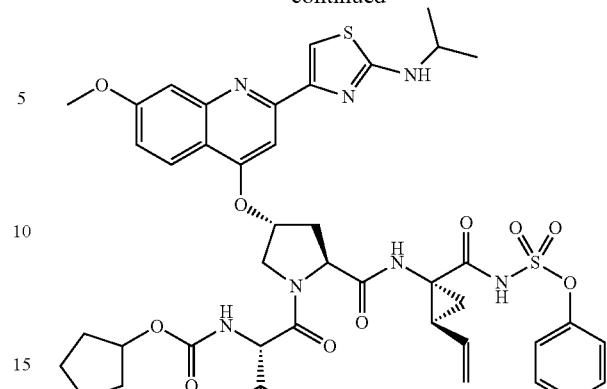
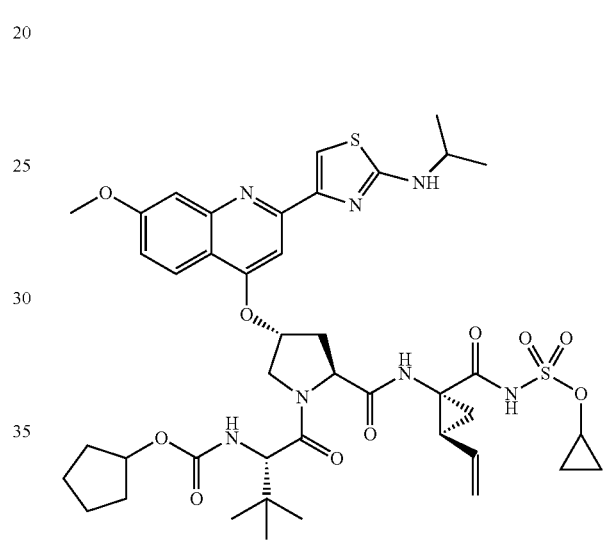
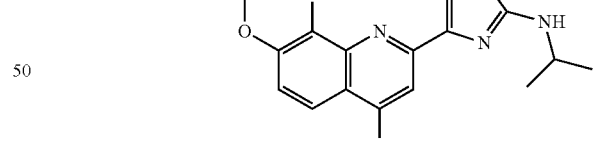
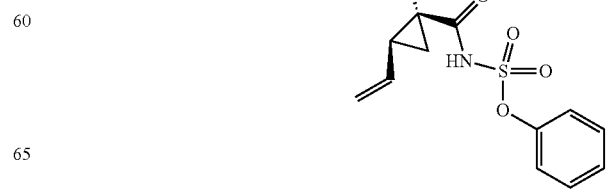

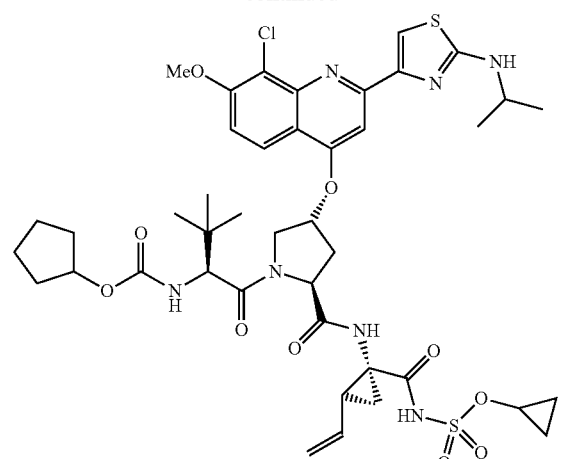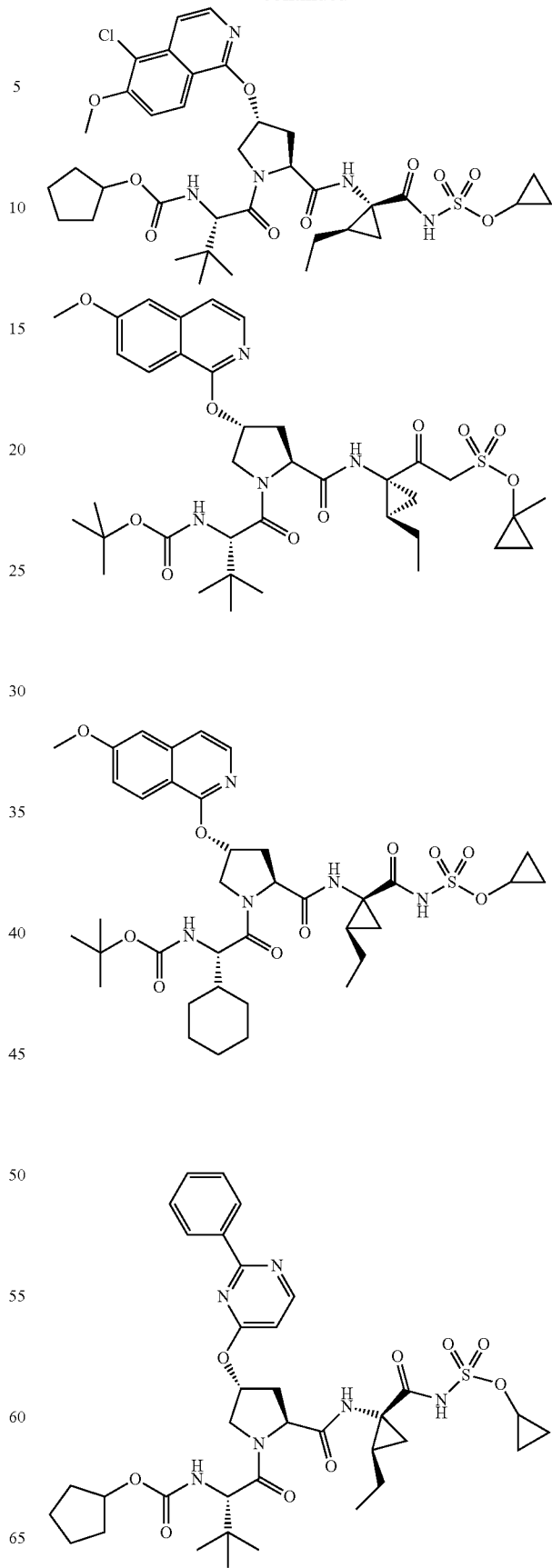

605
-continued
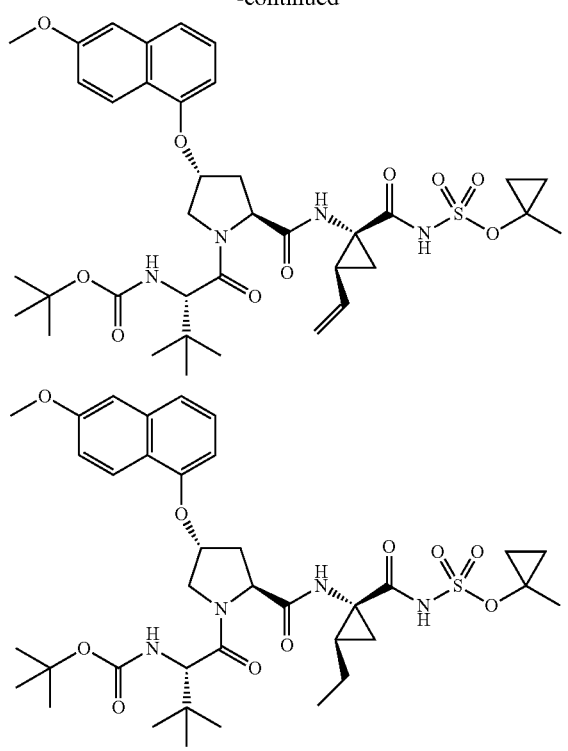
606
-continued
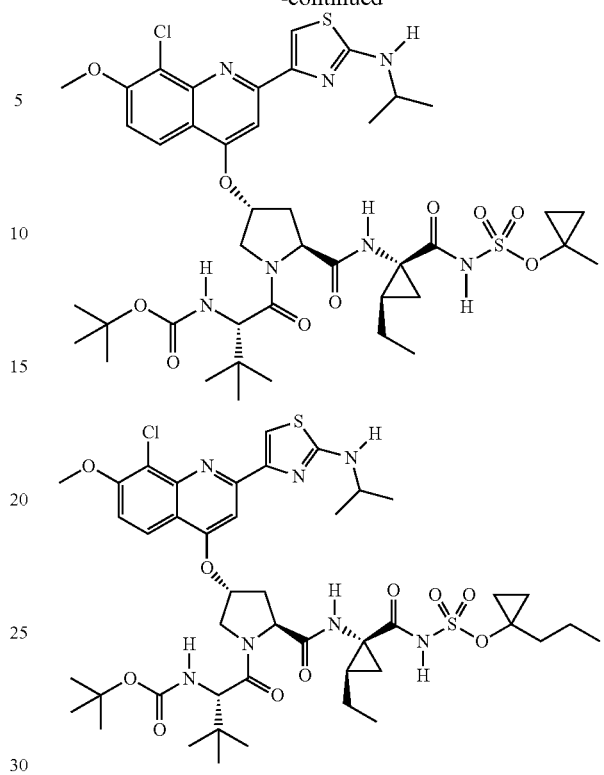
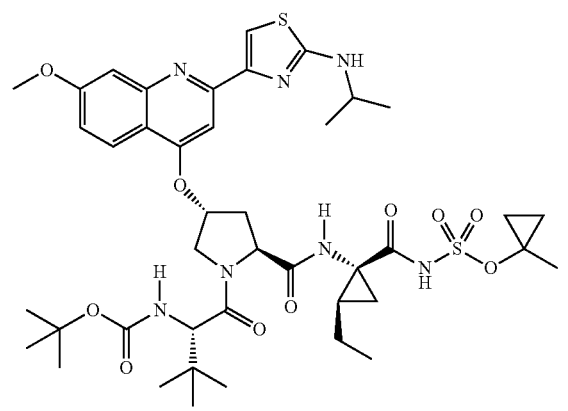
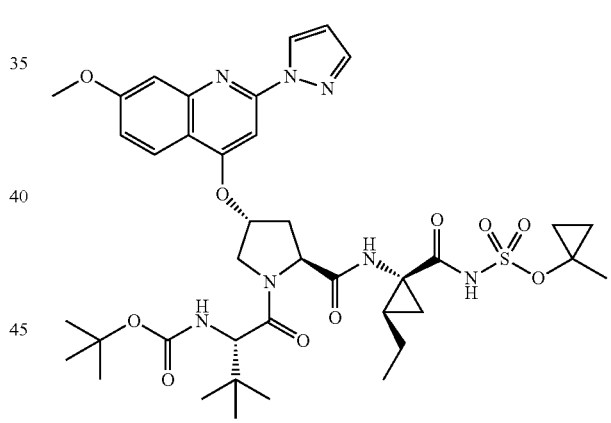
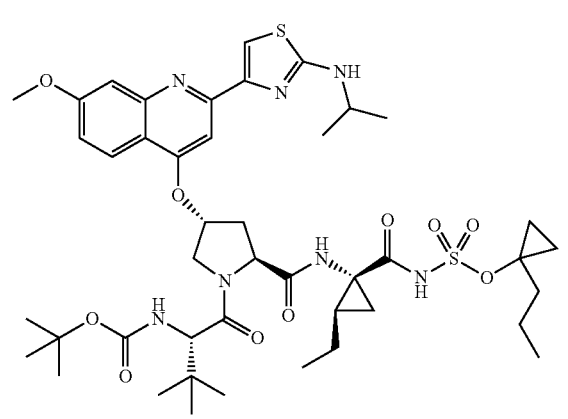
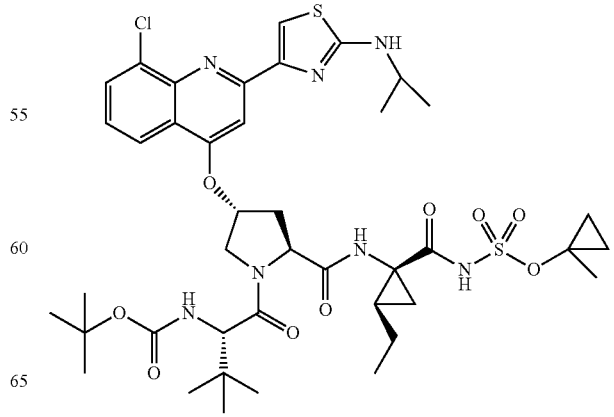

-continued

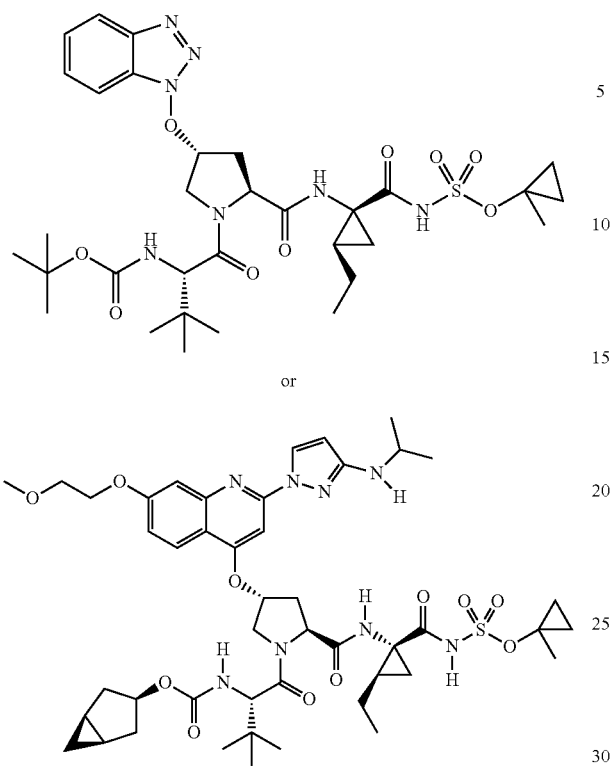

or a pharmaceutically acceptable salt thereof.

5. The compound of formula (I) as described in claim 1 or a pharmaceutically acceptable salt thereof, wherein:

$Z^1$ is:

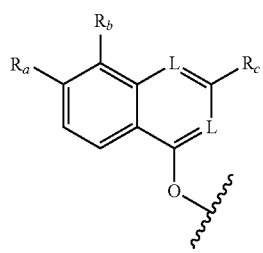

6. The compound of formula (I) as described in claim 5 or a pharmaceutically acceptable salt thereof, wherein $Z^1$ is selected from the following structures:

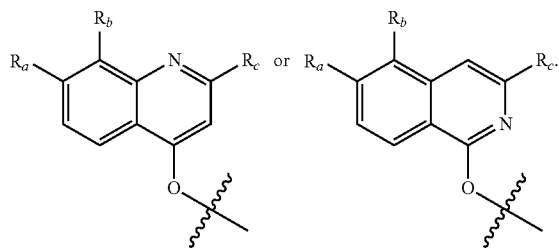

7. The compound of claim 1 wherein $R_c$ is selected from:

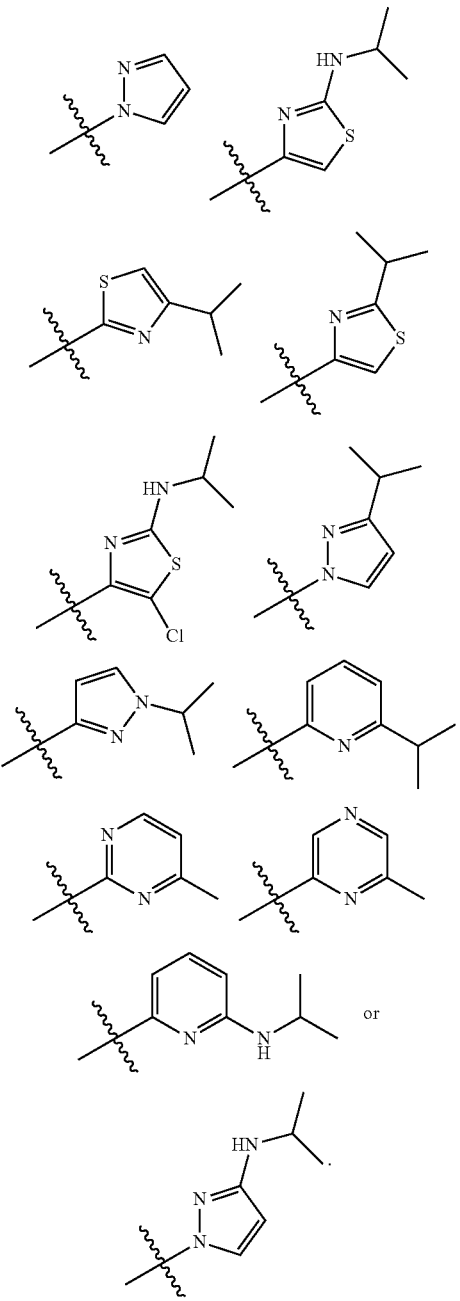

8. The compound of claim 1 wherein $R_c$ is selected from:

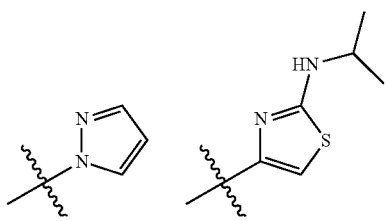

-continued

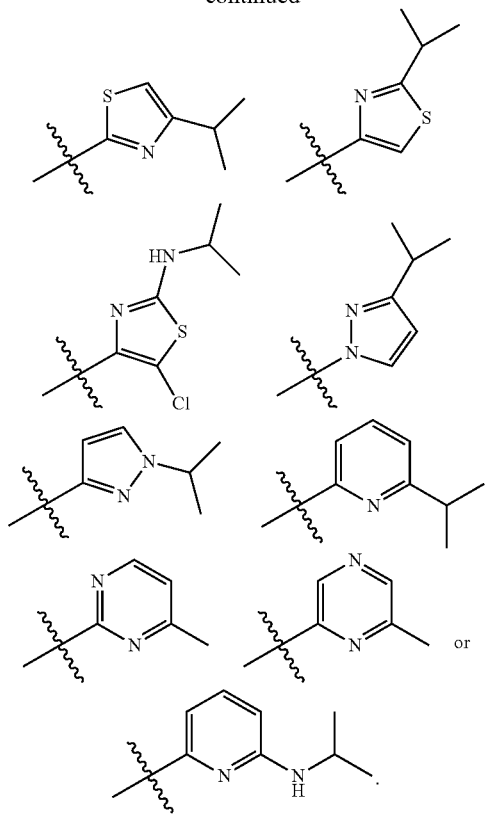

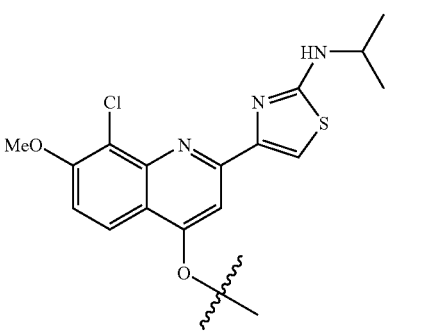

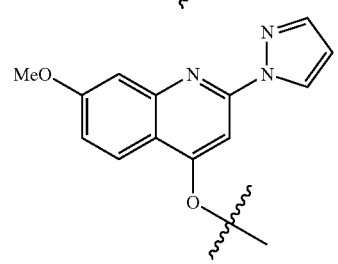

9. The compound of claim 5 wherein $R_a$ is H, methoxy, trifluoromethoxy, chloro, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, or 2-morpholinoethoxy.

10. The compound of claim 1 wherein $Z^1$ is selected from the following structures:

-continued

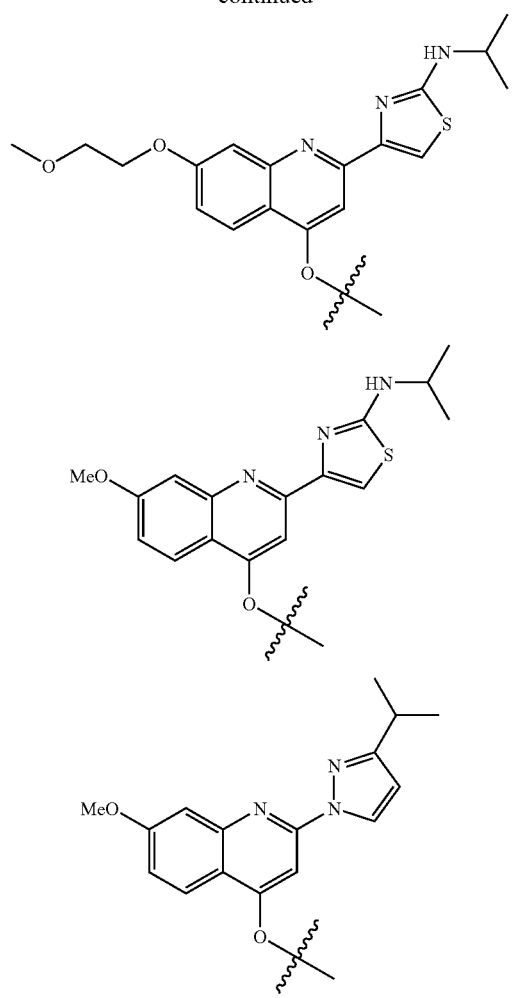

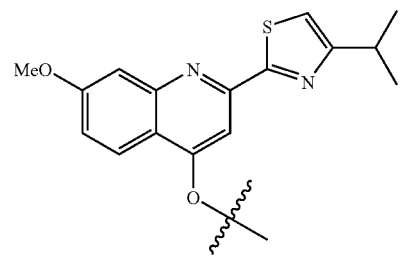

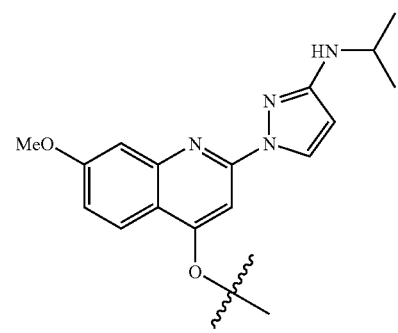

611
-continued
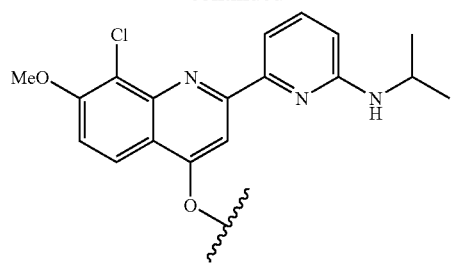
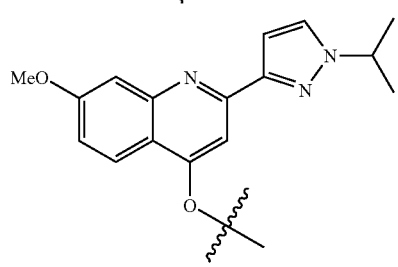
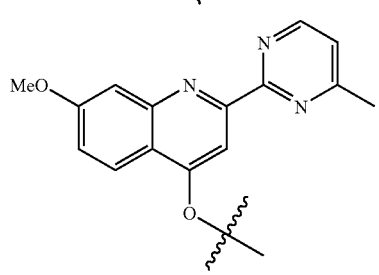
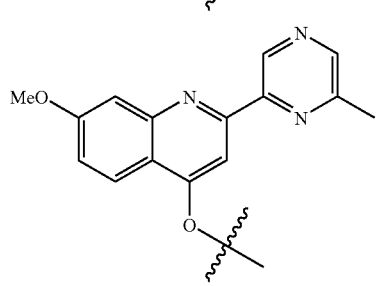
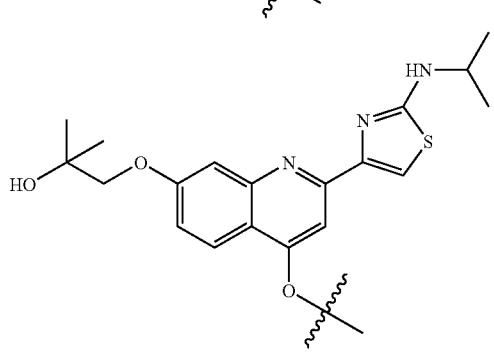
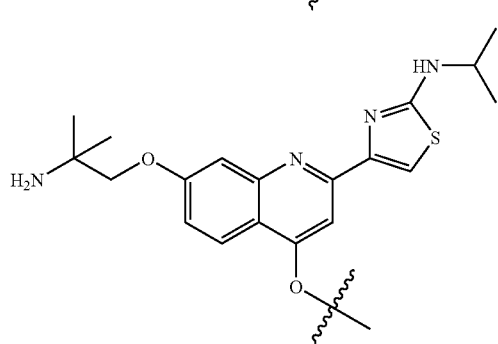
612
-continued
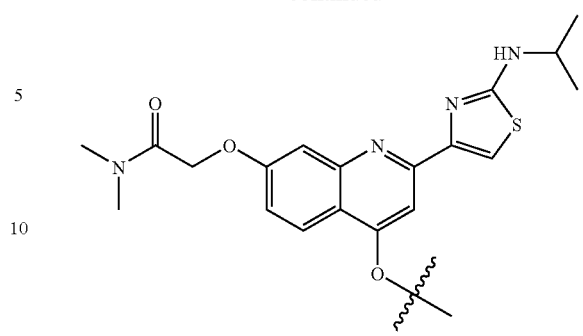
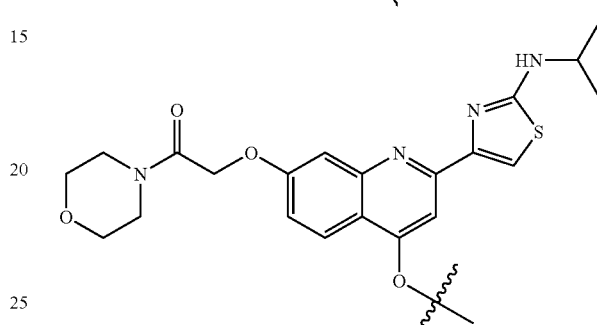
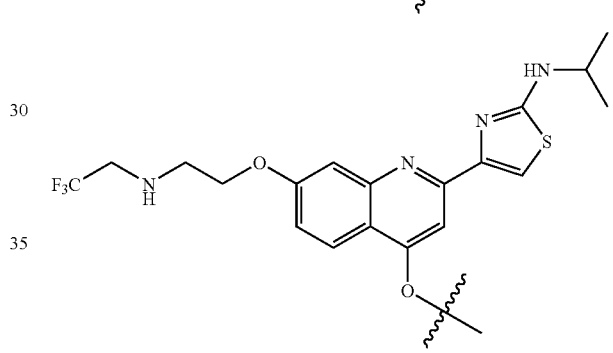
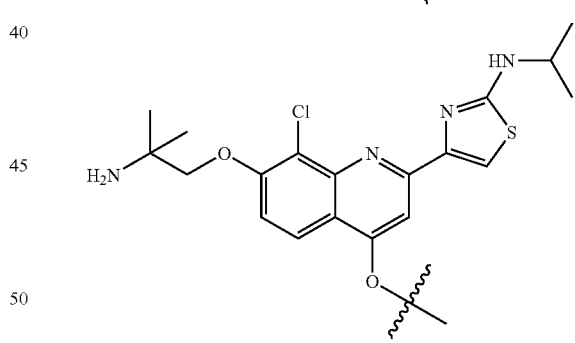
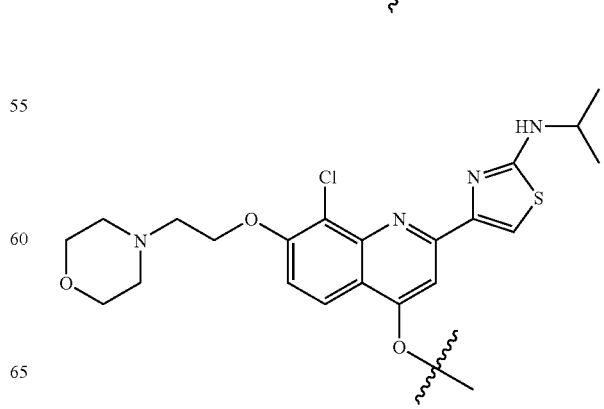

613
-continued

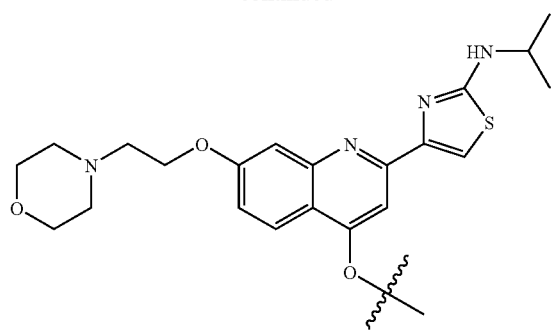

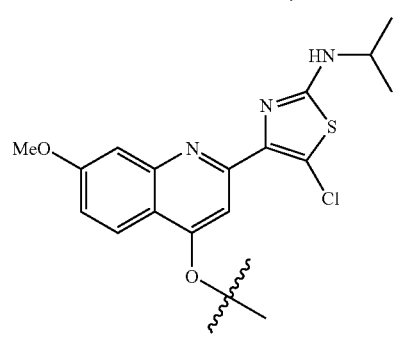

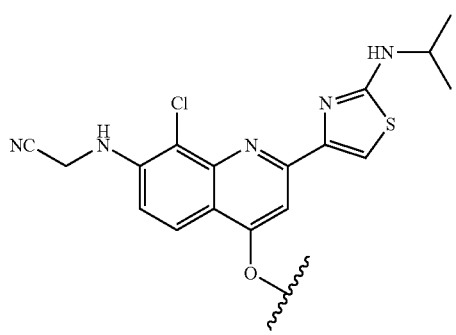

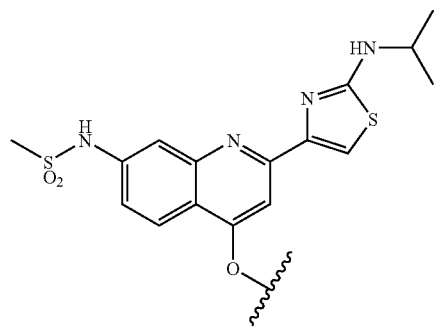

614
-continued

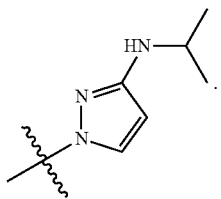 [SMILES: *n1ccc(NC(C)C)n1]

11. The compound of claim 1 wherein $R_c$ is

12. The compound of claim 1 wherein $R^f$ is cyclopropyl optionally substituted by up to three $A^3$.

13. The compound of claim 1 wherein $R^f$ is cyclopropyl optionally substituted by one $A^3$.

14. The compound of claim 1 wherein $R^f$ is phenyl, cyclopropyl, 2-fluorophenyl, 4-chlorophenyl, 2-chlorophenyl, 2,6-dimethylphenyl, 2-methylphenyl, 2,2-dimethylpropyl, 2,2-difluoroethyl, 2,2,2-trifluoroethyl, or 1-methylcyclopropyl.

15. The compound of claim 1 wherein $R^f$ is cyclopropyl.

16. The compound of claim 1 wherein $R^f$ is 1-methylcyclopropyl.

17. A compound of claim 1, wherein the compound of formula I is a compound of formula (II):

(II)

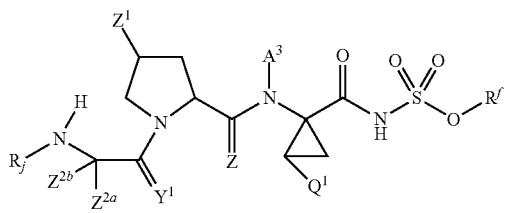

or a pharmaceutically acceptable salt thereof, wherein: $R_j$ is tert-butoxycarbonyl, cyclopentoxycarbonyl, 2,2,2-trifluoro-1,1-dimethylethoxycarbonyl, 1-methylcyclopropoxycarbonyl, 2-(N,N-dimethylamino)-1,1-dimethylethoxycarbonyl, 2-morpholino-1,1-dimethylethoxycarbnyl, tetrahydrofur-3-yloxycarbonyl, or

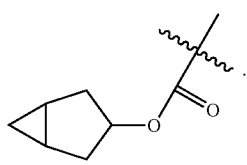 [SMILES: *C(=O)OC1CC2CC2C1 ; "."]

18. The compound of claim 1 wherein $Q^1$ is vinyl, ethyl, cyanomethyl, propyl, 2-fluoroethyl, 2,2-difluoroethyl, or 2-cyanoethyl.

19. The compound of claim 1 wherein $Q^1$ and $Z^{2a}$ taken together with the atoms to which they are attached form a 12-18 membered heterocycle, wherein said heterocycle may optionally be substituted with one or more oxo (=O) or $A^3$.

20. A compound of claim 1, wherein the compound of formula I is a compound of formula (III):

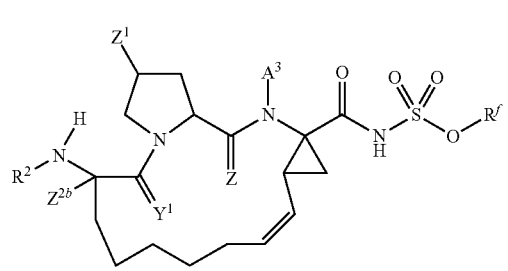
(III)

or a pharmaceutically acceptable salt thereof.

21. A compound of claim 1, wherein the compound of formula I is a compound of formula (IV):

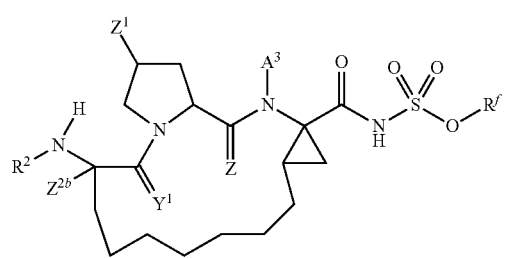
(IV)

or a pharmaceutically acceptable salt thereof.

22. The compound of claim 1 wherein $Z^{2a}$ is tert-butyl, 1-methylcyclohexyl, tetrahydropyran-4-yl, 1-methylcyclohexyl, 4,4-difluorocyclohexyl, 2,2,2-trifluoro-1-trifluoromethylethyl, or cyclopropyl.

23. A pharmaceutical composition comprising the compound as described in claim 1 or a pharmaceutically acceptable salt thereof; and at least one pharmaceutically acceptable carrier.

24. The pharmaceutical composition according to claim 23 for use in treating HCV.

25. The pharmaceutical composition of claim 23, further comprising at least one additional therapeutic agent.

26. The pharmaceutical composition of claim 25, wherein said additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

27. The pharmaceutical composition according to claim 23, further comprising a nucleoside analogue.

28. The pharmaceutical composition according to claim 27, further comprising an interferon or pegylated interferon.

29. The pharmaceutical composition according to claim 28, wherein said nucleoside analogue is selected from ribavirin, viramidine, levovirin, a L-nucleoside, and isatoribine and said interferon is α-interferon or pegylated interferon.

30. A method of treating hepatitis C, said method comprising administering to an individual a pharmaceutical composition which comprises a therapeutically effective amount of the compound as described in claim 1 or a pharmaceutically acceptable salt thereof.

31. A compound of formula (V):

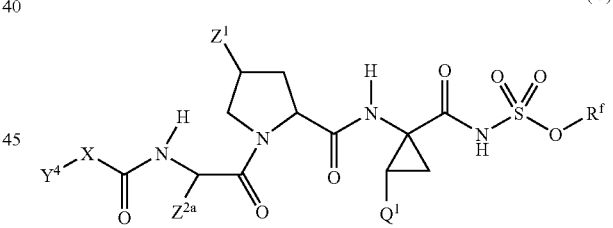
(V)

wherein $Z^1$ is selected from the following structures:

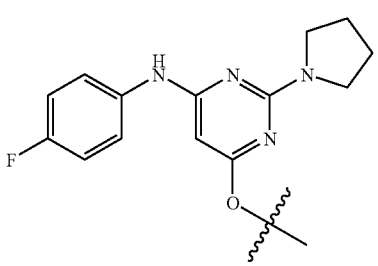

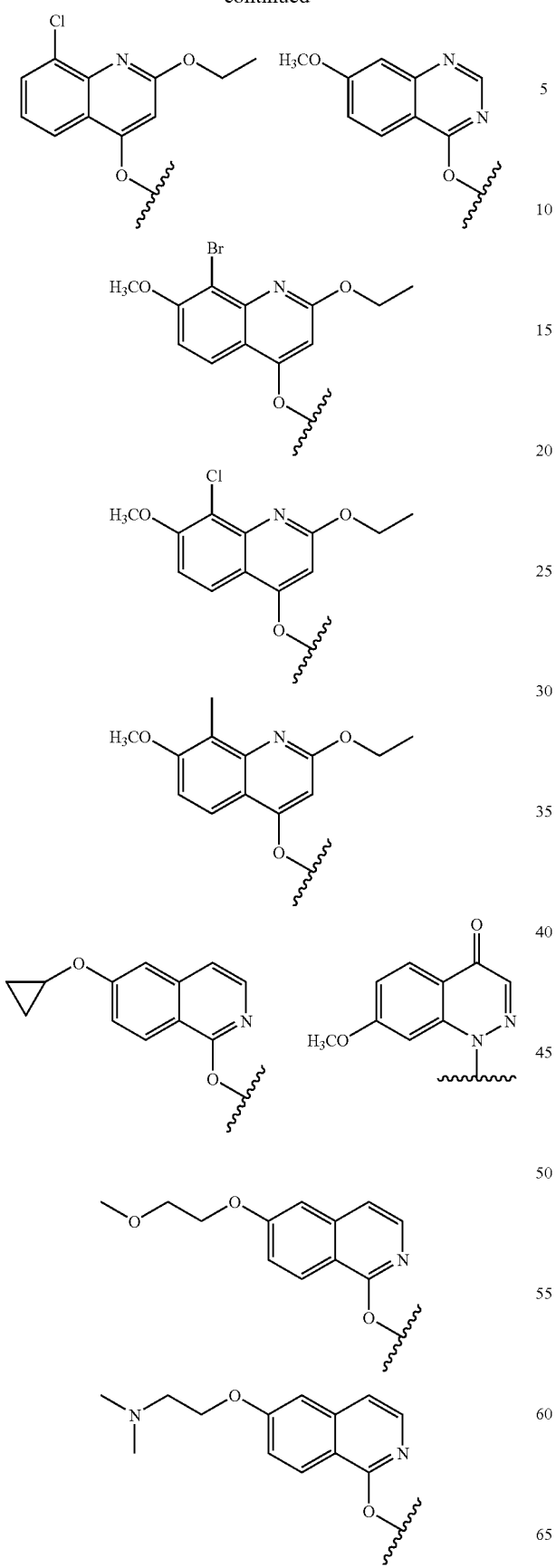
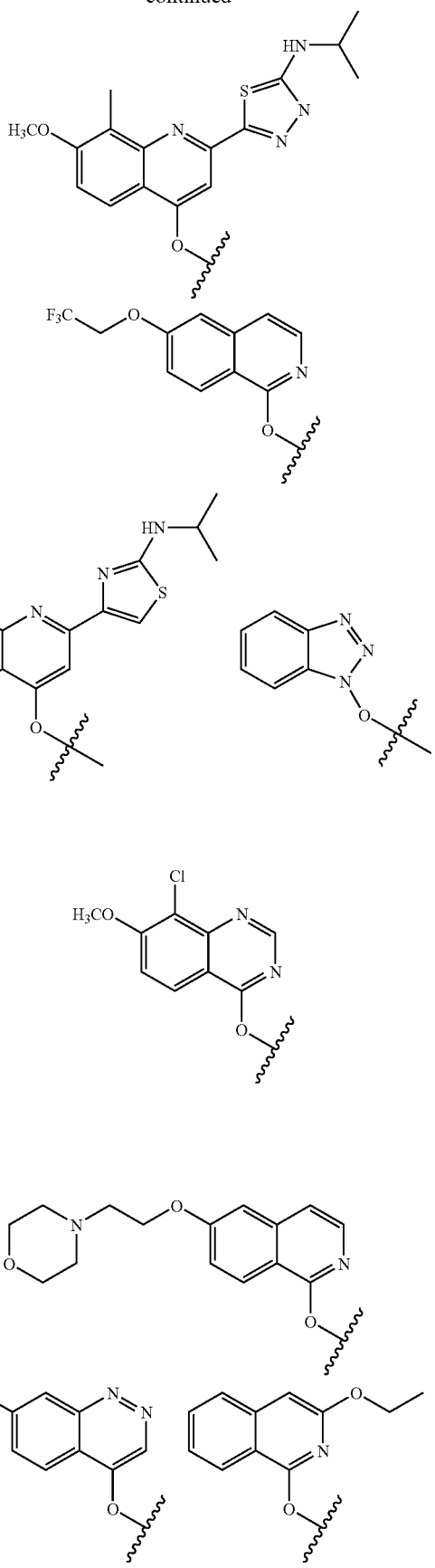

619
-continued

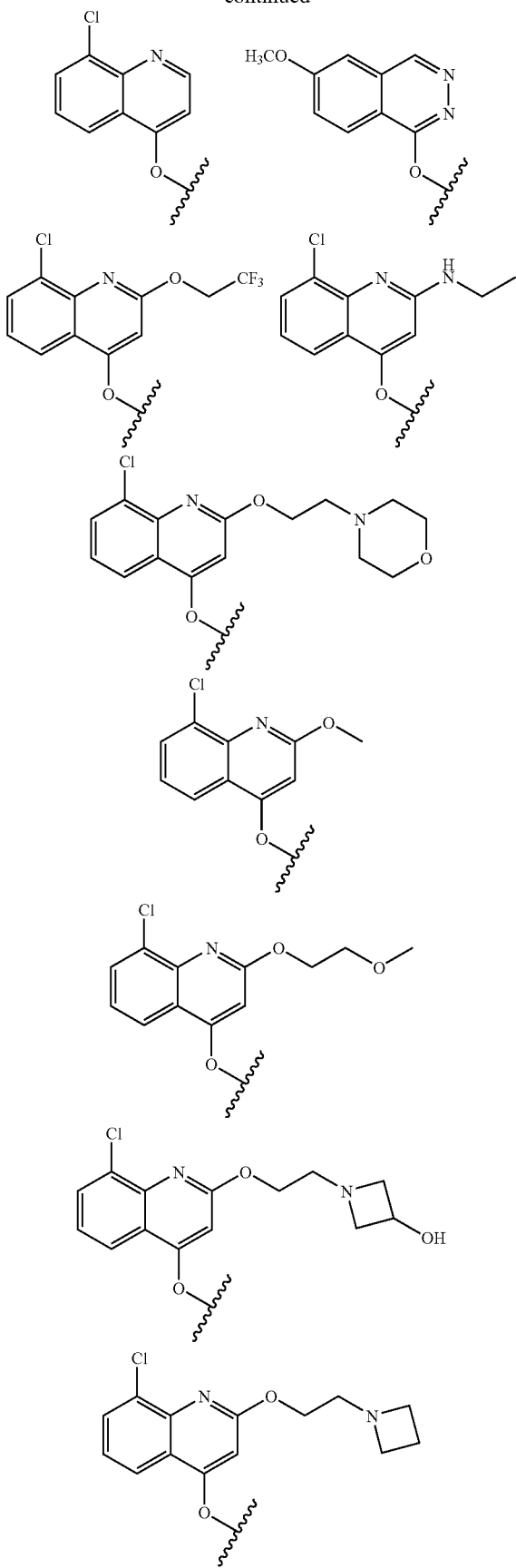

620
-continued

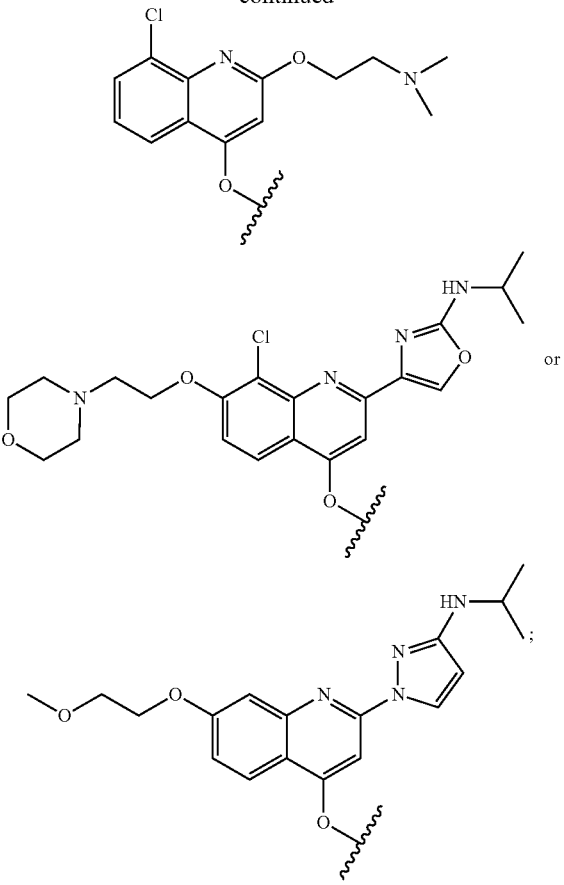

$R^f$ is H, alkyl, alkenyl, alkynyl, aryl, heteroaryl, or cycloalkyl, wherein each alkyl, alkenyl, alkynyl, aryl, heteroaryl, or cycloalkyl is optionally substituted with one or more $R_g$;

$Q^1$ is H, (C1-10)alkyl, (C2-10)alkenyl, or (C2-10)alkynyl wherein said (C1-10)alkyl, (C2-10)alkenyl, or (C2-10)alkynyl is optionally substituted with one or more $R_c$; or $Q^1$ and $Z^{2a}$ taken together with the atoms to which they are attached form a heterocycle, wherein said heterocycle may optionally be substituted with one or more oxo (=O) or halo;

X is a bond, O, S, or NH;

$Y^4$ is (C2-10)alkyl, (C3-7)cycloalkyl, heterocycle, polycarbocycle, or polyheterocycle, wherein said (C2-10) alkyl, (C3-7)cycloalkyl, heterocycle, polycarbocycle, or polyheterocycle is optionally substituted with one or more (C1-10)alkyl, halo, carboxy, hydroxy, (C1-10)alkanoyl, (C1-10)alkoxy, (C1-10)alkanoyloxy, (C1-10)alkoxycarbonyl, trifluoromethyl, $NR_nR_p$, $SR_r$, $S(O)R_r$, or $S(O)_2R_r$;

each $R_c$ is independently cyano, F, Cl, Br, $S(O)_2R_r$, (C1-10)alkoxy, or cycloalkyl;

each $R_d$ is independently H, (C1-10)alkyl, or aryl, wherein each (C1-10)alkyl, or aryl is optionally substituted with one or more halo;

each $R_g$ is independently H, alkyl, alkenyl, alkynyl, halo, hydroxy, cyano, arylthio, cycloalkyl, aryl, heteroaryl, alkoxy, $NR_hR_i$, —C(=O)$NR_hR_i$, or —C(=O)$OR_d$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; wherein each alkyl is optionally substituted with one or more halo, alkoxy, or cyano;

each $R_h$ and $R_i$ is independently H, alkyl, or haloalkyl;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, wherein each (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring; and each $R_r$ is independently (C1-10)alkyl.

32. The compound of claim 31 wherein: X is a bond; and $Y^4$ is pyrrol-1-yl, morpholino, or (C2-10)alkyl.

33. The compound of claim 31 wherein: X is O; and $Y^4$ is tert-butyl, cyclopentyl, 1,1-dimethylethyl, cyclopropyl, tetrahydrofuranyl, isopropyl, 2,2-dimethylpropyl, cyclobutyl or

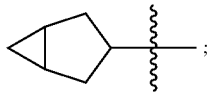 [SMILES: *C1CC2CC2C1]
;

wherein said $Y^4$ is optionally substituted with one or more (C1-10)alkyl, halo, (C1-10)alkoxy, trifluoromethyl, or $NR_nR_p$.

34. The compound of claim 31 wherein: X is NH; and $Y^4$ is (C2-10)alkyl that is optionally substituted with one or more halo.

35. The compound of claim 31 wherein: $R^f$ is alkyl, aryl, or cycloalkyl, optionally substituted with one or more $R_g$ independently selected from alkyl, halo, —C(=O)$OR_d$, and trifluoromethyl, wherein each alkyl of $R_g$ is optionally substituted with one or more halo, alkoxy, or cyano.

36. The compound of claim 31 wherein: $R^f$ is phenyl, cyclopropyl, 2-fluorophenyl, 4-chlorophenyl, 2-chlorophenyl, 2,6-dimethylphenyl, 2-methylphenyl, 2,2-dimethylpropyl, 2,2-difluoroethyl, 2,2,2-trifluoroethyl, 1-methylcyclopropyl, 1-isopropylcyclopropyl, 1-propylcyclopropyl, 2,2,2-trifluoro-1,1-dimethylethyl, 1-(methoxycarbonyl)cyclopropyl, 1-ethylcyclopropyl, 1-trifluoromethylcyclobutyl, 1-(methoxymethyl)cyclopropyl, 1-(2-cyanoethyl)cyclopropyl, or 1-(2,2,2-trifluoroethyl)cyclopropyl.

37. The compound of claim 31 wherein: $Q^1$ is hydrogen, methyl, ethyl, vinyl, cyanomethyl, propyl, 2-fluoroethyl, 2,2-difluoroethyl, 2-cyanoethyl, 2-methoxyethyl, 2-methylsulfonylethyl, or cyclopropyl.

* * * * *

UNITED STATES PATENT AND TRADEMARK OFFICE
CERTIFICATE OF CORRECTION

PATENT NO. : 8,513,186 B2  
APPLICATION NO. : 12/215601  
DATED : August 20, 2013  
INVENTOR(S) : Cottell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1045 days.

Signed and Sealed this
Tenth Day of March, 2015

Michelle K. Lee
*Deputy Director of the United States Patent and Trademark Office*